US011751826B2

(12) United States Patent
Min et al.

(10) Patent No.: US 11,751,826 B2
(45) Date of Patent: Sep. 12, 2023

(54) SYSTEMS, METHODS, AND DEVICES FOR MEDICAL IMAGE ANALYSIS, DIAGNOSIS, RISK STRATIFICATION, DECISION MAKING AND/OR DISEASE TRACKING

(71) Applicant: CLEERLY, INC., Denver, CO (US)

(72) Inventors: James K. Min, Denver, CO (US); James P. Earls, Fairfax Station, VA (US); Hugo Miguel Rodrigues Marques, Lisbon (PT); Ben Hootnick, New York, NY (US)

(73) Assignee: CLEERLY, INC., Denver, CO (US)

( * ) Notice: Subject to any disclaimer, the term of this patent is extended or adjusted under 35 U.S.C. 154(b) by 0 days.

(21) Appl. No.: 17/662,734

(22) Filed: May 10, 2022

(65) Prior Publication Data

US 2022/0386979 A1 Dec. 8, 2022

Related U.S. Application Data

(63) Continuation of application No. 17/367,549, filed on Jul. 5, 2021, now Pat. No. 11,367,190, which is a
(Continued)

(51) Int. Cl.
*A61B 6/00* (2006.01)
*A61B 8/14* (2006.01)
(Continued)

(52) U.S. Cl.
CPC ............ *A61B 6/481* (2013.01); *A61B 5/0066* (2013.01); *A61B 5/0075* (2013.01);
(Continued)

(58) Field of Classification Search
CPC ......... G06T 7/0012; G06T 2207/10081; G06T 2207/10; G06T 2207/101;
(Continued)

(56) References Cited

U.S. PATENT DOCUMENTS 4,945,478 A 7/1990 Merickel et al.
5,722,408 A 3/1998 Dehner et al.
(Continued)

FOREIGN PATENT DOCUMENTS

CA 2368390 C 7/2010
EP 3 431 005 A1 1/2019
(Continued)

OTHER PUBLICATIONS

Abbara et al., "SCCT Guideline for the performance and acquisition of coronary computed tomographic angiography: A report of the society of Cardiovascular Computed Tomography Guidelines Committee: Endorsed by the North American Society for Cardiovascular Imaging (NASCI)." Journal of cardiovascular computed tomography 2016; 10(6):435-449.
(Continued)

*Primary Examiner* — Tom Y Lu
(74) *Attorney, Agent, or Firm* — Knobbe Martens Olson & Bear LLP

(57) ABSTRACT

The disclosure herein relates to systems, methods, and devices for medical image analysis, diagnosis, risk stratification, decision making and/or disease tracking. In some embodiments, the systems, devices, and methods described herein are configured to analyze non-invasive medical images of a subject to automatically and/or dynamically identify one or more features, such as plaque and vessels, and/or derive one or more quantified plaque parameters, such as radiodensity, radiodensity composition, volume, radiodensity heterogeneity, geometry, location, and/or the like. In some embodiments, the systems, devices, and methods described herein are further configured to generate one or more assessments of plaque-based diseases from raw medical images using one or more of the identified features and/or quantified parameters.

30 Claims, 117 Drawing Sheets

Related U.S. Application Data continuation of application No. 17/350,836, filed on Jun. 17, 2021, which is a continuation-in-part of application No. 17/213,966, filed on Mar. 26, 2021, now Pat. No. 11,094,060, which is a continuation of application No. 17/142,120, filed on Jan. 5, 2021, now Pat. No. 11,501,436.

(60) Provisional application No. 63/201,142, filed on Apr. 14, 2021, provisional application No. 63/142,873, filed on Jan. 28, 2021, provisional application No. 63/089,790, filed on Oct. 9, 2020, provisional application No. 63/077,058, filed on Sep. 11, 2020, provisional application No. 63/077,044, filed on Sep. 11, 2020, provisional application No. 63/041,252, filed on Jun. 19, 2020, provisional application No. 62/958,032, filed on Jan. 7, 2020.

(51) Int. Cl.

| | | |
|---|---|---|
| *A61B 6/03* | (2006.01) | |
| *A61B 5/00* | (2006.01) | |
| *G06T 7/00* | (2017.01) | |
| *A61B 8/12* | (2006.01) | |
| *A61B 5/055* | (2006.01) | |
| *A61K 49/04* | (2006.01) | |
| *A61B 5/02* | (2006.01) | |
| *G06F 18/10* | (2023.01) | |
| *G06V 10/74* | (2022.01) | |
| *G06V 10/764* | (2022.01) | |
| *G06V 10/20* | (2022.01) | |
| *G06V 10/24* | (2022.01) | |
| *G06V 40/14* | (2022.01) | |

(52) U.S. Cl.
CPC .......... *A61B 5/02007* (2013.01); *A61B 5/055* (2013.01); *A61B 5/7267* (2013.01); *A61B 5/742* (2013.01); *A61B 5/7475* (2013.01); *A61B 6/032* (2013.01); *A61B 6/037* (2013.01); *A61B 6/504* (2013.01); *A61B 6/5205* (2013.01); *A61B 6/5217* (2013.01); *A61B 8/12* (2013.01); *A61B 8/14* (2013.01); *A61K 49/04* (2013.01); *G06F 18/10* (2023.01); *G06T 7/0012* (2013.01); *G06V 10/20* (2022.01); *G06V 10/245* (2022.01); *G06V 10/761* (2022.01); *G06V 10/764* (2022.01); *G06V 40/14* (2022.01); *G06T 2207/10081* (2013.01); *G06T 2207/10088* (2013.01); *G06T 2207/10101* (2013.01); *G06T 2207/10132* (2013.01); *G06T 2207/20081* (2013.01); *G06T 2207/30048* (2013.01); *G06T 2207/30101* (2013.01); *G06V 10/247* (2022.01)

(58) Field of Classification Search
CPC . G06T 2207/10132; G06T 2207/20081; G06T 2207/30048; G06T 2207/30101; A61B 5/0066; A61B 5/0075; A61B 5/055; A61B 5/7267; A61B 5/742; A61B 5/7475; A61B 6/032; A61B 6/03; A61B 6/504; A61B 6/5205; A61B 8/12; A61B 8/14; A61B 8/522; A61B 6/583; A61B 8/587; A61B 6/5217; A61B 8/0891; A61K 49/04; G06K 9/6298; G06K 9/3216; G06K 9/36; G06K 9/6215; G06K 9/62; G06K 2009/363; G06K 2209/05
See application file for complete search history.

(56) References Cited

U.S. PATENT DOCUMENTS

| | | |
|---|---|---|
| 5,891,030 A | 4/1999 | Johnson et al. |
| 6,047,080 A | 4/2000 | Chen et al. |
| 6,591,004 B1 | 7/2003 | VanEssen et al. |
| 7,535,986 B2 | 5/2009 | Hempel |
| 7,558,611 B2 | 7/2009 | Arnold et al. |
| 7,570,983 B2 | 8/2009 | Becker et al. |
| 7,711,165 B2 | 5/2010 | Lesage et al. |
| 7,715,626 B2 | 5/2010 | Florin et al. |
| 7,805,385 B2 | 9/2010 | Steck et al. |
| 7,813,549 B2 | 10/2010 | Buelow et al. |
| 7,840,062 B2 | 11/2010 | Boroczky et al. |
| 7,860,283 B2 | 12/2010 | Begelman et al. |
| 7,899,764 B2 | 3/2011 | Martin et al. |
| 7,904,977 B1 | 3/2011 | Singh |
| 7,912,528 B2 | 3/2011 | Krishnan et al. |
| 7,940,974 B2 | 5/2011 | Skinner et al. |
| 7,940,977 B2 | 5/2011 | Begelman et al. |
| 7,953,266 B2 | 5/2011 | Gulsun et al. |
| 7,993,274 B2 | 8/2011 | Pruvot et al. |
| 8,046,488 B2 | 10/2011 | Cherukuri et al. |
| 8,068,894 B2 | 11/2011 | Huizenga et al. |
| 8,144,949 B2 | 3/2012 | Simon et al. |
| 8,200,466 B2 | 6/2012 | Spiker et al. |
| 8,386,188 B2 | 2/2013 | Taylor et al. |
| 8,526,699 B2 | 9/2013 | Mittal et al. |
| 8,582,854 B2 | 11/2013 | Zhang et al. |
| 8,605,979 B2 | 12/2013 | Arnold et al. |
| 8,774,479 B2 | 7/2014 | Madabhushi et al. |
| 8,777,854 B2 | 7/2014 | Patwardhan et al. |
| 8,885,905 B2 | 11/2014 | Dey et al. |
| 8,938,106 B2 | 1/2015 | Aulbach et al. |
| 9,008,392 B1 | 4/2015 | Bai et al. |
| 9,058,692 B1 | 6/2015 | Grady et al. |
| 9,070,214 B1 | 6/2015 | Grady et al. |
| 9,081,721 B1 | 7/2015 | Grady et al. |
| 9,129,417 B2 | 9/2015 | Zheng et al. |
| 9,155,512 B2 | 10/2015 | Choi et al. |
| 9,159,159 B2 | 10/2015 | Bai et al. |
| 9,195,801 B1 | 11/2015 | Sankaran et al. |
| 9,220,418 B2 | 12/2015 | Choi et al. |
| 9,220,419 B2 | 12/2015 | Choi et al. |
| 9,235,887 B2 | 1/2016 | Bucker et al. |
| 9,239,905 B1 | 1/2016 | Sankaran et al. |
| 9,280,639 B2 | 3/2016 | Sankaran et al. |
| 9,295,397 B2 | 3/2016 | Liu et al. |
| 9,295,429 B2 | 3/2016 | Ong et al. |
| 9,378,580 B2 | 6/2016 | Grady et al. |
| 9,430,827 B2 | 8/2016 | Kelm et al. |
| 9,538,925 B2 | 1/2017 | Sharma et al. |
| 9,610,272 B2 | 4/2017 | Soni |
| 9,642,586 B2 | 5/2017 | Kelm et al. |
| 9,649,171 B2 | 5/2017 | Sankaran et al. |
| 9,655,563 B2 | 5/2017 | Liu et al. |
| 9,700,219 B2 | 7/2017 | Sharma et al. |
| 9,715,562 B2 | 7/2017 | Goldstein |
| 9,721,340 B2 | 8/2017 | Gillies et al. |
| 9,761,004 B2 | 9/2017 | Mittal et al. |
| 9,767,557 B1 | 9/2017 | Gulsun et al. |
| 9,770,303 B2 | 9/2017 | Choi et al. |
| 9,785,748 B2 | 10/2017 | Koo et al. |
| 9,805,463 B2 | 10/2017 | Choi et al. |
| 9,805,470 B2 | 10/2017 | Bhatia et al. |
| 9,836,653 B2 | 12/2017 | Schnittman |
| 9,839,399 B2 | 12/2017 | Fonte et al. |
| 9,839,484 B2 | 12/2017 | Taylor |
| 9,881,372 B2 | 1/2018 | Gulsun et al. |
| 9,965,891 B2 | 5/2018 | Grady et al. |
| 10,010,255 B2 | 7/2018 | Fonte et al. |
| 10,078,124 B2 | 9/2018 | Horkay et al. |
| 10,082,553 B2 | 9/2018 | Boss |
| 10,170,206 B2 | 1/2019 | Koo et al. |
| 10,176,408 B2 | 1/2019 | Paik et al. |
| 10,354,360 B2 | 7/2019 | Sakamoto |
| 10,398,331 B2 | 9/2019 | Relan |
| 10,456,094 B2 | 10/2019 | Fonte et al. |

(56) References Cited

U.S. PATENT DOCUMENTS

| | | |
|---|---|---|
| 10,478,130 B2 | 11/2019 | Sharma et al. |
| 10,483,006 B2 | 11/2019 | Itu et al. |
| 10,492,755 B2 | 12/2019 | Lin |
| 10,498,755 B2 | 12/2019 | Harris |
| 10,517,677 B2 | 12/2019 | Sankaran et al. |
| 10,695,023 B2 | 6/2020 | Antoniades et al. |
| 10,762,624 B2 | 9/2020 | Daughton et al. |
| 10,776,988 B2 | 9/2020 | Grady et al. |
| 10,813,612 B2 | 10/2020 | Min |
| 10,871,536 B2 | 12/2020 | Golden et al. |
| 10,939,828 B2 | 3/2021 | Fonte et al. |
| 10,939,960 B2 | 3/2021 | Choi et al. |
| 10,943,142 B2 | 3/2021 | Daughton et al. |
| 10,945,606 B2 | 3/2021 | Sanders et al. |
| 10,951,715 B2 | 3/2021 | Hart et al. |
| 10,964,071 B2 | 3/2021 | Grady et al. |
| 10,966,619 B2 | 4/2021 | Fonte et al. |
| 10,973,469 B2 | 4/2021 | Karimabadi |
| 10,973,583 B2 | 4/2021 | Taylor et al. |
| 10,978,210 B2 | 4/2021 | Grady et al. |
| 10,984,535 B2 | 4/2021 | Grady et al. |
| 10,987,010 B2 | 4/2021 | Grady et al. |
| 10,990,652 B2 | 4/2021 | Tayler et al. |
| 10,991,465 B2 | 4/2021 | Grady |
| 11,013,425 B2 | 5/2021 | Fonte et al. |
| 11,017,904 B2 | 5/2021 | Sankaran et al. |
| 11,033,332 B2 | 6/2021 | Taylor |
| 11,042,822 B2 | 6/2021 | Sankaran et al. |
| 11,071,501 B2 * | 7/2021 | Buckler ............... G16H 10/60 |
| 11,083,524 B2 | 8/2021 | Taylor |
| 11,087,459 B2 | 8/2021 | Buckler et al. |
| 11,087,460 B2 | 8/2021 | Buckler et al. |
| 11,087,884 B2 | 8/2021 | Sankaran et al. |
| 11,090,118 B2 | 8/2021 | Taylor |
| 11,094,058 B2 | 8/2021 | Buclker et al. |
| 11,094,060 B1 | 8/2021 | Min et al. |
| 11,094,061 B1 | 9/2021 | Min et al. |
| 11,113,811 B2 | 9/2021 | Min et al. |
| 11,113,812 B2 | 9/2021 | Buckler et al. |
| 11,116,575 B2 | 9/2021 | Taylor |
| 11,120,312 B2 | 9/2021 | Buckler et al. |
| 11,120,549 B2 | 9/2021 | Min et al. |
| 11,120,550 B2 | 9/2021 | Min et al. |
| 11,120,893 B2 | 9/2021 | Choi et al. |
| 11,127,503 B2 | 9/2021 | Rabbat et al. |
| 11,132,796 B2 | 9/2021 | Min et al. |
| 11,135,012 B2 | 10/2021 | Taylor |
| 11,138,337 B2 | 10/2021 | Yousfi et al. |
| 11,154,361 B2 | 10/2021 | Taylor |
| 11,185,368 B2 | 11/2021 | Spilker et al. |
| 11,210,786 B2 | 12/2021 | Min et al. |
| 11,232,564 B2 | 1/2022 | Min et al. |
| 11,238,587 B2 | 2/2022 | Min et al. |
| 11,244,451 B1 | 2/2022 | Min et al. |
| 11,257,584 B2 | 2/2022 | Buckler et al. |
| 11,257,585 B2 | 2/2022 | Bhatia et al. |
| 11,276,170 B2 | 3/2022 | Min et al. |
| 11,288,799 B2 | 3/2022 | Min et al. |
| 11,288,813 B2 | 3/2022 | Grady et al. |
| 11,295,865 B2 | 4/2022 | Rabbat et al. |
| 11,298,187 B2 | 4/2022 | Taylor |
| 11,302,001 B2 | 4/2022 | Min et al. |
| 11,302,002 B2 | 4/2022 | Min et al. |
| 11,308,617 B2 | 4/2022 | Min et al. |
| 11,315,247 B2 | 4/2022 | Min et al. |
| 11,317,883 B2 | 5/2022 | Min et al. |
| 11,321,840 B2 | 5/2022 | Min et al. |
| 11,328,824 B2 | 5/2022 | Fonte |
| 11,341,644 B2 | 5/2022 | Min et al. |
| 11,350,899 B2 | 6/2022 | Min |
| 11,357,469 B2 | 6/2022 | Taylor et al. |
| 11,367,190 B2 * | 6/2022 | Min .................... A61B 8/0891 |
| 11,382,569 B2 | 7/2022 | Grady et al. |
| 11,398,029 B2 | 7/2022 | Grady et al. |
| 11,399,729 B2 | 8/2022 | Fonte et al. |
| 11,423,805 B2 | 8/2022 | Sankaran et al. |
| 11,424,036 B2 | 8/2022 | Fonte et al. |
| 11,424,038 B2 | 8/2022 | Grady et al. |
| 11,430,113 B2 | 8/2022 | Daughton et al. |
| 11,462,329 B2 | 10/2022 | Rabbat et al. |
| 11,482,339 B2 | 10/2022 | Koo et al. |
| 11,494,904 B2 | 11/2022 | Fonte et al. |
| 11,501,436 B2 | 11/2022 | Min et al. |
| 11,501,485 B2 | 11/2022 | Grady et al. |
| 11,504,019 B2 | 11/2022 | Fonte et al. |
| 11,508,063 B2 | 11/2022 | Buckler |
| 11,521,755 B2 | 12/2022 | Taylor et al. |
| 11,540,931 B2 | 1/2023 | Grady et al. |
| 11,547,367 B2 | 1/2023 | Taylor |
| 11,564,746 B2 | 1/2023 | Spilker et al. |
| 11,576,626 B2 | 2/2023 | Fonte et al. |
| 11,583,340 B2 | 2/2023 | Taylor |
| 11,594,319 B2 | 2/2023 | Yousfi et al. |
| 11,605,466 B2 | 3/2023 | Grady et al. |
| 11,642,092 B1 | 5/2023 | Min |
| 2002/0172663 A1 | 11/2002 | Palasis |
| 2004/0101181 A1 | 5/2004 | Giger et al. |
| 2004/0133094 A1 | 7/2004 | Becker et al. |
| 2004/0136491 A1 | 7/2004 | Iatrou et al. |
| 2005/0043614 A1 | 2/2005 | Huizenga et al. |
| 2005/0110791 A1 | 5/2005 | Krishnamoorthy et al. |
| 2005/0118632 A1 | 6/2005 | Chen et al. |
| 2006/0036167 A1 | 2/2006 | Shina |
| 2006/0101075 A1 | 5/2006 | Lehel et al. |
| 2007/0018558 A1 | 1/2007 | Chua et al. |
| 2007/0019778 A1 | 1/2007 | Clouse et al. |
| 2007/0248250 A1 | 10/2007 | Gulsun et al. |
| 2007/0260141 A1 | 11/2007 | Margolis et al. |
| 2008/0100621 A1 | 5/2008 | Aharon et al. |
| 2008/0103389 A1 | 5/2008 | Begelman et al. |
| 2008/0119734 A1 | 5/2008 | Pruvot et al. |
| 2008/0187199 A1 | 8/2008 | Gulsun et al. |
| 2008/0188962 A1 | 8/2008 | Suryanarayanan et al. |
| 2009/0012382 A1 | 1/2009 | Dutta et al. |
| 2009/0016588 A1 | 1/2009 | Slabaugh et al. |
| 2009/0129673 A1 | 5/2009 | Simon et al. |
| 2009/0276161 A1 | 11/2009 | Cobain |
| 2009/0278846 A1 | 11/2009 | Gulsun et al. |
| 2010/0137711 A1 | 6/2010 | Hamilton et al. |
| 2010/0177945 A1 | 7/2010 | Moriya |
| 2010/0201786 A1 | 8/2010 | Schaefer et al. |
| 2010/0215225 A1 | 8/2010 | Kadomura et al. |
| 2010/0278405 A1 | 11/2010 | Kakadiaris et al. |
| 2010/0316274 A1 | 12/2010 | Langheinrich et al. |
| 2011/0026798 A1 | 2/2011 | Madabhushi et al. |
| 2011/0116697 A1 | 5/2011 | Dafni et al. |
| 2011/0206247 A1 | 8/2011 | Dachille et al. |
| 2011/0229002 A1 | 9/2011 | Arnold et al. |
| 2011/0245650 A1 | 10/2011 | Kerwin et al. |
| 2012/0041323 A1 | 2/2012 | Taylor et al. |
| 2012/0076377 A1 | 3/2012 | Dutta et al. |
| 2012/0128132 A1 | 5/2012 | Coolens et al. |
| 2012/0158432 A1 | 6/2012 | Jain |
| 2012/0243764 A1 | 9/2012 | Dey et al. |
| 2012/0263368 A1 | 10/2012 | Nakano et al. |
| 2013/0066188 A1 | 3/2013 | Taerum et al. |
| 2013/0101187 A1 | 4/2013 | Sundar et al. |
| 2013/0190592 A1 | 7/2013 | Coppini et al. |
| 2013/0190595 A1 | 7/2013 | Oraevsky et al. |
| 2013/0246034 A1 | 9/2013 | Sharma et al. |
| 2014/0058715 A1 | 2/2014 | Sharma et al. |
| 2014/0073976 A1 | 3/2014 | Fonte et al. |
| 2014/0114176 A1 | 4/2014 | Hirschenbain et al. |
| 2014/0306961 A1 | 10/2014 | Nagata |
| 2015/0016702 A1 | 1/2015 | Huizenga et al. |
| 2015/0065846 A1 | 3/2015 | Choi |
| 2015/0066818 A1 | 3/2015 | Choi et al. |
| 2015/0164342 A1 | 6/2015 | Choi et al. |
| 2015/0187025 A1 | 7/2015 | Wasserkrug et al. |
| 2015/0193944 A1 | 7/2015 | Lang et al. |
| 2016/0066861 A1 | 3/2016 | Taylor |
| 2016/0078309 A1 | 3/2016 | Feldman |
| 2016/0104281 A1 | 4/2016 | Grady et al. |
| 2016/0203263 A1 | 7/2016 | Maier et al. |

(56) References Cited

U.S. PATENT DOCUMENTS

| | | |
|---|---|---|
| 2016/0239564 A1 | 8/2016 | Sohma |
| 2016/0292372 A1 | 10/2016 | Kamen et al. |
| 2016/0296288 A1 | 10/2016 | Sankaran et al. |
| 2016/0300350 A1 | 10/2016 | Choi et al. |
| 2016/0346043 A1 | 12/2016 | Jaquet et al. |
| 2016/0358333 A1 | 12/2016 | Lee et al. |
| 2017/0014034 A1 | 1/2017 | Koo et al. |
| 2017/0018081 A1 | 1/2017 | Taylor et al. |
| 2017/0046484 A1 | 2/2017 | Buckler et al. |
| 2017/0103525 A1 | 4/2017 | Hu et al. |
| 2017/0119333 A1 | 5/2017 | Zebaze et al. |
| 2017/0202621 A1 | 7/2017 | Taylor |
| 2017/0245821 A1 | 8/2017 | Itu et al. |
| 2017/0258433 A1 | 9/2017 | Gulsun et al. |
| 2017/0265831 A1 | 9/2017 | Sankaran et al. |
| 2017/0265832 A1 | 9/2017 | Antodiades |
| 2017/0337343 A1 | 11/2017 | Kakadiaris et al. |
| 2017/0340393 A1 | 11/2017 | Choi et al. |
| 2018/0165811 A1 | 6/2018 | Flohr et al. |
| 2018/0179189 A1 | 6/2018 | MacPhee et al. |
| 2018/0225847 A1 | 8/2018 | Grady et al. |
| 2018/0243033 A1 | 8/2018 | Tran et al. |
| 2018/0330477 A1 | 11/2018 | Paik et al. |
| 2019/0074082 A1 | 3/2019 | Buckler et al. |
| 2019/0110776 A1 | 4/2019 | Yu et al. |
| 2019/0159737 A1 | 5/2019 | Buckler et al. |
| 2019/0172197 A1 | 6/2019 | Buckler et al. |
| 2019/0174082 A1 | 6/2019 | Taruki et al. |
| 2019/0175130 A1 | 6/2019 | Raman et al. |
| 2019/0180153 A1 | 6/2019 | Buckler et al. |
| 2019/0180438 A1 | 6/2019 | Buckler et al. |
| 2019/0244347 A1 | 8/2019 | Buckler et al. |
| 2019/0244348 A1 | 8/2019 | Buckler et al. |
| 2019/0251713 A1 | 8/2019 | Chen et al. |
| 2019/0282211 A1 | 9/2019 | Merritt et al. |
| 2019/0318476 A1 | 10/2019 | Isgum et al. |
| 2019/0350538 A1 | 11/2019 | Wilson et al. |
| 2020/0069262 A1 | 3/2020 | Fonte et al. |
| 2020/0085501 A1 | 3/2020 | Sankaran et al. |
| 2020/0243076 A1 | 7/2020 | Kim |
| 2020/0273579 A1 | 8/2020 | Wright |
| 2020/0320775 A1 | 10/2020 | Holladay et al. |
| 2020/0372701 A1 | 11/2020 | Grady et al. |
| 2020/0402234 A1 | 12/2020 | Daughton et al. |
| 2021/0007807 A1 | 1/2021 | Sankaran et al. |
| 2021/0030478 A1 | 2/2021 | Hart et al. |
| 2021/0042918 A1 | 2/2021 | Bucker |
| 2021/0042927 A1 | 2/2021 | Amis et al. |
| 2021/0074435 A1 | 3/2021 | Taylor et al. |
| 2021/0077196 A1 | 3/2021 | Jaquet et al. |
| 2021/0082579 A1 | 3/2021 | Grady et al. |
| 2021/0090694 A1 | 3/2021 | Colley et al. |
| 2021/0093384 A1 | 4/2021 | Grady et al. |
| 2021/0153749 A1 | 5/2021 | Fonte et al. |
| 2021/0153945 A1 | 5/2021 | Choi et al. |
| 2021/0185131 A1 | 6/2021 | Hart et al. |
| 2021/0186448 A1 | 6/2021 | Min |
| 2021/0196391 A1 | 7/2021 | Taylor et al. |
| 2021/0202110 A1 | 7/2021 | Grady et al. |
| 2021/0209757 A1 | 7/2021 | Min et al. |
| 2021/0210209 A1 | 7/2021 | Taylor et al. |
| 2021/0212565 A1 | 7/2021 | Gardner et al. |
| 2021/0217534 A1 | 7/2021 | Rabbat et al. |
| 2021/0225006 A1 | 7/2021 | Grady et al. |
| 2021/0228094 A1 | 7/2021 | Grady et al. |
| 2021/0241920 A1 | 8/2021 | Sankaran et al. |
| 2021/0244475 A1 | 8/2021 | Taylor |
| 2021/0267690 A1 | 9/2021 | Taylor |
| 2021/0272030 A1 | 9/2021 | Sankaran et al. |
| 2021/0282719 A1 | 9/2021 | Buckler et al. |
| 2021/0282860 A1 | 9/2021 | Taylor |
| 2021/0312622 A1 | 10/2021 | Buckler et al. |
| 2021/0319558 A1 | 10/2021 | Min et al. |
| 2021/0322102 A1 | 10/2021 | Sankaran et al. |
| 2021/0334961 A1 | 10/2021 | Min et al. |
| 2021/0334962 A1 | 10/2021 | Min et al. |
| 2021/0334966 A1 | 10/2021 | Min et al. |
| 2021/0335497 A1 | 10/2021 | Sankaran et al. |
| 2021/0338333 A1 | 11/2021 | Sankaran et al. |
| 2021/0343010 A1 | 11/2021 | Min et al. |
| 2021/0358634 A1 | 11/2021 | Sankaran et al. |
| 2021/0358635 A1 | 11/2021 | Sankaran et al. |
| 2021/0366111 A1 | 11/2021 | Min et al. |
| 2021/0366112 A1 | 11/2021 | Min et al. |
| 2021/0366113 A1 | 11/2021 | Min et al. |
| 2021/0366114 A1 | 11/2021 | Min et al. |
| 2021/0366115 A1 | 11/2021 | Min et al. |
| 2021/0366116 A1 | 11/2021 | Min et al. |
| 2021/0374969 A1 | 12/2021 | Grady et al. |
| 2021/0375401 A1 | 12/2021 | Choi et al. |
| 2021/0375476 A1 | 12/2021 | Rabbat et al. |
| 2021/0386390 A1 | 12/2021 | Min et al. |
| 2021/0390689 A1 | 12/2021 | Buckler et al. |
| 2021/0397746 A1 | 12/2021 | Yousfi et al. |
| 2022/0079540 A1 | 3/2022 | Sankaran et al. |
| 2022/0079681 A1 | 3/2022 | Grady et al. |
| 2022/0110687 A1 | 4/2022 | Spilker et al. |
| 2022/0110690 A1 | 4/2022 | Sankaran et al. |
| 2022/0122251 A1 | 4/2022 | Min |
| 2022/0139529 A1 | 5/2022 | Bhatia et al. |
| 2022/0211439 A1 | 7/2022 | Sankaran et al. |
| 2022/0230312 A1 | 7/2022 | Choi et al. |
| 2022/0241019 A1 | 8/2022 | Taylor |
| 2022/0253992 A1 | 8/2022 | Buckler et al. |
| 2022/0265239 A1 | 8/2022 | Taylor et al. |
| 2022/0277443 A1 | 9/2022 | Min et al. |
| 2022/0284572 A1 | 9/2022 | Min et al. |
| 2022/0322953 A1 | 10/2022 | Fonte et al. |
| 2022/0327695 A1 | 10/2022 | Min |
| 2022/0327701 A1 | 10/2022 | Grady et al. |
| 2022/0330902 A1 | 10/2022 | Forneris et al. |
| 2022/0335603 A1 | 10/2022 | Min |
| 2022/0335859 A1 | 10/2022 | Sankaran et al. |
| 2022/0359063 A1 | 11/2022 | Tombropoulos et al. |
| 2022/0366562 A1 | 11/2022 | Yu et al. |
| 2022/0367066 A1 | 11/2022 | Grady et al. |
| 2022/0375072 A1 | 11/2022 | Min |
| 2022/0383464 A1 | 12/2022 | Buckler et al. |
| 2022/0383495 A1 | 12/2022 | Peterson et al. |
| 2022/0392065 A1 | 12/2022 | Min |
| 2022/0392070 A1 | 12/2022 | Buckler et al. |
| 2022/0398706 A1 | 12/2022 | Buckler et al. |
| 2022/0400963 A1 | 12/2022 | Buckler et al. |
| 2022/0401050 A1 | 12/2022 | Min |
| 2022/0406459 A1 | 12/2022 | Buckler et al. |
| 2022/0406470 A1 | 12/2022 | Fonte et al. |
| 2022/0409160 A1 | 12/2022 | Buckler et al. |
| 2022/0415519 A1 | 12/2022 | Buckler et al. |
| 2023/0005582 A1 | 1/2023 | Buckler et al. |
| 2023/0005583 A1 | 1/2023 | Buckler et al. |
| 2023/0005622 A1 | 1/2023 | Rabbat et al. |
| 2023/0016104 A1 | 1/2023 | Koo et al. |
| 2023/0033594 A1 | 2/2023 | Grade et al. |
| 2023/0055828 A1 | 2/2023 | Fonte et al. |
| 2023/0117134 A1 | 4/2023 | Clifton et al. |
| 2023/0124826 A1 | 4/2023 | Spilker et al. |
| 2023/0132940 A1 | 5/2023 | Min |
| 2023/0137093 A1 | 5/2023 | Min |
| 2023/0137934 A1 | 5/2023 | Min |
| 2023/0138144 A1 | 5/2023 | Min |
| 2023/0138889 A1 | 5/2023 | Min |
| 2023/0142747 A1 | 5/2023 | Min |
| 2023/0144293 A1 | 5/2023 | Min |
| 2023/0144338 A1 | 5/2023 | Min |
| 2023/0145596 A1 | 5/2023 | Min |
| 2023/0147336 A1 | 5/2023 | Min |
| 2023/0147995 A1 | 5/2023 | Min |

FOREIGN PATENT DOCUMENTS

| | | |
|---|---|---|
| FR | 2908976 A1 | 5/2008 |
| JP | 2003-150703 | 5/2003 |
| JP | 5305821 B2 | 10/2013 |
| JP | 6203410 B2 | 9/2017 |

(56) References Cited

FOREIGN PATENT DOCUMENTS

| WO | WO 09/105530 | 8/2009 |
|---|---|---|
| WO | WO 10/067276 | 6/2010 |
| WO | WO 14/107402 | 7/2014 |
| WO | WO 15/095282 | 6/2015 |
| WO | WO 16/022533 | 2/2016 |
| WO | WO 16 /024128 | 2/2016 |
| WO | WO 17/011555 | 1/2017 |
| WO | WO 17/096407 | 6/2017 |
| WO | WO 17/106819 | 6/2017 |
| WO | WO 19/033098 | 2/2019 |
| WO | WO 19/165432 | 8/2019 |
| WO | WO 19/242227 | 12/2019 |
| WO | WO 21/141135 | 7/2021 |

OTHER PUBLICATIONS

Ahmadi et al., 2018, Lesion-Specific and Vessel-Related Determinants of Fractional Flow Reserve Beyond Coronary Artery Stenosis, JACCL Cardiovascular lmaging, 11(4):521-530

Al'Aref et al. "Clinical Applications of machine learning in cardiovascular disease and its relevance to cardiac imaging." Eur Heart J. Jul. 27, 2018. [Epub ahead of print].

Al'Aref et al., "High-risk atherosclerotic plaque features for cardiovascular risk assessment in the Prospective Multicenter Imaging Study for Evaluation of Chest Pain trial", Cardiovascular Diagnosis and Therapy, vol. 9, No. 1, Feb. 2019. pp. 89-93.

Antonopoulos et al., "Detecting Human coronary inflammation by imaging perivascular fat", Sci. Transl. Med. 9, eaal2658 (2017) Jul. 12, 2017.

Arbab-Zadeh et al., "Contemporary Reviews in Cardiovascular Medicine, Acute Coronary Events", Amercan Heart Association, Inc., Circulation. 2012;125:1147-1156, Mar. 6, 2012, pp. 1147-1156.

Bakhasi, et al. "Comparative Effectiveness of CT-Derived Atherosclerotic Plaque Metrics for Predicting Myocardial Ischemia." JACC Cardiovasc Imaing. Jul. 13, 2018. doi: 10.2013/j.jcmg.2018.05.019. [Epub ahead of print].

Benjamin, et al. "Heart Disease and Stroke Statistics—2018 Update: A Report From the American Hear Association." Circulation. 2018;137: e67-e492.

Bergman "Using Multicoloured Halftsone Screens for Offset Print Quality Monitoring", Linköping Studie in Science and Technology; LiU-TEK-LIC-2005:02.

Budoff MJ, et al. "Diagnostic performance of 64-multidetector row coronary computed tomographic angiography for evaluation of coronary artery stenosis in individuals without know coronary artery disease: results from the prospective multicenter ACCURACY (Assessment by Coronary Computed Tomography of Individuals Undergoing Invasive Coronary Angiography) trial." J Am Coll Cardiol 2008; 52(21): 1724-32.

Bzdok "Classical Statistics and Statistical Learning in lmaging Neuroscience." Front Neurosci. 2017; 11:543.

Calvert, et al. "Association between IVUS Findings and Adverse Outcomes in Patients with Coronary Artery Disease: the VIVA (VH-IVUS in Vulnerable Atherosclerosis) Study." JACC Cardiovasc Imaging. 2011;4: 894-901 .

Cerqueira et al. "Standardized myocardial segmentation and nomenclature for tomographic imaging of the heart. A statement for healthcare professionals from the Cardiac Imaging Committee of the Council on Clinical Cardiology of the American Heart Association." Int J Cardiovasc Imaging 2002; 18(1): 539-42.

Chang et al., "Selective Referral Using CCTA Versus Direct Referral for Individuals Referred to Invasive Coronary Angiography for Suspected CAD", JACC: Cardiovascular Imaging, vol. 12, No. 7, Jul. 2019. pp. 1303-1312.

Costopoulos, et al. "Intravascular Ultrasound and Optical Coherence Tomography Imaging of Coronary Atherosclerosis." Int J Cardiovasc Imaging. 2016;32: 189-200.

Cury, et al. "CAD-RADS TM Coronary Artery Disease- Reporting and Data System. An Expert consensus documents of the Society of Cardiovascular Computed Tomography (SCCT), the American College of Radiology (ACR) and the North American Society for Cardiovascular Imaging (NASCI)." Endorsed by the American College of Cardiology. J Cardiovasc Compute Tomogr. 2016;10: 269-81.

De Graaf, et al. "Automatic Quantification and Characterization of Coronary Atherosclerosis with Computed Tomography Coronary Angiography: Cross-Correlation with Intravascular Ultrasound Virtual Histology", Int J Cardiovasc, pp. 1177-1190, (2013).

Dey, et al. "Comparison of Quantitative Atherosclerotic Plaque Burden from Coronary CT Angiography in Patients with First Acute Coronary Syndrome and Stable CAD" J Cardiovasc Comput tomogr (2014).

Diaz-Zamudio, et al. "Automated Quantitative Plaque Burden from Coronary CT Angiography Non-Invasively Predicts Hemodynamic Significance by Using Fractional Flow Reserve in Intermediate Coronary Lesions." Radiology (2015).

Dwivedi et al., "Evaluation of Atherosclerotic Plaque in Non-invasive Coronary Imaging", Korean Circulation Journal, Feb. 2018. 48(2), pp. 124-133.

Ferencik et al., "Use of High-Risk Coronary Atherosclerotic Plaque Detection for Risk Stratification of Patients With Stable Chest Pain", JAMA Cardiol, Feb. 2018 in 19 pages.

Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons." Journal of the American College of Cardiology 2014;64 (18): 1929-49. doi:10.1016/j.jacc.2014.07.017 [published Online First: Aug. 1, 2014].

Friedman et al., "Additive logistic regression: a statistical view of boosting (With discussion and a rejoinder by the authors)." Ann Statist. 2000; 28(2) pp. 337-407.

Funama, Yoshinori, et al. "Improved estimation of coronary plaque and luminal attenuation using a vendor-specific model-based iterative reconstruction algorithm in contrast-enhanced CT coronary angiography." Academic radiology 24.9.

Goff, et al. "2013 ACC/AHA Guidelines on the Assessment of Cardiovascular Risk: a Report of the American College of Cardiology/American Heart Association Task Force on Practice Guidelines." J Am Coll Cardiol. 2014;63: 2935-59.

Greenwood et al. "Effect of Care Guided by Cardiovascular Magnetic Resonance, Myocardial Perfusion Scintigraphy, or NICE Guidelines on Subsequent Unnecessary Angiography Rates: The CE-MARC 2 Randomized Clinical Trial." JAMA 2016; 316(10): 1051-60. doi: 10.1001/jama.2016.12680 [published Online First: Aug. 30, 2016].

Guyon et al., "An introduction to variable and feature selection." J Mach Learn Res. 2003; 3:1157-1182.

Hadamitzky et al., "Optimized Prognostic Score for Coronary Computed Tomographic Angiography", Journal of the American College of Cardiology, vol. 62, No. 5, 2013, pp. 468-476.

Hall et al., "The WEKA data mining software: an update." SIGKDD Explor News. 2009; 11(1) pp. 10-18

Han et al., "Quantitative measurement of lipid rich plaque by coronary computed tomography angiography: A correlation of histology in sudden cardiac death", Atherosclerosis, 2018 pp. 426-433.

Hausleiter et al. "Estimated radiation dose associated with cardiac CT angiography." JAMA 2009; 301(5): 500-7

Howard G. et al. "Cigarette smoking and progression of atherosclerosis: The Atherosclerosis Risk in Communities (AIRC) Study." JAMA 1998; 279(2) pp. 119-124.

Kang, et al. "Structured Learning Algorithm for Detection of Nonobstructive and Obstructive Coronary Plaque Lesions from Computed Tomography Angiography", Journal of Medical Imaging, (2015).

Klein et al. :Diagnostic quality of time-averaged ECG-Gated CT data, SPIE medical imaging, 2019.

(56) References Cited

OTHER PUBLICATIONS

Koo BK, et al. "Diagnosis of ischemia-causing coronary stenoses by noninvasive fractional flow reserve computed from coronary computed tomographic angiograms. Results from the prospective multicenter Discovery-Flow (Diagnosis of Ischemia-Causes Stenoses Obtained Via Noninvasive Fractional Flow Reserve) study." J Am Coll Cardiol 2011; 58 (19): 1989-97. doi: 10.1016/j.jacc.2011.06.066 [published Online First: Oct. 29, 2011].

Kramer et al. "Standardized cardiovascular magnetic resonance imaging (CMR) protocols, society for cardiovascular magnetic resonance: board oftrustees task force on standardized protocols." J Cardiovasc Magn Reson 2008; 10:35. doi: 10.1186/1532-429X-10-35.

Lee et al., "Identification of High-Risk Plaques Destined to Cause Acute Coronary Syndrome Using Coronary Computed Tomographic Angiography and Computational Fluid Dynamics", JACC: Cardiovascular Imaging, vol. 12, No. 6, Jun. 2019. pp. 1032-1043.

Lee et al., Rationale and design of the Coronary Computed Tomographic Angiography for Selective Cardiac Catheterization: Relation to Cardiovascular Outcomes, Cost Effectiveness and Quality of Life (CONSERVE) trial:, Am Heart J, 2017; vol. 186, pp. 48-55.

Lee et al., "Rationale and design of the Progression of AtheRosclerotic PIAque Determined by Computed TomoGraphic Angiography Imaging (PARADIGM) registry: A comprehensive exploration of plaque progression and its impact on clinical outcomes from a multicenter serial coronary computed tomo-orahic an-oioraoh stud American", Heart Journal, vol. 182. 2016 pp. 72-79.

Lee et al., "Reproducibility in the assessment of noncalcified coronary plaque with 256-slice multi-detector CT and automated plaque analysis software", Int J Cardiovasc Imaging; 2010; 26:237-244.

Libby P. "Mechanisms of acute coronary syndromes and their implications for therapy." N Engl J Med. 2013; 368: 2004-13.

Lu et al., "Central Core Laboratory versus Site Interpretation of Coronary CT Angiography: Agreement and Association with Cardiovascular Events in the PROMISE Trial", Radiology: vol. 287, No. 1, Apr. 2018, pp. 87-95.

Melikian et al. "Fractional flow reserve and myocardial perfusion imaging in patients with angiographic multivessel coronary artery disease." JACC Cardiovasc Interv 2010; 3 (3): 307-14. doi: 10.1016/j.jcin.2009.12.010 [published Online First: Mar. 20, 2010].

Mettler et al. "Effective doses in radiology and diagnostic nuclear medicine: a catalog." Radiology 2008; 248(1): 254-63

Min et al. "Prognostic value of multidetector coronary computed tomographic angiography for predication of all-cause mortality" J Am Coll Cardio 2007; 50(12): 1161-70

Min et al., "The Immediate Effects of Statins on Coronary Atherosclerosis", JACC: Cardiovascular Imaging, vol. 11, No. 6, Jun. 2018. pp. 839-841.

Min, "Chess and Coronary Artery Ischemia: Clinical Implications of Machine-Learning Applications", Circulation: Cardiovascular Imaging, 2018 in 4 pages.

Montalescot et al. "2013 ESC guidelines on the management of stable coronary artery disease: the Task Force on the management of stable coronary artery disease of the European Society of Cardiology." Eur Heart J 2013;34(35: 2949-3003. doi: 10.1093/eurheartj/eht296 [published Online First: Sep. 3, 2013].

Motoyama et al. "Multislice computed tomographic characteristics of coronary lesions in acute coronar syndromes." J Am Coll Cardiol 2007; 50(4): 319-26.

Nakanishi R. et al. "Plaque progression assessed by a novel semi-automated quantitative plaque software on coronary computed tomography angiography between diabetes and non-diabetes patients: A propensity-score matching study." Atherosclerosis 2016; 255 pp. 73-79.

Nakazato et al., "Aggregate Plaque Volume by Coronary Computed Tomography Angiography is Superior and Incremental to Luminal Narrowing for Diagnosis of Ischemic Lesions of Intermediate Stenosis Severity", Journal ofthe American College of Cardiology, vol. 62, No. 5, 2013 pp. 460-467.

Nakazato et al., "Atherosclerotic plaque characterization by CT angiography for identification of high-risk coronary artery lesions: a comparison to optical coherence tomography", European Heart Journal Cardiovascular Imaging, vol. 16, 2015. pp. 373-379.

Nakazato et al., "Relationship of low- and high-density lipoproteins to coronary artery plaque composition by CT angiography", Journal of Cardiovascular Computed Tomography 7, 2013, pp. 83-90.

Neglia et al. "Detection of significant coronary artery disease by noninvasive anatomical and functional imaging." Circ Cardiovasc Imaging 2015; 8 (3) doi: 10.1161/CIRCIMAGING.114.002179 [published Online First: Feb. 26, 2015].

Obaid, D.R., et al. "Atherosclerotic Plaque Composition and Classification Identified by Coronary Computed Tomography: Assessment of CT-Generated Plaque Maps Compared with Virtual Histology Intravascular Ultrasound and Histology." Circulation: Cardiovascular Imaging 6.5 (2013): 655-664. (Year: 2013).

Obaid, Daniel R., et al. "Coronary CT angiography features of ruptured and high-risk atherosclerotic plaques: correlation with intra-vascular ultrasound." Journal of Cardiovascular Computed Tomography 11.6 (2017): 455-461. (Year: 2017).

Okubo, Ryo, et al. "Pericoronary adipose tissue ratio is a stronger associated factor of plaque vulnerability than epicardial adipose tissue on coronary computed tomography angiography." Heart and vessels 32.7 (2017): 813-822. (Year: 2017).

Ovrehus et al., "CT-based total vessel plaque analyses improves prediction of hemodynamic significance lesions as assessed by fractional flow reserve in patients with stable angina pectoris", Journal of Cardiovascular Computed Tomography 12, 2018 pp. 344-349.

Park, et al. "Clinical Feasibility of 3D Automated Coronary Atherosclerotic Plaque Quantification Algorithm on Coronary Computed Tomography Angiography: Comparison with Intravascular Ultrasound"European Radiology (2015), 25: 3073-3083.

Puchner, et al. "High-Risk Plaque Detected on Coronary CT Angiography Predicts Acute Coronary Syndrome Independent of Significant Stenosis in Patients with Acute Chest Pain" *J Am Coll Cardiol* 2014.

Raff, et al. "SCCT guidelines forthe interpretation and reporting of coronary computed tomographic angiography" *J Cardiovasc Comput Tomogr* 2009: 3(2): 122-36.

Rizvi et al., "Diffuse coronary artery disease among other atherosclerotic plaque characteristics by coronary computed tomography angiography for predicting coronary vessel-specific ischemia by fractional flow reserve", Atherosclerosis 258, 2017 pp. 145-151.

Rizvi et al., "Rationale and Design of the CREDENCE Trial: computed Tomographic evaluation of atherosclerotic Determinants of myocardial Ischemia", BMC Cardiovascular Disorders, 2016, in 10 pages.

Seghier et al., "Lesion identification using unified segmentation-normalisation models and fuzzy clustering" NeuroImage 40(2008) 1253-1266.

Shaw et al. "Optimal medical therapy with or without percutaneous coronary intervention to reduce ischemic burden: results from the Clinical Outcomes Utilizing Revascularization and Aggressive Drug Evaluation (COURAGE) trail nuclear substudy." Circulation 2008; 117 (10): 1283-91. doi: 10.116/CIRCULATIONAHA.107.743963.

Siasos, et al. "Local Low Shear Stress and Endothelial Dysfunction in Patients with Nonobstructive Coronary Atherosclerosis." J Am Coll Cardiol. 2018;71: 2092-2102.

Song et al. "Comparison of machine learning techniques with classical statistical models in predicting health outcomes." Stud Health Technol Inform. 2004; 107(Pt 1) pp. 736-740.

Staruch, et al. "Automated Quantitative Plaque Analysis for Discrimination of Coronary Chronic Total Occlusion and Subtotal Occlusion in Computed Tomography Angiography", *J Thoracic Imaging*, (2016).

Thygesen, et al. "Third Universal Definition of Myocardial Infarction." Glob Heart. 2013;7: 275-95.

Tian, et al. "Distinct Morphological Features of Ruptured Culprit Plaque for Acute Coronary Events Compared to those with Silent Rupture and Thin-Cap Fibroatheroma: a Combined Optical Coherence Tomography and Intravascular Ultrasound Study." J Am Coll Cardiol. 2014;63: 2209-16.

(56) References Cited

OTHER PUBLICATIONS

Tilkemeier et al., "American Society of Nuclear Cardiology information statement: Standardized reporting matrix for radionuclide myocardial perfusion imaging." J Nucl Cardiol 2006; 13 (6): e157-71. doi: 10.1016/j.nuclcard.2006.08.014.
Van Rosendael et al., "Maximization of the usage of coronary CTA derived plaque information using a machine learning based algorithm to improve risk stratification; insights from the CONFIRM registry", Journal of Cardiovascular Computed Tomography 12, 2018, pp. 204-209.
Virmani, et al. "Lessons from sudden coronary death: a comprehensive morphological classification scheme for atherosclerotic lesions." Arterioscler Thromb Vasc Biol. 2000;20: 1262-75.
Wei, et al. "Computerized Detection of Noncalcified Plaques in Coronary CT Angiography: Evaluation 01 Topological Soft Gradient Prescreening Method and Luminal Analysis" *Med Phys*, (2014).
Weir-MacCall et al., "Impact of Non-obstructive left main disease on the progression of coronary artery disease: A PARADIGM substudy", Journal of Cardiovascular Computed Tomography 12, 2018, pp. 231-237.
Weisenfeld et al. "Automatic Segmentation of Newborn Brain MRI", NIH PA Author Manuscript 2010.
Williams et al. "Use of Coronary Computed Tomographic Angiography to Guide Management of Patients with Coronary Disease." Journal of American College of Cardiology 2016; 67 (15) : 1759-68. doi: 10.1016/J.Jacc.2016.02.026 [published Online First: Apr. 16, 2016].
Williams et al., "Coronary Artery Plaque Characteristics Associated With Adverse Outcomes in the SCOT-HEART Study", Journal ofthe American College of Cardiology, vol. 73, No. 3, Jan. 29, 2019. pp. 291-301.
Wilson et al. "Prediction of coronary heart disease using risk factor categories" Circulation 1998; 97(18) pp. 1837-1847.
Yokoya K, et al. "Process of progression of coronary artery lesions from mild or moderate stenosis to moderate or severe stenosis: A study based on four serial coronary arteriograms per year." Circulation 1999; 100(9):903-909.
Zeb I et al. "Effect of statin treatment on coronary plaque progression—a serial coronary CT angiography study." Atherosclerosis. 2013; 231 (2):198-204.
International Search Report and Written Opinion for Application No. PCT/US20/15035 dated Apr. 14, 2020, in 20 pages.
International Preliminary Report on Patentability for Application No. PCT/US2020/015035 dated Jul. 27, 2021, in 7 pages.
Abbara et al., "SCCT Guidelines for the performance and acquisition of coronary compted tomographic angiography: A report of the society of Cardiovascular Computed Tomography Guidelines Committee: Endorsed by the North American Society for Cardiovascular Imaging (NASCI)." Journal of cardiovascular compted tomography 2016; 10(6):435-449.
Achenbach et al. "Detection of calcified and noncalcified coronary atherosclerotic plaque by contrast-enhanced, submillimeter multidetector spiral computed tomography: a segment-based comparison with intravascular ultrasound." Circulation 2004; 109(1):14-17.
Ahmadi A. et al. "Do Plaques rapidly progress prior to myocardial infarction? The interplay between plaque vulnerability and progression." Circ Res. 2015; 117(1):99-104.
Ahmadi et al., "Association of Coronary Stenosis and Plaque Morphology with Fractional Flow Reserve and Outcomes." JAMA cardiology 2016; 1 (3):350-357. doi: 10.1001/jamacardio.2016.0263 [published Online First: Jul. 22, 2016].
Ahmadi et al., 2018, Lesion-Specific and Vessel-Related Determinants of Fractional Flow Reserve Beyond Coronary Artery Stenosis, JACCL Cardiovascular Imaging, 11(4):521-530.
Al'Aref et al. "Clinical Application of machine learning in cardiovascular disease and its relevance to cardiac imaging." Eur Heart J. Jul. 27, 2018. [Epub ahead of print].
Al'Ared et al., "High-risk atherosclerotic plaque features for cardiovascular risk assessment in the Prospective Multicenter Imaging Study for Evaluation of Chest Pain Trial", Cardiovascular Diagnosis and Therpay, vol. 9, No. 1, Feb. 2019. pp. 89-93.

Antonopoulos et al., "Detecting Human coronary inflammation by imaging perivascular fat", Aci. Transl. Med. 9, eaal2658 (2017) Jul. 12, 2017.
Arbab-Zadeh et al., "Contemporary Reviews in Cardiovascular Medicine, Acute Coronary Events", American Heart Association, Inc., Circulation. 2012;125:1147-1156, Mar. 6, 2012, pp. 1147-1156.
Arbab-Zadeh, et al. "the myth of the vulnerable plaque: transitioning from a focus on individual lesions to atherosclerotic disease burden for coronary artery disease risk assessment." J Am Coll Cardiol. 2015;65: 846-855.
Bakhasi, et al. "Comparative Effectivness of CT-Derived Atherosclerotic Plaque Metrics for Predicting Myocardial Ischemia." JACC Cardiovasc Imaging. Jul. 13, 2018. doi: 10.2013/j.jcmg.2018.05.019. [Epub ahead of print].
Baskaran et al., "Dense calcium and lesion-specific ischemia: A comparison of CCTA with fractional flow reserve", Atherosclerosis 260, 2017 pp. 163-168.
Benjamin, et al. "Heart Disease and Stroke Statistics-2018 Update: A Report From the American Heart Association." Circulation. 2018;137: e67-e492.
Bergman "Using Multicoloured Halftone Screens for Offset Print Quality Monitoring", Linköping Studies in Science and Technology; LiU-TEK-LIC-2005:02.
Blankstein R. et al. "Coronary CTA in the Evaluation of Stable Chest Pain: Clear Benefits, But Not for All." J Am Coll Cardiol 2017; 69 (14): 1771-73. doi: 10.1016/j.jacc.2017.02.011 [published Online First: Apr. 8, 2017].
Boogers, et al. "Automated Quantification of Coronary Plaque with Computed Tomography: Comparison with Intravascular Ultrasound using a Dedicated Registration Algorithm for Fusion-Based Quantification", Epub, (2012).
Budoff MJ, et al. "Diagnostic performance of 64-multidetector row coronary computed tomographic angiography for evaluation of coronary artery stenosis in individuals without know coronary artery disease: results from the prospective multicenter ACCURACY (Assesment by Coronary Computed Tomograohy of Individuals Undergoing Invasive Coronary Angiography) trial." *J Am Coll Cardiol* 2008; 52(21): 1724-32.
Bzdok "Classical Statistics and Statistical Learning in Imaging Neuroscience." Front Neurosci. 2017; 11:543.
Calvert, et al. "Association between IVUS Finding and Adverse Outcomes in Patients with Coronary Artery Disease: the VIVA (VH-IVUS in Vulnerable Atherosclerosis) Study." JACC Cardiovasc Imaging. 2011;4: 894-901.
Celeng, et al. "Non-invasive and Invasive Imaging of Vulnerable Coronary Plaque." trends Cardiovasc Med. 2016;26-538-47.
Cerqueora et al. "Standardized myocardial segmentation and nomenclature for tomographic imaging of the hear. A statement for healthcare professionals from the Cardiac Imaging Committee of the Council on Clinical Cardiology of the American Heart Association." Int J Cardiovasc Imahing 2002; 18(1): 539-42.
Chang et al., "Coronary Atherosclerotic Precursors of Acute Coronary Syndromes", Journal of the American College of Cardiology, vol. 71, No. 22, Jun. 5, 2018. pp. 2511-2522.
Change et al., "Selective Referral Using CCTA Verses Direct Refferal for Individuals Reddered to Invasive Coronary Angiography for Suspected CAD", JACC: Cardiovascular Imaging, vol. 12, No. 7, Jul. 2019. pp. 1303-1312.
Chung et al. "Image Segmentation Methods for Detecting Blood Vessels in Angiography", 2006 9th Int. Conf. Control, Automation, Robotics and Vision, Singapore, Dec. 5-8, 2006, ICARCV 2006, pp. 1424-1429.
Costopoulos, et al. "Intravascular Ultrasound and Optical Coherence Tomography Imaging of Coronary Atherosclerosis." Int J Cardiovasc Imaging. 2016;32: 18-200.
Cury et al. "CAD-RADS™ Coronary Artery Disease—Reporting and Data System. An Expert consensus documents of the Society of Cardiovascular Computed Tomography (SCCT), the American College of Radiology (ACR) and the North American Society for Cardiovascular Imaging (NASCI)." Endorsed by the American College of Cardiology. J Cardiovasc Compye Tomogr. 2016;10: 269-81.

(56) References Cited

OTHER PUBLICATIONS

Danad et al. "Comparison of Coronary CT Angiography, SPECT, PET, and Hybrid Imaging for Diagnosis of Ischemic Heart Disease Determined by Fractional Flow Reserve." JAMA Cardiol 2017; 2(10): 1100-07. doi 10.1001/jamacardio.2017.2471 [published Online First: Aug. 17, 2017].

De Bruyne B. et al. "Fractional flow reserve-guided PCI for stable coronary artery disease." The New England journal of medicine 2014; 371 (13): 1208-17. doi: 10.1056/NEJMoal408758 [published Online First: Sep. 2, 2014].

De Graaf, et al. "Automatic Quantification and Characterization of Coronary Atherosclerosis with Computed Tomograohy Coronary Angiography: Cross-Correlation with Intravascular Ultrasound Virtual Histology", Int J Cardiovasc, pp. 1177-1190, (2013).

De Graaf, et al. "Feasibility of an Automated Quantitative Computed Tomography Angiography-Derived Risk Stratification of Patients with Suspected CAD." Am J Cardiol (2014).

DeLong ER, et al. "Comparing the areas under two or more correlated receiver operating characteristic curves: a nonparametric approach." Biometrics 1988; 44 (3): 837-45. [published Online First: Sep. 1, 1988].

Dey et al., "Direct Quantitative In Vivo Comparison of Calcified Atherosclerotic Plaque on Vascular MRI and CT by Multimodality Image Registration" Journal of Magnetic Resonance Imaging 23:345-354 (2006).

Dey et al., 2018, Integrated prediction of lesion-specific ischemia from quantitative coronary CT Angiography using machine learning: a multicenter study, European Radiology, 28(6):2655-2664.

Dey, et al. "Comparison of Quantitative Atherosclerotic Plaque Burden fmm Coronary CT Angiography in Patients with First Acute Coronary Syndrome and Stable CAD" *J Cardiovasc Comput tomogr* (2014).

Dey, et al. "Non-Invasive Measurement of Coronary Plaque from Coronary CT Angiography and its Clinical Implication", *Expert Review of Cardiovascular Therapy* (2013).

Diaz-Zamudio, et al. "Automated Quantitative Plaque Burden from Coronary CT Angiography Non-Invasively Predicts Hemodynamic Significance by Using Fractional Flow Reserve in Intermediate Coronary Lesions." *Radiology* (2015).

Douglas et al., "Outcomes of Anatomical versus Functional Testing for Coronary Artery Disease", N Engl J Med. Apr. 2, 2015, p. 1291-1300.

Driessen et al., "Adverse Plaque Characteristic Relate More Strongly With Hyperemic Fractional Flow Reserve and Instantaneous Wave-Free Ratio Than With Resting Instantaneous Wave-Free Ratio", JACC: Cardiovascular Imaging, 2019, in 11 pages.

Driessen et al., "Effect of Plaque Burden and Morphology on Myocardial Blood Flow and Fractional Flow Reserve", Journal of the American College of Cardiology, vol. 71, No. 5, 2018 p. 499-509.

Dwivedi et al., "Evaluation of Atherpsc;erptoc Plaque in Non-Invasive Coronary Imaging", Karean Circulation Journal, Feb. 2018. 48(2), pp. 124-133.

Ehara et al. "Spotty calcification typifies the culprit plaque in patients with acute myocardial infarction: an intravascular ultrasound study." Circulation 2004; 110(22): 3424-9.

Erickson BJ, et al. "Machine Learning for Medical Imaging." Radiographics 2017; 37(2) pp. 505-515.

Ferencik et al., "Use of High-Risk Caronary Atherosclerotic Plaque Detection for Risk Stratification of Patients With Stable Chest Pain", JAMA Cardiol, Feb. 2018 in 19 pages.

Ferencik, et al. "Computed Tomography-Based High-Risk Coronary Plaque Score to Predict ACS Among Patients with Acute Chest Pain" *Journal of Cardiovascular Computed Tomography*, (2015).

Fihn et al. "2012 ACCF/AHA/ACP/AATS/PCNA/SCAI/STS Guideline for the Diagnosis and the Management of Patients With Stable Ischemic Heart Disease: Executive Summary: A Report of the American College of Cardiology Foundation/American Heart Association Task Force on Practice Guidelines, and the American College of Physicians, American Association for Thoracic Surgery, Preventive Cardiovascular Nurses Association, Society for Cardiovascular Angiography and Interventions, and Society of Thoracic Surgeons." J Am Coll Cardio 2012;60(24):2564-603. doi: 10.1016/c.cacc.2012.07.012 [published Online First: Nov. 28, 2012].

Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery; Preventive Cardiovascular Nurses Association, Society for Cardiovascular Angiography and Interventions, and Society of Thoracic Surgeons," Journal of the American Cellege of Cardiology 2614;64 (18): 1929-49. doi:10.1016/j.jacc.2014.07.017 [publiched Online First: Aug. 1, 2014].

Friedman et al., "Additive logistic regression: a statistical view of boasting (With discussion and a rejoinder by the authors)" Ann Statist. 2000: 28(2) pp. 337-407.

Funama, Yoshinori, et al. "Improved estimation of coronary plaque and luminal attenuation using a vendor-specific model-based iterative reconstruction algorithm in contrast-enhanced CT coronary angigraphy." Academic radiology 24.9.

Gaemperli et al. "Cardiac hybrid imaging." Eur Heart J 2011; 32(17): 2100-8.

Gaur et al., "Coronary plaque quantification and fractional flow reserve by coronary computed tomography angiography identify ischaemia-causing lesions", European Heart Journal, 2016 pp. 1220-1227.

Goff, et al. "2013 ACC/AHA Guidelines on the Assessment of Cardiovascular Risk: a Report of the American College of Cardiology/ American Heart Associationn Task Farce on Practice Guideines,"J Am Coll Cardiol. 2014;63: 2935-59.

Gogas, et al. "Assessment of Coronary Atherosclerosis by IVUS and IVUS-based Imaging Modalities: Profession and Regression Studies; Tissue Composition and Beyond." Int J Cardiovasc Imaging. 2011;27: 225-37.

Goldstein et al., "Moving beyond regression techniques in cardiovascular risk prediction: applying machine learning to address analytic challenges." Eur Heart J. 2017; 38(23) pp. 1805-1814.

Greenwood et al. "Effect of Care Guided by Cardiovascular Magnetic Resonance, Myocardial Perfusion Scintigraphy, or NICE Guidelines on Subsequent Unnecessary Angiography Rates: The CE-MARC 2 Randomized Clinical Trial." JAMA 2016; 316(10): 1051-60. doi: 10.1001/jama.2016.12680 [published Onilne First: Aug. 30, 2016.

Guyon et al., "An introduction to variable and features selection." J Mach Learn Res. 2003; 3:1157-1182.

Hadamitzky et al., "Optimized Prognostic Scare for Coronary Computed Tomographic Angiography", Journal of the American College of Cardiology, vol. 62, No. 5, 2013, pp. 458-475.

Hall et al., "Benchmarking attribute selection techniques for discrete clas data mining." IEEE Transaction on Knowledge and Data Engineering 2003; 15(6): pp. 1437-1447.

Hall et al., "The WEKA data mining software: an update." SIGKDD Explor News. 2909; 11(1) pp. 10-18.

Han et al. "Incremental role of resting myocardial computed tomography perfusion for predicting physiologically significant coronary artery disease: A machine learning approach." J Nucl Cardiol. 2018; 25(1) pp. 223-233.

Han et al., "Quantitative measurement of lipid rich plaque by coronary computed tomography angiogrsphy: A correlation of histology in sudden cardiac death", Atherosclerosis, 2018 pp. 426-433.

Hausleiter et al. "Estimated radiatian dose associated with cardiac CT angiography." JAMA 2009; 301(5): 500-7.

Heo et al., "Optimal boundary detection method and window settings for coronary atherosclerotic plaque volume analysis in coronary computed tomography angiography: comparison with intravascular ultrasound", Eur Radiol, (2016) 26:31, pp. 3190-3198.

Hesse et al. "EANM/ESC procedural guidelines for myocardial perfusion imaging in nuclear cardiology." Eur J Nucl Med Mol Imaging 2005; 32 (7): 855-97. doi: 10.1007/s00259-005-1779-y.

Howard G. et al. "Cigarette smoking and pragression of atherosclerosis: The Atherosclerosis Risk in Communities (AIRC) Study." JAMA 1998; 279(2) pp. 119-124.

(56) References Cited

OTHER PUBLICATIONS

Hundley WG et al. "Society for Cardiovascular Magnetic Resonance guidelines for reporting cardiovascular magnetic resonance examinations." J Cardiovasc Magn Reson 2009; 11:5.

Kanamori et al. "Robust Loss Functions for Boosting" Neural Computation. 2007; 19(8) pp. 2183-2244.

Kang, et al. Automated Knowledge-Based Detection of Nonobstructive and Obstructive Arterial Lesions from Coronary CT Angiography. Med Phys.

Kang, et al. "Structured Learning Algorithm for Detection of Nonobstruetive and Obstructive Coronary Plaque Lesions from Computed Tomography Angiegraphy", Journal of Medical Imaging, (2015).

Kim et al., "Natural History of Diabetic Coronary Atherosclerosis by Quantitative Measurement of Serial Coronary Computed Tomographic Angiography", JACC: Cardiovascular Imaging, vol. 11, No. 10, 2018 pp. 1461-1471.

Klass O, et al. "Coronary plaque imaging with 256-slice multidetector computed tomography: interobserver variability of volumetric lesion parameters with semiautomatic plaque analysis software", Int J Cardiovasc Imaging, (2010). 26; pp. 711-720.

Klein et al. :Diagnotic quality of time-average ECG-Gated CT data, SPIE medical imaging, 2019.

Knuiman et al. "An Empirical comparison of multivariable methods for estimating risk of death from coronary heart disease." J. Cardiovasc Risk. 1997; 4(2): pp. 127-134.

Kolossvary, et al. "Radiomic Features Are Superior to Conventional Quantitative Computed Tomographic Metrics to Identify Coronary Plaques with Napkin-Ring Sign." Circ Cardiovasc Imaging. 2017;10.

Koo BK, et al. "Diagnosis of ischemia-causing summary stenoses by neniuvasive fractional flow reserve computed from coronary computed tomographic angiograms. Results from the prospective multicenter DISCOVERY-FLOW (Diagnosis of ischemia-Causes Stenoses Obtained Via Noninvasive Fractional Flow Reserve) study." J Am Coll Cardiol 2011; 58 (19): 1989-97. doi: 10.1016/j.jacc.2011.06.066 [published Online First: Oct. 29, 2011].

Kramer et al. "Standardized cardiovascular magnetic resonance imaging (CMR) protocols, society for cardiovascular magnetic resonance: board of trustees risk task force on standardized protocols." J Cardiovasc Magn Reson 2008; 10:35. doi: 10.1186/1532-429X-10-35.

Kwan et al., "Bridging the gap for lipid lowering therapy: plaque regression, coronary computed tomographic angiography, and imaging-guided personalized medicine." Expert Rev Cardiovasc Ther. 2017; 15(7): pp. 547-558.

Lee et al., "Differences in Progression to Obstructive Lesions per High-Risk Plaque Features and Plaque Volumes With CCTA", JACC: Cardiovascular Imaging, 2019 in 9 pages.

Lee et al., "Effects of Statins on Coronary Atherosclerotic Plaques—The PARADIGM (Progression of AtheRosclerotic PlAque Determined by Computed TomoGraphic Angiography Imaging) Study", JACC: Cardiovascular Imaging, 2018.

Lee et al., "Identification of High-Risk Plaques Destined to Cause Acute Caronary Syndrome Using Coronary Computed Tomographic Angioraphy and Computational Fluid Dynamics", JACC: Cardiovascular Imaing, vol. 12, No. 6, Jun. 2019. pp. 1032-1043.

Lee et al., "Quantification of Coronary Atherosclerosis in the Assessment of Coronary Artery Disease." Circ Cardiovasc Imaging. 2018; 11(7): e007562.

Lee et al., Rationale and design of the Coronary Computed Tomographic Angiography for Selective Cardiac Catheterization: Relation to Cardiovascular Outcomes, Cost Effectiveness and Quality of Life (CONSERVE) trial;, Am Heart J, 2017; vol. 186, pp. 45-55.

Lee et al., "Rationale and design of the Progression of AtheRosclerotic PlAque Determined by Computed Tomo-Graphic Angiography Imaging (PARADIGM) registry: A comptehensive exploration of plaque progression and its impact on clinical outcomes from a multicenter serial coronary computed tomographic angiography study", American Heart Journal, vol. 182. 2016 pp. 72-79.

Lee et al., "Reproducibiluty in the assessment of noncalcified coronary plaque with 256-slice multi-detector CT and aummated plaque analysis software", Int J Cardiovasc Imaging; 2010; 26:237-244.

Leipsic et al. "SCCT guidelines for the interpretation and reporting of coronary CT angiography: a report of the Society of Cardiovascular Computed Tomography Guidelines Committee" J Cardiovasc Comput Tomogr 2014; 8(5): 342-58.

Libby P. "Mechanisms of acute coronary syndromes and their implications for therapy." N Engl J Med. 2013; 268: 2004-13.

Lu et al., "Central Core Laboratory versus Site Interpreation of Coronary CT Angiography: Agreement and Association with Cardiovascular Events in the PROMESE Trial", Radiology: vol. 287, No. 1, Apr. 2018, pp. 87-95.

Lundberg, et al. "A Unified Approach to Interpreting Model Predictions." 31st Conference on Neural Information Processing Systems (NIPS 2017).

Mancio, Jennifer, et al. "Perivascular adipose tissue and coronary atherosclerosis." Hear 104.20 (2018): 1654-1662. (Year: 2018).

Maurovich-Horvat, et al. "Comprehensive Plaque Assessment by Coronary CT Angiography", Nature Reviews, (2014).

Maurovich-Horvat, et al. "The: napkin-ring sign indicates advanced atherosclerotic lesions in coronary CT angiography.", JACC Cardiovasc Imaging 2012; 5(12): 1243-52.

Meijboom et al. "Diagnostic accuracy of 64-slice computed tomography coronary angiography: a prospective, multicenter, multivendor study." J Am Coll Cardiol 2008; 52 (25): 2135-44. doi: 10.1016/j.jacc.2008.08.058.

Melikian et al. "Fractional flow reserve and myacardial perfusion imaging in patients with angiographic multivessel coronary artery disease." JACC Cardiovasc Interv 2010; 3 (3): 307-14. doi: 10.1016/j.jcin.2009.12.010 [published Online FirstL Mar. 20, 2010].

Mettler et al. "Effect doses in radiology and diagnostic nuclear medicine: a catalog." Radiology 2008; 248(1): 254-63.

Miller et al. "Diagnostic performance of coronary angiography by 61-row CT." N Engel J Med 2008; 359 (22): 2324-36. doi: 10.1056/NEJMoa0806576 [published Online First: Nov. 29, 2008].

Min et al. "Prognostic value of multidetector coronary computed tomographic angiography for predication of all-cause mortatlity" J Am Coll Cardio 2007; 50(12): 1161-70.

Min et al., "Atherosclerosis, Stenosis, and Ischemia", JACC: Cardiovascular Imaging, vol. 11, No. 4, Apr. 2018. pp. 531-533.

Min et al., "Diagnostic accuracy of fractional flow reserve from anatomic CT angiography." JAMA 2012; 038 (12): 1237-45. doi: 10.1001/2012.jama.11274 [published Online First: Aug. 28, 2012].

Min et al., "Immediate Effects of Statins on Coronary Atherosclerosis", JACC: Cardiovascular Imaging, vol. 11, No. 6, Jun. 2018. pp. 839-841.

Min, "Atherosclerotic plaque characterization: a need for a paradigm shift for prediction of risk", European Heart Journal—Cardiovascular Imaging, Oct. 2017. pp. 1340-1341.

Min, "Chess and Coronary Artery Ischemia: Clinical Implication of Machine-Learning Applications", Circulation: Cardiovascular Imaging, 2018 in 4 pages.

Min, et al. "Rationale and Design of the CONFIRM (Coronary CT Angiography Evaluation for Clinical Outcomes: An International Multicenter) Registry." J Cardiovasc Comput Tomogr. 2011;5: 84-92.

Mintz GS. "Intravascular Imaging of Coronary Calcification and its Clinical Implications." JACC Cardiovasc Imaging. 2015;8: 461-471.

Montaleacot et al. "2013 ESC guidelines on the management of stable caronary artery disease: the Task Force on the management of stable coronary artery disease of the European Society of Cardiology." Eur Heart J 2013;34(35: 2949-3003. doi: 10.1093/eurheartj/eht296 [published Online First: Sep. 3, 2013].

Motoyama et al. "Atherosclerotic plaque characterization by 0.5-mm-slice multislice computed tomographic imaging." Circ J 2009; 71(3): 363-6.

Motoyama et al. "Computed tomographic angiography characteristics of atherosclerotic plaques subsequently resulting in acute coronary syndrome." J Am Coll Cardiol 2009; 54(1): 49-57.

(56) References Cited

OTHER PUBLICATIONS

Motoyama et al. "Multislice computed tomographic characteristics of coronary lesions in acute coronary syndromes." J Am Coll Cardiol 2007; 50(4): 319-26.

Motwani et al., "Machine learning for prediction of all-cause mortality in patients with suspected coronary artery disease: a 5-year multicentre prospective registry analysis", European Heart Journal, 2017, pp. 500-507.

Naghavi, et al. From Vulnerable Plaque to Vulnerable Patient: a call for new definitions and risk assessment strategies: Part I. Circulation. 2003; 108: 1664-72.

Nair, et al. "Automated Coronary Plaque Characterisation with intravascular ultrasound backscatter: ex vivo validation." EuroIntervention. 2007; 3: 113-20.

Nakamshi R. et al. "Plaque progression assessed by a novel semi-automated quantitative plaque Software on coronary computed tomography angiography between diabetes and non-diabetes patients: A propensity-score matching study." Atheroscierosis 2016; 255 pp. 73-79.

Nakazato et al., "Additive diagnostic value of atherosclerotic plaque characteristics to non-invasive FFR for identification of lesions causing ischaemia; results from a prospective international multicentre trial", http://www.pcronline.com/eurointervention/ahead_of_print/201509-02/ in 9 pages.

Nakazam et al., "Aggregate Plaque Volume by Coronary Computed Tomography Angiography is Superior and Incremental to Luminal Narrowing for Diagnosis of Ischemic Lesions of Intermediate Stenosis Severity", Journal of the American College of Cardiology, vol. 62, No. 5, 2013, pp. 460-467.

Nakazato et al., "Atherosclerotic plaque characterization by CT angiography for identification of high-risk coronary artery lesions: a comparism to optical coherence tomography", European Heart Journal—Cardiovascular Imaging, vol. 16, 2015. pp. 373-379.

Nakazato et al., "Quantification and characterisation of coronary artery plaque volume and adverse plaque features by coronary computed tomographic angiography: a direct comparison to intravascular ultrasound", Eur Radiol (2013) 23, pp. 2109-2117.

Nakazato et al., "Relationshop of low- and high-density lipoproteins to coronary artery plaque composition by CT angiography", Journal of Cardiovascular Computed Tomography 7, 2013, pp. 83-90.

Neglia et al. "Detection of significant coronary artery disease by noninvasive anatomical and functional imaging," Circ Cardiovas Imaging 2015; 8 (3) doi: 10.1161/CIRCIMAGING.114.002179 [published Online First: Feb. 26, 2015].

Newby et al., "Coronary CT Angiography and 5-Year Risk of Myocardial Infarction", The New England Journal of Medicine Aug. 25, 2018, pp. 924-933.

Newby et al., "CT coronary angiography in patients with suspected angina due to coronary heart disease (SCOT-HEART): an open-label, parallel-group, multicentre trial", www.thelancet.com, vol. 385. Jun. 13, 2015, pp. 2383-2391.

Nicholls et al. "Intravascular ultrasound-derived measures of coronary atherosclerotic plaque burden and clinical outcome." J Am Coll Cardiol. 2010; 55(21): pp. 2399-2407.

Nicholls, et al. "Effect of Evolocumab on Coronary Plaque Composition." J Am Coll Cardiol. 2018;72: 2012-2021.

Obaid, D.R., et al. "Atherosclerotic Plaque Composition and Classification Identified by Coronary Computed Tomography: Assessment of CT-Generated Plaque Maps Compared with Virtual-Histology Intravascular Ultrasound and Histology." Circulatian: Cardiovascular Imaging 6.5 (2013): 655-664. (Year: 2013).

Obaid, Daniel R., et al. "Coronary CT angiography features of ruptured and high-risk atherosclerotic plaques: correlation with intra-vascular ultrasound." Journal of Cardiovascular Computed Tomagraphy 11.6 (2017): 455-461. (Year: 2017).

Okuba, Ryo, et al. "Pericoronary adipose tissue ratio is a stronger associated factor of plaque vulnerability than epicardial adipose tissue on coronary computed tomography angiography." Heart and vessels 32.7 (2017): 813-322. (Year: 2017).

Otsuka et al. "Napkin-ring sign on coronary CT angiography for the prediction of acute coronary syndrome." JACC Cardiovasc Imaging 2013; 6(4): 448-57.

Ovrehus et al., "CT-based total vessel plaque analyses improves prediction of hemodynamic significance lesions as assessed by fractional flow reseve in patients with stable angina pectoris", Journal of Cardiovascular Computed Tomography 12, 2018 pp. 344-349.

Ovrehus, et al. "Reproducibility of Semi-Automatic Coronary Plaque Quantification in Coronary CT Angiography with Sub-mSV Radiation Dose." *J Cardiovasc Comput Tomogr*, (2016).

Papadopoulou, et al. "Detection and Quantification of Coronary Atherosclerotic plaque by 64-slice multidetector CT: A systematic head-to-head comparison with intravascular ultrasound." Atherosclerosis. 2011;219: 163-70.

Papadopoulou, et al. Reproducibility of CT Angiography Data Analysis Using Semiautomated Plaque Quantification Software: Implications for the Design of Longitudinal Studies. *Int J Cardiovasc Imaging*.

Park et al., "Atherosclerotic Plaque Characteristics by CT Angiography Identify Coronary Lesions That Cause Ischemia", JACC: Cardiovascular Imaging, vol. 8, No. 1, 2015 in 10 pages.

Park, et al. "Clinical Feasibilty 3D Automated Coronary Atherosclerotic Plaque Quantification Algorithm on Germany Computed Tomography Angiography: Comparison with Intravascular Ultrasound" European Radiology (2015), 25: 3073-3083.

Park, et al. "Visual-functional Mismatch between Coronary Angiography and Fractional Flow Reserve." JACC Cardiovasc Interv. 2012; 5: 1029-36.

Pavlou et al., "A note on obtaining correct marginal predictions from a random intercepts model for binary outcomes." BMC Med Res Methodol 2015; 15:59. doi: 10.1186/s12874-015-004606 [published Online First: Aug. 6, 2015].

Pedregosa, et al. "Scikit-learn: Machine Learning in Python." Journal of Machine Learning Research, 2011;12: 2825-2830.

Picano et al. "The appropriate and justified use of medical radiation in cardiovascular imaging: a position document of the ESC Associations of Cardiovascular Imaging, Percutaneous Cardiovascular Interventions and Electrophysiology." Eur Heart J 2014; 35(10): 665-72.

Puchner, et al. "High-Risk Coronary Plaque at Coronary CT Angiography is Associated with NAFLD, Independent of Coronary Plaque and Stenosis Burden", *J Cardiovasc Comput Tomogr*.

Puehner, et al. "High-Risk Plaque Detected on Coronary CT Angiography Predicts Acute Coronary Syndrome Independent of Significant Stenosis in Patients with Acute Chest Pain" *J Am Coll Cardiol* 2014.

Raff, et al. "SCCT guidelines for the interpretation adn reporting of coronary computed tomographic angiography" *J Cardiovasc Comput Tomogr* 2009: 9(2): 122-36.

Rehani et al. "ICRP Publication 117. Radiological protection in fluoroscopically guided procedures performed outside the imaging department." Ann ICRP 2010; 40(6): 1-102.

Rizvi et al., "Diffuse coronary artery disease among other atherosclerotic plaque characteristics by coronary computed tomography angiography for prediciting coronary vessel-specific ischemia by fractional flow reserve", Atherosclerosis 258, 2017 pp. 145-151.

Rizvi et al., "Rationale and Design of the CREDENCE Trial: computed Tomographic ecaluation of atherosclerotic Determinants of myocardial Ischemia", BMC Cardiovascular Disorders, 2016, in 10 pages.

Roy-Cardinal et al. "Intravascular Ultrasound Image Segmentation: A Three-Dimensional Fast-Marching Method Based on Grey Level Distributions", IEEE Transactions on Medical Imaging, vol. 25, No. 5, May 2006.

Sabir, A et al. Measuring Noncalcified Coronary Atherosclerotic Plaque Using Voxel Analysis with MDCT Angiography: Phantom Validation: American Journal of Roentgenology, Apr. 2008; vol. 190, No. 4, pp. 242-246.

Samady H. et al. "Coronary artery wall shear is associated with progression and transformation of atherosclerotic plaque and arte-

(56) References Cited

OTHER PUBLICATIONS rial remodeling in patients with coronary artery disease." American Heart Association Circulation, vol. 124, Issue 7, Aug. 16, 2011, pp. 779-788.
Schinkel et al. "Noninvasive evaluation of ischaemic heart disease: myocardial perfusion imaging or stress echocardiography?" European Heart Journal (2003) 24, 789-800.
Schlett et al. "How to assess non-calcified plaque in CT angiography: delineation methods affect diagnostic accuracy of low-attenuation plaque by CT for lipid-core plaque in history." Euro Heart J Cardiovasc Imaging 2013; 14(11): 1099-105.
Schuurman, et al. "Prognostic Value of Intravascular Ultrasound in Patients with Coronary Artery Disease." J Am Coll Cardiol. 2018;72: 2003-2011.
Seghier et al., "Lesion identification using unified sagmentation-normalisation models and fuzzy clustering" NeuroImage 40(2008) 1253-1266.
Seifarth, et al. "Histopathological Correlates of the Napkin-Ring Sign Plaque in Coronary CT Angiography." Send to Atherosclerosis. 2012;224: 90-6.
Sharma et al., "Stress Testing Versus CT Angiography in Patients With Diabetes and Suspected Coronary Artery Disease", Journal of the American College of Cardiology, vol. 73, No. 8, 2019 pp. 893-902.
Shaw et al. "Optimal medical therapy with or without percutaneous coronary intervention to reduce ischemic burden: results from the Clinical Outcomes Utilizing Revascularization and Aggressive Drug Evaluation (COURAGE) trail nuclar substudy." Circulation 2008; 117 (10): 1283-91. doi: 10.116/CIRCULATIONAHA.107.743963.
Shaw et al. "Why all the focus on cardiac imaging?" JAAC Cardiovasc Imaging 2010; 3(7): 789-94 doi: 10.16/j.jcmg.2010.05. 004.
Shin S. et al., "Impact of Intensive LDL Cholesterol Lowering on Coronary Artery Atherosclerosis Progression: A Serial CT Angiography Study." JACC Cardiovasc Imaging. 2017; 10(4) pp. 437-446.
Siasos, et al. "Local Low Shear Stess and Endothelial Dysfunction in Patients with Nonobstructive Coronary Atherosclerosis." J Am Coll Cardiol. 2018;71: 2092-2102.
Song et al. "Comparison of machine learning techniques with classical statistical models in predicting heaith outcomes." Stud Health Technol Inform. 2004; 107(Pt 1) pp. 736-740.
Staruch, et al. "Automated Quantitative Plaque Analysis for Discrimination of Coronary Chronic Total Occlusion adn Subtoal Occlusion in Computed Tomography Angiography", *J Thoracic Imaging*, (2016).
Stone, et al. "A prospective natural-history study of coronary atherosclerosis." N Engl J Med 2011; 364(3): 226-35.
Stuijfzand, et al. "Stress Myocardial Perfusion Imaging vs Coronary Computed Tomographic Angiography for Diagnosis of Invasive Vessel-Specific Coronary Physiology Predictive Modeling Results From the Computed Tomographic Evaluation of Atherosclerotic Determinants of Myocardial Ischemia (CREDENCE) Trial", JAMA Cardiology. doi:10.1001/jamacardio.2020.3409, Aug. 19, 2020.
Sun, et al. "Diagnostic Value of Multislice Computed Tomography Angiography in Coronary Artery Disease: a Meta-Analysis." Eur J Radiol. 2006;60: 279-86.
Taylor et al., "Patient-Specific Modeling of Cardiovascular Mechanics", Annu. Rev. Biomed. Eng. 2009.11:109-139.
Thim, et al. "Unreliable Assessment of Necrotic Core by Virtual Histology Intravascular Ultrasound in Porcine Coronary Artery Disease." Circ Cardiovasc Imaging. 2010;3: 384-91.
Thygesen, et al. "Third Universal Definition of Myocardial Infarction." Glob Heart. 2013;7: 275-95.
Tian, et al. "Distinct Morphological Features of Ruptured Culprit Plaque for Acute Coronary Events Compared to those with Silent Rupture and Thin-Cap Fibroatheroma: a Combined Optical Coherence Tomography and Intravascular Ultrasound Study." J Am Coll Cardiol. 2014;63: 2209-16.

Tilkemier et al., "American of Nuclear Cardiology information statement: Standardized reporting matrix for radionuclide myocardial perfusion imaging." J Nucl Cardiol 2006; 13 (6): e157-71. doi: 10.1016/j.nuclcard.2006.08.014.
Tomey MI, et al. "Advances in the understanding of plaque composition and treatment options: year in review." J AM Coll Cardio. 2014; 63(16) pp. 1604-1616.
Tonino et al., "Angiographic versus functional severity of coronary artery stenoses in the FAME study fractional flow reserve versus angiography in multivessel evaluation." Journal of the American College of Cardiology 2010; 55 (25): 2816-21. doi: 10.1016/j.jacc. 2009.11-096 [published Online First: Jun. 29, 2010].
Van Ooijen, et al. "Coronary Artery Imaging with Multidetector CT: Visualization Issues" *RadioGraphics*, vol. 23. (2003).
Van Rosendael et al., "Maximization of the usage of coronary CTA derived plaque information using a machine learning based algorithm to improve risk stratification; insights from the CONFIRM registry", Journao of Cardiovascular Computed Tomography 12, 2018, pp. 204-209.
Van Rosendael et al., "Quantitative Evaluation of High-Risk Coronary Plaque by Coronary CTA and Subsequent Acute Coronary Events", JACC: Cardiovascular Imaging, vol. 12, No. 8, Aug. 2019. pp. 1568-1571.
Versteylen MO, et al. "Additive value of semiautomated quantification of coronary artery disease using cardiac computed tomographic angiography to predict future acute coronary syndrome." J Am Coll Cardiol. 2013: 61(22): pp. 2296-2305.
Virmani, et al. "Atherosclerotic plaque progression and vulnerability to rupture: angiogenesis as a source of intraplaque hemorrhage." Arterioscler Thromb Vasc Biol. 2005; 25: 2054-61.
zvirmani, et al. "Lessons from sudden coronary death: a comprehensive morphological classification scheme for atherosclerotic lesions." Arterioscler Thromg Vasc Biol. 2000;20: 1262-75.
Virmani, et al. "Pathology of the Vulnerable Plaque." J Am Coll Cardiol. 2006; 47: C13-8.
Wei, et al. "Computerized Detection of Noncalcified Plaques in Coronary CT Angiography: Evaluation of Topological Soft Gradient Prescreening Method and Luminal Analysis" *Med Phys*, (2014).
Weir-MacCall et al., "Impact of Non-obstructive left main disease on the pregression of coronary artery disease: A PARADIGM substudy", Journal of Cardiovascular Computed Tomography 12, 2018, pp. 231-237.
Weisenfeld et al. "Automatic Segmentation of Newborn Brain MRI", NIG PA Author Manuscript 2010.
Williams et al. "Use of Coronary Computed Tomographic Angiography to Guide Management of Patients with Coronary Disease". Jaurnal of American College of Cardiology 2016; 67 (15) : 1759-68. doi: 10.1016/J.Jacc.2016.02.026 [published Online First: Apr. 16, 2016].
Williams et al., "Coronary Artery Plaque Characteristics Associated With Adverse Outcomes in the SCOT-HEART Study", Journal of the American College of Cardiology, vol. 73, No. 3, Jan. 29, 2019, pp. 291-3231.
Wilson et al. "Prediction of coronary heart disease using risk factor catrgories" Circulation 1998; 97(18) pp. 1837-1847.
Won et al., "Longitudinal assessment of coronary plaque volume change related to glycemic status using serial coronary computed tomography angiography: A Computed TomoGraphic Angiography Imaging) substudy", Journal of Cardiovascular Computed Tomography 13, 2019 pp. 142-147.
Won et al., "Longitudinal quantitative assessment of coronary plaque progression related to body mass index using serial coronary computed tomography angiography", European Heart Journal—Cardiovascular Imaging, 2019 pp. 591-599.
Yang, et al. "Automatic centerline extraction of coronary arteries in coronary computed tomographic angiography" *The International Journal of Cardiovascular Imaging*, 28:921-933. (2012).
Yokoya K, et al. "Process of progression of coronary artery lesions from mild or moderate stenosis to moderate or severe stenesis: A study based on four serial coronary arteriograms per year. "Circulation 1999; 100(9):903-909.
Zeb I et al. "Effect of statin treatment on coronary plaque progression—a serial coronary CT angiography study." Atherosclerosis. 2013; 231(2):198-264.

(56) References Cited

OTHER PUBLICATIONS

Zhao Z., et al. "Dynamic nature of nonculprit coronary artery lesion morphology in STEMI: a serial IVUS analysis from HORIZONS-AMI trial." JACC Cardiovasc Imaging, 2013; 6(1):86-95.
International Search Report and Written Opinion for Application No. PCT/US20/15035 dated Spr. 14, 2020, in 20 pages.
International Search Report and Written Opinion for Application No. PCT/US2021/012218 dated Mar. 17, 2021, in 11 pages.
International Preliminary Report on Patentabiluty for Application No. PCT/US2020/015035 dated Jul. 27, 2021, in 7 pages.
International Search Report and Written Opinion for Application No. PCT/US2021/037919 dated Oct. 6, 2021, in 12 pages.
Abdelrahman et al., Sep. 8, 2020, Coronary computed tomography angiography from clinical uses to emerging technologies, Journal of the American College of Cardiology, 76(10):1226-1243.
Chrencik et al., Sep. 2019, Quantitative assessment of carotid plaque morphology (geometry and tissue composition) using computed tomography angiography. Journal of Vascular Surgery, 70(3):858-868.
Gupta et al., Apr. 8, 2015, Moving beyond luminal stenosis: imaging strategies for stroke prevention in asymptomatic carotid stenosis, Cerebrovascular Diseases, 39:253-261.
Karlof et al., 2019, Correlation of computed tomography with carotid plaque transcriptomes associates calcification with lesion-stabilization, atherosclerosis, 288:175-185.
Karlof et al., 2021, Carotid plaque phenotyping by correlating plaque morphology from computed tomography angiography with transcriptional profiling, Eur. J. Vas, Endovas. Surg., 62:716-726.
Kwee et al., Apr. 2010, Systematic review on the association between calcification in carotid plaques and clinical ischemic symptoms, Journal of Vascular Surgery, 51(4):1015-1025.
Murgia et al., Aug. 2020, Plaque imaging volume analysis: technique and application, Cardiovasc: Diagn Ther, 10(4):1032-1047.
Oikonomou et al., Aug. 28, 2018, Non-invasive detection of coronary inflammation using computed tomography7 and prediction of residual cardiovascular risk (the CRIPS CT Study): a post-hoc analysis of prospective outcome data, The Lancet, 382(10151):929-393.
Rozie et al., 2009, Atherosclerotic plaque volume and composition in symptomatic carotid arteries assess with the multidetector CT angiography; relationship with severity of stenosis and cardiovascular risk factors, Eur Radiol, 19:2294-2301.
Sheahan et al., Feb. 2018, Atheroscierotic plaque tissue: noninvasive quantitative assessment of characteristics with software-aided measurements from conventional CT angiography, Radiology, 286(2):622-631.
Sun et al., Mar. 2017, Carotid plaque lipidt content and fibrous cap status predict systemic cv outcomes, JACC: Cardiovaseutar Imaging, 10(3):241-249.
U.S. Food and Drug Administration, Nov. 5, 2010, K100868 501(k) Summary, 10 pp.
U.S. Food and Drug Administration, Oct. 2, 2020, K202280 501(k) Summary, 9 pp.
Wintermark et al., May 2008, High-resolution CT imaging of carotid artery atherosciemtic plaques, Am J Neuroradiol, 29:875-882.
Maurovich-Horvat et al., 2014, Comprehensive plaque assessment by coronary CT angiography, Nature Reviews Cardiology, 11(7):390-402.
Oikonomou et al., Aug. 28, 2018, Non-invasive detection of coronary inflammation using computed tomography7 and prediction of residual cardiovascular risk (the CRIPS CT study): a post-hoc analysis of prospective outcome data, The Lancet, 382(10151):929-939.
Sheahan et al., Feb. 2018, Atherosclerotic plaque tissue: noninvasive quantitative assessment of characteristics with software-aided measurements from conventional CT angiography, Radiology, 286(2):622-631.
Sun et al., Mar. 2017, Carotid plaque lipid content and fibrous cap status predict systemic cv outcomes, JACC: Cardiovascular Imaging, 10(3):241-249.
US. Food and Drug Administration, Nov. 5, 2019, K190868 501(k) Summary, 10 pp.
Wintermark et al., May 2008, High-resolution CT imaging of carotid artery atherosclerotic plaques, Am J Neuroradiol, 29:875-882.
Boussoussou et al., 2023, The effect of patient and imaging characteristics on coronary CT angiography assessed perocoronary adipose tissue attenuation and gradient, Journal of Cardiovascular Computed Tomography, 17:34-42.
Budde et al., Sep. 15, 2021, CT-derived fractional flow reserve (FFRct) for functional coronary artery evaluation in the follow-up of patients after heart transplantation, European Radiology, https://doi.org/10/1007/500330-0921-08246-5.
Cury et al., 2022, CAD-RADS™ 2.0-2022 coronary artery disease—reporting and data system an expert consensus document ofthe Society of Cardiovascular Computed Tomography (SCCT), the American College of Cardiology (ACC), the American College of Radiology (ACR) and the North America Society of Cardiovascular Imaging (NASCI), Journal of Cardiovascular Computed Tomography, https://doi.org/10.1016/j.jcct.2022.07.002.
De Bruyne et al., Sep. 13, 2012, Fractional flow reserve-guided PCA versus medical therapy in stable coronary disease, The New England Journal of Medicine, 367(11):991-1001.
Douglas et al., Aug. 2, 2016, 1-year outcomes of FFRCT-guided care in patients with suspected coronary disease, Journal of the American College of Cardiology, 68(5):435-445.
Kanitsar et al., 2002, CPR—curved planar reformation, IEEE Visualization, DOI: 10.1109/VISUAL.2002.1183754, 8 pp.
MacAlpin, Feb. 1980, Contribution of dynamic vascular wall thickening to luminal narrowing during coronary arterial constriction, Circulation, 60(2):296-301.
Michail et al., Jan. 2021, Feasibility and validity of computed tomography-derived fractional flow reserve in patients with severe aortic stenosis, Circ. Cardiovasc., Interv. 14:e009586.
Min et al., 2022, Coronary CTA plaque volume severity stages according to invasive coronary angiography and FFR, Journal of Cardiovascular Computed Tomography, https://doi.org/1o.1016/j.jcct.2002.03.001.
Narula et al., 2021, SCCT 2021 expert consensus document of coronary computed tomographic angiography: a report of the Society of Cardiovascular Computed Tomography, Journal of Cardiovascular Computed Tomography.
Norgaard et al., 2020, Clinical outcomes following real-world computed tomography angiography-derived factional flow reserve testing in chronic coronary syndrome patients with calcification, European Heart Journal-Cardiovascular Imaging, doi:10.1093/ehjc/jeaa173.
Norgaard et al., Apr. 1, 2014, Diagnostic performance of noninvasive fractional flow reserve derived from coronary computed tomography angiography in suspected coronary artery disease, Journal of the American College of Cardiology, 63(12):1145-1155.
Patel et al., 2019, 1-year impact on medical practice and clinical outcomes of FFRCT, JACC: Cardiovascular Imaging, https://doi.org/10.,1016/j.jcmg.2019.03.003, 9 pp.
Tonino et al., Jan. 15, 2009, Fractional flow.reserve versus angiography for guiding percutaneous coronary interventions, The New England Journal of Medicine, 360(3):213-224.
Wu et al., Jun. 11, 2018. Group normalization, arXiv:1803.08494v3, [cs.CV], 10 pp.
Zreik et al., Dec. 10, 2018, A recurrent CNN for automatic detection and classification of coronary artery plaque and stenosis in coronary CT angiography, arXiv:1803/04360v4, 11 pp.
International Search Report and Written Opinion for Application No. PCT/US22/40816 dated Mar. 1, 2023, in 16 pages.

\* cited by examiner

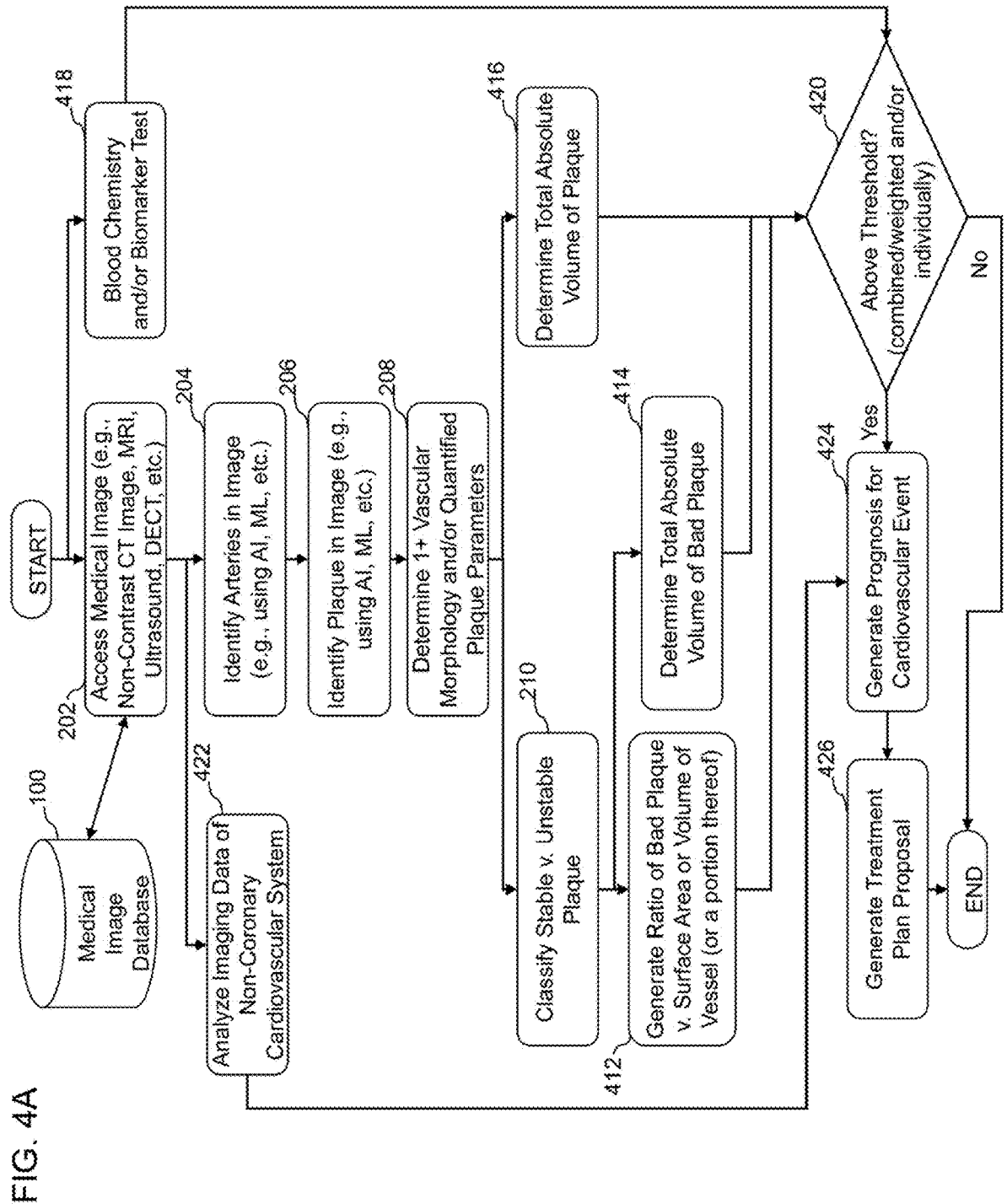

FIG. 5D
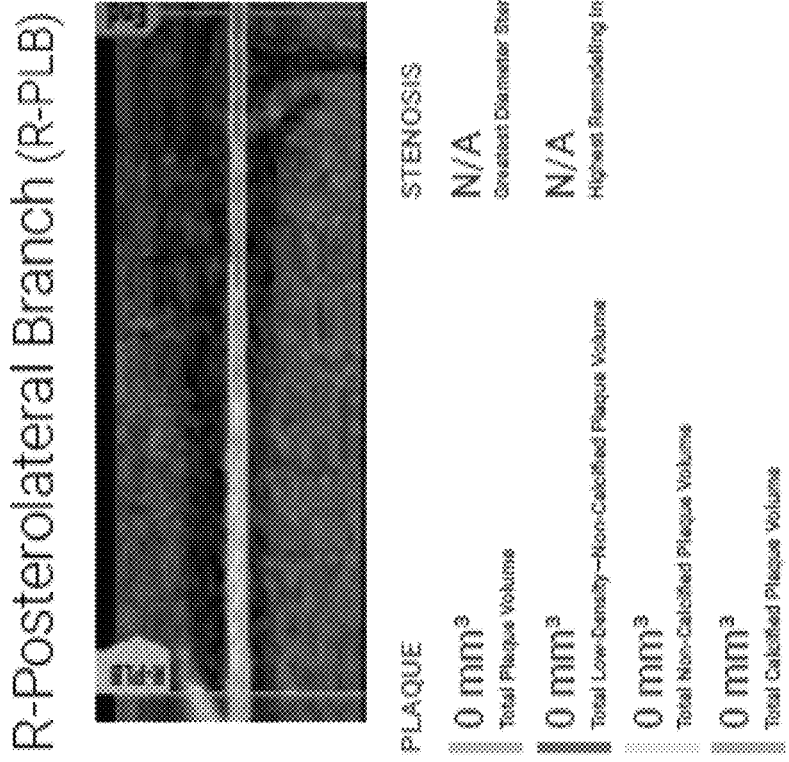
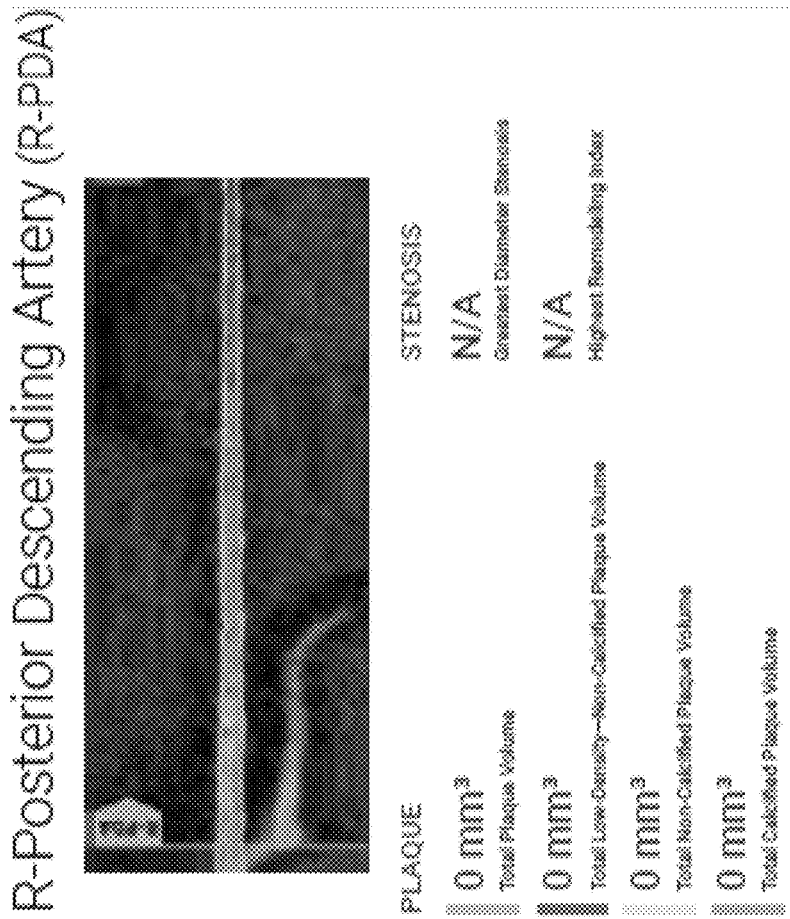

FIG. 5F
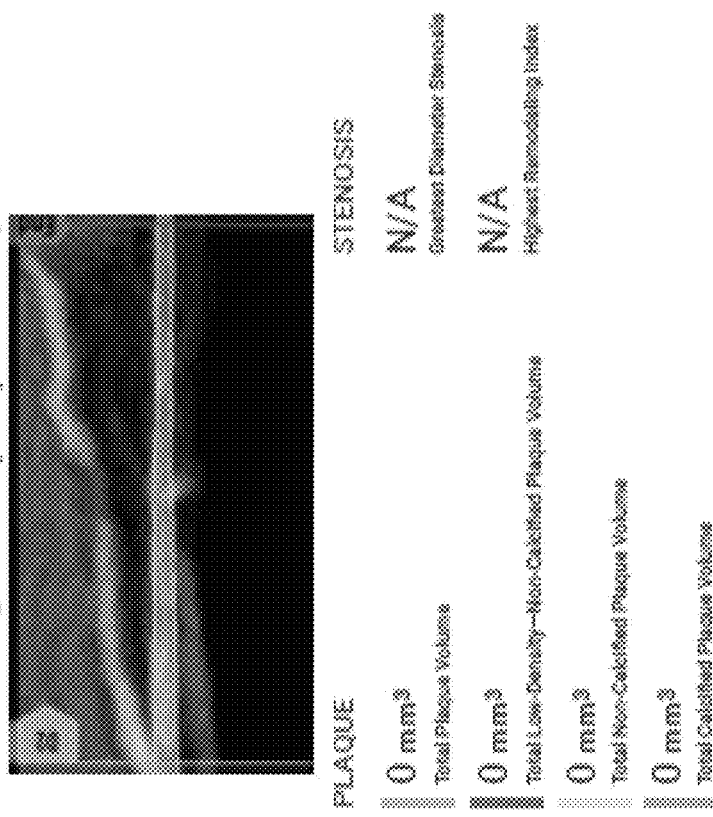
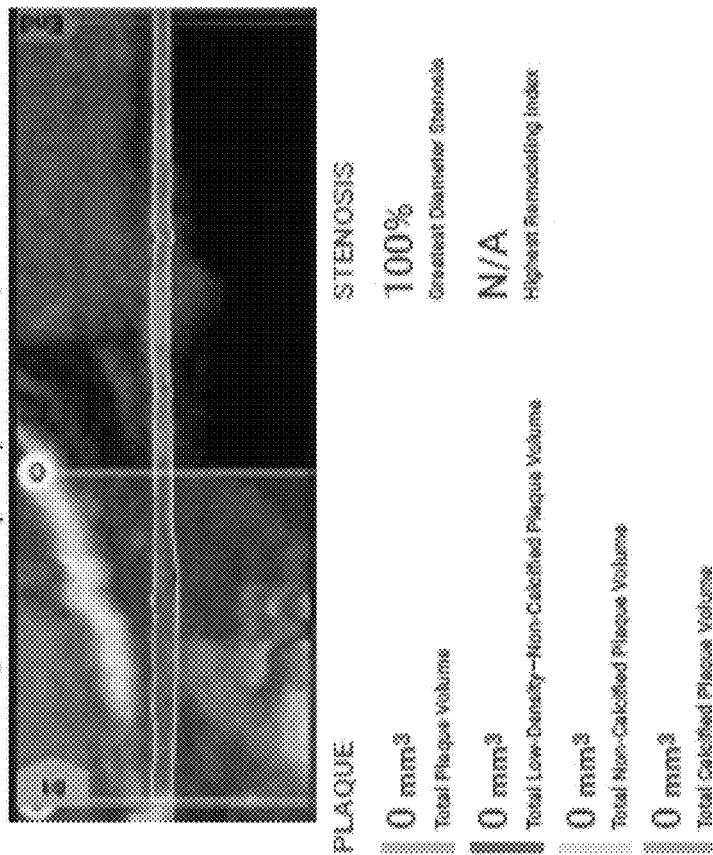

FIG. 5H
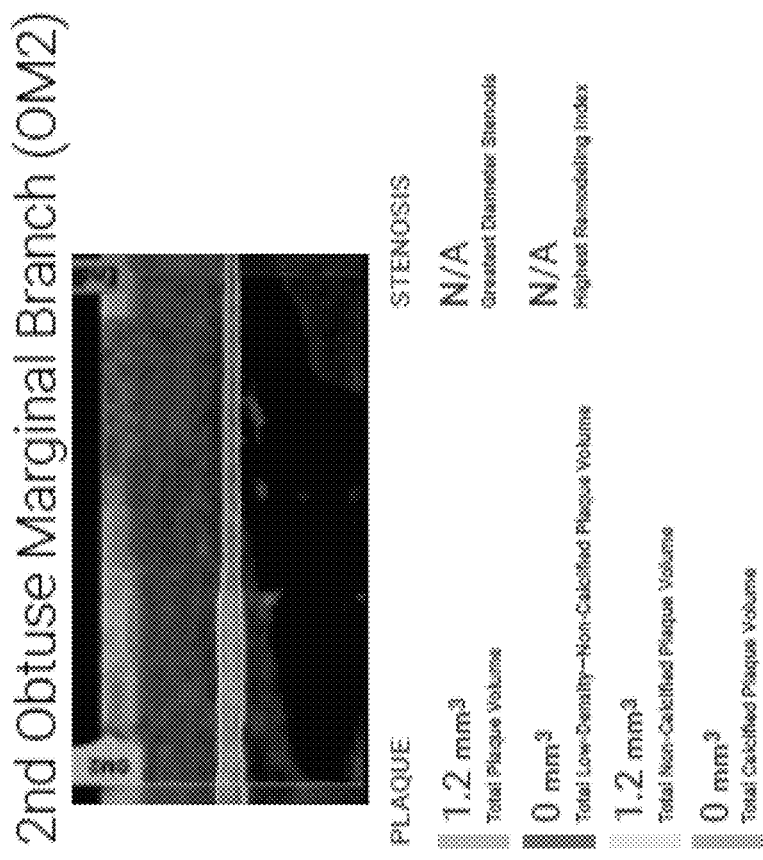
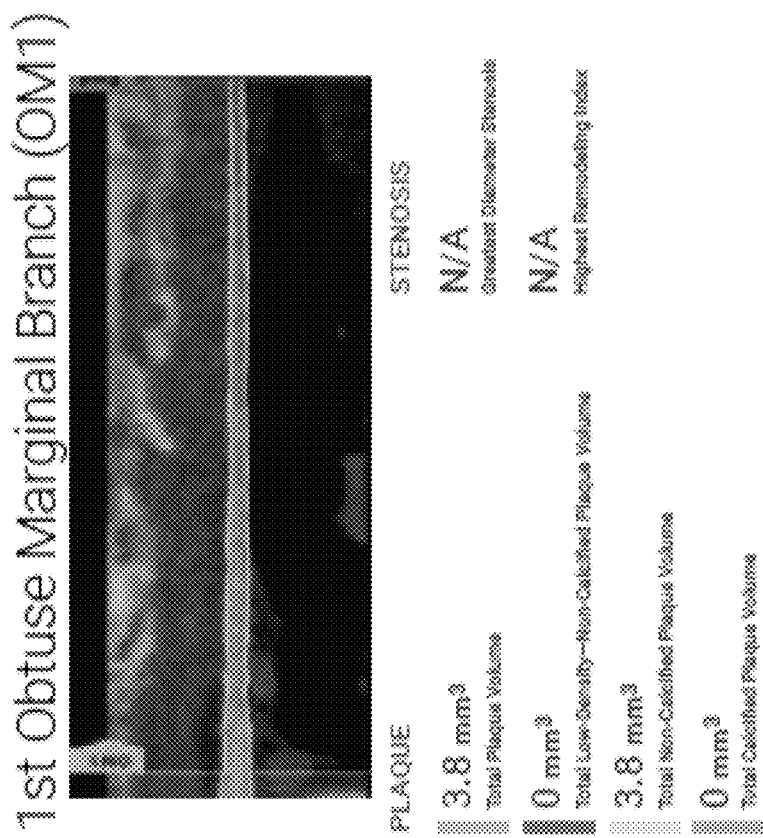

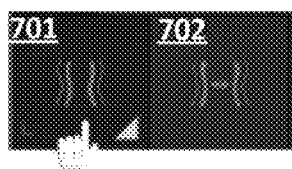 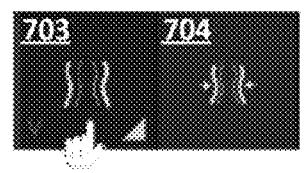
FIG. 7F
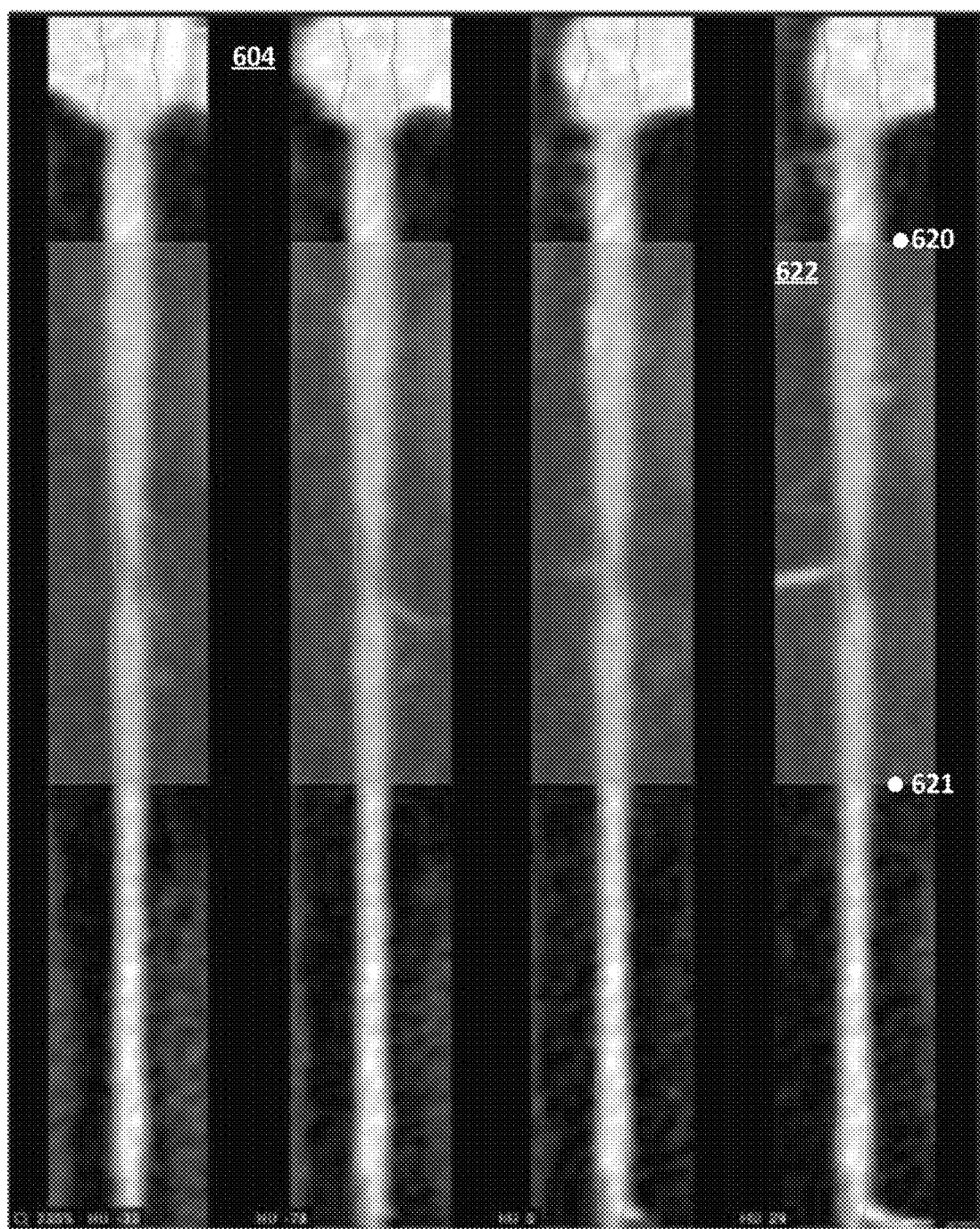
FIG. 7G

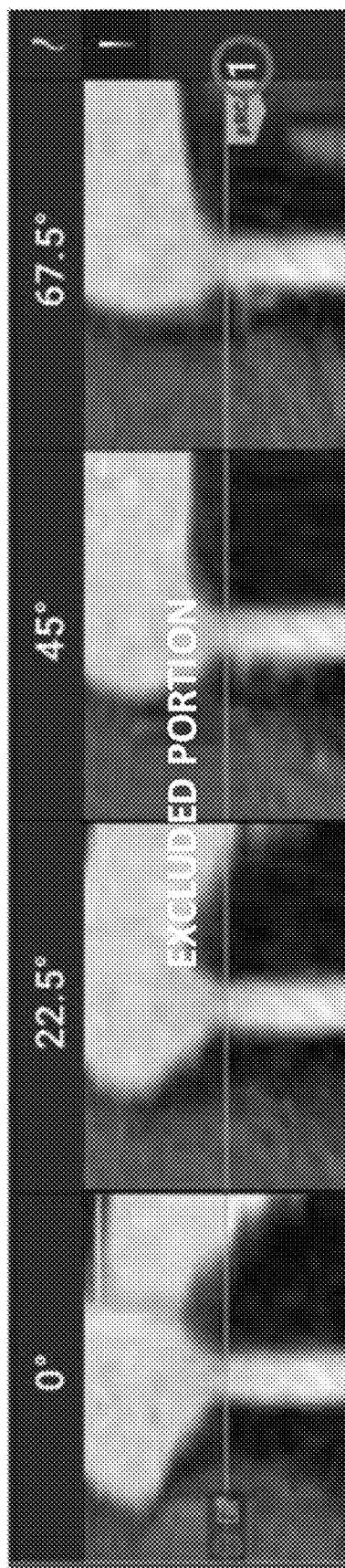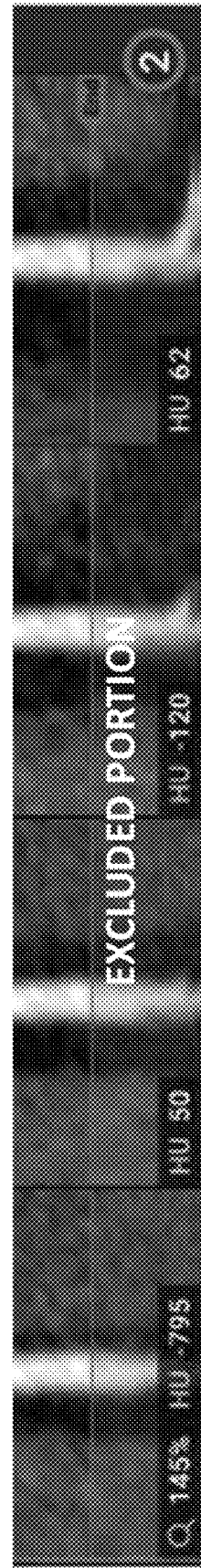
FIG. 7Z
FIG. 7AA

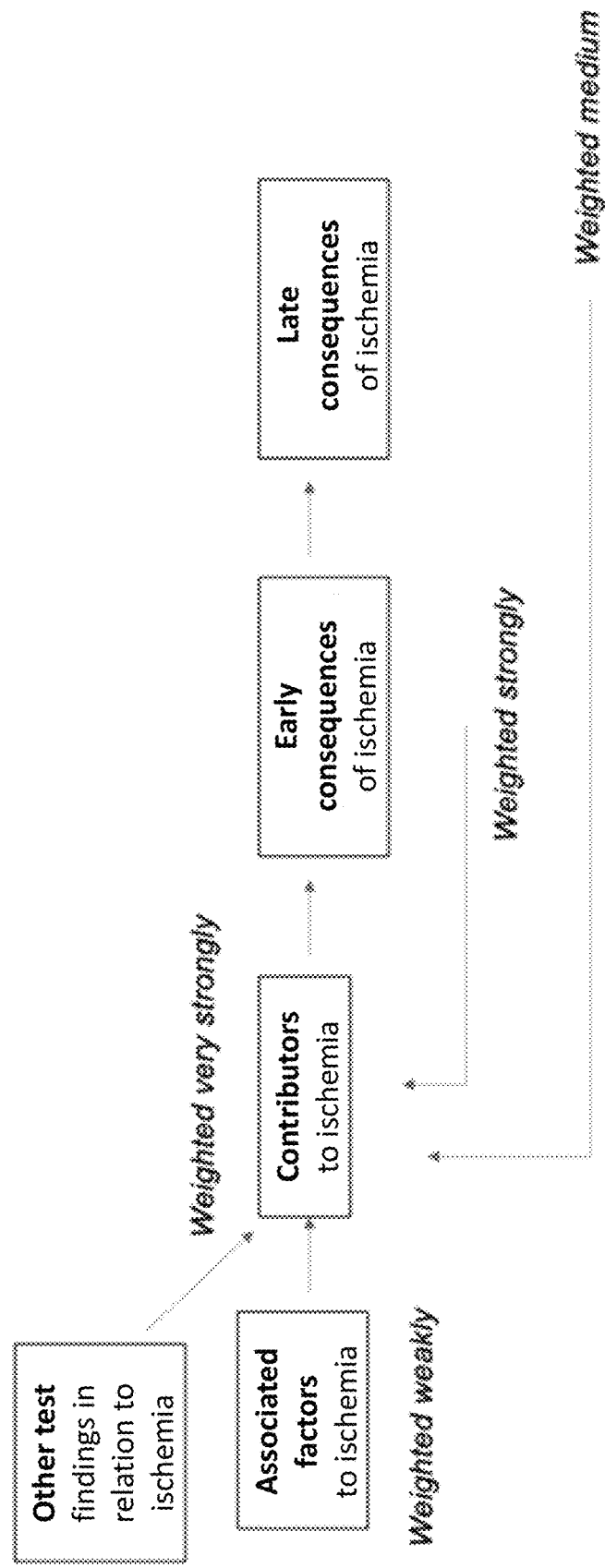

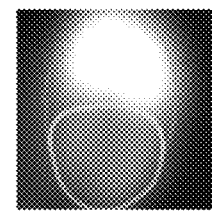
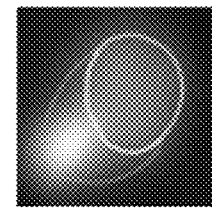
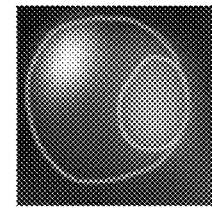
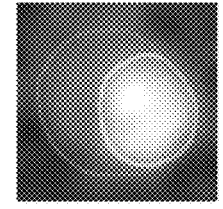
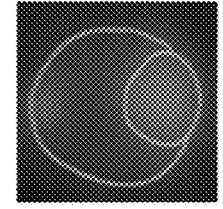
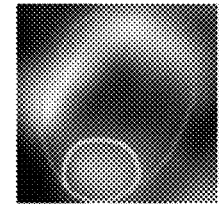
FIG. 22A

FIG. 23B

| Severity | Angiographic Equivalent | Ranges of Plaque Volume | PAV (%) | Plaque Volume (mm³) |
|---|---|---|---|---|
| None | • No stenosis | • 0 mm³ | • 0% | • 0 mm³ |
| Stage 1 | • 1-49% stenosis | • 186 ± 159 mm³ | • 0.1% - 10% | • 1 – 350 mm³ |
| Stage 2 | • 1-vessel CAD >50% stenosis | • 345 ± 291 mm³ | • 10.1% - 20% | • 1 – 350 mm³ |
| Stage 3 | • 2-vessel CAD >50% stenosis | • 486 ± 343 mm³ | • 20.1% - 30% | • 351 – 700 mm³ |
| Stage 4 | • 3-vessel CAD >50% stenosis | • 724 ± 338 mm³ | • >30% | • >700 mm³ |

FIG. 23C

| Severity | Angiographic Equivalent | Ranges of Plaque Volume | PAV (%) | Plaque Volume (mm³) |
|---|---|---|---|---|
| None | • No stenosis | • 0 mm³ | • 0% | • 0 mm³ |
| Stage 1 | • 1-49% stenosis<br>• Future ACS | • 186 ± 159 mm³<br>• 200 mm³ (36% CAC=0) | • 0.1% - 10% | • 1 – 350 mm³ |
| Stage 2 | • 1-vessel CAD >50% stenosis | • 345 ± 291 mm³ | • 10.1% - 20% | • 1 – 350 mm³ |
| Stage 3 | • 2-vessel CAD >50% stenosis | • 486 ± 343 mm³ | • 20.1% - 30% | • 351 – 700 mm³ |
| Stage 4 | • 3-vessel CAD >50% stenosis | • 724 ± 338 mm³ | • >30% | • >700 mm³ |

FIG. 23D

| RAPID PROGRESSION | PROGRESSION WITHOUT STABILIZATION | PROGRESSION WITH STABILIZATION | REGRESSION |
|---|---|---|---|
| 1. >1.0% PAV / year | 1. <1.0% increase in PAV / year; AND Non-calcified plaque represents >50% of total new plaque formation | 1. <1.0% increase in PAV / year; AND Calcified plaque represents >50% of total new plaque formation | 1. Decrease in total PAV |

FIG. 23E

TIME-TO-TREATMENT GOALS:
LDL-to-Goal in 4 weeks (Average is 18 months)

LDL-to-Goal in 4 weeks (Average is 18 months)
- 4+8 weeks
- Easy mathematical calculation for % LDL lowering: Statins + zetia/BA + PCSK9 inhibitor/bempedoic acid
- Treat with what is needed - Minimal titration

Blood Pressure-to-Goal in 12 Weeks
- 12+8 weeks

FIG. 23F
LIPIDS
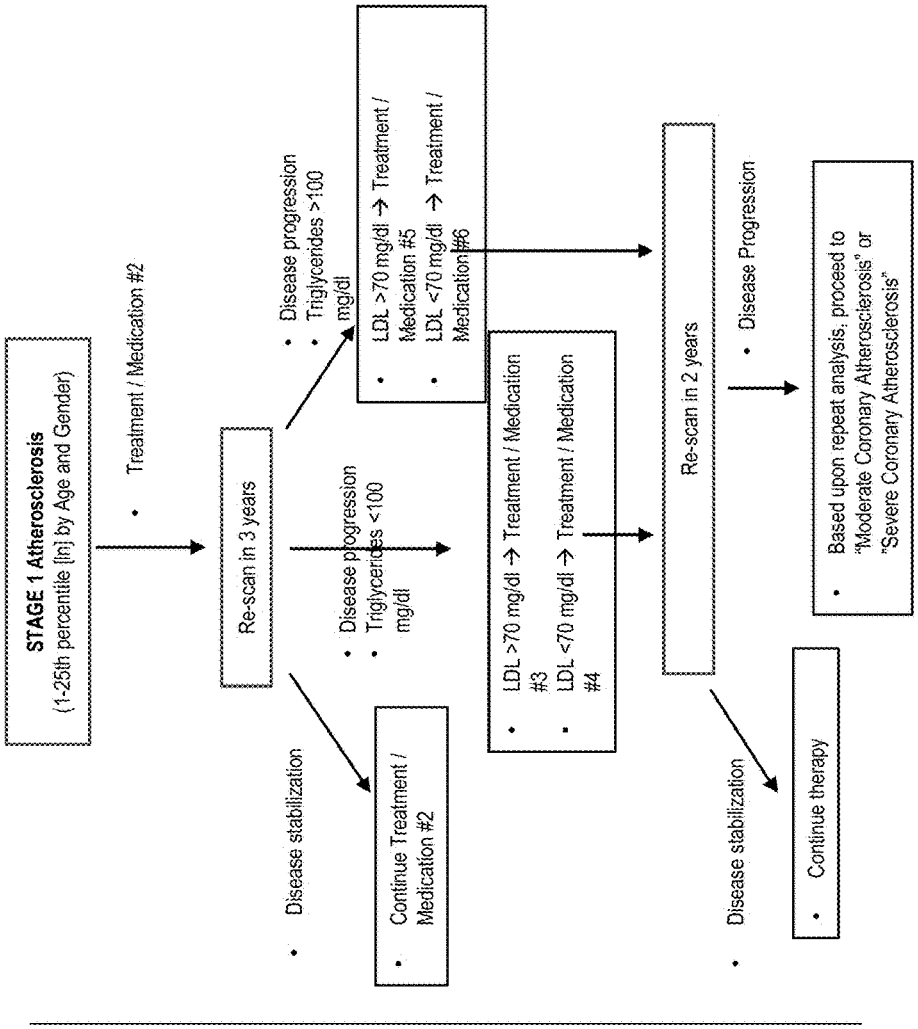
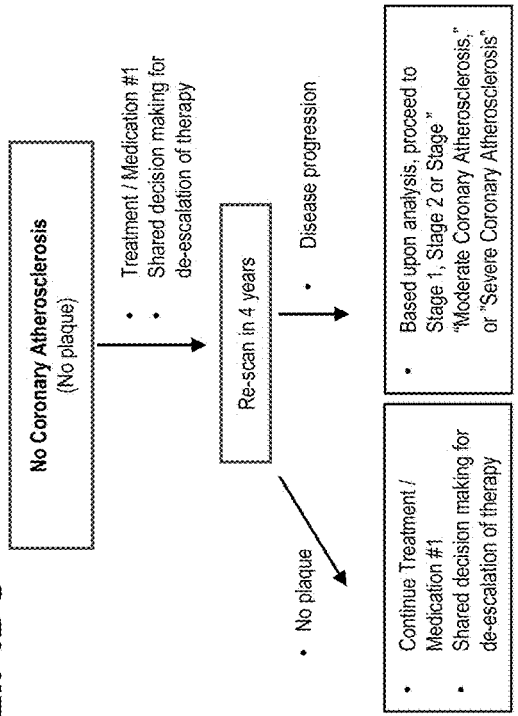

LIPIDS

FIG. 23H
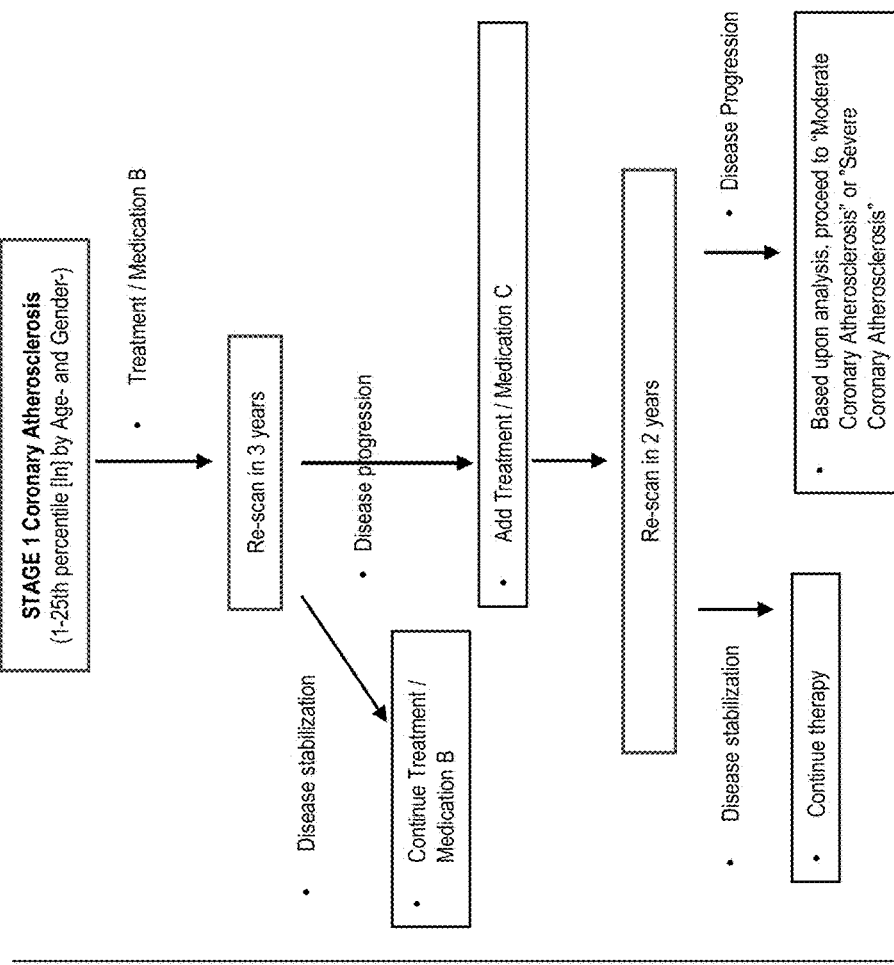
T2 DIABETES
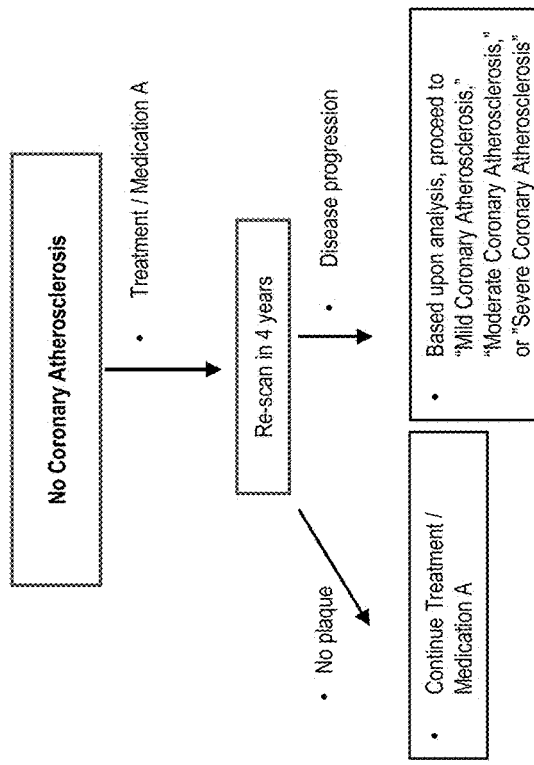

FIG. 23I
T2 DIABETES
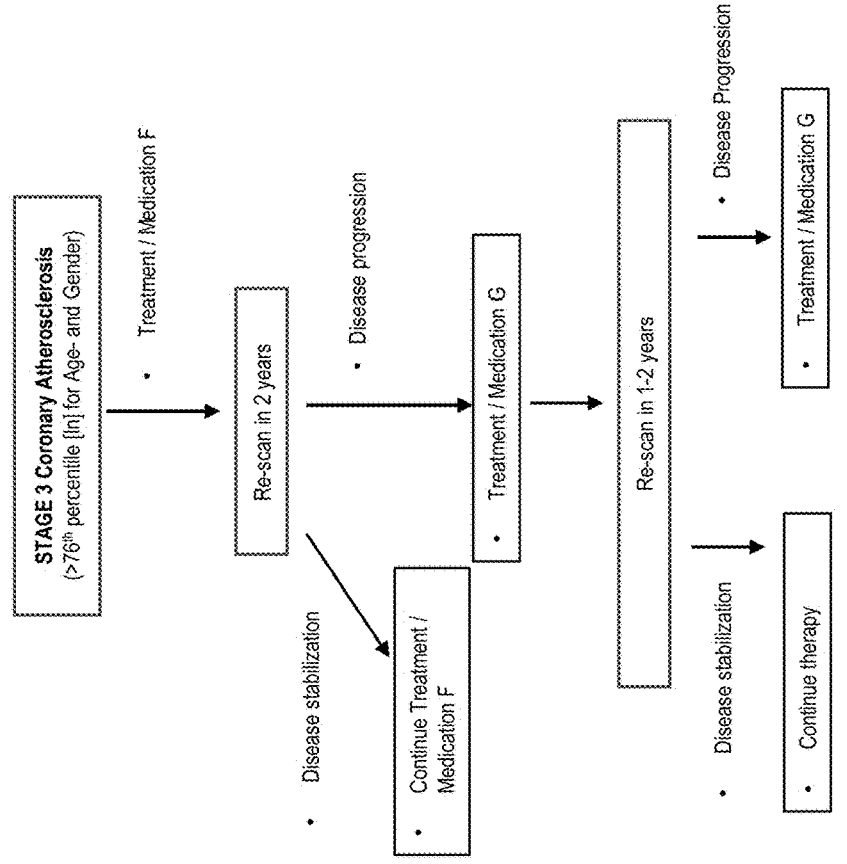
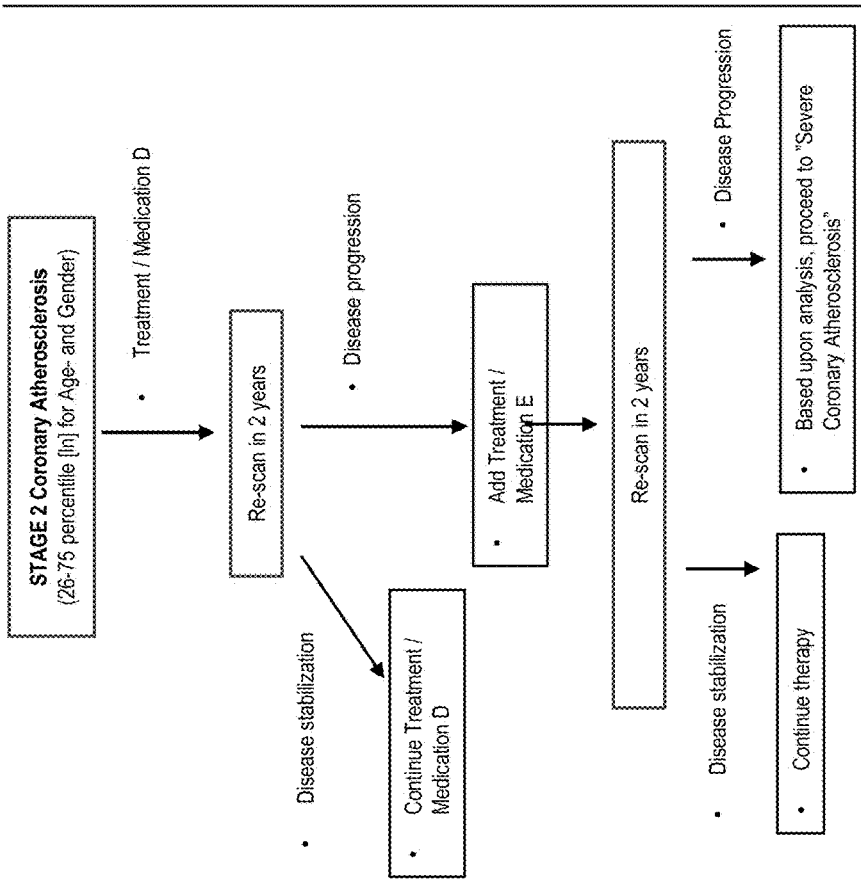

FIG. 24E

| Estimated $R_0$ | Actual R | Lumen | Estimated Stenosis | True stenosis |
|---|---|---|---|---|
| 5 | 3 | 0.5 | 90% | 83% |
| 5 | 3 | 1 | 80% | 67% |
| 5 | 3 | 1.5 | 70% | 50% |
| 5 | 3 | 2 | 60% | 33% |
| 5 | 3 | 2.5 | 50% | 17% |

| Estimated $R_0$ | Actual R | Wall | Estimated Remodeling Index | True Remodeling Index |
|---|---|---|---|---|
| 5 | 3 | 4 | 0.80 | 1.33 |
| 5 | 3 | 4.5 | 0.90 | 1.50 |
| 5 | 3 | 5 | 1.00 | 1.67 |
| 5 | 3 | 5.5 | 1.10 | 1.83 |
| 5 | 3 | 6 | 1.20 | 2.00 |

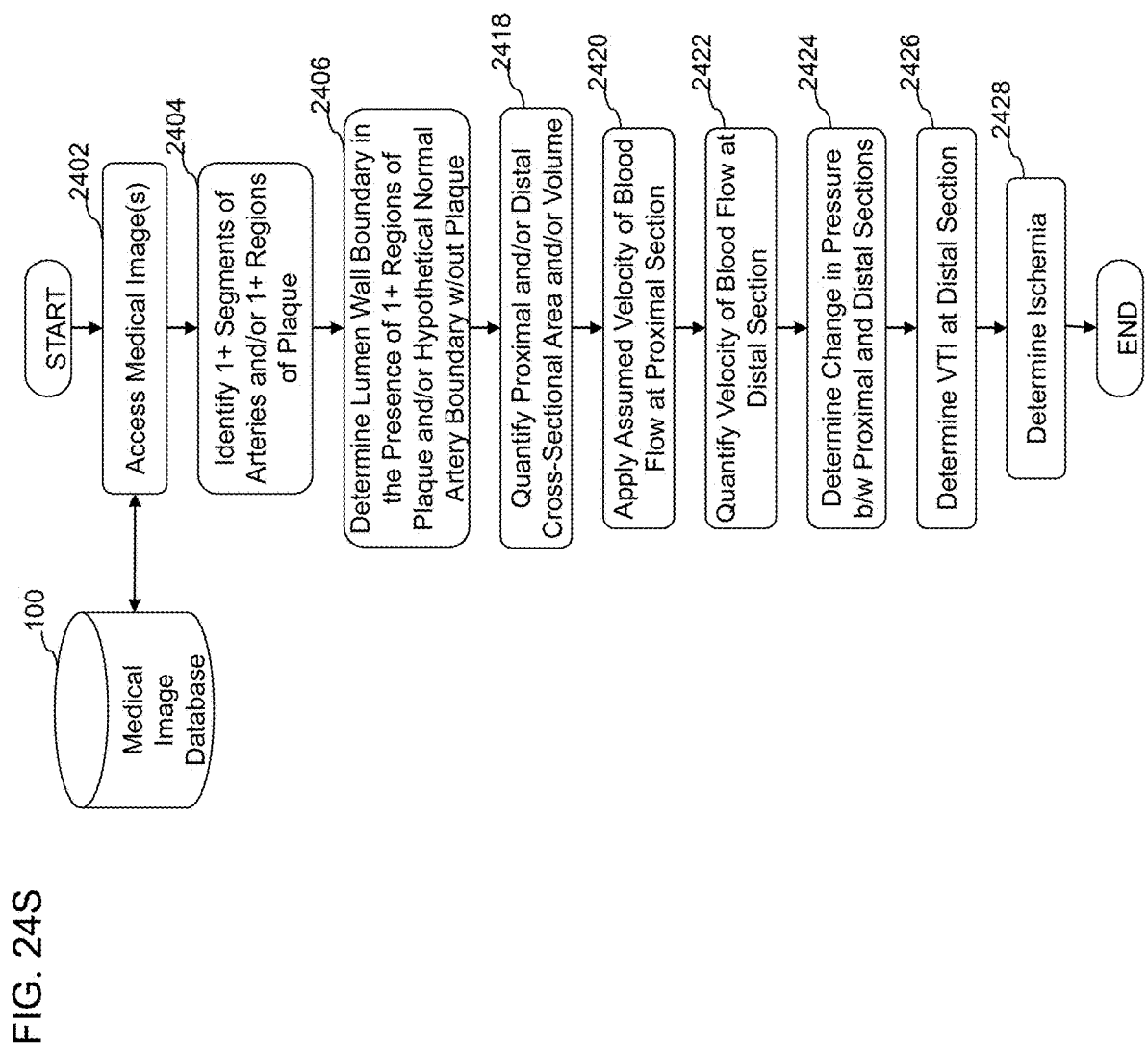

SYSTEMS, METHODS, AND DEVICES FOR MEDICAL IMAGE ANALYSIS, DIAGNOSIS, RISK STRATIFICATION, DECISION MAKING AND/OR DISEASE TRACKING

CROSS-REFERENCE TO RELATED APPLICATIONS

The present application is a continuation of U.S. patent application Ser. No. 17/367,549, filed Jul. 5, 2021, which is a continuation of U.S. patent application Ser. No. 17/350,836, filed Jun. 17, 2021, which is a continuation-in-part of U.S. patent application Ser. No. 17/213,966, filed Mar. 26, 2021, which is a continuation of U.S. patent application Ser. No. 17/142,120, filed Jan. 5, 2021, which claims the benefit of U.S. Provisional Patent Application No. 62/958,032, filed Jan. 7, 2020. This application also claims the benefit of U.S. Provisional Patent Application Nos. 63/201,142, filed Apr. 14, 2021, 63/041,252, filed Jun. 19, 2020, 63/077,044, filed Sep. 11, 2020, 63/077,058, filed Sep. 11, 2020, 63/089,790, filed Oct. 9, 2020, and 63/142,873, filed Jan. 28, 2021, Each one of the above-listed disclosures is incorporated herein by reference in its entirety. Any and all applications for which a foreign or domestic priority claim is identified in the Application Data Sheet as filed with the present application are hereby incorporated by reference under 37 C.F.R. § 1.57.

BACKGROUND

Field

The present application relates to systems, methods, and devices for medical image analysis, diagnosis, risk stratification, decision making and/or disease tracking.

Description

Coronary heart disease affects over 17.6 million Americans. The current trend in treating cardiovascular health issues is generally two-fold. First, physicians generally review a patient's cardiovascular health from a macro level, for example, by analyzing the biochemistry or blood content or biomarkers of a patient to determine whether there are high levels of cholesterol elements in the bloodstream of a patient. In response to high levels of cholesterol, some physicians will prescribe one or more drugs, such as statins, as part of a treatment plan in order to decrease what is perceived as high levels of cholesterol elements in the bloodstream of the patient.

The second general trend for currently treating cardiovascular health issues involves physicians evaluating a patient's cardiovascular health through the use of angiography to identify large blockages in various arteries of a patient. In response to finding large blockages in various arteries, physicians in some cases will perform an angioplasty procedure wherein a balloon catheter is guided to the point of narrowing in the vessel. After properly positioned, the balloon is inflated to compress or flatten the plaque or fatty matter into the artery wall and/or to stretch the artery open to increase the flow of blood through the vessel and/or to the heart. In some cases, the balloon is used to position and expand a stent within the vessel to compress the plaque and/or maintain the opening of the vessel to allow more blood to flow. About 500,000 heart stent procedures are performed each year in the United States.

However, a recent federally funded $100 million study calls into question whether the current trends in treating cardiovascular disease are the most effective treatment for all types of patients. The recent study involved over 5,000 patients with moderate to severe stable heart disease from 320 sites in 37 countries and provided new evidence showing that stents and bypass surgical procedures are likely no more effective than drugs combined with lifestyle changes for people with stable heart disease. Accordingly, it may be more advantageous for patients with stable heart disease to forgo invasive surgical procedures, such as angioplasty and/or heart bypass, and instead be prescribed heart medicines, such as statins, and certain lifestyle changes, such as regular exercise. This new treatment regimen could affect thousands of patients worldwide. Of the estimated 500,000 heart stent procedures performed annually in the United States, it is estimated that a fifth of those are for people with stable heart disease. It is further estimated that 25% of the estimated 100,000 people with stable heart disease, or roughly 23,000 people, are individuals that do not experience any chest pain. Accordingly, over 20,000 patients annually could potentially forgo invasive surgical procedures or the complications resulting from such procedures.

To determine whether a patient should forego invasive surgical procedures and opt instead for a drug regimen, it can be important to more fully understand the cardiovascular disease of a patient. Specifically, it can be advantageous to better understand the arterial vessel health of a patient.

SUMMARY

Various embodiments described herein relate to systems, methods, and devices for medical image analysis, diagnosis, risk stratification, decision making and/or disease tracking.

In particular, in some embodiments, the systems, devices, and methods described herein are configured to utilize non-invasive medical imaging technologies, such as a CT image for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms. In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

In some embodiments, a normalization device configured to normalize a medical image of a coronary region of a subject for an algorithm-based medical imaging analysis comprises: a substrate configured in size and shape to be placed in a medical imager along with a patient so that the normalization device and the patient can be imaged together such that at least a region of interest of the patient and the normalization device appear in a medical image taken by the medical imager; a plurality of compartments positioned on or within the substrate, wherein an arrangement of the plurality of compartments is fixed on or within the substrate; a plurality of samples, each of the plurality of samples positioned within one of the plurality of compartments, and wherein a volume, an absolute density, and a relative density of each of the plurality of samples is known, the plurality of samples comprising: a set of contrast samples, each of the contrast samples comprising a different absolute density than absolute densities of the others of the contrast samples; a set of calcium samples, each of the calcium samples comprising a different absolute density than absolute densities of the others of the calcium samples; and a set of fat samples, each of the fat samples comprising a different absolute density than absolute densities of the others of the fat samples; and wherein the set contrast samples are arranged within the plurality of compartments such that the set of calcium samples and the set of fat samples surround the set of contrast samples.

In some embodiments, the normalization device further comprises an attachment mechanism disposed on the substrate, the attachment mechanism configured to attach the normalization device to the patient so that the normalization device and the patient can be imaged together such that the region of interest of the patient and the normalization device appear in the medical image taken by the medical imager. In some embodiments of the normalization device, the set of contrast samples comprise four contrast samples; the set of calcium samples comprise four calcium samples; and the set of fat samples comprise four fat samples. In some embodiments of the normalization device, the plurality of samples further comprises at least one of an air sample and a water sample. In some embodiments of the normalization device, the volume of a first contrast sample is different than a volume of a second contrast sample; the volume of a first calcium sample is different than a volume of a second calcium sample; and the volume of a first fat sample is different than a volume of a second fat sample. In some embodiments of the normalization device, a first contrast sample is arranged within the plurality of compartments so as to be adjacent to a second contrast sample, a first calcium sample, and a first fat sample. In some embodiments of the normalization device, a first calcium sample is arranged within the plurality of compartments so as to be adjacent to a second calcium sample, a first contrast sample, and a first fat sample. In some embodiments of the normalization device, a first fat sample is arranged within the plurality of compartments so as to be adjacent to a second fat sample, a first contrast sample, and a first calcium sample. In some embodiments of the normalization device, the set of contrast samples, the set of calcium samples, and the set of fat samples are arranged in a manner that mimics a blood vessel.

In some embodiments, a computer implemented method for generating a risk assessment of atherosclerotic cardiovascular disease (ASCVD) using the normalization device, wherein normalization of the medical imaging improves accuracy of the algorithm-based imaging analysis, comprises: receiving a first set of images of a first arterial bed and a first set of images of a second arterial bed, the second arterial bed being noncontiguous with the first arterial bed, and wherein at least one of the first set of images of the first arterial bed and the first set of images of the second arterial bed are normalized using the normalization device; quantifying ASCVD in the first arterial bed using the first set of images of the first arterial bed; quantifying ASCVD in the second arterial bed using the first set of images of the second arterial bed; and determining a first ASCVD risk score based on the quantified ASCVD in the first arterial bed and the quantified ASCVD in the second arterial bed.

In some embodiments, the method for generating a risk assessment of atherosclerotic cardiovascular disease (ASCVD) further comprises: determining a first weighted assessment of the first arterial bed based on the quantified ASCVD of the first arterial bed and weighted adverse events for the first arterial bed; and determining a second weighted assessment of the second arterial bed based on the quantified ASCVD of the second arterial bed and weighted adverse events for the second arterial bed, wherein determining the first ASCVD risk score further comprises determining the ASCVD risk score based on the first weighted assessment and the second weighted assessment. Further, in some embodiments, the method for generating a risk assessment of atherosclerotic cardiovascular disease (ASCVD) further comprises: receiving a second set of images of the first arterial bed and a second set of images of the second arterial bed, the second set of images of the first arterial bed generated subsequent to generating the first set of image of the first arterial bed, and the second set of images of the second arterial bed generated subsequent to generating the first set of image of the second arterial bed; quantifying ASCVD in the first arterial bed using the second set of images of the first arterial bed; quantifying ASCVD in the second arterial bed using the second set of images of the second arterial bed; and determining a second ASCVD risk score based on the quantified ASCVD in the first arterial bed using the second set of images, and the quantified ASCVD in the second arterial bed using the second set of images. In some embodiments of the method for generating a risk assessment of atherosclerotic cardiovascular disease (ASCVD), determining the second ASCVD risk score is further based on the first ASCVD risk score. In some embodiments of the method for generating a risk assessment of atherosclerotic cardiovascular disease (ASCVD), the first arterial bed includes arteries of one of the aorta, carotid arteries, lower extremity arteries, renal arteries, or cerebral arteries, and wherein the second arterial bed includes arteries of one of the aorta, carotid arteries, lower extremity arteries, renal arteries, or cerebral arteries that are different than the arteries of the first arterial bed.

In some embodiments, a computer implemented method of generating a multi-media medical report for a patient that is based on images generated using the normalization device, wherein the normalization device improves accuracy of the non-invasive medical image analysis, the medical report associated with one or more tests of the patient, comprises: receiving an input of a request to generate the medical report for a patient, the request indicating a format for the medical report; receiving patient information relating to the patient, the patient information associated with the report generation request; determining one or more patient characteristics associated with the patient using the patient information; accessing associations between types of medical reports and patient medical information, wherein the patient medical information includes medical images relating to the patient and test results of one or more test that were performed on the patient, the medical images generated using the normalization device; accessing report content associated with the patient's medical information and the medical report requested, wherein the report content comprises multimedia content that is not related to a specific patient, the multimedia content including a greeting segment in the language of the patient, an explanation segment explaining a type of test conducted, a results segment for conveying test results, and an explanation segment explaining results of the test, and a conclusion segment, wherein at least a portion of the multimedia content includes a test result and one or more medical images that are related to a test performed on the patient; and generating, based at least in part on the format of the medical report, the requested medical report using the patient information and report content.

In some embodiments, a computer implemented method of assessing a risk of coronary artery disease (CAD) for a subject by generating one or more CAD risk scores for the subject based on multi-dimensional information derived from non-invasive medical image analysis using the normalization device, wherein the normalization device improves accuracy of the non-invasive medical image analysis, comprises: accessing, by a computer system, a medical image of a coronary region of a subject, wherein the medical image of the coronary region of the subject is obtained non-invasively; identifying, by the computer system, one or more segments of coronary arteries within the medical image of the coronary region of the subject; determining, by the computer system, for each of the identified one or more segments of coronary arteries one or more plaque parameters, vessel parameters, and clinical parameters, wherein the one or more plaque parameters comprise one or more of plaque volume, plaque composition, plaque attenuation, or plaque location, wherein the one or more vessel parameters comprise one or more of stenosis severity, lumen volume, percentage of coronary blood volume, or percentage of fractional myocardial mass, and wherein the one or more clinical parameters comprise one or more of percentile health condition for age or percentile health condition for gender; generating, by the computer system, for each of the identified one or more segments of coronary arteries a weighted measure of the determined one or more plaque parameters, vessel parameters, and clinical parameters, wherein the weighted measure is generated by applying a correction factor; combining, by the computer system, the generated weighted measure of the determined one or more plaque parameters, vessel parameters, and clinical parameters for each of the identified one or more segments of coronary arteries to generate one or more per-vessel, per-vascular territory, or per-subject CAD risk scores; and generating, by the computer system, a graphical plot of the generated one or more per-vessel, per-vascular territory, or per-subject CAD risk scores for visualizing and quantifying risk of CAD for the subject on one or more of a per-vessel, per-vascular, or per-subject basis, wherein the computer system comprises a computer processor and an electronic storage medium.

In some embodiments, a computer implemented method of tracking efficacy of a medical treatment for a plaque-based disease based on non-invasive medical image analysis using the normalization device, wherein the normalization device improves accuracy of the non-invasive medical image analysis, comprises: accessing, by a computer system, a first set of plaque parameters and a first set of vascular parameters associated with a subject, wherein the first set of plaque parameters and the first set of vascular parameters are derived from a first medical image of the subject comprising one or more regions of plaque, wherein the first medical image of the subject is obtained non-invasively at a first point in time, wherein the first set of plaque parameters comprises one or more of density, location, or volume of one or more regions of plaque from the medical image of the subject at the first point in time, and wherein the first set of vascular parameters comprises vascular remodeling of a vasculature at the first point in time; accessing, by the computer system, a second medical image of the subject, wherein the second medical image of the subject is obtained non-invasively at a second point in time after the subject is treated with a medical treatment, the second point in time being later than the first point in time, wherein the second medical image of the subject comprises the one or more regions of plaque; identifying, by the computer system, the one or more regions of plaque from the second medical image; determining, by the computer system, a second set of plaque parameters and a second of vascular parameters associated with the subject by analyzing the one or more regions of plaque from the second medical image, wherein the second set of plaque parameters comprises one or more of density, location, or volume of the one or more regions of plaque from the medical image of the subject at the second point in time, and wherein the second set of vascular parameters comprises vascular remodeling of the vasculature at the second point in time; analyzing, by the computer system, one or more changes between the first set of plaque parameters and the second set of plaque parameters; analyzing, by the computer system, one or more changes between the first set of vascular parameters and the second set of vascular parameters; tracking, by the computer system, progression of the plaque-based disease based on one or more of the analyzed one or more changes between the first set of plaque parameters and the second set of plaque parameters or the analyzed one or more changes between the first set of vascular parameters and the second set of vascular parameters; and determining, by the computer system, efficacy of the medical treatment based on the tracked progression of the plaque-based disease, wherein the computer system comprises a computer processor and an electronic storage medium.

In some embodiments, a computer implemented method of determining continued personalized treatment for a subject with atherosclerotic cardiovascular disease (ASCVD) risk based on coronary CT angiography (CCTA) analysis using one or more quantitative imaging algorithms using the normalization device, wherein the normalization device improves accuracy of the one or more quantitative imaging algorithms, comprises: assessing, by a computer system, a baseline ASCVD risk of the subject by analyzing baseline CCTA analysis results using one or more quantitative imaging algorithms, the baseline CCTA analysis results based at least in part on one or more atherosclerosis parameters or perilesional tissue parameters, the one or more atherosclerosis parameters comprising one or more of presence, locality, extent, severity, or type of atherosclerosis; categorizing, by the computer system, the baseline ASCVD risk of the subject into one or more predetermined categories of ASCVD risk; determining, by the computer system, an initial personalized proposed treatment for the subject based at least in part on the categorized baseline ASCVD risk of the subject, the initial personalized proposed treatment for the subject comprising one or more of medical therapy, lifestyle therapy, or interventional therapy; assessing, by the computer system, subject response to the determined initial personalized proposed treatment by subsequent CCTA analysis using one or more quantitative imaging algorithms and comparing the subsequent CCTA analysis results to the baseline CCTA analysis results, the subsequent CCTA analysis performed after applying the determined initial personalized proposed treatment to the subject, wherein the subject response is assessed based on one or more of progression, stabilization, or regression of ASCVD; and determining, by the computer system, a continued personalized proposed treatment for the subject based at least in part on the assessed subject response, the continued personalized proposed treatment comprising a higher tiered approach than the initial personalized proposed treatment when the assessed subject response comprises progression of ASCVD, the continued personalized proposed treatment comprising one or more of medical therapy, lifestyle therapy, or interventional therapy, wherein the computer system comprises a computer processor and an electronic storage medium.

In some embodiments, a computer implemented method of determining volumetric stenosis severity in the presence of atherosclerosis based on non-invasive medical image analysis for risk assessment of coronary artery disease (CAD) for a subject using the normalization device, wherein the normalization device improves accuracy of the non-invasive medical image analysis, comprises: accessing, by a computer system, a medical image of a coronary region of a subject, wherein the medical image of the coronary region of the subject is obtained non-invasively; identifying, by the computer system, one or more segments of coronary arteries and one or more regions of plaque within the medical image of the coronary region of the subject; determining, by the computer system, for the identified one or more segments of coronary arteries a lumen wall boundary in the presence of the one or more regions of plaque and a hypothetical normal artery boundary in case the one or more regions of plaque were not present, wherein the determined lumen wall boundary and the hypothetical normal artery boundary comprise tapering of the one or more segments of coronary arteries, and wherein the determined lumen wall boundary further comprises a boundary of the one or more regions of plaque; quantifying, by the computer system, for the identified one or more segments of coronary arteries a lumen volume based on the determined lumen wall boundary, wherein the quantified lumen volume takes into account the tapering of the one or more segments of coronary arteries and the boundary of the one or more regions of plaque; quantifying, by the computer system, for the identified one or more segments of coronary arteries a hypothetical normal vessel volume based on the determined hypothetical normal artery boundary, wherein the quantified hypothetical normal vessel volume takes into account the tapering of the one or more segments of coronary arteries; determining, by the computer system, for the identified one or more segments of coronary arteries volumetric stenosis by determining a percentage or ratio of the quantified lumen volume compared to the hypothetical normal vessel volume; and determining, by the computer system, a risk of CAD for the subject based at least in part on the determined volumetric stenosis for the identified one or more segments of coronary arteries, wherein the computer system comprises a computer processor and an electronic storage medium.

In some embodiments, a computer implemented method of quantifying ischemia for a subject based on non-invasive medical image analysis using the normalization device, wherein the normalization device improves accuracy of the non-invasive medical image analysis, comprises: accessing, by a computer system, a medical image of a coronary region of a subject, wherein the medical image of the coronary region of the subject is obtained non-invasively; identifying, by the computer system, one or more segments of coronary arteries and one or more regions of plaque within the medical image of the coronary region of the subject; quantifying, by the computer system, a proximal volume of a proximal section and a distal volume of a distal section along the one or more segments of coronary arteries, wherein the proximal section does not comprise the one or more regions of plaque, and wherein the distal section comprises at least one of the one or more regions of plaque; accessing, by the computer system, an assumed velocity of blood flow at the proximal section; quantifying, by the computer system, a velocity of blood flow at the distal section based at least in part on the assumed velocity of blood flow at the proximal section, the quantified proximal volume of the proximal section, and the distal volume of the distal section along the one or more segments of coronary arteries; determining, by the computer system, a velocity time integral of blood flow at the distal section based at least in part on the quantified velocity of blood flow at the distal section; and quantifying, by the computer system, ischemia along the one or more segments of coronary arteries based at least in part on the determined velocity time integral of blood flow at the distal section, wherein the computer system comprises a computer processor and an electronic storage medium.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

The disclosed aspects will hereinafter be described in conjunction with the accompanying drawings, which are incorporated in and constitute a part of this specification, and are provided to illustrate and provide a further understanding of example embodiments, and not to limit the disclosed aspects. In the drawings, like designations denote like elements unless otherwise stated.

FIG. 4A is a flowchart illustrating an overview of an example embodiment(s) of a method for prognosis of a cardiovascular event based on medical image analysis.

FIGS. 5B-5I illustrate example embodiment(s) of a patient-specific medical report generated based on medical image analysis.

FIG. 7F illustrates the lumen snap tool button (left) in the vessel snap tool button (right) on a user interface which can be used to activate these tools.

FIG. 7G illustrates an example of a panel that can be displayed on the user interface while using the lumen snap tool in the vessel snap tool.

FIG. 7U is an example of a view that can be displayed when extending the centerline of a vessel. FIG. 7V illustrates an example of a view that can be displayed when saving or canceling centerline edits. FIG. 7W is an example of a CMPR view that can be displayed when editing the vessel centerline.

FIGS. 7Z and 7AA illustrates examples of panels that can be displayed while using the exclude tool, which allows a portion of the vessel to be excluded from the analysis, for example, due to image aberrations. A row FIGS. 7AB and 7AC illustrate examples of additional panels that can be displayed while using the exclude tool.

FIG. 7AB illustrates a panel that can be used to add a new exclusion. FIG. 7AC illustrates a panel that can be used to add a reason for the exclusion.

FIGS. 7AD, 7AE, 7AF, and 7AG illustrate examples of panels that can be displayed while using the distance tool, which can be used to measure the distance between two points on an image. For example, FIG. 7AD illustrates the distance tool being used to measure a distance on an SMPR view. FIG. 7AE illustrates the distance tool being used to measure a distance on an CMPR view. FIG. 7AF illustrates the distance will be used to measure a distance on a cross-sectional view of the vessel. FIG. 7AG illustrates the distance tool being used to measure a distance on an axial view.

FIG. 7AH illustrates a "vessel statistics" portion (button) of a panel which can be selected to display the vessel statistics tab.

FIG. 7AI illustrates the vessel statistics tab.

FIG. 7AJ illustrates functionality on the vessel statistics tab that allows a user to click through the details of multiple lesions.

FIG. 7AK further illustrates an example of the vessel panel which the user can use to toggle between vessels.

FIG. 11A illustrates a CT image reconstructed using filtered back projection, while FIG. 11B illustrates the same CT image reconstructed using iterative reconstruction.

FIG. 11C illustrates a CT image reconstructed by using iterative reconstruction, while FIG. 11D illustrates the same image reconstructed using machine learning.

FIG. 20C is a block diagram depicting one or more features of an example embodiment(s) for determining ischemia by weighting different factors differently.

FIG. 22A illustrates an example(s) of tracking the attenuation of plaque for analysis and/or treatment of coronary artery and/or other vascular disease.

FIG. 23J is a flowchart illustrating an overview of an example embodiment(s) of a method for determining treatments for reducing cardiovascular risk and/or events.

FIG. 24A is a schematic illustration of an artery.

FIG. 24B illustrates an embodiment(s) of determining percentage stenosis and remodeling index.

FIG. 24C is a schematic illustration of an artery.

FIG. 24D is a schematic illustration of an artery with long atherosclerotic regions of plaque.

FIG. 24E is a example illustrating how an inaccurately estimated R0 can significantly affect the resulting percent stenosis and/or remodeling index.

FIG. 24F is a schematic illustration of lumen diameter v. outer wall diameter.

FIG. 24G is a schematic illustration of calculation of an estimated reference diameter(s) along a vessel where plaque is present.

FIG. 24H is a schematic illustration of an embodiment(s) of determining volumetric stenosis.

FIG. 24I is a schematic illustration of an embodiment(s) of determining volumetric stenosis.

FIG. 24J is a schematic illustration of an embodiment(s) of determining volumetric remodeling;

FIG. 24K illustrates an embodiment(s) of coronary vessel blood volume assessment based on total coronary volume.

Figure 24A:
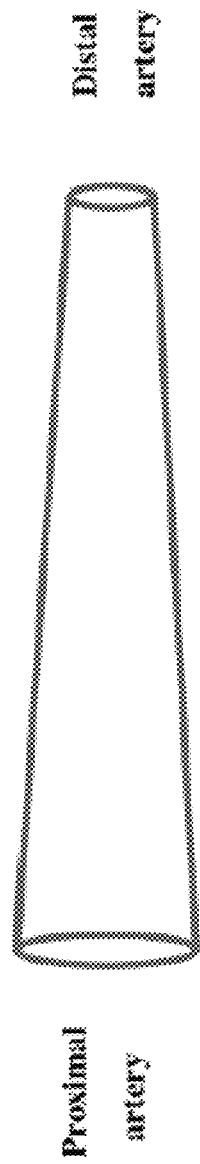
Figure 24B:
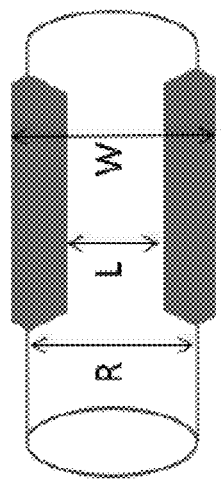
Figure 24C:
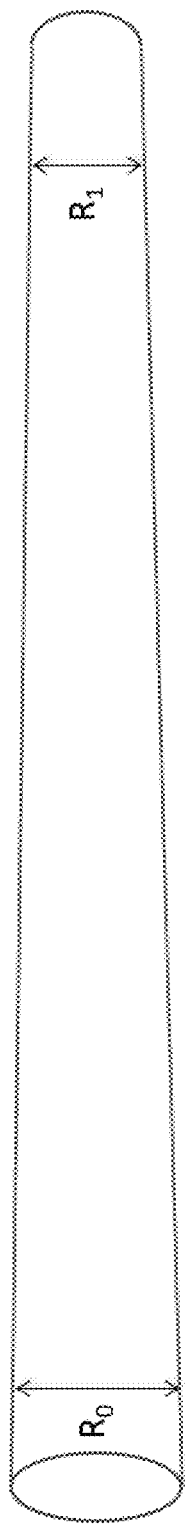
Figure 24D:
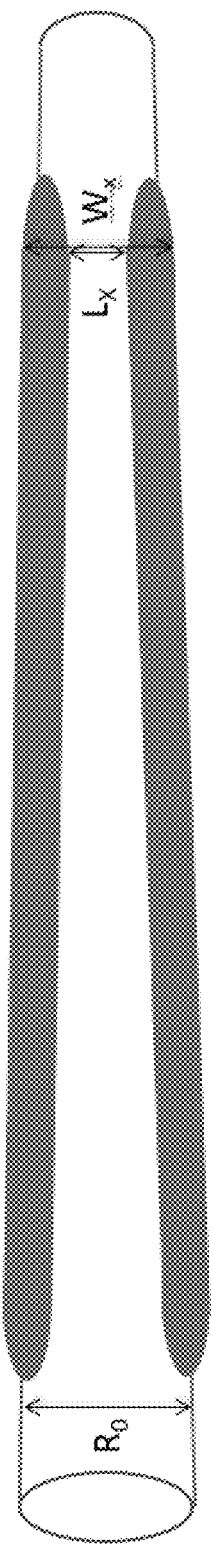
Figure 24F:
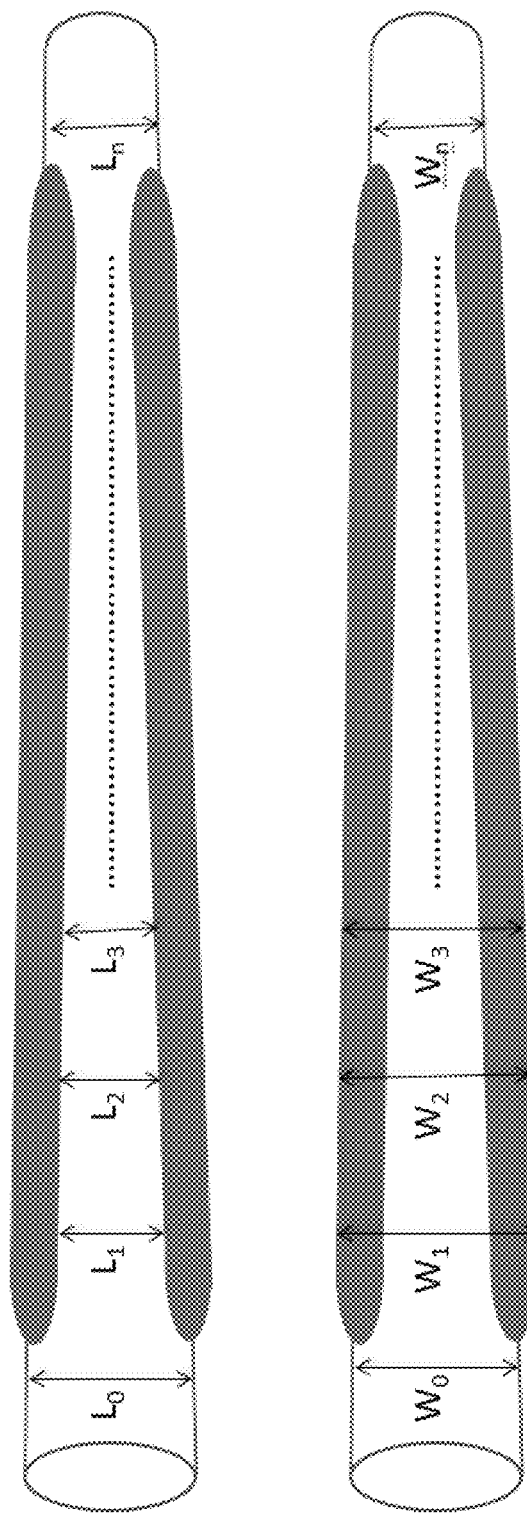
Figure 24G:
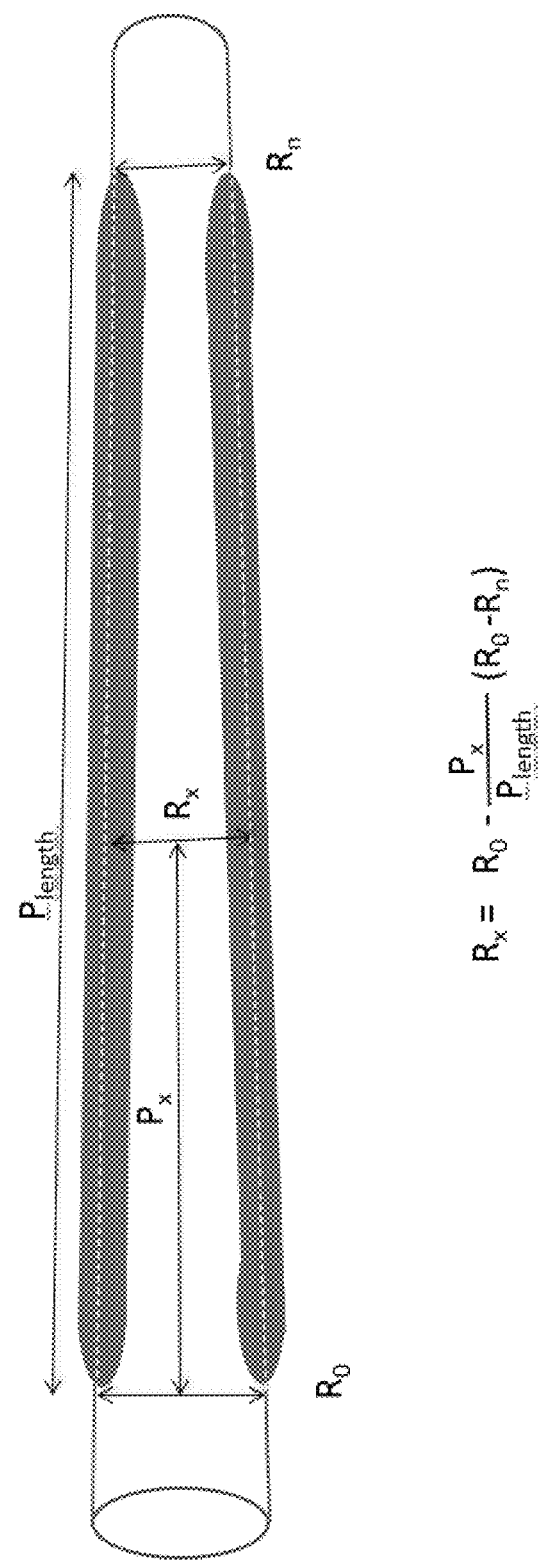
Figure 24H:
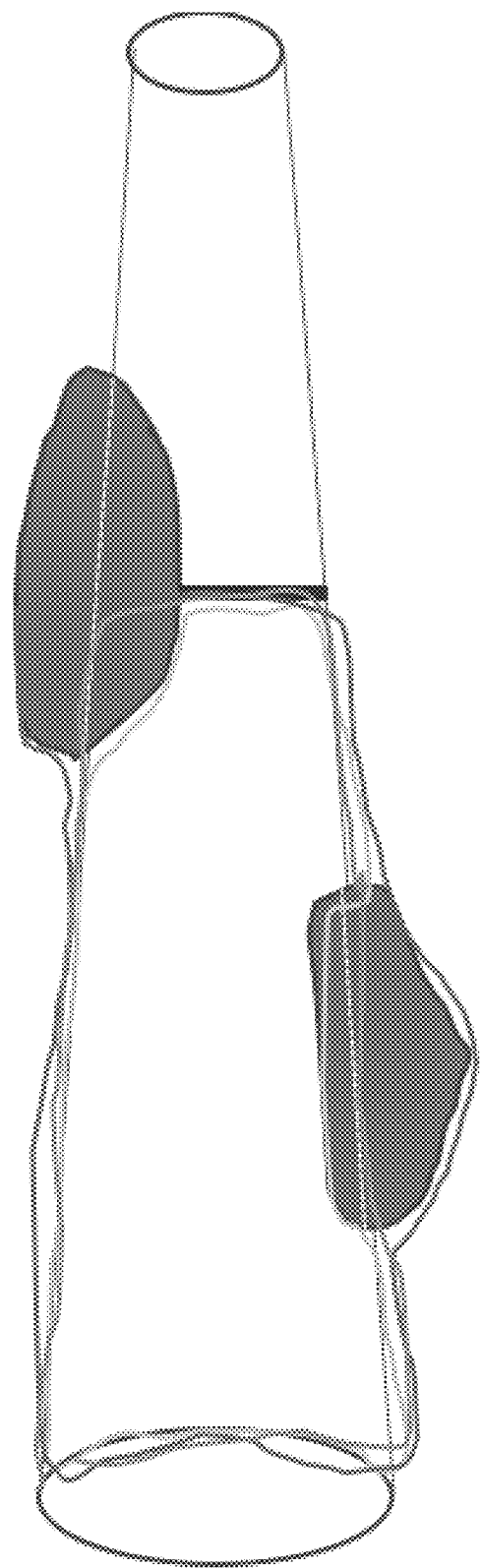
Figure 24I:
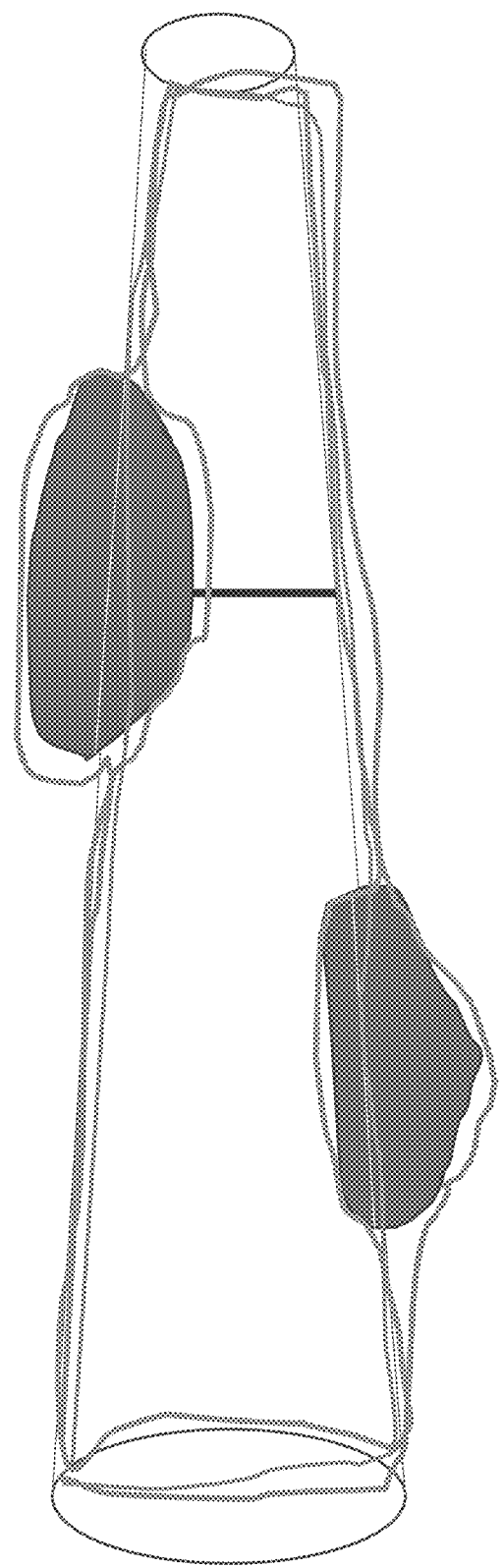
Figure 24J:
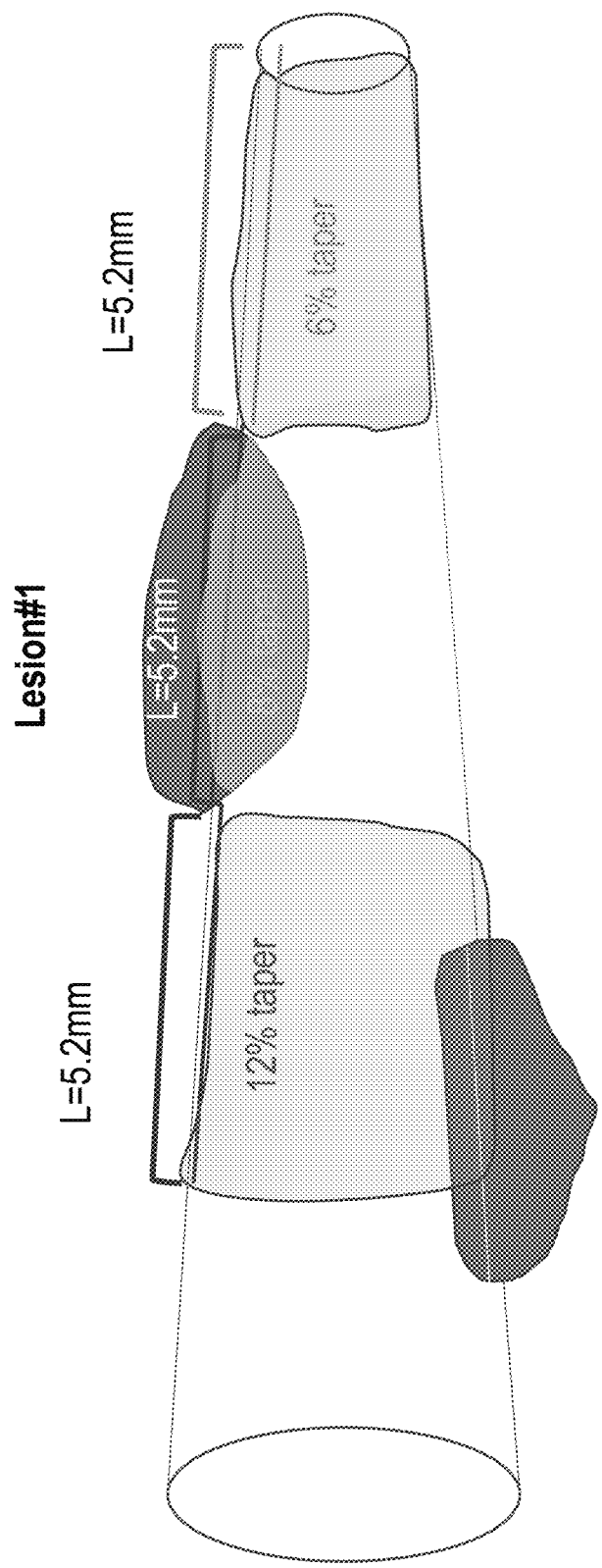
Figure 24K:
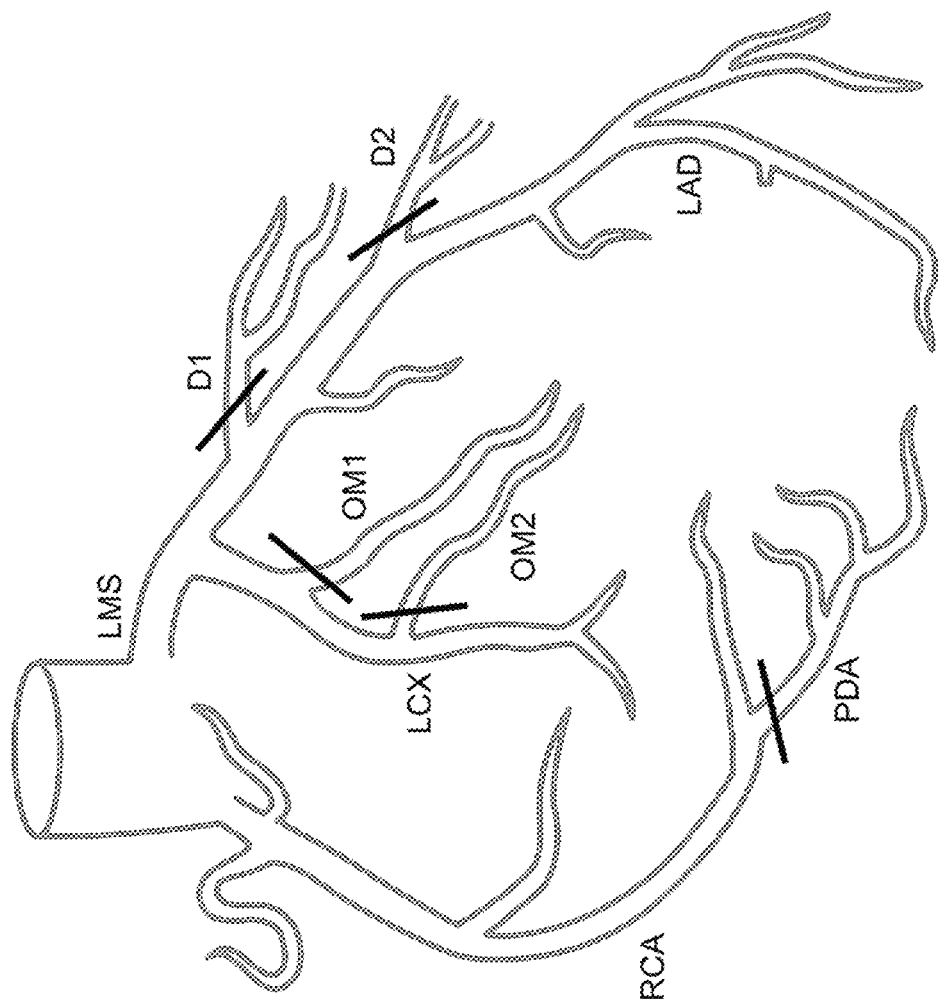
Figure 24L:
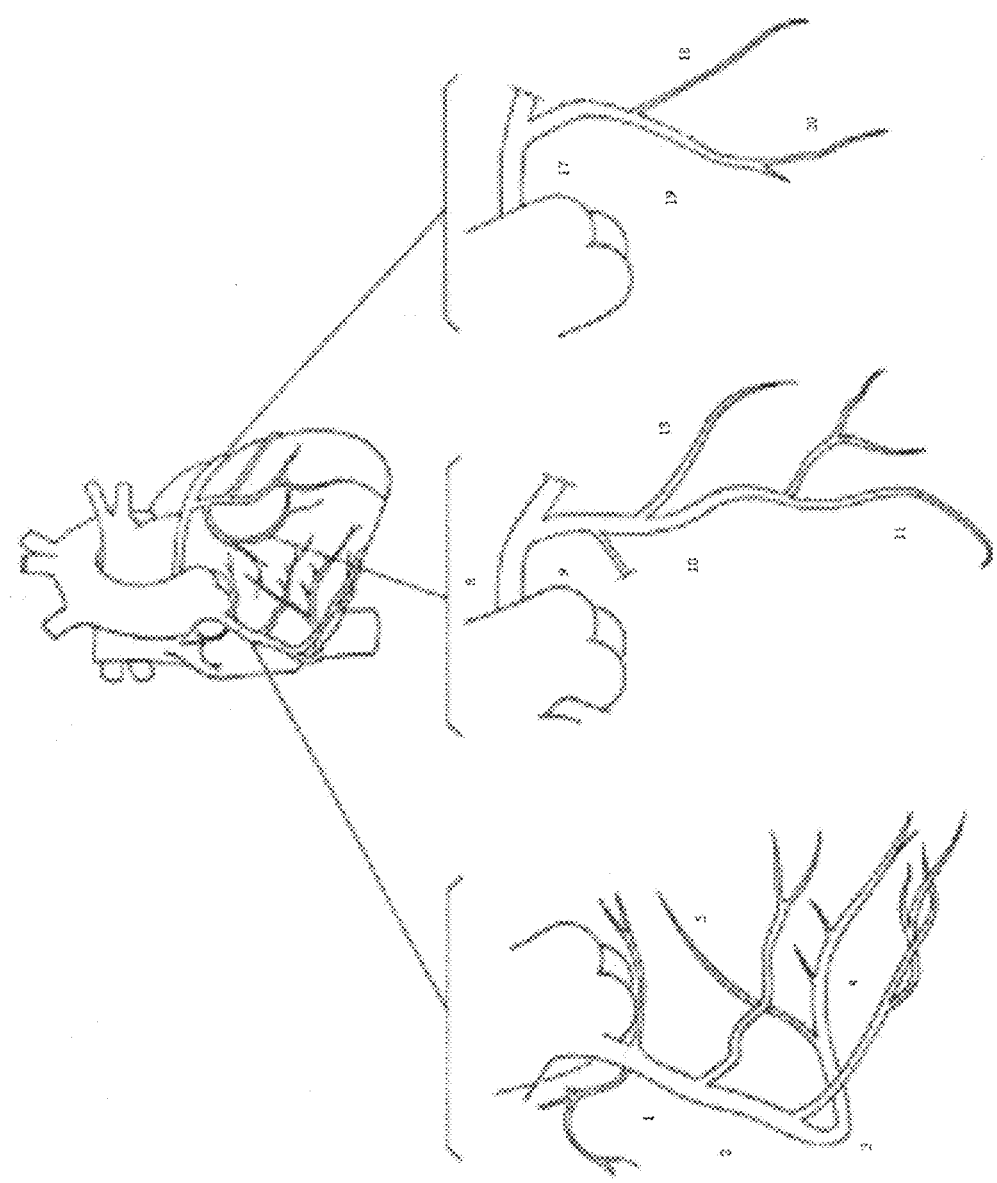

FIG. 24L illustrates an embodiment(s) of coronary vessel blood volume assessment based on territory or artery-specific volume.

Figure 24M:
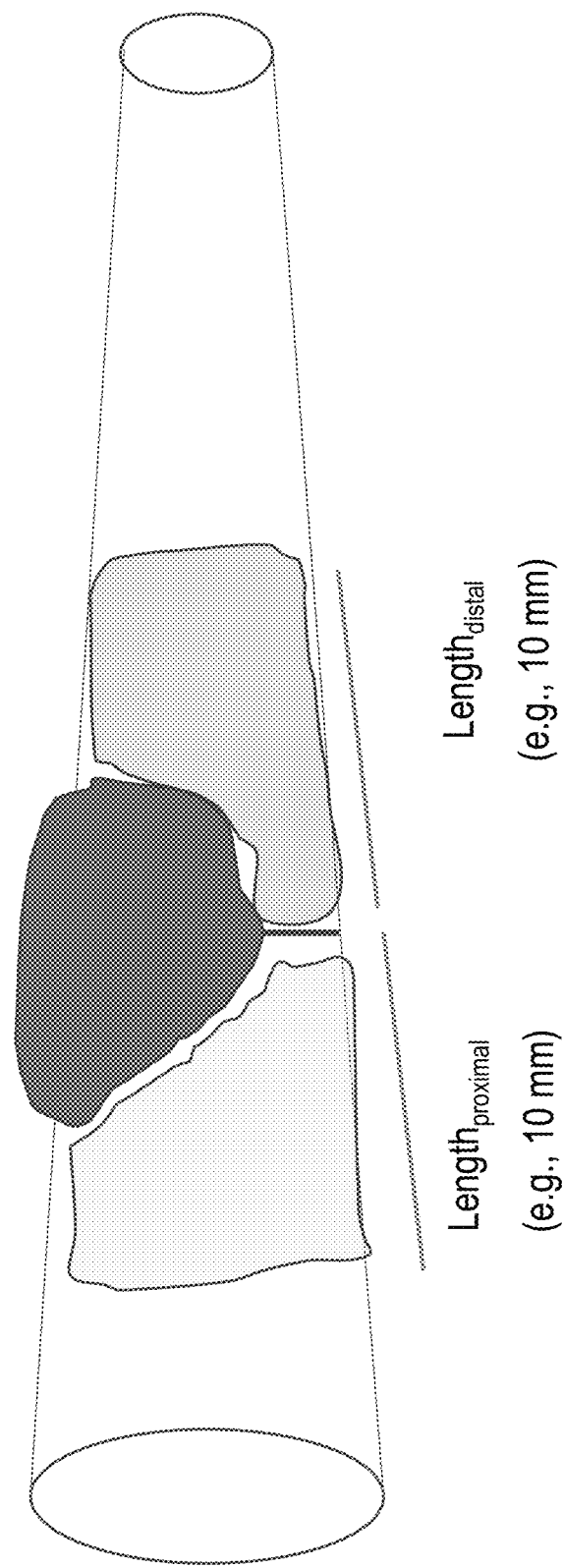

FIG. 24M illustrates an embodiment(s) of coronary vessel blood volume assessment based on within-artery % fractional blood volume.

Figure 24N:
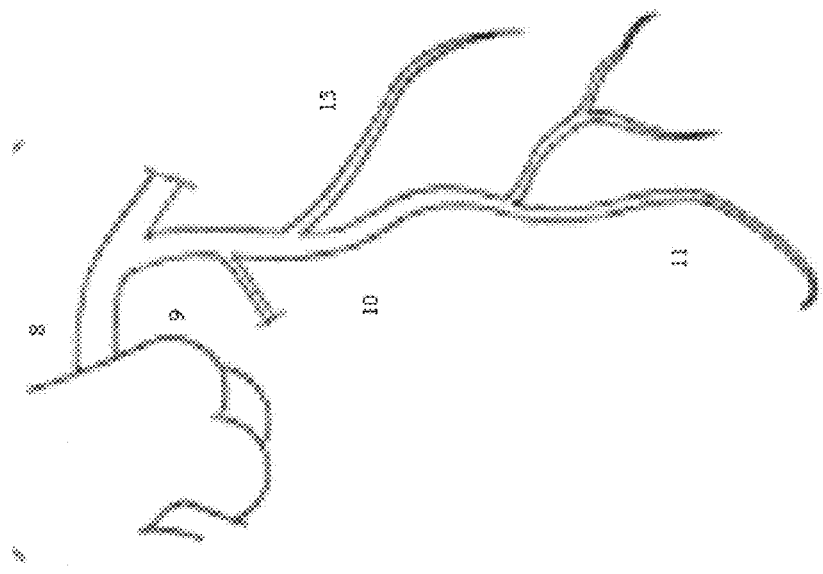
Figure 240:
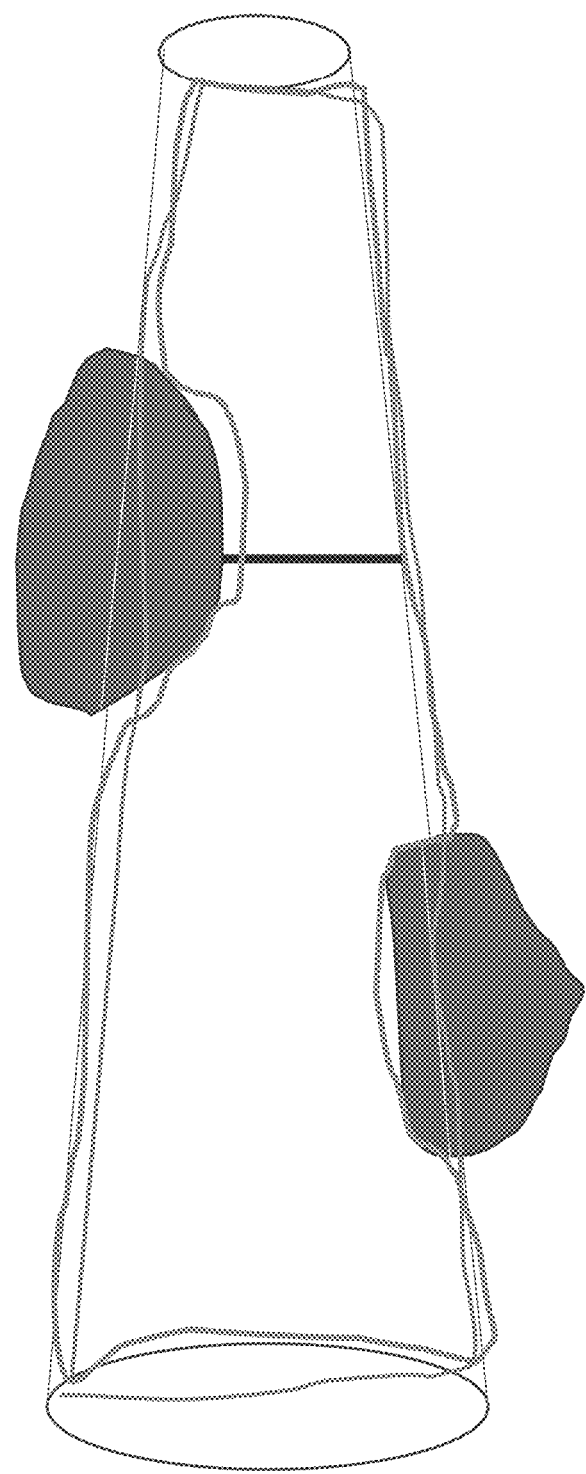

FIG. 24N illustrates an embodiment(s) of assessment of coronary vessel blood volume.

FIG. 24O illustrates an embodiment(s) of assessment of % vessel volume stenosis as a measure of ischemia.

Figure 24P:
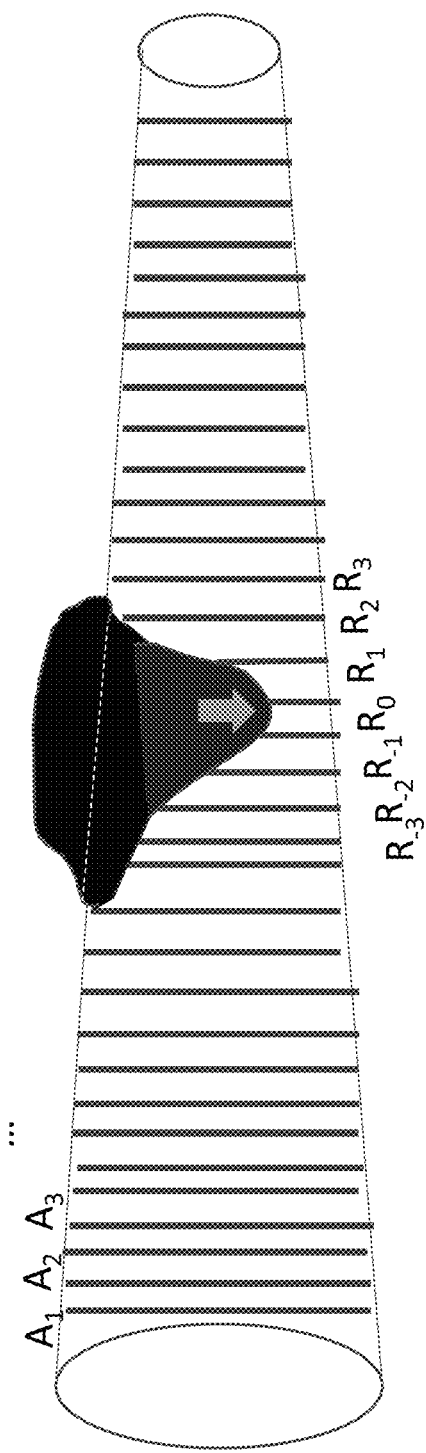

FIG. 24P illustrates an embodiment(s) of assessment of pressure difference across a lesion as a measure of ischemia.

Figure 24Q:
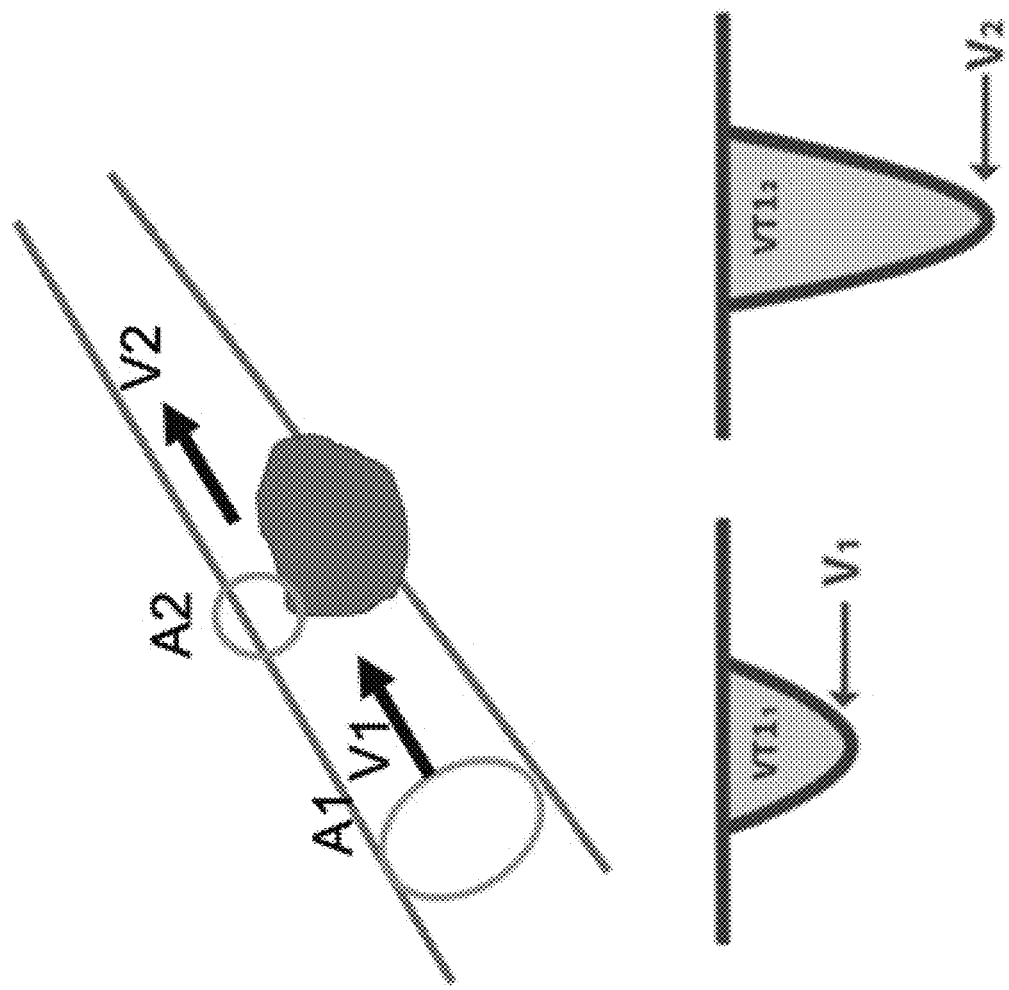

FIG. 24Q illustrates an embodiment(s) of application of the continuity equation to coronary arteries.

Figure 24R:
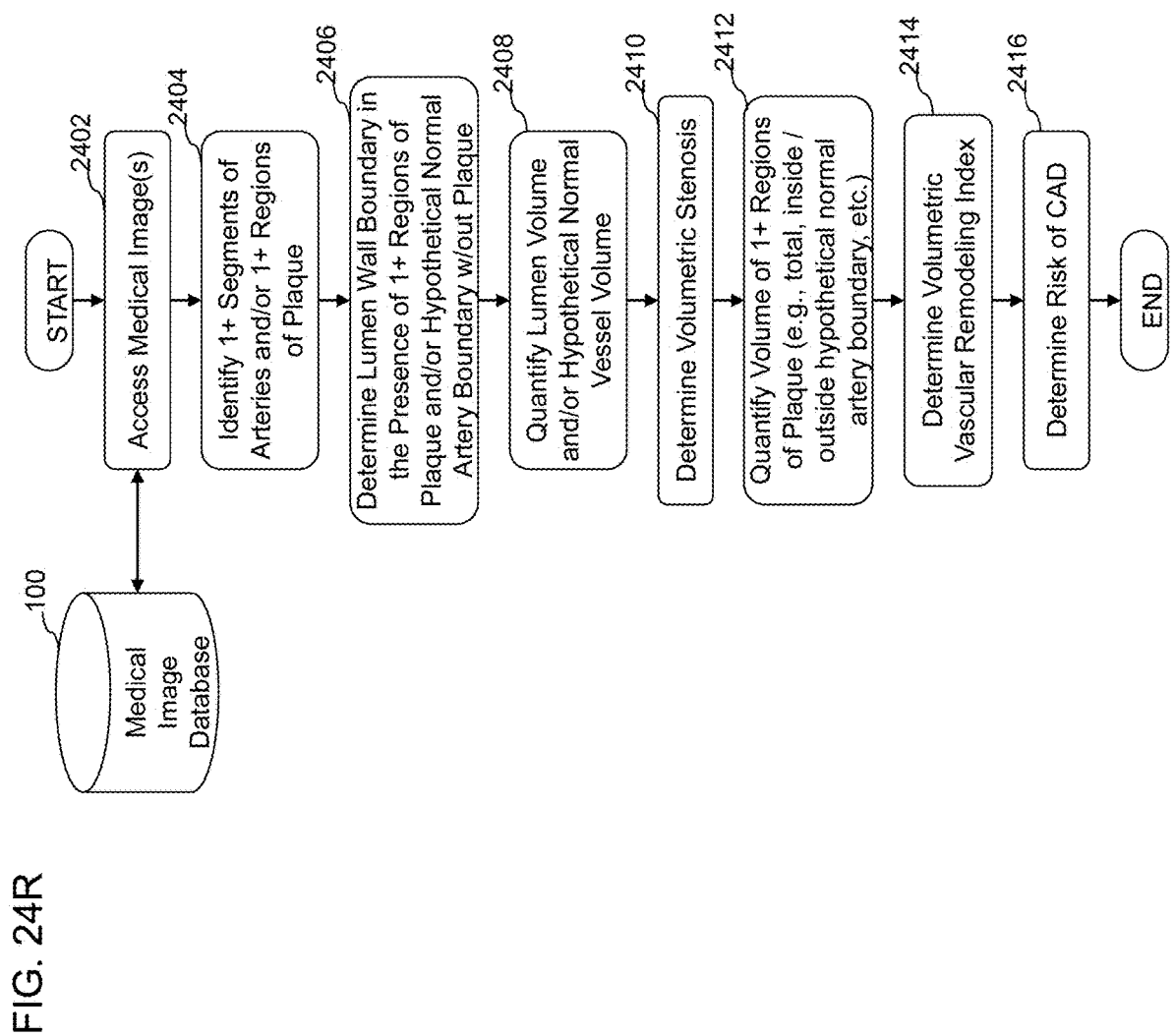

FIG. 24R is a flowchart illustrating an overview of an example embodiment(s) of a method for determining volumetric stenosis and/or volumetric vascular remodeling.

FIG. 24S is a flowchart illustrating an overview of an example embodiment(s) of a method for determining ischemia.

DETAILED DESCRIPTION

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Introduction

Disclosed herein are systems, methods, and devices for medical image analysis, diagnosis, risk stratification, decision making and/or disease tracking. Coronary heart disease affects over 17.6 million Americans. The current trend in treating cardiovascular health issues is generally two-fold. First, physicians generally review a patient's cardiovascular health from a macro level, for example, by analyzing the biochemistry or blood content or biomarkers of a patient to determine whether there are high levels of cholesterol elements in the bloodstream of a patient. In response to high levels of cholesterol, some physicians will prescribe one or more drugs, such as statins, as part of a treatment plan in order to decrease what is perceived as high levels of cholesterol elements in the bloodstream of the patient.

The second general trend for currently treating cardiovascular health issues involves physicians evaluating a patient's cardiovascular health through the use of angiography to identify large blockages in various arteries of a patient. In response to finding large blockages in various arteries, physicians in some cases will perform an angioplasty procedure wherein a balloon catheter is guided to the point of narrowing in the vessel. After properly positioned, the balloon is inflated to compress or flatten the plaque or fatty matter into the artery wall and/or to stretch the artery open to increase the flow of blood through the vessel and/or to the heart. In some cases, the balloon is used to position and expand a stent within the vessel to compress the plaque and/or maintain the opening of the vessel to allow more blood to flow. About 500,000 heart stent procedures are performed each year in the United States.

However, a recent federally funded $100 million study calls into question whether the current trends in treating cardiovascular disease are the most effective treatment for all types of patients. The recent study involved over 5,000 patients with moderate to severe stable heart disease from 320 sites in 37 countries and provided new evidence showing that stents and bypass surgical procedures are likely no more effective than drugs combined with lifestyle changes for people with stable heart disease. Accordingly, it may be more advantageous for patients with stable heart disease to forgo invasive surgical procedures, such as angioplasty and/or heart bypass, and instead be prescribed heart medicines, such as statins, and certain lifestyle changes, such as regular exercise. This new treatment regimen could affect thousands of patients worldwide. Of the estimated 500,000 heart stent procedures performed annually in the United States, it is estimated that a fifth of those are for people with stable heart disease. It is further estimated that 25% of the estimated 100,000 people with stable heart disease, or roughly 23,000 people, are individuals that do not experience any chest pain. Accordingly, over 20,000 patients annually could potentially forgo invasive surgical procedures or the complications resulting from such procedures.

To determine whether a patient should forego invasive surgical procedures and opt instead for a drug regimen and/or to generate a more effective treatment plan, it can be important to more fully understand the cardiovascular disease of a patient. Specifically, it can be advantageous to better understand the arterial vessel health of a patient. For example, it is helpful to understand whether plaque build-up in a patient is mostly fatty matter build-up or mostly calcified matter build-up, because the former situation may warrant treatment with heart medicines, such as statins, whereas in the latter situation a patient should be subject to further periodic monitoring without prescribing heart medicine or implanting any stents. However, if the plaque build-up is significant enough to cause severe stenosis or narrowing of the arterial vessel such that blood flow to heart muscle might be blocked, then an invasive angioplasty procedure to implant a stent may likely be required because heart attack or sudden cardiac death (SCD) could occur in such patients without the implantation of a stent to enlarge the vessel opening. Sudden cardiac death is one of the largest causes of natural death in the United States, accounting for approximately 325,000 adult deaths per year and responsible for nearly half of all deaths from cardiovascular disease. For males, SCD is twice as common as compared to females. In general, SCD strikes people in the mid-30 to mid-40 age range. In over 50% of cases, sudden cardiac arrest occurs with no warning signs.

With respect to the millions suffering from heart disease, there is a need to better understand the overall health of the artery vessels within a patient beyond just knowing the blood chemistry or content of the blood flowing through such artery vessels. For example, in some embodiments of systems, devices, and methods disclosed herein, arteries with "good" or stable plaque or plaque comprising hardened calcified content are considered non-life threatening to patients whereas arteries containing "bad" or unstable plaque or plaque comprising fatty material are considered more life threatening because such bad plaque may rupture within arteries thereby releasing such fatty material into the arteries. Such a fatty material release in the blood stream can cause inflammation that may result in a blood clot. A blood clot within an artery can prevent blood from traveling to heart muscle thereby causing a heart attack or other cardiac event. Further, in some instances, it is generally more difficult for blood to flow through fatty plaque buildup than it is for blood to flow through calcified plaque build-up. Therefore, there is a need for better understanding and analysis of the arterial vessel walls of a patient.

Further, while blood tests and drug treatment regimens are helpful in reducing cardiovascular health issues and mitigating against cardiovascular events (for example, heart attacks), such treatment methodologies are not complete or perfect in that such treatments can misidentify and/or fail to pinpoint or diagnose significant cardiovascular risk areas. For example, the mere analysis of the blood chemistry of a patient will not likely identify that a patient has artery vessels having significant amounts of fatty deposit material bad plaque buildup along a vessel wall. Similarly, an angiogram, while helpful in identifying areas of stenosis or vessel narrowing, may not be able to clearly identify areas of the artery vessel wall where there is significant buildup of bad plaque. Such areas of buildup of bad plaque within an artery vessel wall can be indicators of a patient at high risk of suffering a cardiovascular event, such as a heart attack. In certain circumstances, areas where there exist areas of bad plaque can lead to a rupture wherein there is a release of the fatty materials into the bloodstream of the artery, which in turn can cause a clot to develop in the artery. A blood clot in the artery can cause a stoppage of blood flow to the heart tissue, which can result in a heart attack. Accordingly, there is a need for new technology for analyzing artery vessel walls and/or identifying areas within artery vessel walls that comprise a buildup of plaque whether it be bad or otherwise.

Various systems, methods, and devices disclosed herein are directed to embodiments for addressing the foregoing issues. In particular, various embodiments described herein relate to systems, methods, and devices for medical image analysis, diagnosis, risk stratification, decision making and/or disease tracking. In some embodiments, the systems, devices, and methods described herein are configured to utilize non-invasive medical imaging technologies, such as a CT image for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms. In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

As will be discussed in further detail, the systems, devices, and methods described herein allow for automatic and/or dynamic quantified analysis of various parameters relating to plaque, cardiovascular arteries, and/or other structures. More specifically, in some embodiments described herein, a medical image of a patient, such as a coronary CT image, can be taken at a medical facility. Rather than having a physician eyeball or make a general assessment of the patient, the medical image is transmitted to a backend main server in some embodiments that is configured to conduct one or more analyses thereof in a reproducible manner. As such, in some embodiments, the systems, methods, and devices described herein can provide a quantified measurement of one or more features of a coronary CT image using automated and/or dynamic processes. For example, in some embodiments, the main server system can be configured to identify one or more vessels, plaque, and/or fat from a medical image. Based on the identified features, in some embodiments, the system can be configured to generate one or more quantified measurements from a raw medical image, such as for example radiodensity of one or more regions of plaque, identification of stable plaque and/or unstable plaque, volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like. Based on the identified features and/or quantified measurements, in some embodiments, the system can be configured to generate a risk assessment and/or track the progression of a plaque-based disease or condition, such as for example atherosclerosis, stenosis, and/or ischemia, using raw medical images. Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images. In some embodiments, one or more of the processes can be automated using an AI and/or ML algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures.

As such, in some embodiments, the systems, devices, and methods described herein are able to provide physicians and/or patients specific quantified and/or measured data relating to a patient's plaque that do not exist today. For example, in some embodiments, the system can provide a specific numerical value for the volume of stable and/or unstable plaque, the ratio thereof against the total vessel volume, percentage of stenosis, and/or the like, using for example radiodensity values of pixels and/or regions within a medical image. In some embodiments, such detailed level of quantified plaque parameters from image processing and downstream analytical results can provide more accurate and useful tools for assessing the health and/or risk of patients in completely novel ways.

General Overview

Figure 1:
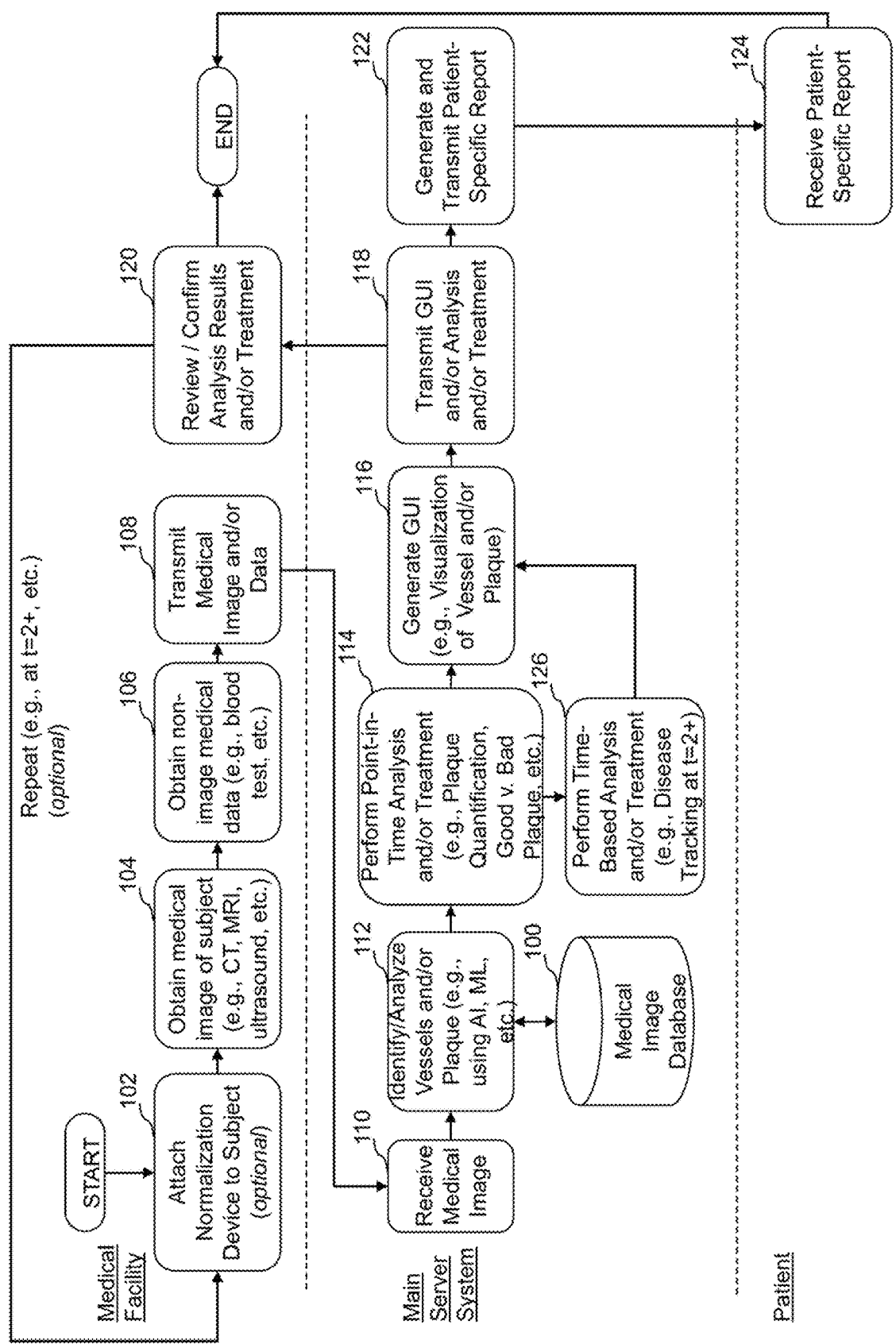
FIG. 1 is a flowchart illustrating an overview of an example embodiment(s) of a method for medical image analysis, visualization, risk assessment, disease tracking, treatment generation, and/or patient report generation.

In some embodiments, the systems, devices, and methods described herein are configured to automatically and/or dynamically perform medical image analysis, diagnosis, risk stratification, decision making and/or disease tracking. FIG. 1 is a flowchart illustrating an overview of an example embodiment(s) of a method for medical image analysis, visualization, risk assessment, disease tracking, treatment generation, and/or patient report generation. As illustrated in FIG. 1, in some embodiments, the system is configured to access and/or analyze one or more medical images of a subject, such as for example a medical image of a coronary region of a subject or patient.

In some embodiments, before obtaining the medical image, a normalization device is attached to the subject and/or is placed within a field of view of a medical imaging scanner at block 102. For example, in some embodiments, the normalization device can comprise one or more compartments comprising one or more materials, such as water, calcium, and/or the like. Additional detail regarding the normalization device is provided below. Medical imaging scanners may produce images with different scalable radiodensities for the same object. This, for example, can depend not only on the type of medical imaging scanner or equipment used but also on the scan parameters and/or environment of the particular day and/or time when the scan was taken. As a result, even if two different scans were taken of the same subject, the brightness and/or darkness of the resulting medical image may be different, which can result in less than accurate analysis results processed from that image. To account for such differences, in some embodiments, a normalization device comprising one or more known elements is scanned together with the subject, and the resulting image of the one or more known elements can be used as a basis for translating, converting, and/or normalizing the resulting image. As such, in some embodiments, a normalization device is attached to the subject and/or placed within the field of view of a medical imaging scan at a medical facility.

In some embodiments, at block 104, the medical facility then obtains one or more medical images of the subject. For example, the medical image can be of the coronary region of the subject or patient. In some embodiments, the systems disclosed herein can be configured to take in CT data from the image domain or the projection domain as raw scanned data or any other medical data, such as but not limited to: x-ray; Dual-Energy Computed Tomography (DECT), Spectral CT, photon-counting detector CT, ultrasound, such as echocardiography or intravascular ultrasound (IVUS); magnetic resonance (MR) imaging; optical coherence tomography (OCT); nuclear medicine imaging, including positron-emission tomography (PET) and single photon emission computed tomography (SPECT); near-field infrared spectroscopy (NIRS); and/or the like. As used herein, the term CT image data or CT scanned data can be substituted with any of the foregoing medical scanning modalities and process such data through an artificial intelligence (AI) algorithm system in order to generate processed CT image data. In some embodiments, the data from these imaging modalities enables determination of cardiovascular phenotype, and can include the image domain data, the projection domain data, and/or a combination of both.

In some embodiments, at block 106, the medical facility can also obtain non-imaging data from the subject. For example, this can include blood tests, biomarkers, panomics and/or the like. In some embodiments, at block 108, the medical facility can transmit the one or more medical images and/or other non-imaging data at block 108 to a main server system. In some embodiments, the main server system can be configured to receive and/or otherwise access the medical image and/or other non-imaging data at block 110.

In some embodiments, at block 112, the system can be configured to automatically and/or dynamically analyze the one or more medical images which can be stored and/or accessed from a medical image database 100. For example, in some embodiments, the system can be configured to take in raw CT image data and apply an artificial intelligence (AI) algorithm, machine learning (ML) algorithm, and/or other physics-based algorithm to the raw CT data in order to identify, measure, and/or analyze various aspects of the identified arteries within the CT data. In some embodiments, the inputting of the raw medical image data involves uploading the raw medical image data into cloud-based data repository system. In some embodiments, the processing of the medical image data involves processing the data in a cloud-based computing system using an AI and/or ML algorithm. In some embodiments, the system can be configured to analyze the raw CT data in about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 30 minutes, about 35 minutes, about 40 minutes, about 45 minutes, about 50 minutes, about 55 minutes, about 60 minutes, and/or within a range defined by two of the aforementioned values.

In some embodiments, the system can be configured to utilize a vessel identification algorithm to identify and/or analyze one or more vessels within the medical image. In some embodiments, the system can be configured to utilize a coronary artery identification algorithm to identify and/or analyze one or more coronary arteries within the medical image. In some embodiments, the system can be configured to utilize a plaque identification algorithm to identify and/or analyze one or more regions of plaque within the medical image. In some embodiments, the vessel identification algorithm, coronary artery identification algorithm, and/or plaque identification algorithm comprises an AI and/or ML algorithm. For example, in some embodiments, the vessel identification algorithm, coronary artery identification algorithm, and/or plaque identification algorithm can be trained on a plurality of medical images wherein one or more vessels, coronary arteries, and/or regions of plaque are pre-identified. Based on such training, for example by use of a Convolutional Neural Network in some embodiments, the system can be configured to automatically and/or dynamically identify from raw medical images the presence and/or parameters of vessels, coronary arteries, and/or plaque.

As such, in some embodiments, the processing of the medical image or raw CT scan data can comprise analysis of the medical image or CT data in order to determine and/or identify the existence and/or nonexistence of certain artery vessels in a patient. As a natural occurring phenomenon, certain arteries may be present in certain patients whereas such certain arteries may not exist in other patients.

In some embodiments, at block 112, the system can be further configured to analyze the identified vessels, coronary arteries, and/or plaque, for example using an AI and/or ML algorithm. In particular, in some embodiments, the system can be configured to determine one or more vascular morphology parameters, such as for example arterial remodeling, curvature, volume, width, diameter, length, and/or the like. In some embodiments, the system can be configured to determine one or more plaque parameters, such as for example volume, surface area, geometry, radiodensity, ratio or function of volume to surface area, heterogeneity index, and/or the like of one or more regions of plaque shown within the medical image. "Radiodensity" as used herein is a broad term that refers to the relative inability of electromagnetic relation (e.g., X-rays) to pass through a material. In reference to an image, radiodensity values refer to values indicting a density in image data (e.g., film, print, or in an electronic format) where the radiodensity values in the image corresponds to the density of material depicted in the image.

In some embodiments, at block 114, the system can be configured to utilize the identified and/or analyzed vessels, coronary arteries, and/or plaque from the medical image to perform a point-in-time analysis of the subject. In some embodiments, the system can be configured to use automatic and/or dynamic image processing of one or more medical images taken from one point in time to identify and/or analyze one or more vessels, coronary arteries, and/or plaque and derive one or more parameters and/or classifications thereof. For example, as will be described in more detail herein, in some embodiments, the system can be configured to generate one or more quantification metrics of plaque and/or classify the identified regions of plaque as good or bad plaque. Further, in some embodiments, at block 114, the system can be configured to generate one or more treatment plans for the subject based on the analysis results. In some embodiments, the system can be configured to utilize one or more AI and/or ML algorithms to identify and/or analyze vessels or plaque, derive one or more quantification metrics and/or classifications, and/or generate a treatment plan.

In some embodiments, if a previous scan or medical image of the subject exists, the system can be configured to perform at block 126 one or more time-based analyses, such as disease tracking. For example, in some embodiments, if the system has access to one or more quantified parameters or classifications derived from previous scans or medical images of the subject, the system can be configured to compare the same with one or more quantified parameters or classifications derived from a current scan or medical image to determine the progression of disease and/or state of the subject.

In some embodiments, at block 116, the system is configured to automatically and/or dynamically generate a Graphical User Interface (GUI) or other visualization of the analysis results at block 116, which can include for example identified vessels, regions of plaque, coronary arteries, quantified metrics or parameters, risk assessment, proposed treatment plan, and/or any other analysis result discussed herein. In some embodiments, the system is configured to analyze arteries present in the CT scan data and display various views of the arteries present in the patient, for example within 10-15 minutes or less. In contrast, as an example, conducting a visual assessment of a CT to identify stenosis alone, without consideration of good or bad plaque or any other factor, can take anywhere between 15 minutes to more than an hour depending on the skill level, and can also have substantial variability across radiologists and/or cardiac imagers.

In some embodiments, at block 118, the system can be configured to transmit the generated GUI or other visualization, analysis results, and/or treatment to the medical facility. In some embodiments, at block 120, a physician at the medical facility can then review and/or confirm and/or revise the generated GUI or other visualization, analysis results, and/or treatment.

In some embodiments, at block 122, the system can be configured to further generate and transmit a patient-specific medical report to a patient, who can receive the same at block 124. In some embodiments, the patient-specific medical report can be dynamically generated based on the analysis results derived from and/or other generated from the medical image processing and analytics. For example, the patient-specific report can include identified vessels, regions of plaque, coronary arteries, quantified metrics or parameters, risk assessment, proposed treatment plan, and/or any other analysis result discussed herein.

In some embodiments, one or more of the process illustrated in FIG. 1 can be repeated, for example for the same patient at a different time to track progression of a disease and/or the state of the patient.

Image Processing-Based Classification of Good v. Bad Plaque

As discussed, in some embodiments, the systems, methods, and devices described herein are configured to automatically and/or dynamically identify and/or classify good v. bad plaque or stable v. unstable plaque based on medical image analysis and/or processing. For example, in some embodiments, the system can be configured to utilize an AI and/or ML algorithm to identify areas in an artery that exhibit plaque buildup within, along, inside and/or outside the arteries. In some embodiments, the system can be configured to identify the outline or boundary of plaque buildup associated with an artery vessel wall. In some embodiments, the system can be configured to draw or generate a line that outlines the shape and configuration of the plaque buildup associated with the artery. In some embodiments, the system can be configured to identify whether the plaque buildup is a certain kind of plaque and/or the composition or characterization of a particular plaque buildup. In some embodiments, the system can be configured to characterize plaque binarily, ordinally and/or continuously. In some embodiments, the system can be configured to determine that the kind of plaque buildup identified is a "bad" kind of plaque due to the dark color or dark gray scale nature of the image corresponding to the plaque area, and/or by determination of its attenuation density (e.g., using a Hounsfield unit scale or other). For example, in some embodiments, the system can be configured to identify certain plaque as "bad" plaque if the brightness of the plaque is darker than a pre-determined level. In some embodiments, the system can be configured to identify good plaque areas based on the white coloration and/or the light gray scale nature of the area corresponding to the plaque buildup. For example, in some embodiments, the system can be configured to identify certain plaque as "good" plaque if the brightness of the plaque is lighter than a pre-determined level. In some embodiments, the system can be configured to determine that dark areas in the CT scan are related to "bad" plaque, whereas the system can be configured to identify good plaque areas corresponding to white areas. In some embodiments, the system can be configured to identify and determine the total area and/or volume of total plaque, good plaque, and/or bad plaque identified within an artery vessel or plurality of vessels. In some embodiments, the system can be configured to determine the length of the total plaque area, good plaque area, and/or bad plaque area identified. In some embodiments, the system can be configured to determine the width of the total plaque area, good plaque area, and/or bad plaque area identified. The "good" plaque may be considered as such because it is less likely to cause heart attack, less likely to exhibit significant plaque progression, and/or less likely to be ischemia, amongst others. Conversely, the "bad" plaque be considered as such because it is more likely to cause heart attack, more likely to exhibit significant plaque progression, and/or more likely to be ischemia, amongst others. In some embodiments, the "good" plaque may be considered as such because it is less likely to result in the no-reflow phenomenon at the time of coronary revascularization. Conversely, the "bad" plaque may be considered as such because it is more likely to cause the no-reflow phenomenon at the time of coronary revascularization.

Figure 2A:
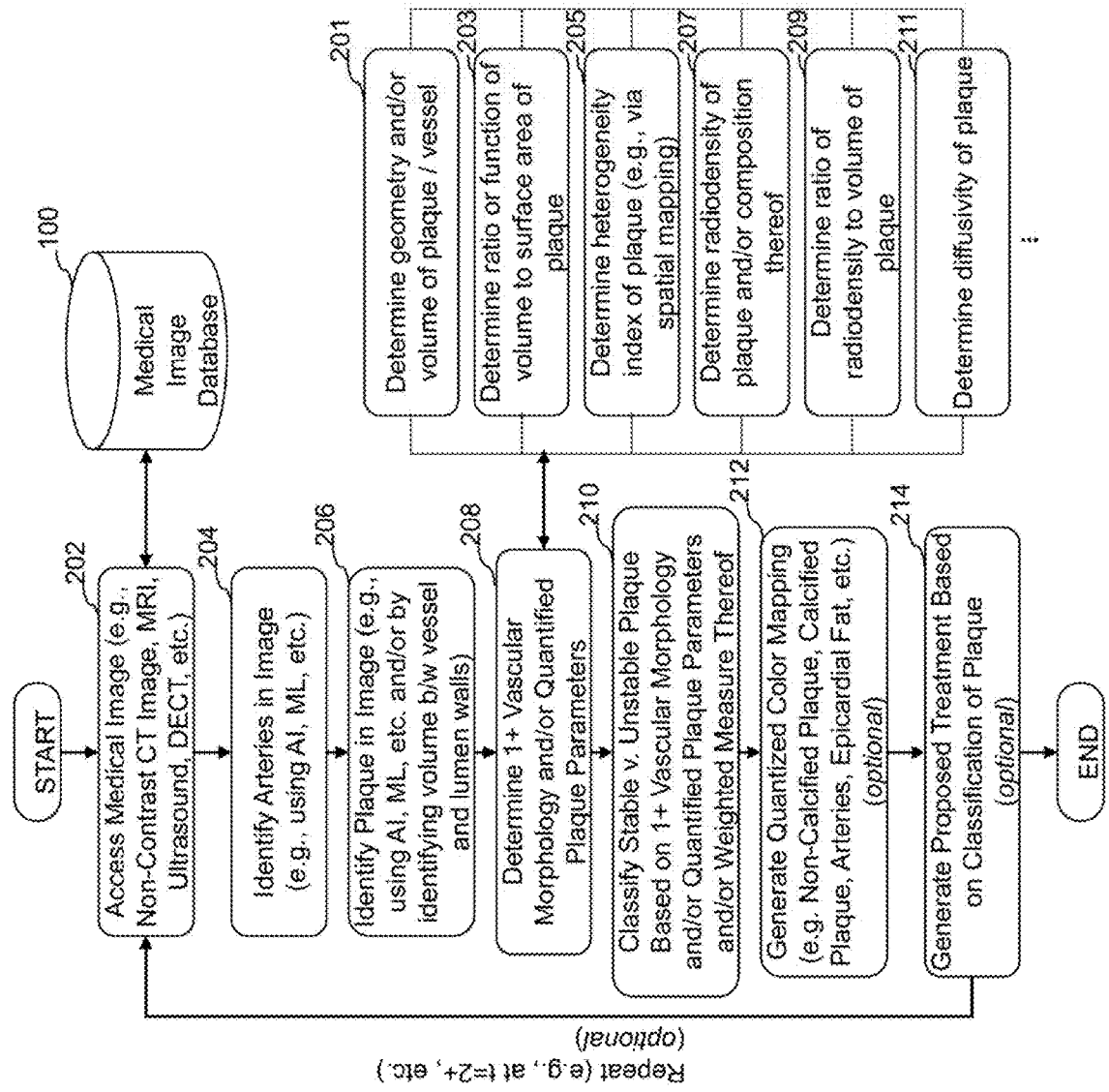
FIG. 2A is a flowchart illustrating an overview of an example embodiment(s) of a method for analysis and classification of plaque from a medical image.

FIG. 2A is a flowchart illustrating an overview of an example embodiment(s) of a method for analysis and classification of plaque from a medical image, which can be obtained non-invasively. As illustrated in FIG. 2A, at block 202, in some embodiments, the system can be configured to access a medical image, which can include a coronary region of a subject and/or be stored in a medical image database 100. The medical image database 100 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 204, the system can be configured to identify one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 206, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system can be configured to identify a vessel wall and a lumen wall for each of the identified coronary arteries in the medical image. In some embodiments, the system is then configured to determine the volume in between the vessel wall and the lumen wall as plaque. In some embodiments, the system can be configured to identify regions of plaque based on the radiodensity values typically associated with plaque, for example by setting a predetermined threshold or range of radiodensity values that are typically associated with plaque with or without normalizing using a normalization device.

In some embodiments, the system is configured to automatically and/or dynamically determine one or more vascular morphology parameters and/or plaque parameters at block 208 from the medical image. In some embodiments, the one or more vascular morphology parameters and/or plaque parameters can comprise quantified parameters derived from the medical image. For example, in some embodiments, the system can be configured to utilize an AI and/or ML algorithm or other algorithm to determine one or more vascular morphology parameters and/or plaque parameters. As another example, in some embodiments, the system can be configured to determine one or more vascular morphology parameters, such as classification of arterial remodeling due to plaque, which can further include positive arterial remodeling, negative arterial remodeling, and/or intermediate arterial remodeling. In some embodiments, the classification of arterial remodeling is determined based on a ratio of the largest vessel diameter at a region of plaque to a normal reference vessel diameter of the same region which can be retrieved from a normal database. In some embodiments, the system can be configured to classify arterial remodeling as positive when the ratio of the largest vessel diameter at a region of plaque to a normal reference vessel diameter of the same region is more than 1.1. In some embodiments, the system can be configured to classify arterial remodeling as negative when the ratio of the largest vessel diameter at a region of plaque to a normal reference vessel diameter is less than 0.95. In some embodiments, the system can be configured to classify arterial remodeling as intermediate when the ratio of the largest vessel diameter at a region of plaque to a normal reference vessel diameter is between 0.95 and 1.1.

Further, as part of block 208, in some embodiments, the system can be configured to determine a geometry and/or volume of one or more regions of plaque and/or one or more vessels or arteries at block 201. For example, the system can be configured to determine if the geometry of a particular region of plaque is round or oblong or other shape. In some embodiments, the geometry of a region of plaque can be a factor in assessing the stability of the plaque. As another example, in some embodiments, the system can be configured to determine the curvature, diameter, length, volume, and/or any other parameters of a vessel or artery from the medical image.

In some embodiments, as part of block 208, the system can be configured to determine a volume and/or surface area of a region of plaque and/or a ratio or other function of volume to surface area of a region of plaque at block 203, such as for example a diameter, radius, and/or thickness of a region of plaque. In some embodiments, a plaque having a low ratio of volume to surface area can indicate that the plaque is stable. As such, in some embodiments, the system can be configured to determine that a ratio of volume to surface area of a region of plaque below a predetermined threshold is indicative of stable plaque.

In some embodiments, as part of block 208, the system can be configured to determine a heterogeneity index of a region of plaque at block 205. For instance, in some embodiments, a plaque having a low heterogeneity or high homogeneity can indicate that the plaque is stable. As such, in some embodiments, the system can be configured to determine that a heterogeneity of a region of plaque below a predetermined threshold is indicative of stable plaque. In some embodiments, heterogeneity or homogeneity of a region of plaque can be determined based on the heterogeneity or homogeneity of radiodensity values within the region of plaque. As such, in some embodiments, the system can be configured to determine a heterogeneity index of plaque by generating spatial mapping, such as a three-dimensional histogram, of radiodensity values within or across a geometric shape or region of plaque. In some embodiments, if a gradient or change in radiodensity values across the spatial mapping is above a certain threshold, the system can be configured to assign a high heterogeneity index. Conversely, in some embodiments, if a gradient or change in radiodensity values across the spatial mapping is below a certain threshold, the system can be configured to assign a low heterogeneity index.

In some embodiments, as part of block 208, the system can be configured to determine a radiodensity of plaque and/or a composition thereof at block 207. For example, a high radiodensity value can indicate that a plaque is highly calcified or stable, whereas a low radiodensity value can indicate that a plaque is less calcified or unstable. As such, in some embodiments, the system can be configured to determine that a radiodensity of a region of plaque above a predetermined threshold is indicative of stable stabilized plaque. In addition, different areas within a region of plaque can be calcified at different levels and thereby show different radiodensity values. As such, in some embodiments, the system can be configured to determine the radiodensity values of a region of plaque and/or a composition or percentage or change of radiodensity values within a region of plaque. For instance, in some embodiments, the system can be configured to determine how much or what percentage of plaque within a region of plaque shows a radiodensity value within a low range, medium range, high range, and/or any other classification.

Similarly, in some embodiments, as part of block 208, the system can be configured to determine a ratio of radiodensity value of plaque to a volume of plaque at block 209. For instance, it can be important to assess whether a large or small region of plaque is showing a high or low radiodensity value. As such, in some embodiments, the system can be configured to determine a percentage composition of plaque comprising different radiodensity values as a function or ratio of volume of plaque.

In some embodiments, as part of block 208, the system can be configured to determine the diffusivity and/or assign a diffusivity index to a region of plaque at block 211. For example, in some embodiments, the diffusivity of a plaque can depend on the radiodensity value of plaque, in which a high radiodensity value can indicate low diffusivity or stability of the plaque.

In some embodiments, at block 210, the system can be configured to classify one or regions of plaque identified from the medical image as stable v. unstable or good v. bad based on the one or more vascular morphology parameters and/or quantified plaque parameters determined and/or derived from raw medical images. In particular, in some embodiments, the system can be configured to generate a weighted measure of one or more vascular morphology parameters and/or quantified plaque parameters determined and/or derived from raw medical images. For example, in some embodiments, the system can be configured weight one or more vascular morphology parameters and/or quantified plaque parameters equally. In some embodiments, the system can be configured weight one or more vascular morphology parameters and/or quantified plaque parameters differently. In some embodiments, the system can be configured weight one or more vascular morphology parameters and/or quantified plaque parameters logarithmically, algebraically, and/or utilizing another mathematical transform. In some embodiments, the system is configured to classify one or more regions of plaque at block 210 using the generated weighted measure and/or using only some of the vascular morphology parameters and/or quantified plaque parameters.

In some embodiments, at block 212, the system is configured to generate a quantized color mapping based on the analyzed and/or determined parameters. For example, in some embodiments, the system is configured to generate a visualization of the analyzed medical image by generating a quantized color mapping of calcified plaque, non-calcified plaque, good plaque, bad plaque, stable plaque, and/or unstable plaque as determined using any of the analytical techniques described herein. Further, in some embodiments, the quantified color mapping can also include arteries and/or epicardial fat, which can also be determined by the system, for example by utilizing one or more AI and/or ML algorithms.

In some embodiments, at block 214, the system is configured to generate a proposed treatment plan for the subject based on the analysis, such as for example the classification of plaque derived automatically from a raw medical image. In particular, in some embodiments, the system can be configured to assess or predict the risk of atherosclerosis, stenosis, and/or ischemia of the subject based on a raw medical image and automated image processing thereof.

In some embodiments, one or more processes described herein in connection with FIG. 2A can be repeated. For example, if a medical image of the same subject is taken again at a later point in time, one or more processes described herein can be repeated and the analytical results thereof can be used for disease tracking and/or other purposes.

Determination of Non-Calcified Plaque from a Non-Contrast CT Image(s)

As discussed herein, in some embodiments, the system can be configured to utilize a CT or other medical image of a subject as input for performing one or more image analysis techniques to assess a subject, including for example risk of a cardiovascular event. In some embodiments, such CT image can comprise a contrast-enhanced CT image, in which case some of the analysis techniques described herein can be directly applied, for example to identify or classify plaque. However, in some embodiments, such CT image can comprise a non-contrast CT image, in which case it can be more difficult to identify and/or determine non-calcified plaque due to its low radiodensity value and overlap with other low radiodensity values components, such as blood for example. As such, in some embodiments, the systems, devices, and methods described herein provide a novel approach to determining non-calcified plaque from a non-contrast CT image, which can be more widely available.

Also, in some embodiments, in addition to or instead of analyzing a contrast-enhanced CT scan, the system can also be configured to examine the attenuation densities within the arteries that are lower than the attenuation density of the blood flowing within them in a non-contrast CT scan. In some embodiments, these "low attenuation" plaques may be differentiated between the blood attenuation density and the fat that sometimes surrounds the coronary artery and/or may represent non-calcified plaques of different materials. In some embodiments, the presence of these non-calcified plaques may offer incremental prediction for whether a previously calcified plaque is stabilizing or worsening or progressing or regressing. These findings that are measurable through these embodiments may be linked to the prognosis of a patient, wherein calcium stabilization (that is, higher attenuation densities) and lack of non-calcified plaque by may associated with a favorable prognosis, while lack of calcium stabilization (that is, no increase in attenuation densities), or significant progression or new calcium formation may be associated with a poorer prognosis, including risk of rapid progression of disease, heart attack or other major adverse cardiovascular event.

Figure 2B:
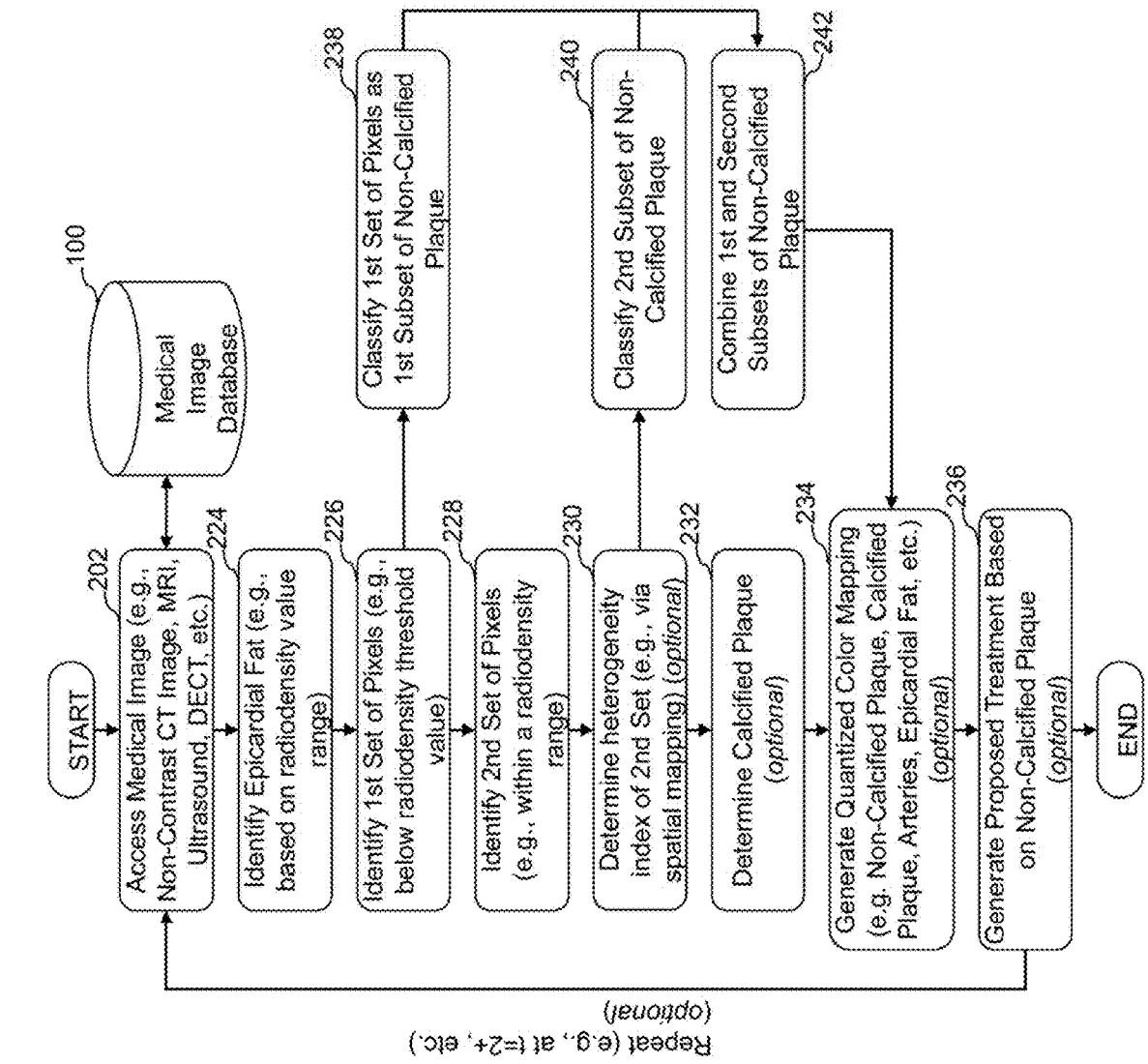
FIG. 2B is a flowchart illustrating an overview of an example embodiment(s) of a method for determination of non-calcified plaque from a non-contrast CT image(s).

FIG. 2B is a flowchart illustrating an overview of an example embodiment(s) of a method for determination of non-calcified and/or low-attenuated plaque from a medical image, such as a non-contrast CT image. As discussed herein and as illustrated in FIG. 2B, in some embodiments, the system can be configured to determine non-calcified and/or low-attenuated plaque from a medical image. In some embodiments, the medical image can be of the coronary region of the subject or patient. In some embodiments, the medical image can be obtained using one or more modalities such as CT, Dual-Energy Computed Tomography (DECT), Spectral CT, x-ray, ultrasound, echocardiography, IVUS, MR, OCT, nuclear medicine imaging, PET, SPECT, NIRS, and/or the like. In some embodiments, the system can be configured to access one or more medical images at block 202, for example from a medical image database 100.

In some embodiments, in order to determine non-calcified and/or low-attenuated plaque from the medical image or non-contrast CT image, the system can be configured to utilize a stepwise approach to first identify areas within the medical image that are clearly non-calcified plaque. In some embodiments, the system can then conduct a more detailed analysis of the remaining areas in the image to identify other regions of non-calcified and/or low-attenuated plaque. By utilizing such compartmentalized or a stepwise approach, in some embodiments, the system can identify or determine non-calcified and/or low-attenuated plaque from the medical image or non-contrast CT image with a faster turnaround rather than having to apply a more complicated analysis to every region or pixel of the image.

In particular, in some embodiments, at block 224, the system can be configured to identify epicardial fat from the medical image. In some embodiments, the system can be configured to identify epicardial fat by determining every pixel or region within the image that has a radiodensity value below a predetermined threshold and/or within a predetermined range. The exact predetermined threshold value or range of radiodensity for identifying epicardial fat can depend on the medical image, scanner type, scan parameters, and/or the like, which is why a normalization device can be used in some instances to normalize the medical image. For example, the system can be configured to identify as epicardial fat pixels and/or regions within the medical image or non-contrast CT image with a radiodensity value that is around −100 Hounsfield units and/or within a range that includes −100 Hounsfield units. In particular, in some embodiments, the system can be configured to identify as epicardial fat pixels and/or regions within the medical image or non-contrast CT image with a radiodensity value that is within a range with a lower limit of about −100 Hounsfield units, about −110 Hounsfield units, about −120 Hounsfield units, about −130 Hounsfield units, about −140 Hounsfield units, about −150 Hounsfield units, about −160 Hounsfield units, about −170 Hounsfield units, about −180 Hounsfield units, about −190 Hounsfield units, or about −200 Hounsfield units, and an upper limit of about 30 Hounsfield units, about 20 Hounsfield units, about 10 Hounsfield units, about 0 Hounsfield units, about −10 Hounsfield units, about −20 Hounsfield units, about −30 Hounsfield units, about −40 Hounsfield units, about −50 Hounsfield units, about −60 Hounsfield units, about −70 Hounsfield units, about −80 Hounsfield units, or about −90 Hounsfield units.

In some embodiments, the system can be configured to identify and/or segment arteries on the medical image or non-contrast CT image using the identified epicardial fat as outer boundaries of the arteries. For example, the system can be configured to first identify regions of epicardial fat on the medical image and assign a volume in between epicardial fat as an artery, such as a coronary artery.

In some embodiments, at block 226, the system can be configured to identify a first set of pixels or regions within the medical image, such as within the identified arteries, as non-calcified or low-attenuated plaque. More specifically, in some embodiments, the system can be configured to identify as an initial set low-attenuated or non-calcified plaque by identifying pixels or regions with a radiodensity value that is below a predetermined threshold or within a predetermined range. For example, the predetermined threshold or predetermined range can be set such that the resulting pixels can be confidently marked as low-attenuated or non-calcified plaque without likelihood of confusion with another matter such as blood. In particular, in some embodiments, the system can be configured to identify the initial set of low-attenuated or non-calcified plaque by identifying pixels or regions with a radiodensity value below around 30 Hounsfield units. In some embodiments, the system can be configured to identify the initial set of low-attenuated or non-calcified plaque by identifying pixels or regions with a radiodensity value at or below around 60 Hounsfield units, around 55 Hounsfield units, around 50 Hounsfield units, around 45 Hounsfield units, around 40 Hounsfield units, around 35 Hounsfield units, around 30 Hounsfield units, around 25 Hounsfield units, around 20 Hounsfield units, around 15 Hounsfield units, around 10 Hounsfield units, around 5 Hounsfield units, and/or with a radiodensity value at or above around 0 Hounsfield units, around 5 Hounsfield units, around 10 Hounsfield units, around 15 Hounsfield units, around 20 Hounsfield units, around 25 Hounsfield units, and/or around 30 Hounsfield units. In some embodiments, the system can be configured classify pixels or regions that fall within or below this predetermined range of radiodensity values as a first set of identified non-calcified or low-attenuated plaque at block 238.

In some embodiments, the system at block 228 can be configured to identify a second set of pixels or regions within the medical image, such as within the identified arteries, that may or may not represent low-attenuated or non-calcified plaque. As discussed, in some embodiments, this second set of candidates of pixels or regions may require additional analysis to confirm that they represent plaque. In particular, in some embodiments, the system can be configured to identify this second set of pixels or regions that may potentially be low-attenuated or non-calcified plaque by identifying pixels or regions of the image with a radiodensity value within a predetermined range. In some embodiments, the predetermined range for identifying this second set of pixels or regions can be between around 30 Hounsfield units and 100 Hounsfield units. In some embodiments, the predetermined range for identifying this second set of pixels or regions can have a lower limit of around 0 Hounsfield units, 5 Hounsfield units, 10 Hounsfield units, 15 Hounsfield units, 20 Hounsfield units, 25 Hounsfield units, 30 Hounsfield units, 35 Hounsfield units, 40 Hounsfield units, 45 Hounsfield units, 50 Hounsfield units, and/or an upper limit of around 55 Hounsfield units, 60 Hounsfield units, 65 Hounsfield units, 70 Hounsfield units, 75 Hounsfield units, 80 Hounsfield units, 85 Hounsfield units, 90 Hounsfield units, 95 Hounsfield units, 100 Hounsfield units, 110 Hounsfield units, 120 Hounsfield units, 130 Hounsfield units, 140 Hounsfield units, 150 Hounsfield units.

In some embodiments, at block 230, the system can be configured conduct an analysis of the heterogeneity of the identified second set of pixels or regions. For example, depending on the range of radiodensity values used to identify the second set of pixels, in some embodiments, the second set of pixels or regions may include blood and/or plaque. Blood can typically show a more homogeneous gradient of radiodensity values compared to plaque. As such, in some embodiments, by analyzing the homogeneity or heterogeneity of the pixels or regions identified as part of the second set, the system can be able to distinguish between blood and non-calcified or low attenuated plaque. As such, in some embodiments, the system can be configured to determine a heterogeneity index of the second set of regions of pixels identified from the medical image by generating spatial mapping, such as a three-dimensional histogram, of radiodensity values within or across a geometric shape or region of plaque. In some embodiments, if a gradient or change in radiodensity values across the spatial mapping is above a certain threshold, the system can be configured to assign a high heterogeneity index and/or classify as plaque. Conversely, in some embodiments, if a gradient or change in radiodensity values across the spatial mapping is below a certain threshold, the system can be configured to assign a low heterogeneity index and/or classify as blood.

In some embodiments, at block 240, the system can be configured to identify a subset of the second set of regions of pixels identified from the medical image as plaque or non-calcified or low-attenuated plaque. In some embodiments, at block 242, the system can be configured to combine the first set of identified non-calcified or low-attenuated plaque from block 238 and the second set of identified non-calcified or low-attenuated plaque from block 240. As such, even using non-contrast CT images, in some embodiments, the system can be configured to identify low-attenuated or non-calcified plaque which can be more difficult to identify compared to calcified or high-attenuated plaque due to possible overlap with other matter such as blood.

In some embodiments, the system can also be configured to determine calcified or high-attenuated plaque from the medical image at block 232. This process can be more straightforward compared to identifying low-attenuated or non-calcified plaque from the medical image or non-contrast CT image. In particular, in some embodiments, the system can be configured to identify calcified or high-attenuated plaque from the medical image or non-contrast CT image by identifying pixels or regions within the image that have a radiodensity value above a predetermined threshold and/or within a predetermined range. For example, in some embodiments, the system can be configured to identify as calcified or high-attenuated plaque regions or pixels from the medical image or non-contrast CT image having a radiodensity value above around 100 Hounsfield units, around 150 Hounsfield units, around 200 Hounsfield units, around 250 Hounsfield units, around 300 Hounsfield units, around 350 Hounsfield units, around 400 Hounsfield units, around 450 Hounsfield units, around 500 Hounsfield units, around 600 Hounsfield units, around 700 Hounsfield units, around 800 Hounsfield units, around 900 Hounsfield units, around 1000 Hounsfield units, around 1100 Hounsfield units, around 1200 Hounsfield units, around 1300 Hounsfield units, around 1400 Hounsfield units, around 1500 Hounsfield units, around 1600 Hounsfield units, around 1700 Hounsfield units, around 1800 Hounsfield units, around 1900 Hounsfield units, around 2000 Hounsfield units, around 2500 Hounsfield units, around 3000 Hounsfield units, and/or any other minimum threshold.

In some embodiments, at block 234, the system can be configured to generate a quantized color mapping of one or more identified matters from the medical image. For example, in some embodiments, the system can be configured assign different colors to each of the different regions associated with different matters, such as non-calcified or low-attenuated plaque, calcified or high-attenuated plaque, all plaque, arteries, epicardial fat, and/or the like. In some embodiments, the system can be configured to generate a visualization of the quantized color map and/or present the same to a medical personnel or patient via a GUI. In some embodiments, at block 236, the system can be configured to generate a proposed treatment plan for a disease based on one or more of the identified non-calcified or low-attenuated plaque, calcified or high-attenuated plaque, all plaque, arteries, epicardial fat, and/or the like. For example, in some embodiments, the system can be configured to generate a treatment plan for an arterial disease, renal artery disease, abdominal atherosclerosis, carotid atherosclerosis, and/or the like, and the medical image being analyzed can be taken from any one or more regions of the subject for such disease analysis.

In some embodiments, one or more processes described herein in connection with FIG. 2B can be repeated. For example, if a medical image of the same subject is taken again at a later point in time, one or more processes described herein can be repeated and the analytical results thereof can be used for disease tracking and/or other purposes.

Further, in some embodiments, the system can be configured to identify and/or determine non-calcified plaque from a DECT or spectral CT image. Similar to the processes described above, in some embodiments, the system can be configured to access a DECT or spectral CT image, identify epicardial fat on the DECT image or spectral CT and/or segment one or more arteries on the DECT image or spectral CT, identify and/or classify a first set of pixels or regions within the arteries as a first set of low-attenuated or non-calcified plaque, and/or identify a second set of pixels or regions within the arteries as a second set of low-attenuated or non-calcified plaque. However, unlike the techniques described above, in some embodiments, such as for example where a DECT or spectral CT image is being analyzed, the system can be configured to identify a subset of those second set of pixels without having to perform a heterogeneity and/or homogeneity analysis of the second set of pixels. Rather, in some embodiments, the system can be configured to distinguish between blood and low-attenuated or non-calcified plaque directly from the image, for example by utilizing the dual or multispectral aspect of a DECT or spectral CT image. In some embodiments, the system can be configured to combine the first set of identified pixels or regions and the subset of the second set of pixels or regions identified as low-attenuated or non-calcified plaque to identify a whole set of the same on the medical image. In some embodiments, even if analyzing a DECT or spectral CT image, the system can be configured to further analyze the second set of pixels or regions by performing a heterogeneity or homogeneity analysis, similar to that described above in relation to block 230. For example, even if analyzing a DECT or spectral CT image, in some embodiments, the distinction between certain areas of blood and/or low-attenuated or non-calcified plaque may not be complete and/or accurate.

Imaging Analysis-Based Risk Assessment

In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images, for example using AI and/or ML algorithms, to provide a full image-based analysis report within minutes.

In particular, in some embodiments, the system can be configured to calculate the total amount of plaque (and/or amounts of specific types of plaque) within a specific artery and/or within all the arteries of a patient. In some embodiments, the system can be configured to determine the total amount of bad plaque in a particular artery and/or within a total artery area across some or all of the arteries of the patient. In some embodiments, the system can be configured to determine a risk factor and/or a diagnosis for a particular patient to suffer a heart attack or other cardiac event based on the total amount of plaque in a particular artery and/or a total artery area across some or all of the arteries of a patient. Other risk factors that can be determined from the amount of "bad" plaque, or the relative amount of "bad" versus "good" plaque, can include the rate of disease progression and/or the likelihood of ischemia. In some embodiments, plaques can be measured by total volume (or area on cross-sectional imaging) as well as by relative amount when normalized to the total vessel volumes, total vessel lengths or subtended myocardium.

In some embodiments, the imaging data of the coronary arteries can include measures of atherosclerosis, stenosis and vascular morphology. In some embodiments, this information can be combined with other cardiovascular disease phenotyping by quantitative characterization of left and right ventricles, left and right atria; aortic, mitral, tricuspid and pulmonic valves; aorta, pulmonary artery, pulmonary vein, coronary sinus and inferior and superior vena cava; epicardial or pericoronary fat; lung densities; bone densities; pericardium and others. As an example, in some embodiments, the imaging data for the coronary arteries may be integrated with the left ventricular mass, which can be segmented according to the amount and location of the artery it is subtended by. This combination of left ventricular fractional myocardial mass to coronary artery information may enhance the prediction of whether a future heart attack will be a large one or a small one. As another example, in some embodiments, the vessel volume of the coronary arteries can be related to the left ventricular mass as a measure of left ventricular hypertrophy, which can be a common finding in patients with hypertension. Increased left ventricular mass (relative or absolute) may indicate disease worsening or uncontrolled hypertension. As another example, in some embodiments, the onset, progression, and/or worsening of atrial fibrillation may be predicted by the atrial size, volume, atrial free wall mass and thickness, atrial function and fat surrounding the atrium. In some embodiments, these predictions may be done with a ML or AI algorithm or other algorithm type.

Sequentially, in some embodiments, the algorithms that allow for segmentation of atherosclerosis, stenosis and vascular morphology—along with those that allow for segmentation of other cardiovascular structures, and thoracic structures—may serve as the inputs for the prognostic algorithms. In some embodiments, the outputs of the prognostic algorithms, or those that allow for image segmentation, may be leveraged as inputs to other algorithms that may then guide clinical decision making by predicting future events. As an example, in some embodiments, the integrated scoring of atherosclerosis, stenosis, and/or vascular morphology may identify patients who may benefit from coronary revascularization, that is, those who will achieve symptom benefit, reduced risk of heart attack and death. As another example, in some embodiments, the integrated scoring of atherosclerosis, stenosis and vascular morphology may identify individuals who may benefit from specific types of medications, such as lipid lowering medications (such as statin medications, PCSK-9 inhibitors, icosopent ethyl, and others); Lp(a) lowering medications; anti-thrombotic medications (such as clopidogrel, rivoroxaban and others). In some embodiments, the benefit that is predicted by these algorithms may be for reduced progression, determination of type of plaque progression (progression, regression or mixed response), stabilization due to the medical therapy, and/or need for heightened intensified therapy. In some embodiments, the imaging data may be combined with other data to identify areas within a coronary vessel that are normal and without plaque now but may be at higher likelihood of future plaque formation.

In some embodiments, an automated or manual co-registration method can be combined with the imaging segmentation data to compare two or more images over time. In some embodiments, the comparison of these images can allow for determination of differences in coronary artery atherosclerosis, stenosis and vascular morphology over time, and can be used as an input variable for risk prediction.

In some embodiments, the imaging data of the coronary arteries for atherosclerosis, stenosis, and vascular morphology—coupled or not coupled to thoracic and cardiovascular disease measurements—can be integrated into an algorithm that determines whether a coronary vessel is ischemia, or exhibits reduced blood flow or pressure (either at rest or hyperemic states).

In some embodiments, the algorithms for coronary atherosclerosis, stenosis and ischemia can be modified by a computer system and/or other to remove plaque or "seal" plaque. In some embodiments, a comparison can be made before or after the system has removed or sealed the plaque to determine whether any changes have occurred. For example, in some embodiments, the system can be configured to determine whether coronary ischemia is removed with the plaque sealing.

In some embodiments, the characterization of coronary atherosclerosis, stenosis and/or vascular morphology can enable relating a patient's biological age to their vascular age, when compared to a population-based cohort of patients who have undergone similar scanning. As an example, a 60-year old patient may have X units of plaque in their coronary arteries that is equivalent to the average 70-year old patient in the population-based cohort. In this case, the patient's vascular age may be 10 years older than the patient's biological age.

In some embodiments, the risk assessment enabled by the image segmentation prediction algorithms can allow for refined measures of disease or death likelihood in people being considered for disability or life insurance. In this scenario, the risk assessment may replace or augment traditional actuarial algorithms.

In some embodiments, imaging data may be combined with other data to augment risk assessment for future adverse events, such as heart attacks, strokes, death, rapid progression, non-response to medical therapy, no-reflow phenomenon and others. In some embodiments, other data may include a multi-omic approach wherein an algorithm integrates the imaging phenotype data with genotype data, proteomic data, transcriptomic data, metabolomic data, microbiomic data and/or activity and lifestyle data as measured by a smart phone or similar device.

Figure 3A:
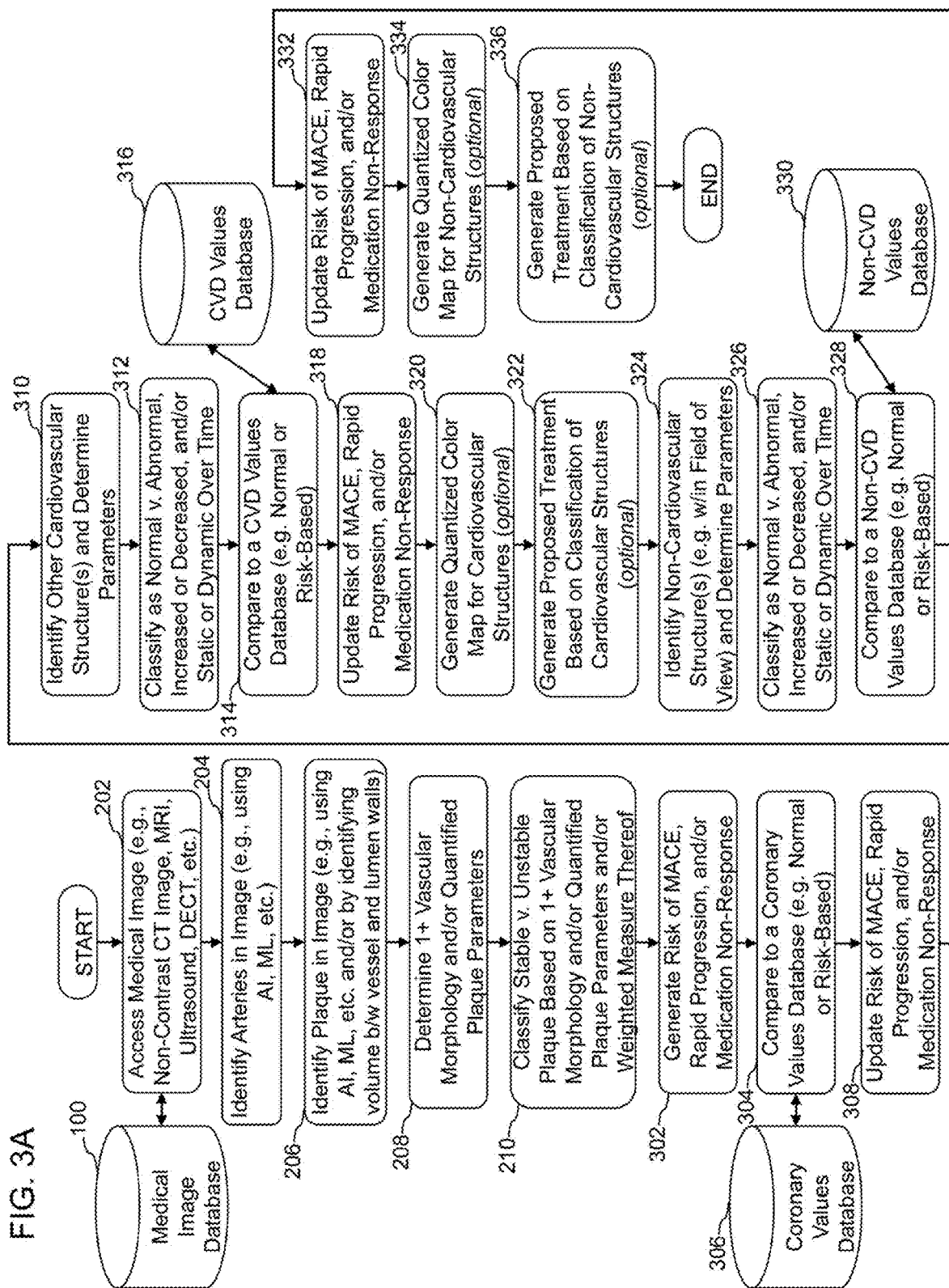
FIG. 3A is a flowchart illustrating an overview of an example embodiment(s) of a method for risk assessment based on medical image analysis.

FIG. 3A is a flowchart illustrating an overview of an example embodiment(s) of a method for risk assessment based on medical image analysis. As illustrated in FIG. 3A, in some embodiments, the system can be configured to access a medical image at block 202. Further, in some embodiments, the system can be configured to identify one or more arteries at block 204 and/or one or more regions of plaque at block 206. In addition, in some embodiments, the system can be configured to determine one or more vascular morphology and/or quantified plaque parameters at block 208 and/or classify stable or unstable plaque based on the determined one or more vascular morphology and/or quantified plaque parameters and/or a weighted measure thereof at block 210. Additional detail regarding the processes and techniques represented in blocks 202, 204, 206, 208, and 210 can be found in the description above in relation to FIG. 2A.

In some embodiments, the system can automatically and/or dynamically determine and/or generate a risk of cardiovascular event for the subject at block 302, for example using the classified stable and/or unstable regions of plaque. More specifically, in some embodiments, the system can utilize an AI, ML, or other algorithm to generate a risk of cardiovascular event, MACE, rapid plaque progression, and/or non-response to medication at block 302 based on the image analysis.

In some embodiments, at block 304, the system can be configured to compare the determined one or more vascular morphology parameters, quantified plaque parameters, and/or classified stable v. unstable plaque and/or values thereof, such as volume, ratio, and/or the like, to one or more known datasets of coronary values derived from one or more other subjects. The one or more known datasets can comprise one or more vascular morphology parameters, quantified plaque parameters, and/or classified stable v. unstable plaque and/or values thereof, such as volume, ratio, and/or the like, derived from medical images taken from other subjects, including healthy subjects and/or subjects with varying levels of risk. For example, the one or more known datasets of coronary values can be stored in a coronary values database 306 that can be locally accessible by the system and/or remotely accessible via a network connection by the system.

In some embodiments, at block 308, the system can be configured to update the risk of cardiovascular event for the subject based on the comparison to the one or more known datasets. For example, based on the comparison, the system may increase or decrease the previously generated risk assessment. In some embodiments, the system may maintain the previously generated risk assessment even after comparison. In some embodiments, the system can be configured to generate a proposed treatment for the subject based on the generated and/or updated risk assessment after comparison with the known datasets of coronary values.

In some embodiments, at block 310, the system can be configured to further identify one or more other cardiovascular structures from the medical image and/or determine one or more parameters associated with the same. For example, the one or more additional cardiovascular structures can include the left ventricle, right ventricle, left atrium, right atrium, aortic valve, mitral valve, tricuspid valve, pulmonic valve, aorta, pulmonary artery, inferior and superior vena cava, epicardial fat, and/or pericardium.

In some embodiments, parameters associated with the left ventricle can include size, mass, volume, shape, eccentricity, surface area, thickness, and/or the like. Similarly, in some embodiments, parameters associated with the right ventricle can include size, mass, volume, shape, eccentricity, surface area, thickness, and/or the like. In some embodiments, parameters associated with the left atrium can include size, mass, volume, shape, eccentricity, surface area, thickness, pulmonary vein angulation, atrial appendage morphology, and/or the like. In some embodiments, parameters associated with the right atrium can include size, mass, volume, shape, eccentricity, surface area, thickness, and/or the like.

Further, in some embodiments, parameters associated with the aortic valve can include thickness, volume, mass, calcifications, three-dimensional map of calcifications and density, eccentricity of calcification, classification by individual leaflet, and/or the like. In some embodiments, parameters associated with the mitral valve can include thickness, volume, mass, calcifications, three-dimensional map of calcifications and density, eccentricity of calcification, classification by individual leaflet, and/or the like. In some embodiments, parameters associated with the tricuspid valve can include thickness, volume, mass, calcifications, three-dimensional map of calcifications and density, eccentricity of calcification, classification by individual leaflet, and/or the like. In some embodiments, parameters associated with the pulmonic valve can include thickness, volume, mass, calcifications, three-dimensional map of calcifications and density, eccentricity of calcification, classification by individual leaflet, and/or the like.

In some embodiments, parameters associated with the aorta can include dimensions, volume, diameter, area, enlargement, outpouching, and/or the like. In some embodiments, parameters associated with the pulmonary artery can include dimensions, volume, diameter, area, enlargement, outpouching, and/or the like. In some embodiments, parameters associated with the inferior and superior vena cava can include dimensions, volume, diameter, area, enlargement, outpouching, and/or the like.

In some embodiments, parameters associated with epicardial fat can include volume, density, density in three dimensions, and/or the like. In some embodiments, parameters associated with the pericardium can include thickness, mass, and/or the like.

In some embodiments, at block 312, the system can be configured to classify one or more of the other identified cardiovascular structures, for example using the one or more determined parameters thereof. In some embodiments, for one or more of the other identified cardiovascular structures, the system can be configured to classify each as normal v. abnormal, increased or decreased, and/or static or dynamic over time.

In some embodiments, at block 314, the system can be configured to compare the determined one or more parameters of other cardiovascular structures to one or more known datasets of cardiovascular structure parameters derived from one or more other subjects. The one or more known datasets of cardiovascular structure parameters can include any one or more of the parameters mentioned above associated with the other cardiovascular structures. In some embodiments, the cardiovascular structure parameters of the one or more known datasets can be derived from medical images taken from other subjects, including healthy subjects and/or subjects with varying levels of risk. In some embodiments, the one or more known datasets of cardiovascular structure parameters can be stored in a cardiovascular structure values or cardiovascular disease (CVD) database 316 that can be locally accessible by the system and/or remotely accessible via a network connection by the system.

In some embodiments, at block 318, the system can be configured to update the risk of cardiovascular event for the subject based on the comparison to the one or more known datasets of cardiovascular structure parameters. For example, based on the comparison, the system may increase or decrease the previously generated risk assessment. In some embodiments, the system may maintain the previously generated risk assessment even after comparison.

In some embodiments, at block 320, the system can be configured to generate a quantified color map, which can include color coding for one or more other cardiovascular structures identified from the medical image, stable plaque, unstable plaque, arteries, and/or the like. In some embodiments, at block 322, the system can be configured to generate a proposed treatment for the subject based on the generated and/or updated risk assessment after comparison with the known datasets of cardiovascular structure parameters.

In some embodiments, at block 324, the system can be configured to further identify one or more non-cardiovascular structures from the medical image and/or determine one or more parameters associated with the same. For example, the medical image can include one or more non-cardiovascular structures that are in the field of view. In particular, the one or more non-cardiovascular structures can include the lungs, bones, liver, and/or the like.

In some embodiments, parameters associated with the non-cardiovascular structures can include volume, surface area, ratio or function of volume to surface area, heterogeneity of radiodensity values, radiodensity values, geometry (such as oblong, spherical, and/or the like), spatial radiodensity, spatial scarring, and/or the like. In addition, in some embodiments, parameters associated with the lungs can include density, scarring, and/or the like. For example, in some embodiments, the system can be configured to associate a low Hounsfield unit of a region of the lungs with emphysema. In some embodiments, parameters associated with bones, such as the spine and/or ribs, can include radiodensity, presence and/or extent of fractures, and/or the like. For example, in some embodiments, the system can be configured to associate a low Hounsfield unit of a region of bones with osteoporosis. In some embodiments, parameters associated with the liver can include density for non-alcoholic fatty liver disease which can be assessed by the system by analyzing and/or comparing to the Hounsfield unit density of the liver.

In some embodiments, at block 326, the system can be configured to classify one or more of the identified non-cardiovascular structures, for example using the one or more determined parameters thereof. In some embodiments, for one or more of the identified non-cardiovascular structures, the system can be configured to classify each as normal v. abnormal, increased or decreased, and/or static or dynamic over time.

In some embodiments, at block 328, the system can be configured to compare the determined one or more parameters of non-cardiovascular structures to one or more known datasets of non-cardiovascular structure parameters or non-CVD values derived from one or more other subjects. The one or more known datasets of non-cardiovascular structure parameters or non-CVD values can include any one or more of the parameters mentioned above associated with non-cardiovascular structures. In some embodiments, the non-cardiovascular structure parameters or non-CVD values of the one or more known datasets can be derived from medical images taken from other subjects, including healthy subjects and/or subjects with varying levels of risk. In some embodiments, the one or more known datasets of non-cardiovascular structure parameters or non-CVD values can be stored in a non-cardiovascular structure values or non-CVD database 330 that can be locally accessible by the system and/or remotely accessible via a network connection by the system.

In some embodiments, at block 332, the system can be configured to update the risk of cardiovascular event for the subject based on the comparison to the one or more known datasets of non-cardiovascular structure parameters or non-CVD values. For example, based on the comparison, the system may increase or decrease the previously generated risk assessment. In some embodiments, the system may maintain the previously generated risk assessment even after comparison.

In some embodiments, at block 334, the system can be configured to generate a quantified color map, which can include color coding for one or more non-cardiovascular structures identified from the medical image, as well as for the other cardiovascular structures identified from the medical image, stable plaque, unstable plaque, arteries, and/or the like. In some embodiments, at block 336, the system can be configured to generate a proposed treatment for the subject based on the generated and/or updated risk assessment after comparison with the known datasets of non-cardiovascular structure parameters or non-CVD values.

In some embodiments, one or more processes described herein in connection with FIG. 3A can be repeated. For example, if a medical image of the same subject is taken again at a later point in time, one or more processes described herein can be repeated and the analytical results thereof can be used for tracking of risk assessment of the subject based on image processing and/or other purposes.

Quantification of Atherosclerosis

In some embodiments, the system is configured to analyze one or more arteries present in a medical image, such as CT scan data, to automatically and/or dynamically quantify atherosclerosis. In some embodiments, the system is configured to quantify atherosclerosis as the primary disease process, while stenosis and/or ischemia can be considered surrogates thereof. Prior to the embodiments described herein, it was not feasible to quantify the primary disease due to the lengthy manual process and manpower needed to do so, which could take anywhere from 4 to 8 or more hours. In contrast, in some embodiments, the system is configured to quantify atherosclerosis based on analysis of a medical image and/or CT scan using one or more AI, ML, and/or other algorithms that can segment, identify, and/or quantify atherosclerosis in less than about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 25 minutes, about 30 minutes, about 40 minutes, about 50 minutes, and/or about 60 minutes. In some embodiments, the system is configured to quantify atherosclerosis within a time frame defined by two of the aforementioned values. In some embodiments, the system is configured to calculate stenosis rather than simply eyeballing, thereby allowing users to better understand whole heart atherosclerosis and/or guaranteeing the same calculated stenosis result if the same medical image is used for analysis. Importantly, the type of atherosclerosis can also be quantified and/or classified by this method. Types of atherosclerosis can be determined binarily (calcified vs. non-calcified plaque), ordinally (dense calcified plaque, calcified plaque, fibrous plaque, fibrofatty plaque, necrotic core, or admixtures of plaque types), or continuously (by attenuation density on a Hounsfield unit scale or similar).

Figure 3B:
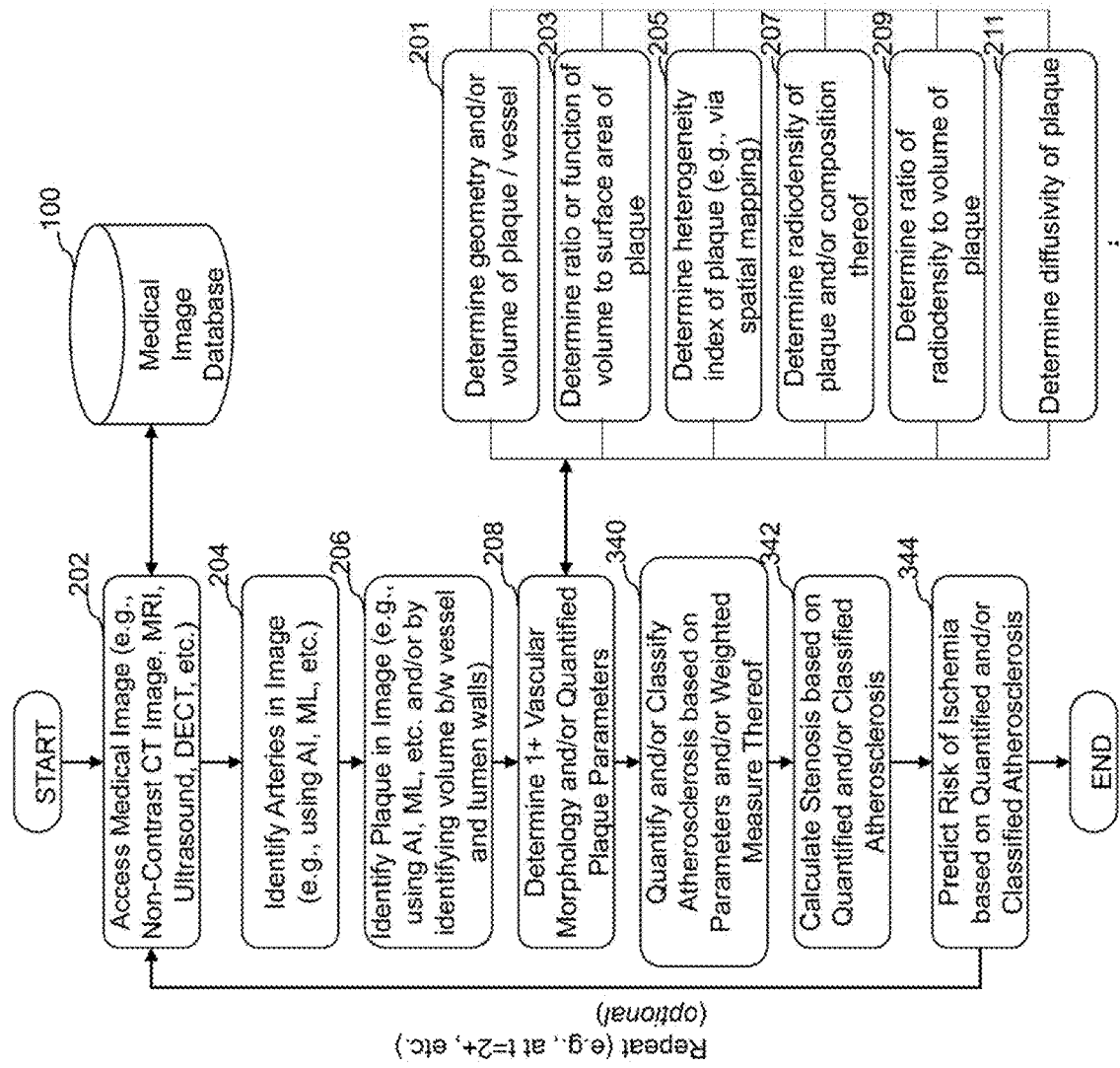
FIG. 3B is a flowchart illustrating an overview of an example embodiment(s) of a method for quantification of atherosclerosis based on medical image analysis.

FIG. 3B is a flowchart illustrating an overview of an example embodiment(s) of a method for quantification and/or classification of atherosclerosis based on medical image analysis. As illustrated in FIG. 3B, in some embodiments, the system can be configured to access a medical image at block 202, such as a CT scan of a coronary region of a subject. Further, in some embodiments, the system can be configured to identify one or more arteries at block 204 and/or one or more regions of plaque at block 206. In addition, in some embodiments, the system can be configured to determine one or more vascular morphology and/or quantified plaque parameters at block 208. For example, in some embodiments, the system can be configured to determine a geometry and/or volume of a region of plaque and/or a vessel at block 201, a ratio or function of volume to surface area of a region of plaque at block 203, a heterogeneity or homogeneity index of a region of plaque at block 205, radiodensity of a region of plaque and/or a composition thereof by ranges of radiodensity values at block 207, a ratio of radiodensity to volume of a region of plaque at block 209, and/or a diffusivity of a region of plaque at block 211. Additional detail regarding the processes and techniques represented in blocks 202, 204, 206, 208, 201, 203, 205, 207, 209, and 211 can be found in the description above in relation to FIG. 2A.

In some embodiments, the system can be configured quantify and/or classify atherosclerosis at block 340 based on the determined one or more vascular morphology and/or quantified plaque parameters. In some embodiments, the system can be configured to generate a weighted measure of one or more vascular morphology parameters and/or quantified plaque parameters determined and/or derived from raw medical images. For example, in some embodiments, the system can be configured to weight one or more vascular morphology parameters and/or quantified plaque parameters equally. In some embodiments, the system can be configured weight one or more vascular morphology parameters and/or quantified plaque parameters differently. In some embodiments, the system can be configured weight one or more vascular morphology parameters and/or quantified plaque parameters logarithmically, algebraically, and/or utilizing another mathematical transform. In some embodiments, the system is configured to quantify and/or classify atherosclerosis at block 340 using the weighted measure and/or using only some of the vascular morphology parameters and/or quantified plaque parameters.

In some embodiments, the system is configured to generate a weighted measure of the one or more vascular morphology parameters and/or quantified plaque parameters by comparing the same to one or more known vascular morphology parameters and/or quantified plaque parameters that are derived from medical images of other subjects. For example, the one or more known vascular morphology parameters and/or quantified plaque parameters can be derived from one or more healthy subjects and/or subjects at risk of coronary vascular disease.

In some embodiments, the system is configured to classify atherosclerosis of a subject based on the quantified atherosclerosis as one or more of high risk, medium risk, or low risk. In some embodiments, the system is configured to classify atherosclerosis of a subject based on the quantified atherosclerosis using an AI, ML, and/or other algorithm. In some embodiments, the system is configured to classify atherosclerosis of a subject by combining and/or weighting one or more of a ratio of volume of surface area, volume, heterogeneity index, and radiodensity of the one or more regions of plaque.

In some embodiments, a plaque having a low ratio of volume to surface area or a low absolute volume itself can indicate that the plaque is stable. As such, in some embodiments, the system can be configured to determine that a ratio of volume to surface area of a region of plaque below a predetermined threshold is indicative of a low risk atherosclerosis. Thus, in some embodiments, the system can be configured to take into account the number and/or sides of a plaque. For example, if there are a higher number of plaques with smaller sides, then that can be associated with a higher surface area or more irregularity, which in turn can be associated with a higher surface area to volume ratio. In contrast, if there are fewer number of plaques with larger sides or more regularity, then that can be associated with a lower surface area to volume ratio or a higher volume to surface area ratio. In some embodiments, a high radiodensity value can indicate that a plaque is highly calcified or stable, whereas a low radiodensity value can indicate that a plaque is less calcified or unstable. As such, in some embodiments, the system can be configured to determine that a radiodensity of a region of plaque above a predetermined threshold is indicative of a low risk atherosclerosis. In some embodiments, a plaque having a low heterogeneity or high homogeneity can indicate that the plaque is stable. As such, in some embodiments, the system can be configured to determine that a heterogeneity of a region of plaque below a predetermined threshold is indicative of a low risk atherosclerosis.

In some embodiments, at block 342, the system is configured to calculate or determine a numerical calculation or representation of coronary stenosis based on the quantified and/or classified atherosclerosis derived from the medical image. In some embodiments, the system is configured to calculate stenosis using the one or more vascular morphology parameters and/or quantified plaque parameters derived from the medical image of a coronary region of the subject.

In some embodiments, at block 344, the system is configured to predict a risk of ischemia for the subject based on the quantified and/or classified atherosclerosis derived from the medical image. In some embodiments, the system is configured to calculate a risk of ischemia using the one or more vascular morphology parameters and/or quantified plaque parameters derived from the medical image of a coronary region of the subject.

In some embodiments, the system is configured to generate a proposed treatment for the subject based on the quantified and/or classified atherosclerosis, stenosis, and/or risk of ischemia, wherein all of the foregoing are derived automatically and/or dynamically from a raw medical image using image processing algorithms and techniques.

In some embodiments, one or more processes described herein in connection with FIG. 3A can be repeated. For example, if a medical image of the same subject is taken again at a later point in time, one or more processes described herein can be repeated and the analytical results thereof can be used for tracking of quantified atherosclerosis for a subject and/or other purposes.

Quantification of Plaque, Stenosis, and/or CAD-RADS Score

As discussed herein, in some embodiments, the system is configured to take the guesswork out of interpretation of medical images and provide substantially exact and/or substantially accurate calculations or estimates of stenosis percentage, atherosclerosis, and/or Coronary Artery Disease-Reporting and Data System (CAD-RADS) score as derived from a medical image. As such, in some embodiments, the system can enhance the reads of the imagers by providing comprehensive quantitative analyses that can improve efficiency, accuracy, and/or reproducibility.

Figure 3C:
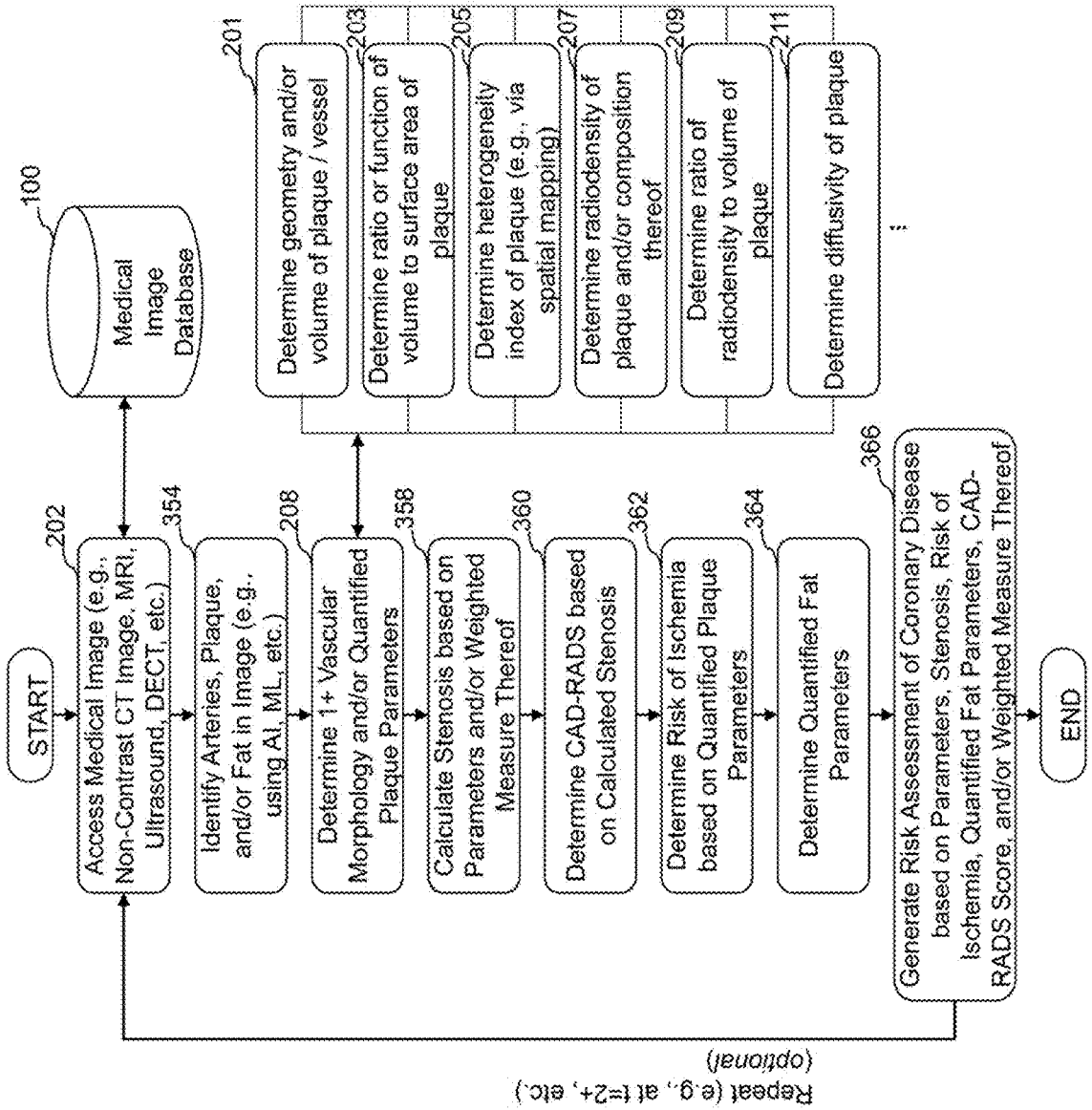
FIG. 3C is a flowchart illustrating an overview of an example embodiment(s) of a method for quantification of stenosis and generation of a CAD-RADS score based on medical image analysis.

FIG. 3C is a flowchart illustrating an overview of an example embodiment(s) of a method for quantification of stenosis and generation of a CAD-RADS score based on medical image analysis. As illustrated in FIG. 3A, in some embodiments, the system can be configured to access a medical image at block 202. Additional detail regarding the types of medical images and other processes and techniques represented in block 202 can be found in the description above in relation to FIG. 2A.

In some embodiments, at block 354, the system is configured to identify one or more arteries, plaque, and/or fat in the medical image, for example using AI, ML, and/or other algorithms. The processes and techniques for identifying one or more arteries, plaque, and/or fat can include one or more of the same features as described above in relation to blocks 204 and 206. In particular, in some embodiments, the system can be configured to utilize one or more AI and/or ML algorithms to automatically and/or dynamically identify one or more arteries, including for example coronary arteries, carotid arteries, aorta, renal artery, lower extremity artery, and/or cerebral artery. In some embodiments, one or more AI and/or ML algorithms can be trained using a Convolutional Neural Network (CNN) on a set of medical images on which arteries have been identified, thereby allowing the AI and/or ML algorithm automatically identify arteries directly from a medical image. In some embodiments, the arteries are identified by size and/or location.

Further, in some embodiments, the system can be configured to identify one or more regions of plaque in the medical image, for example using one or more AI and/or ML algorithms to automatically and/or dynamically identify one or more regions of plaque. In some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system can be configured to identify a vessel wall and a lumen wall for each of the identified coronary arteries in the medical image. In some embodiments, the system is then configured to determine the volume in between the vessel wall and the lumen wall as plaque. In some embodiments, the system can be configured to identify regions of plaque based on the radiodensity values typically associated with plaque, for example by setting a predetermined threshold or range of radiodensity values that are typically associated with plaque with or without normalizing using a normalization device.

Similarly, in some embodiments, the system can be configured to identify one or more regions of fat, such as epicardial fat, in the medical image, for example using one or more AI and/or ML algorithms to automatically and/or dynamically identify one or more regions of fat. In some embodiments, the one or more AI and/or ML algorithms can be trained using a Convolutional Neural Network (CNN) on a set of medical images on which regions of fat have been identified, thereby allowing the AI and/or ML algorithm automatically identify regions of fat directly from a medical image. In some embodiments, the system can be configured to identify regions of fat based on the radiodensity values typically associated with fat, for example by setting a predetermined threshold or range of radiodensity values that are typically associated with fat with or without normalizing using a normalization device.

In some embodiments, the system can be configured to determine one or more vascular morphology and/or quantified plaque parameters at block 208. For example, in some embodiments, the system can be configured to determine a geometry and/or volume of a region of plaque and/or a vessel at block 201, a ratio or function of volume to surface area of a region of plaque at block 203, a heterogeneity or homogeneity index of a region of plaque at block 205, radiodensity of a region of plaque and/or a composition thereof by ranges of radiodensity values at block 207, a ratio of radiodensity to volume of a region of plaque at block 209, and/or a diffusivity of a region of plaque at block 211. Additional detail regarding the processes and techniques represented in blocks 208, 201, 203, 205, 207, 209, and 211 can be found in the description above in relation to FIG. 2A.

In some embodiments, at block 358, the system is configured to calculate or determine a numerical calculation or representation of coronary stenosis based on the one or more vascular morphology parameters and/or quantified plaque parameters derived from the medical image of a coronary region of the subject. In some embodiments, the system can be configured to generate a weighted measure of one or more vascular morphology parameters and/or quantified plaque parameters determined and/or derived from raw medical images. For example, in some embodiments, the system can be configured weight one or more vascular morphology parameters and/or quantified plaque parameters equally. In some embodiments, the system can be configured to weight one or more vascular morphology parameters and/or quantified plaque parameters differently. In some embodiments, the system can be configured weight one or more vascular morphology parameters and/or quantified plaque parameters logarithmically, algebraically, and/or utilizing another mathematical transform. In some embodiments, the system is configured to calculate stenosis at block 358 using the weighted measure and/or using only some of the vascular morphology parameters and/or quantified plaque parameters. In some embodiments, the system can be configured to calculate stenosis on a vessel-by-vessel basis or a region-by-region basis.

In some embodiments, based on the calculated stenosis, the system is configured to determine a CAD-RADS score at block 360. This is in contrast to preexisting methods of determining a CAD-RADS based on eyeballing or general assessment of a medical image by a physician, which can result in unreproducible results. In some embodiments described herein, however, the system can be configured to generate a reproducible and/or objective calculated CAD-RADS score based on automatic and/or dynamic image processing of a raw medical image.

In some embodiments, at block 362, the system can be configured to determine a presence or risk of ischemia based on the calculated stenosis, one or more quantified plaque parameters and/or vascular morphology parameters derived from the medical image. For example, in some embodiments, the system can be configured to determine a presence or risk of ischemia by combining one or more of the foregoing parameters, either weighted or not, or by using some or all of these parameters on an individual basis. In some embodiments, the system can be configured to determine a presence of risk of ischemia by comparing one or more of the calculated stenosis, one or more quantified plaque parameters and/or vascular morphology parameters to a database of known such parameters derived from medical images of other subjects, including for example healthy subjects and/or subjects at risk of a cardiovascular event. In some embodiments, the system can be configured to calculate presence or risk of ischemia on a vessel-by-vessel basis or a region-by-region basis.

In some embodiments, at block 364, the system can be configured to determine one or more quantified parameters of fat for one or more regions of fat identified from the medical image. For example, in some embodiments, the system can utilize any of the processes and/or techniques discussed herein in relation to deriving quantified parameters of plaque, such as those described in connection with blocks 208, 201, 203, 205, 207, 209, and 211. In particular, in some embodiments, the system can be configured to determine one or more parameters of fat, including volume, geometry, radiodensity, and/or the like of one or more regions of fat within the medical image.

In some embodiments, at block 366, the system can be configured to generate a risk assessment of cardiovascular disease or event for the subject. In some embodiments, the generated risk assessment can comprise a risk score indicating a risk of coronary disease for the subject. In some embodiments, the system can generate a risk assessment based on an analysis of one or more vascular morphology parameters, one or more quantified plaque parameters, one or more quantified fat parameters, calculated stenosis, risk of ischemia, CAD-RADS score, and/or the like. In some embodiments, the system can be configured to generate a weighted measure of one or more vascular morphology parameters, one or more quantified plaque parameters, one or more quantified fat parameters, calculated stenosis, risk of ischemia, and/or CAD-RADS score of the subject. For example, in some embodiments, the system can be configured weight one or more of the foregoing parameters equally. In some embodiments, the system can be configured weight one or more of these parameters differently. In some embodiments, the system can be configured weight one or more of these parameters logarithmically, algebraically, and/or utilizing another mathematical transform. In some embodiments, the system is configured to generate a risk assessment of coronary disease or cardiovascular event for the subject at block 366 using the weighted measure and/or using only some of these parameters.

In some embodiments, the system can be configured to generate a risk assessment of coronary disease or cardiovascular event for the subject by combining one or more of the foregoing parameters, either weighted or not, or by using some or all of these parameters on an individual basis. In some embodiments, the system can be configured to generate a risk assessment of coronary disease or cardiovascular event by comparing one or more vascular morphology parameters, one or more quantified plaque parameters, one or more quantified fat parameters, calculated stenosis, risk of ischemia, and/or CAD-RADS score of the subject to a database of known such parameters derived from medical images of other subjects, including for example healthy subjects and/or subjects at risk of a cardiovascular event.

Further, in some embodiments, the system can be configured to automatically and/or dynamically generate a CAD-RADS modifier based on one or more of the determined one or more vascular morphology parameters, the set of quantified plaque parameters of the one or more regions of plaque, the quantified coronary stenosis, the determined presence or risk of ischemia, and/or the determined set of quantified fat parameters. In particular, in some embodiments, the system can be configured to automatically and/or dynamically generate one or more applicable CAD-RADS modifiers for the subject, including for example one or more of nondiagnostic (N), stent (S), graft (G), or vulnerability (V), as defined by and used by CAD-RADS. For example, N can indicate that a study is non-diagnostic, S can indicate the presence of a stent, G can indicate the presence of a coronary artery bypass graft, and V can indicate the presence of vulnerable plaque, for example showing a low radiodensity value.

In some embodiments, the system can be configured to generate a proposed treatment for the subject based on the generated risk assessment of coronary disease, one or more vascular morphology parameters, one or more quantified plaque parameters, one or more quantified fat parameters, calculated stenosis, risk of ischemia, CAD-RADS score, and/or CAD-RADS modifier derived from the raw medical image using image processing.

In some embodiments, one or more processes described herein in connection with FIG. 3B can be repeated. For example, if a medical image of the same subject is taken again at a later point in time, one or more processes described herein can be repeated and the analytical results thereof can be used for tracking of quantified plaque, calculated stenosis, CAD-RADS score and/or modifier derived from a medical image(s), risk determined risk of ischemia, quantified fat parameters, generated risk assessment of coronary disease for a subject, and/or other purposes.

Disease Tracking

In some embodiments, the systems, methods, and devices described herein can be configured to track the progression and/or regression of an arterial and/or plaque-based disease, such as a coronary disease. For example, in some embodiments, the system can be configured to track the progression and/or regression of a disease by automatically and/or dynamically analyzing a plurality of medical images obtained from different times using one or more techniques discussed herein and comparing different parameters derived therefrom. As such, in some embodiments, the system can provide an automated disease tracking tool using non-invasive raw medical images as an input, which does not rely on subjective assessment.

In particular, in some embodiments, the system can be configured to utilize a four-category system to determine whether plaque stabilization or worsening is occurring in a subject. For example, in some embodiments, these categories can include: (1) "plaque progression" or "rapid plaque progression"; (2) "mixed response—calcium dominant" or "non-rapid calcium dominant mixed response"; (3) "mixed response—non-calcium dominant" or "non-rapid non-calcium dominant mixed response"; or (4) "plaque regression."

In some embodiments, in "plaque progression" or "rapid plaque progression," the overall volume or relative volume of plaque increases. In some embodiments, in "mixed response—calcium dominant" or "non-rapid calcium dominant mixed response," the plaque volume remains relatively constant or does not increase to the threshold level of "rapid plaque progression" but there is a general progression of calcified plaque and a general regression of non-calcified plaque. In some embodiments, in "mixed response—non-calcium dominant" or "non-rapid non-calcium dominant mixed response," the plaque volume remains relatively constant but there is a general progression of non-calcified plaque and a general regression of calcified plaque. In some embodiments, in "plaque regression," the overall volume or relative volume of plaque decreases.

In some embodiments, these 4 categories can be expanded to be more granular, for example including for higher vs. lower density calcium plaques (e.g., for those >vs. <1000 Hounsfield units) and/or to categorize more specifically in calcium-dominant and non-calcified plaque-dominant mixed response. For example, for the non-calcified plaque-dominant mixed response, the non-calcified plaque can further include necrotic core, fibrofatty plaque and/or fibrous plaque as separate categories within the overall umbrella of non-calcified plaque. Similarly, calcified plaques can be categorized as lower density calcified plaques, medium density calcified plaques and high density calcified plaques.

Figure 3D:
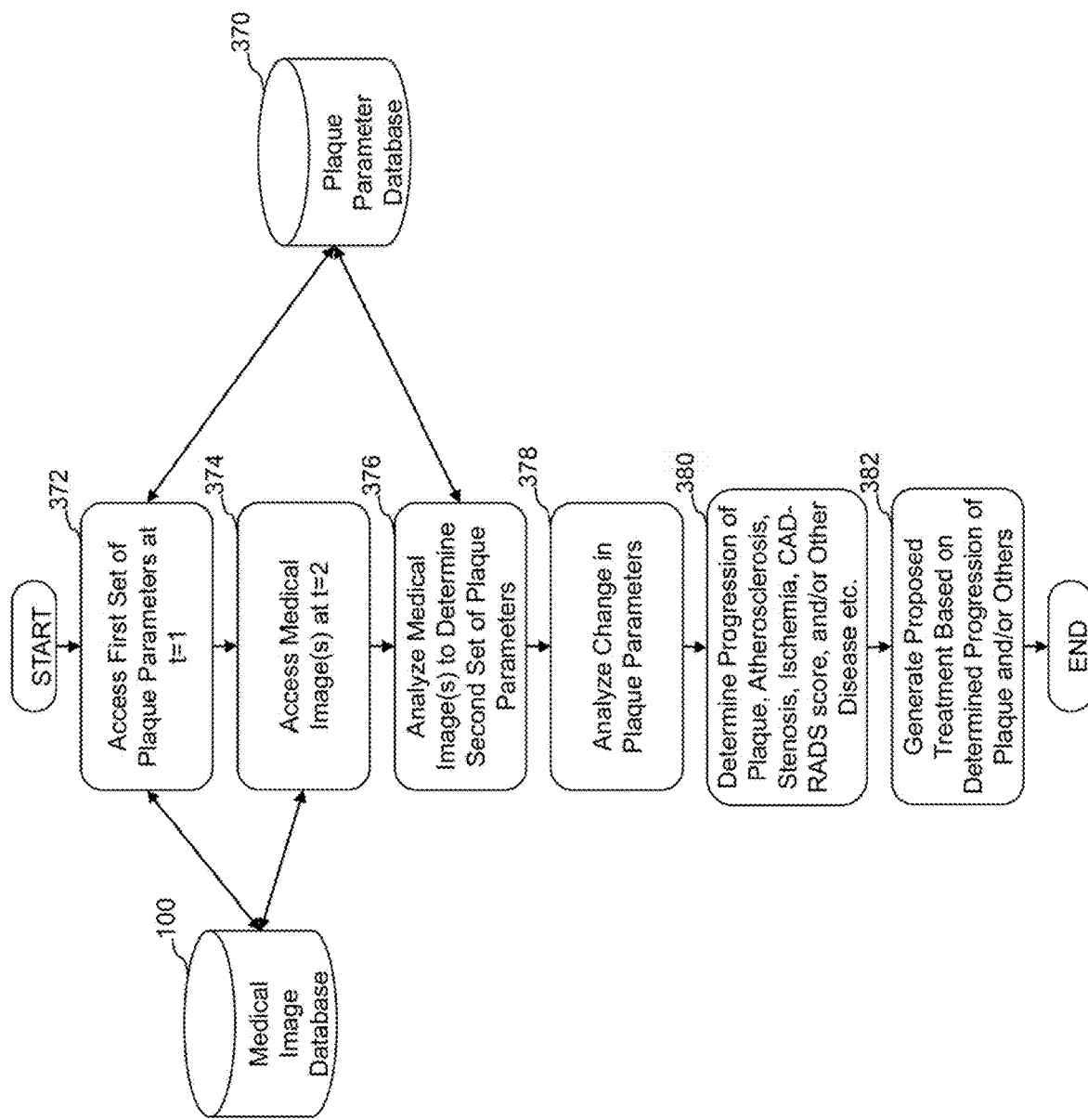
FIG. 3D is a flowchart illustrating an overview of an example embodiment(s) of a method for disease tracking based on medical image analysis.

FIG. 3D is a flowchart illustrating an overview of an example embodiment(s) of a method for disease tracking based on medical image analysis. For example, in some embodiments, the system can be configured to track the progression and/or regression of a plaque-based disease or condition, such as a coronary disease relating to or involving atherosclerosis, stenosis, ischemia, and/or the like, by analyzing one or more medical images obtained non-invasively.

As illustrated in FIG. 3D, in some embodiments, the system at block 372 is configured to access a first set of plaque parameters derived from a medical image of a subject at a first point in time. In some embodiments, the medical image can be stored in a medical image database 100 and can include any of the types of medical images described above, including for example CT, non-contrast CT, contrast-enhanced CT, MR, DECT, Spectral CT, and/or the like. In some embodiments, the medical image of the subject can comprise the coronary region, coronary arteries, carotid arteries, renal arteries, abdominal aorta, cerebral arteries, lower extremities, and/or upper extremities of the subject. In some embodiments, the set of plaque parameters can be stored in a plaque parameter database 370, which can include any of the quantified plaque parameters discussed above in relation to blocks 208, 201, 203, 205, 207, 209, and/or 211.

In some embodiments, the system can be configured to directly access the first set of plaque parameters that were previously derived from a medical image(s) and/or stored in a plaque parameter database 370. In some embodiments, the plaque parameter database 370 can be locally accessible and/or remotely accessible by the system via a network connection. In some embodiments, the system can be configured to dynamically and/or automatically derive the first set of plaque parameters from a medical image taken from a first point in time.

In some embodiments, at block 374, the system can be configured to access a second medical image(s) of the subject, which can be obtained from the subject at a later point in time than the medical image from which the first set of plaque parameters were derived. In some embodiments, the medical image can be stored in a medical image database 100 and can include any of the types of medical images described above, including for example CT, non-contrast CT, contrast-enhanced CT, MR, DECT, Spectral CT, and/or the like.

In some embodiments, at block 376, the system can be configured to dynamically and/or automatically derive a second set of plaque parameters from the second medical image taken from the second point in time. In some embodiments, the second set of plaque parameters can include any of the quantified plaque parameters discussed above in relation to blocks 208, 201, 203, 205, 207, 209, and/or 211. In some embodiments, the system can be configured to store the derived or determined second set of plaque parameters in the plaque parameter database 370.

In some embodiments, at block 378, the system can be configured to analyze changes in one or more plaque parameters between the first set derived from a medical image taken at a first point in time to the second set derived from a medical image taken at a later point in time. For example, in some embodiments, the system can be configured to compare a quantified plaque parameter between the two scans, such as for example radiodensity, volume, geometry, location, ratio or function of volume to surface area, heterogeneity index, radiodensity composition, radiodensity composition as a function of volume, ratio of radiodensity to volume, diffusivity, any combinations or relations thereof, and/or the like of one or more regions of plaque. In some embodiments, the system can be configured to determine the heterogeneity index of one or more regions of plaque by generating a spatial mapping or a three-dimensional histogram of radiodensity values across a geometric shape of one or more regions of plaque. In some embodiments, the system is configured to analyze changes in one or more non-image based metrics, such as for example serum biomarkers, genetics, omics, transcriptomics, microbiomics, and/or metabolomics.

In some embodiments, the system is configured to determine a change in plaque composition in terms of radiodensity or stable v. unstable plaque between the two scans. For example, in some embodiments, the system is configured to determine a change in percentage of higher radiodensity or stable plaques v. lower radiodensity or unstable plaques between the two scans. In some embodiments, the system can be configured to track a change in higher radiodensity plaques v. lower radiodensity plaques between the two scans. In some embodiments, the system can be configured to define higher radiodensity plaques as those with a Hounsfield unit of above 1000 and lower radiodensity plaques as those with a Hounsfield unit of below 1000.

In some embodiments, at block 380, the system can be configured to determine the progression or regression of plaque and/or any other related measurement, condition, assessment, or related disease based on the comparison of the one or more parameters derived from two or more scans and/or change in one or more non-image based metrics, such as serum biomarkers, genetics, omics, transcriptomics, microbiomics, and/or metabolomics. For example, in some embodiments, the system can be configured to determine the progression and/or regression of plaque in general, atherosclerosis, stenosis, risk or presence of ischemia, and/or the like. Further, in some embodiments, the system can be configured to automatically and/or dynamically generate a CAD-RADS score of the subject based on the quantified or calculated stenosis, as derived from the two medical images. Additional detail regarding generating a CAD-RADS score is described herein in relation to FIG. 3C. In some embodiments, the system can be configured to determine a progression or regression in the CAD-RADS score of the subject. In some embodiments, the system can be configured to compare the plaque parameters individually and/or combining one or more of them as a weighted measure. For example, in some embodiments, the system can be configured to weight the plaque parameters equally, differently, logarithmically, algebraically, and/or utilizing another mathematical transform. In some embodiments, the system can be configured to utilize only some or all of the quantified plaque parameters.

In some embodiments, the state of plaque progression as determined by the system can include one of four categories, including rapid plaque progression, non-rapid calcium dominant mixed response, non-rapid non-calcium dominant mixed response, or plaque regression. In some embodiments, the system is configured to classify the state of plaque progression as rapid plaque progression when a percent atheroma volume increase of the subject is more than 1% per year. In some embodiments, the system is configured to classify the state of plaque progression as non-rapid calcium dominant mixed response when a percent atheroma volume increase of the subject is less than 1% per year and calcified plaque represents more than 50% of total new plaque formation. In some embodiments, the system is configured to classify the state of plaque progression as non-rapid non-calcium dominant mixed response when a percent atheroma volume increase of the subject is less than 1% per year and non-calcified plaque represents more than 50% of total new plaque formation. In some embodiments, the system is configured to classify the state of plaque progression as plaque regression when a decrease in total percent atheroma volume is present.

In some embodiments, at block 382, the system can be configured to generate a proposed treatment plan for the subject. For example, in some embodiments, the system can be configured to generate a proposed treatment plan for the subject based on the determined progression or regression of plaque and/or any other related measurement, condition, assessment, or related disease based on the comparison of the one or more parameters derived from two or more scans.

In some embodiments, one or more processes described herein in connection with FIG. 3D can be repeated. For example, one or more processes described herein can be repeated and the analytical results thereof can be used for continued tracking of a plaque-based disease and/or other purposes.

Determination of Cause of Change in Calcium

In some embodiments, the systems, methods and devices disclosed herein can be configured to generate analysis and/or reports that can determine the likely cause of an increased calcium score. A high or increased calcium score alone is not representative of any specific cause, either positive or negative. Rather, in general, there can be various possible causes for a high or increased calcium score. For example, in some cases, a high or increased calcium score can be an indicator of significant heart disease and/or that the patient is at increased risk of a heart attack. Also, in some cases, a high or increased calcium score can be an indicator that the patient is increasing the amount of exercise performed, because exercise can convert fatty material plaque within the artery vessel. In some cases, a high or increased calcium score can be an indicator of the patient beginning a statin regimen wherein the statin is converting the fatty material plaque into calcium. Unfortunately, a blood test alone cannot be used to determine which of the foregoing reasons is the likely cause of an increased calcium score. In some embodiments, by utilizing one or more techniques described herein, the system can be configured to determine the cause of an increased or high calcium score.

More specifically, in some embodiments, the system can be configured to track a particular segment of an artery wall vessel of a patient in such a way to monitor the conversion of a fatty deposit material plaque lesion to a mostly calcified plaque deposit, which can be helpful in determining the cause of an increase calcium score, such as one or more of the causes identified above. In addition, in some embodiments, the system can be configured to determine and/or use the location, size, shape, diffusivity and/or the attenuation radiodensity of one or more regions of calcified plaque to determine the cause of an increase in calcium score. As a non-limiting example, if a calcium plaque increases in density, this may represent a stabilization of plaque by treatment or lifestyle, whereas if a new calcium plaque forms where one was not there before (particularly with a lower attenuation density), this may represent an adverse finding of disease progression rather than stabilization. In some embodiments, one or more processes and techniques described herein may be applied for non-contrast CT scans (such as an ECG gated coronary artery calcium score or non-ECG gated chest CT) as well as contrast-enhanced CT scans (such as a coronary CT angiogram).

As another non-limiting example, the CT scan image acquisition parameters can be altered to improve understanding of calcium changes over time. As an example, traditional coronary artery calcium imaging is done using a 2.5-3.0 mm slice thickness and detecting voxels/pixels that are 130 Hounsfield units or greater. An alternative may be to do "thin" slice imaging with 0.5 mm slice thickness or similar; and detecting all Hounsfield units densities below 130 and above a certain threshold (e.g., 100) that may identify less dense calcium that may be missed by an arbitrary 130 Hounsfield unit threshold.

Figure 3E:
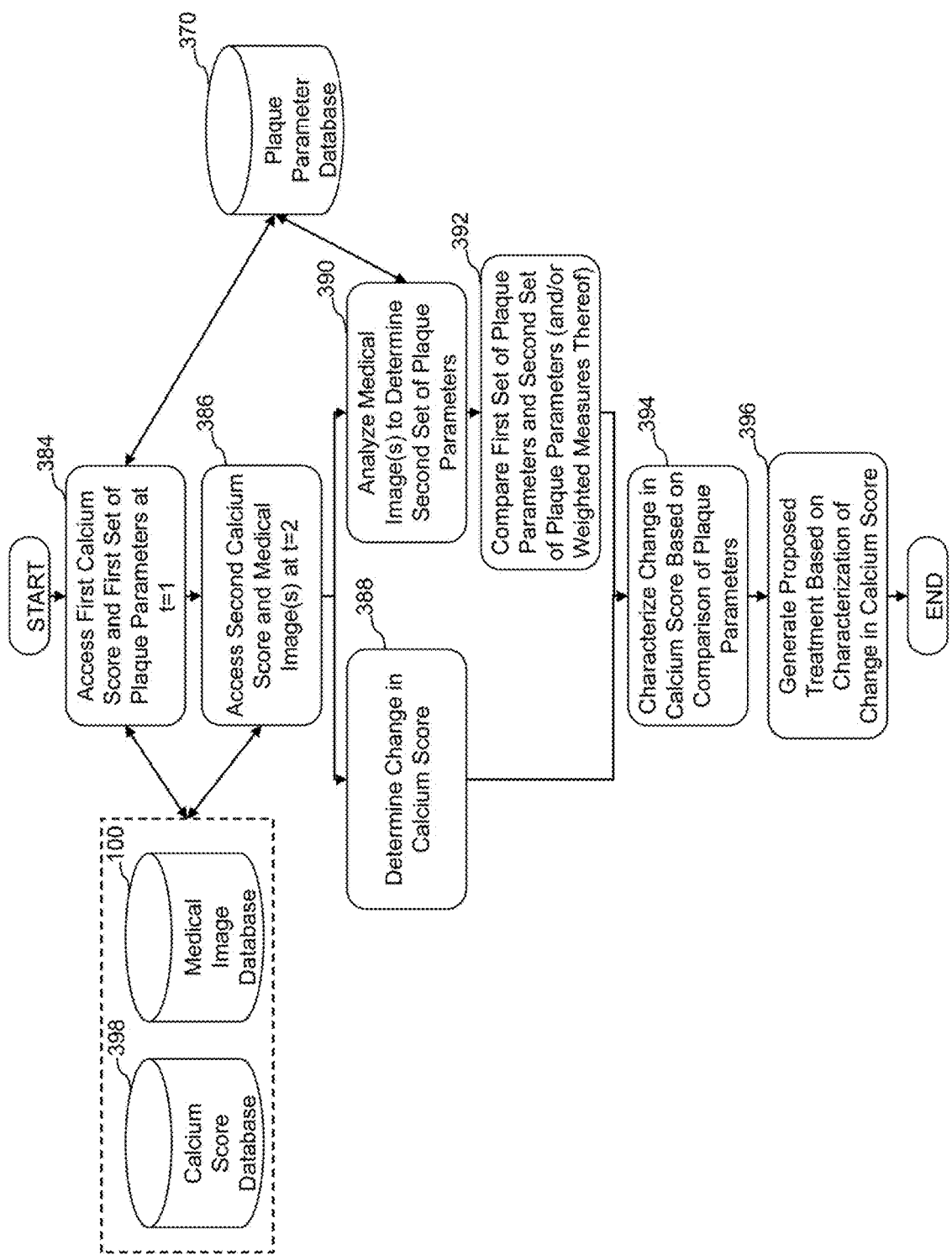
FIG. 3E is a flowchart illustrating an overview of an example embodiment(s) of a method for determination of cause of change in calcium score based on medical image analysis.

FIG. 3E is a flowchart illustrating an overview of an example embodiment(s) of a method for determination of cause of change in calcium score, whether an increase or decrease, based on medical image analysis.

As illustrated in FIG. 3E, in some embodiments, the system can be configured to access a first calcium score and/or a first set of plaque parameters of a subject at block 384. The first calcium score and/or a first set of plaque parameters can be derived from a medical image of a subject and/or from a blood test at a first point in time. In some embodiments, the medical image can be stored in a medical image database 100 and can include any of the types of medical images described above, including for example CT, non-contrast CT, contrast-enhanced CT, MR, DECT, Spectral CT, and/or the like. In some embodiments, the medical image of the subject can comprise the coronary region, coronary arteries, carotid arteries, renal arteries, abdominal aorta, cerebral arteries, lower extremities, and/or upper extremities of the subject. In some embodiments, the set of plaque parameters can be stored in a plaque parameter database 370, which can include any of the quantified plaque parameters discussed above in relation to blocks 208, 201, 203, 205, 207, 209, and/or 211.

In some embodiments, the system can be configured to directly access and/or retrieve the first calcium score and/or first set of plaque parameters that are stored in a calcium score database 398 and/or plaque parameter database 370 respectively. In some embodiments, the plaque parameter database 370 and/or calcium score database 298 can be locally accessible and/or remotely accessible by the system via a network connection. In some embodiments, the system can be configured to dynamically and/or automatically derive the first set of plaque parameters and/or calcium score from a medical image and/or blood test of the subject taken from a first point in time.

In some embodiments, at block 386, the system can be configured to access a second calcium score and/or second medical image(s) of the subject, which can be obtained from the subject at a later point in time than the first calcium score and/or medical image from which the first set of plaque parameters were derived. For example, in some embodiments, the second calcium score can be derived from the second medical image and/or a second blood test taken of the subject at a second point in time. In some embodiments, the second calcium score can be stored in the calcium score database 398. In some embodiments, the medical image can be stored in a medical image database 100 and can include any of the types of medical images described above, including for example CT, non-contrast CT, contrast-enhanced CT, MR, DECT, Spectral CT, and/or the like.

In some embodiments, at block 388, the system can be configured to compare the first calcium score to the second calcium score and determine a change in the calcium score. However, as discussed above, this alone typically does not provide insight as to the cause of the change in calcium score, if any. In some embodiments, if there is no statistically significant change in calcium score between the two readings, for example if any difference is below a predetermined threshold value, then the system can be configured to end the analysis of the change in calcium score. In some embodiments, if there is a statistically significant change in calcium score between the two readings, for example if the difference is above a predetermined threshold value, then the system can be configured to continue its analysis.

In particular, in some embodiments, at block 390, the system can be configured to dynamically and/or automatically derive a second set of plaque parameters from the second medical image taken from the second point in time. In some embodiments, the second set of plaque parameters can include any of the quantified plaque parameters discussed above in relation to blocks 208, 201, 203, 205, 207, 209, and/or 211. In some embodiments, the system can be configured to store the derived or determined second set of plaque parameters in the plaque parameter database 370.

In some embodiments, at block 392, the system can be configured to analyze changes in one or more plaque parameters between the first set derived from a medical image taken at a first point in time to the second set derived from a medical image taken at a later point in time. For example, in some embodiments, the system can be configured to compare a quantified plaque parameter between the two scans, such as for example radiodensity, volume, geometry, location, ratio or function of volume to surface area, heterogeneity index, radiodensity composition, radiodensity composition as a function of volume, ratio of radiodensity to volume, diffusivity, any combinations or relations thereof, and/or the like of one or more regions of plaque and/or one or more regions surrounding plaque. In some embodiments, the system can be configured to determine the heterogeneity index of one or more regions of plaque by generating a spatial mapping or a three-dimensional histogram of radiodensity values across a geometric shape of one or more regions of plaque. In some embodiments, the system is configured to analyze changes in one or more non-image based metrics, such as for example serum biomarkers, genetics, omics, transcriptomics, microbiomics, and/or metabolomics.

In some embodiments, the system is configured to determine a change in plaque composition in terms of radiodensity or stable v. unstable plaque between the two scans. For example, in some embodiments, the system is configured to determine a change in percentage of higher radiodensity or stable plaques v. lower radiodensity or unstable plaques between the two scans. In some embodiments, the system can be configured to track a change in higher radiodensity plaques v. lower radiodensity plaques between the two scans. In some embodiments, the system can be configured to define higher radiodensity plaques as those with a Hounsfield unit of above 1000 and lower radiodensity plaques as those with a Hounsfield unit of below 1000.

In some embodiments, the system can be configured to compare the plaque parameters individually and/or combining one or more of them as a weighted measure. For example, in some embodiments, the system can be configured to weight the plaque parameters equally, differently, logarithmically, algebraically, and/or utilizing another mathematical transform. In some embodiments, the system can be configured to utilize only some or all of the quantified plaque parameters.

In some embodiments, at block 394, the system can be configured to characterize the change in calcium score of the subject based on the comparison of the one or more plaque parameters, whether individually and/or combined or weighted. In some embodiments, the system can be configured to characterize the change in calcium score as positive, neutral, or negative. For example, in some embodiments, if the comparison of one or more plaque parameters reveals that plaque is stabilizing or showing high radiodensity values as a whole for the subject without generation of any new plaque, then the system can report that the change in calcium score is positive. In contrast, if the comparison of one or more plaque parameters reveals that plaque is destabilizing as a whole for the subject, for example due to generation of new unstable regions of plaque with low radiodensity values, without generation of any new plaque, then the system can report that the change in calcium score is negative. In some embodiments, the system can be configured to utilize any or all techniques of plaque quantification and/or tracking of plaque-based disease analysis discussed herein, include those discussed in connection with FIGS. 3A, 3B, 3C, and 3D.

As a non-limiting example, in some embodiments, the system can be configured to characterize the cause of a change in calcium score based on determining and comparing a change in ratio between volume and radiodensity of one or more regions of plaque between the two scans. Similarly, in some embodiments, the system can be configured to characterize the cause of a change in calcium score based on determining and comparing a change in diffusivity and/or radiodensity of one or more regions of plaque between the two scans. For example, if the radiodensity of a region of plaque has increased, the system can be configured to characterize the change or increase in calcium score as positive. In some embodiments, if the system identifies one or more new regions of plaque in the second image that were not present in the first image, the system can be configured to characterize the change in calcium score as negative. In some embodiments, if the system determines that the volume to surface area ratio of one or more regions of plaque has decreased between the two scans, the system can be configured to characterize the change in calcium score as positive. In some embodiments, if the system determines that a heterogeneity or heterogeneity index of a region is plaque has decreased between the two scans, for example by generating and/or analyzing spatial mapping of radiodensity values, then the system can be configured to characterize the change in calcium score as positive.

In some embodiments, the system is configured to utilize an AI, ML, and/or other algorithm to characterize the change in calcium score based on one or more plaque parameters derived from a medical image. For example, in some embodiments, the system can be configured to utilize an AI and/or ML algorithm that is trained using a CNN and/or using a dataset of known medical images with identified plaque parameters combined with calcium scores. In some embodiments, the system can be configured to characterize a change in calcium score by accessing known datasets of the same stored in a database. For example, the known dataset may include datasets of changes in calcium scores and/or medical images and/or plaque parameters derived therefrom of other subjects in the past. In some embodiments, the system can be configured to characterize a change in calcium score and/or determine a cause thereof on a vessel-by-vessel basis, segment-by-segment basis, plaque-by-plaque basis, and/or a subject basis.

In some embodiments, at block 396, the system can be configured to generate a proposed treatment plan for the subject. For example, in some embodiments, the system can be configured to generate a proposed treatment plan for the subject based on the change in calcium score and/or characterization thereof for the subject.

In some embodiments, one or more processes described herein in connection with FIG. 3E can be repeated. For example, one or more processes described herein can be repeated and the analytical results thereof can be used for continued tracking and/or characterization of changes in calcium score for a subject and/or other purposes.

Prognosis of Cardiovascular Event

In some embodiments, the systems, devices, and methods described herein are configured to generate a prognosis of a cardiovascular event for a subject based on one or more of the medical image-based analysis techniques described herein. For example, in some embodiments, the system is configured to determine whether a patient is at risk for a cardiovascular event based on the amount of bad plaque buildup in the patient's artery vessels. For this purpose, a cardiovascular event can include clinical major cardiovascular events, such as heart attack, stroke or death, as well as disease progression and/or ischemia.

In some embodiments, the system can identify the risk of a cardiovascular event based on a ratio of the amount and/or volume of bad plaque buildup versus the total surface area and/or volume of some or all of the artery vessels in a patient. In some embodiments, if the foregoing ratio exceeds a certain threshold, the system can be configured to output a certain risk factor and/or number and/or level associated with the patient. In some embodiments, the system is configured to determine whether a patient is at risk for a cardiovascular event based on an absolute amount or volume or a ratio of the amount or volume bad plaque buildup in the patient's artery vessels compared to the total volume of some or all of the artery vessels. In some embodiments, the system is configured to determine whether a patient is at risk for a cardiovascular event based on results from blood chemistry or biomarker tests of the patient, for example whether certain blood chemistry or biomarker tests of the patient exceed certain threshold levels. In some embodiments, the system is configured to receive as input from the user or other systems and/or access blood chemistry or biomarker tests data of the patient from a database system. In some embodiments, the system can be configured to utilize not only artery information related to plaque, vessel morphology, and/or stenosis but also input from other imaging data about the non-coronary cardiovascular system, such as subtended left ventricular mass, chamber volumes and size, valvular morphology, vessel (e.g., aorta, pulmonary artery) morphology, fat, and/or lung and/or bone health. In some embodiments, the system can utilize the outputted risk factor to generate a treatment plan proposal. For example, the system can be configured to output a treatment plan that involves the administration of cholesterol reducing drugs, such as statins, in order to transform the soft bad plaque into hard plaque that is safer and more stable for a patient. In general, hard plaque that is largely calcified can have a significant lower risk of rupturing into the artery vessel thereby decreasing the chances of a clot forming in the artery vessel which can decrease a patient's risk of a heart attack or other cardiac event.

FIG. 4A is a flowchart illustrating an overview of an example embodiment(s) of a method for prognosis of a cardiovascular event based on and/or derived from medical image analysis.

As illustrated in FIG. 4A, in some embodiments, the system can be configured to access a medical image at block 202, such as a CT scan of a coronary region of a subject, which can be stored in a medical image database 100. Further, in some embodiments, the system can be configured to identify one or more arteries at block 204 and/or one or more regions of plaque at block 206. In addition, in some embodiments, the system can be configured to determine one or more vascular morphology and/or quantified plaque parameters at block 208. For example, in some embodiments, the system can be configured to determine a geometry and/or volume of a region of plaque and/or a vessel, a ratio or function of volume to surface area of a region of plaque, a heterogeneity or homogeneity index of a region of plaque, radiodensity of a region of plaque and/or a composition thereof by ranges of radiodensity values, a ratio of radiodensity to volume of a region of plaque, and/or a diffusivity of a region of plaque. In addition, in some embodiments, at block 210, the system can be configured to classify one or more regions of plaque as stable v. unstable or good v. bad based on the one or more vascular morphology parameters and/or quantified plaque parameters determined and/or derived from raw medical images. Additional detail regarding the processes and techniques represented in blocks 202, 204, 206, 208, and 210 can be found in the description above in relation to FIG. 2A.

In some embodiments, the system at block 412 is configured to generate a ratio of bad plaque to the vessel on which the bad plaque appears. More specifically, in some embodiments, the system can be configured to determine a total surface area of a vessel identified on a medical image and a surface area of all regions of bad or unstable plaque within that vessel. Based on the foregoing, in some embodiments, the system can be configured to generate a ratio of surface area of all bad plaque within a particular vessel to the surface area of the entire vessel or a portion thereof shown in a medical image. Similarly, in some embodiments, the system can be configured to determine a total volume of a vessel identified on a medical image and a volume of all regions of bad or unstable plaque within that vessel. Based on the foregoing, in some embodiments, the system can be configured to generate a ratio of volume of all bad plaque within a particular vessel to the volume of the entire vessel or a portion thereof shown in a medical image.

In some embodiments, at block 414, the system is further configured to determine a total absolute volume and/or surface area of all bad or unstable plaque identified in a medical image. Also, in some embodiments, at block 416, the system is configured to determine a total absolute volume of all plaque, including good plaque and bad plaque, identified in a medical image. Further, in some embodiments, at block 418, the system can be configured to access or retrieve results from a blood chemistry and/or biomarker test of the patient and/or other non-imaging test results. Furthermore, in some embodiments, at block 422, the system can be configured to access and/or analyze one or more non-coronary cardiovascular system medical images.

In some embodiments, at block 420, the system can be configured to analyze one or more of the generated ratio of bad plaque to a vessel, whether by surface area or volume, total absolute volume of bad plaque, total absolute volume of plaque, blood chemistry and/or biomarker test results, and/or analysis results of one or more non-coronary cardiovascular system medical images to determine whether one or more of these parameters, either individually and/or combined, is above a predetermined threshold. For example, in some embodiments, the system can be configured to analyze one or more of the foregoing parameters individually by comparing them to one or more reference values of healthy subjects and/or subjects at risk of a cardiovascular event. In some embodiments, the system can be configured to analyze a combination, such as a weighted measure, of one or more of the foregoing parameters by comparing the combined or weighted measure thereof to one or more reference values of healthy subjects and/or subjects at risk of a cardiovascular event. In some embodiments, the system can be configured to weight one or more of these parameters equally. In some embodiments, the system can be configured to weight one or more of these parameters differently. In some embodiments, the system can be configured to weight one or more of these parameters logarithmically, algebraically, and/or utilizing another mathematical transform. In some embodiments, the system can be configured to utilize only some of the aforementioned parameters, either individually, combined, and/or as part of a weighted measure.

In some embodiments, at block 424, the system is configured to generate a prognosis for a cardiovascular event for the subject. In particular, in some embodiments, the system is configured to generate a prognosis for cardiovascular event based on one or more of the analysis results of the generated ratio of bad plaque to a vessel, whether by surface area or volume, total absolute volume of bad plaque, total absolute volume of plaque, blood chemistry and/or biomarker test results, and/or analysis results of one or more non-coronary cardiovascular system medical images. In some embodiments, the system is configured to generate the prognosis utilizing an AI, ML, and/or other algorithm. In some embodiments, the generated prognosis comprises a risk score or risk assessment of a cardiovascular event for the subject. In some embodiments, the cardiovascular event can include one or more of atherosclerosis, stenosis, ischemia, heart attack, and/or the like.

In some embodiments, at block 426, the system can be configured to generate a proposed treatment plan for the subject. For example, in some embodiments, the system can be configured to generate a proposed treatment plan for the subject based on the change in calcium score and/or characterization thereof for the subject. In some embodiments, the generated treatment plan can include use of statins, lifestyle changes, and/or surgery.

In some embodiments, one or more processes described herein in connection with FIG. 4A can be repeated. For example, one or more processes described herein can be repeated and the analytical results thereof can be used for continued prognosis of a cardiovascular event for a subject and/or other purposes.

Patient-Specific Stent Determination

In some embodiments, the systems, methods, and devices described herein can be used to determine and/or generate one or more parameters for a patient-specific stent and/or selection or guidance for implantation thereof. In particular, in some embodiments, the systems disclosed herein can be used to dynamically and automatically determine the necessary stent type, length, diameter, gauge, strength, and/or any other stent parameter for a particular patient based on processing of the medical image data, for example using AI, ML, and/or other algorithms.

In some embodiments, by determining one or more patient-specific stent parameters that are best suited for a particular artery area, the system can reduce the risk of patient complications and/or insurance risks because if too large of a stent is implanted, then the artery wall can be stretched too thin resulting in a possible rupture, or undesirable high flow, or other issues. On the other hand, if too small of a stent is implanted, then the artery wall might not be stretched open enough resulting in too little blood flow or other issues.

In some embodiments, the system is configured to dynamically identify an area of stenosis within an artery, dynamically determine a proper diameter of the identified area of the artery, and/or automatically select a stent from a plurality of available stent options. In some embodiments, the selected stent can be configured to prop open the artery area after implantation to the determined proper artery diameter. In some embodiments, the proper artery diameter is determined to be equivalent or substantially equivalent to what the diameter would naturally be without stenosis. In some embodiments, the system can be configured to dynamically generate a patient-specific surgical plan for implanting the selected stent in the identified artery area. For example, the system can be configured to determine whether a bifurcation of the artery is near the identified artery area and generate a patient-specific surgical plan for inserting two guidewires for handling the bifurcation and/or determining the position for jailing and inserting a second stent into the bifurcation.

Figure 4B:
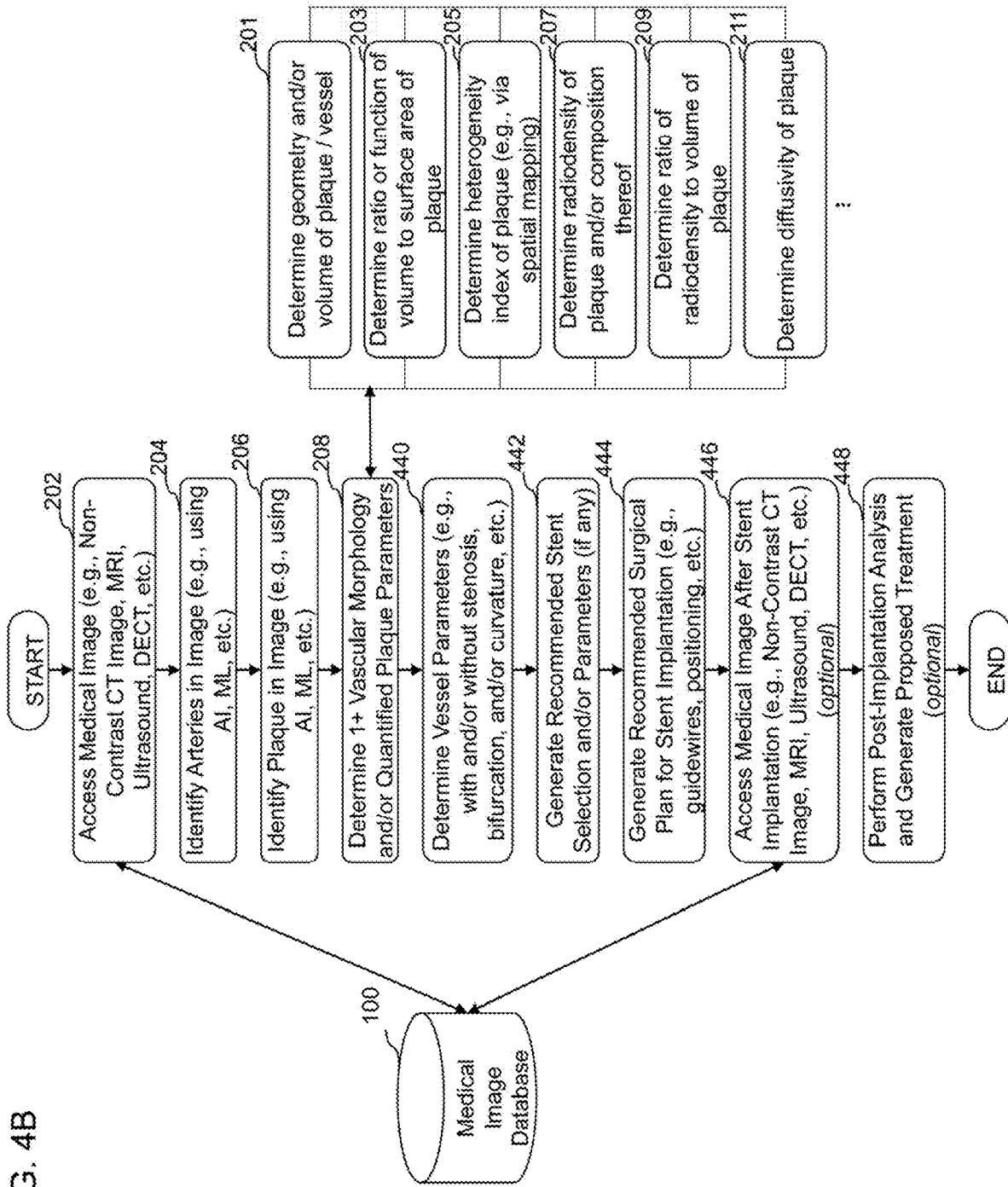
FIG. 4B is a flowchart illustrating an overview of an example embodiment(s) of a method for determination of patient-specific stent parameters based on medical image analysis.

FIG. 4B is a flowchart illustrating an overview of an example embodiment(s) of a method for determination of patient-specific stent parameters based on medical image analysis.

As illustrated in FIG. 4B, in some embodiments, the system can be configured to access a medical image at block 202, such as a CT scan of a coronary region of a subject. Further, in some embodiments, the system can be configured to identify one or more arteries at block 204 and/or one or more regions of plaque at block 206. In addition, in some embodiments, the system can be configured to determine one or more vascular morphology and/or quantified plaque parameters at block 208. For example, in some embodiments, the system can be configured to determine a geometry and/or volume of a region of plaque and/or a vessel at block 201, a ratio or function of volume to surface area of a region of plaque at block 203, a heterogeneity or homogeneity index of a region of plaque at block 205, radiodensity of a region of plaque and/or a composition thereof by ranges of radiodensity values at block 207, a ratio of radiodensity to volume of a region of plaque at block 209, and/or a diffusivity of a region of plaque at block 211. Additional detail regarding the processes and techniques represented in blocks 202, 204, 206, 208, 201, 203, 205, 207, 209, and 211 can be found in the description above in relation to FIG. 2A.

In some embodiments, at block 440, the system can be configured to analyze the medical image to determine one or more vessel parameters, such as the diameter, curvature, vascular morphology, vessel wall, lumen wall, and/or the like. In some embodiments, the system can be configured to determine or derive from the medical image one or more vessel parameters as shown in the medical image, for example with stenosis at certain regions along the vessel. In some embodiments, the system can be configured to determine one or more vessel parameters without stenosis. For example, in some embodiments, the system can be configured to graphically and/or hypothetically remove stenosis or plaque from a vessel to determine the diameter, curvature, and/or the like of the vessel if stenosis did not exist.

In some embodiments, at block 442, the system can be configured to determine whether a stent is recommended for the subject and, if so, one or more recommended parameters of a stent specific for that patient based on the medical analysis. For example, in some embodiments, the system can be configured to analyze one or more of the identified vascular morphology parameters, quantified plaque parameters, and/or vessel parameters. In some embodiments, the system can be configured to utilize an AI, ML, and/or other algorithm. In some embodiments, the system is configured to analyze one or more of the aforementioned parameters individually, combined, and/or as a weighted measure. In some embodiments, one or more of these parameters derived from a medical image, either individually or combined, can be compared to one or more reference values derived or collected from other subjects, including those who had a stent implanted and those who did not. In some embodiments, based on the determined parameters of a patient-specific stent, the system can be configured to determine a selection of a preexisting stent that matches those parameters and/or generate manufacturing instructions to manufacture a patient-specific stent with stent parameters derived from a medical image. In some embodiments, the system can be configured to recommend a diameter of a stent that is less than or substantially equal to the diameter of an artery if stenosis did not exist.

In some embodiments, at block 444, the system can be configured to generate a recommended surgical plan for stent implantation based on the analyzed medical image. For example, in some embodiments, the system can be configured to determine whether a bifurcation exists based on the medical image and/or generate guidelines for the positioning of guidewires and/or stent for the patient prior to surgery. As such, in some embodiments, the system can be configured to generate a detailed surgical plan that is specific to a particular patient based on medical image analysis of plaque and/or other parameters.

In some embodiments, at block 446, the system is configured to access or retrieve one or more medical images after stent implantation. In some embodiments, at block 448, the system can be configured to analyze the accessed medical image to perform post-implantation analysis. For example, in some embodiments, the system can be configured to derive one or more vascular morphology and/or plaque parameters, including any of those discussed herein in relation to block 208, after stent implantation. Based on analysis of the foregoing, in some embodiments, the system can generate further proposed treatment in some embodiments, such as for example recommended use of statins or other medications, lifestyle change, further surgery or stent implantation, and/or the like.

In some embodiments, one or more processes described herein in connection with FIG. 4B can be repeated. For example, one or more processes described herein can be repeated and the analytical results thereof can be used to determine the need for and/or parameters of an additional patient-specific stent for a patient and/or other purposes.

Patient-Specific Report

In some embodiments, the system is configured to dynamically generate a patient-specific report based on the analysis of the processed data generated from the raw CT scan data. In some embodiments, the patient specific report is dynamically generated based on the processed data. In some embodiments, the written report is dynamically generated based on selecting and/or combining certain phrases from a database, wherein certain words, terms, and/or phrases are altered to be specific to the patient and the identified medical issues of the patient. In some embodiments, the system is configured to dynamically select one or more images from the image scanning data and/or the system generated image views described herein, wherein the selected one or more images are dynamically inserted into the written report in order to generate a patient-specific report based on the analysis of the processed data.

In some embodiments, the system is configured to dynamically annotate the selected one or more images for insertion into the patient specific report, wherein the annotations are specific to patient and/or are annotations based on the data processing performed by the devices, methods, and systems disclosed herein, for example, annotating the one or more images to include markings or other indicators to show where along the artery there exists bad plaque buildup that is significant.

In some embodiments, the system is configured to dynamically generate a report based on past and/or present medical data. For example, in some embodiments, the system can be configured to show how a patient's cardiovascular health has changed over a period. In some embodiments, the system is configured to dynamically generate phrases and/or select phrases from a database to specifically describe the cardiovascular health of the patient and/or how the cardiovascular disease has changed within a patient.

In some embodiments, the system is configured to dynamically select one or more medical images from prior medical scanning and/or current medical scanning for insertion into the medical report in order to show how the cardiovascular disease has changed over time in a patient, for example, showing past and present images juxtaposed to each other, or for example, showing past images that are superimposed on present images thereby allowing a user to move or fade or toggle between past and present images.

In some embodiments, the patient-specific report is an interactive report that allows a user to interact with certain images, videos, animations, augmented reality (AR), virtual reality (VR), and/or features of the report. In some embodiments, the system is configured to insert into the patient-specific report dynamically generated illustrations or images of patient artery vessels in order to highlight specific vessels and/or portions of vessels that contain or are likely to contain vascular disease that require review or further analysis. In some embodiments, the dynamically generated patient-specific report is configured to show a user the vessel walls using AR and/or VR.

In some embodiments, the system is configured to insert into the dynamically generated report any ratios and/or dynamically generated data using the methods, systems, and devices disclosed herein. In some embodiments, the dynamically generated report comprises a radiology report. In some embodiments, the dynamically generated report is in an editable document, such as Microsoft Word®, in order to allow the physician to make edits to the report. In some embodiments, the dynamically generated report is saved into a PACS (Picture Archiving and Communication System) or other EMR (electronic medical records) system.

In some embodiments, the system is configured to transform and/or translate data from the imaging into drawings or infographics in a video format, with or without audio, in order to transmit accurately the information in a way that is better understandable to any patient to improve literacy. In some embodiments, this method of improving literacy is coupled to a risk stratification tool that defines a lower risk with higher literacy, and a higher risk with lower literacy. In some embodiments, these report outputs may be patient-derived and/or patient-specific. In some embodiments, real patient imaging data (for example, from their CT) can be coupled to graphics from their CT and/or drawings from the CT to explain the findings further. In some embodiments, real patient imaging data, graphics data and/or drawings data can be coupled to an explaining graphic that is not from the patient but that can help the patient better understand (for example, a video about lipid-rich plaque).

In some embodiments, these patient reports can be imported into an application that allows for following disease over time in relation to control of heart disease risk factors, such as diabetes or hypertension. In some embodiments, an app and/or user interface can allow for following of blood glucose and blood pressure over time and/or relate the changes of the image over time in a way that augments risk prediction.

In some embodiments, the system can be configured to generate a video report that is specific to the patient based on the processed data generated from the raw CT data. In some embodiments, the system is configured to generate and/or provide a personalized cinematic viewing experience for a user, which can be programmed to automatically and dynamically change content based upon imaging findings, associated auto-calculated diagnoses, and/or prognosis algorithms. In some embodiments, the method of viewing, unlike traditional reporting, is through a movie experience which can be in the form of a regular 2D movie and/or through a mixed reality movie experience through AR or VR. In some embodiments, in the case of both 2D and mixed reality, the personalized cinematic experience can be interactive with the patient to predict their prognosis, such as risk of heart attack, rate of disease progression, and/or ischemia.

In some embodiments, the system can be configured to dynamically generate a video report that comprises both cartoon images and/or animation along with audio content in combination with actual CT image data from the patient. In some embodiments, the dynamically generated video medical report is dynamically narrated based on selecting phrases, terms and/or other content from a database such that a voice synthesizer or pre-made voice content can be used for playback during the video report. In some embodiments, the dynamically generated video medical report is configured to comprise any of the images disclosed herein. In some embodiments, the dynamically generated video medical report can be configured to dynamically select one or more medical images from prior medical scanning and/or current medical scanning for insertion into the video medical report in order to show how the cardiovascular disease has changed over time in a patient. For example, in some embodiments, the report can show past and present images juxtaposed next to each other. In some embodiments, the repot can show past images that are superimposed on present images thereby allowing a user to toggle or move or fade between past and present images. In some embodiments, the dynamically generated video medical report can be configured to show actual medical images, such as a CT medical image, in the video report and then transition to an illustrative view or cartoon view (partial or entirely an illustrative or cartoon view) of the actual medical images, thereby highlighting certain features of the patient's arteries. In some embodiments, the dynamically generated video medical report is configured to show a user the vessel walls using AR and/or VR.

Figure 5A:
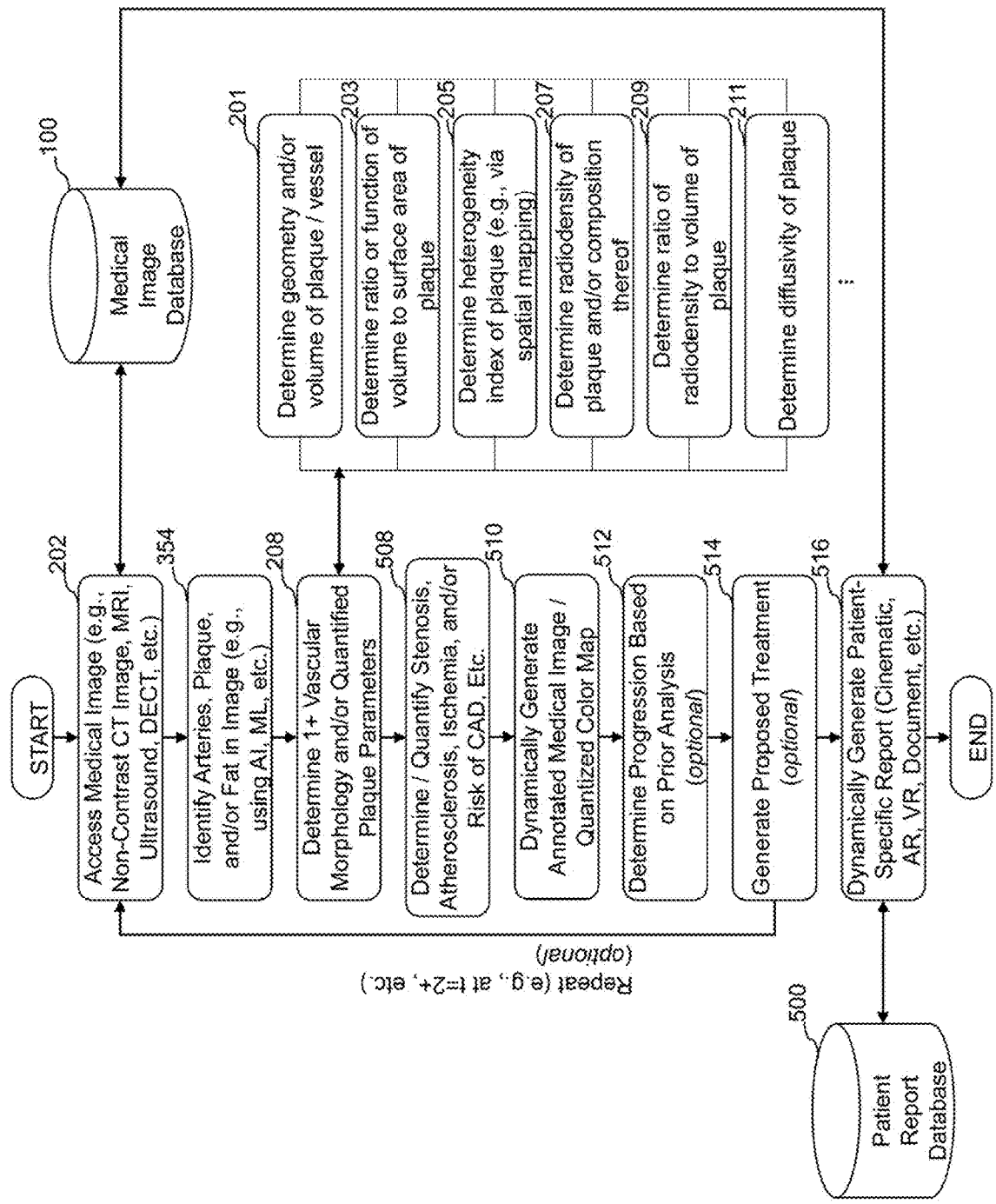
FIG. 5A is a flowchart illustrating an overview of an example embodiment(s) of a method for generation of a patient-specific medical report based on medical image analysis.

FIG. 5A is a flowchart illustrating an overview of an example embodiment(s) of a method for generation of a patient-specific medical report based on medical image analysis. As illustrated in FIG. 5A, in some embodiments, the system can be configured to access a medical image at block 202. In some embodiments, the medical image can be stored in a medical image database 100. Additional detail regarding the types of medical images and other processes and techniques represented in block 202 can be found in the description above in relation to FIG. 2A.

In some embodiments, at block 354, the system is configured to identify one or more arteries, plaque, and/or fat in the medical image, for example using AI, ML, and/or other algorithms. Additional detail regarding the types of medical images and other processes and techniques represented in block 354 can be found in the description above in relation to FIG. 3C.

In some embodiments, at block 208, the system can be configured to determine one or more vascular morphology and/or quantified plaque parameters. For example, in some embodiments, the system can be configured to determine a geometry and/or volume of a region of plaque and/or a vessel at block 201, a ratio or function of volume to surface area of a region of plaque at block 203, a heterogeneity or homogeneity index of a region of plaque at block 205, radiodensity of a region of plaque and/or a composition thereof by ranges of radiodensity values at block 207, a ratio of radiodensity to volume of a region of plaque at block 209, and/or a diffusivity of a region of plaque at block 211. Additional detail regarding the processes and techniques represented in blocks 208, 201, 203, 205, 207, 209, and 211 can be found in the description above in relation to FIG. 2A.

In some embodiments, at block 508, the system can be configured to determine and/or quantify stenosis, atherosclerosis, risk of ischemia, risk of cardiovascular event or disease, and/or the like. The system can be configured to utilize any techniques and/or algorithms described herein, including but not limited to those described above in connection with block 358 and block 366 of FIG. 3C.

In some embodiments, at block 510, the system can be configured to generate an annotated medical image and/or quantized color map using the analysis results derived from the medical image. For example, in some embodiments, the system can be configured to generate a quantized map showing one or more arteries, plaque, fat, good plaque, bad plaque, vascular morphologies, and/or the like.

In some embodiments, at block 512, the system can be configured to determine a progression of plaque and/or disease of the patient, for example based on analysis of previously obtained medical images of the subject. In some embodiments, the system can be configured to utilize any algorithms or techniques described herein in relation to disease tracking, including but not limited to those described in connection with block 380 and/or FIG. 3D generally.

In some embodiments, at block 514, the system can be configured to generate a proposed treatment plan for the patient based on the determined progression of plaque and/or disease. In some embodiments, the system can be configured to utilize any algorithms or techniques described herein in relation to disease tracking and treatment generation, including but not limited to those described in connection with block 382 and/or FIG. 3D generally.

In some embodiments, at block 516, the system can be configured to generate a patient-specific report. The patient-specific report can include one or more medical images of the patient and/or derived graphics thereof. For example, in some embodiments, the patient report can include one or more annotated medical images and/or quantized color maps. In some embodiments, the patient-specific report can include one or more vascular morphology and/or quantified plaque parameters derived from the medical image. In some embodiments, the patient-specific report can include quantified stenosis, atherosclerosis, ischemia, risk of cardiovascular event or disease, CAD-RADS score, and/or progression or tracking of any of the foregoing. In some embodiments, the patient-specific report can include a proposed treatment, such as statins, lifestyle changes, and/or surgery.

In some embodiments, the system can be configured to access and/or retrieve from a patient report database 500 one or more phrases, characterizations, graphics, videos, audio files, and/or the like that are applicable and/or can be used to generate the patient-specific report. In generating the patient-specific report, in some embodiments, the system can be configured to compare one or more parameters, such as those mentioned above and/or derived from a medical image of the patient, with one or more parameters previously derived from other patients. For example, in some embodiments, the system can be configured to compare one or more quantified plaque parameters derived from the medical image of the patient with one or more quantified plaque parameters derived from medical images of other patients in the similar or same age group. Based on the comparison, in some embodiments, the system can be configured to determine which phrases, characterizations, graphics, videos, audio files, and/or the like to include in the patient-specific report, for example by identifying similar previous cases. In some embodiments, the system can be configured to utilize an AI and/or ML algorithm to generate the patient-specific report. In some embodiments, the patient-specific report can include a document, AR experience, VR experience, video, and/or audio component.

Figure 5B:
Figure 5C:
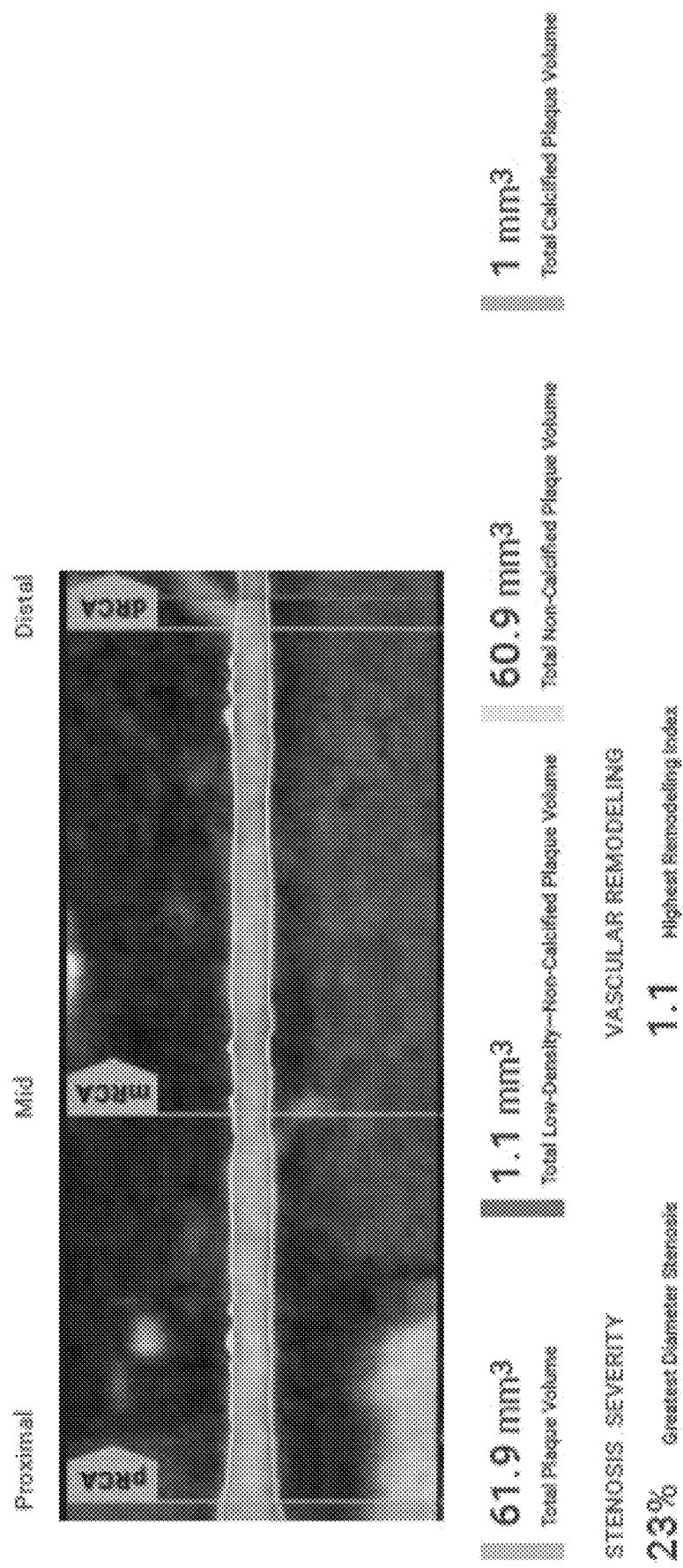
Figure 5E:
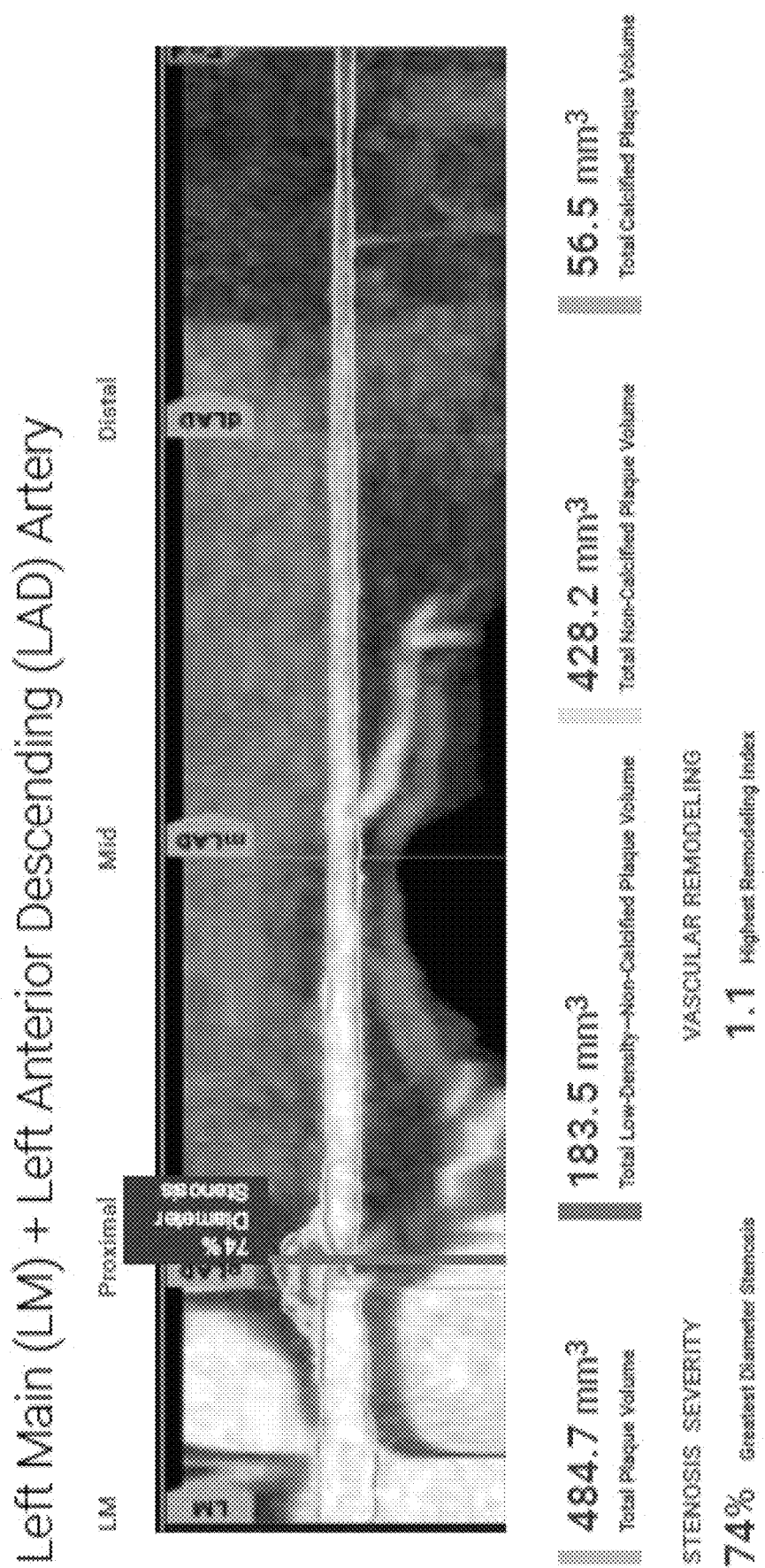
Figure 5G:
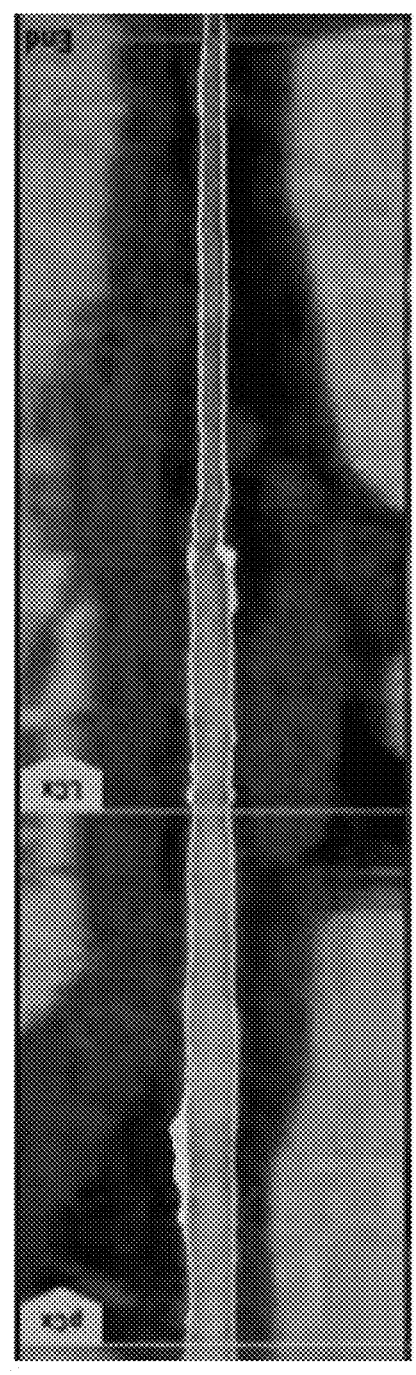
Figure 51:
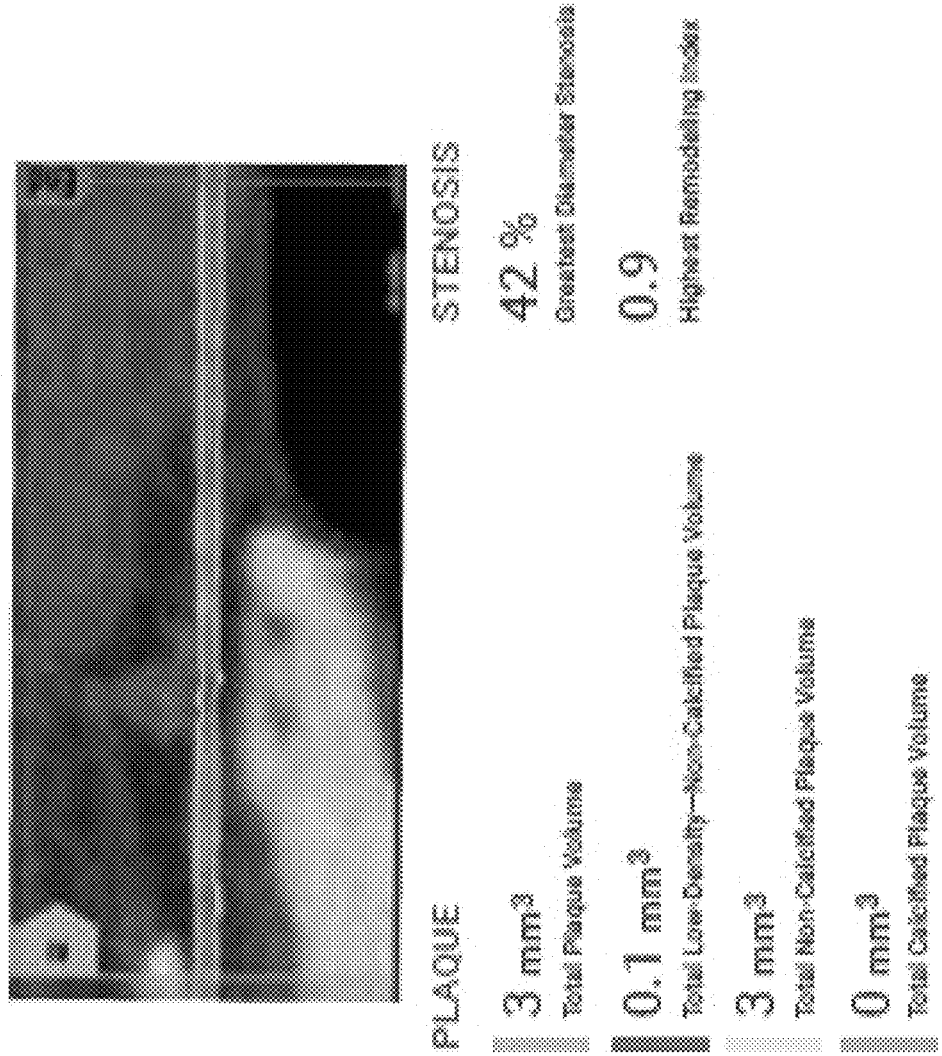

FIGS. 5B-5I illustrate example embodiment(s) of a patient-specific medical report generated based on medical image analysis. In particular, FIG. 5B illustrates an example cover page of a patient-specific report.

FIGS. 5C-5I illustrate portions of an example patient-specific report(s). In some embodiments, a patient-specific report generated by the system may include only some or all of these illustrated portions. As illustrated in FIGS. 5C-5I, in some embodiments, the patient-specific report includes a visualization of one or more arteries and/or portions thereof, such as for example, the Right Coronary Artery (RCA), R-Posterior Descending Artery (R-PDA), R-Posterolateral Branch (R-PLB), Left Main (LM) and Left Anterior Descending (LAD) Artery, 1st Diagonal (D1) Artery, 2nd Diagonal (D2) Artery, Circumflex (Cx) Artery, 1st Obtuse Marginal Branch (OM1), 2nd Obtuse Marginal Branch (OM2), Ramus Intermedius (RI), and/or the like. In some embodiments, for each of the arteries included in the report, the system is configured to generate a straightened view for easy tracking along the length of the vessel, such as for example at the proximal, mid, and/or distal portions of an artery.

In some embodiments, a patient-specific report generated by the system includes a quantified measure of various plaque and/or vascular morphology-related parameters shown within the vessel. In some embodiments, for each or some of the arteries included in the report, the system is configured to generate and/or derive from a medical image of the patient and include in a patient-specific report a quantified measure of the total plaque volume, total low-density or non-calcified plaque volume, total non-calcified plaque value, and/or total calcified plaque volume. Further, in some embodiments, for each or some of the arteries included in the report, the system is configured to generate and/or derive from a medical image of the patient and include in a patient-specific report a quantified measure of stenosis severity, such as for example a percentage of the greatest diameter stenosis within the artery. In some embodiments, for each or some of the arteries included in the patient-specific report, the system is configured to generate and/or derive from a medical image of the patient and include in a patient-specific report a quantified measure of vascular remodeling, such as for example the highest remodeling index.

Visualization/GUI

Atherosclerosis, the buildup of fats, cholesterol and other substances in and on your artery walls (e.g., plaque), which can restrict blood flow. The plaque can burst, triggering a blood clot. Although atherosclerosis is often considered a heart problem, it can affect arteries anywhere in the body. However, determining information about plaque in coronary arteries can be difficult due in part to imperfect imaging data, aberrations that can be present in coronary artery images (e.g., due to movement of the patient), and differences in the manifestation of plaque in different patients. Accordingly, neither calculated information derived from CT images, or visual inspection of the CT images, alone provide sufficient information to determine conditions that exist in the patient's coronary arteries. Portions of this disclosure describe information they can be determined from CT images using automatic or semiautomatic processes. For example, using a machine learning process has been trained on thousands of CT scans determine information depicted in the CT images, and/or utilizing analyst to review and enhance the results of the machine learning process, and the example user interfaces described herein can provide the determined information to another analyst or a medical practitioner. While the information determined from the CT images is invaluable in assessing the condition of a patient's coronary arteries, visual analysis of the coronary arteries by skilled medical practitioner, with the information determined from the CT images in-hand, allows a more comprehensive assessment of the patient's coronary arteries. As indicated herein, embodiments of the system facilitate the analysis and visualization of vessel lumens, vessel walls, plaque and stenosis in and around coronary vessels. This system can display vessels in multi-planar formats, cross-sectional views, 3D coronary artery tree view, axial, sagittal, and coronal views based on a set of computerized tomography (CT) images, e.g., generated by a CT scan of a patient's vessels. The CT images can be Digital Imaging and Communications in Medicine (DICOM) images, a standard for the communication and management of medical imaging information and related data. CT images, or CT scans, as used herein, is a broad term that refers to pictures of structures within the body created by computer controlled scanner. For example, by a scanner that uses an X-ray beam. However, it is appreciated that other radiation sources and/or imaging systems may produce a set of CT-like images. Accordingly, the use of the term "CT images" herein may refer to any type of imaging system having any type of imaging source that produces a set of images depicting "slices" of structures within a body, unless otherwise indicated. One key aspect of the user interface described herein is the precise correlation of the views and information that is displayed of the CT images. Locations in the CT images displayed on portions (or "panels") of the user interface are correlated precisely by the system such that the same locations are displayed concurrently in a different views. By simultaneously displaying a portion of the coronary vessel in, for example, two, three, four, five or six views simultaneously, and allowing a practitioner to explore particular locations of a coronary vessel in one view while the other 2-6 views correspondingly show the exact same location provides an enormous amount of insight into the condition of the vessel and allows the practitioner/analyst to quickly and easily visually integrate the presented information to gain a comprehensive and accurate understanding of the condition of the coronary vessel being examined.

Advantageously, the present disclosure allows CT images and data to be analyzed in a more useful and accurate way, for users to interact and analyze images and data in a more analytically useful way and/or for computation analysis to be performed in a more useful way, for example to detect conditions requiring attention. The graphical user interfaces in the processing described herein allow a user to visualize otherwise difficult to define relationships between different information and views of coronary arteries. In an example, displaying a portion of a coronary artery simultaneously in a CMPR view, a SMPR view, and a cross-sectional view can provide insight to an analyst of plaque or stenosis associated with the coronary artery that may not otherwise be perceivable using a fewer number of views. Similarly, displaying the portion of the coronary artery in an axial view, a sagittal view, and a coronal view, in addition to the CMPR view, the SMPR view, and the cross-sectional view can provide further information to the analyst that would not otherwise be perceivable with a fewer number of views of the coronary artery. In various embodiments, any of the information described or illustrated herein, determined by the system or an analyst interacting with the system, and other information (for example, from another outside source, e.g., an analyst) that relates to coronary arteries/vessels associated with the set of CT images ("artery information") including information indicative of stenosis and plaque of segments of the coronary vessels in the set of CT images, and information indicative of identification and location of the coronary vessels in the set of CT images, can be stored on the system and presented in various panels of the user interface and in reports. The present disclosure allows for easier and quicker analysis of a patient's coronary arteries and features associate with coronary arteries. The present disclosure also allows faster analysis of coronary artery data by allowing quick and accurate access to selected portions of coronary artery data. Without using the present system and methods of the disclosure, quickly selecting, displaying, and analyzing CT images and coronary artery information, can be cumbersome and inefficient, and may lead to analyst missing critical information in their analysis of a patient's coronary arteries, which may lead to inaccurate evaluation of a patient's condition.

In various embodiments, the system can identify a patient's coronary arteries either automatically (e.g., using a machine learning algorithm during the preprocessing step of set of CT images associated with a patient), or interactively (e.g., by receiving at least some input form a user) by an analyst or practitioner using the system. As described herein, in some embodiments, the processing of the raw CT scan data can comprise analysis of the CT data in order to determine and/or identify the existence and/or nonexistence of certain artery vessels in a patient. As a natural occurring phenomenon, certain arteries may be present in certain patients whereas such certain arteries may not exist in other patients. In some embodiments, the system can be configured to identify and label the artery vessels detected in the scan data. In certain embodiments, the system can be configured to allow a user to click upon a label of an identified artery within the patient, and thereby allowing that artery to be highlighted in an electronic representation of a plurality of artery vessels existing in the patient. In some embodiments, the system is configured to analyze arteries present in the CT scan data and display various views of the arteries present in the patient, for example within 10-15 minutes or less. In contrast, as an example, conducting a visual assessment of a CT to identify stenosis alone, without consideration of good or bad plaque or any other factor, can take anywhere between 15 minutes to more than an hour depending on the skill level, and can also have substantial variability across radiologists and/or cardiac imagers.

Although some systems may allow an analyst to view the CT images associated with a patient, they lack the ability to display all of the necessary views, in real or near real-time, with correspondence between 3-D artery tree views of coronary arteries specific to a patient, multiple SMPR views, and a cross-sectional, as well as an axial view, a sagittal view, and/or the coronal view. Embodiments of the system can be configured this display one or more of the use, or all of the use, which provides unparalleled visibility of a patient's coronary arteries, and allows an analyst or practitioner to perceive features and information that is simply may not be perceivable without these views. That is, a user interface configured to show all of these views, as well as information related to the displayed coronary vessel, allows an analyst or practitioner to use their own experience in conjunction with the information that the system is providing, to better identify conditions of the arteries which can help them make a determination on treatments for the patient. In addition, the information that is determined by the system and displayed by the user interface that cannot be perceived by an analyst or practitioner is presented in such a manner that is easy to understand and quick to assimilate. As an example, the knowledge of actual radiodensity values of plaque is not something that analyst and determine simply by looking at the CT image, but the system can and present a full analysis of all plaque is found.

In general, arteries vessels are curvilinear in nature. Accordingly, the system can be configured to straighten out such curvilinear artery vessels into a substantially straightline view of the artery, and in some embodiments, the foregoing is referred to as a straight multiplanar reformation (MPR) view. In some embodiments, the system is configured to show a dashboard view with a plurality of artery vessels showing in a straight multiplanar reformation view. In some embodiments, the linear view of the artery vessels shows a cross-sectional view along a longitudinal axis (or the length of the vessel or a long axis) of the artery vessel. In some embodiments, the system can be configured to allow the user to rotate in a 360° fashion about the longitudinal axis of the substantially linear artery vessels in order for the user to review the vessel walls from various views and angles. In some embodiments, the system is configured to not only show the narrowing of the inner vessel diameter but also characteristics of the inner and/or outer vessel wall itself. In some embodiments, the system can be configured to display the plurality of artery vessels in a multiple linear views, e.g., in an SMPR view.

In some embodiments, the system can be configured to display the plurality of artery vessels in a perspective view in order to better show the user the curvatures of the artery vessels. In some embodiments, the perspective view is referred to as a curved multiplanar reformation view. In some embodiments, the perspective view comprises the CT image of the heart and the vessels, for example, in an artery tree view. In some embodiments, the perspective view comprises a modified CT image showing the artery vessels without the heart tissue displayed in order to better highlight the vessels of the heart. In some embodiments, the system can be configured to allow the user to rotate the perspective view in order to display the various arteries of the patient from different perspectives. In some embodiments, the system can be configured to show a cross-sectional view of an artery vessel along a latitudinal axis (or the width of the vessel or short axis). In contrast to the cross-sectional view along a longitudinal axis, in some embodiments, the system can allow a user to more clearly see the stenosis or vessel wall narrowing by viewing the artery vessel from a cross-sectional view across a latitudinal axis.

In some embodiments, the system is configured to display the plurality of artery vessels in an illustrative view or cartoon view. In the illustrative view of the artery vessels, in some embodiments, the system can utilize solid coloring or grey scaling of the specific artery vessels or sections of specific artery vessels to indicate varying degrees of risk for a cardiovascular event to occur in a particular artery vessel or section of artery vessel. For example, the system can be configured to display a first artery vessel in yellow to indicate a medium risk of a cardiovascular event occurring in the first artery vessel while displaying a second artery vessel in red to indicate a high risk of a cardiovascular event occurring in the second artery vessel. In some embodiments, the system can be configured to allow the user to interact with the various artery vessels and/or sections of artery vessels in order to better understand the designated risk associated with the artery vessel or section of artery vessel. In some embodiments, the system can allow the user to switch from the illustrative view to a CT view of the arteries of the patient.

In some embodiments, the system can be configured to display in a single dashboard view all or some of the various views described herein. For example, the system can be configured to display the linear view with the perspective view. In another example, the system can be configured to display the linear view with the illustrative view.

In some embodiments, the processed CT image data can result in allowing the system to utilize such processed data to display to a user various arteries of a patient. As described above, the system can be configured to utilize the processed CT data in order to generate a linear view of the plurality of artery vessels of a patient. In some embodiments, the linear view displays the arteries of a patient as in a linear fashion to resemble a substantially straight line. In some embodiments, the generating of the linear view requires the stretching of the image of one or more naturally occurring curvilinear artery vessels. In some embodiments, the system can be configured to utilize such processed data to allow a user to rotate a displayed linear view of an artery in a 360° rotatable fashion. In some embodiments, the processed CT image data can visualize and compare the artery morphologies over time, i.e., throughout the cardiac cycle. The dilation of the arteries, or lack thereof, may represent a healthy versus sick artery that is not capable of vasodilation. In some embodiments, a prediction algorithm can be made to determine the ability of the artery to dilate or not, by simply examining a single point in time.

As mentioned above, aspects of the system can help to visualize a patient's coronary arteries. In some embodiments, the system can be configured to utilize the processed data from the raw CT scans in order to dynamically generate a visualization interface for a user to interact with and/or analyze the data for a particular patient. The visualization system can display multiple arteries associated with a patient's heart. The system can be configured to display multiple arteries in a substantially linear fashion even though the arteries are not linear within the body of the patient. In some embodiments, the system can be configured to allow the user to scroll up and down or left to right along the length of the artery in order to visualize different areas of the artery. In some embodiments, the system can be configured to allow a user to rotate in a 360° fashion an artery in order to allow the user to see different portions of the artery at different angles.

Advantageously, the system can be configured to comprise or generate markings in areas where there is an amount of plaque buildup that exceeds a threshold level. In some embodiments, the system can be configured to allow the user to target a particular area of the artery for further examination. The system can be configured to allow the user to click on one or more marked areas of the artery in order to display the underlying data associated with the artery at a particular point along the length of the artery. In some embodiments, the system can be configured to generate a cartoon rendition of the patient's arteries. In some embodiments, the cartoon or computer-generated representation of the arteries can comprise a color-coded scheme for highlighting certain areas of the patient's arteries for the user to examine further. In some embodiments, the system can be configured to generate a cartoon or computer-generated image of the arteries using a red color, or any other graphical representation, to signify arteries that require further analysis by the user. In some embodiments, the system can label the cartoon representation of the arteries, and the 3D representation of the arteries described above, with stored coronary vessel labels according to the labeling scheme. If a user desires, the labeling scheme can be changed or refined and preferred labels may be stored and used label coronary arteries.

In some embodiments, the system can be configured to identify areas in the artery where ischemia is likely to be found. In some embodiments, the system can be configured to identify the areas of plaque in which bad plaque exists. In some embodiments, the system can be configured to identify bad plaque areas by determining whether the coloration and/or the gray scale level of the area within the artery exceeds a threshold level. In an example, the system can be configured to identify areas of plaque where the image of a plaque area is black or substantially black or dark gray. In an example, the system can be configured to identify areas of "good" plaque by the designation of whiteness or light grey in a plaque area within the artery.

In some embodiments, the system is configured to identify portions of an artery vessel where there is high risk for a cardiac event and/or draw an outline following the vessel wall or profiles of plaque build-up along the vessel wall. In some embodiments, the system is further configured to display this information to a user and/or provide editing tools for the user to change the identified portions or the outline designations if the user thinks that the AI algorithm incorrectly drew the outline designations. In some embodiments, the system comprises an editing tool referred to as "snap-to-lumen," wherein the user selects a region of interest by drawing a box around a particular area of the vessel and selecting the snap-to-lumen option and the system automatically redraws the outline designation to more closely track the boundaries of the vessel wall and/or the plaque build-up, wherein the system is using image processing techniques, such as but not limited to edge detection. In some embodiments, the AI algorithm does not process the medical image data with complete accuracy and therefore editing tools are necessary to complete the analysis of the medical image data. In some embodiments, the final user editing of the medical image data allows for faster processing of the medical image data than using solely AI algorithms to process the medical image data.

In some embodiments, the system is configured to replicate images from higher resolution imaging. As an example, in CT, partial volume artifacts from calcium are a known artifact of CT that results in overestimation of the volume of calcium and the narrowing of an artery. By training and validating a CT artery appearance to that of intravascular ultrasound or optical coherence tomography or histopathology, in some embodiments, the CT artery appearance may be replicated to be similar to that of IVUS or OCT and, in this way, de-bloom the coronary calcium artifacts to improve the accuracy of the CT image.

In some embodiments, the system is configured to provide a graphical user interface for displaying a vessel from a beginning portion to an ending portion and/or the tapering of the vessel over the course of the vessel length. Many examples of panels that can be displayed in a graphical user interface are illustrated and described in reference to FIGS. 6A-9N. In some embodiments, portions of the user interface, panels, buttons, or information displayed on the user interface be arranged differently than what is described herein and illustrated in the Figures. For example, a user may have a preference for arranging different views of the arteries in different portions of the user interface.

In some embodiments, the graphical user interface is configured to annotate the displayed vessel view with plaque build-up data obtained from the AI algorithm analysis in order to show the stenosis of the vessel or a stenosis view. In some embodiments, the graphical user interface system is configured to annotate the displayed vessel view with colored markings or other markings to show areas of high risk or further analysis, areas of medium risk, and/or areas of low risk. For example, the graphical user interface system can be configured to annotate certain areas along the vessel length in red markings, or other graphical marking, to indicate that there is significant bad fatty plaque build-up and/or stenosis. In some embodiments, the annotated markings along the vessel length are based on one or more variable such as but not limited to stenosis, biochemistry tests, biomarker tests, AI algorithm analysis of the medical image data, and/or the like. In some embodiments, the graphical user interface system is configured to annotate the vessel view with an arthrosclerosis view. In some embodiments, the graphical user interface system is configured to annotate the vessel view with an ischemia view. In some embodiments, the graphical user interface is configured to allow the user to rotate the vessel 180 degrees or 360 degrees in order to display the vessel and the annotated plaque build-up views from different angles. From this view, the user can manually determine the stent length and diameter for addressing the stenosis, and in some embodiments, the system is configured to analyze the medical image information to determine the recommended stent length and diameter, and display the proposed stent for implantation in the graphical user interface to illustrate to the user how the stent would address the stenosis within the identified area of the vessel. In some embodiments, the systems, methods, and devices disclosed herein can be applied to other areas of the body and/or other vessels and/or organs of a subject, whether the subject is human or other mammal.

Illustrative Example

One of the main uses of such systems can be to determine the presence of plaque in vessels, for example but not limited to coronary vessels. Plaque type can be visualized based on Hounsfield Unit density for enhanced readability for the user. Embodiments of the system also provide quantification of variables related to stenosis and plaque composition at both the vessel and lesion levels for the segmented coronary artery.

In some embodiments, the system is configured as a web-based software application that is intended to be used by trained medical professionals as an interactive tool for viewing and analyzing cardiac CT data for determining the presence and extent of coronary plaques (i.e., atherosclerosis) and stenosis in patients who underwent Coronary Computed Tomography Angiography (CCTA) for evaluation of coronary artery disease (CAD), or suspected CAD. This system post processes CT images obtained using a CT scanner. The system is configured to generate a user interface that provides tools and functionality for the characterization, measurement, and visualization of features of the coronary arteries.

Features of embodiments of the system can include, for example, centerline and lumen/vessel extraction, plaque composition overlay, user identification of stenosis, vessel statistics calculated in real time, including vessel length, lesion length, vessel volume, lumen volume, plaque volume (non-calcified, calcified, low-density-non-calcified plaque and total), maximum remodeling index, and area/diameter stenosis (e.g., a percentage), two dimensional (2D) visualization of multi-planar reformatted vessel and cross-sectional views, interactive three dimensional (3D) rendered coronary artery tree, visualization of a cartoon artery tree that corresponds to actual vessels that appear in the CT images, semi-automatic vessel segmentation that is user modifiable, and user identification of stents and Chronic Total Occlusion (CTO).

In an embodiment, the system uses 18 coronary segments within the coronary vascular tree (e.g., in accordance with the guidelines of the Society of Cardiovascular Computed Tomography). The coronary segment labels include:

pRCA—proximal right coronary artery
mRCA—mid right coronary artery
dRCA—distal right coronary artery
R-PDA—right posterior descending artery
LM—left main artery
pLAD—proximal left descending artery
mLAD—mid left anterior descending artery
dLAD—distal left anterior descending artery
D1—first diagonal
D2—second diagonal
pCx—proximal left circumflex artery
OM1—first obtuse marginal
LCx—distal left circumflex
OM2—second obtuse marginal
L-PDA—left posterior descending artery
R-PLB—right posterior lateral branch
RI—ramus intermedius artery
L-PLB—left posterior lateral branch Other embodiments can include more, or fewer, coronary segment labels. The coronary segments present in an individual patient are dependent on whether they are right or left coronary dominant. Some segments are only present when there is right coronary dominance, and some only when there is a left coronary dominance. Therefore, in many, if not all instances, no single patient may have all 18 segments. The system will account for most known variants.

In one example of performance of the system, CT scans were processed by the system, and the resulting data was compared to ground truth results produced by expert readers. Pearson Correlation Coefficients and Bland-Altman Agreements between the systems results and the expert reader results is shown in the table below:

| Output | Pearson Correlation | Bland-Altman Agreement |
|---|---|---|
| Lumen Volume | 0.91 | 96% |
| Vessel Volume | 0.93 | 97% |
| Total Plaque Volume | 0.85 | 95% |
| Calcified Plaque Volume | 0.94 | 95% |
| Non-Calcified Plaque Volume | 0.74 | 95% |
| Low-Density-Non-Calcified Plaque Volume | 0.53 | 97% |

FIGS. 6A-9N illustrate an embodiment of the user interface of the system, and show examples of panels, graphics, tools, representations of CT images, and characteristics, structure, and statistics related to coronary vessels found in a set of CT images. In various embodiments, the user interface is flexible and that it can be configured to show various arrangements of the panels, images, graphics representations of CT images, and characteristics, structure, and statistics. For example, based on an analyst's preference. The system has multiple menus and navigational tools to assist in visualizing the coronary arteries. Keyboard and mouse shortcuts can also be used to navigate through the images and information associated with a set of CT images for patient.

Figure 6A:
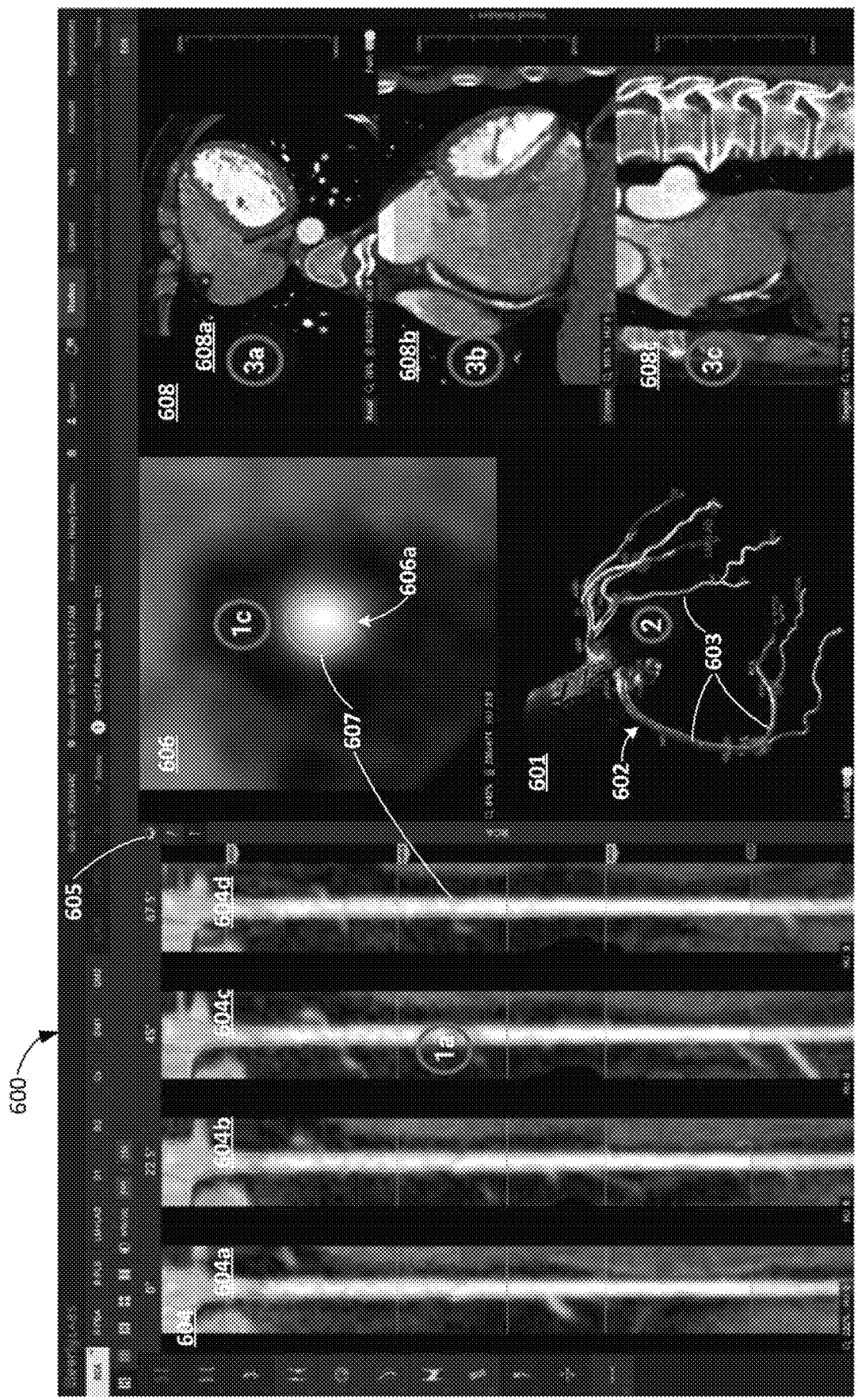
FIG. 6A illustrates an example of a user interface that can be generated and displayed on the system, the user interface having multiple panels (views) that can show various corresponding views of a patient's arteries.

FIG. 6A illustrates an example of a user interface 600 that can be generated and displayed on a CT image analysis system described herein, the user interface 600 having multiple panels (views) that can show various corresponding views of a patient's arteries and information about the arteries. In an embodiment, the user interface 600 shown in FIG. 6A can be a starting point for analysis of the patient's coronary arteries, and is sometimes referred to herein as the "Study Page" (or the Study Page 600). In some embodiments, the Study Page can include a number of panels that can be arranged in different positions on the user interface 600, for example, based on the preference the analyst. In various instances of the user interface 600, certain panels of the possible panels that may be displayed can be selected to be displayed (e.g., based on a user input).

The example of the Study Page 600 shown in FIG. 6A includes a first panel 601 (also shown in the circled "2") including an artery tree 602 comprising a three-dimensional (3D) representation of coronary vessels based on the CT images and depicting coronary vessels identified in the CT images, and further depicting respective segment labels. While processing the CT images, the system can determine the extent of the coronary vessels are determined and the artery tree is generated. Structure that is not part of the coronary vessels (e.g., heart tissue and other tissue around the coronary vessels) are not included in the artery tree 602. Accordingly, the artery tree 602 in FIG. 6A does not include any heart tissue between the branches (vessels) 603 of the artery tree 602 allowing visualization of all portions of the artery tree 602 without them being obscured by heart tissue.

This Study Page 600 example also includes a second panel 604 (also shown in the circled "1a") illustrating at least a portion of the selected coronary vessel in at least one straightened multiplanar reformat (SMPR) vessel view. A SMPR view is an elevation view of a vessel at a certain rotational aspect. When multiple SMPR views are displayed in the second panel 604 each view can be at a different rotational aspect. For example, at any whole degree, or at a half degree, from 0° to 259.5°, where 360° is the same view as 0°. In this example, the second panel 604 includes four straightened multiplanar vessels 604a-d displayed in elevation views at a relative rotation of 0°, 22.5°, 45°, and 67.5°, the rotation indicated that the upper portion of the straightened multiplanar vessel. In some embodiments, the rotation of each view can be selected by the user, for example, at the different relative rotation interval. The user interface includes the rotation tool 605 that is configured to receive an input from a user, and can be used to adjust rotation of a SMPR view (e.g., by one or more degrees). One or more graphics related to the vessel shown in the SMPR view can also be displayed. For example, a graphic representing the lumen of the vessel, a graphic representing the vessel wall, and/or a graphic representing plaque.

This Study Page 600 example also includes the third panel 606 (also indicated by the circled "1c"), which is configured to show a cross-sectional view of a vessel 606a generated based on a CT image in the set of CT images of the patient. The cross-sectional view corresponds to the vessel shown in the SMPR view. The cross-sectional view also corresponds to a location indicated by a user (e.g., with a pointing device) on a vessel in the SMPR view. The user interfaces configured such that a selection of a particular location along the coronary vessel in the second panel 604 displays the associated CT image in a cross-sectional view in the third panel 606. In this example, a graphic 607 is displayed on the second panel 604 and the third panel 606 indicating the extent of plaque in the vessel.

This Study Page 600 example also includes a fourth panel 608 that includes anatomical plane views of the selected coronary vessel. In this embodiment, the Study Page 600 includes an axial plane view 608a (also indicated by the circled "3a"), a coronal plane view 608b (also indicated by the circled "3b"), and a sagittal plane view 608c (also indicated by the circled "3c"). The axial plane view is a transverse or "top" view. The coronal plane view is a front view. The sagittal plane view is a side view. The user interface is configured to display corresponding views of the selected coronary vessel. For example, views of the selected coronary vessel at a location on the coronary vessel selected by the user (e.g., on one of the SMPR views in the second panel 604.

Figure 6B:
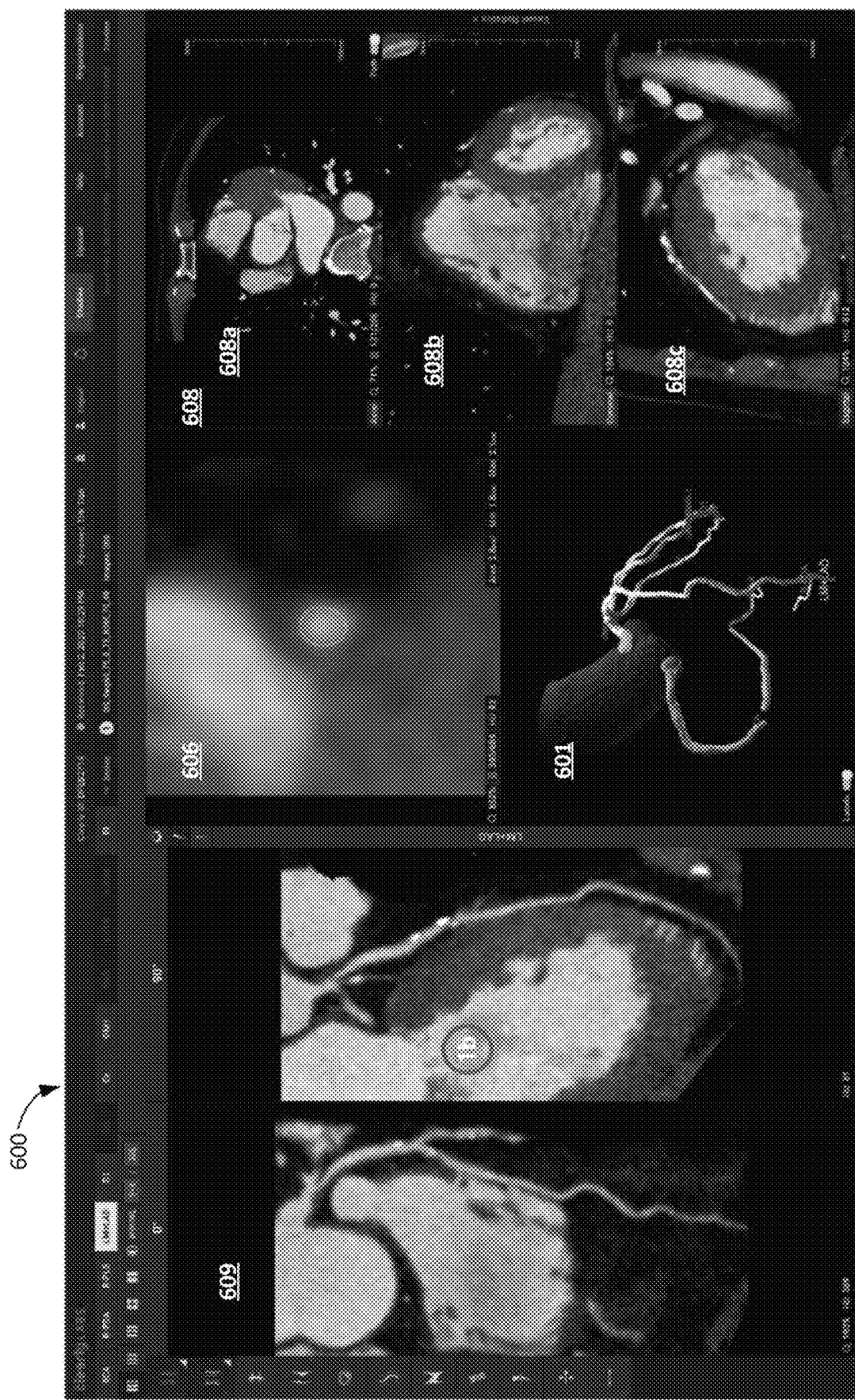
FIG. 6B illustrates an example of a user interface that can be generated and displayed on the system, the user interface having multiple panels that can show various corresponding views of a patient's arteries.

FIG. 6B illustrates another example of the Study Page (user interface) 600 that can be generated and displayed on the system, the user interface 600 having multiple panels that can show various corresponding views of a patient's arteries. In this example, the user interface 600 displays an 3D artery tree in the first panel 601, the cross-sectional view in the third panel 606, and axial, coronal, and sagittal plane views in the fourth panel 608. Instead of the second panel 604 shown in FIG. 6A, the user interface 600 includes a fifth panel 609 showing curved multiplanar reformat (CMPR) vessel views of a selected coronary vessel. The fifth panel 609 can be configured to show one or more CMPR views. In this example, two CMPR views were generated and are displayed, a first CMPR view 609a at 0° and a second CMPR view 609b at 90°. The CMPR views can be generated and displayed at various relative rotations, for example, from 0° to 259.5°. The coronary vessel shown in the CMPR view corresponds to the selected vessel, and corresponds to the vessel displayed in the other panels. When a location on the vessel in one panel is selected (e.g., the CMPR view), the views in the other panels (e.g., the cross-section, axial, sagittal, and coronal views) can be automatically updated to also show the vessel at that the selected location in the respective views, thus greatly enhancing the information presented to a user and increasing the efficiency of the analysis.

Figure 6C:
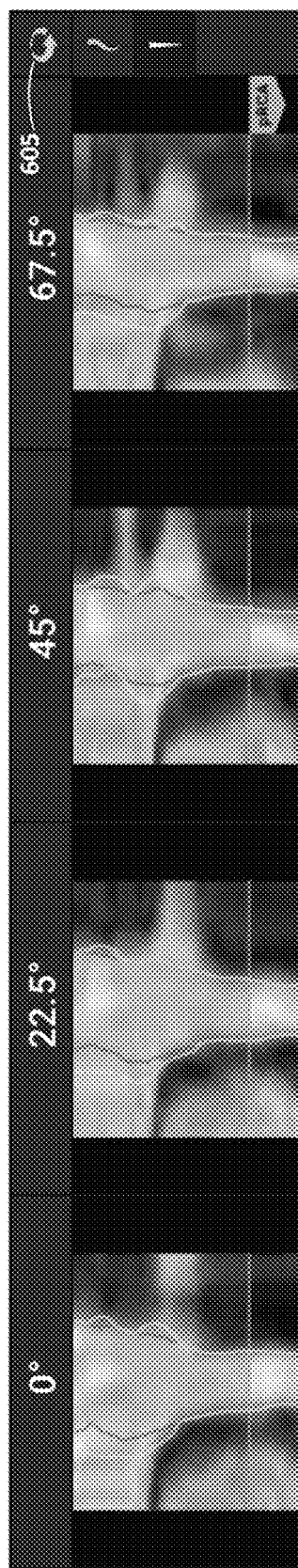
FIGS. 6C, 6D, and 6E illustrate certain details of a multiplanar reformat (MPR) vessel view in the second panel, and certain functionality associated with this view.
Figure 6D:
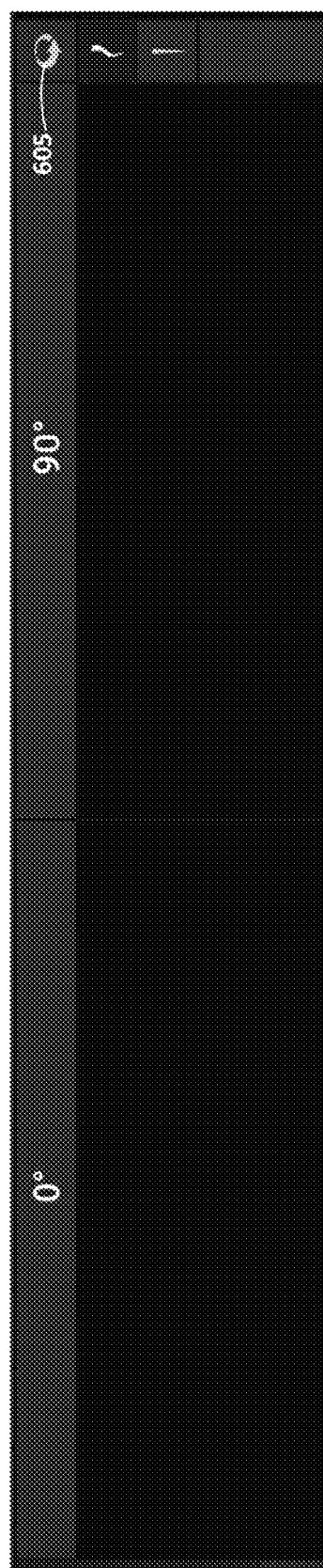
Figure 6E:

FIGS. 6C, 6D, and 6E illustrate certain details of a multiplanar reformat (MPR) vessel view in the second panel, and certain functionality associated with this view. After a user verifies the accuracy of the segmentation of the coronary artery tree in panel 602, they can proceed to interact with the MPR views where edits can be made to the individual vessel segments (e.g., the vessel walls, the lumen, etc.) In the SMPR and CMPR views, the vessel can be rotated in increments (e.g., 22.5°) by using the arrow icon 605, illustrated in FIGS. 6C and 6D. Alternatively, the vessel can be rotated continuously by 1 degree increments in 360 degrees by using the rotation command 610, as illustrated in FIG. 6E. The vessels can also be rotated by pressing the COMMAND or CTRL button and left clicking+dragging the mouse on the user interface 600.

Figure 6F:
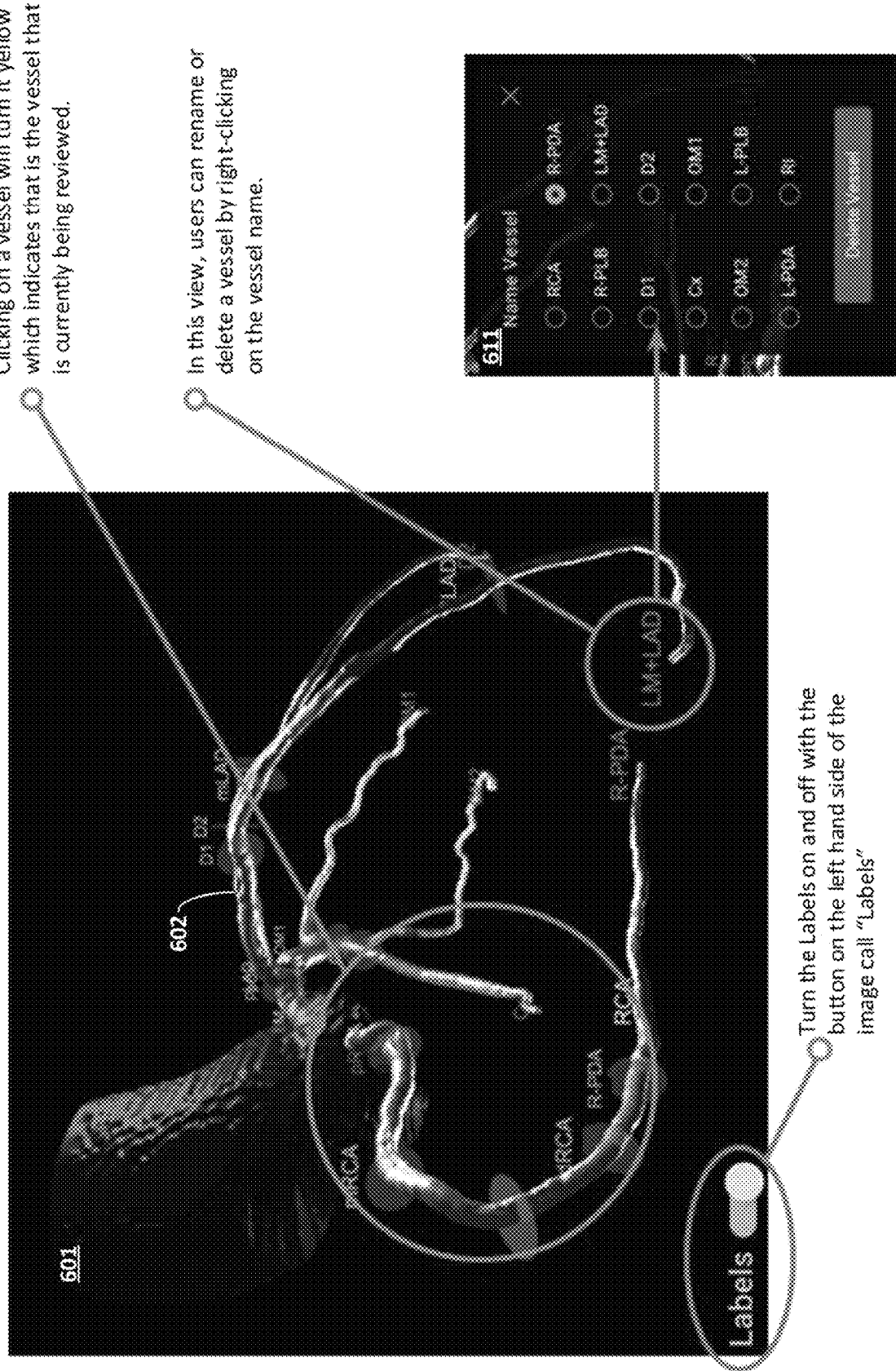
FIG. 6F illustrates an example of a three-dimensional (3D) rendering of a coronary artery tree that allows a user to view the vessels and modify the labels of a vessel.
Figure 6G:
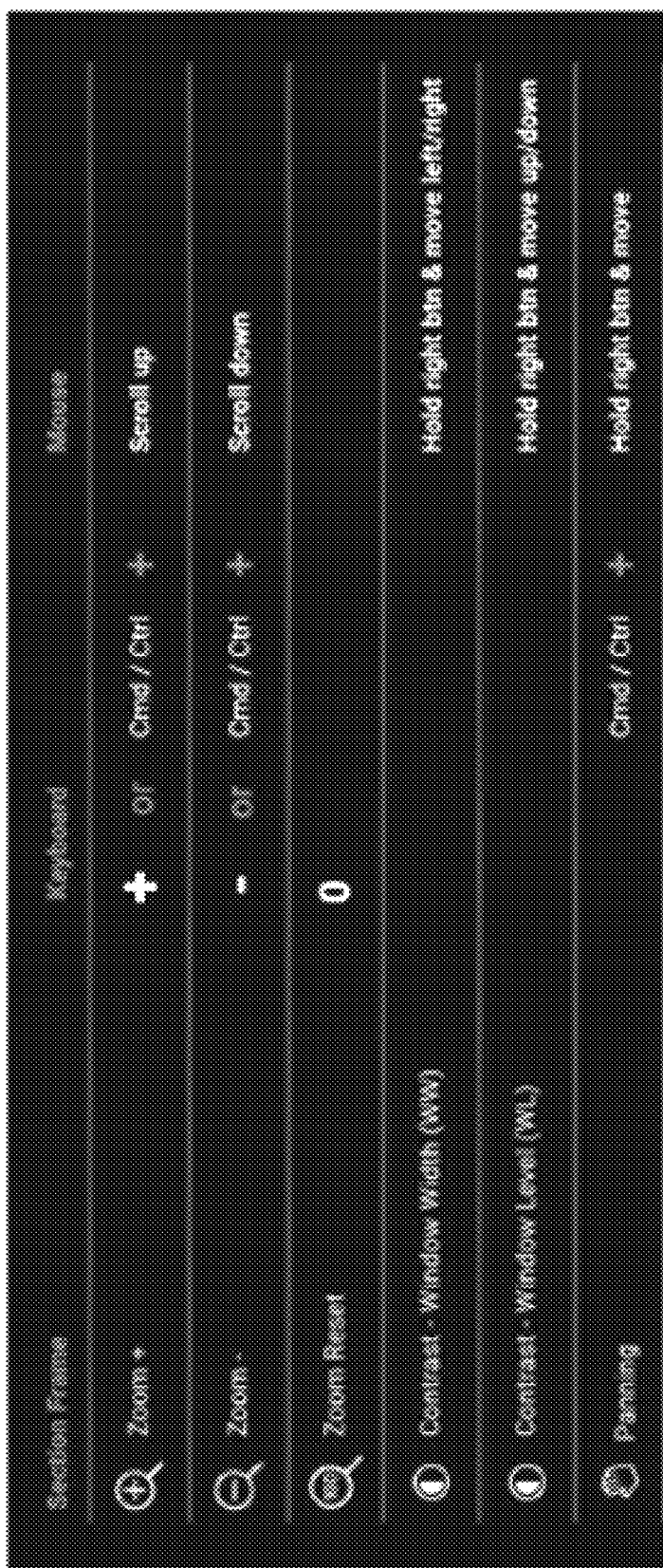
FIG. 6G illustrates an example of a panel of the user interface that provides shortcut commands that a user may employ while analyzing information in the user interface in a coronary artery tree view, an axial view, a sagittal view, and a coronal view.
Figures 6H, 6I:
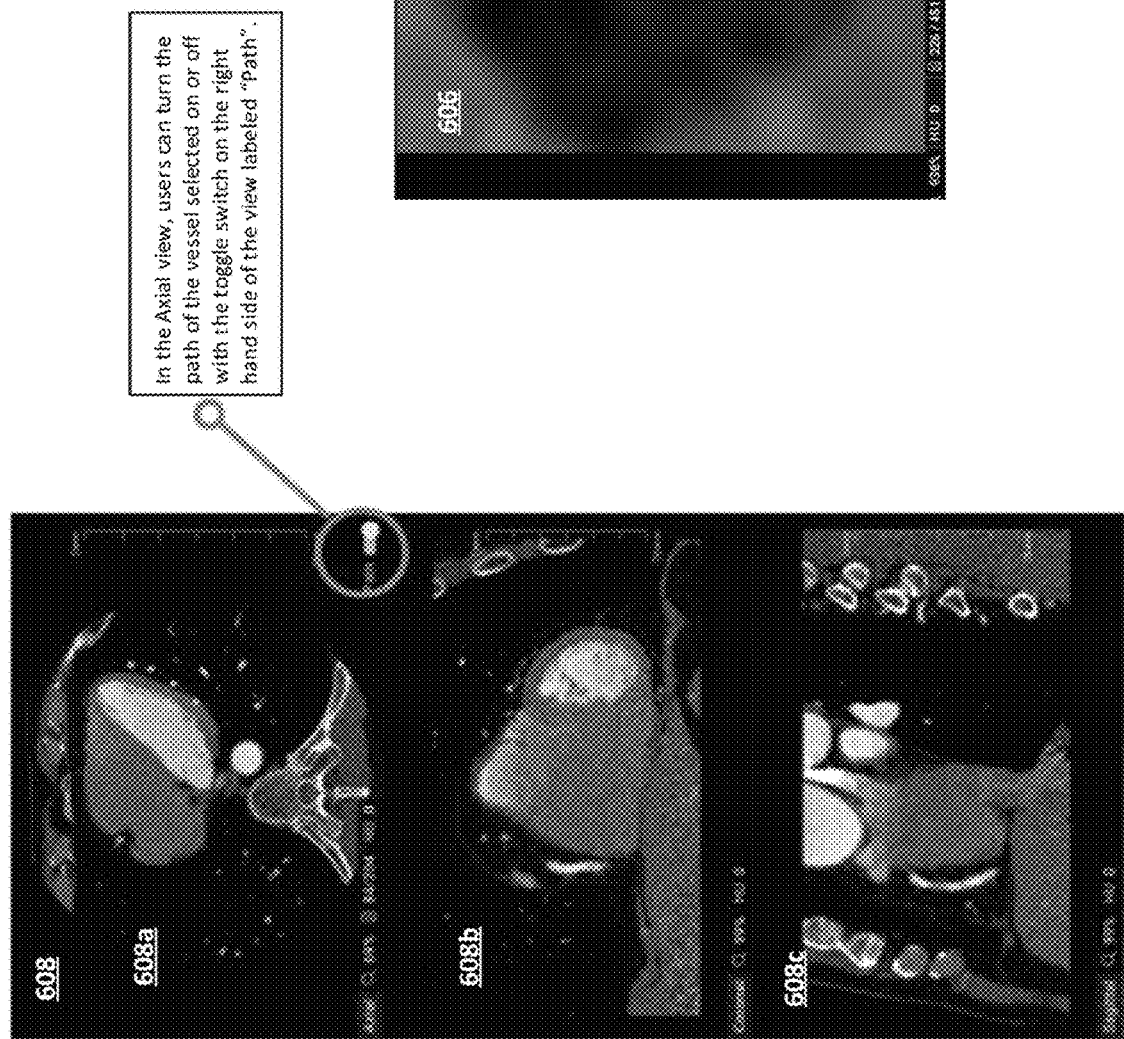
FIG. 6H illustrates examples of panels of the user interface for viewing DICOM images in three anatomical planes: axial, coronal, and sagittal.
FIG. 6I illustrates an example of a panel of the user interface showing a cross-sectional view of a vessel, in the graphical overlay of an extracted feature of the vessel.

FIG. 6F illustrates additional information of the three-dimensional (3D) rendering of the coronary artery tree 602 on the first panel 601 that allows a user to view the vessels and modify the labels of a vessel. FIG. 6G illustrates shortcut commands for the coronary artery tree 602, axial view 608a, sagittal view 608b, and coronal view 608c. In panel 601 shown in FIG. 6F, a user can rotate the artery tree as well as zoom in and out of the 3D rendering using commands selected in the user interface illustrated in FIG. 6G. Clicking on a vessel will turn it yellow which indicates that is the vessel that is currently being reviewed. In this view, users can rename or delete a vessel by right-clicking on the vessel name which opens panel 611, which is configured to receive an input from a user to rename the vessel. Panel 601 also includes a control that can be activated to turn the displayed labels "on" or "off." FIG. 6H further illustrates panel 608 of the user interface for viewing DICOM images in three anatomical planes: axial, coronal, and sagittal. FIG. 6I illustrates panel 606 showing a cross-sectional view of a vessel. The scroll, zoom in/out, and pan commands can also be used on these views.

Figure 6J:
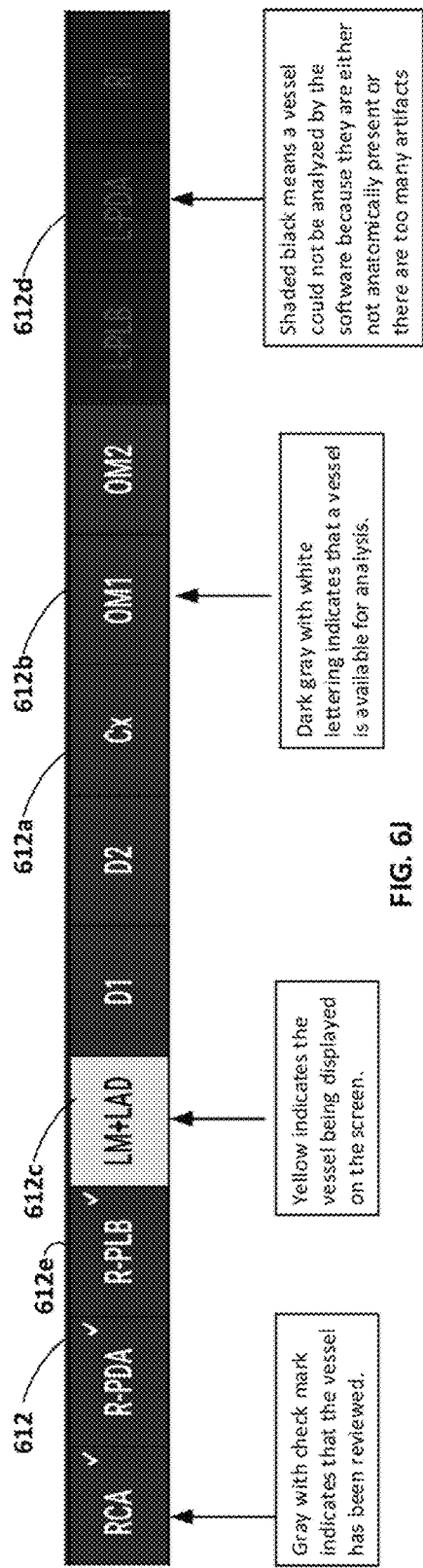
FIG. 6J illustrates an example of a toolbar that allows a user to select different vessels for review and analysis.
Figure 6K:
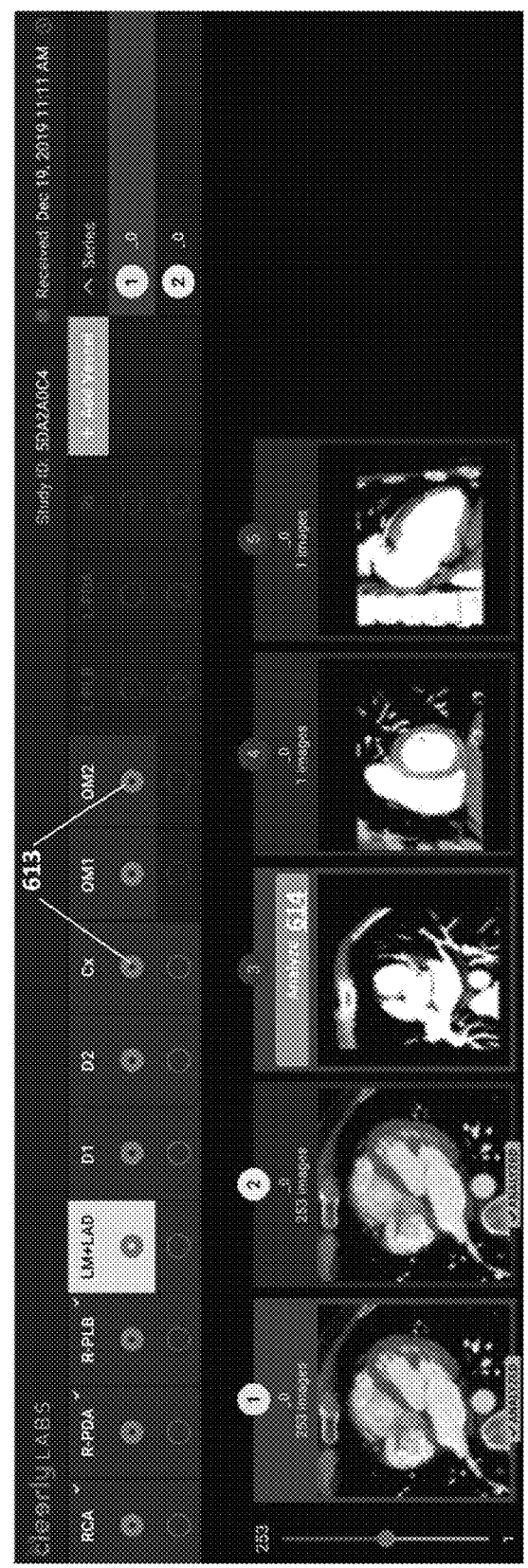
FIG. 6K illustrates an example of a series selection panel of the user interface in an expanded view of the toolbar illustrated in FIG. 6J, which allows a user to expand the menu to view all the series (set of images) that are available for review and analysis for a particular patient.

FIGS. 6J and 6K illustrate certain aspects of the toolbar 612 and menu navigation functionality of the user interface 600. FIG. 6J illustrates a toolbar of the user interface for navigating the vessels. The toolbar 612 includes a button 612a, 612b etc. for each of the vessels displayed on the screen. The user interface 600 is configured to display the buttons 612a-n to indicate various information to the user. In an example, when a vessel is selected, the corresponding button is highlighted (e.g., displayed in yellow), for example, button 612c. In another example, a button being dark gray with white lettering indicates that a vessel is available for analysis. In an example, a button 612d that is shaded black means a vessel could not be analyzed by the software because they are either not anatomically present or there are too many artifacts. A button 612e that is displayed as gray with check mark indicates that the vessel has been reviewed.

Figure 6L:
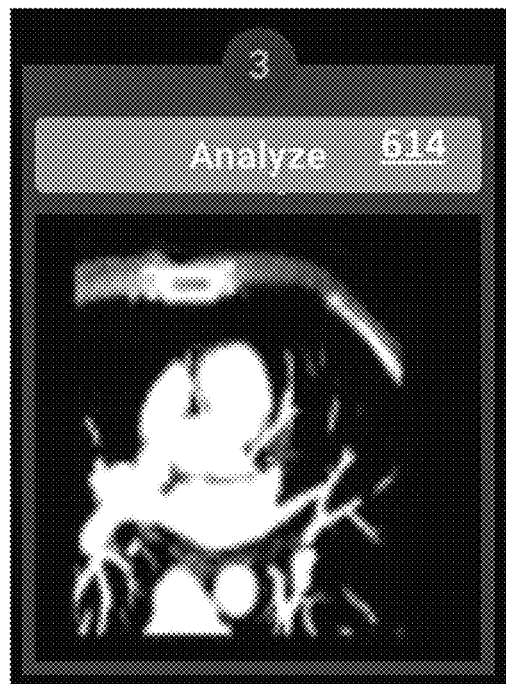
FIG. 6L illustrates an example of a selection panel that can be displayed on the user interface that may be uses to select a vessel segment for analysis.

FIG. 6K illustrates a view of the user interface 600 with an expanded menu to view all the series (of images) that are available for review and analysis. If the system has provided more than one of the same vessel segment from different series of images for analysis, the user interface is configured to receive a user input to selected the desired series for analysis. In an example, an input can be received indicating a series for review by a selection on one of the radio buttons 613 from the series of interest. The radio buttons will change from gray to purple when it is selected for review. In an embodiment, the software, by default, selects the two series of highest diagnostic quality for analysis however, all series are available for review. The user can use clinical judgment to determine if the series selected by the system is of diagnostic quality that is required for the analysis, and should select a different series for analysis if desired. The series selected by the system is intended to improve workflow by prioritizing diagnostic quality images. The system is not intended to replace the user's review of all series and selection of a diagnostic quality image within a study. Users can send any series illustrated in FIG. 6K for the system to suggest vessel segmentations by hovering the mouse over the series and select an "Analyze" button 614 as illustrated in FIG. 6L.

Figure 6M:
FIG. 6M illustrates an example of a panel that can be displayed on the user interface to add a new vessel on the image.
Figure 6N:
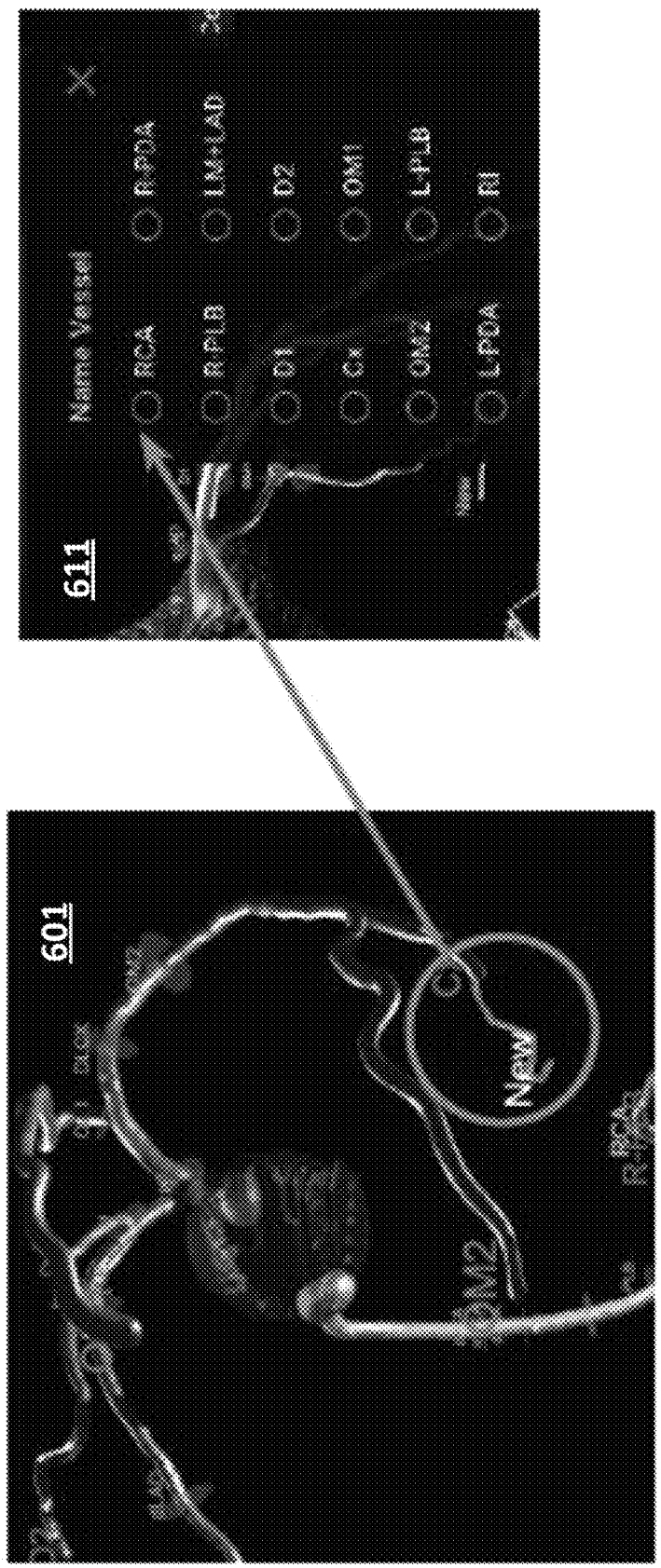
FIG. 6N illustrates examples of two panels that can be displayed on the user interface to name, or to rename, a vessel in the 3-D artery tree view.

FIG. 6M illustrates a panel that can be displayed on the user interface 600 to add a new vessel on the image, according to one embodiment. To add a new vessel on the image, the user interface 600 can receive a user input via a "+Add Vessel" button on the toolbar 612. The user interface will display a "create Mode" 615 button appear in the fourth panel 608 on the axial, coronal and sagittal view. Then the vessel can be added on the image by scrolling and clicking the left mouse button to create multiple dots (e.g., green dots). As the new vessel is being added, it will preview as a new vessel in the MPR, cross-section, and 3D artery tree view. The user interface is configured to receive a "Done" command to indicate adding the vessel has been completed. Then, to segment the vessels utilizing the system's semi-automatic segmentation tool, click "Analyze" on the tool bar and the user interface displays suggested segmentation for review and modification. The name of the vessel can be chosen by selecting "New" in the 3D artery tree view in the first panel 601, which activates the name panel 611 and the name of the vessel can be selected from panel 611, which following is a listing and description of the available editing tools. Hovering over each button (icon) will display the name of each tool. These tools can be activated and deactivated by clicking on it. If the color of the tool is gray, it is deactivated. If the software has identified any of these characteristics in the vessel, the annotations will already be on the image when the tool is activated. The editing tools in the toolbar can include one or more of the following tools: Lumen Wall 701, Snap to Vessel Wall 702, Vessel Wall 703, Snap to Lumen Wall 704, Segments 705, Stenosis 706, Plaque Overlay 707, Centerline 708, Chronic Total Occlusion (CTO) 709, Stent 710, Exclude By 711, Tracker 712, and Distance 713. The user interface 600 is configured to activate each of these tools by receiving a user selection on the respective toll icon (shown in the table below and in FIG. 7A) and are configured to provide functionality described in the Editing Tools Description Table below:

| | | Editing Tools Description Table |
|---|---|---|
| L | LUMEN WALL. | USERS CAN ADJUST OR DRAW NEW LUMEN WALL CONTOURS TO IMPROVE THE ACCURACY OF THE LOCATION AND MEASUREMENTS OFTHE LUMEN |
| | SNAP TO VESSELWALL | USERS CAN DRAG A SHADED AREA AND RELEASE IT IN ORDER TO SNAP THE LUMEN WALL TO THE VESSELWALL FOR HEALTHY VESSELS AREAS |
| V | VESSELWALL | USERS CAN ADJUST OR DRAW NEW VESSELWALL CONTOURS TO REFINE THE EXTERIOR OF THE VESSELWALL |
| | SNAP TO LUMEN WALL | USERS CAN DRAG A SHADED AREA AND RELEASE IT IN ORDER TO SNAP THE VESSEL WALL TO THE LUMEN WALL FOR HEALTHY VESSELS AREAS |
| S | SEGMENTS | USERS CAN ADD SEGMENT MARKERS TO DEFINE THE BOUNDARIES OF EACH OF THE 18 CORONARY SEGMENTS. NEW OR ALREADY EXISTNG MARKERS CAN BE DRAGGED UP AND DOWN TO ADJUST TO THE EXACT SEGMENT BOUNDARIES. |
| E | STENOSIS | THIS TOOLCONSISTS OF 5 MARKERS THAT ALLOW USERS TO MARK REGIONS OF STENOSIS ON THE VESSEL, USERS CAN ADD NEW STENOSIS MARP MARKERS AND NEW OR ALREADY EXISTINC MARKERS CAN BE DRAGGED UPDOWN |
| F | PLAQUE OVERLAY | THIS TOOL OVERLAYS THE SMPR AND THE CROSS SECTION VIEWS WITH COLORIZED AREAS OF PLAQUE BASED UPON THE PLAQUES HOUNSFIELD ATTENUATION |
| C | CENTERLINE | USERS CAN ADJUST THE CENTERLINE OF THE VESSEL IN THE CMPR OR CROSS-SECTION VIEW ADJUSTMENTS WLL BE PROPAGATED TO THE SMPR VIEW |
| G | CTO | CHRONIC TOTAL OCCLUSION TOOL CONSISTS OF TWO MARKERS THAT IDENTIFY THE START AND END OF A SECTION OF AN ARTERY THAT IS TOTALLY OCCLUDED. MULTIPLE CTOS CAN BE ADDED AND DRAGGED TO THE AREA OF INTEREST. |
| N | STENT | THE STENT TOOL ALLOW USERS TO IDENTIFY THE PRESENCE OF STENT(S) IN THE CORONARY ARTERIES. USERS CAN ADD STENT MARKERS AND DRAG EXISTING MARKERS UP OR DOWN TO THE EXACT STENT BOUNDARIES. |
| X | EXCLUDE | BY USING THIS TOOL SECTIONS OF A VESSEL CAN BE REMOVED FROM THE FINAL CALCULATIONS/ANALYSIS. REMOVAL OF THESE SECTIONS IS OFTEN DUE TO THE PRESENCE OF ARTIFACTS. USUALLY DUE TO MOTION OR MISLIGNMENT ISSUES AMONG OTHERS. |
| T | TRACKER | THE TRACKER ORIENTS AND ALLOWS USERS TO CORRELATE THE MPR, CROSS-SECTIONA, AXIAL, CORONAL SAGITTAL, AND 3 DARTERY TREE VIEWS. |
| D | DISTANCE | THE TOOL IS USED ON THE MPR. CROSS-SECTION AXIAL CORONAL, OR SAGITTALVIEWS TO MEASURE DISTANCES BETWEEN POINTS THE TOQL PROVIDES ACCURATE READINGS IN MILLMETERS ALLOWING FOR QUICK REVIEW AND ESTIMATION ON AREAS OF INTEREST. | then stores the new vessel and its name. In an embodiment, if the software is unable to identify the vessel which has been added by the user, it will return straight vessel lines connecting the user-added green dots, and the user can adjust the centerline. The pop-up menu 611 of the user interface allows new vessels to be identified and named according to a standard format quickly and consistently.

Figure 7A:
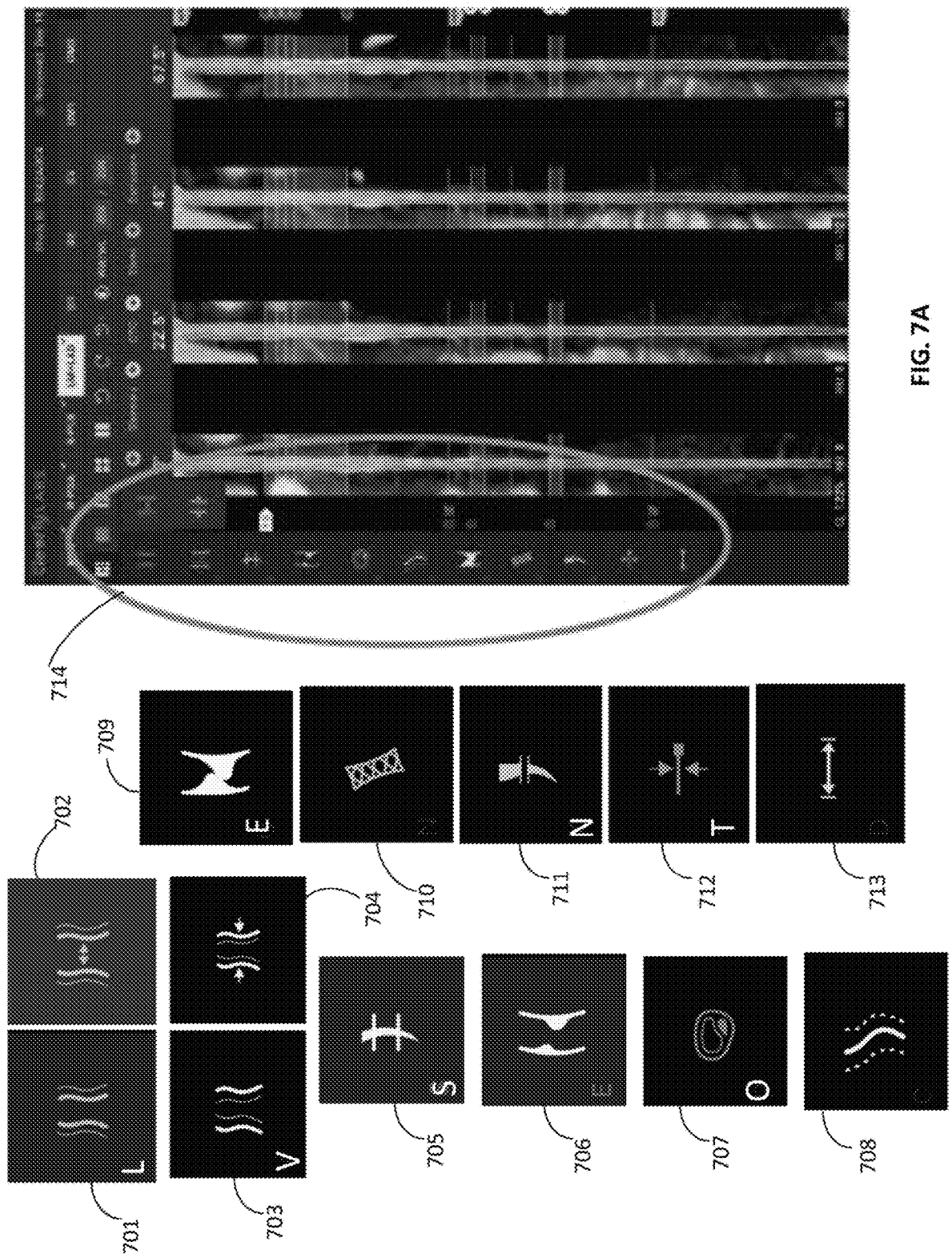
FIG. 7A illustrates an example of an editing toolbar which allows users to modify and improve the accuracy of the findings resulting from processing CT scans with a machine learning algorithm and then by an analyst.
Figure 7B:
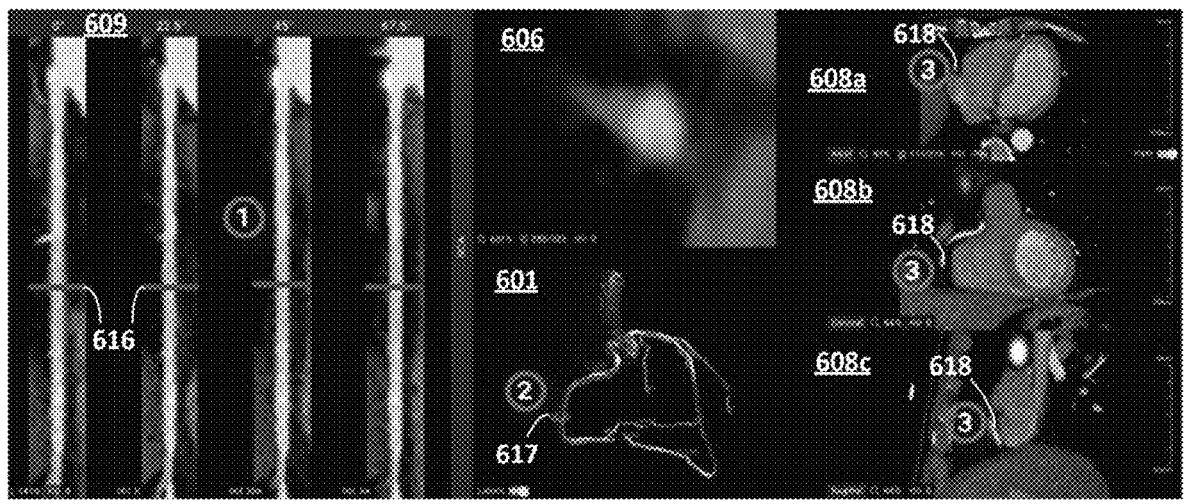
FIGS. 7B and 7C illustrate examples of certain functionality of the tracker tool.
Figure 7C:
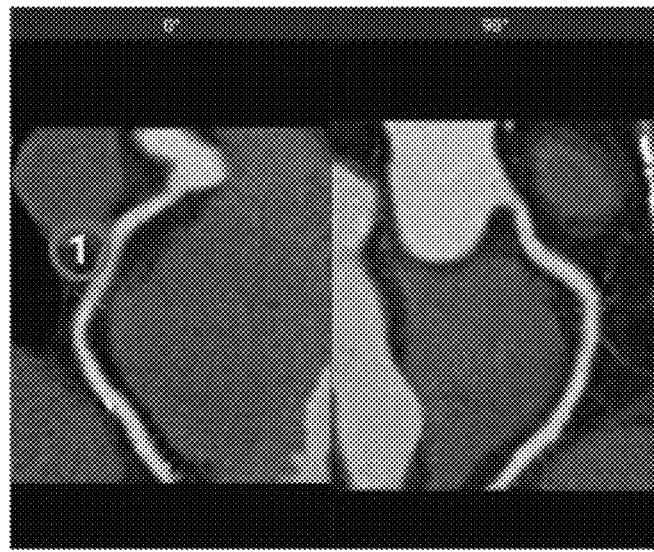

FIG. 7A illustrates an example of an editing toolbar 714 that includes editing tools which allow users to modify and improve the accuracy of the findings resulting from processing CT scans with a machine learning algorithm, and then processing the CT scans, and information generated by the machine learning algorithm, by an analyst. In some embodiments, the user interface includes editing tools that can be used to modify and improve the accuracy of the findings. In some embodiments, the editing tools are located on the left-hand side of the user interface, as shown in FIG. 7A. The FIGS. 7B and 7C illustrate certain functionality of the Tracker tool. The Tracker tool 712 orients and allows user to correlate the views shown in the various panels of the user interface 600, for example, in the SMPR, CMPR, cross-section, axial, coronal, sagittal, and the 3D artery tree views. To activate, the tracker icon is selected on the editing toolbar. When the Tracker tool 712 is activated, the user interface generates and displays a line 616 (e.g., a red line) on the SMPR or CMPR view. The system generates on the user interface a corresponding (red) disc 617 which is displayed on the 3D artery tree in the first panel 601 in a corresponding location as the line 616. The system generates on the user interface a corresponding (red) dot which his displayed on the axial, sagittal and coronal views in the fourth panel 608 in a corresponding location as the line 616. The line 616, disc 617, and dots 618 are location indicators all referencing the same location in the different views, such that scrolling any of the trackers up and down will also result in the same movement of the location indicator in other views. Also, the user interface 600 displays the cross-sectional image in panel 606 corresponding to the location indicated by the location indicators.

Figure 7D:
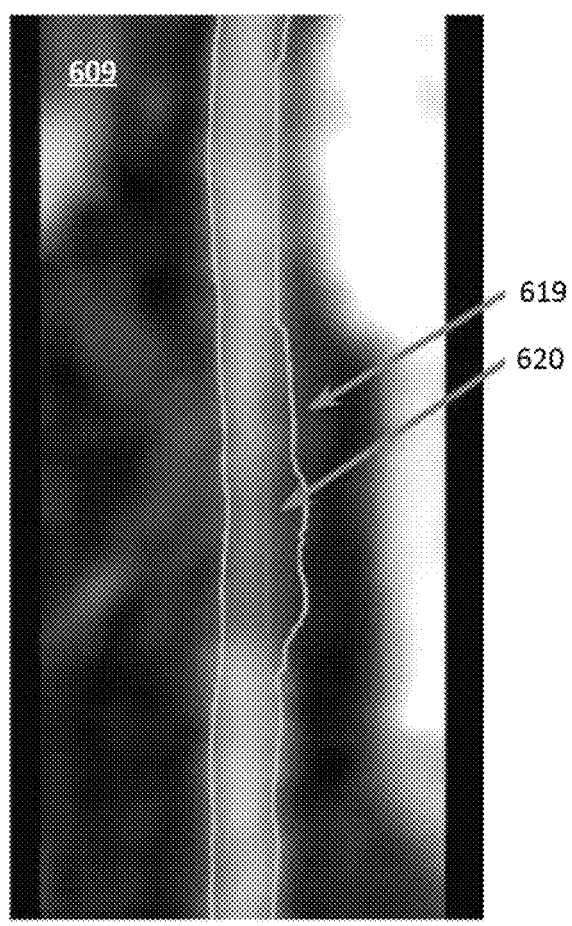
FIGS. 7D and 7E illustrate certain functionality of the vessel and lumen wall tools, which are used to modify the lumen and vessel wall contours.
Figure 7E:
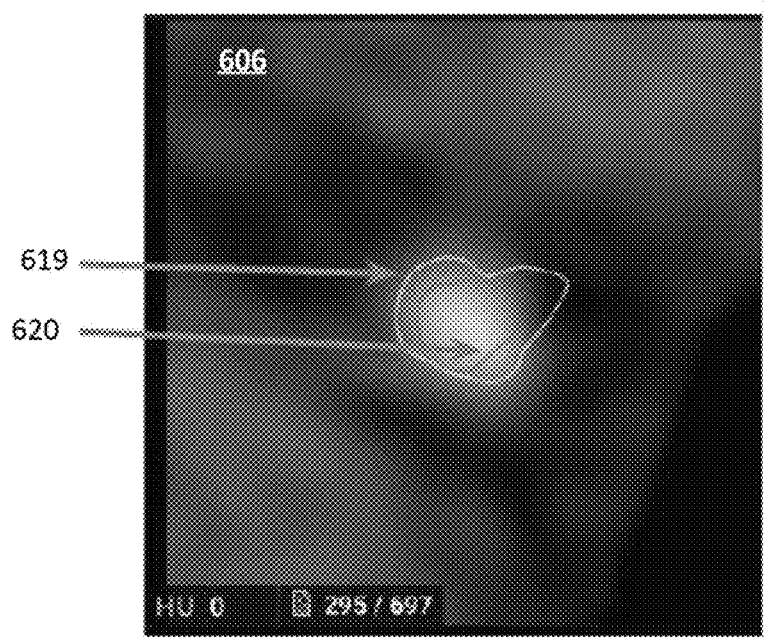

FIGS. 7D and 7E illustrate certain functionality of the vessel and lumen wall tools, which are used to modify the lumen and vessel wall contours. The Lumen Wall tool 701 and the Vessel Wall tool 703 are configured to modify the lumen and vessel walls (also referred to herein as contours, boundaries, or features) that were previously determined for a vessel (e.g., determined by processing the CT images using a machine learning process. These tool are used by the system for determining measurements that are output or displayed. By interacting with the contours generated by the system with these tools, a user can refine the accuracy of the location of the contours, and any measurements that are derived from those contours. These tools can be used in the SMPR and cross-section view. The tools are activated by selecting the vessel and lumen icons 701, 703 on the editing toolbar. The vessel wall 619 will be displayed in the MPR view and the cross-section view in a graphical "trace" overlay in a color (e.g., yellow). The lumen wall 629 will be displayed in a graphical "trace" overly in a different color (e.g., purple). In an embodiment, the user interface is configured to refine the contours through interactions with a user. For example, to refine the contours, the user can hover above the contour with a pointing device (e.g., mouse, stylus, finger) so it highlights the contour, click on the contour for the desired vessel or lumen wall and drag the displayed trace to a different location setting a new boundary. The user interface 600 is configured to automatically save any changes to these tracings. The system re-calculates any measurements derived from the changes contours in real time, or near real time. Also, the changes made in one panel on one view are displayed correspondingly in the other views/panels.

FIG. 7F illustrates the lumen wall button 701 and the snap to vessel wall button 702 (left) and the vessel wall button 703 and the snap to lumen wall button 704 (right) of the user interface 600 which can be used to activate the Lumen Wall/Snap to Vessel tools 701, 702, and the Vessel Wall/Snap to Lumen Wall 703, 704 tools, respectively. The user interface provides these tools to modify lumen and vessel wall contours that were previously determined. The Snap to Vessel/Lumen Wall tools are used to easily and quickly close the gap between lumen and vessel wall contours, that is, move a trace of the lumen contour and a trace of the vessel contour to be the same, or substantially the same, saving interactive editing time. The user interface 600 is configured to activate these tools when a user hovers of the tools with a pointing device, which reveals the snap to buttons. For example, hovering over the Lumen Wall button 701 reveals the Snap to Vessel button 702 to the right-side of the Lumen wall button, and hovering over the Vessel Wall button 703 reveals the Snap to Lumen Wall button 704 beside the Vessel Wall button 703. A button is selected to activate the desired tool. In reference to Figure G, a pointing device can be used to click at a first point 620 and drag along the intended part of the vessel to edit to a second point 621, and an area 622 will appear indicating where the tool will run. Once the end of the desired area 622 is drawn, releasing the selection will snap the lumen and vessel walls together.

Figure 7H:
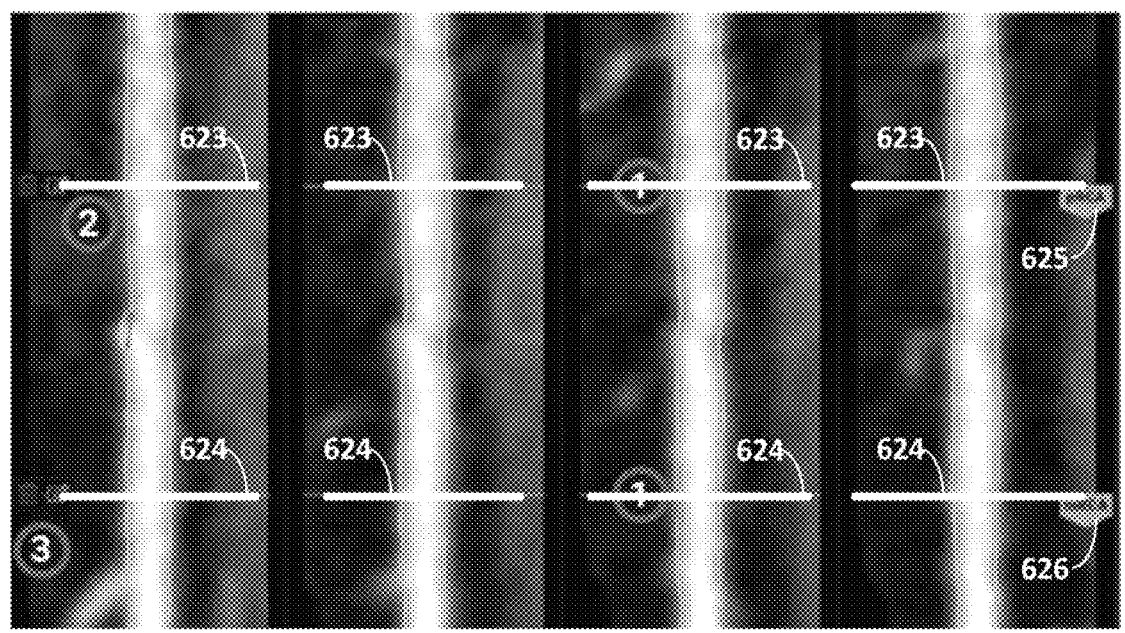
FIG. 7H illustrates an example of a panel of the user interface that can be displayed while using the segment tool which allows for marking the boundaries between individual coronary segments on the MPR.
Figure 7I:
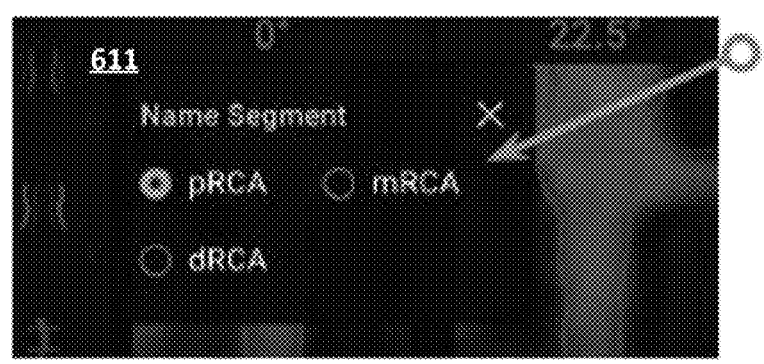
FIG. 7I illustrates an example of a panel of the user interface that allows a different name to be selected for a segment.

FIG. 7H illustrates an example of the second panel 602 that can be displayed while using the Segment tool 705 which allows for marking the boundaries between individual coronary segments on the MPR. The user interface 600 is configured such that when the Segment tool 705 is selected, lines (e.g., lines 623, 624) appear on the vessel image in the second panel 602 on the vessels in the SMPR view. The lines indicate segment boundaries that were determined by the system. The names are displayed in icons 625, 626 adjacent to the respective line 623, 624. To edit the name of the segment, click on an icon 625, 626 and label appropriately using the name panel 611, illustrated in FIG. 7I. A segment can also be deleted, for example, by selecting a trashcan icon. The lines 623, 624 can be moved up and down to define the segment of interest. If a segment is missing, the user can add a new segment using a segment addition button, and labeled using the labeling feature in the segment labeling pop-up menu 611.

Figure 7J:
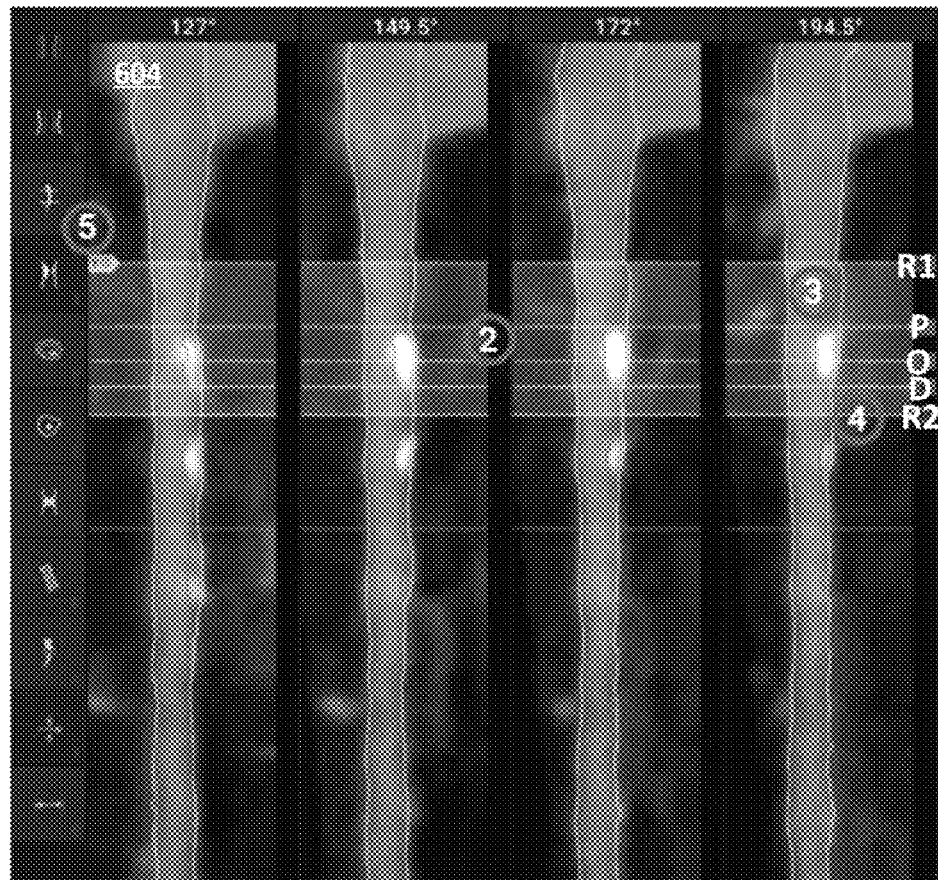
FIG. 7J illustrates an example of a panel of the user interface that can be displayed while using the stenosis tool, which allows a user to indicate markers to mark areas of stenosis on a vessel.
Figure 7K:
FIG. 7K illustrates an example of a stenosis button of the user interface which can be used to drop five evenly spaced stenosis markers.
Figure 7L:
FIG. 7L illustrates an example of a stenosis button of the user interface which can be used to drop stenosis markers based on the user edited lumen and vessel wall contours.
Figure 7M:
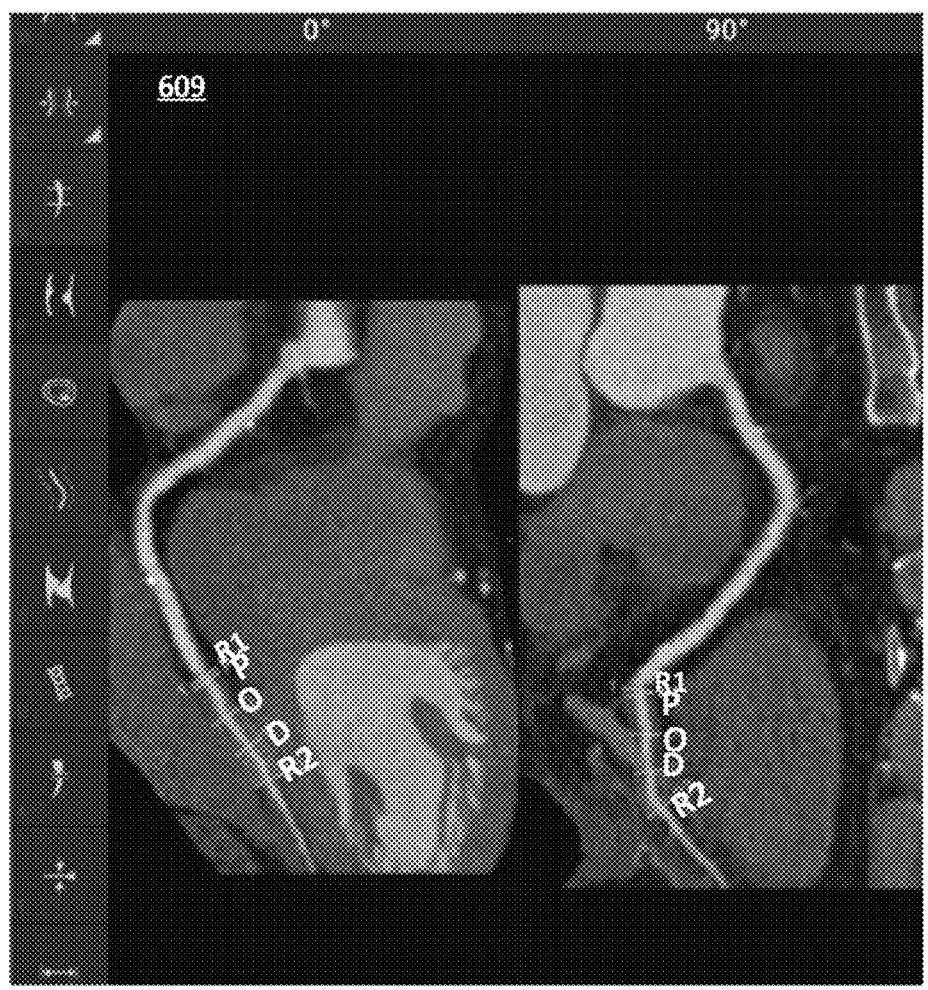
FIG. 7M illustrates the stenosis markers on segments on a curved multiplanar vessel (CMPR) view.

FIGS. 7J-7M illustrate an example of using the stenosis tool 706 on the user interface 600. For example, FIG. 7L illustrates a stenosis button which can be used to drop stenosis markers based on the user edited lumen and vessel wall contours. FIG. 7M illustrates the stenosis markers on segments on a curved multiplanar vessel (CMPR) view. The second panel 604 can be displayed while using the stenosis tool 706 which allows a user to indicate markers to mark areas of stenosis on a vessel. In an embodiment, the stenosis tool contains a set of five markers that are used to mark areas of stenosis on the vessel. These markers are defined as:

R1: Nearest proximal normal slice to the stenosis/lesion
P: Most proximal abnormal slice of the stenosis/lesion
O: Slice with the maximum occlusion
D: Most distal abnormal slice of the stenosis/lesion
R2: Nearest distal normal slice to the stenosis/lesion In an embodiment, there are two ways to add stenosis markers to the multiplanar view (straightened and curved). After selecting the stenosis tool 706, a stenosis can be added by activating the stenosis button shown in FIG. 7K or FIG. 7L: to drop 5 evenly spaced stenosis markers (i) click on the Stenosis "+" button (FIG. 7K); (ii) a series of 5 evenly spaced yellow lines will appear on the vessel; the user must edit these markers to the applicable position; (iii) move all 5 markers at the same time by clicking inside the highlighted area encompassed by the markers and dragging them up/down; (iv) move the individual markers by clicking on the individual yellow lines or tags and move up and down; (v) to delete a stenosis, click on the red trashcan icon. To drop stenosis markers based on the user-edited lumen and vessel wall contours, click on the stenosis "⟳" button (see FIG. 7L). A series of 5 yellow lines will appear on the vessel. The positions are based on the user-edited contours. The user interface 600 provides functionality for a user to edit the stenosis markers, e.g., can move the stenosis markers FIG. 7J illustrates the stenosis markers R1, P, O, D, and R2 placed on vessels in a SMPR view. FIG. 7M illustrates the markers R1, P, O, D, and R2 placed on vessels in a CMPR view.

Figure 7N:
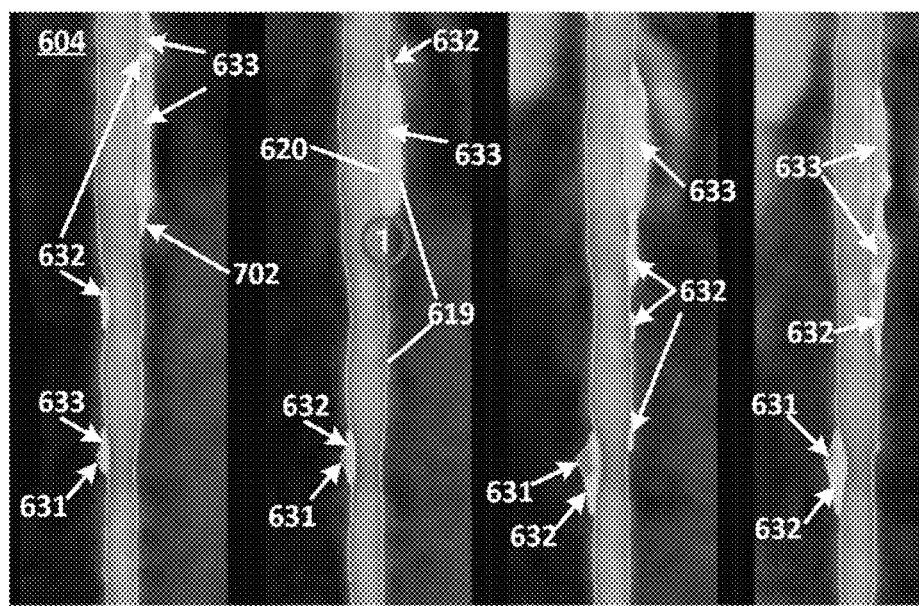
FIG. 7N illustrates an example of a panel of the user interface that can be displayed while using the plaque overlay tool.
Figure 7O:
FIGS. 7O and 7P illustrate a button on the user interface that can be selected to the plaque thresholds.

FIG. 7N illustrates an example of a panel that can be displayed while using the Plaque Overlay tool 707 of the user interface. In an embodiment and in reference to FIG. 7N, "Plaque" is categorized as: low-density-non-calcified plaque (LD-NCP) 701, non-calcified plaque (NCP) 632, or calcified plaque (CP) 633. Selecting the Plaque Overlay tool 707 on the editing toolbar activates the tool. When activated, the Plaque Overlay tool 707 overlays different colors on vessels in the SMPR view in the second panel 604, and in the cross-section the SMPR, and cross-section view in the third panel 606 (see for example, FIG. 7R) with areas of plaque based on Hounsfield Unit (HU) density. In addition, a legend opens in the cross-section view corresponding to plaque type to plaque overlay color as illustrated in FIGS.

Figure 7P:

7O and 7Q. Users can select different HU ranges for the three different types of plaque by clicking on the "Edit Thresholds" button located in the top right corner of the cross-section view as illustrated in FIG. 7P. In one embodiment, plaque thresholds default to the values shown in the table below:

| Plaque Type | Hounsfield Unit (HU) |
|---|---|
| LD-NCP | −189 to 30 |
| NCP | −139 to 353 |
| CP | 350 to 2500 |

Figure 7Q:
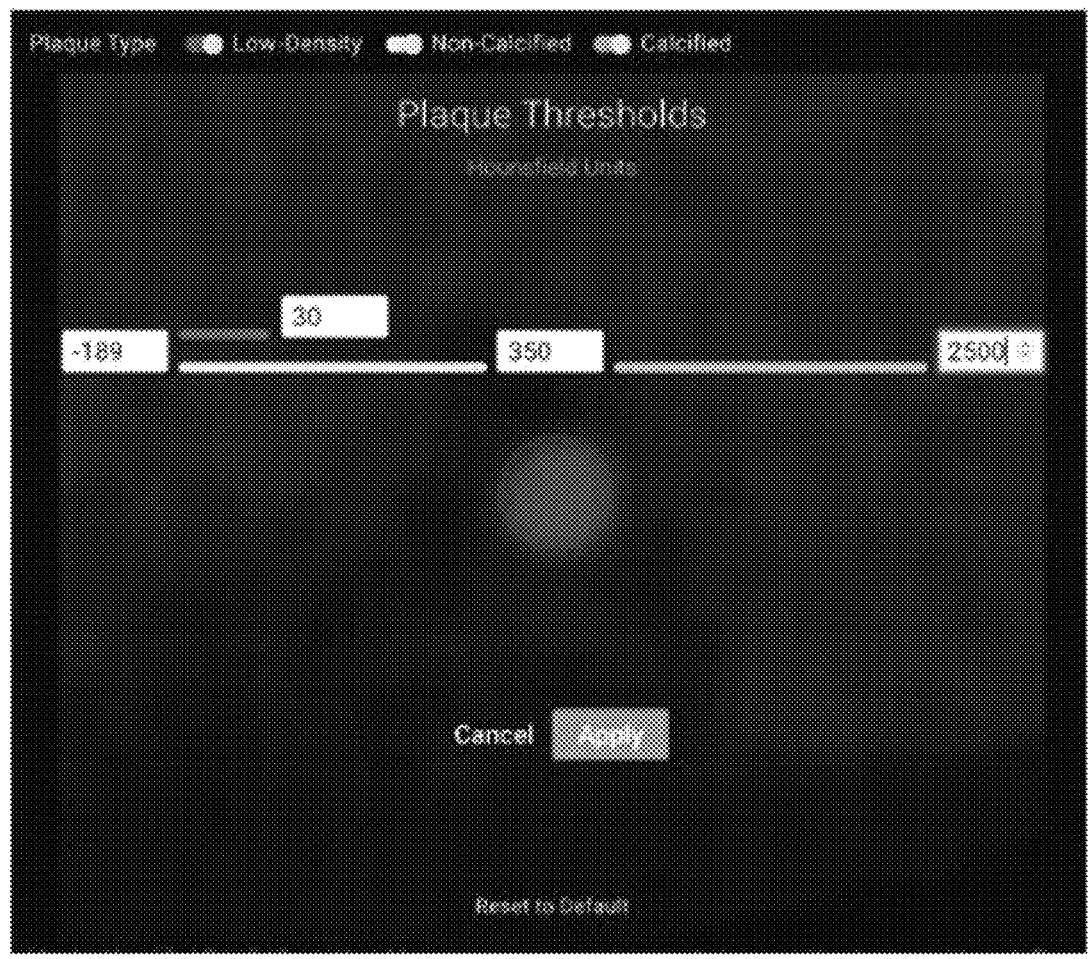
FIG. 7Q illustrates a panel of the user interface which can receive a user input to adjust plaque threshold levels for low-density plaque, non-calcified plaque, and calcified plaque.
Figure 7S:
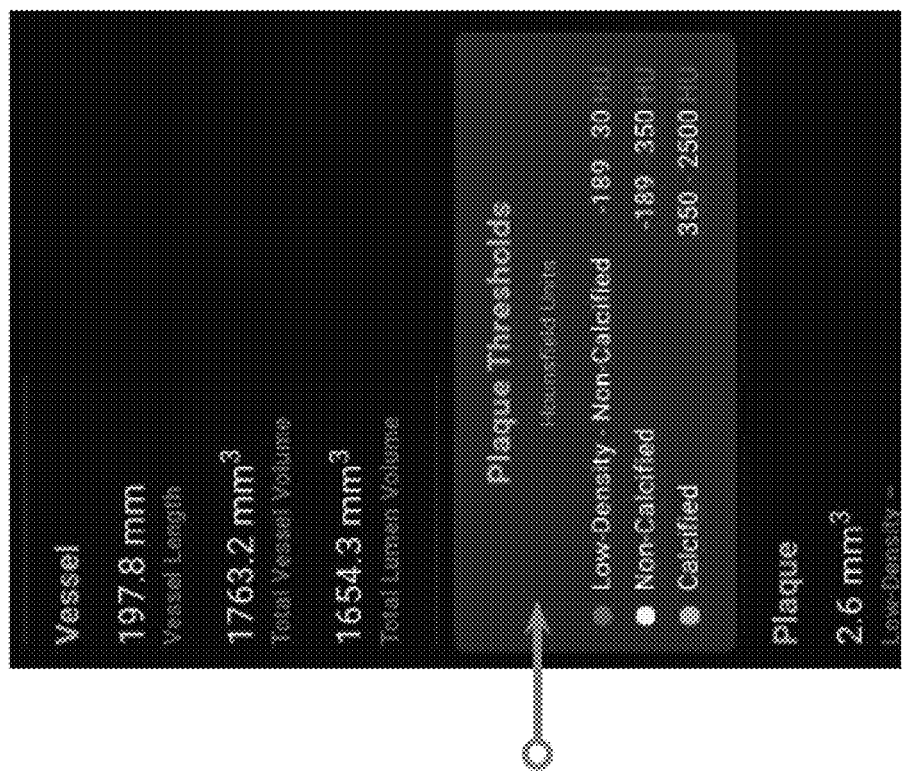
FIG. 7S illustrates a panel can be displayed showing plaque thresholds in a vessel statistics panel that includes information on the vessel being viewed.
Figure 7R:
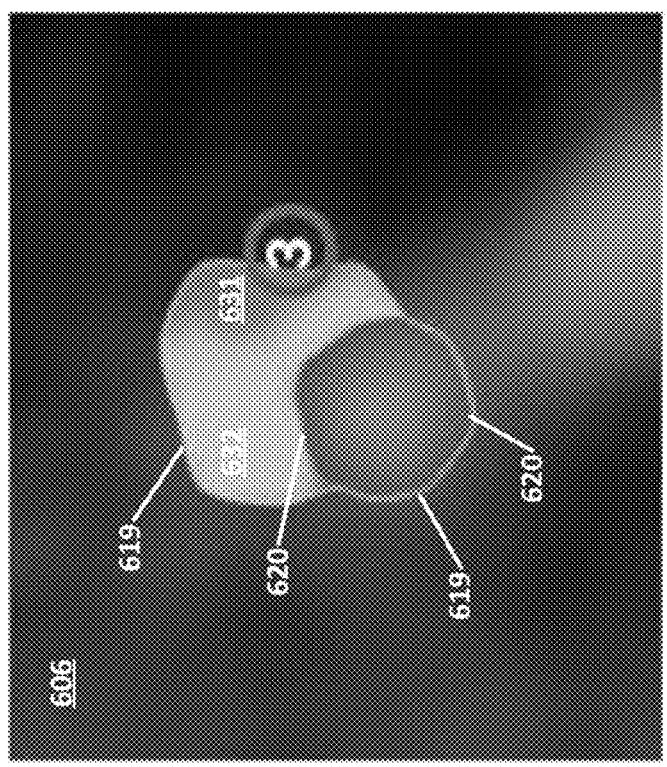
FIG. 7R illustrates a cross-sectional view of a vessel indicating areas of plaque which are displayed in the user interface in accordance with the plaque thresholds.
Figure 7U:
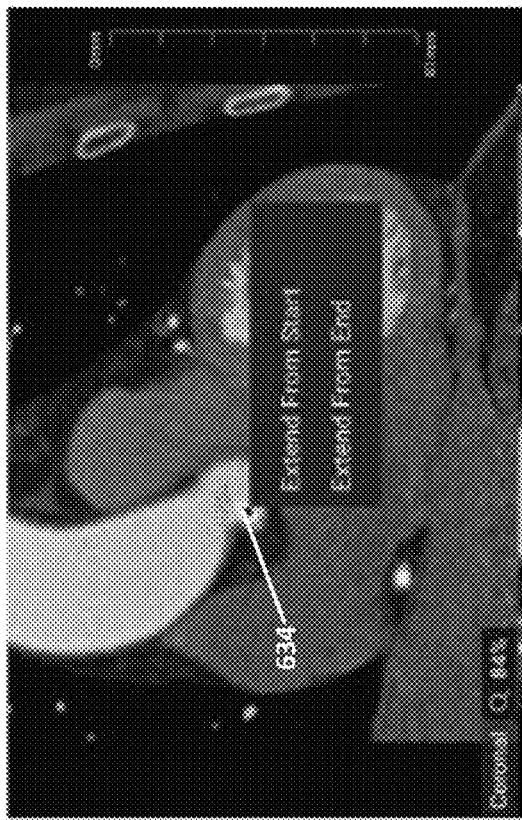
FIGS. 7U, 7V, 7W illustrate examples of panels showing other views of a vessel that can be displayed when using the centerline tool.
Figure 7W:
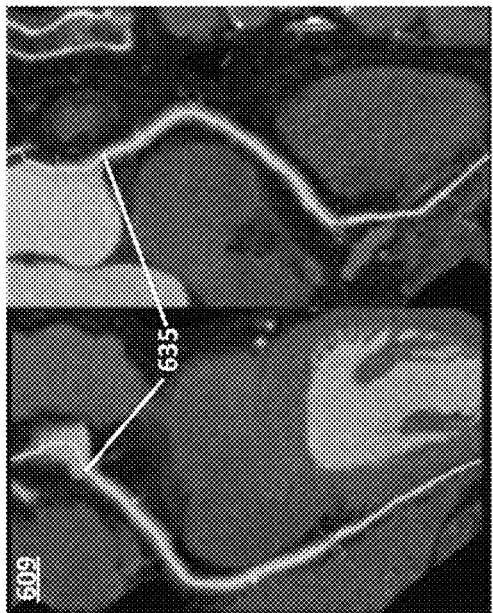
Figure 7T:
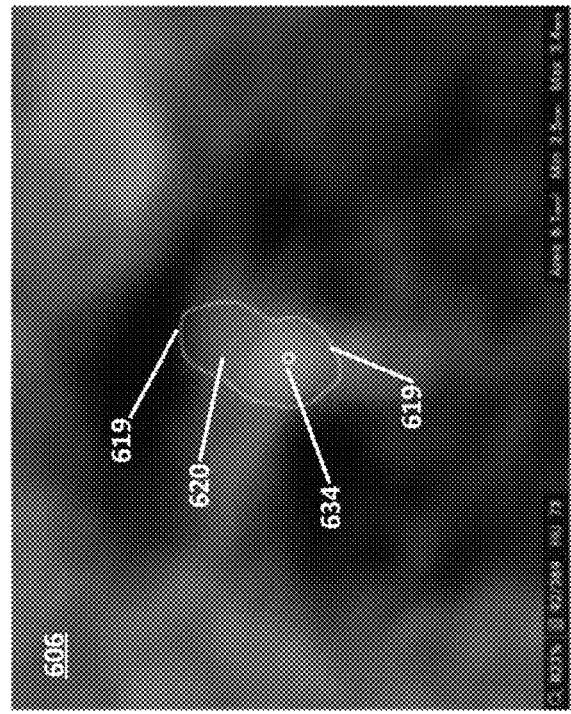
FIG. 7T illustrates a panel showing a cross-sectional view of a vessel that can be displayed while using the centerline tool, which allows adjustment of the center of the lumen.
Figure 7V:

The default values can be revised, if desired, for example, using the Plaque Threshold interface shown in FIG. 7Q. Although default values are provided, users can select different plaque thresholds based on their clinical judgment. Users can use the cross-section view of the third panel 606, illustrated in FIG. 7R, to further examine areas of interest. Users can also view the selected plaque thresholds in a vessel statistics panel of the user interface 600, illustrated in FIG. 7S.

The Centerline tool 708 allows users to adjust the center of the lumen. Changing a center point (of the centerline) may change the lumen and vessel wall and the plaque quantification. if present. The Centerline tool 708 is activated by selecting it on the user interface 600. A line 635 (e.g., a yellow line) will appear on the CMPR view 609 and a point 634 (e.g., a yellow point) will appear in the cross-section view on the third panel 606. The centerline can be adjusted as necessary by clicking and dragging the line/point. Any changes made in the CMPR view will be reflected in the cross-section view, and vice-versa. The user interface 600 provides for several ways to extend the centerline of an existing vessel. For example, a user can extend the centerline by: (1) right-clicking on the dot 634 delineated vessel on the axial, coronal, or sagittal view (see FIG. 7U); (2) select "Extend from Start" or "Extend from End" (see FIG. 7U), the view will jump to the start or end of the vessel; (3) add (green) dots to extend the vessel (see FIG. 7V); (4) when finished, select the (blue) check mark button, to cancel the extension, select the (red) "x" button (see for example, FIG. 7V). The user interface then extends the vessel according to the changes made by the user. A user can then manually edit the lumen and vessel walls on the SMPR or cross-section views (see for example, FIG. 7W). If the user interface is unable to identify the vessel section which has been added by the user, it will return straight vessel lines connecting the user-added dots. The user can then adjust the centerline.

Figure 7X:
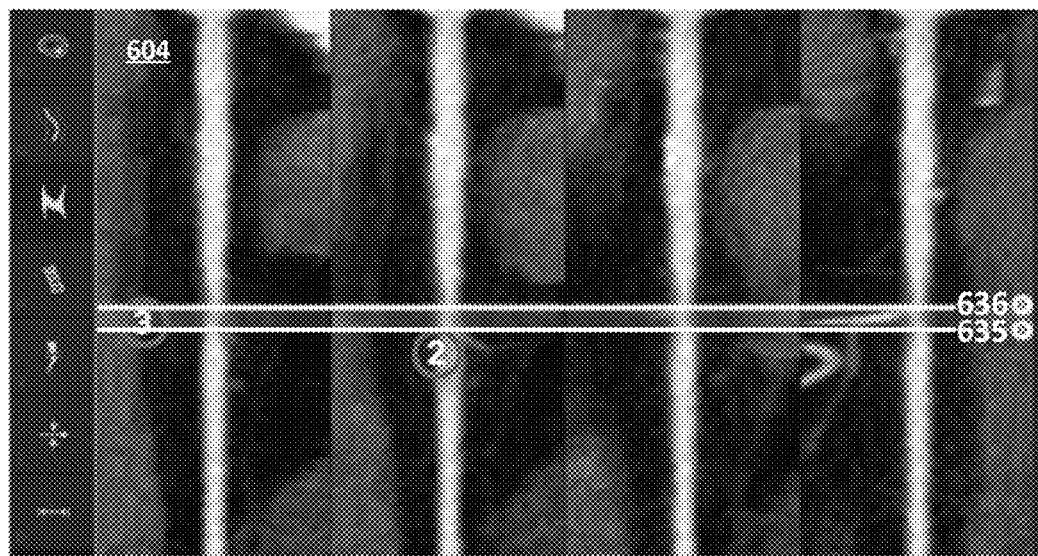
FIG. 7X illustrates an example of a panel that can be displayed while using the chronic total occlusion (CTO) tool, which is used to indicate a portion of artery with 100% stenosis and no detectable blood flow.

The user interface 600 also provides a Chronic Total Occlusion (CTO) tool 709 to identify portions of an artery with a chronic total occlusion (CTO), that is, a portion of artery with 100% stenosis and no detectable blood flow. Since it is likely to contain a large amount of thrombus, the plaque within the CTO is not included in overall plaque quantification. To activate, click on the CTO tool 709 on the editing toolbar 612. To add a CTO, click on the CTO "+" button on the user interface. Two lines (markers) 636, 637 will appear on the MPR view in the second panel 604, as illustrated in FIG. 7X indicating a portion of the vessel of the CTO. The markers 636, 637 can be moved to adjust the extent of the CTO. If more than one CTO is present, additional CTO's can be added by again activating the CTO "+" button on the user interface. A CTO can also be deleted, if necessary. The location of the CTO is stored. In addition, portions of the vessel that are within the designated CTO are not included in the overall plaque calculation, and the plaque quantification determination is re-calculated as necessary after CTO's are identified.

Figure 7Y:
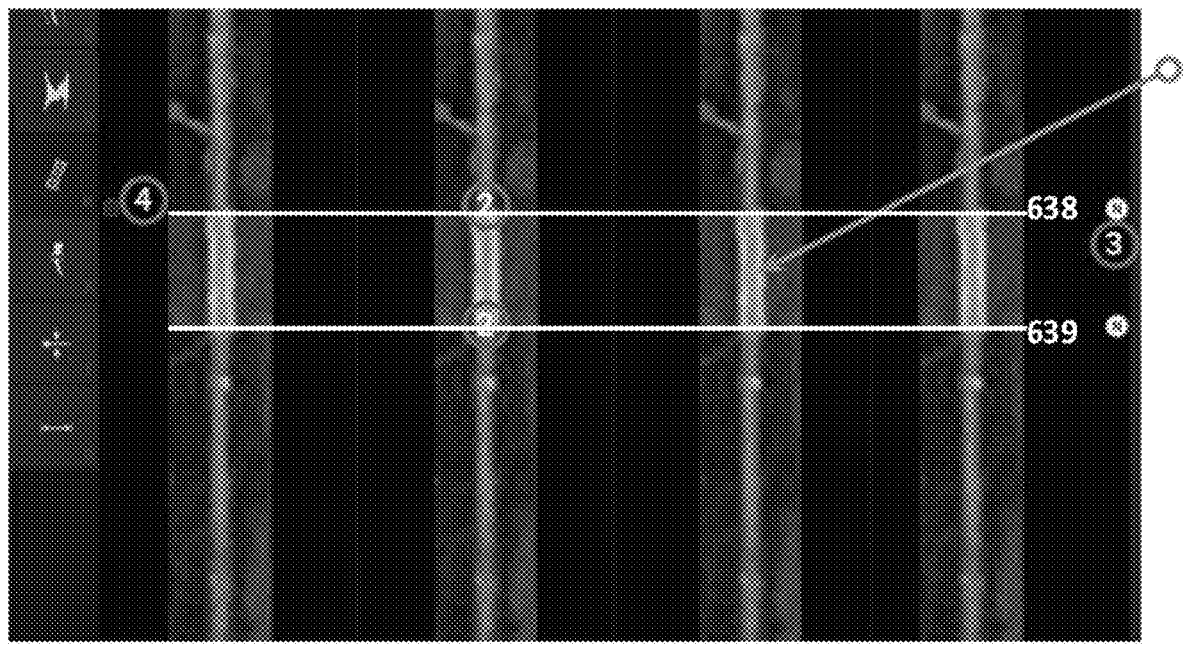
FIG. 7Y illustrates an example of a panel that can be displayed while using the stent tool, which allows a user to mark the extent of a stent in a vessel.
Figure 7A:
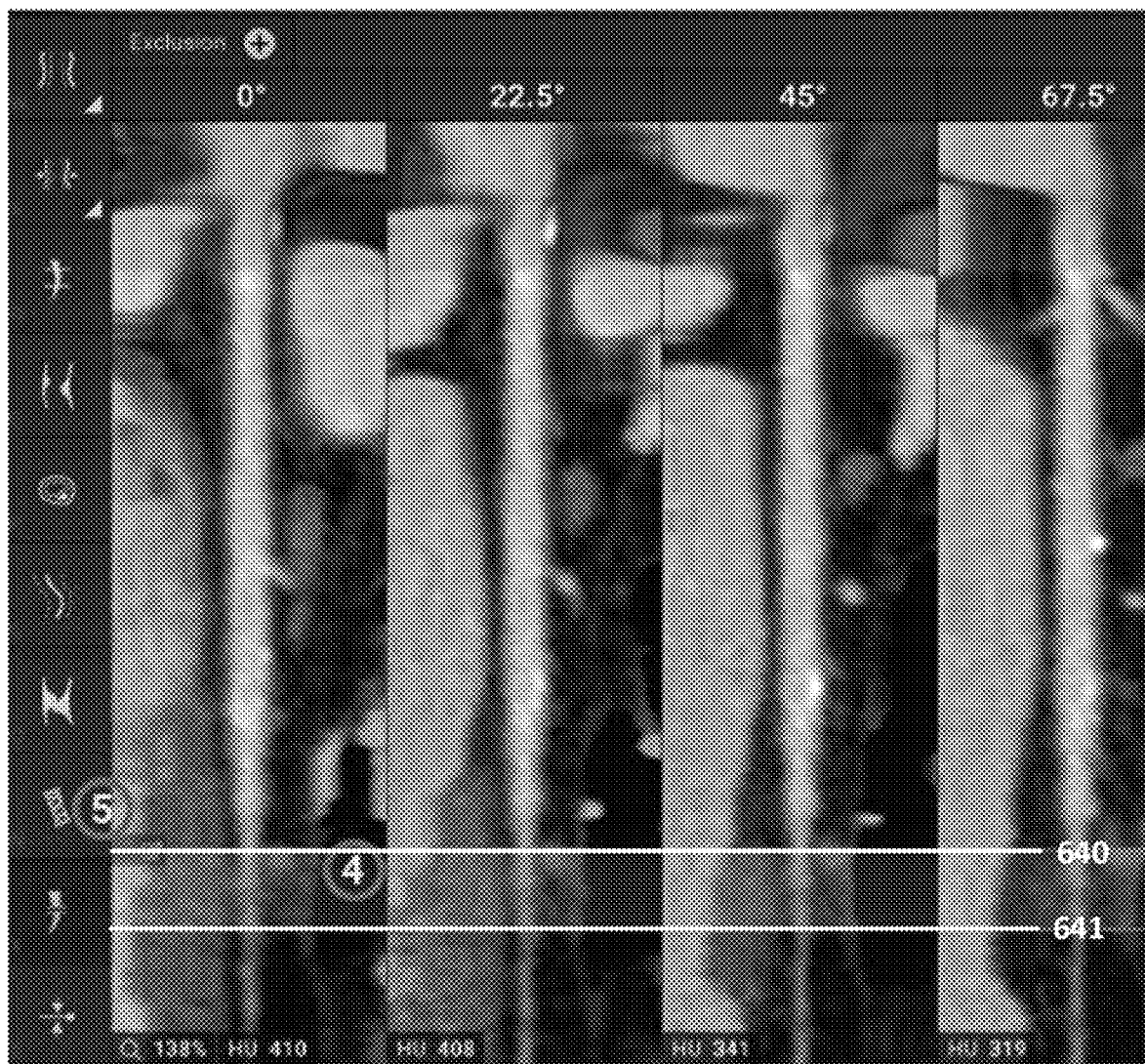
Figure 7A:
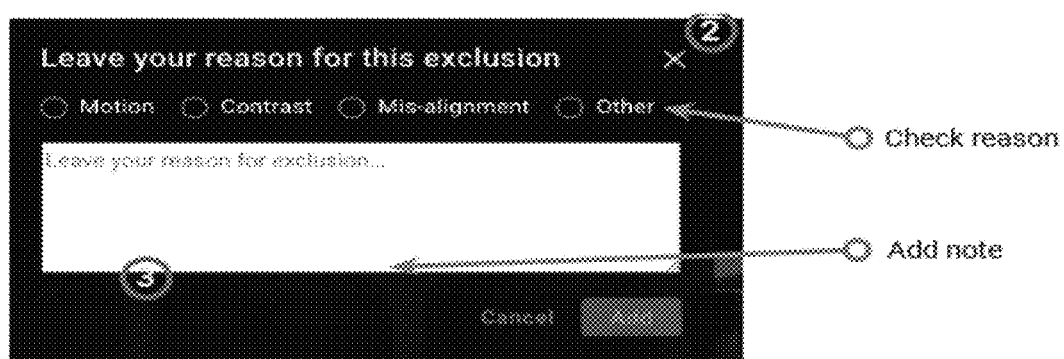
Figure 7A:
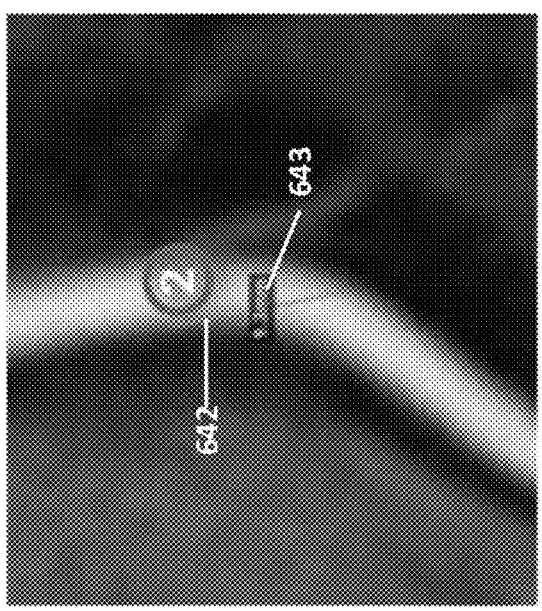
Figure 7A:
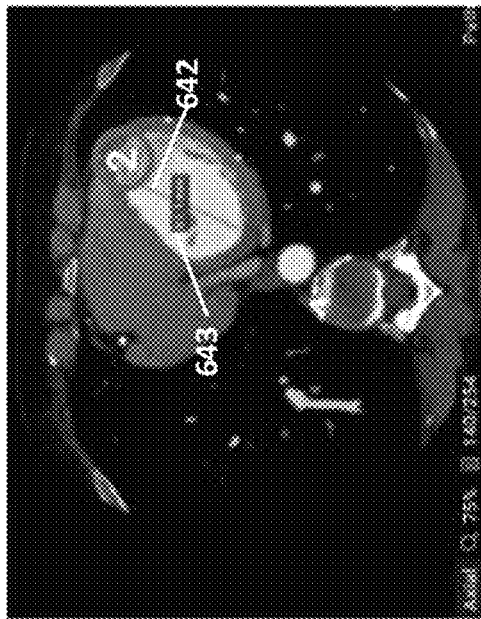
Figure 7A:
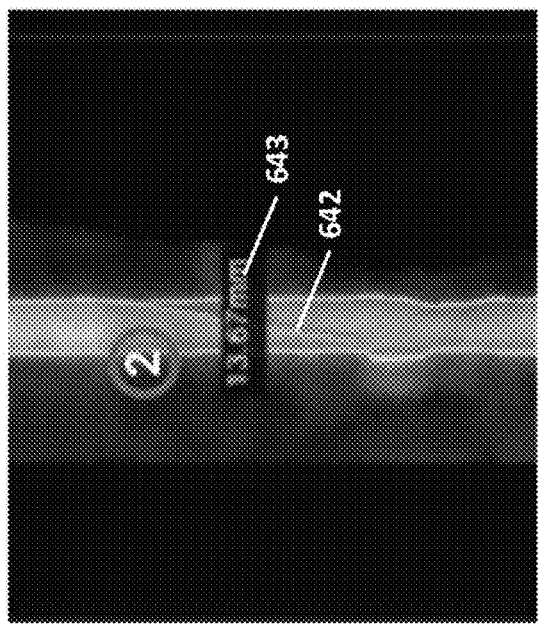
Figure 7A:
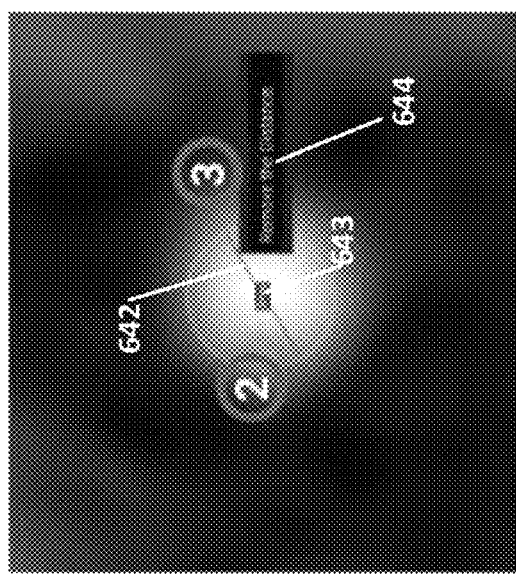
Figure 7A:
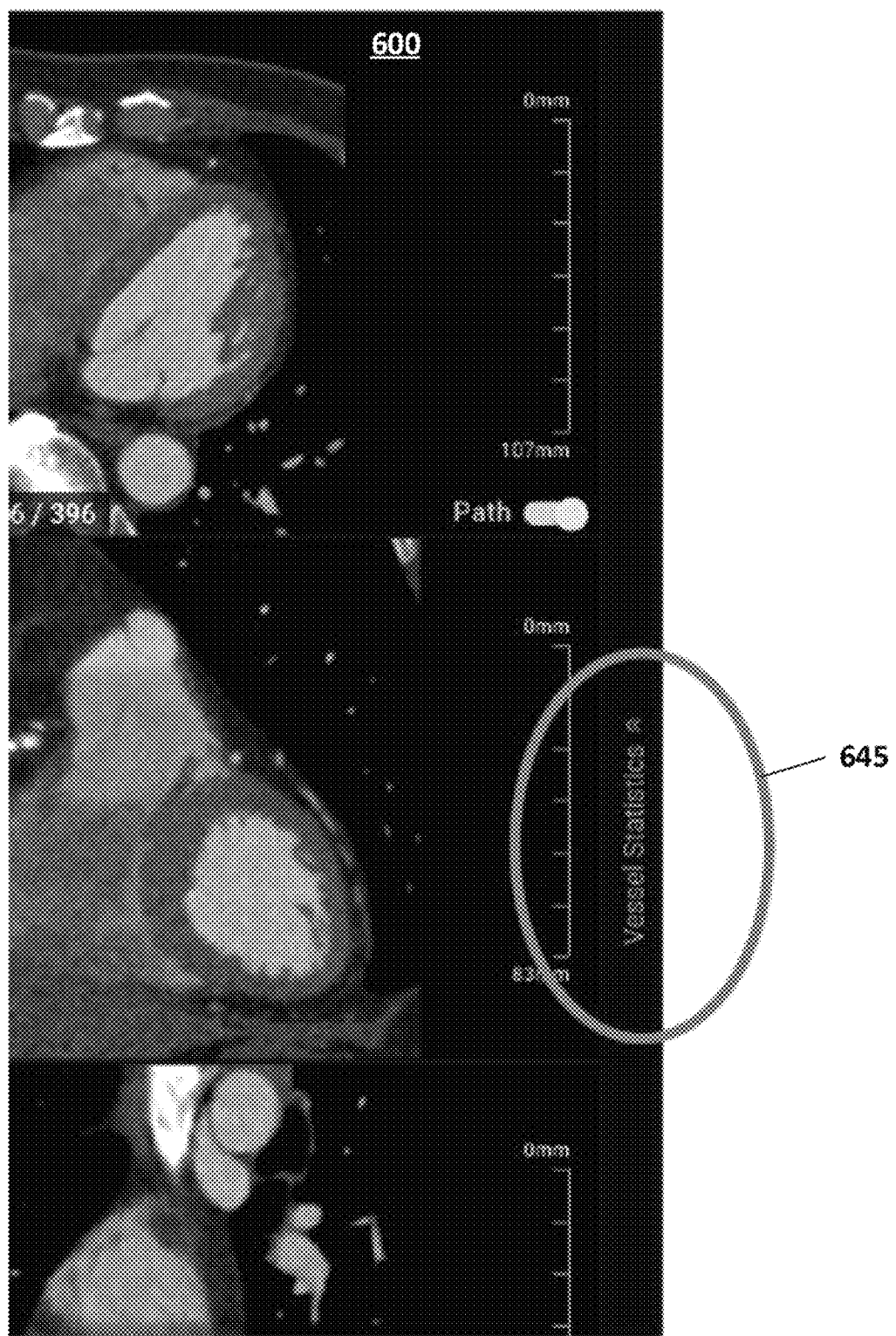
Figure 7A:
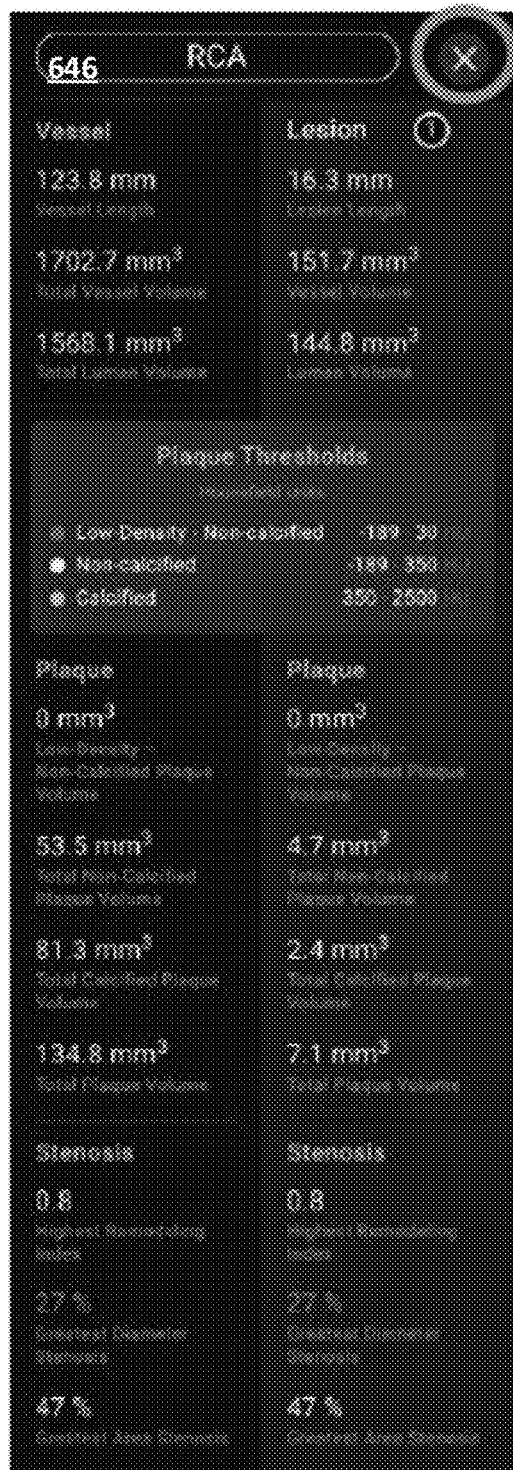
Figure 7A:
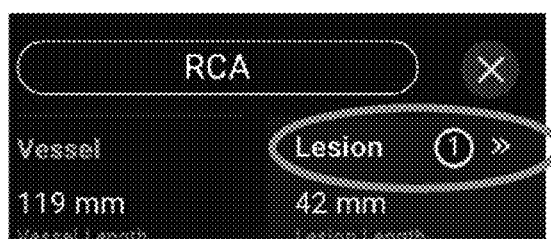
Figure 7A:
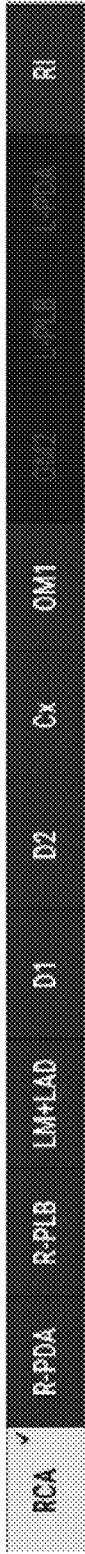

The user interface 600 also provides a Stent tool 710 to indicate where in vessel a stent exists. The Stent tool is activated by a user selection of the Stent tool 710 on the toolbar 612. To add a stent, click on the Stent "+" button provided on the user interface. Two lines 638, 639 (e.g., purple lines) will appear on of the MPR view as illustrated in FIG. 7Y, and the lines 638, 639 can be moved to indicate the extend of the stent by clicking on the individual lines 638, 639 and moving them up and down along the vessel to the ends of the stent. Overlapping with the stent (or the CTO/Exclusion/Stenosis) markers is not permitted by the user interface 600. A stent can also be deleted.

The user interface 600 also provides an Exclude tool 711 that is configured to indicate a portion of a vessel to exclude from the analysis due to blurring caused by motion, contrast, misalignment, or other reasons. Excluding poor quality images will improve the overall quality of the results of the analysis for the non-excluded portions of the vessels. To exclude the top or bottom portion of a vessel, activate the segment tool 705 and the exclude tool 711 in the editing toolbar 612. FIG. 7Z illustrates the use of the exclusion tool to exclude a portion from the top of the vessel. FIG. 7AA illustrates the use of the exclusion tool to exclude a bottom portion of the vessel. A first segment marker acts as the exclusion marker for the top portion of the vessel. The area enclosed by exclusion markers is excluded from all vessel statistic calculations. An area can be excluded by dragging the top segment marker to the bottom of the desired area of exclusion. The excluded area will be highlighted. Or the "End" marker can be dragged to the top of the desired area of exclusion. The excluded area will be highlighted, and a user can enter the reason for an exclusion in the user interface (see FIG. 7AC). To add a new exclusion to the center of the vessel, activate the exclude tool 711 on the editing toolbar 612. Click on the Exclusion "+" button. A pop-up window on the user interface will appear for the reason of the exclusion (FIG. 7AC), and the reason can be entered and it is stored in reference to the indicated excluded area. Two markers 640, 641 will appear on the MPR as shown in FIG. 7AB. Move both markers at the same time by clicking inside the highlighted area. The user can move the individual markers by clicking and dragging the lines 640, 641. The user interface 600 tracks the locations of the of the exclusion marker lines 640, 641 (and previously defined features) and prohibits overlap of the area defined by the exclusion lines 640, 641 with any previously indicated portions of the vessel having a CTO, stent or stenosis. The user interface 600 also is configured to delete a designated exclusion.

Now referring to FIGS. 7AD-7AG, the user interface 600 also provides a Distance tool 713, which is used to measure the distance between two points on an image. It is a drag and drop ruler that captures precise measurements. The Distance tool works in the MPR, cross-section, axial, coronal, and sagittal views. To activate, click on the distance tool 713 on the editing toolbar 612. Then, click and drag between the desired two points. A line 642 and measurement 643 will appear on the image displayed on the user interface 600. Delete the measurement by right-clicking on the distance line 642 or measurement 643 and selecting "Remove the Distance" button 644 on the user interface 600 (see FIG. 7AF). FIG. 7AD illustrates an example of measuring a distance of a straightened multiplanar vessel (SMPR). FIG.

7AE illustrates an example of measuring the distance 642 of a curved multiplanar vessel (CMPR). FIG. 7AF illustrates an example of measuring a distance 642 of a cross-section of the vessel. FIG. 7AG illustrates an example of measuring the distance 642 on an Axial View of a patient's anatomy.

An example of a vessel statistics panel of the user interface 600 is described in reference to FIGS. 7AH-7AK. FIG. 7AH illustrates a "vessel statistics" portion 645 of the user interface 600 (e.g., a button) of a panel which can be selected to display the vessel statistics panel 646 (or "tab"), illustrated in FIG. 7AI. FIG. 7AJ illustrates certain functionality on the vessel statistics tab that allows a user to click through the details of multiple lesions. FIG. 7AK further illustrates the vessel panel which the user can use to toggle between vessels. For example, Users can hide the panel by clicking on the "X" on the top right hand side of the panel, illustrated in FIG. 7AI. Statistics are shown at the per-vessel and per-lesion (if present) level, as indicated in FIG. 7AJ.

If more than one lesion is marked by the user, the user can click through each lesion's details. To view the statistics for each vessel, the users can toggle between vessels on the vessel panel illustrated in FIG. 7AK.

General information pertaining to the length and volume are presented for the vessel and lesion (if present) in the vessel statistics panel 646, along with the plaque and stenosis information on a per-vessel and per-lesion level. Users may exclude artifacts from the image they do not want to be considered in the calculations by using the exclusion tool. The following tables indicate certain statistics that are available for vessels, lesions, plaque, and stenosis.

Vessel

| Term | Definition |
|---|---|
| Vessel Length (mm) | Length of a linear coronary vessel |
| Total Vessel Volume (mm3) | The volume of consecutive slices of vessel contours. |
| Total Lumen Volume (mm3) | The volume of consecutive slices of lumen contours |

Lesion

| Term | Definition |
|---|---|
| Lesion Length (mm) | Linear distance from the start of a coronary lesion to the end of a coronary lesion. |
| Vessel Volume (mm3) | The volume of consecutive slices of vessel contours. |
| Lumen Volume (mm3) | The volume of consecutive slices of lumen contours. |

Plaque

| Term | Definition |
|---|---|
| Total Calcified Plaque Volume (mm3) | Calcified plaque is defined as plaque in between the lumen and vessel wall with an attenuation of greater than 350 HU, or as defined by the user, and is reported in absolute measures by plaque volume. Calcified plaques are identified in each coronary artery ≥1.5 mm in mean vessel diameter. |
| Total Non-Calcified Plaque Volume (mm3) | Non-calcified plaque is defined as plaque in between the lumen and vessel wall with an attenuation of less than or equal to 350, or as defined by the user, HU and is reported in absolute measures by plaque volume. The total non-calcified plaque volume is the sum total of all non-calcified plaques identified in each coronary artery ≥1.5 mm in mean vessel diameter. Non-calcified plaque data reported is further broken down into low-density plaque, based on HU density thresholds. |
| Low-Density Non-Calcified Plaque Volume (mm3) | Low-Density--Non-Calcified Plaque is defined as plaque in between the lumen and vessel wall with an attenuation of less than or equal to 30 HU or as defined by the user and is reported in absolute measures by plaque volume. |
| Total Plaque Volume (mm3) | Plaque volume is defined as plaque in between the lumen and vessel wall reported in absolute measures. The total plaque volume is the sum total of all plaque identified in each coronary artery ≥1.5 mm in mean vessel diameter or wherever the user places the "End" marker. |

Stenosis

| Term | Definition |
|---|---|
| Remodeling Index | Remodeling Index is defined as the mean vessel diameter at a denoted slice divided by the mean vessel diameter at a reference slice. |
| Greatest Diameter Stenosis (%) | The deviation of the mean lumen diameter at the denoted slice from a reference slice, expressed in percentage. |
| Greatest Area Stenosis (%) | The deviation of the lumen area at the denoted slice to a reference area, expressed in percentage |

A quantitative variable that is used in the system and displayed on various portions of the user interface 600, for example, in reference to low-density non-calcified plaque, non-calcified plaque, and calcified plaque, is the Hounsfield unit (HU). As is known, a Hounsfield Unit scale is a quantitative scale for describing radiation, and is frequently used in reference to CT scans as a way to characterize radiation attenuation and thus making it easier to define what a given finding may represent. A Hounsfield Unit measurement is presented in reference to a quantitative scale. Examples of Hounsfield Unit measurements of certain materials are shown in the following table:

| Material | HU |
|---|---|
| Air | −1000 |
| Fat | −50 |
| Distilled Water | 0 |
| Soft Tissue | +40 |
| Blood | +40 to 80 |
| Calcified Plaques | 350-1000+ |
| Bone | +1000 |

Figure 8B:
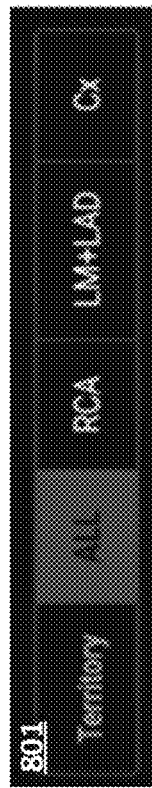
FIG. 8B illustrates an example of a portion of a panel displayed on the user interface that allows selection of a territory or combination of territories (e.g., left main artery (LM), left anterior descending artery (LAD), left circumflex artery (LCx), right coronary artery (RCA), according to various embodiments.
Figure 8A:
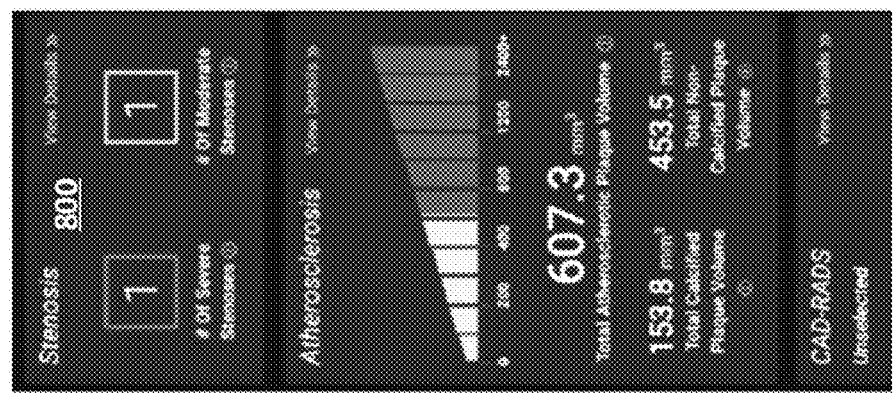
FIG. 8A illustrates an example of a panel of the user interface that shows stenosis, atherosclerosis, and CAD-RADS results of the analysis.
Figure 8C:
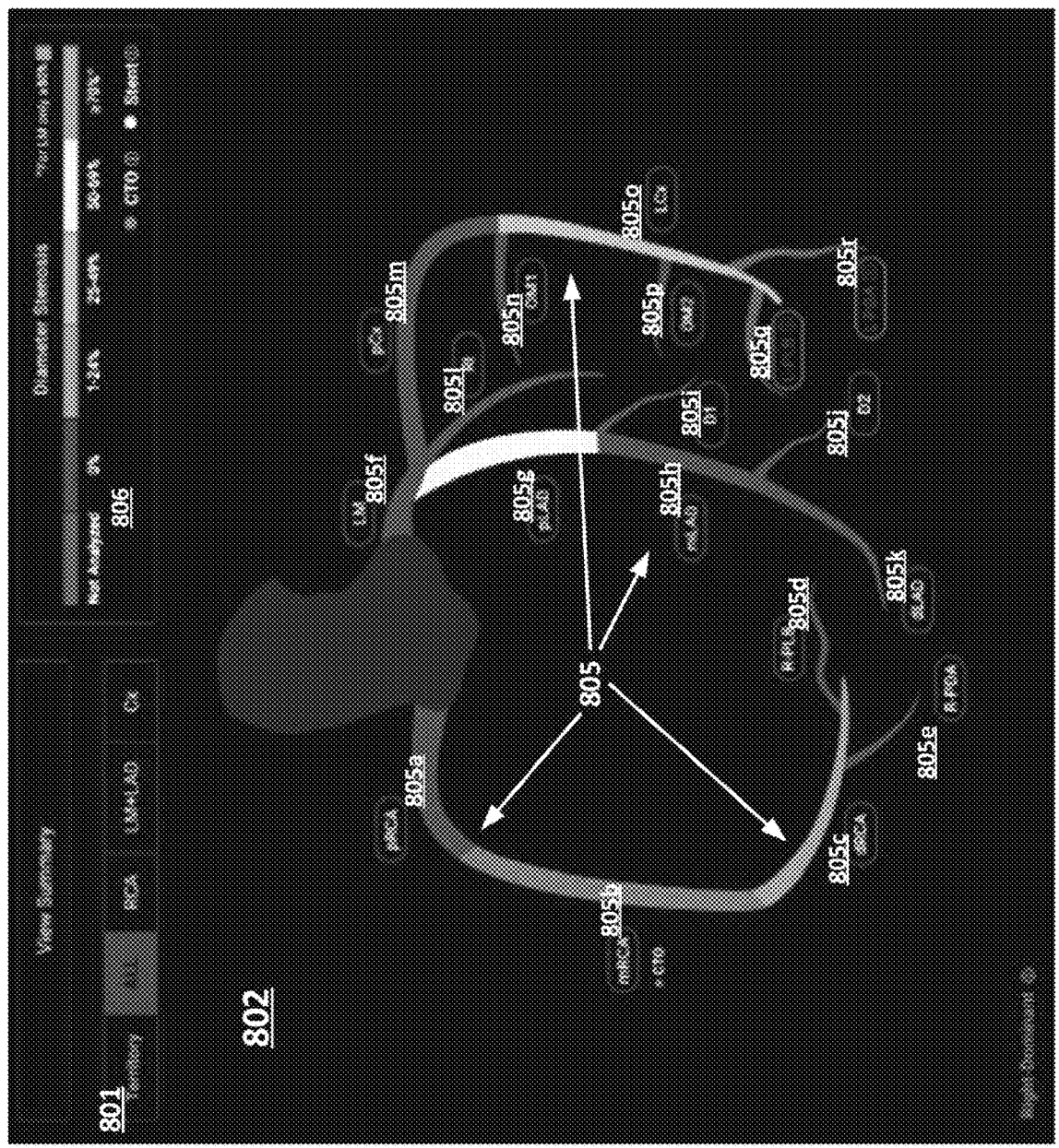
FIG. 8C illustrates an example of a panel that can be displayed on the user interface showing a cartoon representation of a coronary artery tree ("cartoon artery tree").

In an embodiment, information that the system determines relating to stenosis, atherosclerosis, and CAD-RADS details are included on panel 800 of the user interface 600, as illustrated in FIG. 8A. By default, the CAD-RADS score may be unselected and requires the user to manually select the score on the CAD-RADS page. Hovering over the "#" icons causes the user interface 600 to provide more information about the selected output. To view more details about the stenosis, atherosclerosis, and CAD-RADS outputs, click the "View Details" button in the upper right of panel 800—this will navigate to the applicable details page. In an embodiment, in the center of a centerpiece page view of the user interface 600 there is a non-patient specific rendition of a coronary artery tree 805 (a "cartoon artery tree" 805) broken into segments 805a-855r based on the SCCT coronary segmentation, as illustrated in panel 802 in FIG. 8C. All analyzed vessels are displayed in color according to the legend 806 based on the highest diameter stenosis within that vessel. Greyed out segments/vessels in the cartoon artery tree 805, for example, segment 805q and 805r, were not anatomically available or not analyzed in the system (all segments may not exist in all patients). Per-territory and per-segment information can be viewed by clicking the territory above the tree (RCA, LM+LAD, etc.) using, for example, the user interface 600 selection buttons in panel 801, as illustrated in FIGS. 8B and 8C. Or my selecting a segment 805a-805r within the cartoon coronary tree 805.

Figure 8D:
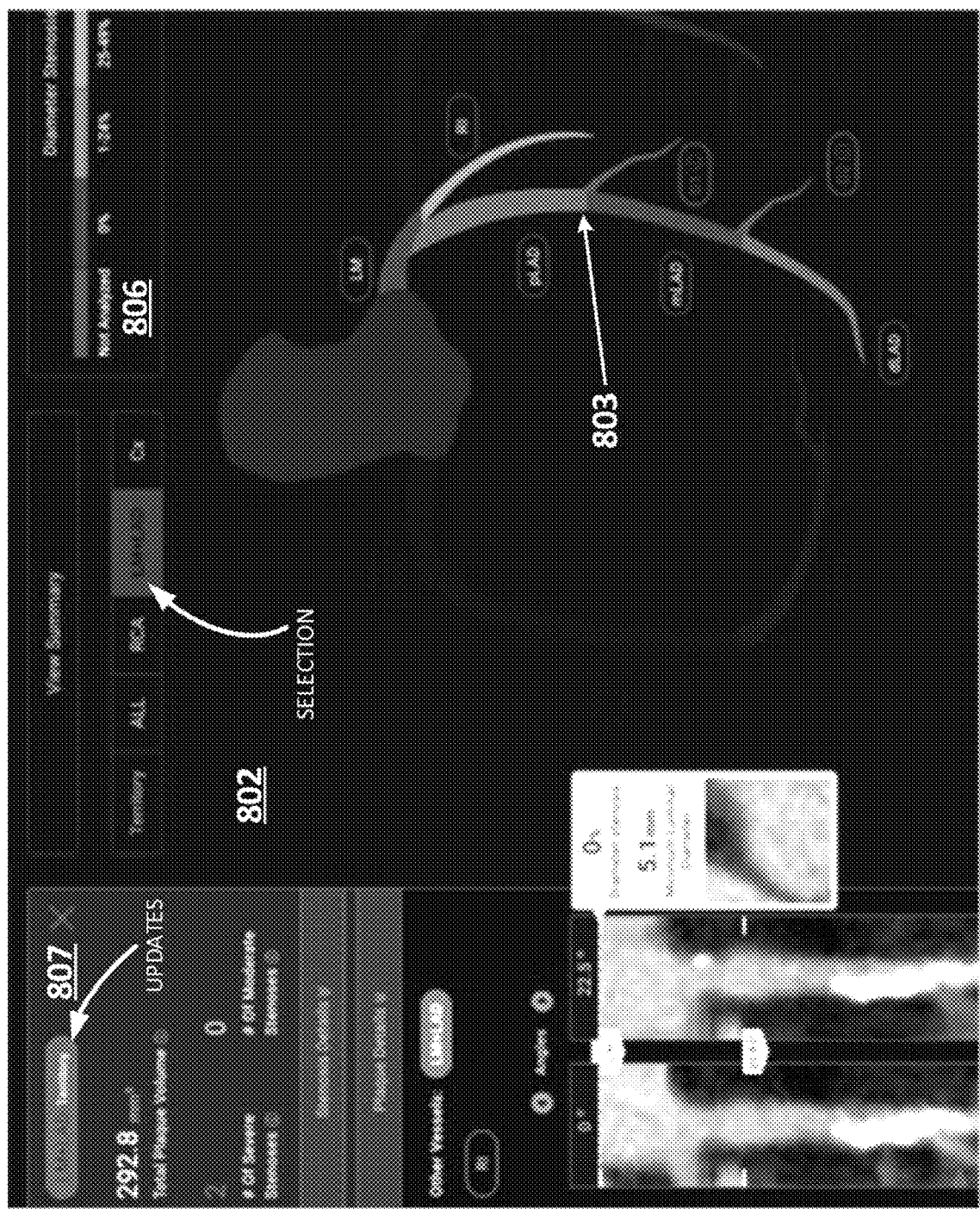
FIG. 8D illustrates an example of a panel that can be displayed on the user interface illustrating territory selection using the cartoon artery tree.
Figure 8F:
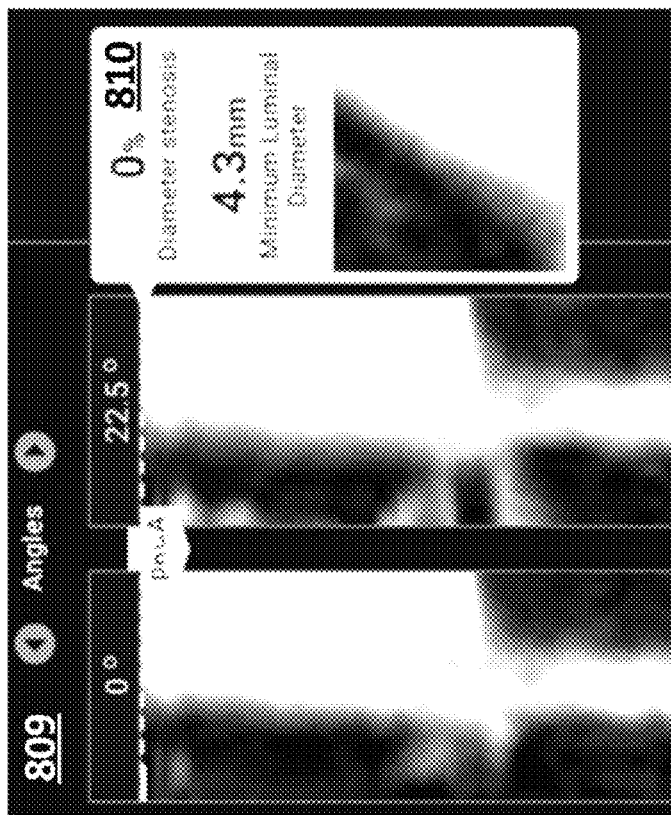
FIG. 8F illustrates an example panel that can be displayed on the user interface showing a SMPR view of a selected vessel, and corresponding statistics of the selected vessel.
Figure 8I:
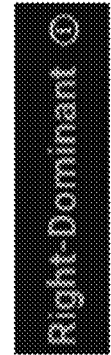
FIG. 8I illustrates an example of a portion of a panel that can be displayed in the user interface indicating left or right dominance of the patient.
Figure 8E:
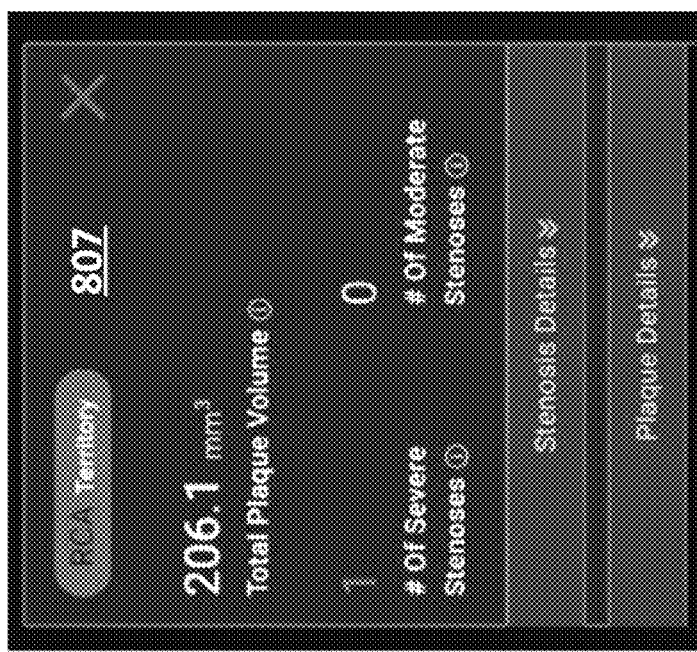
FIG. 8E illustrates an example panel that can be displayed on the user interface showing per-territory summaries.
Figure 8H:
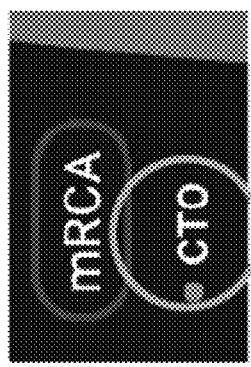
FIG. 8H illustrates an example of a portion of a panel that can be displayed in the user interface indicating CTO presence at the segment level.
Figure 8G:
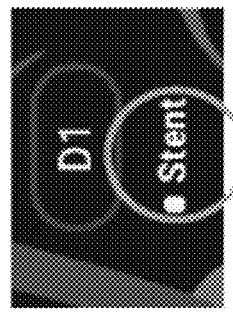
FIG. 8G illustrates an example of a portion of a panel that can be displayed in the user interface indicating the presence of a stent, which is displayed at the segment level.
Figure 8J:
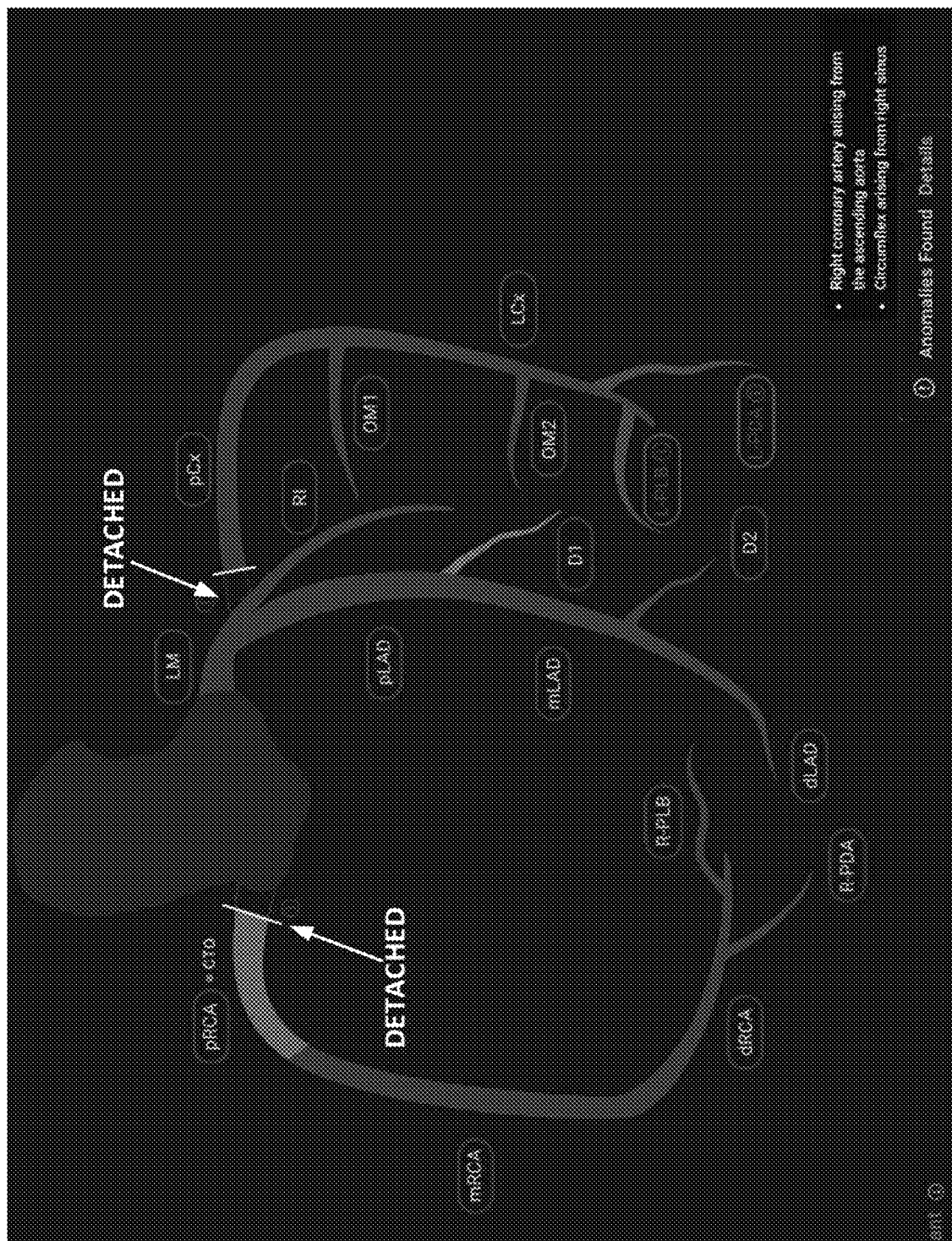
FIG. 8J illustrates an example of a panel that can be displayed on the user interface showing cartoon artery tree with indications of anomalies that were found.
Figure 8K:
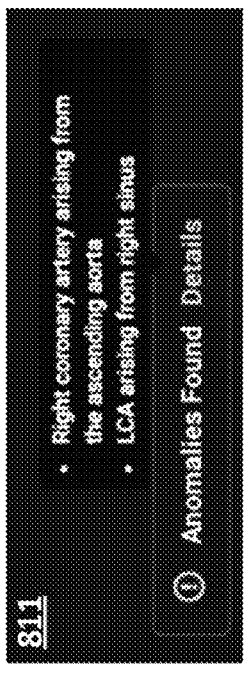
FIG. 8K illustrates an example of a portion of a panel that can be displayed on the panel of FIG. 8J that can be selected to show details of an anomaly.

Stenosis and atherosclerosis data displayed on the user interface in panel 807 will update accordingly as various segments are selected, as illustrated in FIG. 8D. FIG. 8E illustrates an example of a portion of the per-territory summary panel 807 of the user interface. FIG. 8F also illustrates an example of portion of panel 807 showing the SMPR of a selected vessel and its associated statistics along the vessel at indicated locations (e.g., at locations indicated by a pointing device as it is moved along the SMPR visualization). That is, the user interface 600 is configured to provide plaque details and stenosis details in an SMPR visualization in panel 809 and a pop-up panel 810 that displays information as the user interface receives location information long the displayed vessel from the user, e.g., via a pointing device. The presence of a chronic total occlusion (CT)) and/or a stent are indicated at the vessel segment level. For example, FIG. 8G illustrates the presence of a stent in the D1 segment. FIG. 8H indicates the presence of a CTO in the mRCA segment. Coronary dominance and any anomalies can be displayed below the coronary artery tree as illustrated in FIG. 8I. The anomalies that were selected in the analysis can be displayed, for example, by "hovering" with a pointing device over the "details" button. If plaque thresholds were changed in the analysis, an alert can be displayed on the user interface, or on a generated report, that indicates the plaque thresholds were changed. When anomalies are present, the coronary vessel segment 805 associated with each anomaly will appear detached from the aorta as illustrated in FIG. 8J. In an embodiment, a textual summary of the analysis can also be displayed below the coronary tree, for example, as illustrated in the panel 811 in FIG. 8K.

Figure 9A:
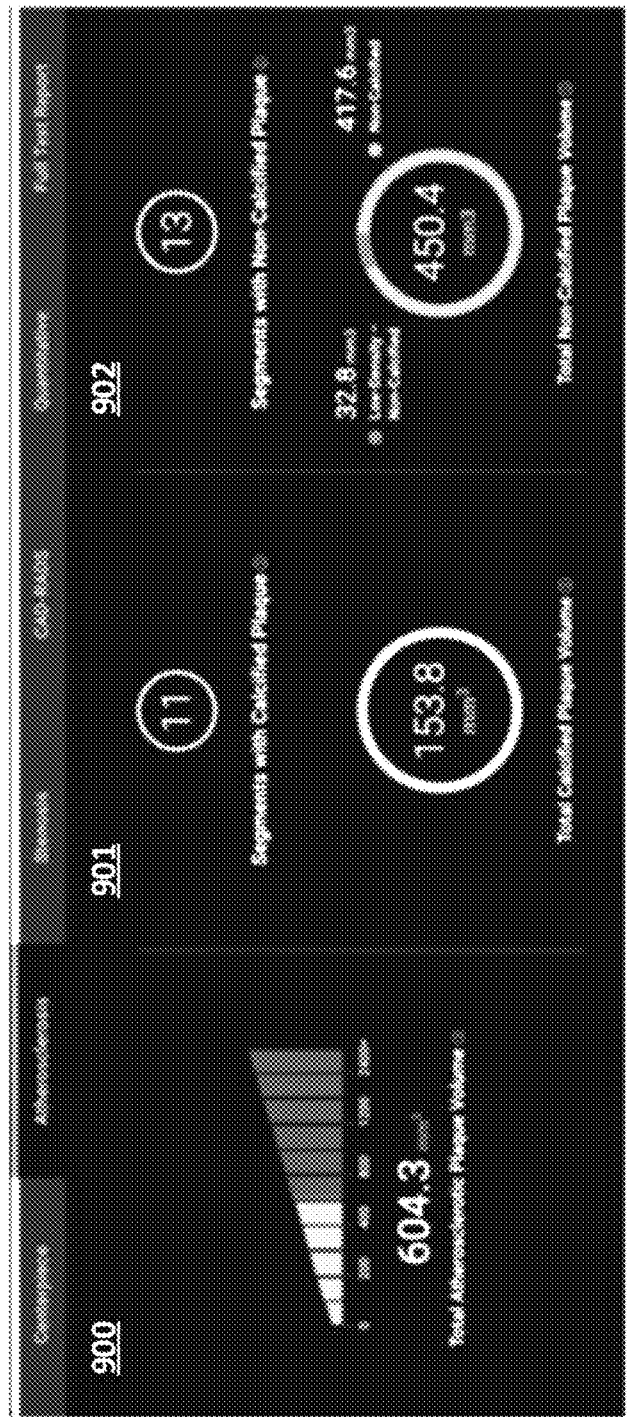
FIG. 9A illustrates an example of an atherosclerosis panel that can be displayed on the user interface which displays a summary of atherosclerosis information based on the analysis.
Figure 9B:
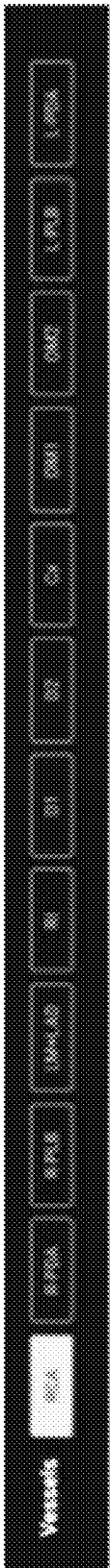
FIG. 9B illustrates an example of a vessel selection panel which can be used to select a vessel such that the summary of atherosclerosis information is displayed on a per segment basis.

FIG. 9A illustrates an atherosclerosis panel 900 that can be displayed on the user interface, which displays a summary of atherosclerosis information based on the analysis. FIG. 9B illustrates the vessel selection panel which can be used to select a vessel such that the summary of atherosclerosis information is displayed on a per segment basis. The top section of the atherosclerosis panel 900 contains per-patient data, as illustrated in FIG. 9A. When a user "hovers" over the "Segments with Calcified Plaque" on panel 901, or hovers over the "Segments with Non-Calcified Plaque" in panel 902, the segment names with the applicable plaque are displayed. Below the patient specific data, users may access per-vessel and per-segment atherosclerosis data by clicking on one of the vessel buttons, illustrated in FIG. 9B.

Figure 9C:
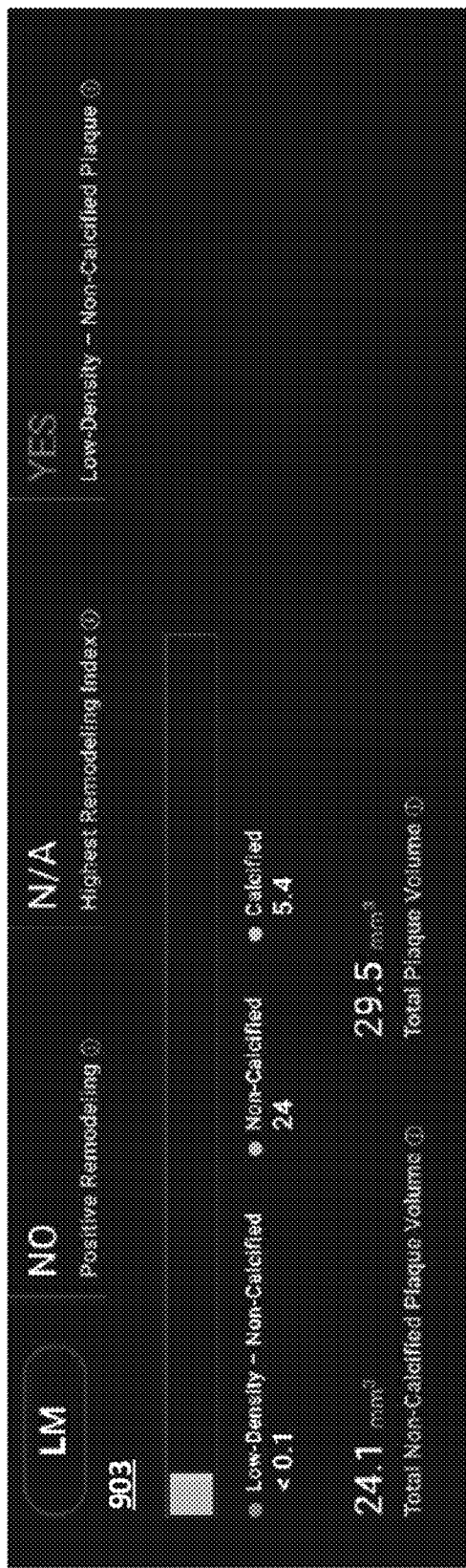
FIG. 9C illustrates an example of a panel that can be displayed on the user interface which shows per segment atherosclerosis information.

FIG. 9C illustrates a panel 903, that can be generated and displayed on the user interface, which shows atherosclerosis information determined by the system on a per segment basis. The presence of positive remodeling, the highest remodeling index, and the presence of Low-Density—Non-Calcified Plaque are reported for each segment in the panel 903 illustrated in FIG. 9C. For example, plaque data can be displayed below on a per-segment basis, and plaque composition volumes can be displayed on a per-segment in the panel 903 illustrated in FIG. 9C.

Figure 9D:
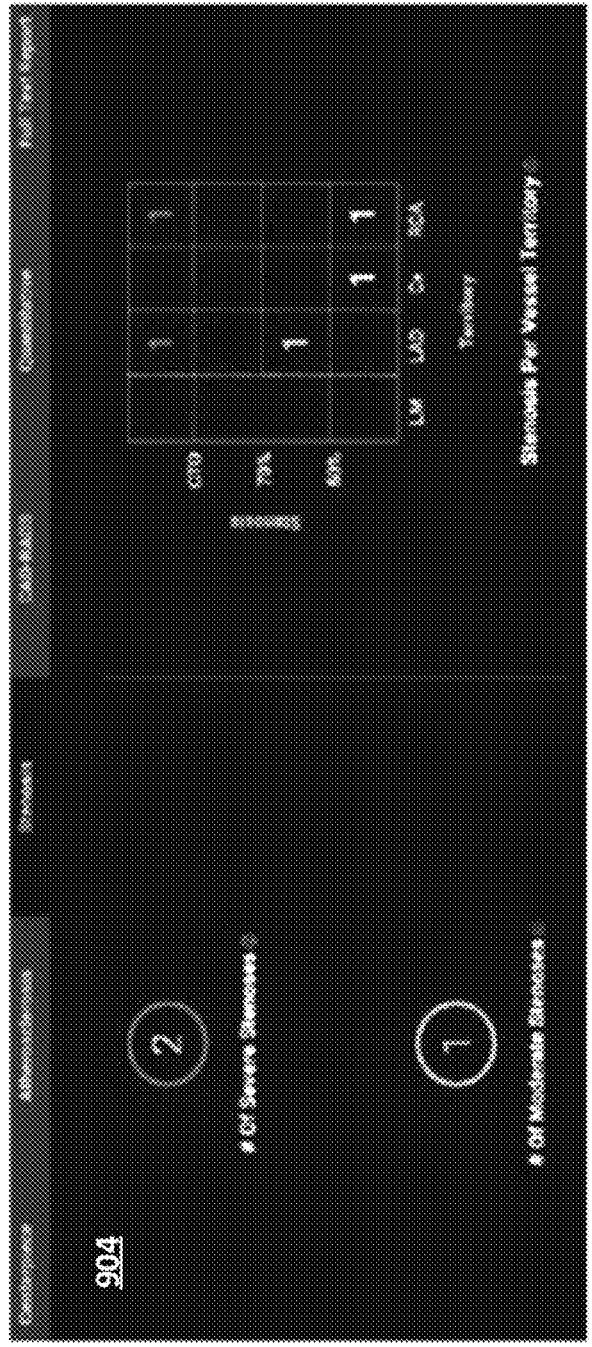
FIG. 9D illustrates an example of a panel that can be displayed on the user interface that contains stenosis per patient data.
Figure 9E:
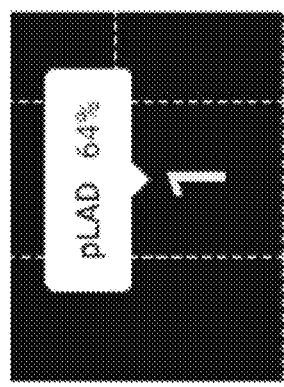
FIG. 9E illustrates an example of a portion of a panel that can be displayed on the user interface that when a count is selected (e.g., by hovering over the number) segment details are displayed.

FIG. 9D illustrates a panel 904 that can be displayed on the user interface that contains stenosis per patient data. The top section of the stenosis panel 904 contains per-patient data. Further details about each count can be displayed by hovering with a pointing device over the numbers, as illustrated in FIG. 9E. Vessels included in each territory are shown in the table below:

| Vessel Territory | Segment Name |
| --- | --- |
| LM (Left Main Artery) | LM |
| LAD (Left Anterior Descending) | pLAD |
| | mLAD |
| | dLAD |
| | D1 |
| | D2 |
| | RI |
| LCx (Left Circumflex Artery) | pCx |
| | LCx |
| | OM1 |
| | OM2 |
| | L-PLB |
| | L-PDA |
| RCA (Right Coronary Artery) | pRCA |
| | mRCA |
| | dRCA |
| | R-PLB |
| | R-PDA |

Figure 9F:
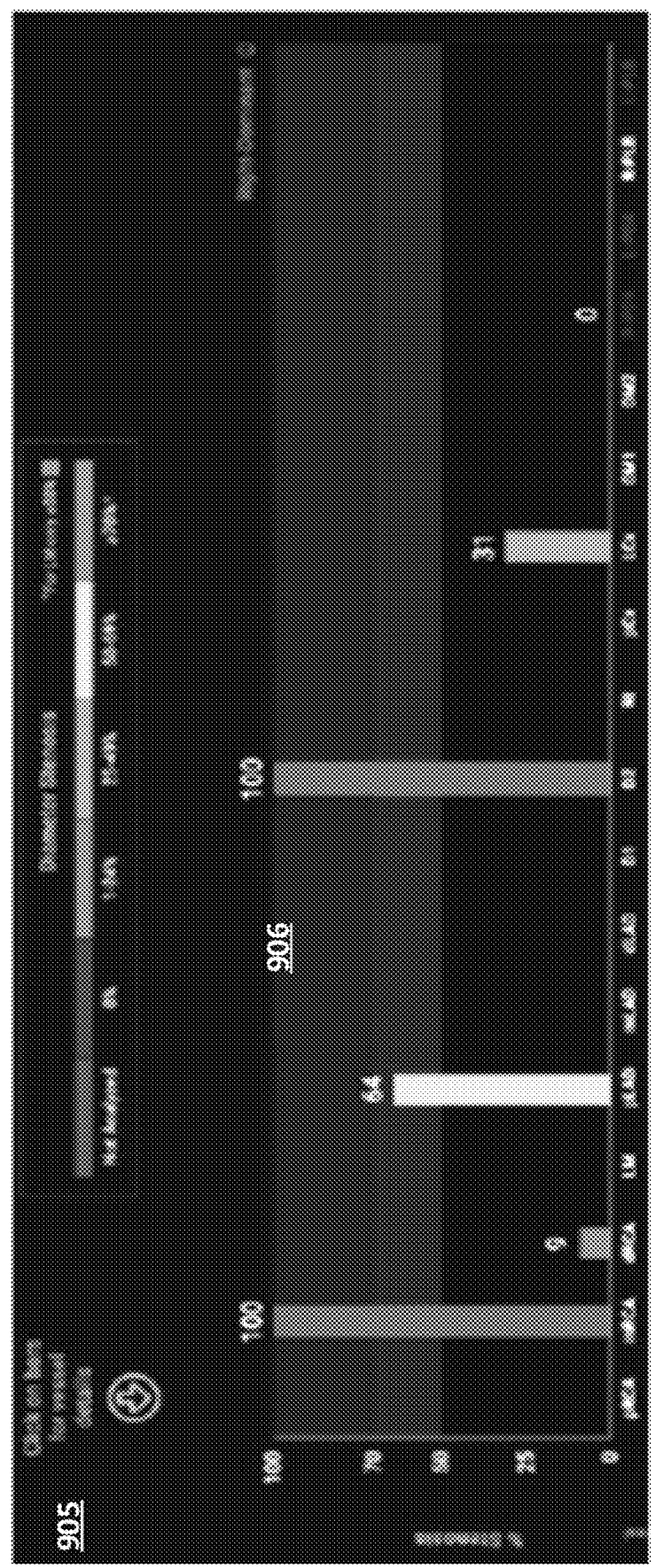
FIG. 9F illustrates an example of a portion of a panel that can be displayed on the user interface that shows stenosis per segment in a graphical format, for example, in a stenosis per segment bar graph.
Figure 9G:
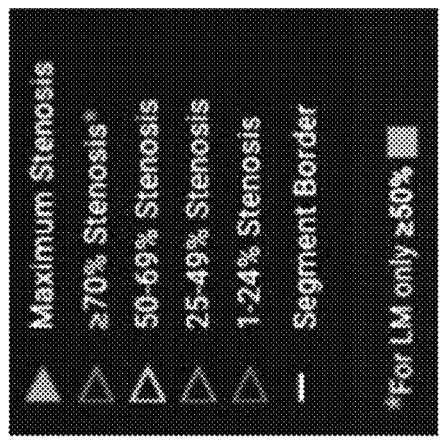
FIG. 9G illustrates another example of a panel that can be displayed on the user interface showing information of the vessel, for example, diameter stenosis and minimum luminal diameter.

In an embodiment, a percentage Diameter Stenosis bar graph 906 can be generated and displayed in a panel 905 of the user interface, as illustrated in FIG. 9F. The percentage Diameter Stenosis bar graph 906 displays the greatest diameter stenosis in each segment. If a CTO has been marked on the segment, it will display as a 100% diameter stenosis. If more than one stenosis has been marked on a segment, the highest value outputs are displayed by default and the user can click into each stenosis bar to view stenosis details and interrogate smaller stenosis (if present) within that segment. The user can also scroll through each cross-section by dragging the grey button in the center of a SMPR view of the vessel, and view the lumen diameter and % diameter stenosis at each cross-section at any selected location, as illustrated in FIG. 9G.

Figure 9H:
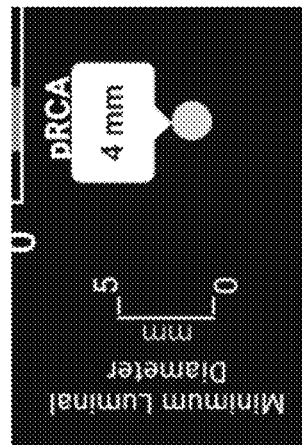
FIG. 9H illustrates an example of a portion of a panel that can be displayed on the user interface indicating a diameter stenosis legend.
Figure 9J:
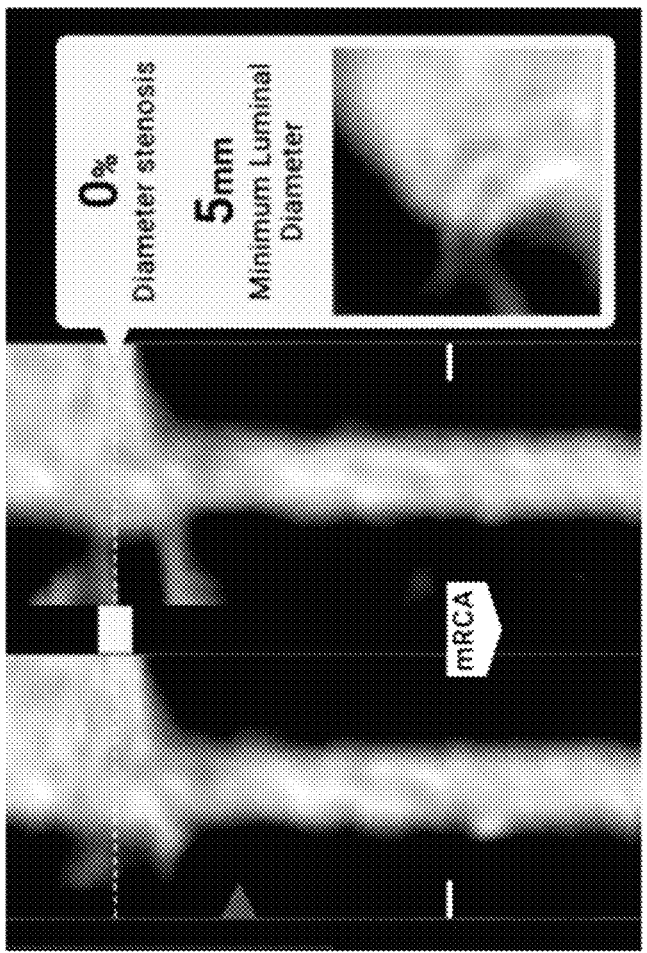
FIG. 9J illustrates a portion of the panel shown in FIG. 9I, and shows how specific minimum lumen diameter details can be quickly and efficiently displayed by selecting (e.g., by hovering over) a desired graphic of a lumen.
Figure 9I:
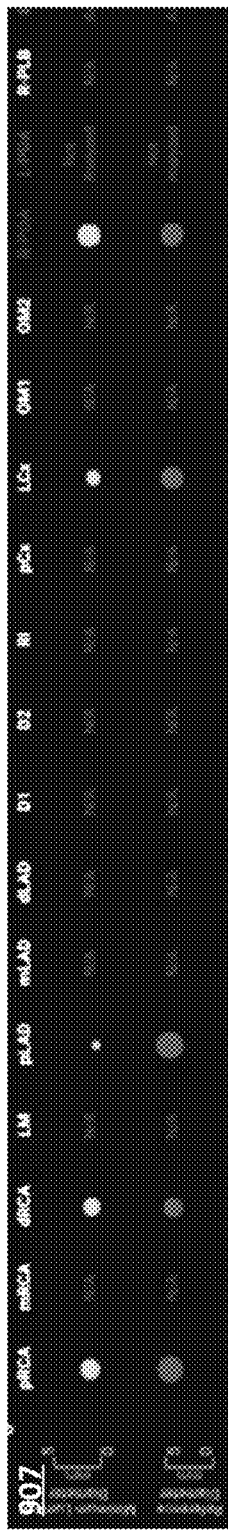
FIG. 9I illustrates an example of a panel that can be displayed on the user interface indicating minimum and reference lumen diameters.

FIG. 9H illustrates a panel showing categories of the one or more stenosis marked on the SMPR based on the analysis. Color can be used to enhance the displayed information. In an example, stenosis in the LM>=50% diameter stenosis are marked in red. As illustrated in a panel 907 of the user interface in FIG. 9I, for each segment's greatest percentage diameter stenosis the minimum luminal diameter and lumen diameter at the reference can be displayed when a pointing device is "hovered" above the graphical vessel cross-section representation, as illustrated in FIG. 9J. If a segment was not analyzed or is not anatomically present, the segment will be greyed out and will display "Not Analyzed". If a segment was analyzed but did not have any stenosis marked, the value will display "N/A".

Figure 9K:
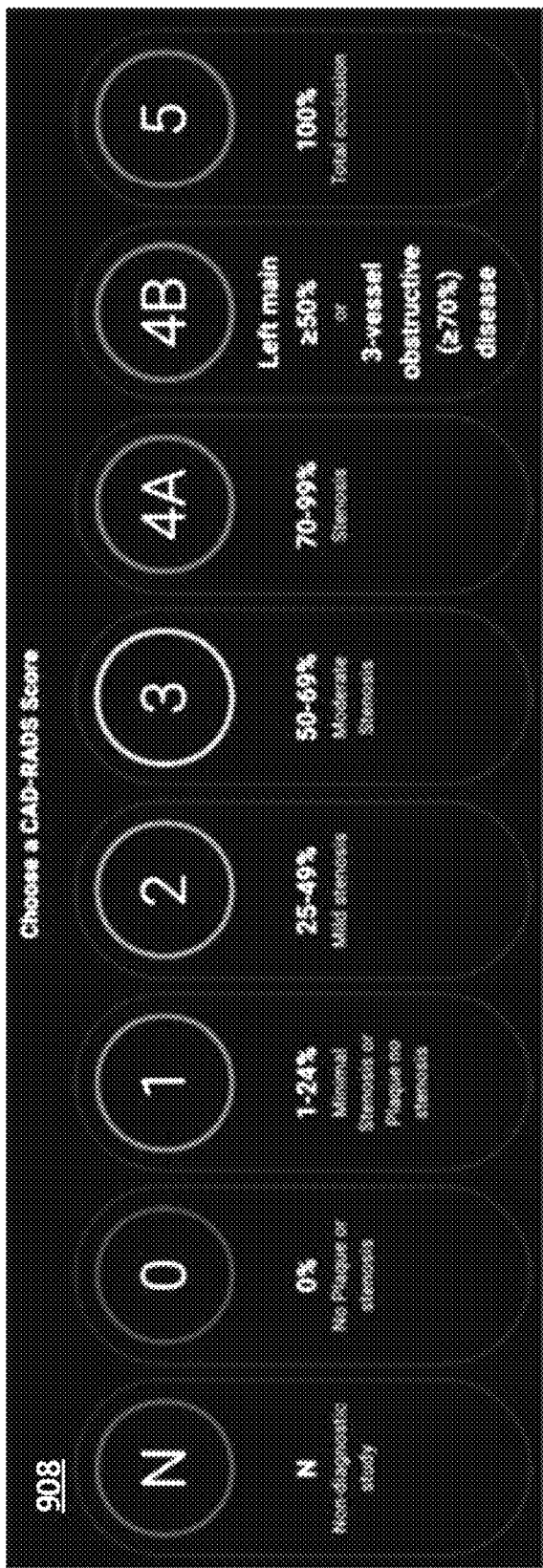
FIG. 9K illustrates an example of a panel that can be displayed in user interface indicating CADS-RADS score selection.
Figure 9L:
FIG. 9L illustrates an example of a panel that can be displayed in the user interface showing further CAD-RADS details generated in the analysis.

FIG. 9K illustrates a panel 908 of the user interface that indicates CADS-RADS score selection. The CAD-RADS panel displays the definitions of CAD-RADS as defined by "Coronary Artery Disease—Reporting and Data System (CAD-RADS) An Expert Consensus Document of SCCT, ACR and NASCI: Endorsed by the ACC". The user is in full control of selecting the CAD-RADS score. In an embodiment, no score will be suggested by the system. In another embodiment, a CAD-RADS score can be suggested. Once a CAD-RADS score is selected on this page, the score will display in both certain user interface panels and full text report pages. Once a CAD-RADS score is selected, the user has the option of selecting modifiers and the presentation of symptoms. Once a presentation is selected, the interpretation, further cardiac investigation and management guidelines can be displayed to the user on the user interface, for example, as illustrated in the panel 909 illustrated in FIG. 9L. These guidelines reproduce the guidelines found in "Coronary Artery Disease-Reporting and Data System (CAD-RADS) An Expert Consensus Document of SCCT, ACR and NASCI: Endorsed by the ACC."

Figure 9M:
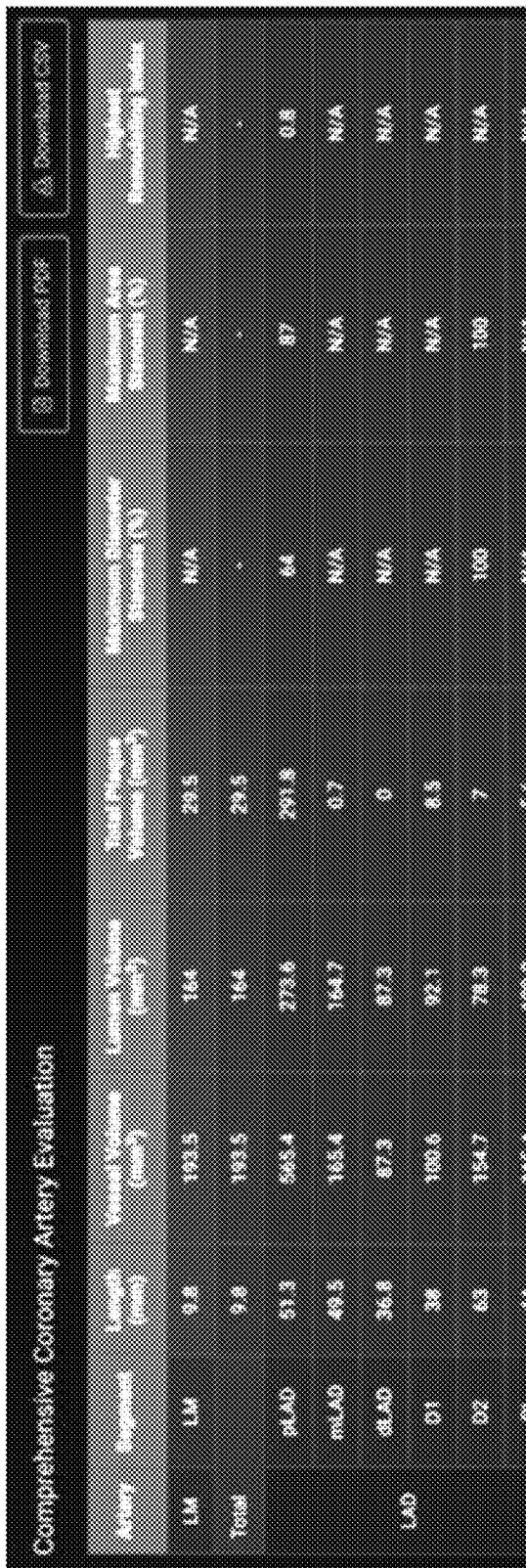
FIG. 9M illustrates an example of a panel that can be displayed in the user interface showing a table indicating quantitative stenosis and vessel outputs which are determined during the analysis.
Figure 9N:
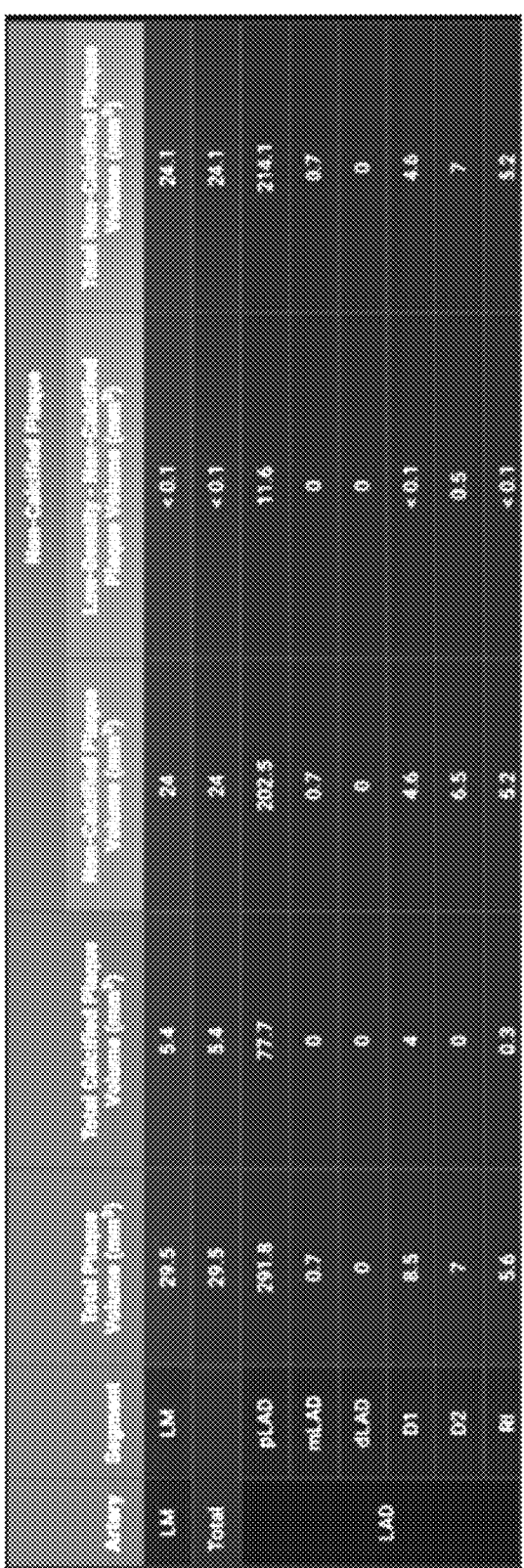
FIG. 9N illustrates an example of a panel that can be displayed in the user interface showing a table indicating quantitative plaque outputs.

FIGS. 9M and 9N illustrate tables that can be generated and displayed on a panel of the user interface, and/or included in a report. FIG. 9M illustrates quantitative stenosis and vessel outputs. FIG. 9N illustrates quantitative plaque outputs. In these quantitative tables, a user can view quantitative per-segment stenosis and atherosclerosis outputs from the system analysis. The quantitative stenosis and vessel outputs table (FIG. 9M) includes information for the evaluated arteries and segments. Totals are given for each vessel territory. Information can include, for example, length, vessel volume, lumen volume, total plaque volume, maximum diameter stenosis, maximum area stenosis, and highest remodeling index. The quantitative plaque outputs table (FIG. 9N) includes information for the evaluated arteries and segments. Information can include, for example, total plaque volume, total calcified plaque volume, non-calcified plaque volume, low-density non-calcified plaque volume, and total non-calcified plaque volume. The user is also able to download a PDF or CSV file of the quantitative outputs is a full text Report. The full text Report presents a textual summary of the atherosclerosis, stenosis, and CAD-RADS measures. The user can edit the report, as desired. Once the user chooses to edit the report, the report will not update the CAD-RADS selection automatically.

Figure 10:
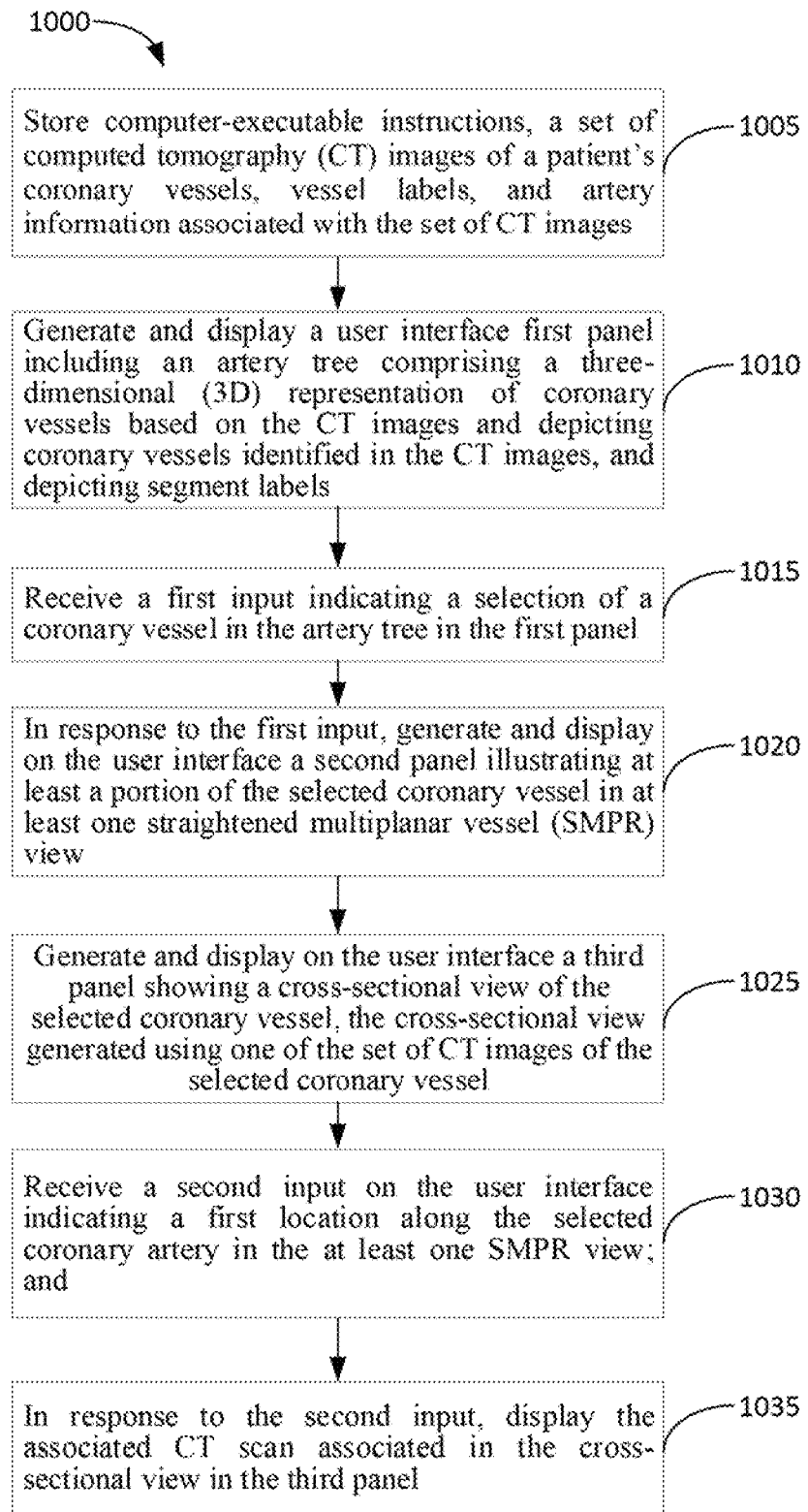
FIG. 10 is a flowchart illustrating a process 1000 for analyzing and displaying CT images and corresponding information.

FIG. 10 is a flowchart illustrating a process 1000 for analyzing and displaying CT images and corresponding information. At block 1005, the process 1000 stores computer-executable instructions, a set of CT images of a patient's coronary vessels, vessel labels, and artery information associated with the set of CT images including information of stenosis, plaque, and locations of segments of the coronary vessels. All of the steps of the process can be performed by embodiments of the system described herein, for example, on embodiments of the systems described in FIG. 13. For example, by one or more computer hardware processors in communication with the one or more non-transitory computer storage mediums, executing the computer-executable instructions stored on one or more non-transitory computer storage mediums. In various embodiments, the user interface can include one or more portions, or panels, that are configured to display one or more of images, in various views (e.g., SMPR, CMPR, cross-sectional, axial, sagittal, coronal, etc.) related to the CT images of a patient's coronary arteries, a graphical representation of coronary arteries, features (e.g., a vessel wall, the lumen, the centerline, the stenosis, plaque, etc.) that have been extracted or revised by machine learning algorithm or by an analyst, and information relating to the CT images that has been determined by the system, by an analyst, or by an analyst interacting with the system (e.g., measurements of features in the CT images. In various embodiments, panels of the user interface can be arranged differently than what is described herein and what is illustrated in the corresponding figures. A user can make an input to the user interface using a pointing device or a user's finger on a touchscreen. In an embodiment, the user interface can receive input by determining the selection of a button/icon/portion of the user interface. In an embodiment, the user interface can receive an input in a defined field of the user interface.

At block 1010, the process 1000 can generate and display in a user interface a first panel including an artery tree comprising a three-dimensional (3D) representation of coronary vessels based on the CT images and depicting coronary vessels identified in the CT images, and depicting segment labels, the artery tree not including heart tissue between branches of the artery tree. An example of such an artery tree 602 is shown in panel 601 in FIG. 6A. In various embodiments, panel 601 can be positioned in locations of the user interface 600 other than what is shown in FIG. 6A.

At block 1015, the process 1000 can receive a first input indicating a selection of a coronary vessel in the artery tree in the first panel. For example, the first input can be received by the user interface 600 of a vessel in the artery tree 602 in panel 601. At block 1020, in response to the first input, the process 1000 can generate and display on the user interface a second panel illustrating at least a portion of the selected coronary vessel in at least one straightened multiplanar vessel (SMPR) view. In an example, the SMPR view is displayed in panel 604 of FIG. 6A.

At block 1025, the process 1000 can generate and display on the user interface a third panel showing a cross-sectional view of the selected coronary vessel, the cross-sectional view generated using one of the set of CT images of the selected coronary vessel. Locations along the at least one SMPR view are each associated with one of the CT images in the set of CT images such that a selection of a particular location along the coronary vessel in the at least one SMPR view displays the associated CT image in the cross-sectional view in the third panel. In an example, the cross-sectional view can be displayed in panel 606 as illustrated in FIG. 6A. At block 1030, the process 1000 can receive a second input on the user interface indicating a first location along the selected coronary artery in the at least one SMPR view. In an example, user may use a pointing device to select a different portion of the vessel shown in the SMPR view in panel 604. At block 1030, the process 1000, in response to the second input, displays the associated CT scan associated in the cross-sectional view in the third panel, panel 606. That is, the cross-sectional view that correspond to the first input is replaced by the cross-sectional view that corresponds to the second input on the SMPR view.

Normalization Device

In some instances, medical images processed and/or analyzed as described throughout this application can be normalized using a normalization device. As will be described in more detail in this section, the normalization device may comprise a device including a plurality of samples of known substances that can be placed in the medical image field of view so as to provide images of the known substances, which can serve as the basis for normalizing the medical images. In some instances, the normalization device allows for direct within image comparisons between patient tissue and/or other substances (e.g., plaque) within the image and known substances within the normalization device.

As mentioned briefly above, in some instances, medical imaging scanners may produce images with different scalable radiodensities for the same object. This, for example, can depend not only on the type of medical imaging scanner or equipment used but also on the scan parameters and/or environment of the particular day and/or time when the scan was taken. As a result, even if two different scans were taken of the same subject, the brightness and/or darkness of the resulting medical image may be different, which can result in less than accurate analysis results processed from that image. To account for such differences, in some embodiments, the normalization device comprising one or more known samples of known materials can be scanned together with the subject, and the resulting image of the one or more known elements can be used as a basis for translating, converting, and/or normalizing the resulting image.

Normalizing the medical images that will be analyzed can be beneficial for several reasons. For example, medical images can be captured under a wide variety of conditions, all of which can affect the resulting medical images. In instances where the medical imager comprises a CT scanner, a number of different variables can affect the resulting image. Variable image acquisition parameters, for example, can affect the resulting image. Variable image acquisition parameters can comprise one or more of a kilovoltage (kV), kilovoltage peak (kVp), a milliamperage (mA), or a method of gating, among others. In some embodiments, methods of gating can include prospective axial triggering, retrospective ECG helical gating, and fast pitch helical, among others. Varying any of these parameters, may produce slight differences in the resulting medical images, even if the same subject is scanned.

Figure 11B:
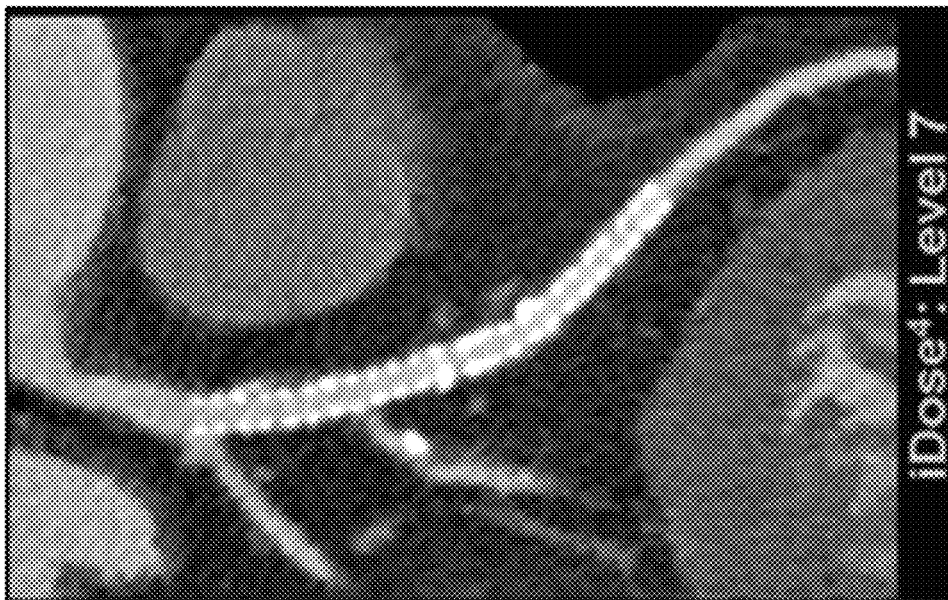
FIGS. 11A and 11B are example CT images illustrating how plaque can appear differently depending on the image acquisition parameters used to capture the CT images.
Figure 11A:
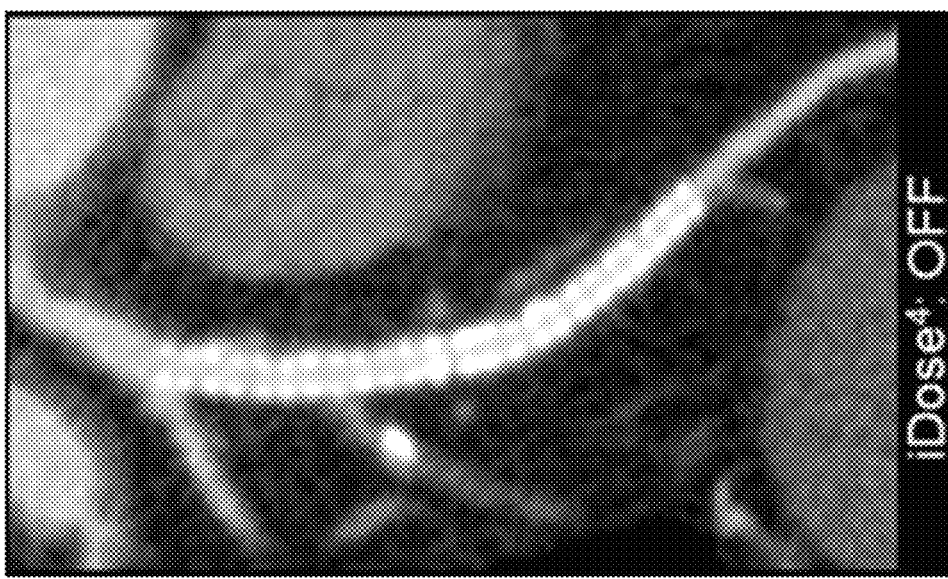
Figure 11C:
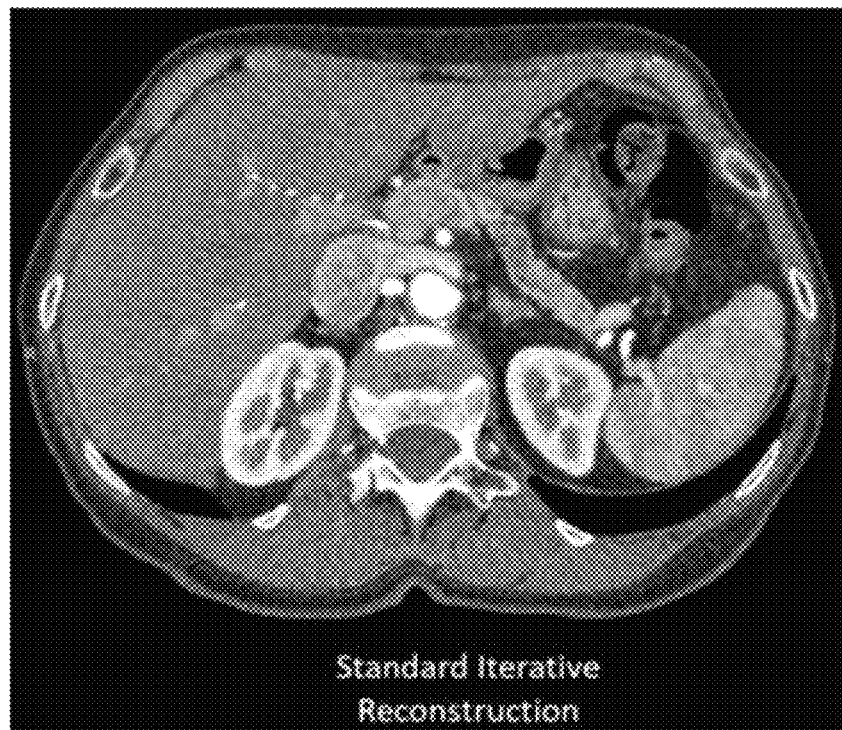
FIGS. 11C and 11D provide another example that illustrates that plaque can appear differently in CT images depending on the image acquisition parameters used to capture the CT images.
Figure 11D:
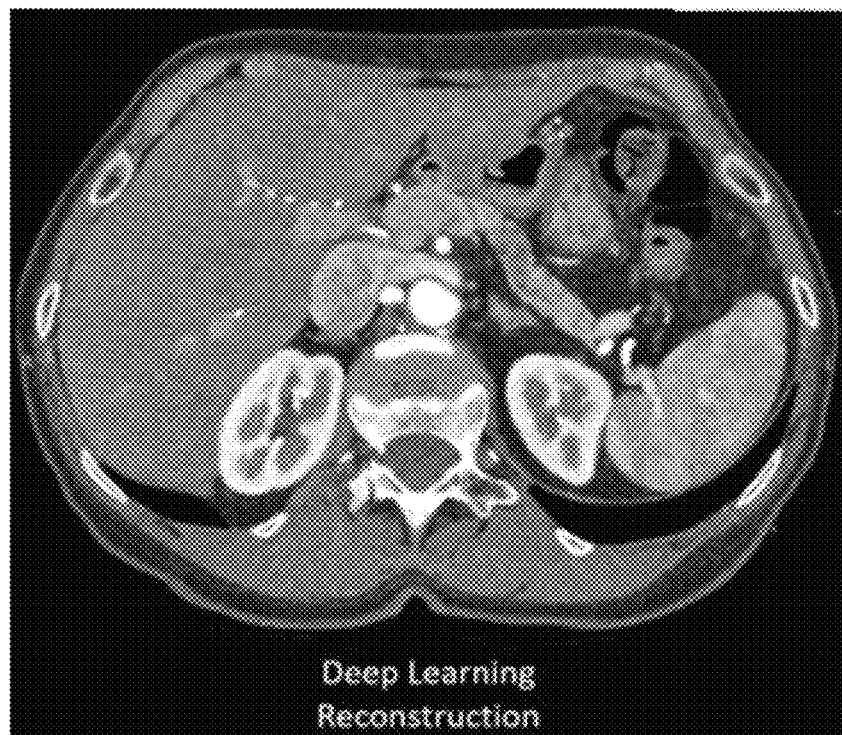

Additionally, the type of reconstruction used to prepare the image after the scan may provide differences in medical images. Example types of reconstruction can include iterative reconstruction, non-iterative reconstruction, machine learning-based reconstruction, and other types of physics-based reconstruction among others. FIGS. 11A-11D illustrate different images reconstructed using different reconstruction techniques. In particular, FIG. 11A illustrates a CT image reconstructed using filtered back projection, while FIG. 11B illustrates the same CT image reconstructed using iterative reconstruction. As shown, the two images appear slightly different. The normalization device described below can be used to help account for these differences by providing a method for normalizing between the two. FIG. 11C illustrates a CT image reconstructed by using iterative reconstruction, while FIG. 11D illustrates the same image reconstructed using machine learning. Again, one can see that the images include slight differences, and the normalization device described herein can advantageously be useful in normalizing the images to account for the two differences.

As another example, various types of image capture technologies can be used to capture the medical images. In instances where the medical imager comprises a CT scanner, such image capture technologies may include a dual source scanner, a single source scanner, dual energy, monochromatic energy, spectral CT, photon counting, and different detector materials, among others. As before, images captured using difference parameters may appear slightly different, even if the same subject is scanned. In addition to CT scanners, other types of medical imagers can also be used to capture medical images. These can include, for example, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS). Use of the normalization device can facilitate normalization of images such that images captured on these different imaging devices can be used in the methods and systems described herein.

Additionally, new types of medical imaging technologies are currently being developed. Use of the normalization device can allow the methods and systems described herein to be used even with medical imaging technologies that are currently being developed or that will be developed in the future. Use of different or emerging medical imaging technologies can also cause slight differences between images.

Another factor that can cause differences in medical images that can be accounted for using the normalization device can be use of different contrast agents during medical imaging. Various contrast agents currently exist, and still others are under development. Use of the normalization device can facilitate normalization of medical images regardless of the type of contrast agent used and even in instances where no contrast agent is used.

These slight differences can, in some instances, negatively impact analysis of the image, especially where analysis of the image is performed by artificial intelligence or machine learning algorithms that were trained or developed using medical images captured under different conditions. In some embodiments, the methods and systems described throughout this application for analyzing medical images can include the use of artificial intelligence and/or machine learning algorithms. Such algorithms can be trained using medical images. In some embodiments, the medical images that are used to train these algorithms can include the normalization device such that the algorithms are trained based on normalized images. Then, by normalizing subsequent images by also including the normalization device in those images, the machine learning algorithms can be used to analyze medical images captured under a wide variety of parameters, such as those described above.

In some embodiments, the normalization device described herein is distinguishable from a conventional phantom. In some instances, conventional phantoms can be used to verify if a CT machine is operating in a correct manner. These conventional phantoms can be used periodically to verify the calibration of the CT machine. For example, in some instances, conventional phantoms can be used prior to each scan, weekly, monthly, yearly, or after maintenance on the CT machine to ensure proper functioning and calibration. Notably, however, the conventional phantoms do not provide a normalization function that allows for normalization of the resulting medical images across different machines, different parameters, different patients, etc.

In some embodiments, the normalization device described herein can provide this functionality. The normalization device can allow for the normalization of CT data or other medical imaging data generated by various machine types and/or for normalization across different patients. For example, different CT devices manufactured by various manufacturers, can produce different coloration and/or different gray scale images. In another example, some CT scanning devices can produce different coloration and/or different gray scale images as the CT scanning device ages or as the CT scanning device is used or based on the environmental conditions surrounding the device during the scanning. In another example, patient tissue types or the like can cause different coloration and/or gray scale levels to appear differently in medical image scan data. Normalization of CT scan data can be important in order to ensure that processing of the CT scan data or other medical imaging data is consistent across various data sets generated by various machines or the same machines used at different times and/or across different patients. In some embodiments, the normalization device needs to be used each time a medical image scan is performed because scanning equipment can change over time and/or patients are different with each scan. In some embodiments, the normalization device is used in performing each and every scan of patient in order to normalize the medical image data of each patient for the AI algorithm(s) used to analyze the medical image data of the patient. In other words, in some embodiments, the normalization device is used to normalize to each patient as opposed to each scanner. In some embodiments, the normalization device may have different known materials with different densities adjacent to each other (e.g., as described with reference to FIG. 12F). This configuration may address an issue present in some CT images where the density of a pixel influences the density of the adjacent pixels and that influence changes with the density of each of the individual pixel. One example of such an embodiment can include different contrast densities in the coronary lumen influencing the density of the plaque pixels. The normalization device can address this issue by having known volumes of known substances to help to correctly evaluate volumes of materials/lesions within the image correcting in some way the influence of the blooming artifact on quantitative CT image analysis/measures. In some instances, the normalization device might have moving known materials with known volume and known and controllable motion. This may allow to exclude or reduce the effect of motion on quantitative CT image analysis/measures.

Accordingly, the normalization device, in some embodiments, is not a phantom in the traditional sense because the normalization device is not just calibrating to a particular scanner but is also normalizing for a specific patient at a particular time in a particular environment for a particular scan, for particular scan image acquisition parameters, and/or for specific contrast protocols. Accordingly, in some embodiments, the normalization device can be considered a reverse phantom. This can be because, rather than providing a mechanism for validating a particular medical imager as a conventional phantom would, the normalization device can provide a mechanism for normalizing or validating a resulting medical image such that it can be compared with other medical images taken under different conditions. In some embodiments, the normalization device is configured to normalize the medical image data being examined with the medical image data used to train, test, and/or validate the AI algorithms used for analyzing the to be examined medical image data.

In some embodiments, the normalization of medical scanning data can be necessary for the AI processing methods disclosed herein because in some instances AI processing methods can only properly process medical scanning data when the medical scanning data is consistent across all medical scanning data being processed. For example, in situations where a first medical scanner produces medical images showing fatty material as dark gray or black, whereas a second medical scanner produces medical image showing the same fatty material as medium or light gray, then the AI processing methodologies of the systems, methods, and devices disclosed herein may misidentify and/or not fully identify the fatty materials in one set or both sets of the medical images produced by the first and second medical scanners. This can be even more problematic as the relationship of specific material densities may not be not constant, and even may change in an non linear way depending on the material and on the scanning parameters. In some embodiments, the normalization device enables the use of AI algorithms trained on certain medical scanner devices to be used on medical images generated by next-generation medical scanner devices that may have not yet even been developed.

Figure 12A:
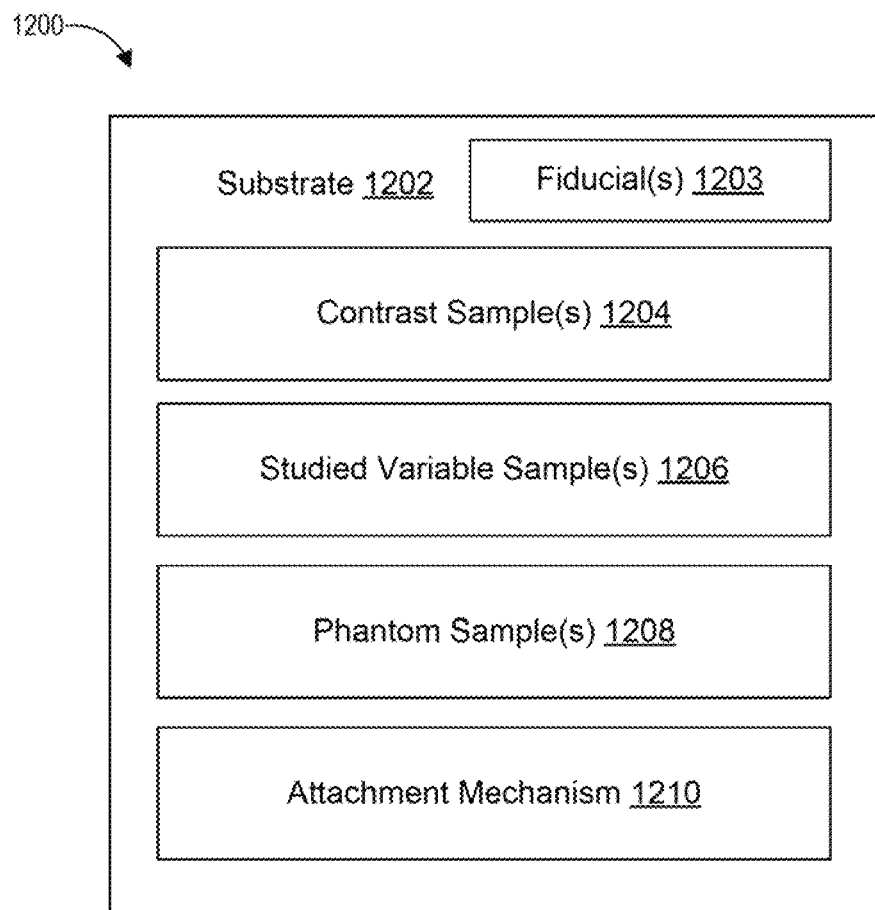
FIG. 12A is a block diagram representative of an embodiment of a normalization device that can be configured to normalize medical images for use with the methods and systems described herein.

FIG. 12A is a block diagram representative of an embodiment of a normalization device 1200 that can be configured to normalize medical images for use with the methods and systems described herein. In the illustrated embodiment, the normalization device 1200 can include a substrate 1202. The substrate 1202 can provide the body or structure for the normalization device 1200. In some embodiments, the normalization device 1200 can comprise a square or rectangular or cube shape, although other shapes are possible. In some embodiments, the normalization device 1200 is configured to be bendable and/or be self-supporting. For example, the substrate 1202 can be bendable and/or self-supporting. A bendable substrate 1202 can allow the normalization device to fit to the contours of a patient's body. In some embodiments, the substrate 1202 can comprise one or more fiducials 1203. The fiducials 1203 can be configured to facilitate determination of the alignment of the normalization device 1200 in an image of the normalization device such that the position in the image of each of the one or more compartments holding samples of known materials can be determined.

The substrate 1202 can also include a plurality of compartments (not shown in FIG. 12A, but see, for example, compartments 1216 of FIGS. 12C-12F). The compartments 1216 can be configured to hold samples of known materials, such as contrast samples 1204, studied variable samples 1206, and phantom samples 1208. In some embodiments, the contrast samples 1204 comprise samples of contrast materials used during capture of the medical image. In some embodiments, the samples of the contrast materials 1204 comprise one or more of iodine, Gad, Tantalum, Tungsten, Gold, Bismuth, or Ytterbium. These samples can be provided within the compartments 1216 of the normalization device 1200 at various concentrations. The studied variable samples 1206 can includes samples of materials representative of materials to be analyzed systems and methods described herein. In some examples, the studied variable samples 1206 comprise one or more of calcium 1000HU, calcium 220 HU, calcium 150 HU, calcium 130 HU, and a low attenuation (e.g., 30 HU) material. Other studied variable samples 1206 provided at different concentrations can also be included. In general, the studied variable samples 1206 can correspond to the materials for which the medical image is being analyzed. The phantom samples 1208 can comprise samples of one or more phantom materials. In some examples, the phantom samples 1208 comprise one or more of water, fat, calcium, uric acid, air, iron, or blood. Other phantom samples 1208 can also be used.

In some embodiments, the more materials contained in the normalization device 1200, or the more compartments 1216 with different materials in the normalization device 1200, the better the normalization of the data produced by the medical scanner. In some embodiments, the normalization device 1200 or the substrate 1202 thereof is manufactured from flexible and/or bendable plastic. In some embodiments, the normalization device 1200 is adapted to be positioned within or under the coils of an MR scanning device. In some embodiments, the normalization device 1200 or the substrate 1202 thereof is manufactured from rigid plastic.

In the illustrated embodiment of FIG. 12A, the normalization device 1200 also includes an attachment mechanism 1210. The attachment mechanism 1210 can be used to attach the normalization device 1200 to the patient. For example, in some embodiments, the normalization device 1200 is attached to the patient near the coronary region to be imaged prior to image acquisition. In some embodiments, the normalization device 1200 can be adhered to the skin of a patient using an adhesive or Velcro or some other fastener or glue. In some embodiments, the normalization device 1200 can be applied to a patient like a bandage. For example, in some embodiments, a removable Band-Aid or sticker is applied to the skin of the patient, wherein the Band-Aid can comprise a Velcro outward facing portion that allows the normalization device having a corresponding Velcro mating portion to adhere to the Band-Aid or sticker that is affixed to the skin of the patient (see, for example, the normalization device of FIG. 12G, described below).

In some embodiments, the attachment mechanism 1210 can be omitted, such that the normalization device 1200 need not be affixed to the patient. Rather, in some embodiments, the normalization device can be placed in a medical scanner with or without a patient. In some embodiments, the normalization device can be configured to be placed alongside a patient within a medical scanner.

In some embodiments, the normalization device 1200 can be a reusable device or be a disposable one-time use device. In some embodiments, the normalization device 1200 comprises an expiration date, for example, the device can comprise a material that changes color to indicate expiration of the device, wherein the color changes over time and/or after a certain number of scans or an amount of radiation exposure (see, for example, FIGS. 12H and 12I, described below). In some embodiments, the normalization device 1200 requires refrigeration between uses, for example, to preserve one or more of the samples contained therein. In some embodiments, the normalization device 1200 can comprise an indicator, such as a color change indicator, that notifies the user that the device has expired due to heat exposure or failure to refrigerate.

In certain embodiments, the normalization device 1200 comprises a material that allows for heat transfer from the skin of the patient in order for the materials within the normalization device 1200 to reach the same or substantially the same temperature of the skin of the patient because in some cases the temperature of the materials can affect the resulting coloration or gray-scale of the materials produced by the image scanning device. For example, the substrate 1202 can comprise a material with a relatively high heat transfer coefficient to facilitate heat transfer from the patient to the samples within the substrate 1202. In some embodiments, the normalization device 1200 can be removably coupled to a patient's skin by using an adhesive that can allow the device to adhere to the skin of a patient.

In some embodiments, the normalization device 1200 can be used in the imaging field of view or not in the imaging field of view. In some embodiments, the normalization device 1200 can be imaged simultaneously with the patient image acquisition or sequentially. Sequential use can comprise first imaging the normalization device 1200 and the imaging the patient shortly thereafter using the same imaging parameters (or vice versa). In some embodiments, the normalization device 1200 can be static or programmed to be in motion or movement in sync with the image acquisition or the patient's heart or respiratory motion. In some embodiments, the normalization device 1200 can utilize comparison to image domain-based data or projection domain-based data. In some embodiments, the normalization device 1200 can be a 2D (area), or 3D (volume), or 4D (changes with time) device. In some embodiments, two or more normalization devices 1200 can be affixed to and/or positioned alongside a patient during medical image scanning in order to account for changes in coloration and/or gray scale levels at different depths within the scanner and/or different locations within the scanner.

Figure 12B:
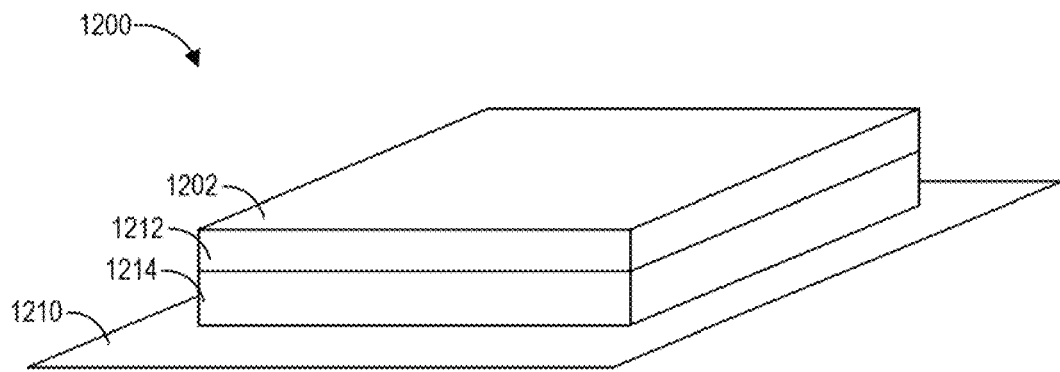
FIG. 12B is a perspective view of an embodiment of a normalization device including a multilayer substrate.
Figure 12C:
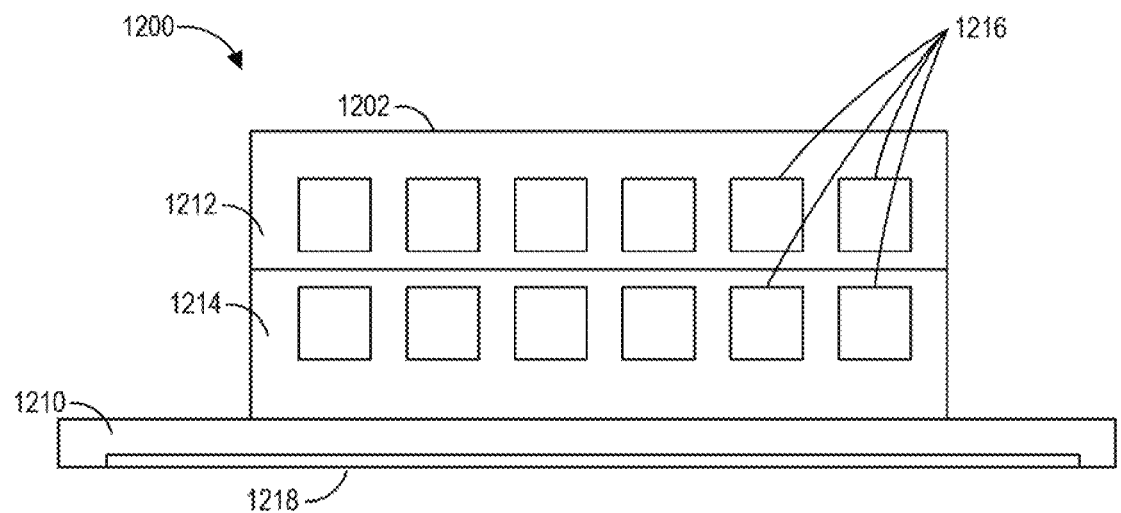
FIG. 12C is a cross-sectional view of the normalization device of FIG. 12B illustrating various compartments positioned therein for holding samples of known materials for use during normalization.

In some embodiments, the normalization device 1200 can comprise one or more layers, wherein each layer comprises compartments for holding the same or different materials as other layers of the device. FIG. 12B, for example, illustrates a perspective view of an embodiment of a normalization device 1200 including a multilayer substrate 1202. in the illustrated embodiment, the substrate 1202 comprises a first layer 1212 and a second layer 1214. The second layer 1214 can be positioned above the first layer 1212. In other embodiments, one or more additional layers may be positioned above the second layer 1214. Each of the layers 1212, 1214 can be configured with compartments for holding the various known samples, as shown in FIG. 12C. In some embodiments, the various layers 1212, 1214 of the normalization device 1200 allow for normalization at various depth levels for various scanning machines that perform three-dimensional scanning, such as MR and ultrasound. In some embodiments, the system can be configured to normalize by averaging of coloration and/or gray scale level changes in imaging characteristics due to changes in depth.

FIG. 12C is a cross-sectional view of the normalization device 1200 of FIG. 12B illustrating various compartments 1216 positioned therein for holding samples of known materials for use during normalization. The compartments 1216 can be configured to hold, for example, the contrast samples 1204, the studied variable samples 1206, and the phantom samples 1208 illustrated in FIG. 12A. The compartments 1216 may comprise spaces, pouches, cubes, spheres, areas, or the like, and within each compartment 1216 there is contained one or more compounds, fluids, substances, elements, materials, and the like. In some embodiments, each of the compartments 1216 can comprise a different substance or material. In some embodiments, each compartment 1216 is air-tight and sealed to prevent the sample, which may be a liquid, from leaking out.

Figure 12D:
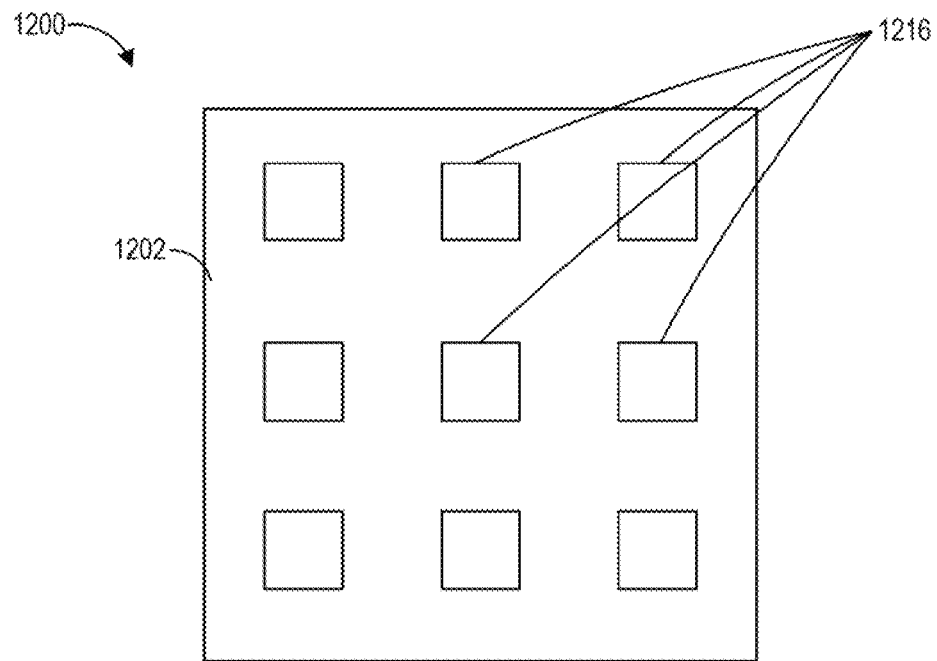
FIG. 12D illustrates a top down view of an example arrangement of a plurality of compartments within a normalization device. In the illustrated embodiment, the plurality of compartments are arranged in a rectangular or grid-like pattern.
Figure 12E:
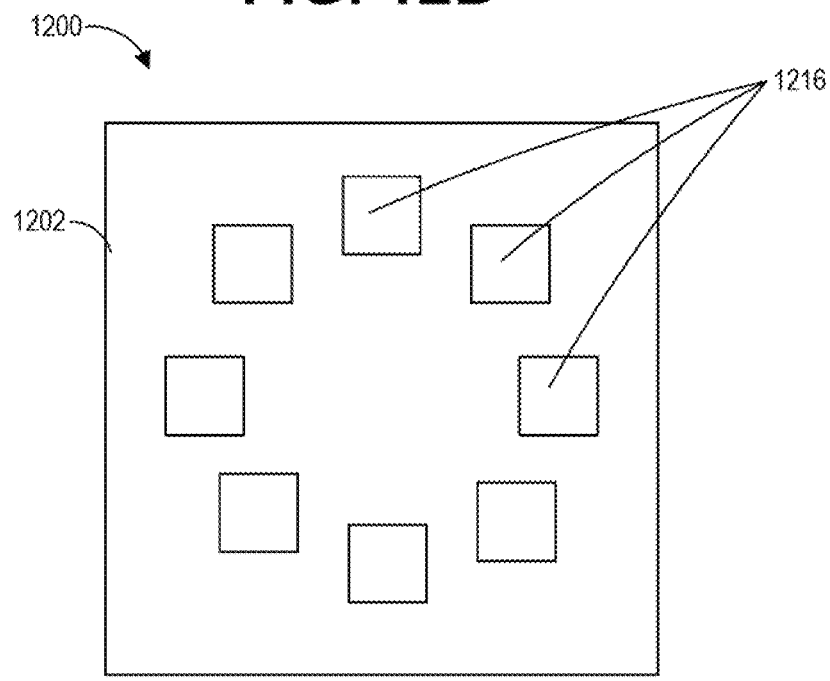
FIG. 12E illustrates a top down view of another example arrangement of a plurality of compartments within a normalization device. In the illustrated embodiment, the plurality of compartments are arranged in a circular pattern.

Within each layer 1212, 1214, or within the substrate 1202, the normalization device 1200 may include different arrangements for the compartments 1216. FIG. 12D illustrates a top down view of an example arrangement of a plurality of compartments 1216 within the normalization device 1200. In the illustrated embodiment, the plurality of compartments 1216 are arranged in a rectangular or grid-like pattern. FIG. 12E illustrates a top down view of another example arrangement of a plurality of compartments 1216 within a normalization device 1200. In the illustrated embodiment, the plurality of compartments 1216 are arranged in a circular pattern. Other arrangements are also possible.

Figure 12F:
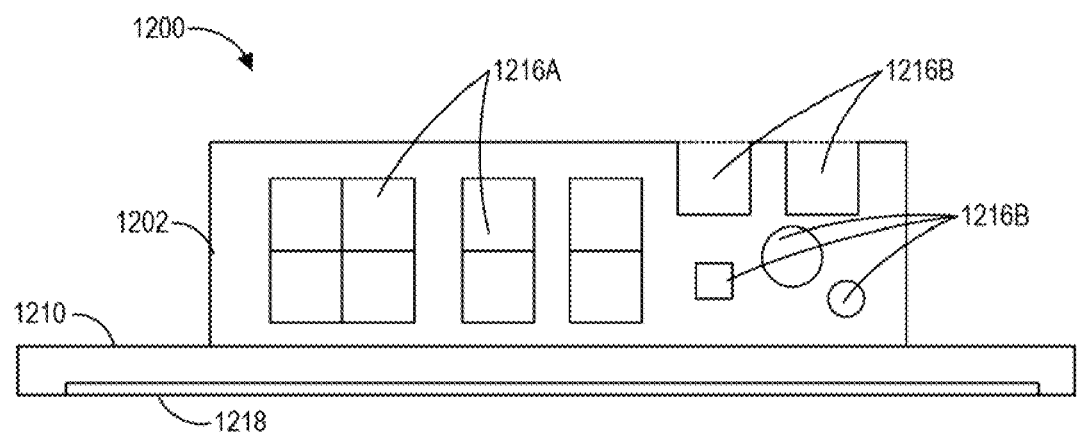
FIG. 12F is a cross-sectional view of another embodiment of a normalization device illustrating various features thereof, including adjacently arranged compartments, self-sealing fillable compartments, and compartments of various sizes.

FIG. 12F is a cross-sectional view of another embodiment of a normalization device 1200 illustrating various features thereof, including adjacently arranged compartments 1216A, self-sealing fillable compartments 1216B, and compartments of various sizes and shapes 1216C. As shown in FIG. 12F, one or more of the compartments 1216A can be arranged so as to be adjacent to each other so that materials within the compartments 1216A can be in contact with and/or in close proximity to the materials within the adjacent compartments 1216A. In some embodiments, the normalization device 1200 comprises high density materials juxtaposed to low density materials in order to determine how a particular scanning device displays certain materials, thereby allowing normalization across multiple scanning devices. In some embodiments, certain materials are positioned adjacent or near other materials because during scanning certain materials can influence each other. Examples of materials that can be placed in adjacently positioned compartments 1216A can include iodine, air, fat material, tissue, radioactive contrast agent, gold, iron, other metals, distilled water, and/or water, among others.

In some embodiments, the normalization device 1200 is configured receive material and/or fluid such that the normalization device is self-sealing. Accordingly, FIG. 12F illustrates compartments 1216B that are self-sealing. These can allow a material to be injected into the compartment 1216B and then sealed therein. For example, a radioactive contrast agent can be injected in a self-sealing manner into a compartment 1216B of the normalization device 1200, such that the medical image data generated from the scanning device can be normalized over time as the radioactive contrast agent decays over time during the scanning procedure. In some embodiments, the normalization device can be configured to contain materials specific for a patient and/or a type of tissue being analyzed and/or a disease type and/or a scanner machine type.

In some embodiments, the normalization device 1200 can be configured measure scanner resolution and type of resolution by configuring the normalization device 1200 with a plurality of shapes, such as a circle. Accordingly, the compartments 1216C can be provided with different shapes and sizes. FIG. 12F illustrates an example wherein compartments 1216C are provided with different shapes (cubic and spherical) and different sizes. In some embodiments, all compartments 1216 can be the same shape and size.

In some embodiments, the size of one or more compartment 1216 of the normalization device 1200 can be configured or selected to correspond to the resolution of the medical image scanner. For example, in some embodiments, if the spatial resolution of a medical image scanner is 0.5 mm×0.5 mm×0.5 mm, then the dimension of the compartments of the normalization device can also be 0.5 mm×0.5 mm×0.5 mm. In some embodiments, the sizes of the compartments range from 0.5 mm to 0.75 mm. In some embodiments, the width of the compartments of the normalization device can be about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1.0 mm, and/or within a range defined by two of the aforementioned values. In some embodiments, the length of the compartments of the normalization device can be about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1.0 mm, and/or within a range defined by two of the aforementioned values. In some embodiments, the height of the compartments of the normalization device can be about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1.0 mm, and/or within a range defined by two of the aforementioned values.

In some embodiments, the dimensions of each of the compartments 1216 in the normalization device 1200 are the same or substantially the same for all of the compartments 1216. In some embodiments, the dimensions of some or all of the compartments 1216 in the normalization device 1200 can be different from each other in order for a single normalization device 1200 to have a plurality of compartments having different dimensions such that the normalization device 1200 can be used in various medical image scanning devices having different resolution capabilities (for example, as illustrated in FIG. 12F). In some embodiments, a normalization device 1200 having a plurality of compartments 1216 with differing dimensions enable the normalization device to be used to determine the actual resolution capability of the scanning device. In some embodiments, the size of each compartment 1216 may extend up to 10 mm, and the sizes of each compartment may be variable depending upon the material contained within.

Figure 12G:
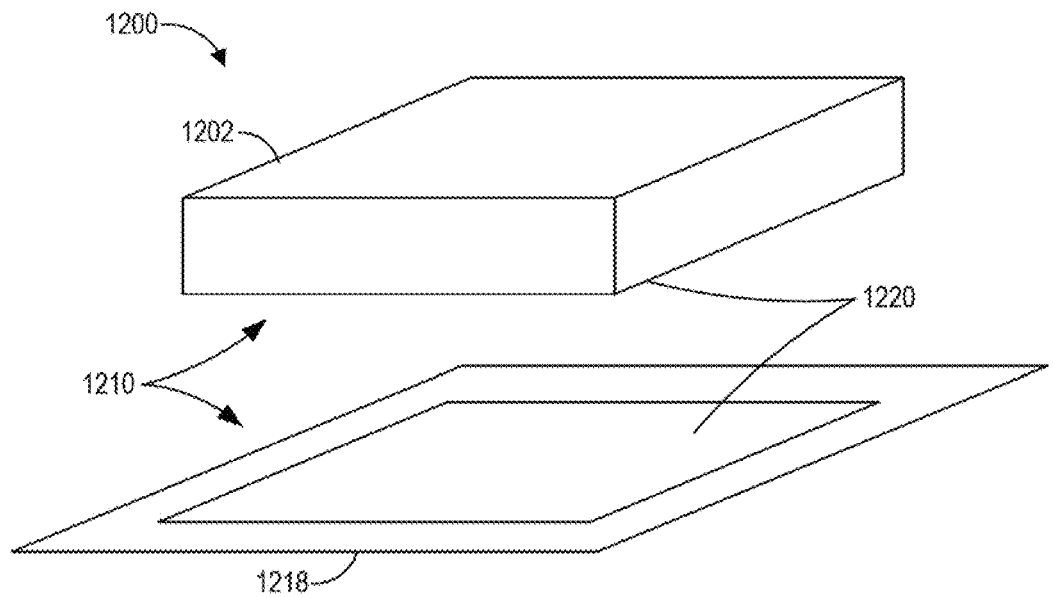
FIG. 12G is a perspective view illustrating an embodiment of an attachment mechanism for a normalization device that uses hook and loop fasteners to secure a substrate of the normalization device to a fastener of the normalization device.

In the illustrated embodiment of FIGS. 12C and 12F, the normalization device 1200 includes an attachment mechanism 1210 which includes an adhesive surface 1218. The adhesive surface 1218 can be configured to affix (e.g., removably affix) the normalization device 1200 to the skin of the patient. FIG. 12G is a perspective view illustrating an embodiment of an attachment mechanism 1210 for a normalization device 1200 that uses hook and loop fasteners 1220 to secure a substrate of the normalization device to a fastener of the normalization device 1200. In the illustrated embodiment, an adhesive surface 1218 can be configured to be affixed to the patient. The adhesive surface 1218 can include a first hook and loop fastener 1220. A corresponding hook and loop fastener 1220 can be provided on a lower surface of the substrate 1202 and used to removably attach the substrate 1202 to the adhesive surface 1218 via the hook and loop fasteners 1220.

Figure 12H:
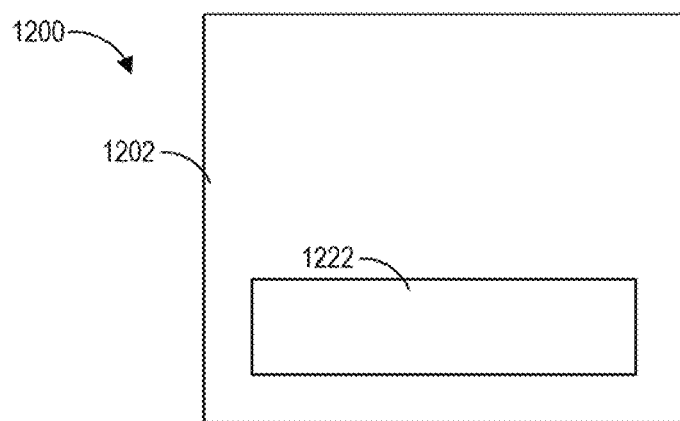
FIGS. 12H and 12I illustrate an embodiment of a normalization device that includes an indicator configured to indicate an expiration status of the normalization device.
Figure 12I:
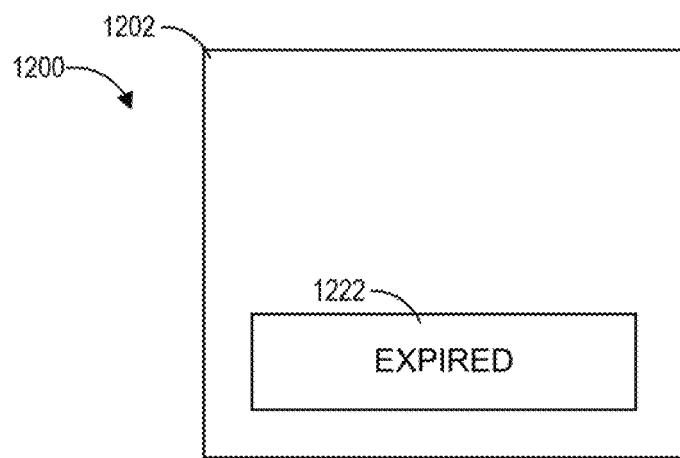

FIGS. 12H and 12I illustrate an embodiment of a normalization device 1200 that includes an indicator 1222 configured to indicate an expiration status of the normalization device 1200. The indicator 1222 can comprise a material that changes color or reveals a word to indicate expiration of the device, wherein the color or text changes or appears over time and/or after a certain number of scans or an amount of radiation exposure. FIG. 12H illustrates the indicator 1222 in a first state representative of a non-expired state, and FIG. 12I illustrates the indicator 1222 in a second state representative of an expired state. In some embodiments, the normalization device 1200 requires refrigeration between uses. In some embodiments, the indicator 1222, such as a color change indicator, can notify the user that the device has expired due to heat exposure or failure to refrigerate.

In some embodiments, the normalization device 1200 can be used with a system configured to set distilled water to a gray scale value of zero, such that if a particular medical image scanning device registers the compartment of the normalization device 1200 comprising distilled water as having a gray scale value of some value other than zero, then the system can utilize an algorithm to transpose or transform the registered value to zero. In some embodiments, the system is configured to generate a normalization algorithm based on known values established for particular substances in the compartments of the normalization device 1200, and on the detected/generated values by a medical image scanning device for the same substances in the compartments

1216 of the normalization device 1200. In some embodiments, the normalization device 1200 can be configured to generate a normalization algorithm based on a linear regression model to normalize medical image data to be analyzed. In some embodiments, the normalization device 1200 can be configured to generate a normalization algorithm based on a non-linear regression model to normalize medical image data to be analyzed. In some embodiments, the normalization device 1200 can be configured to generate a normalization algorithm based on any type of model or models, such as an exponential, logarithmic, polynomial, power, moving average, and/or the like, to normalize medical image data to be analyzed. In some embodiments, the normalization algorithm can comprise a two-dimensional transformation. In some embodiments, the normalization algorithm can comprise a three-dimensional transformation to account for other factors such as depth, time, and/or the like.

By using the normalization device 1200 to scan known substances using different machines or the same machine at different times, the system can normalize CT scan data across various scanning machines and/or the same scanning machine at different times. In some embodiments, the normalization device 1200 disclosed herein can be used with any scanning modality including but not limited to x-ray, ultrasound, echocardiogram, magnetic resonance (MR), optical coherence tomography (OCT), intravascular ultrasound (IVUS) and/or nuclear medicine imaging, including positron-emission tomography (PET) and single photon emission computed tomography (SPECT).

In some embodiments, the normalization device 1200 contains one or more materials that form plaque (e.g., studied variable samples 1206) and one or more materials that are used in the contrast that is given to the patient through a vein during examination (e.g., contrast samples 1204). In some embodiments, the materials within the compartments 1216 include iodine of varying concentrations, calcium of varying densities, non-calcified plaque materials or equivalents of varying densities, water, fat, blood or equivalent density material, iron, uric acid, air, gadolinium, tantalum, tungsten, gold, bismuth, ytterbium, and/or other material. In some embodiments, the training of the AI algorithm can be based at least in part on data relating to the density in the images of the normalization device 1200. As such, in some embodiments, the system can have access to and/or have stored pre-existing data on how the normalization device 1200 behaved or was shown in one or more images during the training of the AI algorithm. In some embodiments, the system can use such prior data as a baseline to determine the difference with how the normalization device 1200 behaves in the new or current CT scan to which the AI algorithm is applied to. In some embodiments, the determined difference can be used to calibrate, normalize, and/or map one or more densities in recently acquired image(s) to one or more images that were obtained and/or used during training of the AI algorithm.

As a non-limiting example, in some embodiments, the normalization device 1200 comprises calcium. If, for example, the calcium in the CT or normalization device 1200 that was used to train the AI algorithm(s) showed a density of 300 Hounsfield Units (HU), and if the same calcium showed a density of 600 HU in one or more images of a new scan, then the system, in some embodiments, may be configured to automatically divide all calcium densities in half to normalize or transform the new CT image(s) to be equivalent to the old CT image(s) used to train the AI algorithm.

In some embodiments, as discussed above, the normalization device 1200 comprises a plurality or all materials that may be relevant, which can be advantageous as different materials can change densities in different amounts across scans. For example, if the density of calcium changes 2× across scans, the density of fat may change around 10% across the same scans. As such, it can be advantageous for the normalization device 1200 to comprise a plurality of materials, such as for example one or more materials that make up plaque, blood, contrast, and/or the like.

As described above, in some embodiments, the system can be configured to normalize, map, and/or calibrate density readings and/or CT images obtained from a particular scanner and/or subject proportionally according to changes or differences in density readings and/or CT images obtained from one or more materials of a normalization device 1200 using a baseline scanner compared to density readings and/or CT images obtained from one or more same materials of a normalization device 1200 using the particular scanner and/or subject. As a non-limiting example, for embodiments in which the normalization device 1200 comprises calcium, the system can be configured to apply the same change in density of known calcium between the baseline scan and the new scan, for example 2×, to all other calcium readings of the new scan to calibrate and/or normalize the readings.

In some embodiments, the system can be configured to normalize, map, and/or calibrate density readings and/or CT images obtained from a particular scanner and/or subject by averaging changes or differences between density readings and/or CT images obtained from one or more materials of a normalization device 1200 using a baseline scanner compared to density readings and/or CT images obtained from one or more materials or areas of a subject using the same baseline scanner. As a non-limiting example, for embodiments in which the normalization device 1200 comprises calcium, the system can be configured to determine a difference, or a ratio thereof, in density readings between calcium in the normalization device 1200 and other areas of calcium in the subject during the baseline scan. In some embodiments, the system can be configured to similarly determine a difference, or a ratio thereof, in density readings between calcium in the normalization device 1200 and other areas of calcium in the subject during the new scan; dividing the value of calcium from the device to the value of calcium anywhere else in the image can cancel out any change as the difference in conditions can affect the same material in the same manner.

In some embodiments, the device will account for scan parameters (such as mA or kVp), type and number of x-ray sources within a scanner (such as single source or dual source), temporal resolution of a scanner, spatial resolution of scanner or image, image reconstruction method (such as adaptive statistical iterative reconstruction, model-based iterative reconstruction, machine learning-based iterative reconstruction or similar); image reconstruction method (such as from different types of kernels, overlapping slices from retrospective ECG-helical studies, non-overlapping slices from prospective axial triggered studies, fast pitch helical studies, or half vs. full scan integral reconstruction); contrast density accounting for internal factors (such as oxygen, blood, temperature, and others); contrast density accounting for external factors (such as contrast density, concentration, osmolality and temporal change during the scan); detection technology (such as material, collimation and filtering); spectral imaging (such as polychromatic, monochromatic and spectral imaging along with material basis decomposition and single energy imaging); photon counting; and/or scanner brand and model.

In some embodiments, the normalization device 1200 can be applied to MRI studies, and account for one or more of: type of coil; place of positioning, number of antennas; depth from coil elements; image acquisition type; pulse sequence type and characteristics; field strength, gradient strength, slew rate and other hardware characteristics; magnet vendor, brand and type; imaging characteristics (thickness, matrix size, field of view, acceleration factor, reconstruction methods and characteristics, 2D, 3D, 4D [cine imaging, any change over time], temporal resolution, number of acquisitions, diffusion coefficients, method of populating k-space); contrast (intrinsic [oxygen, blood, temperature, etc.] and extrinsic types, volume, temporal change after administration); static or moving materials; quantitative imaging (including T1 T2 mapping, ADC, diffusion, phase contrast, and others); and/or administration of pharmaceuticals during image acquisition.

In some embodiments, the normalization device 1200 can be applied to ultrasound studies, and account for one or more of: type and machine brands; transducer type and frequency; greyscale, color, and pulsed wave doppler; B- or M-mode doppler type; contrast agent; field of view; depth from transducer; pulsed wave deformity (including elastography), angle; imaging characteristics (thickness, matrix size, field of view, acceleration factor, reconstruction methods and characteristics, 2D, 3D, 4D [cine imaging, any change over time]; temporal resolution; number of acquisitions; gain, and/or focus number and places, amongst others.

In some embodiments, the normalization device 1200 can be applied to nuclear medicine studies, such as PET or SPECT and account for one or more of: type and machine brands; for PET/CT all CT applies; for PET/MR all MR applies; contrast (radiopharmaceutical agent types, volume, temporal change after administration); imaging characteristics (thickness, matrix size, field of view, acceleration factor, reconstruction methods and characteristics, 2D, 3D, 4D [cine imaging, any change over time]; temporal resolution; number of acquisitions; gain, and/or focus number and places, amongst others.

In some embodiments, the normalization device may have different known materials with different densities adjacent to each other. This may address any issue present in some CT images where the density of a pixel influences the density of the adjacent pixels and that influence changes with the density of each of the individual pixel. One example of this embodiment being different contrast densities in the coronary lumen influencing the density of the plaque pixels. In some embodiments, the normalization device may include known volumes of known substances to help to correctly evaluate volumes of materials/lesions within the image in order to correct the influence of the blooming artifact on quantitative CT image analysis/measures. In some embodiments, the normalization device might have moving known materials with known volume and known and controllable motion. This would allow to exclude or reduce the effect of motion on quantitative CT image analysis/measures.

In some embodiments, having a known material on the image in the normalization device might also be helpful for material specific reconstructions from the same image. For example, it can be possible to use only one set of images to display only known materials, not needing multiple kV/spectral image hardware.

Figure 12J:
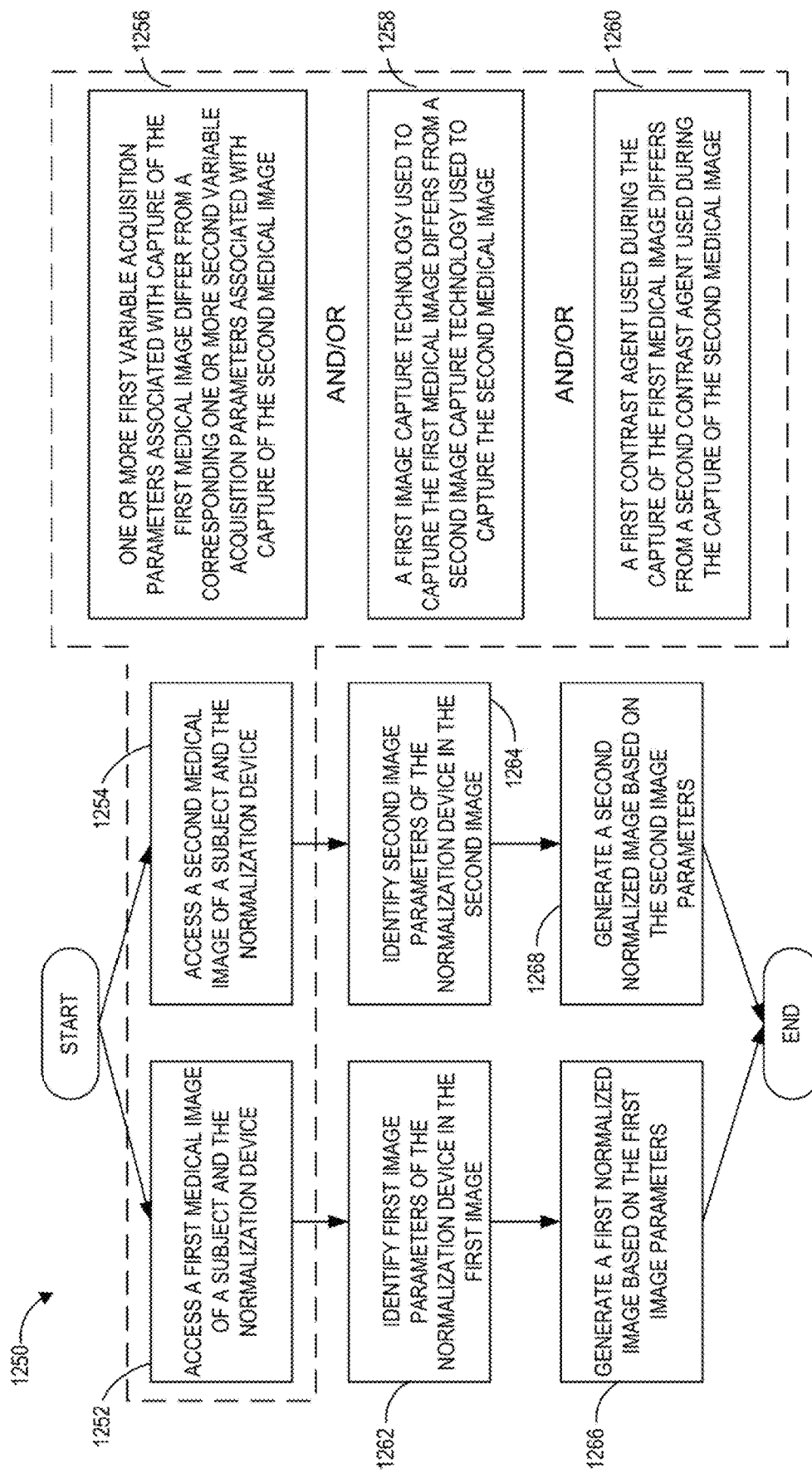
FIG. 12J is a flowchart illustrating an example method for normalizing medical images for an algorithm-based medical imaging analysis, wherein normalization of the medical images improves accuracy of the algorithm-based medical imaging analysis.

FIG. 12J is a flowchart illustrating an example method 1250 for normalizing medical images for an algorithm-based medical imaging analysis such as the analyses described herein. Use of the normalization device can improve accuracy of the algorithm-based medical imaging analysis. The method 1250 can be a computer-implemented method, implemented on a system that comprises a processor and an electronic storage medium. The method 1250 illustrates that the normalization device can be used to normalize medical images captured under different conditions. For example, at block 1252, a first medical image of a coronary region of a subject and the normalization device is accessed. The first medical image can be obtained non-invasively. The normalization device can comprise a substrate comprising a plurality of compartments, each of the plurality of compartments holding a sample of a known material, for example as described above. At block 1254, a second medical image of a coronary region of a subject and the normalization device is captured. The second medical image can be obtained non-invasively. Although the method 1250 is described with reference to a coronary region of a patient, the method is also applicable to all body parts and not only the vessels as the same principles apply to all body parts, all time points and all imaging devices. This can even include "live" type of images such as fluoroscopy or MR real time image.

As illustrated by the portion within the dotted lines, the first medical image and the second medical image can comprise at least one of the following: (1) one or more first variable acquisition parameters associated with capture of the first medical image differ from a corresponding one or more second variable acquisition parameters associated with capture of the second medical image, (2) a first image capture technology used to capture the first medical image differs from a second image capture technology used to capture the second medical image, and (3) a first contrast agent used during the capture of the first medical image differs from a second contrast agent used during the capture of the second medical image.

In some embodiments, the first medical image and the second medical image each comprise a CT image and the one or more first variable acquisition parameters and the one or more second variable acquisition parameters comprise one or more of a kilovoltage (kV), kilovoltage peak (kVp), a milliamperage (mA), or a method of gating. In some embodiments, the method of gating comprises one of prospective axial triggering, retrospective ECG helical gating, and fast pitch helical. In some embodiments, the first image capture technology and the second image capture technology each comprise one of a dual source scanner, a single source scanner, dual energy, monochromatic energy, spectral CT, photon counting, and different detector materials. In some embodiments, the first contrast agent and the second contrast agent each comprise one of an iodine contrast of varying concentration or a non-iodine contrast agent. In some embodiments, the first image capture technology and the second image capture technology each comprise one of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

In some embodiments, a first medical imager that captures the first medical imager is different than a second medical image that capture the second medical image. In some embodiments, the subject of the first medical image is different than the subject of the first medical image. In some embodiments, wherein the subject of the first medical image is the same as the subject of the second medical image. In some embodiments, wherein the subject of the first medical image is different than the subject of the second medical image. In some embodiments, wherein the capture of the first medical image is separated from the capture of the second medical image by at least one day. In some embodiments, wherein the capture of the first medical image is separated from the capture of the second medical image by at least one day. In some embodiments, wherein a location of the capture of the first medical image is geographically separated from a location of the capture of the second medical image.

Accordingly, it is apparent that the first and second medical images can be acquired under different conditions that can cause differences between the two images, even if the subject of each image is the same. The normalization device can help to normalize and account for these differences.

The method 1250 then moves to blocks 1262 and 1264, at which image parameters of the normalization device within the first medical image and which image parameters of the normalization device within the second medical image are identified, respectively. Due to different circumstances under which the first and second medical images were captured, the normalization device may appear differently in each image, even though the normalization device includes the same known samples.

Next, at blocks 1266 and 1268, the method generates a normalized first medical image for the algorithm-based medical imaging analysis based in part on the first identified image parameters of the normalization device within the first medical image and generates a normalized second medical image for the algorithm-based medical imaging analysis based in part on the second identified image parameters of the normalization device within the second medical image, respectively. In these blocks, each image is normalized based on the appearance or determined parameters of the normalization device in each image.

In some embodiments, the algorithm-based medical imaging analysis comprises an artificial intelligence or machine learning imaging analysis algorithm, and the artificial intelligence or machine learning imaging analysis algorithm was trained using images that included the normalization device.

System Overview

Figure 13:
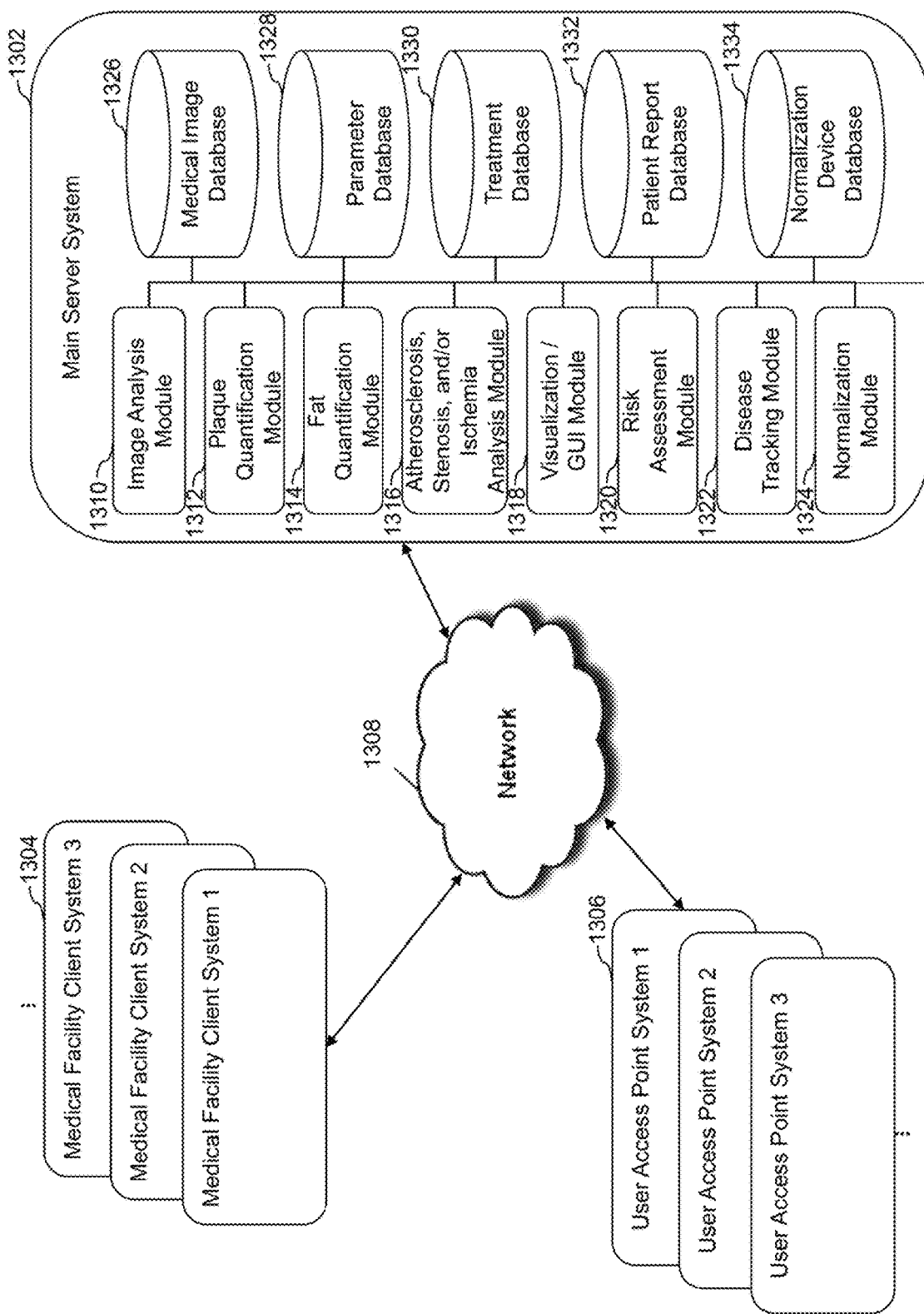
FIG. 13 is a block diagram depicting an embodiment(s) of a system for medical image analysis, visualization, risk assessment, disease tracking, treatment generation, and/or patient report generation.

In some embodiments, the systems, devices, and methods described herein are implemented using a network of one or more computer systems, such as the one illustrated in FIG. 13. FIG. 13 is a block diagram depicting an embodiment(s) of a system for medical image analysis, visualization, risk assessment, disease tracking, treatment generation, and/or patient report generation.

As illustrated in FIG. 13, in some embodiments, a main server system 1302 is configured to perform one or more processes, analytics, and/or techniques described herein, some of which relating to medical image analysis, visualization, risk assessment, disease tracking, treatment generation, and/or patient report generation. In some embodiments, the main server system 1302 is connected via an electronic communications network 1308 to one or more medical facility client systems 1304 and/or one or more user access point systems 1306. For example, in some embodiments, one or more medical facility client systems 1304 can be configured to access a medical image taken at the medical facility of a subject, which can then be transmitted to the main server system 1302 via the network 1308 for further analysis. After analysis, in some embodiments, the analysis results, such as for example quantified plaque parameters, assessed risk of a cardiovascular event, generated report, annotated and/or derived medical images, and/or the like, can be transmitted back to the medical facility client system 1304 via the network 1308. In some embodiments, the analysis results, such as for example quantified plaque parameters, assessed risk of a cardiovascular event, generated report, annotated and/or derived medical images, and/or the like, can be transmitted also to a user access point system 1306, such as a smartphone or other computing device of the patient or subject. As such, in some embodiments, a patient can be allowed to view and/or access a patient-specific report and/or other analyses generated and/or derived by the system from the medical image on the patient's computing device.

In some embodiments, the main server system 1302 can comprise and/or be configured to access one or more modules and/or databases for performing the one or more processes, analytics, and/or techniques described herein. For example, in some embodiments, the main server system 1302 can comprise an image analysis module 1310, a plaque quantification module 1312, a fat quantification module 1314, an atherosclerosis, stenosis, and/or ischemia analysis module 1316, a visualization/GUI module 1318, a risk assessment module 1320, a disease tracking module 1322, a normalization module 1324, a medical image database 1326, a parameter database 1328, a treatment database 1330, a patient report database 1332, a normalization device database 1334, and/or the like.

In some embodiments, the image analysis module 1310 can be configured to perform one or more processes described herein relating to image analysis, such as for example vessel and/or plaque identification from a raw medical image. In some embodiments, the plaque quantification module 1312 can be configured to perform one or more processes described herein relating to deriving or generating quantified plaque parameters, such as for example radiodensity, volume, heterogeneity, and/or the like of plaque from a raw medical image. In some embodiments, the fat quantification module 1314 can be configured to perform one or more processes described herein relating to deriving or generating quantified fat parameters, such as for example radiodensity, volume, heterogeneity, and/or the like of fat from a raw medical image. In some embodiments, the atherosclerosis, stenosis, and/or ischemia analysis module 1316 can be configured to perform one or more processes described herein relating to analyzing and/or generating an assessment or quantification of atherosclerosis, stenosis, and/or ischemia from a raw medical image. In some embodiments, the visualization/GUI module 1318 can be configured to perform one or more processes described herein relating to deriving or generating one or more visualizations and/or GUIs, such as for example a straightened view of a vessel identifying areas of good and/or bad plaque from a raw medical image. In some embodiments, the risk assessment module 1320 can be configured to perform one or more processes described herein relating to deriving or generating risk assessment, such as for example of a cardiovascular event or disease from a raw medical image. In some embodiments, the disease tracking module 1322 can be configured to perform one or more processes described herein relating to tracking a plaque-based disease, such as for example atherosclerosis, stenosis, ischemia, and/or the like from a raw medical image. In some embodiments, the normalization module 1324 can be configured to perform one or more processes described herein relating to normalizing and/or translating a medical image, for example based on a medical image of a normalization device comprising known materials, for further processing and/or analysis.

In some embodiments, the medical image database 1326 can comprise one or more medical images that are used for one or more of the various analysis techniques and processes described herein. In some embodiments, the parameter database 1328 can comprise one or more parameters derived from raw medical images by the system, such as for example one or more vessel morphology parameters, quantified plaque parameters, quantified fat parameters, and/or the like. In some embodiments, the treatment database 1328 can comprise one or more recommended treatments derived from raw medical images by the system. In some embodiments, the patient report database 1332 can comprise one or more patient-specific reports derived from raw medical images by the system and/or one or more components thereof that can be used to generate a patient-specific report based on medical image analysis results. In some embodiments, the normalization database 1334 can comprise one or more historical data points and/or datasets of normalizing various medical images and/or the specific types of medical imaging scanners and/or specific scan parameters used to obtain those images, as well as previously used normalization variables and/or translations for different medical images.

Computer System

Figure 14:
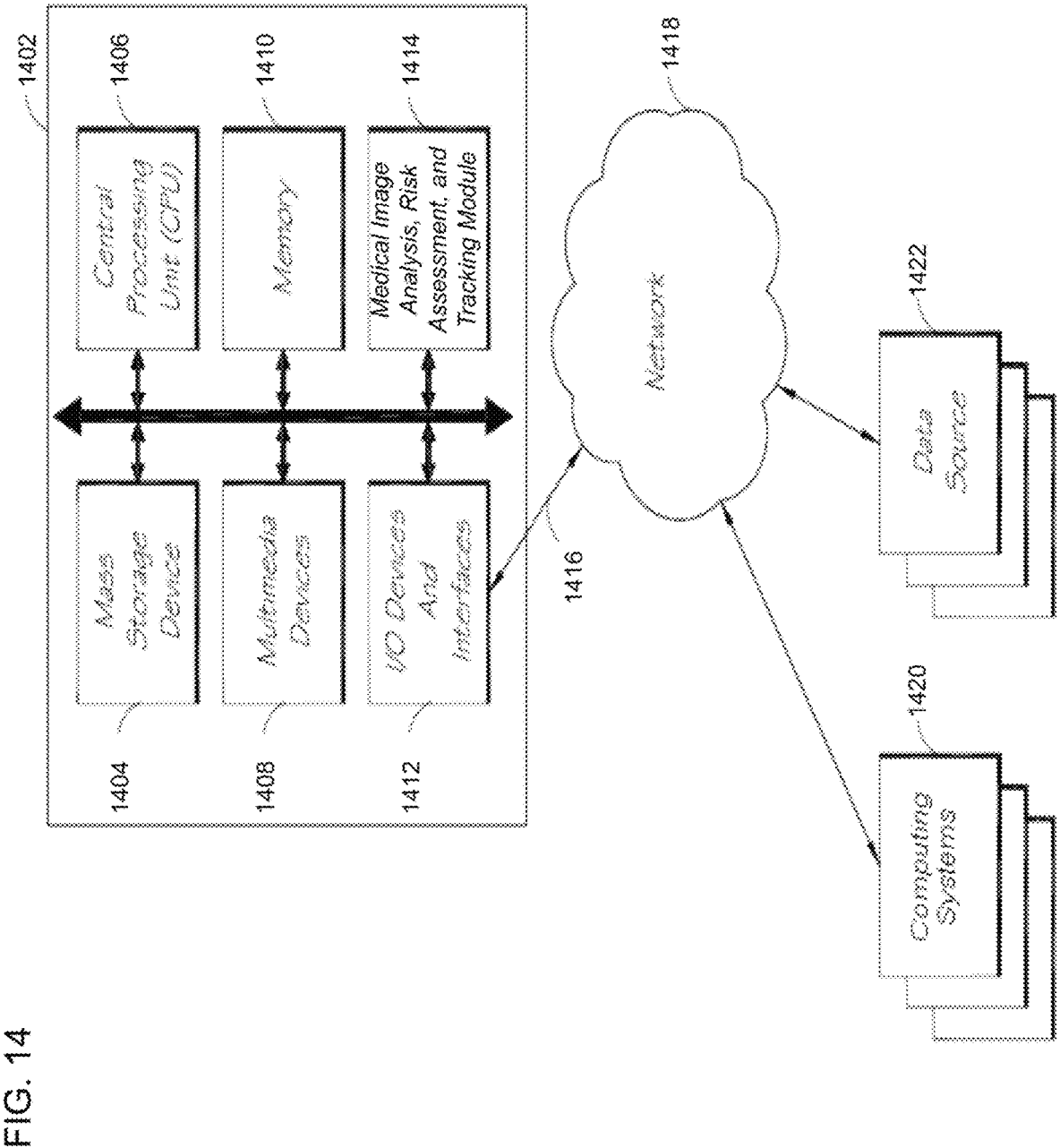
FIG. 14 is a block diagram depicting an embodiment(s) of a computer hardware system configured to run software for implementing one or more embodiments of a system for medical image analysis, visualization, risk assessment, disease tracking, treatment generation, and/or patient report generation.

In some embodiments, the systems, processes, and methods described herein are implemented using a computing system, such as the one illustrated in FIG. 14. The example computer system 1402 is in communication with one or more computing systems 1420 and/or one or more data sources 1422 via one or more networks 1418. While FIG. 14 illustrates an embodiment of a computing system 1402, it is recognized that the functionality provided for in the components and modules of computer system 1402 may be combined into fewer components and modules, or further separated into additional components and modules.

The computer system 1402 can comprise a Medical Analysis, Risk Assessment, and Tracking Module 1414 that carries out the functions, methods, acts, and/or processes described herein. The Medical Analysis, Risk Assessment, and Tracking Module 1414 is executed on the computer system 1402 by a central processing unit 1406 discussed further below.

In general the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1402 includes one or more processing units (CPU) 1406, which may comprise a microprocessor. The computer system 1402 further includes a physical memory 1410, such as random access memory (RAM) for temporary storage of information, a read only memory (ROM) for permanent storage of information, and a mass storage device 1404, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1402 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1402 includes one or more input/output (I/O) devices and interfaces 1412, such as a keyboard, mouse, touch pad, and printer. The I/O devices and interfaces 1412 can include one or more display devices, such as a monitor, that allows the visual presentation of data to a user. More particularly, a display device provides for the presentation of GUIs as application software data, and multi-media presentations, for example. The I/O devices and interfaces 1412 can also provide a communications interface to various external devices. The computer system 1402 may comprise one or more multi-media devices 1408, such as speakers, video cards, graphics accelerators, and microphones, for example.

The computer system 1402 may run on a variety of computing devices, such as a server, a Windows server, a Structure Query Language server, a Unix Server, a personal computer, a laptop computer, and so forth. In other embodiments, the computer system 1402 may run on a cluster computer system, a mainframe computer system and/or other computing system suitable for controlling and/or communicating with large databases, performing high volume transaction processing, and generating reports from large databases. The computing system 1402 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1402 illustrated in FIG. 14 is coupled to a network 1418, such as a LAN, WAN, or the Internet via a communication link 1416 (wired, wireless, or a combination thereof). Network 1418 communicates with various computing devices and/or other electronic devices. Network 1418 is communicating with one or more computing systems 1420 and one or more data sources 1422. The Medical Analysis, Risk Assessment, and Tracking Module 1414 may access or may be accessed by computing systems 1420 and/or data sources 1422 through a web-enabled user access point. Connections may be a direct physical connection, a virtual connection, and other connection type. The web-enabled user access point may comprise a browser module that uses text, graphics, audio, video, and other media to present data and to allow interaction with data via the network 1418.

Access to the Medical Analysis, Risk Assessment, and Tracking Module 1414 of the computer system 1402 by computing systems 1420 and/or by data sources 1422 may be through a web-enabled user access point such as the computing systems' 1420 or data source's 1422 personal computer, cellular phone, smartphone, laptop, tablet computer, e-reader device, audio player, or other device capable of connecting to the network 1418. Such a device may have a browser module that is implemented as a module that uses text, graphics, audio, video, and other media to present data and to allow interaction with data via the network 1418.

The output module may be implemented as a combination of an all-points addressable display such as a cathode ray tube (CRT), a liquid crystal display (LCD), a plasma display, or other types and/or combinations of displays. The output module may be implemented to communicate with input devices 1412 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1402 may comprise a physical or logical connection established between a remote microprocessor and a mainframe host computer for the express purpose of uploading, downloading, or viewing interactive data and databases on-line in real time. The remote microprocessor may be operated by an entity operating the computer system 1402, including the client server systems or the main server system, and/or may be operated by one or more of the data sources 1422 and/or one or more of the computing systems 1420. In some embodiments, terminal emulation software may be used on the microprocessor for participating in the micro-mainframe link.

In some embodiments, computing systems 1420 who are internal to an entity operating the computer system 1402 may access the Medical Analysis, Risk Assessment, and Tracking Module 1414 internally as an application or process run by the CPU 1406.

The computing system 1402 may include one or more internal and/or external data sources (for example, data sources 1422). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1402 may also access one or more databases 1422. The databases 1422 may be stored in a database or data repository. The computer system 1402 may access the one or more databases 1422 through a network 1418 or may directly access the database or data repository through I/O devices and interfaces 1412. The data repository storing the one or more databases 1422 may reside within the computer system 1402.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Example Embodiments

The following are non-limiting examples of certain embodiments of systems and methods of characterizing coronary plaque. Other embodiments may include one or more other features, or different features, that are discussed herein.

Embodiment 1: A computer-implemented method of quantifying and classifying coronary plaque within a coronary region of a subject based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; generating, by the computer system, a weighted measure of the determined one or more vascular morphology parameters and the set of quantified plaque parameters of the one or more regions of plaque; and classifying, by the computer system, the one or more regions of plaque within the medical image as stable plaque or unstable plaque based at least in part on the generated weighted measure of the determined one or more vascular morphology parameters and the determined set of quantified plaque parameters, wherein the computer system comprises a computer processor and an electronic storage medium.

Embodiment 2: The computer-implemented method of Embodiment 1, wherein one or more of the coronary artery identification algorithm or the plaque identification algorithm comprises an artificial intelligence or machine learning algorithm.

Embodiment 3: The computer-implemented method of any one of Embodiments 1 or 2, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 4: The computer-implemented method of any one of Embodiments 1-3, wherein the one or more coronary arteries are identified by size.

Embodiment 5: The computer-implemented method of any one of Embodiments 1-4, wherein a ratio of volume to surface area of the one or more regions of plaque below a predetermined threshold is indicative of stable plaque.

Embodiment 6: The computer-implemented method of any one of Embodiments 1-5, wherein a radiodensity of the one or more regions of plaque above a predetermined threshold is indicative of stable plaque.

Embodiment 7: The computer-implemented method of any one of Embodiments 1-6, wherein a heterogeneity of the one or more regions of plaque below a predetermined threshold is indicative of stable plaque.

Embodiment 8: The computer-implemented method of any one of Embodiments 1-7, wherein the set of quantified plaque parameters further comprises diffusivity of the one or more regions of plaque.

Embodiment 9: The computer-implemented method of any one of Embodiments 1-8, wherein the set of quantified plaque parameters further comprises a ratio of radiodensity to volume of the one or more regions of plaque.

Embodiment 10: The computer-implemented method of any one of Embodiments 1-9, further comprising generating, by the computer system, a proposed treatment for the subject based at least in part on the classified one or more regions of plaque.

Embodiment 11: The computer-implemented method of any one of Embodiments 1-10, further comprising generating, by the computer system, an assessment of the subject for one or more of atherosclerosis, stenosis, or ischemia based at least in part on the classified one or more regions of plaque.

Embodiment 12: The computer-implemented method of any one of Embodiments 1-11, wherein the medical image comprises a Computed Tomography (CT) image.

Embodiment 13: The computer-implemented method of Embodiment 12, wherein the medical image comprises a non-contrast CT image.

Embodiment 14: The computer-implemented method of Embodiment 12, wherein the medical image comprises a contrast-enhanced CT image.

Embodiment 15: The computer-implemented method of any one of Embodiments 1-11, wherein the medical image comprises a Magnetic Resonance (MR) image.

Embodiment 16: The computer-implemented method of any one of Embodiments 1-11, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 17: The computer-implemented method of any one of Embodiments 1-16, wherein the heterogeneity index of one or more regions of plaque is determined by generating a three-dimensional histogram of radiodensity values across a geometric shape of the one or more regions of plaque.

Embodiment 18: The computer-implemented method of any one of Embodiments 1-17, wherein the heterogeneity index of one or more regions of plaque is determined by generating spatial mapping of radiodensity values across the one or more regions of plaque.

Embodiment 19: The computer-implemented method of any one of Embodiments 1-18, wherein the set of quantified plaque parameters comprises a percentage composition of plaque comprising different radiodensity values.

Embodiment 20: The computer-implemented method of any one of Embodiments 1-19, wherein the set of quantified plaque parameters comprises a percentage composition of plaque comprising different radiodensity values as a function of volume of plaque.

Embodiment 21: The computer-implemented method of any one of Embodiments 1-20, wherein the geometry of the one or more regions of plaque comprises a round or oblong shape.

Embodiment 22: The computer-implemented method of any one of Embodiments 1-21, wherein the one or more vascular morphology parameters comprises a classification of arterial remodeling.

Embodiment 23: The computer-implemented method of Embodiment 22, wherein the classification of arterial remodeling comprises positive arterial remodeling, negative arterial remodeling, and intermediate arterial remodeling.

Embodiment 24: The computer-implemented method of Embodiment 22, wherein the classification of arterial remodeling is determined based at least in part on a ratio of a largest vessel diameter at the one or more regions of plaque to a normal reference vessel diameter.

Embodiment 25: The computer-implemented method of Embodiment 23, wherein the classification of arterial remodeling comprises positive arterial remodeling, negative arterial remodeling, and intermediate arterial remodeling, and wherein positive arterial remodeling is determined when the ratio of the largest vessel diameter at the one or more regions of plaque to the normal reference vessel diameter is more than 1.1, wherein negative arterial remodeling is determined when the ratio of the largest vessel diameter at the one or more regions of plaque to the normal reference vessel diameter is less than 0.95, and wherein intermediate arterial remodeling is determined when the ratio of the largest vessel diameter at the one or more regions of plaque to the normal reference vessel diameter is between 0.95 and 1.1.

Embodiment 26: The computer-implemented method of any one of Embodiments 1-25, wherein the function of volume to surface area of the one or more regions of plaque comprises one or more of a thickness or diameter of the one or more regions of plaque.

Embodiment 27: The computer-implemented method of any one of Embodiments 1-26, wherein the weighted measure is generated by weighting the one or more vascular morphology parameters and the set of quantified plaque parameters of the one or more regions of plaque equally.

Embodiment 28: The computer-implemented method of any one of Embodiments 1-26, wherein the weighted measure is generated by weighting the one or more vascular morphology parameters and the set of quantified plaque parameters of the one or more regions of plaque differently.

Embodiment 29: The computer-implemented method of any one of Embodiments 1-26, wherein the weighted measure is generated by weighting the one or more vascular morphology parameters and the set of quantified plaque parameters of the one or more regions of plaque logarithmically, algebraically, or utilizing another mathematical transform.

Embodiment 30: A computer-implemented method of quantifying and classifying vascular plaque based on non-invasive medical image analysis, the method comprising: accessing, by a computer system, a medical image of a subject, wherein the medical image of the subject is obtained non-invasively; identifying, by the computer system utilizing an artery identification algorithm, one or more arteries within the medical image of the subject, wherein the artery identification algorithm is configured to utilize raw medical images as input; identifying, by the computer system utilizing a plaque identification algorithm, one or more regions of plaque within the one or more arteries identified from the medical image of the subject, wherein the plaque identification algorithm is configured to utilize raw medical images as input; determining, by the computer system, one or more vascular morphology parameters and a set of quantified plaque parameters of the one or more identified regions of plaque from the medical image of the subject, wherein the set of quantified plaque parameters comprises a ratio or function of volume to surface area, heterogeneity index, geometry, and radiodensity of the one or more regions of plaque from the medical image; generating, by the computer system, a weighted measure of the determined one or more vascular morphology parameters and the set of quantified plaque parameters of the one or more regions of plaque; and classifying, by the computer system, the one or more regions of plaque within the medical image as stable plaque or unstable plaque based at least in part on the generated weighted measure of the determined one or more vascular morphology and the determined set of quantified plaque parameters, wherein the computer system comprises a computer processor and an electronic storage medium.

Embodiment 31: The computer-implemented method of Embodiment 30, wherein the identified one or more arteries comprise one or more of carotid arteries, aorta, renal artery, lower extremity artery, or cerebral artery.

Embodiment 32: A computer-implemented method of determining non-calcified plaque from a non-contrast Computed Tomography (CT) image, the method comprising: accessing, by a computer system, a non-contrast CT image of a coronary region of a subject; identifying, by the computer system, epicardial fat on the non-contrast CT image; segmenting, by the computer system, arteries on the non-contrast CT image using the identified epicardial fat as outer boundaries of the arteries; identifying, by the computer system, a first set of pixels within the arteries on the non-contrast CT image comprising a Hounsfield unit radiodensity value below a predetermined radiodensity threshold; classifying, by the computer system, the first set of pixels as a first subset of non-calcified plaque; identifying, by the computer system, a second set of pixels within the arteries on the non-contrast CT image comprising a Hounsfield unit radiodensity value within a predetermined radiodensity range; determining, by the computer system, a heterogeneity index of the second set of pixels and identifying a subset of the second set of pixels comprising a heterogeneity index above a heterogeneity index threshold; classifying, by the computer system, the subset of the second set of pixels as a second subset of non-calcified plaque; and determining, by the computer system, non-calcified plaque from the non-contrast CT image by combining the first subset of non-calcified plaque and the second subset of non-calcified plaque, wherein the computer system comprises a computer processor and an electronic storage medium.

Embodiment 33: The computer-implemented method of Embodiment 32, wherein the predetermined radiodensity threshold comprises a Hounsfield unit radiodensity value of 30.

Embodiment 34: The computer-implemented method of any one of Embodiments 32-33, wherein the predetermined radiodensity range comprises Hounsfield unit radiodensity values between 30 and 100.

Embodiment 35: The computer-implemented method of any one of Embodiments 32-34, wherein identifying epicardial fat on the non-contrast CT image further comprises: determining a Hounsfield unit radiodensity value of each pixel within the non-contrast CT image; and classifying as epicardial fat pixels within the non-contrast CT image with a Hounsfield unit radiodensity value within a predetermined epicardial fat radiodensity range, wherein the predetermined epicardial fat radiodensity range comprises a Hounsfield unit radiodensity value of −100.

Embodiment 36: The computer-implemented method of any one of Embodiments 32-35, wherein the heterogeneity index of the second set of pixels is determined by generating spatial mapping of radiodensity values of the second set of pixels.

Embodiment 37: The computer-implemented method of any one of Embodiments 32-36, wherein the heterogeneity index of the second set of pixels is determined by generating a three-dimensional histogram of radiodensity values across a geometric region within the second set of pixels.

Embodiment 38: The computer-implemented method of any one of Embodiments 32-37, further comprising classifying, by the computer system, a subset of the second set of pixels comprising a heterogeneity index below the heterogeneity index threshold as blood.

Embodiment 39: The computer-implemented method of any one of Embodiments 32-38, further comprising generating a quantized color map of the coronary region of the subject by assigning a first color to the identified epicardial fat, assigning a second color to the segmented arteries, and assigning a third color to the determined non-calcified plaque.

Embodiment 40: The computer-implemented method of any one of Embodiments 32-39, further comprising: identifying, by the computer system, a third set of pixels within the arteries on the non-contrast CT image comprising a Hounsfield unit radiodensity value above a predetermined calcified radiodensity threshold; and classifying, by the computer system, the third set of pixels as calcified plaque.

Embodiment 41: The computer-implemented method of any one of Embodiments 32-40, further comprising determining, by the computer system, a proposed treatment based at least in part on the determined non-calcified plaque.

Embodiment 42: A computer-implemented method of determining low-attenuated plaque from a medical image of a subject, the method comprising: accessing, by a computer system, a medical image of a subject; identifying, by the computer system, epicardial fat on the medical image of the subject by: determining a radiodensity value of each pixel within the medical image of the subject; and classifying as epicardial fat pixels within the medical image of the subject with a radiodensity value within a predetermined epicardial fat radiodensity range; segmenting, by the computer system, arteries on the medical image of the subject using the identified epicardial fat as outer boundaries of the arteries; identifying, by the computer system, a first set of pixels within the arteries on the medical image of the subject comprising a radiodensity value below a predetermined radiodensity threshold; classifying, by the computer system, the first set of pixels as a first subset of low-attenuated plaque; identifying, by the computer system, a second set of pixels within the arteries on the non-contrast CT image comprising a radiodensity value within a predetermined radiodensity range; determining, by the computer system, a heterogeneity index of the second set of pixels and identifying a subset of the second set of pixels comprising a heterogeneity index above a heterogeneity index threshold; classifying, by the computer system, the subset of the second set of pixels as a second subset of low-attenuated plaque; and determining, by the computer system, low-attenuated plaque from the medical image of the subject by combining the first subset of low-attenuated plaque and the second subset of low-attenuated plaque, wherein the computer system comprises a computer processor and an electronic storage medium.

Embodiment 43: The computer-implemented method of Embodiment 42, wherein the medical image comprises a Computed Tomography (CT) image.

Embodiment 44: The computer-implemented method of Embodiment 42, wherein the medical image comprises a Magnetic Resonance (MR) image.

Embodiment 45: The computer-implemented method of Embodiment 42, wherein the medical image comprises an ultrasound image.

Embodiment 46: The computer-implemented method of any one of Embodiments 42-45, wherein the medical image comprises an image of a coronary region of the subject.

Embodiment 47: The computer-implemented method of any one of Embodiments 42-46, further comprising determining, by the computer system, a proposed treatment for a disease based at least in part on the determined low-attenuated plaque.

Embodiment 48: The computer-implemented method of Embodiment 47, wherein the disease comprises one or more of arterial disease, renal artery disease, abdominal atherosclerosis, or carotid atherosclerosis.

Embodiment 49: The computer-implemented method of any one of Embodiments 42-48, wherein the heterogeneity index of the second set of pixels is determined by generating spatial mapping of radiodensity values of the second set of pixels.

Embodiment 50: A computer-implemented method of determining non-calcified plaque from a Dual-Energy Computed Tomography (DECT) image or spectral Computed Tomography (CT) image, the method comprising: accessing, by a computer system, a DECT or spectral CT image of a coronary region of a subject; identifying, by the computer system, epicardial fat on the DECT image or spectral CT; segmenting, by the computer system, arteries on the DECT image or spectral CT; identifying, by the computer system, a first set of pixels within the arteries on the DECT or spectral CT image comprising a Hounsfield unit radiodensity value below a predetermined radiodensity threshold; classifying, by the computer system, the first set of pixels as a first subset of non-calcified plaque; identifying, by the computer system, a second set of pixels within the arteries on the DECT or spectral CT image comprising a Hounsfield unit radiodensity value within a predetermined radiodensity range; classifying, by the computer system, a subset of the second set of pixels as a second subset of non-calcified plaque; and determining, by the computer system, non-calcified plaque from the DECT image or spectral CT by combining the first subset of non-calcified plaque and the second subset of non-calcified plaque, wherein the computer system comprises a computer processor and an electronic storage medium.

Embodiment 51: The computer-implemented method of Embodiment 50, wherein the subset of the second set of pixels is identified by determining, by the computer system, a heterogeneity index of the second set of pixels and identifying the subset of the second set of pixels comprising a heterogeneity index above a heterogeneity index threshold.

Embodiment 52: A computer-implemented method of assessing risk of a cardiovascular event for a subject based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; generating, by the computer system, a weighted measure of the determined one or more vascular morphology parameters and the set of quantified plaque parameters of the one or more regions of plaque; classifying, by the computer system, the one or more regions of plaque within the medical image as stable plaque or unstable plaque based at least in part on the generated weighted measure of the determined one or more vascular morphology parameters and the determined set of quantified plaque parameters; generating, by the computer system, a risk of cardiovascular event for the subject based at least in part on the one or more regions of plaque classified as stable plaque or unstable plaque; accessing, by the computer system, a coronary values database comprising one or more known datasets of coronary values derived from one or more other subjects and comparing the one or more regions of plaque classified as stable plaque or unstable plaque to the one or more known datasets of coronary values; updating, by the computer system, the generated risk of cardiovascular event for the subject based at least in part on the comparison of the one or more regions of plaque classified as stable plaque or unstable plaque to the one or more known datasets of coronary values; and generating, by the computer system, a proposed treatment for the subject based at least in part on the comparison of the one or more regions of plaque classified as stable plaque or unstable plaque to the one or more known datasets of coronary values, wherein the computer system comprises a computer processor and an electronic storage medium.

Embodiment 53: The computer-implemented method of Embodiment 52, wherein the cardiovascular event comprises one or more of a Major Adverse Cardiovascular Event (MACE), rapid plaque progression, or non-response to medication.

Embodiment 54: The computer-implemented method of any one of Embodiments 52-53, wherein the one or more known datasets of coronary values comprises one or more parameters of stable plaque and unstable plaque derived from medical images of healthy subjects.

Embodiment 55: The computer-implemented method of any one of Embodiments 52-54, wherein the one or more other subjects are healthy.

Embodiment 56: The computer-implemented method of any one of Embodiments 52-55, wherein the one or more other subjects have a heightened risk of a cardiovascular event.

Embodiment 57: The computer-implemented method of any one of Embodiments 52-57, further comprising: identifying, by the computer system, one or more additional cardiovascular structures within the medical image, wherein the one or more additional cardiovascular structures comprise one or more of the left ventricle, right ventricle, left atrium, right atrium, aortic valve, mitral valve, tricuspid valve, pulmonic valve, aorta, pulmonary artery, inferior and superior vena cava, epicardial fat, or pericardium; determining, by the computer system, one or more parameters associated with the identified one or more additional cardiovascular structures; classifying, by the computer system, the one or more additional cardiovascular structures based at least in part on the determined one or more parameters; accessing, by the computer system, a cardiovascular structures values database comprising one or more known datasets of cardiovascular structures parameters derived from medical images of one or more other subjects and comparing the classified one or more additional cardiovascular structures to the one or more known datasets of cardiovascular structures parameters; and updating, by the computer system, the generated risk of cardiovascular event for the subject based at least in part on the comparison of the classified one or more additional cardiovascular structures to the one or more known datasets of cardiovascular structures parameters.

Embodiment 58: The computer-implemented method of Embodiment 57, wherein the one or more additional cardiovascular structures are classified as normal or abnormal.

Embodiment 59: The computer-implemented method of Embodiment 57, wherein the one or more additional cardiovascular structures are classified as increased or decreased.

Embodiment 60: The computer-implemented method of Embodiment 57, wherein the one or more additional cardiovascular structures are classified as static or dynamic over time.

Embodiment 61: The computer-implemented method of any one of Embodiments 57-60, further comprising generating, by the computer system, a quantized color map for the additional cardiovascular structures.

Embodiment 62: The computer-implemented method of any one of Embodiments 57-61, further comprising updating, by the computer system, the proposed treatment for the subject based at least in part on the comparison of the classified one or more additional cardiovascular structures to the one or more known datasets of cardiovascular structures parameters.

Embodiment 63: The computer-implemented method of any one of Embodiments 57-62, further comprising: identifying, by the computer system, one or more non-cardiovascular structures within the medical image, wherein the one or more non-cardiovascular structures comprise one or more of the lungs, bones, or liver; determining, by the computer system, one or more parameters associated with the identified one or more non-cardiovascular structures; classifying, by the computer system, the one or more non-cardiovascular structures based at least in part on the determined one or more parameters; accessing, by the computer system, a non-cardiovascular structures values database comprising one or more known datasets of non-cardiovascular structures parameters derived from medical images of one or more other subjects and comparing the classified one or more non-cardiovascular structures to the one or more known datasets of non-cardiovascular structures parameters; and updating, by the computer system, the generated risk of cardiovascular event for the subject based at least in part on the comparison of the classified one or more non-cardiovascular structures to the one or more known datasets of non-cardiovascular structures parameters.

Embodiment 64: The computer-implemented method of Embodiment 63, wherein the one or more non-cardiovascular structures are classified as normal or abnormal.

Embodiment 65: The computer-implemented method of Embodiment 63, wherein the one or more non-cardiovascular structures are classified as increased or decreased.

Embodiment 66: The computer-implemented method of Embodiment 63, wherein the one or more non-cardiovascular structures are classified as static or dynamic over time.

Embodiment 67: The computer-implemented method of any one of Embodiments 63-66, further comprising generating, by the computer system, a quantized color map for the non-cardiovascular structures.

Embodiment 68: The computer-implemented method of any one of Embodiments 63-67, further comprising updating, by the computer system, the proposed treatment for the subject based at least in part on the comparison of the classified one or more non-cardiovascular structures to the one or more known datasets of non-cardiovascular structures parameters.

Embodiment 69: The computer-implemented method of any one of Embodiments 63-68, wherein the one or more parameters associated with the identified one or more non-cardiovascular structures comprises one or more of ratio of volume to surface area, heterogeneity, radiodensity, or geometry of the identified one or more non-cardiovascular structures.

Embodiment 70: The computer-implemented method of any one of Embodiments 52-69, wherein the medical image comprises a Computed Tomography (CT) image.

Embodiment 71: The computer-implemented method of any one of Embodiments 52-69, wherein the medical image comprises a Magnetic Resonance (MR) image.

Embodiment 72: A computer-implemented method of quantifying and classifying coronary atherosclerosis within a coronary region of a subject based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; generating, by the computer system, a weighted measure of the determined one or more vascular morphology parameters and the set of quantified plaque parameters of the one or more regions of plaque; quantifying, by the computer system, coronary atherosclerosis of the subject based at least in part on the set of generated weighted measure of the determined one or more vascular morphology parameters and the determined quantified plaque parameters; and classifying, by the computer system, coronary atherosclerosis of the subject as one or more of high risk, medium risk, or low risk based at least in part on the quantified coronary atherosclerosis of the subject, wherein the computer system comprises a computer processor and an electronic storage medium.

Embodiment 73: The computer-implemented method of Embodiment 72, wherein one or more of the coronary artery identification algorithm or the plaque identification algorithm comprises an artificial intelligence or machine learning algorithm.

Embodiment 74: The computer-implemented method of any one of Embodiments 72 or 73, further comprising determining a numerical calculation of coronary stenosis of the subject based at least in part on the one or more vascular morphology parameters and/or set of quantified plaque parameters determined from the medical image of the coronary region of the subject.

Embodiment 75: The computer-implemented method of any one of Embodiments 72-74, further comprising assessing a risk of ischemia for the subject based at least in part on the one or more vascular morphology parameters and/or set of quantified plaque parameters determined from the medical image of the coronary region of the subject.

Embodiment 76: The computer-implemented method of any one of Embodiments 72-75, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 77: The computer-implemented method of any one of Embodiments 72-76, wherein the one or more coronary arteries are identified by size.

Embodiment 78: The computer-implemented method of any one of Embodiments 72-77, wherein a ratio of volume to surface area of the one or more regions of plaque below a predetermined threshold is indicative of low risk.

Embodiment 79: The computer-implemented method of any one of Embodiments 72-78, wherein a radiodensity of the one or more regions of plaque above a predetermined threshold is indicative of low risk.

Embodiment 80: The computer-implemented method of any one of Embodiments 72-79, wherein a heterogeneity of the one or more regions of plaque below a predetermined threshold is indicative of low risk.

Embodiment 81: The computer-implemented method of any one of Embodiments 72-80, wherein the set of quantified plaque parameters further comprises diffusivity of the one or more regions of plaque.

Embodiment 82: The computer-implemented method of any one of Embodiments 72-81, wherein the set of quantified plaque parameters further comprises a ratio of radiodensity to volume of the one or more regions of plaque.

Embodiment 83: The computer-implemented method of any one of Embodiments 72-82, further comprising generating, by the computer system, a proposed treatment for the subject based at least in part on the classified atherosclerosis.

Embodiment 84: The computer-implemented method of any one of Embodiments 72-83, wherein the coronary atherosclerosis of the subject is classified by the computer system using a coronary atherosclerosis classification algorithm, wherein the coronary atherosclerosis classification algorithm is configured to utilize a combination of the ratio of volume of surface area, volume, heterogeneity index, and radiodensity of the one or more regions of plaque as input.

Embodiment 85: The computer-implemented method of any one of Embodiments 72-84, wherein the medical image comprises a Computed Tomography (CT) image.

Embodiment 86: The computer-implemented method of Embodiment 85, wherein the medical image comprises a non-contrast CT image.

Embodiment 87: The computer-implemented method of Embodiment 85, wherein the medical image comprises a contrast CT image.

Embodiment 88: The computer-implemented method of any one of Embodiments 72-84, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 89: The computer-implemented method of any one of Embodiments 72-88, wherein the heterogeneity index of one or more regions of plaque is determined by generating a three-dimensional histogram of radiodensity values across a geometric shape of the one or more regions of plaque.

Embodiment 90: The computer-implemented method of any one of Embodiments 72-89, wherein the heterogeneity index of one or more regions of plaque is determined by generating spatial mapping of radiodensity values across the one or more regions of plaque.

Embodiment 91: The computer-implemented method of any one of Embodiments 72-90, wherein the set of quantified plaque parameters comprises a percentage composition of plaque comprising different radiodensity values.

Embodiment 92: The computer-implemented method of any one of Embodiments 72-91, wherein the set of quantified plaque parameters comprises a percentage composition of plaque comprising different radiodensity values as a function of volume of plaque.

Embodiment 93: The computer-implemented method of any one of Embodiments 72-92, wherein the weighted measure of the determined one or more vascular morphology parameters and the set of quantified plaque parameters of the one or more regions of plaque is generated based at least in part by comparing the determined set of quantified plaque parameters to one or more predetermined sets of quantified plaque parameters.

Embodiment 94: The computer-implemented method of Embodiment 93, wherein the one or more predetermined sets of quantified plaque parameters are derived from one or more medical images of other subjects.

Embodiment 95: The computer-implemented method of Embodiment 93, wherein the one or more predetermined sets of quantified plaque parameters are derived from one or more medical images of the subject.

Embodiment 96: The computer-implemented method of any one of Embodiments 72-95, wherein the geometry of the one or more regions of plaque comprises a round or oblong shape.

Embodiment 97: The computer-implemented method of any one of Embodiments 72-96, wherein the one or more vascular morphology parameters comprises a classification of arterial remodeling.

Embodiment 98: The computer-implemented method of Embodiment 97, wherein the classification of arterial remodeling comprises positive arterial remodeling, negative arterial remodeling, and intermediate arterial remodeling.

Embodiment 99: The computer-implemented method of Embodiment 97, wherein the classification of arterial remodeling is determined based at least in part on a ratio of a largest vessel diameter at the one or more regions of plaque to a normal reference vessel diameter.

Embodiment 100: The computer-implemented method of Embodiment 99, wherein the classification of arterial remodeling comprises positive arterial remodeling, negative arterial remodeling, and intermediate arterial remodeling, and wherein positive arterial remodeling is determined when the ratio of the largest vessel diameter at the one or more regions of plaque to the normal reference vessel diameter is more than 1.1, wherein negative arterial remodeling is determined when the ratio of the largest vessel diameter at the one or more regions of plaque to the normal reference vessel diameter is less than 0.95, and wherein intermediate arterial remodeling is determined when the ratio of the largest vessel diameter at the one or more regions of plaque to the normal reference vessel diameter is between 0.95 and 1.1.

Embodiment 101: The computer-implemented method of any one of Embodiments 72-100, wherein the function of volume to surface area of the one or more regions of plaque comprises one or more of a thickness or diameter of the one or more regions of plaque.

Embodiment 102: The computer-implemented method of any one of Embodiments 72-101, wherein the weighted measure is generated by weighting the one or more vascular morphology parameters and the set of quantified plaque parameters of the one or more regions of plaque equally.

Embodiment 103: The computer-implemented method of any one of Embodiments 72-101, wherein the weighted measure is generated by weighting the one or more vascular morphology parameters and the set of quantified plaque parameters of the one or more regions of plaque differently.

Embodiment 104: The computer-implemented method of any one of Embodiments 72-101, wherein the weighted measure is generated by weighting the one or more vascular morphology parameters and the set of quantified plaque parameters of the one or more regions of plaque logarithmically, algebraically, or utilizing another mathematical transform.

Embodiment 105: A computer-implemented method of quantifying a state of coronary artery disease based on quantification of plaque, ischemia, and fat inflammation based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; identifying, by the computer system utilizing a fat identification algorithm, one or more regions of fat within the medical image of the coronary region of the subject, wherein the fat identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; quantifying, by the computer system, coronary stenosis based at least in part on the set of quantified plaque parameters determined from the medical image of the coronary region of the subject; and determining, by the computer system, a presence or risk of ischemia based at least in part on the set of quantified plaque parameters determined from the medical image of the coronary region of the subject; determining, by the computer system, a set of quantified fat parameters of the one or more identified regions of fat within the medical image of the coronary region of the subject, wherein the set of quantified fat parameters comprises volume, geometry, and radiodensity of the one or more regions of fat within the medical image; generating, by the computer system, a weighted measure of the determined one or more vascular morphology parameters, the set of quantified plaque parameters of the one or more regions of plaque, the quantified coronary stenosis, the determined presence or risk of ischemia, and the determined set of quantified fat parameters; and generating, by the computer system, a risk assessment of coronary disease of the subject based at least in part on the generated weighted measure of the determined one or more vascular morphology parameters, the set of quantified plaque parameters of the one or more regions of plaque, the quantified coronary stenosis, the determined presence or risk of ischemia, and the determined set of quantified fat parameters, wherein the computer system comprises a computer processor and an electronic storage medium.

Embodiment 106: The computer-implemented method of Embodiment 105, wherein one or more of the coronary artery identification algorithm, plaque identification algorithm, or fat identification algorithm comprises an artificial intelligence or machine learning algorithm.

Embodiment 107: The computer-implemented method of any one of Embodiments 105 or 106, further comprising automatically generating, by the computer system, a Coronary Artery Disease Reporting & Data System (CAD-RADS) classification score of the subject based at least in part on the quantified coronary stenosis.

Embodiment 108: The computer-implemented method of any one of Embodiments 105-107, further comprising automatically generating, by the computer system, a CAD-RADS modifier of the subject based at least in part on one or more of the determined one or more vascular morphology parameters, the set of quantified plaque parameters of the one or more regions of plaque, the quantified coronary stenosis, the determined presence or risk of ischemia, and the determined set of quantified fat parameters, wherein the CAD-RADS modifier comprises one or more of nondiagnostic (N), stent (S), graft (G), or vulnerability (V).

Embodiment 109: The computer-implemented method of any one of Embodiments 105-108, wherein the coronary stenosis is quantified on a vessel-by-vessel basis.

Embodiment 110: The computer-implemented method of any one of Embodiments 105-109, wherein the presence or risk of ischemia is determined on a vessel-by-vessel basis.

Embodiment 111: The computer-implemented method of any one of Embodiments 105-110, wherein the one or more regions of fat comprises epicardial fat.

Embodiment 112: The computer-implemented method of any one of Embodiments 105-111, further comprising generating, by the computer system, a proposed treatment for the subject based at least in part on the generated risk assessment of coronary disease.

Embodiment 113: The computer-implemented method of any one of Embodiments 105-112, wherein the medical image comprises a Computed Tomography (CT) image.

Embodiment 114: The computer-implemented method of Embodiment 113, wherein the medical image comprises a non-contrast CT image.

Embodiment 115: The computer-implemented method of Embodiment 113, wherein the medical image comprises a contrast CT image.

Embodiment 116: The computer-implemented method of any one of Embodiments 113-115, wherein the determined set of plaque parameters comprises one or more of a percentage of higher radiodensity calcium plaque or lower radiodensity calcium plaque within the one or more regions of plaque, wherein higher radiodensity calcium plaque comprises a Hounsfield radiodensity unit of above 1000, and wherein lower radiodensity calcium plaque comprises a Hounsfield radiodensity unit of below 1000.

Embodiment 117: The computer-implemented method of any one of Embodiments 105-112, wherein the medical image comprises a Magnetic Resonance (MR) image.

Embodiment 118: The computer-implemented method of any one of Embodiments 105-112, wherein the medical image comprises an ultrasound image.

Embodiment 119: The computer-implemented method of any one of Embodiments 105-112, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 120: The computer-implemented method of any one of Embodiments 105-119, wherein the heterogeneity index of one or more regions of plaque is determined by generating a three-dimensional histogram of radiodensity values across a geometric shape of the one or more regions of plaque.

Embodiment 121: The computer-implemented method of any one of Embodiments 105-119, wherein the heterogeneity index of one or more regions of plaque is determined by generating spatial mapping of radiodensity values across the one or more regions of plaque.

Embodiment 122: The computer-implemented method of any one of Embodiments 105-121, wherein the set of quantified plaque parameters comprises a percentage composition of plaque comprising different radiodensity values.

Embodiment 123: The computer-implemented method of any one of Embodiments 105-122, wherein the set of quantified plaque parameters further comprises diffusivity of the one or more regions of plaque.

Embodiment 124: The computer-implemented method of any one of Embodiments 105-123, wherein the set of quantified plaque parameters further comprises a ratio of radiodensity to volume of the one or more regions of plaque.

Embodiment 125: The computer-implemented method of any one of Embodiments 105-124, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 126: The computer-implemented method of any one of Embodiments 105-125, wherein the one or more coronary arteries are identified by size.

Embodiment 127: The computer-implemented method of any one of Embodiments 105-126, wherein the generated risk assessment of coronary disease of the subject comprises a risk score.

Embodiment 128: The computer-implemented method of any one of Embodiments 105-127, wherein the geometry of the one or more regions of plaque comprises a round or oblong shape.

Embodiment 129: The computer-implemented method of any one of Embodiments 105-128, wherein the one or more vascular morphology parameters comprises a classification of arterial remodeling.

Embodiment 130: The computer-implemented method of Embodiment 129, wherein the classification of arterial remodeling comprises positive arterial remodeling, negative arterial remodeling, and intermediate arterial remodeling.

Embodiment 131: The computer-implemented method of Embodiment 129, wherein the classification of arterial remodeling is determined based at least in part on a ratio of a largest vessel diameter at the one or more regions of plaque to a normal reference vessel diameter.

Embodiment 132: The computer-implemented method of Embodiment 131, wherein the classification of arterial remodeling comprises positive arterial remodeling, negative arterial remodeling, and intermediate arterial remodeling, and wherein positive arterial remodeling is determined when the ratio of the largest vessel diameter at the one or more regions of plaque to the normal reference vessel diameter is more than 1.1, wherein negative arterial remodeling is determined when the ratio of the largest vessel diameter at the one or more regions of plaque to the normal reference vessel diameter is less than 0.95, and wherein intermediate arterial remodeling is determined when the ratio of the largest vessel diameter at the one or more regions of plaque to the normal reference vessel diameter is between 0.95 and 1.1.

Embodiment 133: The computer-implemented method of any of Embodiments 105-132, wherein the function of volume to surface area of the one or more regions of plaque comprises one or more of a thickness or diameter of the one or more regions of plaque.

Embodiment 134: The computer-implemented method of any one of Embodiments 105-133, wherein the weighted measure is generated by weighting the one or more vascular morphology parameters, the set of quantified plaque parameters of the one or more regions of plaque, the quantified coronary stenosis, the determined presence or risk of ischemia, and the determined set of quantified fat parameters equally.

Embodiment 135: The computer-implemented method of any one of Embodiments 105-133, wherein the weighted measure is generated by weighting the one or more vascular morphology parameters, the set of quantified plaque parameters of the one or more regions of plaque, the quantified coronary stenosis, the determined presence or risk of ischemia, and the determined set of quantified fat parameters differently.

Embodiment 136: The computer-implemented method of any one of Embodiments 105-133, wherein the weighted measure is generated by weighting the one or more vascular morphology parameters, the set of quantified plaque parameters of the one or more regions of plaque, the quantified coronary stenosis, the determined presence or risk of ischemia, and the determined set of quantified fat parameters logarithmically, algebraically, or utilizing another mathematical transform.

Embodiment 137: A computer-implemented method of tracking a plaque-based disease based at least in part on determining a state of plaque progression of a subject using non-invasive medical image analysis, the method comprising: accessing, by a computer system, a first set of plaque parameters associated with a region of a subject, wherein the first set of plaque parameters are derived from a first medical image of the subject, wherein the first medical image of the subject is obtained non-invasively at a first point in time; accessing, by a computer system, a second medical image of the subject, wherein the second medical image of the subject is obtained non-invasively at a second point in time, the second point in time being later than the first point in time; identifying, by the computer system, one or more regions of plaque from the second medical image; determining, by the computer system, a second set of plaque parameters associated with the region of the subject by analyzing the second medical image and the identified one or more regions of plaque from the second medical image; analyzing, by the computer system, a change in one or more plaque parameters by comparing one or more of the first set of plaque parameters against one or more of the second set of plaque parameters; determining, by the computer system, a state of plaque progression associated with a plaque-based disease for the subject based at least in part on the analyzed change in the one or more plaque parameters, wherein the determined state of plaque progression comprises one or more of rapid plaque progression, non-rapid calcium dominant mixed response, non-rapid non-calcium dominant mixed response, or plaque regression; and tracking, by the computer system, progression of the plaque-based disease based at least in part on the determined state of plaque progression, wherein the computer system comprises a computer processor and an electronic storage medium.

Embodiment 138: The computer-implemented method of Embodiment 137, wherein rapid plaque progression is determined when a percent atheroma volume increase of the subject is more than 1% per year, wherein non-rapid calcium dominant mixed response is determined when a percent atheroma volume increase of the subject is less than 1% per year and calcified plaque represents more than 50% of total new plaque formation, wherein non-rapid non-calcium dominant mixed response is determined when a percent atheroma volume increase of the subject is less than 1% per year and non-calcified plaque represents more than 50% of total new plaque formation, and wherein plaque regression is determined when a decrease in total percent atheroma volume is present.

Embodiment 139: The computer-implemented method of any one of Embodiments 137-138, further comprising generating, by the computer system, a proposed treatment for the subject based at least in part on the determined state of plaque progression of the plaque-based disease.

Embodiment 140: The computer-implemented method of any one of Embodiments 137-139, wherein the medical image comprises a Computed Tomography (CT) image.

Embodiment 141: The computer-implemented method of Embodiment 140, wherein the medical image comprises a non-contrast CT image.

Embodiment 142: The computer-implemented method of Embodiment 140, wherein the medical image comprises a contrast CT image.

Embodiment 143: The computer-implemented method of any one of Embodiments 140-142, wherein the determined state of plaque progression further comprises one or more of a percentage of higher radiodensity plaques or lower radiodensity plaques, wherein higher radiodensity plaques comprise a Hounsfield unit of above 1000, and wherein lower radiodensity plaques comprise a Hounsfield unit of below 1000.

Embodiment 144: The computer-implemented method of any one of Embodiments 137-139, wherein the medical image comprises a Magnetic Resonance (MR) image.

Embodiment 145: The computer-implemented method of any one of Embodiments 137-139, wherein the medical image comprises an ultrasound image.

Embodiment 146: The computer-implemented method of any one of Embodiments 137-145, wherein the region of the subject comprises a coronary region of the subject.

Embodiment 147: The computer-implemented method of any one of Embodiments 137-145, wherein the region of the subject comprises one or more of carotid arteries, renal arteries, abdominal aorta, cerebral arteries, lower extremities, or upper extremities.

Embodiment 148: The computer-implemented method of any one of Embodiments 137-147, wherein the plaque-based disease comprises one or more of atherosclerosis, stenosis, or ischemia.

Embodiment 149: The computer-implemented method of any one of Embodiments 137-148, further comprising: determining, by the computer system, a first Coronary Artery Disease Reporting & Data System (CAD-RADS) classification score of the subject based at least in part on the first set of plaque parameters; determining, by the computer system, a second CAD-RADS classification score of the subject based at least in part on the second set of plaque parameters; and tracking, by the computer system, progression of a CAD-RADS classification score of the subject based on comparing the first CAD-RADS classification score and the second CAD-RADS classification score.

Embodiment 150: The computer-implemented method of any one of Embodiments 137-149, wherein the plaque-based disease is further tracked by the computer system by analyzing one or more of serum biomarkers, genetics, omics, transcriptomics, microbiomics, or metabolomics.

Embodiment 151: The computer-implemented method of any one of Embodiments 137-150, wherein the first set of plaque parameters comprises one or more of a volume, surface area, geometric shape, location, heterogeneity index, and radiodensity of one or more regions of plaque within the first medical image.

Embodiment 152: The computer-implemented method of any one of Embodiments 137-151, wherein the second set of plaque parameters comprises one or more of a volume, surface area, geometric shape, location, heterogeneity index, and radiodensity of one or more regions of plaque within the second medical image.

Embodiment 153: The computer-implemented method of any one of Embodiments 137-152, wherein the first set of plaque parameters and the second set of plaque parameters comprise a ratio of radiodensity to volume of one or more regions of plaque.

Embodiment 154: The computer-implemented method of any one of Embodiments 137-153, wherein the first set of plaque parameters and the second set of plaque parameters comprise a diffusivity of one or more regions of plaque.

Embodiment 155: The computer-implemented method of any one of Embodiments 137-154, wherein the first set of plaque parameters and the second set of plaque parameters comprise a volume to surface area ratio of one or more regions of plaque.

Embodiment 156: The computer-implemented method of any one of Embodiments 137-155, wherein the first set of plaque parameters and the second set of plaque parameters comprise a heterogeneity index of one or more regions of plaque.

Embodiment 157: The computer-implemented method of Embodiment 156, wherein the heterogeneity index of one or more regions of plaque is determined by generating a three-dimensional histogram of radiodensity values across a geometric shape of the one or more regions of plaque.

Embodiment 158: The computer-implemented method of Embodiment 156, wherein the heterogeneity index of one or more regions of plaque is determined by generating spatial mapping of radiodensity values across the one or more regions of plaque.

Embodiment 159: The computer-implemented method of any one of Embodiments 137-158, wherein the first set of plaque parameters and the second set of plaque parameters comprise a percentage composition of plaque comprising different radiodensity values.

Embodiment 160: The computer-implemented method of any one of Embodiments 137-159, wherein the first set of plaque parameters and the second set of plaque parameters comprise a percentage composition of plaque comprising different radiodensity values as a function of volume of plaque.

Embodiment 161: A computer-implemented method of characterizing a change in coronary calcium score of a subject, the method comprising: accessing, by the computer system, a first coronary calcium score of a subject and a first set of plaque parameters associated with a coronary region of a subject, the first coronary calcium score and the first set of parameters obtained at a first point in time, wherein the first set of plaque parameters comprises volume, surface area, geometric shape, location, heterogeneity index, and radiodensity for one or more regions of plaque within the coronary region of the subject; generating, by the computer system, a first weighted measure of the accessed first set of plaque parameters; accessing, by a computer system, a second coronary calcium score of the subject and one or more medical images of the coronary region of the subject, the second coronary calcium score and the one or more medical images obtained at a second point in time, the second point in time being later than the first point in time, wherein the one or more medical images of the coronary region of the subject comprises the one or more regions of plaque; determining, by the computer system, a change in coronary calcium score of the subject by comparing the first coronary calcium score and the second coronary calcium score; identifying, by the computer system, the one or more regions of plaque from the one or more medical images; determining, by the computer system, a second set of plaque parameters associated with the coronary region of the subject by analyzing the one or more medical images, wherein the second set of plaque parameters comprises volume, surface area, geometric shape, location, heterogeneity index, and radiodensity for the one or more regions of plaque; generating, by the computer system, a second weighted measure of the determined second set of plaque parameters; analyzing, by the computer system, a change in the first weighted measure of the accessed first set of plaque parameters and the second weighted measure of the determined second set of plaque parameters; and characterizing, by the computer system, the change in coronary calcium score of the subject based at least in part on the identified one or more regions of plaque and the analyzed change in the first weighted measure of the accessed first set of plaque parameters and the second weighted measure of the determined second set of plaque parameters, wherein the change in coronary in coronary calcium score is characterized as positive, neutral, or negative, wherein the computer system comprises a computer processor and an electronic storage medium.

Embodiment 162: The computer-implemented method of Embodiment 161, wherein radiodensity of the one or more regions of plaque is determined from the one or more medical images by analyzing a Hounsfield unit of the identified one or more regions of plaque.

Embodiment 163: The computer-implemented method of any one of Embodiments 161-162, further comprising determining a change in ratio between volume and radiodensity of the one or more regions of plaque within the coronary region of the subject, and wherein the change in coronary calcium score of the subject is further characterized based at least in part the determined change in ratio between volume and radiodensity of one or more regions of plaque within the coronary region of the subject.

Embodiment 164: The computer-implemented method of any one of Embodiments 161-163, wherein the change in coronary calcium score of the subject is characterized for each vessel.

Embodiment 165: The computer-implemented method of any one of Embodiments 161-164, wherein the change in coronary calcium score of the subject is characterized for each segment.

Embodiment 166: The computer-implemented method of any one of Embodiments 161-165, wherein the change in coronary calcium score of the subject is characterized for each plaque.

Embodiment 167: The computer-implemented method of any one of Embodiments 161-166, wherein the first set of plaque parameters and the second set of plaque parameters further comprise a diffusivity of the one or more regions of plaque.

Embodiment 168: The computer-implemented method of any one of Embodiments 161-167, wherein the change in coronary calcium score of the subject is characterized as positive when the radiodensity of the one or more regions of plaque is increased.

Embodiment 169: The computer-implemented method of any one of Embodiments 161-168, wherein the change in coronary calcium score of the subject is characterized as negative when one or more new regions of plaque are identified from the one or more medical images.

Embodiment 170: The computer-implemented method of any one of Embodiments 161-169, wherein the change in coronary calcium score of the subject is characterized as positive when a volume to surface area ratio of the one or more regions of plaque is decreased.

Embodiment 171: The computer-implemented method of any one of Embodiments 161-170, wherein the heterogeneity index of the one or more regions of plaque is determined by generating a three-dimensional histogram of radiodensity values across a geometric shape of the one or more regions of plaque.

Embodiment 172: The computer-implemented method of any one of Embodiments 161-171, wherein the change in coronary calcium score of the subject is characterized as positive when the heterogeneity index of the one or more regions of plaque is decreased.

Embodiment 173: The computer-implemented method of any one of Embodiments 161-172, wherein the second coronary calcium score of the subject is determined by analyzing the one or more medical images of the coronary region of the subject.

Embodiment 174: The computer-implemented method of any one of Embodiments 161-172, wherein the second coronary calcium score of the subject is accessed from a database.

Embodiment 175: The computer-implemented method of any one of Embodiments 161-174, wherein the one or more medical images of the coronary region of the subject comprises an image obtained from a non-contrast Computed Tomography (CT) scan.

Embodiment 176: The computer-implemented method of any one of Embodiments 161-174, wherein the one or more medical images of the coronary region of the subject comprises an image obtained from a contrast-enhanced CT scan.

Embodiment 177: The computer-implemented method of Embodiment 176, wherein the one or more medical images of the coronary region of the subject comprises an image obtained from a contrast-enhanced CT angiogram.

Embodiment 178: The computer-implemented method of any one of Embodiments 161-177, wherein a positive characterization of the change in coronary in coronary calcium score is indicative of plaque stabilization.

Embodiment 179: The computer-implemented method of any one of Embodiments 161-178, wherein the first set of plaque parameters and the second set of plaque parameters further comprise radiodensity of a volume around plaque Embodiment 180: The computer-implemented method of any one of Embodiments 161-179, wherein the change in coronary calcium score of the subject is characterized by a machine learning algorithm utilized by the computer system.

Embodiment 181: The computer-implemented method of any one of Embodiments 161-180, wherein the first weighted measure is generated by weighting the accessed first set of plaque parameters equally.

Embodiment 182: The computer-implemented method of any one of Embodiments 161-180, wherein the first weighted measure is generated by weighting the accessed first set of plaque parameters differently.

Embodiment 183: The computer-implemented method of any one of Embodiments 161-180, wherein the first weighted measure is generated by weighting the accessed first set of plaque parameters logarithmically, algebraically, or utilizing another mathematical transform.

Embodiment 184: A computer-implemented method of generating prognosis of a cardiovascular event for a subject based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, a set of quantified plaque parameters of the one or more identified regions of plaque within the medical image of the coronary region of the subject, wherein the set of quantified plaque parameters comprises volume, surface area, ratio of volume to surface area, heterogeneity index, geometry, and radiodensity of the one or more regions of plaque within the medical image; classifying, by the computer system, the one or more regions of plaque within the medical image as stable plaque or unstable plaque based at least in part on the determined set of quantified plaque parameters; determining, by the computer system, a volume of unstable plaque classified within the medical image and a total volume of the one or more coronary arteries within the medical image; determining, by the computer system, a ratio of volume of unstable plaque to the total volume of the one or more coronary arteries; generating, by the computer system, a prognosis of a cardiovascular event for the subject based at least in part on analyzing the ratio of volume of unstable plaque to the total volume of the one or more coronary arteries, the volume of the one or more regions of plaque, and the volume of unstable plaque classified within the medical image, wherein the analyzing comprises conducting a comparison to a known dataset of one or more ratios of volume of unstable plaque to total volume of one or more coronary arteries, volume of one or more regions of plaque, and volume of unstable plaque, wherein the known dataset is collected from other subjects; and generating, by the computer system, treatment plan for the subject based at least in part on the generated prognosis of cardiovascular event for the subject, wherein the computer system comprises a computer processor and an electronic storage medium.

Embodiment 185: The computer-implemented method of Embodiment 184, further comprising generating, by the computer system, a weighted measure of the ratio of volume of unstable plaque to the total volume of the one or more coronary arteries, the volume of the one or more regions of plaque, and the volume of unstable plaque classified within the medical image, wherein the prognosis of cardiovascular event is further generated by comparing the weighted measure to one or more weighted measures derived from the known dataset.

Embodiment 186: The computer-implemented method of Embodiment 185, wherein the weighted measure is generated by weighting the ratio of volume of unstable plaque to the total volume of the one or more coronary arteries, the volume of the one or more regions of plaque, and the volume of unstable plaque classified within the medical image equally.

Embodiment 187: The computer-implemented method of Embodiment 185, wherein the weighted measure is generated by weighting the ratio of volume of unstable plaque to the total volume of the one or more coronary arteries, the volume of the one or more regions of plaque, and the volume of unstable plaque classified within the medical image differently.

Embodiment 188: The computer-implemented method of Embodiment 185, wherein the weighted measure is generated by weighting the ratio of volume of unstable plaque to the total volume of the one or more coronary arteries, the volume of the one or more regions of plaque, and the volume of unstable plaque classified within the medical image logarithmically, algebraically, or utilizing another mathematical transform.

Embodiment 189: The computer-implemented method of any one of Embodiments 184-188, further comprising analyzing, by the computer system, a medical image of a non-coronary cardiovascular system of the subject, and wherein the prognosis of a cardiovascular event for the subject is further generated based at least in part on the analyzed medical image of the non-coronary cardiovascular system of the subject.

Embodiment 190: The computer-implemented method of any one of Embodiments 184-189, further comprising accessing, by the computer system, results of a blood chemistry or biomarker test of the subject, and wherein the prognosis of a cardiovascular event for the subject is further generated based at least in part on the results of the blood chemistry or biomarker test of the subject.

Embodiment 191: The computer-implemented method of any one of Embodiments 184-190, wherein the generated prognosis of a cardiovascular event for the subject comprises a risk score of a cardiovascular event for the subject.

Embodiment 192: The computer-implemented method of any one of Embodiments 184-191, wherein the prognosis of a cardiovascular event is generated by the computer system utilizing an artificial intelligence or machine learning algorithm.

Embodiment 193: The computer-implemented method of any one of Embodiments 184-192, wherein the cardiovascular event comprises one or more of atherosclerosis, stenosis, or ischemia.

Embodiment 194: The computer-implemented method of any one of Embodiments 184-193, wherein the generated treatment plan comprises one or more of use of statins, lifestyle changes, or surgery.

Embodiment 195: The computer-implemented method of any one of Embodiments 184-194, wherein one or more of the coronary artery identification algorithm or the plaque identification algorithm comprises an artificial intelligence or machine learning algorithm.

Embodiment 196: The computer-implemented method of any one of Embodiments 184-195, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 197: The computer-implemented method of any one of Embodiments 184-196, wherein the medical image comprises a Computed Tomography (CT) image.

Embodiment 198: The computer-implemented method of Embodiment 197, wherein the medical image comprises a non-contrast CT image.

Embodiment 199: The computer-implemented method of Embodiment 197, wherein the medical image comprises a contrast CT image.

Embodiment 200: The computer-implemented method of any one of Embodiments 184-196, wherein the medical image comprises a Magnetic Resonance (MR) image.

Embodiment 201: The computer-implemented method of any one of Embodiments 184-196, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 202: A computer-implemented method of determining patient-specific stent parameters and guidance for implantation based on non-invasive medical image analysis, the method comprising: accessing, by a computer system, a medical image of a coronary region of a patient, wherein the medical image of the coronary region of the patient is obtained non-invasively; identifying, by the computer system utilizing a coronary artery identification algorithm, one or more coronary arteries within the medical image of the coronary region of the patient, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the patient, wherein the plaque identification algorithm is configured to utilize raw medical images as input; determining, by the computer system, a set of quantified plaque parameters of the one or more identified regions of plaque from the medical image of the coronary region of the patient, wherein the set of quantified plaque parameters comprises a ratio or function of volume to surface area, heterogeneity index, location, geometry, and radiodensity of the one or more regions of plaque within the medical image; determining, by the computer system, a set of stenosis vessel parameters of the one or more coronary arteries within the medical image of the coronary region of the patient, wherein the set of vessel parameters comprises volume, curvature, vessel wall, lumen wall, and diameter of the one or more coronary arteries within the medical image in the presence of stenosis; determining, by the computer system, a set of normal vessel parameters of the one or more coronary arteries within the medical image of the coronary region of the patient, wherein the set of vessel parameters comprises volume, curvature, vessel wall, lumen wall, and diameter of the one or more coronary arteries within the medical image without stenosis, wherein the set of normal vessel parameters are determined by graphically removing from the medical image of the coronary region of the patient the identified one or more regions of plaque; determining, by the computer system, a predicted effectiveness of stent implantation for the patient based at least in part on the set of quantified plaque parameters and the set of vessel parameters; generating, by the computer system, patient-specific stent parameters for the patient when the predicted effectiveness of stent implantation for the patient is above a predetermined threshold, wherein the patient-specific stent parameters are generated based at least in part on the set of quantified plaque parameters, the set of vessel parameters, and the set of normal vessel parameters; and generating, by the computer system, guidance for implantation of a patient-specific stent comprising the patient-specific stent parameters, wherein the guidance for implantation of the patient-specific stent is generated based at least in part on the set of quantified plaque parameters and the set of vessel parameters, wherein the generated guidance for implantation of the patient-specific stent comprises insertion of guidance wires and positioning of the patient-specific stent, wherein the computer system comprises a computer processor and an electronic storage medium.

Embodiment 203: The computer-implemented method of Embodiment 202, further comprising accessing, by the computer system, a post-implantation medical image of the coronary region of the patient and performing post-implantation analysis.

Embodiment 204: The computer-implemented method of Embodiment 203, further comprising generating, by the computer system, a treatment plan for the patient based at least in part on the post-implantation analysis.

Embodiment 205: The computer-implemented method of Embodiment 204, wherein the generated treatment plan comprises one or more of use of statins, lifestyle changes, or surgery.

Embodiment 206: The computer-implemented method of any one of Embodiments 202-205, wherein the set of stenosis vessel parameters comprises a location, curvature, and diameter of bifurcation of the one or more coronary arteries.

Embodiment 207: The computer-implemented method of any one of Embodiments 202-206, wherein the patient-specific stent parameters comprise a diameter of the patient-specific stent.

Embodiment 208: The computer-implemented method of Embodiment 207, wherein the diameter of the patient-specific stent is substantially equal to the diameter of the one or more coronary arteries without stenosis.

Embodiment 209: The computer-implemented method of Embodiment 207, wherein the diameter of the patient-specific stent is less than the diameter of the one or more coronary arteries without stenosis.

Embodiment 210: The computer-implemented method of any one of Embodiments 202-209, wherein the predicted effectiveness of stent implantation for the patient is determined by the computer system utilizing an artificial intelligence or machine learning algorithm.

Embodiment 211: The computer-implemented method of any one of Embodiments 202-210, wherein the patient-specific stent parameters for the patient are generated by the computer system utilizing an artificial intelligence or machine learning algorithm.

Embodiment 212: The computer-implemented method of any one of Embodiments 202-211, wherein one or more of the coronary artery identification algorithm or the plaque identification algorithm comprises an artificial intelligence or machine learning algorithm.

Embodiment 213: The computer-implemented method of any one of Embodiments 202-212, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 214: The computer-implemented method of any one of Embodiments 202-213, wherein the medical image comprises a Computed Tomography (CT) image.

Embodiment 215: The computer-implemented method of Embodiment 214, wherein the medical image comprises a non-contrast CT image.

Embodiment 216: The computer-implemented method of Embodiment 214, wherein the medical image comprises a contrast CT image.

Embodiment 217: The computer-implemented method of any one of Embodiments 202-213, wherein the medical image comprises a Magnetic Resonance (MR) image.

Embodiment 218: The computer-implemented method of any one of Embodiments 202-213, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 219: A computer-implemented method of generating a patient-specific report on coronary artery disease for a patient based on non-invasive medical image analysis, the method comprising: accessing, by a computer system, a medical image of a coronary region of a patient, wherein the medical image of the coronary region of the patient is obtained non-invasively; identifying, by the computer system utilizing a coronary artery identification algorithm, one or more coronary arteries within the medical image of the coronary region of the patient, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the patient, wherein the plaque identification algorithm is configured to utilize raw medical images as input; determining, by the computer system, one or more vascular morphology parameters and a set of quantified plaque parameters of the one or more identified regions of plaque from the medical image of the coronary region of the patient, wherein the set of quantified plaque parameters comprises a ratio or function of volume to surface area, volume, heterogeneity index, location, geometry, and radiodensity of the one or more regions of plaque within the medical image; quantifying, by the computer system, stenosis and atherosclerosis of the patient based at least in part on the set of quantified plaque parameters determined from the medical image; generating, by the computer system, one or more annotated medical images based at least in part on the medical image, the quantified stenosis and atherosclerosis of the patient, and the set of quantified plaque parameters determined from the medical image; determining, by the computer system, a risk of coronary artery disease for the patient based at least in part by comparing the quantified stenosis and atherosclerosis of the patient and the set of quantified plaque parameters determined from the medical image to a known dataset of one or more quantified stenosis and atherosclerosis and one or more quantified plaque parameters derived from one or more medial images of healthy subjects within an age group of the patient; dynamically generating, by the computer system, a patient-specific report on coronary artery disease for the patient, wherein the generated patient-specific report comprises the one or more annotated medical images, one or more of the set of quantified plaque parameters, and determined risk of coronary artery disease, wherein the computer system comprises a computer processor and an electronic storage medium.

Embodiment 220: The computer-implemented method of Embodiment 219, wherein the patient-specific report comprises a cinematic report.

Embodiment 221: The computer-implemented method of Embodiment 220, wherein the patient-specific report comprises content configured to provide an Augmented Reality (AR) or Virtual Reality (VR) experience.

Embodiment 222: The computer-implemented method of any one of Embodiments 219-221, wherein the patient-specific report comprises audio dynamically generated for the patient based at least in part on the quantified stenosis and atherosclerosis of the patient, the set of quantified plaque parameters determined from the medical image, and determined risk of coronary artery disease.

Embodiment 223: The computer-implemented method of any one of Embodiments 219-222, wherein the patient-specific report comprises phrases dynamically generated for the patient based at least in part on the quantified stenosis and atherosclerosis of the patient, the set of quantified plaque parameters determined from the medical image, and determined risk of coronary artery disease.

Embodiment 224: The computer-implemented method of any one of Embodiments 219-223, further comprising generating, by the computer system, a treatment plan for the patient based at least in part on the quantified stenosis and atherosclerosis of the patient, the set of quantified plaque parameters determined from the medical image, and determined risk of coronary artery disease, wherein the patient-specific report comprises the generated treatment plan.

Embodiment 225: The computer-implemented method of Embodiment 224, wherein the generated treatment plan comprises one or more of use of statins, lifestyle changes, or surgery.

Embodiment 226: The computer-implemented method of any one of Embodiments 219-225, further comprising tracking, by the computer system, progression of coronary artery disease for the patient based at least in part on comparing one or more of the set of quantified plaque parameters determined from the medical image against one or more previous quantified plaque parameters derived from a previous medical image of the patient, wherein the patient-specific report comprises the tracked progression of coronary artery disease.

Embodiment 227: The computer-implemented method of any one of Embodiments 219-226, wherein one or more of the coronary artery identification algorithm or the plaque identification algorithm comprises an artificial intelligence or machine learning algorithm.

Embodiment 228: The computer-implemented method of any one of Embodiments 219-227, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 229: The computer-implemented method of any one of Embodiments 219-228, wherein the medical image comprises a Computed Tomography (CT) image.

Embodiment 230: The computer-implemented method of Embodiment 229, wherein the medical image comprises a non-contrast CT image.

Embodiment 231: The computer-implemented method of Embodiment 229, wherein the medical image comprises a contrast CT image.

Embodiment 232: The computer-implemented method of any one of Embodiments 219-228, wherein the medical image comprises a Magnetic Resonance (MR) image.

Embodiment 233: The computer-implemented method of any one of Embodiments 219-228, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 234: A system comprising: at least one non-transitory computer storage medium configured to at least store computer-executable instructions, a set of computed tomography (CT) images of a patient's coronary vessels, vessel labels, and artery information associated with the set of CT images including information of stenosis, plaque, and locations of segments of the coronary vessels; one or more computer hardware processors in communication with the at least one non-transitory computer storage medium, the one or more computer hardware processors configured to execute the computer-executable instructions to at least: generate and display a user interface a first panel including an artery tree comprising a three-dimensional (3D) representation of coronary vessels depicting coronary vessels identified in the CT images, and including segment labels related to the artery tree, the artery tree not including heart tissue between branches of the artery tree; in response to an input on the user interface indicating the selection of a coronary vessel in the artery tree in the first panel, generate and display on the user interface a second panel illustrating at least a portion of the selected coronary vessel in at least one straightened multiplanar vessel (SMPR) view; generate and display on the user interface a third panel showing a cross-sectional view of the selected coronary vessel, the cross-sectional view generated using one of the set of CT images of the selected coronary vessel, wherein locations along the at least one SMPR view are each associated with one of the CT images in the set of CT images such that a selection of a particular location along the coronary vessel in the at least one SMPR view displays the associated CT image in the cross-sectional view in the third panel; and in response to an input on the third panel indicating a first location along the selected coronary artery in the at least one SMPR view, display a cross-sectional view associated with the selected coronary artery at the first location in the third panel.

Embodiment 235: The system of embodiment 234, wherein the one or more computer hardware processors are further configured to execute the computer-executable instructions to, in response to an input on the second panel pf the user interface indicating a second location along the selected coronary artery in the at least one SMPR view, display the associated CT scan associated with the second location in a cross-sectional view in the third panel.

Embodiment 236: The system of embodiment 234, wherein the one or more computer hardware processors are further configured to execute the computer-executable instructions to: in response to a second input on the user interface indicating the selection of a second coronary vessel in the artery tree displayed in the first panel, generate and display in the second panel least a portion of the selected second coronary vessel in at least one straightened multi-planar vessel (SMPR) view, and generate and display on the third panel a cross-sectional view of the selected second coronary vessel, the cross-sectional view generated using one of the set of CT images of the selected second coronary vessel, wherein locations along the selected second coronary artery in the at least one SMPR view are each associated with one of the CT images in the set of CT images such that a selection of a particular location along the second coronary vessel in the at least one SMPR view displays the associated CT image in the cross-sectional view in the third panel.

Embodiment 237: The system of embodiment 234, wherein the one or more computer hardware processors are further configured to identify the vessel segments using a machine learning algorithm that processes the CT images prior to storing the artery information on the at least one non-transitory computer storage medium.

Embodiment 238: The system of embodiment 234, wherein the one or more computer hardware processors are further configured to execute the computer-executable instructions to generate and display on the user interface in a fourth panel a cartoon artery tree, the cartoon artery tree comprising a non-patient specific graphical representation of a coronary artery tree, and wherein in response to a selection of a vessel segment in the cartoon artery tree, a view of the selected vessel segment is displayed in a panel of the user interface in a SMPR view, and upon selection of a location of the vessel segment displayed in the SMPR view, generate and display in the user interface a panel that displays information about the selected vessel at the selected location.

Embodiment 239: The system of embodiment 238, wherein the displayed information includes information relating to stenosis and plaque of the selected vessel.

Embodiment 240: The system of embodiment 234, wherein the one or more computer hardware processors are further configured to execute the computer-executable instructions to generate and segment name labels, proximal to a respective segment on the artery tree, indicative of the name of the segment.

Embodiment 241: The system of embodiment 240, wherein the one or more computer hardware processors are further configured to execute the computer-executable instructions to, in response to an input selection of a first segment name label displayed on the user interface, generate and display on the user interface a panel having a list of vessel segment names and indicating the current name of the selected vessel segment; and in response to an input selection of a second segment name label on the list, replace the first segment name label with the second segment name label of the displayed artery tree in the user interface.

Embodiment 242: The system of embodiment 234, wherein the at least one SMPR view of the selected coronary vessel comprises at least two SMPR views of the selected coronary vessel displayed adjacently at a rotational interval.

Embodiment 243: The system of embodiment 234, wherein the at least one SMPR view include four SMPR views displayed at a relative rotation of 0°, 22.5°, 45°, and 67.5°.

Embodiment 244: The system of embodiment 234, wherein the one or more computer hardware processors are further configured to execute the computer-executable instructions to, in response to a user input, rotate the at least one SMPR view in increments of 1°.

Embodiment 245: The system of embodiment 234, wherein the artery tree, the at least one SMPR view, and the cross-sectional view are displayed concurrently on the user interface.

Embodiment 246: The system of embodiment 245, wherein the artery tree is displayed in a center portion of the user panel, the cross-sectional view is displayed in a center portion of the user interface above or below the artery tree, and the at least one SMPR view are displayed on one side of the center portion of the user interface.

Embodiment 247: The system of embodiment 246, wherein the one or more computer hardware processors are further configured to generate and display, on one side of the center portion of the user interface, one or more anatomical plane views corresponding to the selected coronary artery, the anatomical plane views of the selected coronary vessel based on the CT images Embodiment 248: The system of embodiment 247, wherein the anatomical plane views comprise three anatomical plane views.

Embodiment 249: The system of embodiment 247, wherein the anatomical plane views comprise at least one of an axial plane view, a coronal plane view, or a sagittal plane view.

Embodiment 250: The system of embodiment 234, wherein the one or more computer hardware processors are further configured to receive a rotation input on the user interface, and rotate the at least one SMPR views incrementally based on the rotation input.

Embodiment 251: The system of embodiment 234, wherein the at least one non-transitory computer storage medium is further configured to at least store vessel wall information including information indicative of the lumen and the vessel walls of the coronary artery vessels, and wherein the one or more computer hardware processors are further configured to graphically display lumen and vessel wall information corresponding to the coronary vessel displayed in the cross-sectional view in the third panel.

Embodiment 252: The system of embodiment 251, wherein and one or more computer hardware processors are further configured to display information of the lumen and the vessel wall on the user interface based on the selected portion of the coronary vessel in the at least one SMPR view.

Embodiment 253: The system of embodiment 251, wherein and one or more computer hardware processors are further configured to display information of plaque based on the selected portion of the coronary vessel in the at least one SMPR view.

Embodiment 254: The system of embodiment 251, wherein and one or more computer hardware processors are further configured to display information of stenosis based on the selected portion of the coronary vessel in the at least one SMPR view.

Embodiment 255: The system of embodiment 234, wherein the one or more computer hardware processors are further configured to execute the computer-executable instructions to generate and display on the user interface a cartoon artery tree, the cartoon artery tree being a non-patient specific graphical representation of an artery tree, wherein portions of the artery tree are displayed in a color that corresponds to a risk level.

Embodiment 256: The system of embodiment 255, wherein the risk level is based on stenosis.

Embodiment 257: The system of embodiment 255, wherein the risk level is based on a plaque.

Embodiment 258: The system of embodiment 255, wherein the risk level is based on ischemia.

Embodiment 259: The system of embodiment 255, wherein the one or more computer hardware processors are further configured to execute the computer-executable instructions to, in response to selecting a portion of the cartoon artery tree, displaying on the second panel a SMPR view of the vessel corresponding to the selected portion of the cartoon artery tree, and displaying on the third panel a cross-sectional view of corresponding to the selected portion of the cartoon artery tree.

Embodiment 269: A system comprising: means for storing computer-executable instructions, a set of computed tomography (CT) images of a patient's coronary vessels, vessel labels, and artery information associated with the set of CT images including information of stenosis, plaque, and locations of segments of the coronary vessels; and means for executing the computer-executable instructions to at least: generate and display a user interface a first panel including an artery tree comprising a three-dimensional (3D) representation of coronary vessels based on the CT images and depicting coronary vessels identified in the CT images, and depicting segment labels, the artery tree not including heart tissue between branches of the artery tree; in response to an input on the user interface indicating the selection of a coronary vessel in the artery tree in the first panel, generate and display on the user interface a second panel illustrating at least a portion of the selected coronary vessel in at least one straightened multiplanar vessel (SMPR) view; generate and display on the user interface a third panel showing a cross-sectional view of the selected coronary vessel, the cross-sectional view generated using one of the set of CT images of the selected coronary vessel, wherein locations along the at least one SMPR view are each associated with one of the CT images in the set of CT images such that a selection of a particular location along the coronary vessel in the at least one SMPR view displays the associated CT image in the cross-sectional view in the third panel; and in response to an input on the user interface indicating a first location along the selected coronary artery in the at least one SMPR view, display the associated CT scan associated with the in the cross-sectional view in the third panel.

Embodiment 261: A method for analyzing CT images and corresponding information, the method comprising: storing computer-executable instructions, a set of computed tomography (CT) images of a patient's coronary vessels, vessel labels, and artery information associated with the set of CT images including information of stenosis, plaque, and locations of segments of the coronary vessels; generating and displaying in a user interface a first panel including an artery tree comprising a three-dimensional (3D) representation of coronary vessels based on the CT images and depicting coronary vessels identified in the CT images, and depicting segment labels, the artery tree not including heart tissue between branches of the artery tree; receiving a first input indicating a selection of a coronary vessel in the artery tree in the first panel; in response to the first input, generating and displaying on the user interface a second panel illustrating at least a portion of the selected coronary vessel in at least one straightened multiplanar vessel (SMPR) view; generating and displaying on the user interface a third panel showing a cross-sectional view of the selected coronary vessel, the cross-sectional view generated using one of the set of CT images of the selected coronary vessel, wherein locations along the at least one SMPR view are each associated with one of the CT images in the set of CT images such that a selection of a particular location along the coronary vessel in the at least one SMPR view displays the associated CT image in the cross-sectional view in the third panel; receiving a second input on the user interface indicating a first location along the selected coronary artery in the at least one SMPR view; and in response to the second input, displaying the associated CT scan associated in the cross-sectional view in the third panel, wherein the method is performed by one or more computer hardware processors executing computer-executable instructions in communication stored on one or more non-transitory computer storage mediums.

Embodiment 262: The method of embodiment 261, further comprising, in response to an input on the second panel pf the user interface indicating a second location along the selected coronary artery in the at least one SMPR view, display the associated CT scan associated with the second location in a cross-sectional view in the third panel.

Embodiment 263: The method of any one of embodiments 261 and 262, further comprising: in response to a second input on the user interface indicating the selection of a second coronary vessel in the artery tree displayed in the first panel, generating and displaying in the second panel least a portion of the selected second coronary vessel in at least one straightened multiplanar vessel (SMPR) view, and generating and displaying on the third panel a cross-sectional view of the selected second coronary vessel, the cross-sectional view generated using one of the set of CT images of the selected second coronary vessel, wherein locations along the selected second coronary artery in the at least one SMPR view are each associated with one of the CT images in the set of CT images such that a selection of a particular location along the second coronary vessel in the at least one SMPR view displays the associated CT image in the cross-sectional view in the third panel.

Embodiment 264: The method of any one embodiments 261-263, further comprising generating and displaying on the user interface in a fourth panel a cartoon artery tree, the cartoon artery tree comprising a non-patient specific graphical representation of a coronary artery tree, and wherein in response to a selection of a vessel segment in the cartoon artery tree, a view of the selected vessel segment is displayed in a panel of the user interface in a SMPR view, and upon selection of a location of the vessel segment displayed in the SMPR view, generating and displaying in the user interface a panel that displays information about the selected vessel at the selected location.

Embodiment 265: The method of embodiment 264, wherein the displayed information includes information relating to stenosis and plaque of the selected vessel.

Embodiment 266: The method of any one of embodiments 261-265, further comprising generating and displaying segment name labels, proximal to a respective segment on the artery tree, indicative of the name of the segment, using the stored artery information.

Embodiment 267: The method of any one of embodiments 261-266, further comprising, in response to an input selection of a first segment name label displayed on the user interface, generating and displaying on the user interface a panel having a list of vessel segment names and indicating the current name of the selected vessel segment, and in response to an input selection of a second segment name label on the list, replacing the first segment name label with the second segment name label of the displayed artery tree in the user interface.

Embodiment 268: The method of any one of embodiments 261-267, further comprising generating and displaying a tool bar on a fourth panel of the user interface, the tool bar comprising tools to add, delete, or revise artery information displayed on the user interface.

Embodiment 269: The method of embodiment 268, wherein the tools on the toolbar include a lumen wall tool, a snap to vessel wall tool, a snap to lumen wall tool, vessel wall tool, a segment tool, a stenosis tool, a plaque overlay tool a snap to centerline tool, chronic total occlusion tool, stent tool, an exclude tool, a tracker tool, or a distance measurement tool.

Embodiment 270: The method of embodiment 268, wherein the tools on the toolbar include a lumen wall tool, a snap to vessel wall tool, a snap to lumen wall tool, vessel wall tool, a segment tool, a stenosis tool, a plaque overlay tool a snap to centerline tool, chronic total occlusion tool, stent tool, an exclude tool, a tracker tool, and a distance measurement tool.

Embodiment 271: A normalization device configured to facilitate normalization of medical images of a coronary region of a subject for an algorithm-based medical imaging analysis, the normalization device comprising: a substrate having a width, a length, and a depth dimension, the substrate having a proximal surface and a distal surface, the proximal surface adapted to be placed adjacent to a surface of a body portion of a patient; a plurality of compartments positioned within the substrate, each of the plurality of compartments configured to hold a sample of a known material, wherein: a first subset of the plurality of compartments hold samples of a contrast material with different concentrations, a second subset of the plurality of compartments hold samples of materials representative of materials to be analyzed by the algorithm-based medical imaging analysis, and a third subset of the plurality of compartments hold samples of phantom materials.

Embodiment 272: The normalization device of Embodiment 271, wherein the contrast material comprises one of iodine, Gad, Tantalum, Tungsten, Gold, Bismuth, or Ytterbium.

Embodiment 273: The normalization device of any of Embodiments 271-272, wherein the samples of materials representative of materials to be analyzed by the algorithm-based medical imaging analysis comprise at least two of calcium 1000 HU, calcium 220 HU, calcium 150 HU, calcium 130 HU, and a low attenuation (e.g., 30 HU) material.

Embodiment 274: The normalization device of any of Embodiments 271-273, wherein the samples of phantom materials comprise one more of water, fat, calcium, uric acid, air, iron, or blood.

Embodiment 275: The normalization device of any of Embodiments 271-274, further comprising one or more fiducials positioned on or in the substrate for determining the alignment of the normalization device in an image of the normalization device such that the position in the image of each of the one or more compartments in the first arrangement can be determined using the one or more fiducials.

Embodiment 276: The normalization device of any of Embodiments 271-275, wherein the substrate comprises a first layer, and at least some of the plurality of compartments are positioned in the first layer in a first arrangement.

Embodiment 277: The normalization device of Embodiment 276, wherein the substrate further comprises a second layer positioned above the first layer, and at least some of the plurality of compartments are positioned in the second layer including in a second arrangement.

Embodiment 278: The normalization device of Embodiment 277, further comprising one or more additional layers positioned above the second layer, and at least some of the plurality of compartments are positioned within the one or more additional layers.

Embodiment 279: The normalization device of any one of Embodiments 271-278, wherein at least one of the compartments is configured to be self-sealing such that the material can be injected into the self-sealing compartment and the compartment seals to contain the injected material.

Embodiment 280: The normalization device of any of Embodiments 271-279, further comprising an adhesive on the proximal surface of the substrate and configured to adhere the normalization device to the body portion patient.

Embodiment 281: The normalization device of any of Embodiments 271-280, further comprising a heat transfer material designed to transfer heat from the body portion of the patient to the material in the one or more compartments.

Embodiment 282: The normalization device of any of Embodiments 271-280, further comprising an adhesive strip having a proximal side and a distal side, the proximal side configured to adhere to the body portion, the adhesive strip including a fastener configured to removably attach to the proximal surface of the substrate.

Embodiment 283: The normalization device of Embodiment 282, wherein the fastener comprises a first part of a hook-and-loop fastener, and the first layer comprises a corresponding second part of the hook-and-loop fastener.

Embodiment 284: The normalization device of any of Embodiments 271-283, wherein substrate a flexible material to allow the substrate to conform to the shape of the body portion.

Embodiment 285: The normalization device of any of Embodiments 271-284, wherein the first arrangement includes a circular-shaped arrangements of the compartments.

Embodiment 286: The normalization device of any of Embodiments 271-284, wherein the first arrangement includes a rectangular-shaped arrangements of the compartments.

Embodiment 287: The normalization device of any of Embodiments 271-286, wherein the material in at least two compartments is the same.

Embodiment 288: The normalization device of any of Embodiments 271-287, wherein at least one of a length, a width or a depth dimension of a compartment is less than 0.5 mm.

Embodiment 289: The normalization device of any of Embodiments 271-287, wherein a width dimension the compartments is between 0.1 mm and 1 mm.

Embodiment 290: The normalization device of Embodiment 289, wherein a length dimension the compartments is between 0.1 mm and 1 mm.

Embodiment 291: The normalization device of Embodiment 290, wherein a depth dimension the compartments is between 0.1 mm and 1 mm.

Embodiment 292: The normalization device of any of Embodiments 271-287, wherein at least one of the length, width or depth dimension of a compartment is greater than 1.0 mm.

Embodiment 293: The normalization device of any of Embodiments 271-287, wherein dimensions of some or all of the compartments in the normalization device are different from each other allowing a single normalization device to have a plurality of compartments having different dimensions such that the normalization device can be used in various medical image scanning devices having different resolution capabilities.

Embodiment 294: The normalization device of any of Embodiments 271-287, wherein the normalization device includes a plurality of compartments with differing dimensions such that the normalization device can be used to determine the actual resolution capability of the scanning device.

Embodiment 295: A normalization device, comprising: a first layer having a width, length, and depth dimension, the first layer having a proximal surface and a distal surface, the proximal surface adapted to be placed adjacent to a surface of a body portion of a patient, the first layer including one or more compartments positioned in the first layer in a first arrangement, each of the one or more compartments containing a known material; and one or more fiducials for determining the alignment of the normalization device in an image of the normalization device such that the position in the image of each of the one or more compartments in the first arrangement be the determined using the one or more fiducials.

Embodiment 296: The normalization device of Embodiment 295, further comprising a second layer having a width, length, and depth dimension, the second layer having a proximal surface and a distal surface, the proximal surface adjacent to the distal surface of the first layer, the second layer including one or more compartments positioned in the second layer in a second arrangement, each of the one or more compartments of the second layer containing a known material.

Embodiment 297: The normalization device of Embodiment 296, further comprising one or more additional layers each having a width, length, and depth dimension, the one or more additional layers having a proximal surface and a distal surface, the proximal surface facing the second layer and each of the one or more layers positioned such that the second layer is between the first layer and the one or more additional layers, each of the one or more additional layers respectively including one or more compartments positioned in each respective one or more additional layers layer in a second arrangement, each of the one or more compartments of the one or more additional layers containing a known material.

Embodiment 298: The normalization device of any one of Embodiments 295-297, wherein at least one of the compartments is configured to be self-sealing such that the material can be injected into the self-sealing compartment and the compartment seals to contain the injected material.

Embodiment 299: The normalization device of Embodiment 295, further comprising an adhesive on the proximal surface of the first layer.

Embodiment 300: The normalization device of Embodiment 295, further comprising a heat transfer material designed to transfer heat from the body portion of the patient to the material in the one or more compartments.

Embodiment 301: The normalization device of Embodiment 295, further comprising an adhesive strip having a proximal side and a distal side, the proximal side configured to adhere to the body portion, the adhesive strip including a fastener configured to removably attach to the proximal surface of the first layer.

Embodiment 302: The normalization device of Embodiment 301, wherein the fastener comprises a first part of a hook-and-loop fastener, and the first layer comprises a corresponding second part of the hook-and-loop fastener.

Embodiment 303: The normalization device of Embodiment 295, wherein the normalization device comprises a flexible material to allow the normalization device to conform to the shape of the body portion.

Embodiment 304: The normalization device of Embodiment 295, wherein the first arrangement includes a circular-shaped arrangements of the compartments.

Embodiment 305: The normalization device of Embodiment 295, wherein the first arrangement includes a rectangular-shaped arrangements of the compartments.

Embodiment 306: The normalization device of Embodiment 295, wherein the material in at least two compartments of the first layer is the same.

Embodiment 307: The normalization device of any of Embodiments 296 or 297, wherein the material in at least two compartments of any of the layers is the same.

Embodiment 308: The normalization device of Embodiment 295, wherein at least one of the one or more compartments include a contrast material.

Embodiment 309: The normalization device of Embodiment 308, wherein the contrast material comprises one of iodine, Gad, Tantalum, Tungsten, Gold, Bismuth, or Ytterbium.

Embodiment 310: The normalization device of Embodiment 295, wherein at least one of the one or more compartments include a material representative of a studied variable.

Embodiment 311: The normalization device of Embodiment 309, wherein the studied variable is representative of calcium 1000 HU, calcium 220 HU, calcium 150 HU, calcium 130 HU, or a low attenuation (e.g., 30 HU) material.

Embodiment 312: The normalization device of Embodiment 295, wherein at least one of the one or more compartments include a phantom.

Embodiment 313: The normalization device of Embodiment 312, wherein the phantom comprises one of water, fat, calcium, uric acid, air, iron, or blood.

Embodiment 314: The normalization device of Embodiment 295, wherein the first arrangement includes at least one compartment that contains a contrast agent, at least one compartment that includes a studied variable and at least one compartment that includes a phantom.

Embodiment 315: The normalization device of Embodiment 295, wherein the first arrangement includes at least one compartment that contains a contrast agent and at least one compartment that includes a studied variable.

Embodiment 316: The normalization device of Embodiment 295, wherein the first arrangement includes at least one compartment that contains a contrast agent and at least one compartment that includes a phantom.

Embodiment 317: The normalization device of Embodiment 295, wherein the first arrangement includes at least one compartment that contains a studied variable and at least one compartment that includes a phantom.

Embodiment 318: The normalization device of Embodiment 271, wherein the first arrangement of the first layer includes at least one compartment that contains a contrast agent, at least one compartment that includes a studied variable and at least one compartment that includes a phantom, and the second arrangement of the second layer includes at least one compartment that contains a contrast agent, at least one compartment that includes a studied variable and at least one compartment that includes a phantom.

Embodiment 319: The normalization device of Embodiment 295, wherein at least one of the length, width or depth dimension of a compartment is less than 0.5 mm.

Embodiment 320: The normalization device of Embodiment 295, wherein the width dimension the compartments is between 0.1 mm and 1 mm.

Embodiment 321: The normalization device of Embodiment 295, wherein the length dimension the compartments is between 0.1 mm and 1 mm.

Embodiment 322: The normalization device of Embodiment 295, wherein the depth (or height) dimension the compartments is between 0.1 mm and 1 mm.

Embodiment 323: The normalization device of Embodiment 295, wherein at least one of the length, width or depth dimension of a compartment is greater than 1.0 mm.

Embodiment 324: The normalization device of any one of Embodiments 295-297, wherein the dimensions of some or all of the compartments in the normalization device are different from each other allowing a single normalization device to have a plurality of compartments having different dimension such that the normalization device can be used in various medical image scanning devices having different resolution capabilities.

Embodiment 325: The normalization device of any one of Embodiments 295-297, wherein the normalization device includes a plurality of compartments with differing dimensions such that the normalization device can be used to determine the actual resolution capability of the scanning device.

Embodiment 326: A computer-implemented method for normalizing medical images for an algorithm-based medical imaging analysis, wherein normalization of the medical images improves accuracy of the algorithm-based medical imaging analysis, the method comprising: accessing, by a computer system, a first medical image of a region of a subject and the normalization device, wherein the first medical image is obtained non-invasively, and wherein the normalization device comprises a substrate comprising a plurality of compartments, each of the plurality of compartments holding a sample of a known material; accessing, by the computer system, a second medical image of a region of a subject and the normalization device, wherein the second medical image is obtained non-invasively, and wherein the first medical image and the second medical image comprise at least one of the following: one or more first variable acquisition parameters associated with capture of the first medical image differ from a corresponding one or more second variable acquisition parameters associated with capture of the second medical image, a first image capture technology used to capture the first medical image differs from a second image capture technology used to capture the second medical image, and a first contrast agent used during the capture of the first medical image differs from a second contrast agent used during the capture of the second medical image; identifying, by the computer system, image parameters of the normalization device within the first medical image; generating a normalized first medical image for the algorithm-based medical imaging analysis based in part on the first identified image parameters of the normalization device within the first medical image; identifying, by the computer system, image parameters of the normalization device within the second medical image; and generating a normalized second medical image for the algorithm-based medical imaging analysis based in part on the second identified image parameters of the normalization device within the second medical image, wherein the computer system comprises a computer processor and an electronic storage medium.

Embodiment 327: The computer-implemented method of Embodiment 326, wherein the algorithm-based medical imaging analysis comprises an artificial intelligence or machine learning imaging analysis algorithm, and wherein the artificial intelligence or machine learning imaging analysis algorithm was trained using images that included the normalization device.

Embodiment 328: The computer-implemented method of any of Embodiments 326-327, wherein the first medical image and the second medical image each comprise a CT image and the one or more first variable acquisition parameters and the one or more second variable acquisition parameters comprise one or more of a kilovoltage (kV), kilovoltage peak (kVp), a milliamperage (mA), or a method of gating.

Embodiment 329: The computer-implemented method of Embodiment 328, wherein the method of gating comprises one of prospective axial triggering, retrospective ECG helical gating, and fast pitch helical.

Embodiment 330: The computer-implemented method of any of Embodiments 326-329, wherein the first image capture technology and the second image capture technology each comprise one of a dual source scanner, a single source scanner, Dual source vs. single source scanners dual energy, monochromatic energy, spectral CT, photon counting, and different detector materials.

Embodiment 331: The computer-implemented method of any of Embodiments 326-330, wherein the first contrast agent and the second contrast agent each comprise one of an iodine contrast of varying concentration or a non-iodine contrast agent.

Embodiment 332: The computer-implemented method of any of Embodiments 326-327, wherein the first image capture technology and the second image capture technology each comprise one of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 333: The computer-implemented method of any of Embodiments 326-332, wherein a first medical imager that captures the first medical imager is different than a second medical image that capture the second medical image.

Embodiment 334: The computer-implemented method of any of Embodiments 326-333, wherein the subject of the first medical image is different than the subject of the first medical image.

Embodiment 335: The computer-implemented method of any of Embodiments 326-333, wherein the subject of the first medical image is the same as the subject of the second medical image.

Embodiment 336: The computer-implemented method of any of Embodiments 326-333, wherein the subject of the first medical image is different than the subject of the second medical image.

Embodiment 337: The computer-implemented method of any of Embodiments 326-336, wherein the capture of the first medical image is separated from the capture of the second medical image by at least one day.

Embodiment 338: The computer-implemented method of any of Embodiments 326-337, wherein the capture of the first medical image is separated from the capture of the second medical image by at least one day.

Embodiment 339: The computer-implemented method of any of Embodiments 326-338, wherein a location of the capture of the first medical image is geographically separated from a location of the capture of the second medical image.

Embodiment 340: The computer-implemented method of any of Embodiments 326-339, wherein the normalization device comprises the normalization device of any of Embodiments 271-325.

Embodiment 340: The computer-implemented method of any of Embodiments 326-339, wherein the normalization device comprises the normalization device of any of Embodiments 271-325.

Embodiment 341: The computer-implemented method of any of Embodiments 326-340, wherein the region of the subject comprises a coronary region of the subject.

Embodiment 342: The computer-implemented method of any of Embodiments 326-341, wherein the region of the subject comprises one or more coronary arteries of the subject.

Embodiment 343: The computer-implemented method of any of Embodiments 326-340, wherein the region of the subject comprises one or more of carotid arteries, renal arteries, abdominal aorta, cerebral arteries, lower extremities, or upper extremities of the subject.

Additional Detail—Normalization Device

As described above and throughout this application, in some embodiments, a normalization device may be used to normalize and/or calibrate a medical image of a patient before that image is analyzed by an algorithm-based medical imaging analysis. This section provides additional detail regarding embodiments of the normalization device and embodiments of the use thereof.

In general, the normalization device can be configured to provide at least two functions: (1) the normalization device can be used to normalize and calibrate a medical image to a known relative spectrum; and (2) the normalization device can be used to calibrate a medical image such that pixels within the medical image representative of various materials can be normalized and calibrated to materials of known absolute density—this can facilitate and allow identification of materials within the medical image. In some embodiments, each of these two functions play a role in providing accurate algorithm-based medical imaging analysis as will be described below.

For example, it can be important to normalize and calibrate a medical image to a known relative spectrum. As a specific example, a CT scan generally produces a medical image comprising pixels represented in gray scale. However, when two CT scans are taken under different conditions, the gray scale spectrum in the first image may not (and likely will not) match the gray scale spectrum of the second image. That is, even if the first and second CT images represent the same subject, the specific grayscale values in the two images, even for the same structure may not (and likely will not) match. A pixel or group of pixels within the first image that represents a calcified plaque buildup within a blood vessel, may (and likely will) appear different (a different shade of gray, for example, darker or lighter) than a pixel or group of pixels within the second image, even if the pixel or groups of pixels within the first and second images is representative of the same calcified plaque buildup.

Moreover, the differences between the first and second images may not be linear. That is, the second image may not be uniformly lighter or darker than the first image, such that it is not possible to use a simple linear transform to cause the two images to correspond. Rather, it is possible that, for example, some regions in the first image may appear lighter than corresponding regions in the second image, while at the same time, other regions in the first image may appear darker than corresponding regions in the second image. In order to normalize the two medical images such that each appears on the same grayscale spectrum, a non-linear transform may be necessary. Use of the normalization device can facilitate and enable such a non-linear transform such that different medical images, that otherwise would not appear to have the same grayscale spectrum, are adjusted so that the same grayscale spectrum is used in each image.

A wide variety of factors can contribute to different medical images, even of the same subject, falling on different grayscale spectrums. This can include, for example, different medical imaging machine parameters, different parameters associated with the patient, differences in contrast agents used, and/or different medical image acquisition parameters.

It can be important to normalize and calibrate a medical image to a known relative spectrum to facilitate the algorithm-based analysis of the medical image. As described herein, some algorithm-based medical image analysis can be performed using artificial intelligence and/or machine learning systems. Such artificial intelligence and/or machine learning systems can be trained using a large number of medical images. The training and performance of such artificial intelligence and/or machine learning systems can be improved when the medical images are all normalized and calibrated to the same or similar relative scale.

Additionally, the normalization device can be used to normalize or calibrate a medical image such that pixels within the medical image representative of various materials can be normalized and calibrated to materials of known absolute density. For example, when analyzing an image of a coronary region of to characterize, for example, calcified plaque buildup, it can be important to accurately determine which pixels or groups of pixels within the medical image correspond to regions of calcified plaque buildup. Similarly, it can be important to be able to accurately identify contrast agents, blood, vessel walls, fat, and other samples within the image. The use of normalization device can facilitate and enable identification of specific materials within the medical image.

The normalization devices described throughout this application can be configured to achieve these two functions. In particular, a normalization device can include a substrate or body configured with compartments that hold different samples. The arrangement (e.g., the spatial arrangement) of the samples is known, as well as other characteristics associated with each of the samples, such as the material of sample, the volume of the sample, the absolute density of the sample, and the relative density of the sample relative to that of the other samples in the normalization device. During use, in some embodiments, the normalization device can be included in the medical imager with the patient, such that an image of the normalization device—including the known samples positioned therein—appears in the image. An image-processing algorithm can be configured to recognize the normalization device within the image and use the known samples of the normalization device to perform the two functions described above.

For example, the image-processing algorithm can detect the known samples within the medical image and use the known samples to adjust the medical image such that it uses a common or desired relative spectrum. For example, if the normalization device includes a sample of calcium of a given density, then that sample of calcium will appear with a certain grayscale value within the image. Due to the various different conditions under which the medical image was taken, however, the particular grayscale value within the image will likely not correspond to the desired relative spectrum. The image-processing algorithm can then adjust the grayscale value in the image such that it falls at the appropriate location on the desired relative spectrum. At the same time, the image-processing algorithm can adjust other pixels within the image that do not correspond to the normalization device but that share the same grayscale value within the medical image, such that those pixels fall at the appropriate location on the desired relative spectrum. This can be done for all pixels in the image. As noted previously, this transformation may not be linear. Once complete, however, the pixels of the medical image will be adjusted such that they all fall on the desired relative grayscale spectrum. In this way, two images of the same subject captured under different conditions, and thus initially appearing differently, can be adjusted so that they appear the same (e.g., appearing on the same relative grayscale spectrum).

Additionally, the normalization device can be used to identify particular materials within the medical image. For example, because the samples of the normalization device are known (e.g., known material, volume, position, absolute density, and/or relative density), pixels representative of the patient's anatomy can be compared against the materials of the normalization device (or a scale established by the materials of the normalization device) such that the materials of the patient's anatomy corresponding to the pixels can be identified. As a simple example, the normalization device can include a sample of calcium of a given density. Pixels that appear the same as the pixels that correspond to the sample of calcium can be identified as representing calcium having the same density as the sample.

In some embodiments, the normalization device is designed such that the samples contained therein correspond to the disease or condition for which the resulting image will be analyzed, the materials within the region of interest of the patient's anatomy, and/or the type of medical imager that will be used. By using a normalization device within the image, the image-processing algorithms described throughout this application can be easily expanded for use with other imaging modalities, including new imaging modalities now under development or yet to be developed. This is because, when these new imaging modalities come online, suitable normalization devices can be designed for use therewith.

Further, although this application primarily describes use of the normalization device for diagnosis and treatment of coronary conditions, other normalization devices can be configured for use in other types of medical procedures or diagnosis. This can be done by selecting samples that are most relevant to the procedure to be performed or disease to be analyzed.

The normalization devices described in this application are distinguishable from conventional phantom devices that are commonly used in medical imaging applications. Conventional phantom devices are typically used to calibrate a medical imager to ensure that it is working properly. For example, conventional phantom devices are often imaged by themselves to ensure that the medical image produces an accurate representation of the phantom device. Conventional phantom devices are imaged periodically to verify and calibrate the machine itself. These phantom devices, are not, however, imaged with the patient and/or used to calibrate or normalize an image of the patient.

In contrast, the normalization device is often imaged directly with the patient, especially where the size of the normalization device and the imaging modality permit the normalization device and the patient to be imaged concurrently. If concurrent image is not possible, or in other embodiments, the normalization device can be imaged separately from the patient. However, in these cases, it is important that the image of the patient and the image of the normalization device be imaged under the same conditions. Rather than verifying that the imaging device is functioning properly, the normalization device is used during an image-processing algorithm to calibrate and normalize the image, providing the two functions discussed above.

To further illustrate the difference between conventional phantom devices and the normalization device, it will be noted that use of the normalization device does not replace the use of a conventional phantom. Rather, both may be used during an imaging procedure. For example, first, a conventional phantom can be imaged alone. The resulting image of the phantom can be reviewed and analyzed to determine whether the imaging device is correctly calibrated. If it is, the normalization device and the patient can be imaged together. The resulting image can be analyzed to detect the normalization device within the image, adjust the pixels of the image based on the representation of the normalization device within the image, and then, identify specific materials within the image using the normalization device as described above.

Figure 15:
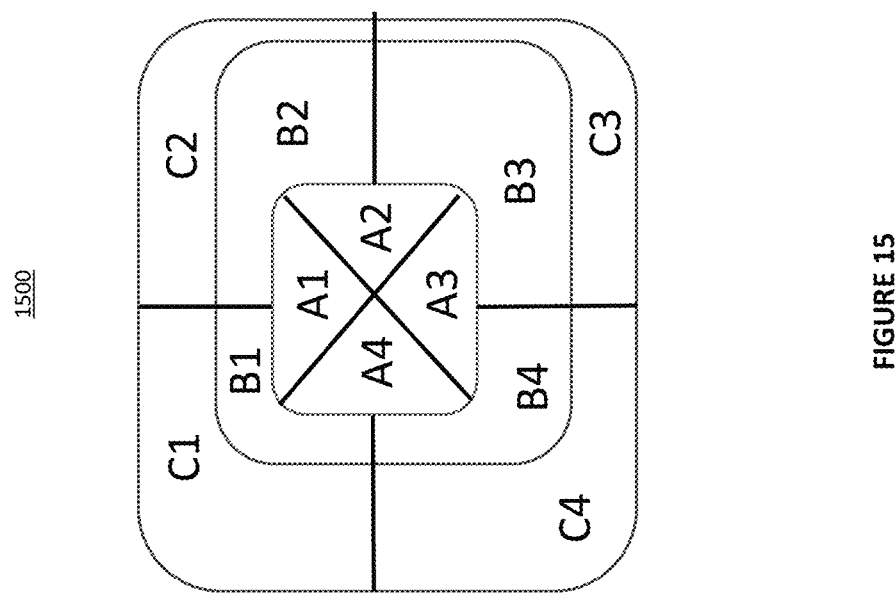
FIG. 15 illustrates an embodiment of a normalization device.

Several embodiments of normalization devices have been described above with reference to FIGS. 12A-12I. FIG. 15 present another embodiment of a normalization device 1500. In the illustrated embodiment, the normalization device 1500 is configured for use with medical images of a coronary region of a patient for analysis and diagnosis of coronary conditions; however, the normalization device 1500 may also be used or may be modified for use with other types of medical images and for other types of medical conditions. As will be described below, in the illustrated embodiment, the normalization device 1500 is configured so as to mimic a blood vessel of a patient, and thus may be particularly suitable for use with analysis and diagnosis of conditions involving a patient's blood vessels.

As shown in FIG. 15, the normalization device 1500 comprises a substrate having a plurality of compartments holding samples formed therein. In the illustrated embodiment, the samples are labeled A1-A4, B1-B4, and C1-C4. As shown in FIG. 15, the samples A1-A4 are positioned towards the center of the normalization device 1500, while the samples B1-B4 and C1-C4 are generally arranged around the samples A1-A4. For each of the samples, the material, volume, absolute density, relative density, and spatial configuration is known.

The samples themselves can be selected such that normalization device 1500 generally corresponds to a cross-sectional blood sample. For example, in one embodiment, the samples A1-A4 comprise samples of contrast agents having different densities or concentrations. Examples of different contrast agents have been provided previously and those contrast agents (or others) can be used here. In general, during a procedure, contrast agents flow through a blood vessel. Accordingly, this can be mimicked by placing the contrast agents as samples A1-A4, which are at the center of the normalization device. In some embodiments, one or more of the samples A1-A4 can be replaced with other samples that may flow through a blood vessel, such as blood.

The samples B1-B4 can be selected to comprise samples that would generally be found on or around an inner blood vessel wall. For example, in some embodiments, one or more of the samples B1-B4 comprise samples of calcium of different densities, and/or one or more of the samples of B1-B4 comprise samples of fat of different densities. Similarly, the samples C1-C4 can be selected to comprise samples that would generally be found on or around an outer blood vessel wall. For example, in some embodiments, one or more of the samples C1-C4 comprise samples of calcium of different densities, and/or one or more of the samples of C1-C4 comprise samples of fat of different densities. In one example, the samples B1, B3, and C4 comprise fat samples of different densities, and the samples B2, B4, C1, C2, and C3, comprise calcium samples of different densities. Other arrangements are also possible, and, in some embodiments, one or more of the compartments may hold other samples, such as, for example, air, tissue, radioactive contrast agents, gold, iron, other metals, distilled water, water, or others.

The embodiment of the normalization device 1500 of FIG. 15, further illustrates several additional features that may be present in some normalization devices. One such feature is represented by the different sized compartments or volumes for the samples. For example, in the illustrated embodiment the sample B1 has a smaller volume than the sample B2. Similarly, the sample C4 has a volume that is larger than the sample C3. This illustrates that, in some embodiments, the volumes of the samples need to be all of the same size. In other embodiments, the volumes of the samples may be the same size.

The embodiment of FIG. 15 also illustrates that various samples can be placed adjacent to (e.g., immediately adjacent to or juxtaposed with) other samples. This can be important because, in some cases of medical imaging, the radiodensity of one pixel may affect the radiodensity of an adjacent pixel. Accordingly, in some embodiments, it can be advantageous to configure the normalization device such that material samples that are likely to be found in proximity to each other are similarly located in proximity to or adjacent to each other on the normalization device. The blood vessel-like arrangement of the normalization device 1500 may advantageously provide such a configuration.

In the illustrated embodiment, each sample A1-A4 is positioned so as to be adjacent to two other samples A1-A4 and to two samples B1-B4. Samples C1-C4 are each positioned so at to be adjacent to two other samples C1-C4 and to a sample B1-B4. Although a particular configuration is illustrated, various other configurations for placing samples adjacent to one another can be provided. Although the normalization device 1500 is illustrated within a plane, the normalization device 1500 will also include a depth dimension such that each of the samples A1-A4, B1-B4, and C1-C4 comprises a three-dimensional volume.

As noted previously, the normalization device can be calibrated specifically for different types of medical imagers, as well as for different types of diseases. The described embodiment of the normalization device 1500 may be suitable for use with CT scans and for the analysis of coronary conditions.

When configuring the normalization device for use with other types of medical imagers, the specific characteristics of the medical imager must be accounted for. For example, in an Mill machine, it can be important to calibrate for the different depths or distances to the coils. Accordingly, a normalization device configured for use with MM may have a sufficient depth or thickness that generally corresponds to the thickness of the body (e.g., from front to back) that will be imaged. In these cases, the normalization device can be placed adjacent to the patient such that a top of the normalization device is positioned at the same height as the patient's chest, while the bottom of the normalization device is positioned at the same height as the patient's back. In this way, the distances between the patient's anatomy and the coils can be mirrored by the distances between the normalization device and the coils.

In some embodiments, the sample material can be inserted within tubes positioned within the normalization device.

As noted previously, in some embodiments, the normalization device may be configured to account for various time-based changes. That is, in addition to providing a three-dimensional (positional) calibration tool, the normalization device may provide four-dimensional (positional plus time) calibration tool. This can help to account for changes that occur in time, for example, as caused by patient movement due to respiration, heartbeat, blood flow, etc. To account for heartbeat, for example, the normalization device may include a mechanical structure that causes it to beat at the same frequency as the patient's heart. As another example of a time-based change, the normalization device can be configured to simulate spreading of a contrast agent through the patient's body. For example, as the contrast agent is injected into the body, a similar sample of contrast agent can be injected into or ruptured within the normalization device, allowing for a time-based mirroring of the spread.

Accounting for time-based changes can be particularly important where patient images are captured over sufficiently large time steps that, for example, cause the image to appear blurry. In some embodiments, artificial intelligence or other image-processing algorithms can be used to reconstruct clear images from such blurry images. In these cases, the algorithms can use the normalization device as a check to verify that the transformation of the image is successful. For example, if the normalization device (which has a known configuration) appears correctly within the transformed image, then an assumption can be made that the rest of the image has been transformed correctly as well.

Medical Reports Overview

Traditional reporting of medical information is designated for physician or other provider consumption and use. Diagnostic imaging studies, laboratory blood tests, pathology reports, EKG readings, etc. are all interpreted and presented in a manner which is often difficult to understand or even unintelligible by most patients. The text, data and images from a typically report usually assumes that the reader has significant medical experience and education, or at least familiarity with medical jargon that, while understandable by medical professionals, are often opaque to the non-medical layperson patient. To be concise, the medical reports do not include any sort of background educational content and it assumes that the reader has formal medical education and understands the meaning of all of the findings in the report as well as the clinical implications of those findings for the patient. Further, often findings are seen in concert with each other for specific disease states (e.g., reduced ejection fraction is often associated with elevated left ventricular volumes), and these relationships are not typically reported as being as part of a constellation of symptoms associated with a disease state or syndrome, so the non-medical layperson patient cannot understand the relationship of findings to his/her disease state.

It is then the responsibility and role of the medical provider to "translate" the reports into simple language which is typically verbally communicated with the patient at the time of their encounter with the provider be it in person or more recently during telehealth visits. The provider explains what the test does, how it works, what its limitations may be, what the patient's results were and finally what those results might mean for the patient's future. Unfortunately, patients frequently are unable to fully interpret and retain all the information that the provider might discuss with them in a short 10-15 typical patient encounter. The patients are then left confused and only partly educated on the results of their medical reports. Often the provider will give the patient a copy of the report both for their records as well as to be able to review on their own after the patient encounter.

Even with the patient report in hand and after hearing the physician's explanation, the patient often remains incompletely informed regarding the results and their meaning. This can be a major source of frustration for both the provider as well as the patient. The patient does not understand fully the results of the study and their implications. Frequently patients will either reach out to friends and family to help understand the results of their examination or they will perform searches on the Internet for additional background education and meaning. Frequently however this is not successful as the patient may not understand even what they are supposed to be searching for or asking about the disease process and many online health information sites maybe inaccurate or misleading. All of this can impact current medical status of the patient, his relation with the health provider, but also future health implications including but not only therapeutic and future diagnostic test adherence.

In response to this, providers sometimes refer patients to websites or provide them with written materials that may help explain their test findings and how this may relate to disease. But these are "generic" material that are not patient-specific, do not incorporate patient specific findings, and do not relate to a patient's specific conditions or symptoms. To date, however, no methods have been devised or described that combines patient facing educational content as well as the patient's specific individual report findings in a way that can be easily accessed, reviewed, and is available at the patient's leisure for repeated consumption as they may require. Thus, it is advantageous for systems and methods that enable communication of these findings beyond a simple paper report by leveraging patient-specific information for generation of reports in the forms of more advanced and contemporary technology, such as movies, mixed reality or holographic environments.

Various aspects of systems and methods of generating a medical report dataset and a corresponding medical report for a specific patient are disclosed herein. In one example, a process includes receiving selection of a report generation request, for a patient, for display on a display of a computing system having one or more computer processors and one or more displays, receiving patient information from a patient information source storing said patient information, the patient information associated with the report generation request, determining patient characteristics associated with the report generation request based on the patient information, accessing a data structure storing associations between patient characteristics and respective patient medical information, medical images, and test results of one or more test performed on the patient, and storing associations between patient characteristics and multimedia report data that is not related to a specific patient, selecting from the data structure a report package associated with the patient medical information and the report generation request, wherein the selected report package comprises a patient greeting in the language of the patient and presented by an avatar selected based on the patient data, a multimedia presentation conveying an explanation of the test performed, of the results of the test, an explanation of the results of the test, and a conclusion segment presented by the avatar, wherein at least a portion of the multimedia presentation includes report multimedia data from the report data source, test results from the results information source, medical information from the medical information source, and medical images related to the test from the medical image source, automatically generating the selected report package, and displaying the selected report package on the one or more displays, wherein the selected reports are configured to receive input from a user of the computing system that is usable in interacting with the selected parent report.

Systems for generating medical report can utilize existing patient medical information, new images and test data, and/or contemporaneous information of the patient received from, for example, the medical wearable device monitoring one or more physiological conditions or characteristics of the patient. Such systems can be configured to automatically generate a desired report. In some embodiments, the systems may use medical practitioner and/or patient interactive inputs to the determine certain aspects to include in the medical report. In one example, a system for automatically generating a medical report can include a patient information source providing stored patient information patient information format, a medical information source providing medical information in a medical information format, and a medical image source providing medical images in a medical image format. The medical images can be any images depicting a portion of a patient's anatomy, for example, an arterial bed. one or more arterial beds. In an example, an arterial bed includes arteries of one of the aorta, carotid arteries, lower extremity arteries, renal arteries, or cerebral arteries. The medical images can be any images depicting one or more arterial beds. In an example, a first arterial bed includes arteries of one of the aorta, carotid arteries, lower extremity arteries, renal arteries, or cerebral arteries, and a second arterial bed includes arteries of one of the aorta, carotid arteries, lower extremity arteries, renal arteries, or cerebral arteries that are different than the arteries of the first arterial bed. In some embodiments, a normalization device (e.g., as described herein) is used when generating the medical images, and the information from the normalization device is used when processing the medical images. The medical images can be processes using any of the methods, processes, and/or systems described herein, or other methods, processes, and/or systems. Any of the methods described herein can be based on imaging using the normalization device to improve quality of the automatic image assessment of the generated images. The system for automatically generating a medical report can also include a test results information source providing test results of one or more test performed on the patient in a results information format, a report data source, the report data source providing multimedia data for including in a medical report, the multimedia data indexed by at least some of the stored patient information relating to non-medical characteristics of the patient, a report generation interface unit to receive said patient information, the patient information including non-medical characteristics of a patient including characteristics indicative of the patients age, gender, language, race, education level, and/or culture, and the like, wherein said report generation interface unit can be adapted to automatically create medical report data links associated with said patient characteristics and associated with report multimedia data on the report data source that is indexed by said respective patient characteristics based on a received report generation request associated with the patient and a test, and wherein the report generation interface unit is further adapted to automatically create links to patient information, medical information, medical images, and test results associated with the patient and the test based on the report generation request. The system further includes a medical report dataset generator adapted to automatically access and retrieve the report multimedia data, patient information, medical information, medical images, the test results using the medical report data links, and automatically generate a medical report associated with the test and the patient based on the report multimedia data, patient information, medical information, medical images, the test results, the medical report conveying a patient greeting in the language of the patient and presented by an avatar selected based on the patient data, a multimedia presentation conveying an explanation of the test performed, of the results of the test, an explanation of the results of the test, and a conclusion segment presented by the avatar, wherein at least a portion of the multimedia presentation includes report multimedia data from the report data source, test results from the results information source, medical information from the medical information source, and medical images related to the test from the medical image source.

As described herein, one innovation relates to generating interactive medical data reports. More particularly, the present application describes methods and systems for generating interactive coronary artery medical reports that are optimized for interactive presentation and clearer understanding by the patient. One innovation includes a method of generating a medical report of a medical test associated with one or more patient tests. The method can include receiving an input of a request of a medical report to generate for a particular patient, the request indicating a selection of a format of the medical report, and receiving patient information from a patient information source storing said patient information, where the patient information is associated with the report generation request. The method can include determining patient characteristics associated with the patient based on the patient information, and accessing one or more data structures storing associations of types of medical reports, patient characteristics and respective patient medical information, medical images, and test results of one or more test performed on the patient. The data structures are structured to store associations between patient characteristics and multimedia report data that is not related to a specific patient. Such methods can include accessing report content associated with the patient's medical information and the medical report request using the one or more data structures.

The content of the medical report can include multimedia content including a greeting in the language of the patient, an explanation segment of a type of test conducted, a results segment for conveying test results, an explanation segment explaining results of the test, and a conclusion segment, wherein at least a portion of the multimedia content includes report data from the report data source, test results from the results information source, medical information from the medical information source, and medical images related to the test from the medical image source. Such methods can also include automatically generating the requested medical report using the accessed report content based at least in part on the selected format of the medical report. Such methods can also include displaying the medical report to the patient. In some embodiments, the multimedia information further comprises data for generating and displaying an avatar on a display, the avatar being included in the medical report. In some embodiments, the method further comprising generating the avatar based on one or more patient characteristics. In some embodiments, the patient characteristics include one or more of age, race, and gender.

In some embodiments of such methods, a method can include displaying the medical report on one or more displays of a computer system, receiving user input while the medical report can be displayed, and changing at least one portion of the medical report based on said received user input. In some embodiments, displaying the medical report comprises displaying the medical report on the patient's smart device. In some embodiments, the method includes storing the medical report. In some embodiments, the one or more data structures is configured to store information representative of the severity of the patient's medical condition, wherein selection of the content of the segments of the medical report are based on in part on the stored information representative of the severity of the patient's medical condition.

Such methods can also include selecting a greeting segment for the medical report based on one or more of the patient's race, age, gender, ethnicity, culture, language, education, geographic location, and severity of prognosis. The method can also include selecting multimedia content for the explanation segment based on one or more of the patient's race, age, gender, ethnicity, culture, language, education, geographic location, and severity of prognosis. The method can also include selecting multimedia content for the explanation of the results segment based on one or more of the patient's race, age, gender, ethnicity, culture, language, education, geographic location, and severity of prognosis. The method can also include selecting multimedia content for the conclusion segment based on one or more of the patient's race, age, gender, ethnicity, culture, language, education, geographic location, and severity of prognosis. In some embodiments, the one or more data structures are configured to store associations related to normality, risk, treatment type, and treatment benefit of medical conditions, and wherein the method further includes automatically determining normality, risk, treatment type, and treatment benefit to include in the report based on the patients test results, and the stored associations related to normality, risk, treatment type, and treatment benefits. In some embodiments, the method can further include generating an updated medical report based on a previously generated medical report, new test results, and an input by a medical practitioner.

Example System and Method for Automatically Generating Coronary Artery Medical Data Described herein are systems and methods for generating medical reports that provides an in-depth explanation of what the medical test or examination was intended to look for, the results of the patient's specific medical findings, and what those findings may mean to the patient. The medical reports can be automatically generated, understandable educational empowering movie of individualized adapted personal aggregated medical information. As an example, a computer implemented method of generating a multi-media medical report for a patient, the medical report associated with one or more tests of the patient. One or more images used to determine information for the medical report, and/or one or more of the images used in the medical report, can be based on images generated using a normalization device described herein, the normalization device improving accuracy of the non-invasive medical image analysis. In an example, a method comprises receiving an input of a request to generate the medical report for a patient, the request indicating a format for the medical report, receiving patient information relating to the patient, the patient information associated with the report generation request, determining one or more patient characteristics associated with the patient using the patient information, accessing associations between types of medical reports and patient medical information, wherein the patient medical information includes medical images relating to the patient and test results of one or more test that were performed on the patient, the medical images generated using the normalization device, and accessing report content associated with the patient's medical information and the medical report requested. The report content can include multimedia content that is not related to a specific patient. For example, the multimedia content can include a greeting segment in the language of the patient, an explanation segment explaining a type of test conducted, a results segment for conveying test results, and an explanation segment explaining results of the test, and a conclusion segment, wherein at least a portion of the multimedia content includes a test result and one or more medical images that are related to a test performed on the patient. the method can further include generating, based at least in part on the format of the medical report, the requested medical report using the patient information and report content.

Certain components of certain embodiments of such systems and methods are described herein. An example of cardiac CT study imaging in a single examination is provided.

1) Transform individual patient specific medical information into an understandable movie. This invention combines patient facing medical education with patient specific medical results in a manner that has not been previously performed. While many online sites explain medical disease processes, they do not have the results of the patients' medical tests and the patients often do not know if they are even looking in the right area. By combining patient facing educational background as well as specific analysis of their test results and meaning, the patients will be educated in a manner that empowers them to make better health decisions. This approach can then combine additional materials beyond just the present test findings, including additional information derived from patient history, physical, clinical electronic medical record, wearable fitness and wellness trackers, patient-specific web browser search history and so on.

2) Provide an in-depth explanation of the test performed. To understand what the results of a test may be, patients must understand what the test was intended to do, an explanation regarding how it works, as well as the potential range of results, both normal and abnormal. An explanation of the test performed would include simple understandable methods of what the test is intended to find and what the range of possibilities of the results may be. In the example provided a coronary artery CT angiogram is intended to evaluate if there are blockages or plaque within the patient's coronary arteries. In order to understand the results, a patient needs to understand that the test is intended to evaluate the blood vessels that feed the heart muscle, that by injecting contrast and doing CT images their coronary arteries can be evaluated for the presence of plaque and associated blockages. This understanding can be conveyed to the patient using a patient's actual images so that there is increased engagement and understanding.

3) Provide the results of the patient's individual patient specific examination. Having educated the patient regarding what test they had as well as the range of all possible results, they are now better empowered to understand what their specific results are in the context of the range of potential results from the examination. Combining the results of the patient's findings with an explanation of what the test was looking for enables the patient to better understand the meaning of those results. The patient's individual results, whether they are quantitative values from a blood test, images and resulting interpretation from a diagnostic imaging study such as CT, MM, ultrasound etc., results from an ECG exam etc. Quantitative results, images, PDFs, or other results can be uploaded and presented within the movie.

4) Give explanations of the results. In addition to presenting the results directly to the patient, an explanation of the meaning of the results can then be presented simultaneously. This is performed using defined aggregation algorithms with previously recorded definitions and discussions of the range of results expected for an individual test. For example, in the case of the cardiac CT angiogram report, we will develop short explanations of the significance of the result of narrowing of a blood vessel. If there is no narrowing present then a short, animated video discussion will explain that no narrowing was present and what that means, if there is a mild narrowing which is clinically defined as a narrowing between one and 24%, then a different video will be played. If the narrowing is between 24 and 49%, another video is played etc. Previously created video explanations of the range of expected results will have been created and are available to then be placed within the video depending on the individual results of the examination. In some cases, there may only be a binary result, and therefore only two explanations are necessary. In other cases, it may be many videos depending on the initial test and the range of possible clinically significant results. The patient specific results can sometimes even be compared to what would be expected to an average patient of the same age and sex or to what age that result would be considered "average—normal". Specifically, in this step, the patient's test findings can be linked to clinical treatment or additional diagnostic recommendations that can be based upon professional societal practice guidelines or contemporary research science, such as that derived from large-scale registries and trials. In this way, this approach can also be educational to the medical professional and may allow for improved and contemporary clinical decision support. This will allow for a shared decision-making moment for the patient and the medical professional, without the need for them to read through scientific literature.

5) Use animation that is patient friendly and non-threatening. The animation selected for the video will be intended to be professional but friendly and non-threatening to the patient in order to put them more at ease and make them more open to hearing and understanding the explanations. The animated physician or other explainer in the video can also be matched to the patience sex, age, and race and even be presented in the patient's primary language. Alternatively, the patient's own countenance can be the patient within the video in a manner that is from a photography or, alternatively, rendered as a cartoon or avatar.

6) Can be delivered via web based and non-web-based methods. The method of delivery to the patient can be via encrypted HIPAA compliant web-based methods or non-web-based methods such as computer disks, other storage media, etc.

7) Can be viewed on computers, cell phones, and other devices. In this manner, all patients will have access to the reports regardless of their socioeconomic status. Not all patients have access to the Internet, cell phones or other devices. Making it available on multiple media platforms increases the degree of access.

8) Uses mixed reality for explanations. The use of advanced computer graphics an augmented or virtual reality may make some of the explanations easier for the patients to understand. For example, a virtual reality trip into the body and through a blood vessel then demonstrating the blood flow slowing down and or stopping at the sight of a blockage will help the patient to understand the significance of having that blockage in their body. Demonstrating the deployment of a stent in that blood vessel at the sight of that blockage will then help the patient understand how their pathology may be treated and why. This could also be done in a 3D/4D virtual reality manner; or as a hologram; or by other visual display. Similarly, this information can be conveyed by audio methods, such as a podcast or others.

9) Can be saved by the patient for future reference. The patient specific movie containing an explanation of the test, their results and additional information becomes property of the patient that they can store for future use.

10) Can be compared to a normal reference population value. In some cases, there may be findings that, to maximize patient understanding, can be compared to normative reference values that are derived from population-based cohorts or other disease cohorts. This may be provided in percentile, by age comparison (e.g., heart age versus biological age), or by visual display (e.g., on a bell-shaped curve or histogram).

11) Can be compared to prior studies. In some cases, the patient may have 2 studies (either the same test, e.g., CT-CT or different tests CT-ultrasound) that can be automatically compared for differences and reported as described above in #1-10. This will allow a patient to understand his/her progress over time in response to lifestyle or medical therapy or interventional therapies. In other cases, the test findings can be conveyed as in #1-10 as a function of heritability (e.g., from genomics or other 'omics or family history), susceptibility (e.g., from lab markers over time, or from environmental lifestyle insults, such as smoking).

12) Can be configured to communicate the likelihood of success. In some cases, the video generated will estimate the likelihood of success or failure of any given intervention by calculating the likelihood through risk calculators or using clinical trial data or practice guidelines; and this can be reported in the movie.

Examples of Medical Report Generation Systems and Methods

Figure 16:
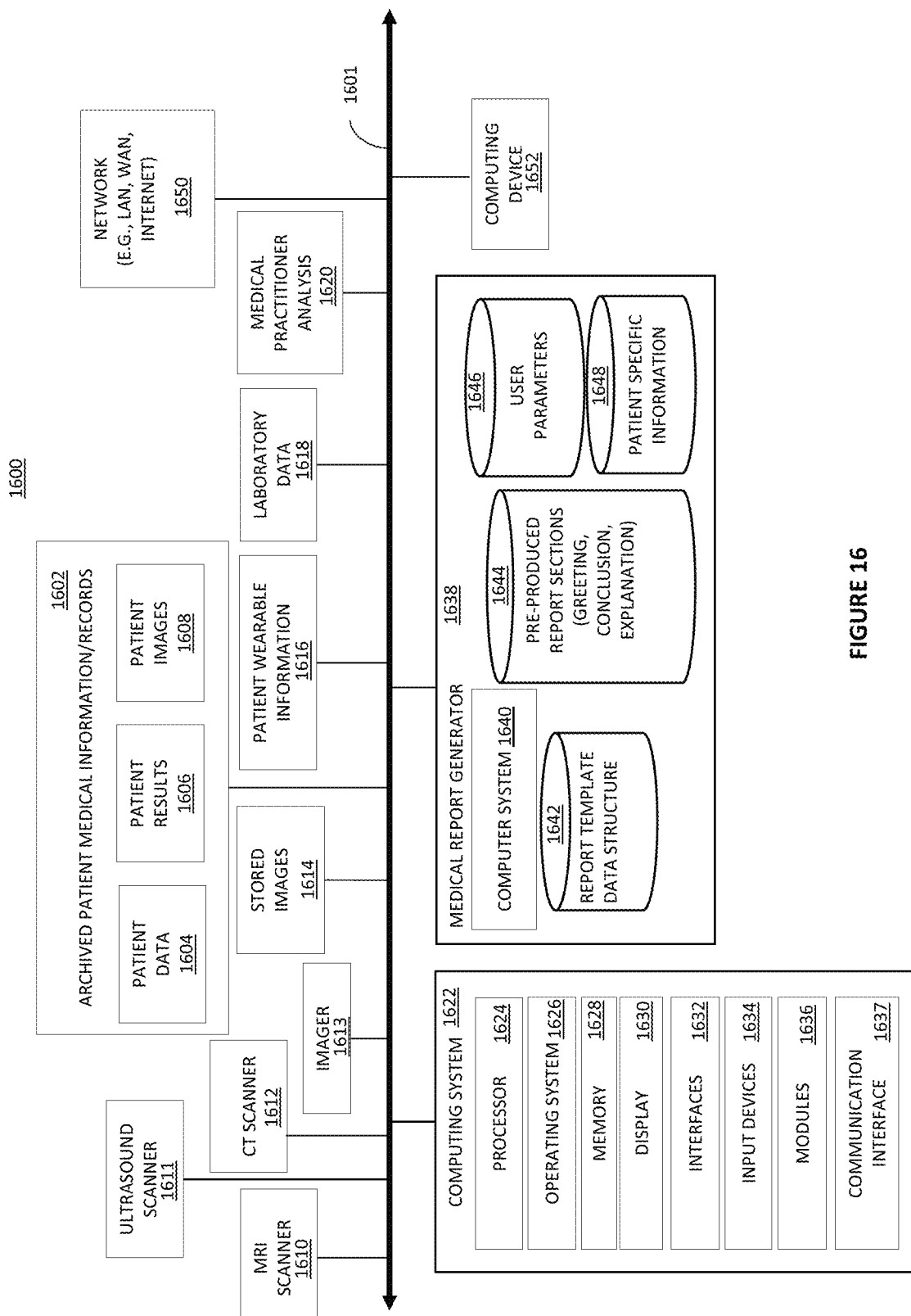
FIG. 16 is a system diagram which shows various components of an example of a system for automatically generating patient medical reports, for example, patient medical reports based on CT scans and analysis, utilizing certain systems and methods described herein.

FIG. 16 is a system diagram which shows various components of an example of a system 1600 for automatically generating patient medical reports, for example, patient medical reports based on CT scans and analysis, utilizing certain systems and methods described herein. Various embodiments of such systems may include fewer components than is shown in FIG. 16, additional components, or different components. In this example, the system 1600 includes an MM scanner 16160, an ultrasound scanner 1611, the CT scanner 1612, and other types of imaging devices 1613. Information from scanners and imaging devices is provided to other components of the system through one or more communication links 1601 or other communication mechanism for communicating information. The communication link is also connected to other components the system illustrated in FIG. 16.

The system 1600 further includes archived patient medical information and records 1602 which may have been collected in a variety of sources and over a period of time. The information and records may include patient data 1604, patient results 1606, patient images 1608, (e.g., stored images of CT scans, ultrasound scans, MRI scans, or other imaging data.

The system 1600 further includes stored images 1614 (which may or may not be patient related). The system 1600 further includes patient wearable information 1616 which may be collected one or more devices worn by patient, devices sensing or measuring one or more types of physiological data or a characteristic of the patient, typically over a period of time. The system 1600 can further include laboratory data 1618 (e.g., recent blood analysis results), and medical practitioner analysis 1620 of any patient related data (e.g., images, laboratory data, wearable information, etc.). The system 1600 may communicate with other systems and devices over a network 1650 which is in communication with communication links 1601.

System 1600 may further include a computing system 1622 which may be used perform any of the functionality related to communicating, analyzing, gathering, or viewing information on the system 1600. The computing system 1622 can include a bus (not shown) that is coupled to the illustrated components of the computing system 1622 (e.g., processor 1624, memory 1628, display 1630, interfaces 1632, input/output devices 1634, communication link 1601, and may also be coupled to other components of the computing system 1622. The computing system 1622 may include a processor 1624 or multiple processors for processing information and executing computer instructions. Hardware processor 1624 may be, for example, one or more general purpose microprocessors. Computer system 1622 also includes memory (e.g., a main memory) 1628, such as a random-access memory (RAM), cache and/or other dynamic storage devices, for storing information and instructions to be executed by processor 1624. Memory 1628 also may be used for storing temporary variables or other intermediate information during execution of instructions to be executed by processor 1624. Such instructions, when stored in storage media accessible to processor 1624, render computer system 1622 into a special-purpose machine that is customized to perform the operations specified in the instructions. The memory 1628 may, for example, include instructions to allow a user to manipulate time-series data to store the patient information and medical data, for example as described in reference to FIGS. 16 and 17. The memory 1628 can include read only memory (ROM) or other static storage device(s) coupled in communication with the processor 1624 storing static information and instructions for processor 1624. Memory 1628 can also include a storage device, such as a magnetic disk, optical disk, or USB thumb drive (Flash drive), etc., coupled the processor 1628 and configured for storing information and instructions.

The computer system 1622 may be coupled via a bus to a display 1630, for example, a cathode ray tube (CRT), light emitting diode (LED), or a liquid crystal display (LCD). The display may include a touchscreen interface. The computing system 1622 may include an input device 1634, including alphanumeric and other keys, is coupled to bus for communicating information and command selections to processor 1622. Another type of user input device is cursor control, such as a mouse, a trackball, or cursor direction keys for communicating direction information and command selections to processor 1622 and for controlling cursor movement on display 1630. The input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 1622 may include a user interface module 1632 to implement a GUI that may be stored in a mass storage device as computer executable program instructions that are executed by the computing device(s). Computer system 1622 may further, implement the techniques described herein using customized hard-wired logic, one or more ASICs or FPGAs, firmware and/or program logic which in combination with the computer system causes or programs computer system 1622 to be a special-purpose machine. According to one embodiment, the techniques herein are performed by computer system 1622 in response to processor(s) 1624 executing one or more sequences of one or more computer readable program instructions contained in memory 1628. Such instructions may be read into memory 1628 from another storage medium. Execution of the sequences of instructions contained in the memory 1628 causes processor(s) 1624 to perform the process steps described herein. In alternative embodiments, hard-wired circuitry may be used in place of or in combination with software instructions.

Various forms of computer readable storage media may be involved in carrying one or more sequences of one or more computer readable program instructions to processor 1624 for execution. The instructions received by memory 1628 may optionally be stored before or after execution by processor 1624.

Computer system 1622 also includes a communication interface 1637 coupled to other components of the computer system and to communication link 1601. Communication interface 1637 provides a two-way data communication coupling to a network link that is connected to a communication link 1601. For example, communication interface 1637 may be an integrated services digital network (ISDN) card, cable modem, satellite modem, or a modem to provide a data communication connection to a corresponding type of telephone line. As another example, communication interface 1637 may be a local area network (LAN) card to provide a data communication connection to a compatible LAN (or WAN component to communicate with a WAN). Wireless links may also be implemented. In any such implementation, communication interface 1637 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). An ISP in turn provides data communication services through the worldwide packet data communication network now commonly referred to as the "Internet." Computer system 1622 can send messages and receive data, including program code, through the network(s), communication link 1601 and communication interface 1637. In the Internet example, a server might transmit a requested code for an application program through the Internet, ISP, local network communication link 1601, and a communication interface. The received code may be executed by processor 1624 as it is received, and/or stored in memory 1628, or other non-volatile storage for later execution. The processor 1624, operating system 1626, memory components 1628, one or more displays 1630, one or more interfaces 1632, input devices 1634, and modules 1636, which may be hardware or software, or a combination of hardware and software, that when utilized performs functionality for the system. For example, the modules 1626 may include computer executable instructions that are executed by processor 1624 to perform the functionality of system 1600.

The system 1600 may further include medical report generation system 1638 ("or medical report generator") which can include various components that are used to generate medical report data set for a particular patient for a requested type of report. Medical report generation system 1638 may include a computing system, e.g., a server or a computing system 1640. In some embodiments, the computing system 1640 includes a server. The medical report generation system also includes collected or determined patient specific information 1648, and a report template data structure 1642 which includes associations between a patient, the patient information 1648 (images, medical analysis and test results associated with the patient), and report segments, report elements, reports of elements for the desired. Medical report generation system 1638 further includes user parameters 1646 that may be specific to a medical practitioner and/or to a patient or entered by a medical practitioner and/or the patient.

The system 1600 may also include one or more computing devices 1652 communication with the components of the system via a communication link(s) 1601. Communication link(s) 1601 may include wired and wireless links. Computing device 1652 may be a tablet computer, laptop computer, a desktop computer, a smart phone, or another mobile device.

Figure 17:
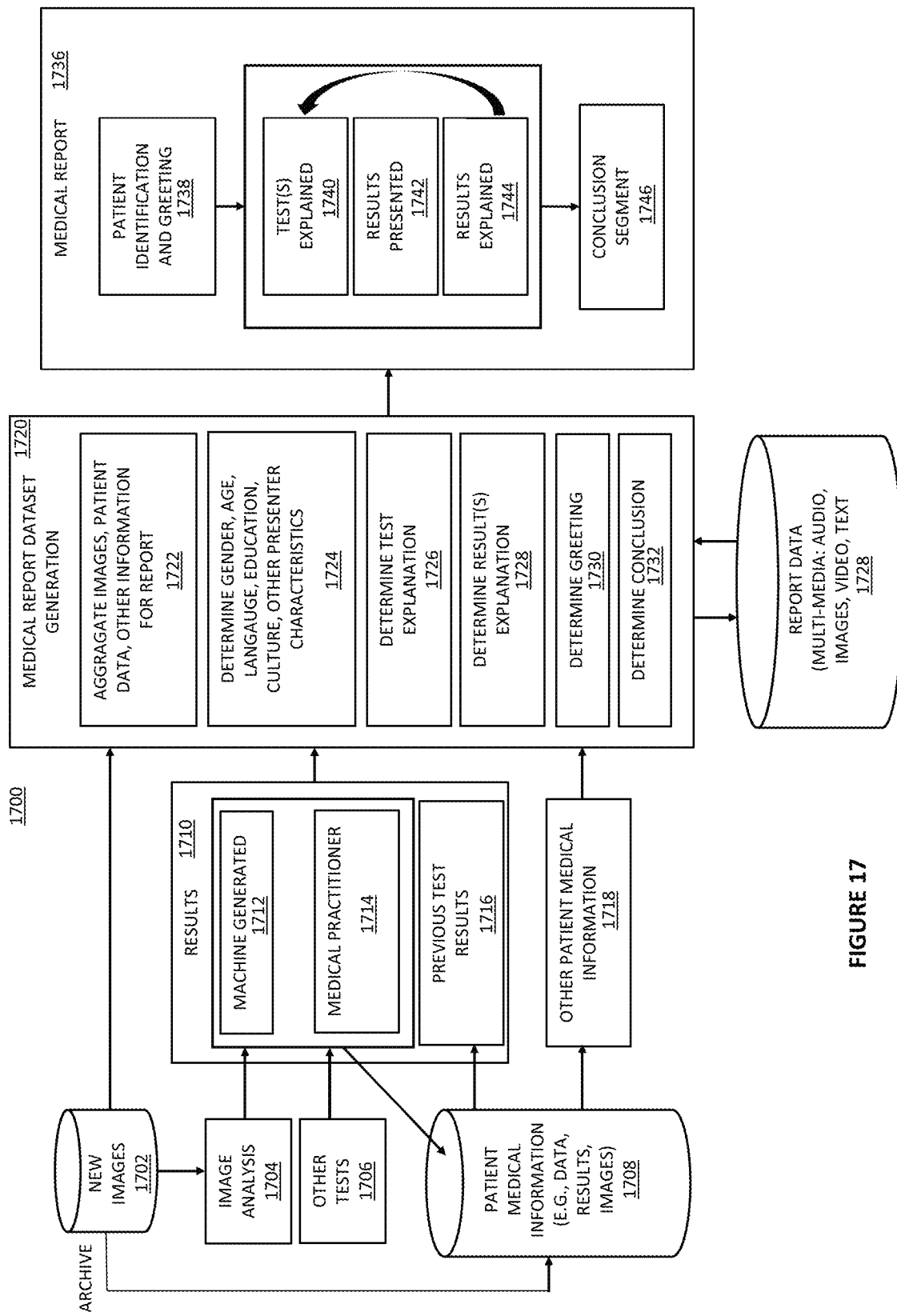
FIG. 17 is a block diagram that shows an example of data flow functionality for generating the patient medical report based on one or more scans of the patient, patient information, medical practitioner's analysis of the scans, and/or previous test results.

FIG. 17 is a block diagram that shows an example of data flow and functionality 1700 for generating the patient medical report based on one or more scans of the patient, patient information, medical practitioner's analysis of the scans, and/or previous test results. At the beginning of this data flow new medical images 1702 are received by the system or are generated by a scanner. The images can be generated using a normalization device described herein. Information derived from images generated and processed using the normalization device can be more consistent and/or accurate, as described herein. The images can be from a CT, MRI, ultrasound, or other type of scanner. The images depict a target feature of a patient's body, for example, coronary arteries. The images may be archived in a patient medical information storage component 1708, which stores other types of patient data (for example, previously generated images, patient test results, patient specific information that can include age, gender, race, BMI, medication, blood pressure, heart rate, weight, height, body habitus, smoking, diabetes, hypertension, prior CAD, family history, lab test results, and the like). The new images 1702 are provided for image analysis 1704, which may include analysis of the images using artificial intelligence/machine learning algorithms that have been trained to detect features in certain characteristics in the images. Other test 1706 may also have been conducted on the patient (e.g., blood work or another test).

The new images 1702, machine generated results to 1712, results determined by medical practitioners 1714, and previous test results 1716 are collected in a results phase 1710, and this information is communicated to medical report data set generation block 1720. Other patient medical information 1718 can also be provided to medical report data set generation 1720. As indicated above, this information may include, for example, a patient's age, gender, race, BMI, medication, blood pressure, heart rate, weight, height, body habitus, smoking, diabetes, hypertension, prior CAD, family history, lab test results, and the like. In addition to the results 1710 and the other patient medical information 1718, medical report data set generation 1720 can also receive report data 1728. Report data 1728 can include multimedia information used for the report. For example, audio, images, sequences of images (i.e., video), text, backgrounds, avatars, or anything else for the report that is not related to the specific patient's medical information.

Medical report data set generation 1720 can use the new images 1702, the results 1710, other patient medical information 1718, and report data 1728 to generate a medical report dataset for a requested type of report. The medical report data set generation 1770 can be interactive, and a medical practitioner can provide input identified what type of report is being generated. At block 1722, during the medical report data set generation, all of the information that is needed for the requested report, is aggregated and the medical report is generated. For example, images, patient data, and other information needed for the report are identified collected from the various inputs. At block 1724, the process uses certain patient information to tailor the report for the particular patient. For example, one or more characteristics of an avatar that presents information in the report to the patient can be identified from the patient data such that the avatar is created to best convey report information to the patient. In some examples, such information includes the gender, age, language, education, culture, and the like, characteristics of the patient. At block 1726, the process determines the test explanation that is best used for the report. For example, there may be ten different explanations for a particular test, and one of the ten explanations is selected for the report. The determination of the test explanation may be based on patient and/or the diagnosis or prognosis of results of the test. In other words, the same test may be explained in various ways based on what the results of the test turned out to be. At block 1728, the process determines results explanation. There can be multiple explanations for the same results, and one of the explanations the selected port. The selection of the results explanation can be based on, for example, patient information, the substance of the results, or other information.

At block 1730, the process determines a greeting to be used in the report. The greeting selected for the report may be one of numerous possible greetings. In various embodiments, the greeting may be selected based on patient information, user input, or the results the test. For example, if the test results indicate great news for the patient, a first type of greeting may be selected. If the test results are unfavorable to the patient, a second type of greeting may be selected is more appropriate for subsequently delivered results.

At block 1732, the process determines the conclusion to be used in the report. The conclusion selected for the report may be one of numerous possible conclusions. In various embodiments, inclusion may be selected based on patient information, user input, or the results of the test. For example, the test results indicate great is for the patient the first type of the selected. The test results are unfavorable to the patient, the second type of conclusion selected is more appropriate for the previously reported unfavorable results.

The medical report data set generation 1720 provides a medical report 1736. In some embodiments, the medical report is a video that includes a patient identification greeting 1738, and for each test, an explanation of the test 1740 results of the test 1742 and explanation of the results 1744. For medical reports that include multiple tests, the report may iteratively present a test explanation, present the results, and present an explanation results for each test conducted. The medical report also includes a conclusion segment 1746. In some embodiments, the medical report is displayed on the display to the patient/patient's family. In some embodiments, the medical report is provided as a video for the patient to view at their home or anywhere else on a computer. In some embodiments, medical report can be provided is a paper copy.

Figure 18A:
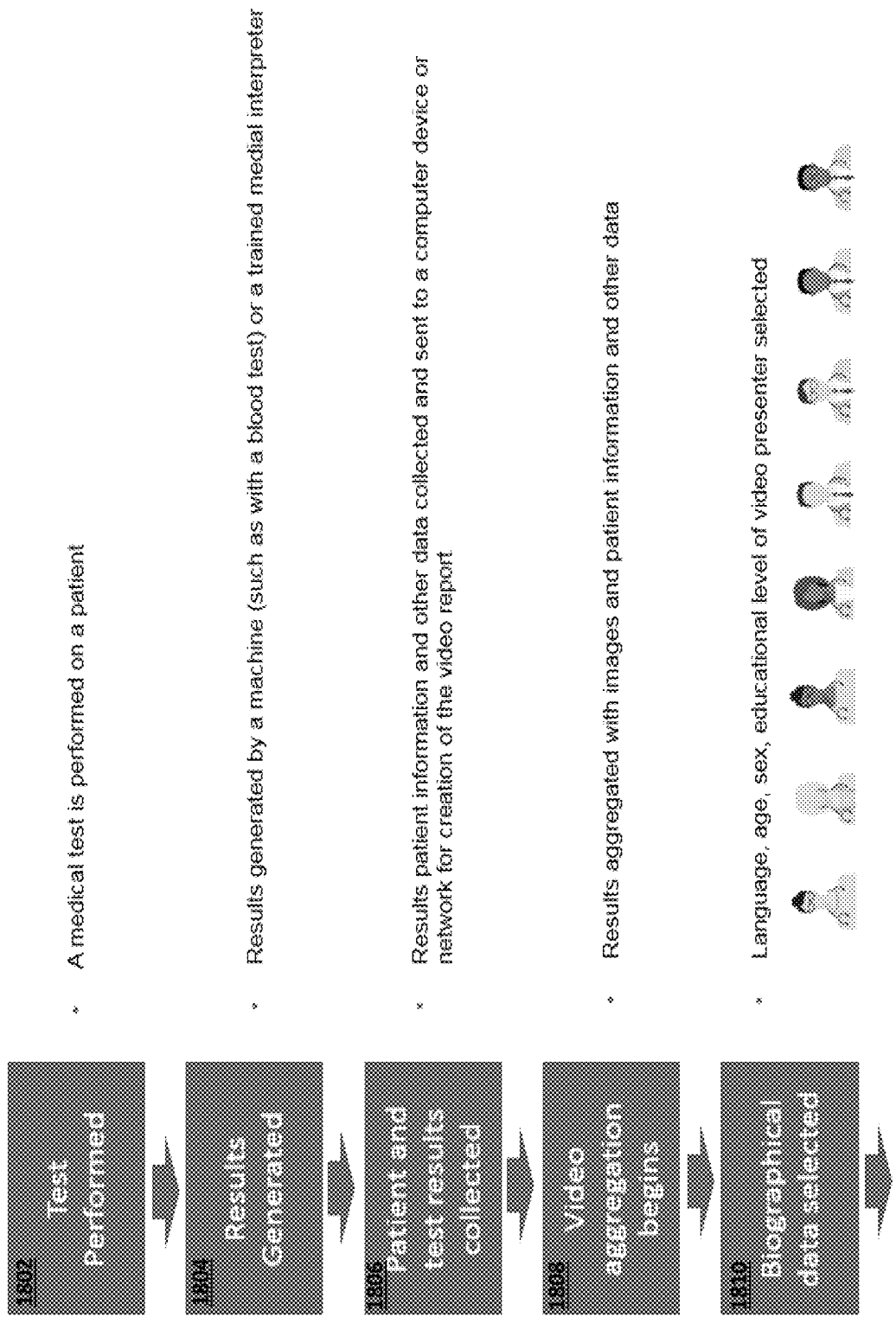
FIG. 18A is a block diagram of a first portion of a process for generating medical report using the functionality and data described in reference to FIG. 2, according to some embodiments.

FIG. 18A is a block diagram of an example of a first portion of a process for generating medical report using the functionality and data described in reference to FIG. 17, according to some embodiments. At block 1802, one or more medical tests are performed on a patient. At block 1804, results are generated by machine (e.g., a blood test), the train medical interpreter, and/or are automatically/semi-automatically determined based on artificial intelligence/machine learning algorithms. At block 1806, results, patient information, and other data is collected and sent to a computer device or network for creation of the medical report. At block 1808, results are aggregated with images, patient information, other data, multimedia information and the like to generate a medical related portion of report. At block 1810, the process generates the video presenter (e.g., an avatar) of the report using certain selected patient information, for example, biographical data of the patient. For example, when the patient is a child, patient information may be used to create child avatar which presents the report to the child. In some embodiments, the child avatar may have been avatar pet which also helps present the report to the child, making the report more interesting and more fun for the child. When the patient is a highly educated adult, patient information may be used to create an avatar that is appropriate to present the report to that patient. In some embodiments, the avatar may mirror certain characteristics of the patient (e.g., race, age, or gender) or be a determined complementary avatar to certain characteristics of patient.

Figure 18B:
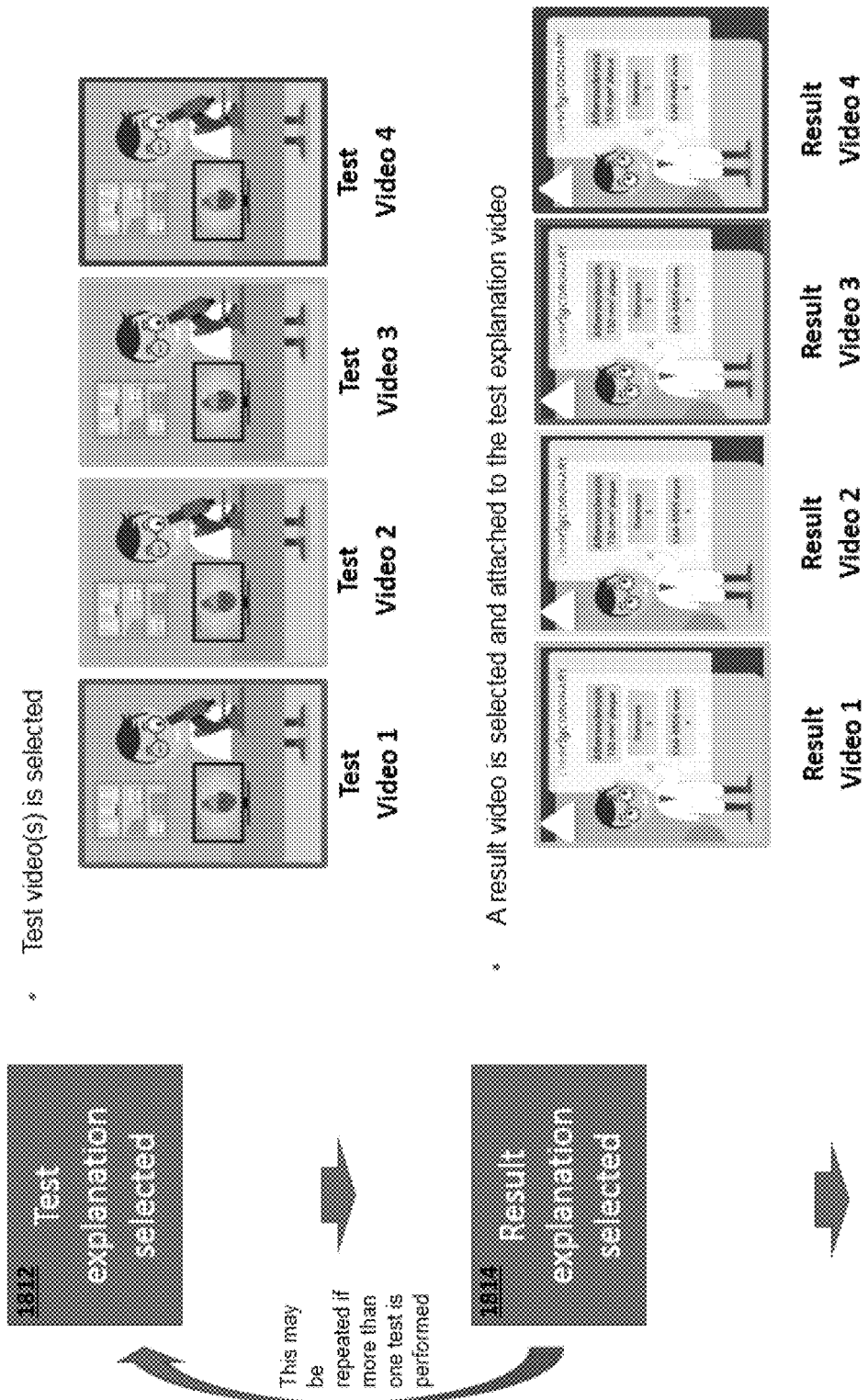
FIG. 18B is a block diagram of a second portion of a process for generating medical report using the functionality and data described in reference to FIG. 2, according to some embodiments.

FIG. 18B is a block diagram of an example of a second portion of a process for generating medical report using the functionality and data described in reference to FIG. 17, according to some embodiments. At block 1812, the process selects a test explanation to be used for the report. The selection of the test explanation can be based on the patient information the severity of injury or disease, and/or the seriousness of the report (e.g., the final diagnosis). In one example, a certain test explanation may be selected from one of four test explanation videos. At block 1814, the process selects explanation results to be used for the report. The selection of the results can also be based on the patient information, severity of the injury or disease, and/or seriousness of report (e.g., the final diagnosis). In one example, the certain results explanation may be selected from one of four results explanation videos.

Figure 18C:
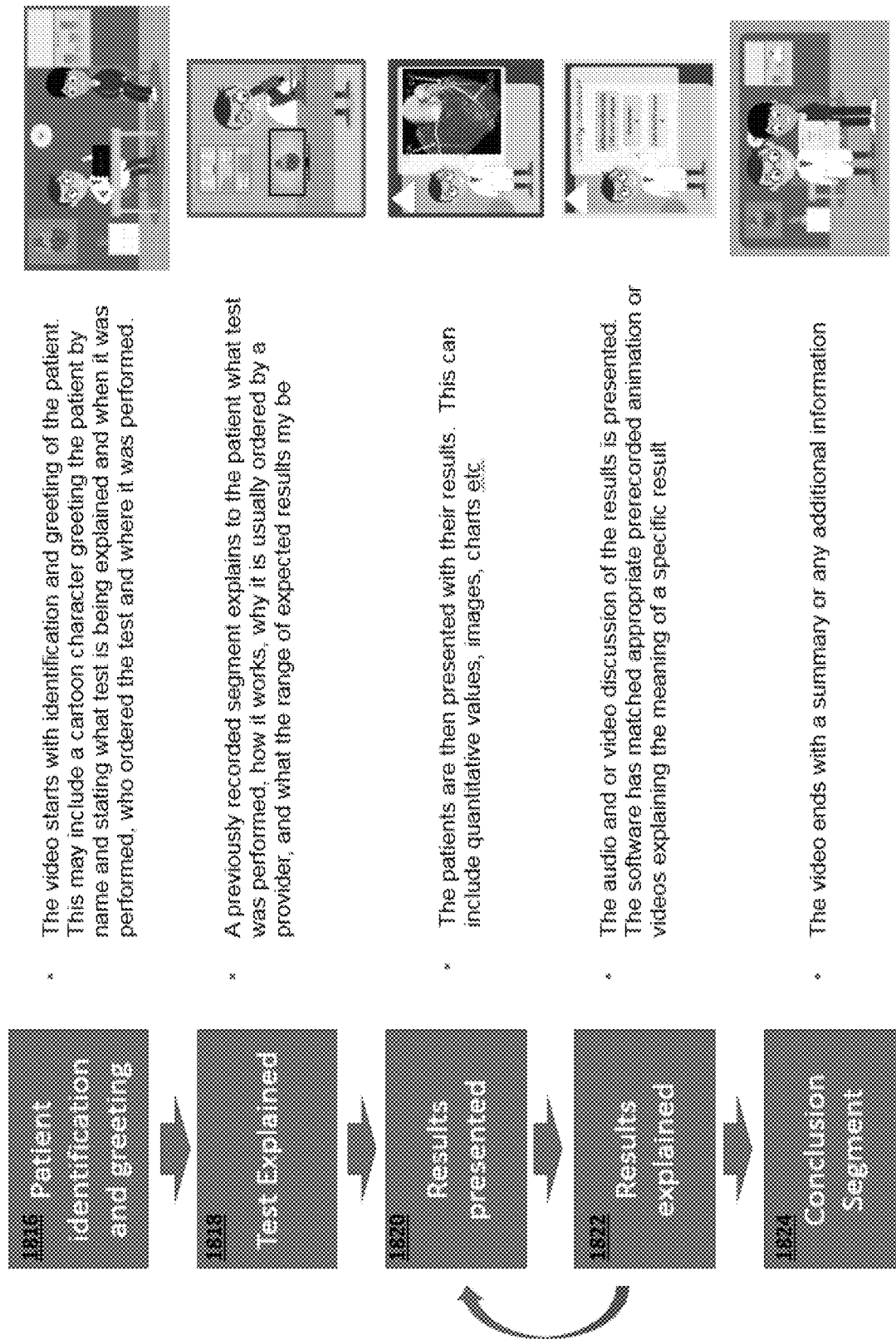
FIG. 18C is a block diagram of a third portion of a process for generating medical report using the functionality and data described in reference to FIG. 2, according to some embodiments.

FIG. 18C is a block diagram of an example of a third portion of a process for generating medical report using the functionality and data described in reference to FIG. 17, according to some embodiments. At block 1816, the process selects patient identification greeting. The report and start with identification reading of the patient this may include a cartoon character, or avatar, reading the patient by name and stating what test does been explained and when it was performed, who ordered the test and where it was performed. At block 1818, the process explains the test conducted on the patient. A previously recorded segment explains, for example, the patient what test was performed, how it works, why it is usually ordered by a provider, and what the range of expected results may be. At block 1820, the report then presents the results to the patient. The results can include quantitative values, images, charts, videos, and other types of data that may help to convey the results to the patient. At block 1822, the report may present a discussion of results to help clarify to the patient exactly what the results mean in some examples, appropriate prerecorded animation of videos explains the meaning of a result. If multiple tests were performed on the patient, the process may iteratively explain each test, present the test results, and then explain the results. At block 1824, the process presents a conclusion segment that may summarize information for the patient, provide additional information, and/or provide guidance on the next steps taken by the patient or that will be taken by the medical practitioner. For all the parts of the report, medical report generation functionality uses a combination of patient information, actual images and or test results, and other multimedia information to present a comprehensive clear explanation of each test that was performed in the results of the test.

Figure 18D:
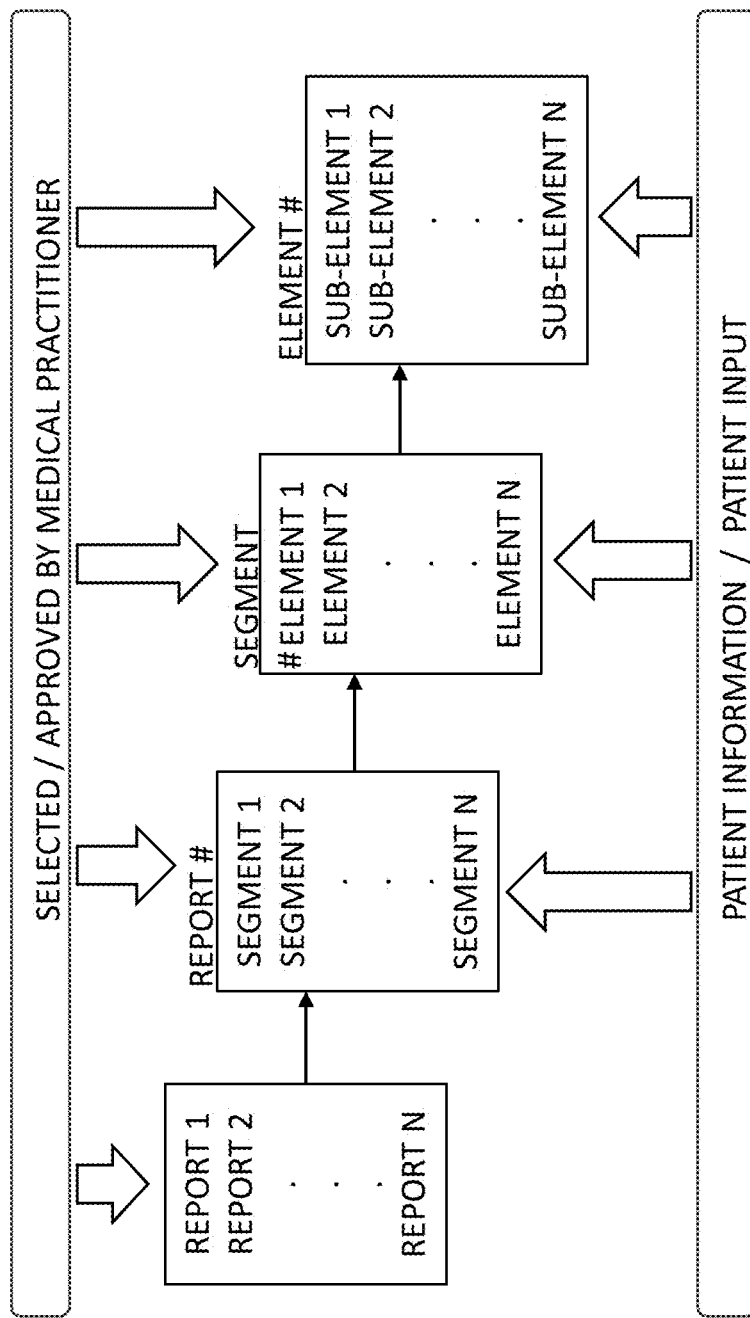
FIG. 18D is a diagram illustrating various portions that can make up the medical report, and input can be provided by the medical practitioner and by patient information or patient input.

FIG. 18D is a diagram illustrating various portions that can make up the medical report, and input can be provided by the medical practitioner and by patient information or patient input. As shown in FIG. 18D, the medical practitioner can interactively select a type of medical report to be generated (e.g., report 1, report 2, etc.). Each medical report is a collection of data and information that can be collected and presented in various segments of the report. For example, the segments can include a greeting, an explanation of the test(s) performed, results, an explanation of the results, and a conclusion. Medical reports that include multiple tests can include multiple segments that present an explanation of each test performed, the results of each test, and an explanation of the results of each test. In some embodiments, all or portions of the segment are automatically generated based on patient information, types of test performed, and the results of each test. In some embodiments, the medical practitioner can select or prove information to use for each segment. In some embodiments, the report can be interactive in a patient's input can help determine what information to use to generate a segment or present a portion of the report. Each segment may include a number of elements. Each of the elements can include one or more sub elements. For example, a segment of test results may include an element for each of the test results to be included in the report. In some embodiments, the medical practitioner can select or approve of what information to use for an element and/or a sub-element. In some embodiments, the elements and/or the sub-elements can be at least partially determined based on the patient information and/or the patient input. Typically, the medical practitioner can interactively select and/or approve of all material that is used in the report. In some embodiments, contents of the report are based on predetermined algorithms that use the combination of patient information, medical tests, medical results, and medical practitioners' preferences to determine the elements in each segment of the medical report.

Figure 18E:
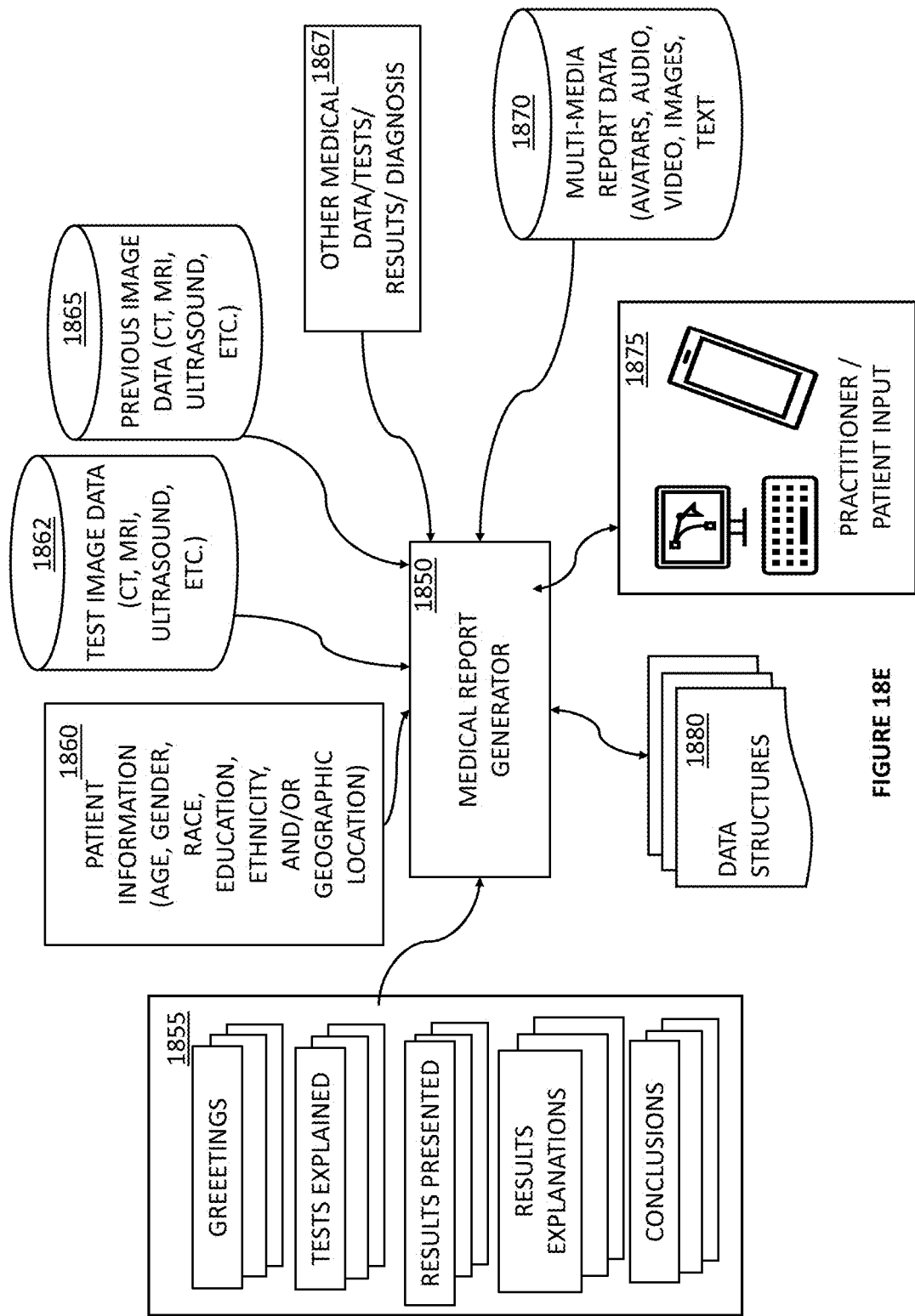
FIG. 18E is a schematic illustrating an example of a medical report generation data flow and communication of data used to generate a report.

FIG. 18E is a schematic illustrating an example of a medical report generation data flow and communication of data used to generate a report. As illustrated components and data related to the components and data illustrated in FIGS. 16-18D. A medical report generator 1850 receives plurality of inputs which it uses to generate a particular medical report for particular patient. This medical report is generated to educate and inform a patient, and a patient's caregivers, of a specific patient's medical tests and results. This medical reporting is a process that transforms individual medical information in an understandable movie. The movie is made with the patient's avatar or avatar like (e.g., matched by sex, age ethnicity, etc.). Viewing of the report can be done anywhere on a computer that a medical facility or on a patient's computer (e.g., a smart phone, tablet, laptop, etc.). Report may contain multimedia data audio, text, images, and/or video. The video may contain, cartoon, real life videos. Animation can include virtual reality for example video enters body, see heart pumping with blood flowing, centered at vessels, see blood through vessels flowing and showing plaque with changes in velocity and flowing—go to plaque and see its distinct types. In some embodiments, augmented reality may be used to simulate, age, pharmacological changes, pharmacological agents available where the exam is done, different degrees of disease, the effect of interventions such as stents and bypass, behavior changes and exercise. The report may be shareable allowing a user able to share with anyone with a defined time of availability or forever. For example, it can be transformed and condensed in a PDF, DICOM, or Word document, or another format, for printing. The language used in the report can be the patient's native language. In some embodiments, subtitles can be used for hearing impaired in native language, or braille for the blind. In embodiments using avatar, the avatar narration can be individualized for the patient, to include age, gender, ethnicity—change in patient look, level of understanding—change in language and depth of information.

The medical report generator 1850 can receive input 1875 from a medical practitioner indicating to generate a particular type of report for particular patient. In some embodiments, a medical practitioner can provide inputs to determine certain aspects of the report. For example, the medical practitioner may indicate which image data to use in which test results to include in the report. In another example, the medical practitioner can, based on the test results and/or the severity of the diagnosis, the medical practitioner can influence the "tone" or seriousness of the report such that is appropriate for reporting the test results in the diagnosis.

In some embodiments, the medical practitioner can provide inputs to approve tentative automatically selected material to include in the report. The medical report generator 1800 in communication with data structures 1880 which store associations related to report generation. In some embodiments, the data structures 1880 include associations between the particular medical practitioner and characteristics of medical reports that he prefers to generate. The associations may be dynamic and may interactively or automatically change over time. The data structures 1880 can also include associations that relate to all of material that can be used to generate a report. For example, after a medical practitioner indicates that a certain medical report generated for certain patient, the medical report generator 1880 receives patient information 1880 based on the associations data structures begins to it needs to generate the medical report.

As illustrated in FIG. 18E, medical report generator 1850 can receive pre-existing portions of a report 1855 (segments, elements, sub-elements) that can include multi-media greetings, explanation of a test, presentation of results, explanation results, and conclusions. This material can be combined with other inputs the medical report generator 1850 to generate the report. For example, the medical report generator 1850 can receive patient information 1860 that includes the patient's age, gender, race, education, ethnicity, geographic location, in any other characteristic of pertinent information of the patient which may be used to tailor the medical report such that the information in the medical report is best conveyed to the particular patient. Medical report generator 1850 can also receive image data 1862 related to recent test performed on the patient (e.g., CT, MRI, ultrasound scans, or other image data), and/or previously collected image data 1865 (e.g., previously collected CT, MRI, ultrasound scans, or other image data). For example, the previously collected image data 1865 can include image data that was taken over a period of time (for example, days, weeks, months, or years). The medical report generator 1850 can also receive other medical data 1867 including but not limited to test, results, diagnosis of the patient. The medical report generator 1850 can also receive multimedia report data 1870 which is used to form portions of medical report. The multimedia report data 1870 can include information relating to avatars, audio information, video information, images, and text that may be included in the report.

The medical report can apply to and/or discuss test results—imaging and non-imaging tests, and other medical information isolated or aggregated with or without therapeutic approach. For example, for a gallstone surgery, the medical report can aggregate information from lab tests, objective observation, medical history, imaging tests, include surgery proposal, surgery explanation, virtual surgery, pathological findings (more important in cancer), and explain after surgery recuperation until normal life or treatment FUP (ex: chemotherapy in cancer). A medical report can also be educational, and generic and adapted to a patient, a disease, and/or a treatment, a test, and address disease, risk factors, treatment, behavior, and behavior changes. Some examples, medical report can be generated to form part of a patient's complete electronic medical record (EMR) information. In some examples, the medical report generator 1850 can generate a comprehensive medical report per patient showing the patient "your medical life movie report."

The medical report generator 1850 can be configured to generate the medical report in many different formats. For example, a movie, augmented reality, virtual reality, the hologram, a podcast (audio only), a webcast (video), or for access using an interactive web-based portal. In some embodiments, the information generated for the medical report can be stored in the data structures 1880 (e.g., the data structures 1880 can be revised or updated to include information from any of the inputs to the medical report generator 1850). In some embodiments, the medical report, or the information from the medical report stored in the data structures 1880 can be used to determine eligibility of the patient for additional trials test through an auto calculation feature. In such cases, the data structures 1880 are configured to store information that is needed for determining (or auto-calculating) such eligibility, including for example information relating to the patient's age, gender, ethnicity, and/or race, wellness, allergies, pre-existing conditions, medical diagnosis, etc. In some examples, information stored in the data structures 1880 can be used to determine whether a patient fits inclusion criteria for large-scale randomized trials, determine whether patient fit criteria for appropriate use criteria or professional societal guidelines (e.g., AHA/ACC practice guidelines), determines whether patient's insurance will cover certain medications (e.g., statins vs. PCSK9 inhibitors), and determine whether a patient qualifies for certain employee benefits (e.g., exercise program). In some embodiments, the information used in the data structures 1880 can be used to determine/indicate a patient's normality, risk, treatment type and treatment benefits, and such information can be included in the medical report, for example, based on medical practitioners' preferences. Accordingly, in various embodiments, in addition to the predetermined video/information 1855 relating to greetings, test explanations, results presented, results explanation, and conclusions, the medical report generator 1850 can be configured to generate a medical report that includes information to help the medical practitioner explain the results and best way forward, the information being based at least in part on the patient's specific data (e.g., test data), including:

a. patient-specific findings.
b. comparison to normal values (age, gender, ethnicity, race-specific values of population-based norms).
c. comparison to abnormal values (e.g., comparing someone's CAD results to database of those who experienced heart attack; or another database of similar).
d. comparison to outcomes (e.g., identifying inclusion criteria for trials and medication treatments therein, and auto-calculating Kaplan Meier curves or other visual representations showing the probability of an event respective time interval (e.g., survival rate).
e. comparison to identify benefits of treatment (e.g., auto-linking to clinical trials or clinical data in order to examine the relative benefits of specific types of treatment, e.g., medication therapy with statins vs. PCSK9 inhibitors; medication treatment vs. percutaneous intervention; PCI vs. surgical bypass).
f. calculations of previously published (or unpublished) scores, e.g., CONFIRM score, SYNTAX score, etc.
g. comparisons from serial studies.
h. auto-links to EMR or patient-entered data to enable patient-specific explanation of medications and other treatments.
i. can include "test" or "quiz" at the end to promote patient engagement and ensure patient literacy.
j. interactive patient satisfaction surveys.
k. interactive with patients through patient input 1875, allowing a patient to select which information they want to view and better understand.
l. ethnically, racially and gender diversity, and allow dynamic changes in language, content based upon gender, race and ethnicity that is used to convey report to patient; and
m. adaptations for age allowing changes in language and content based upon age, timeframe born (millennial vs. baby boomer).

In some embodiments, the medical report generator 1850 can be configured to check for updates/received updates over time (e.g., auto-updating) such that the medical reports change over time and include the latest available reports. In some embodiments, the medical report generator 1850 can communicate via a network or web-based portal to include information from other medical or wearable devices. In some embodiments, the medical report generator 1850 can be configured to provide the patient patient-specific education based upon published scientific evidence and specifically curated to the patient's medical report, and auto-update the report based upon serial changes.

Figure 18F:
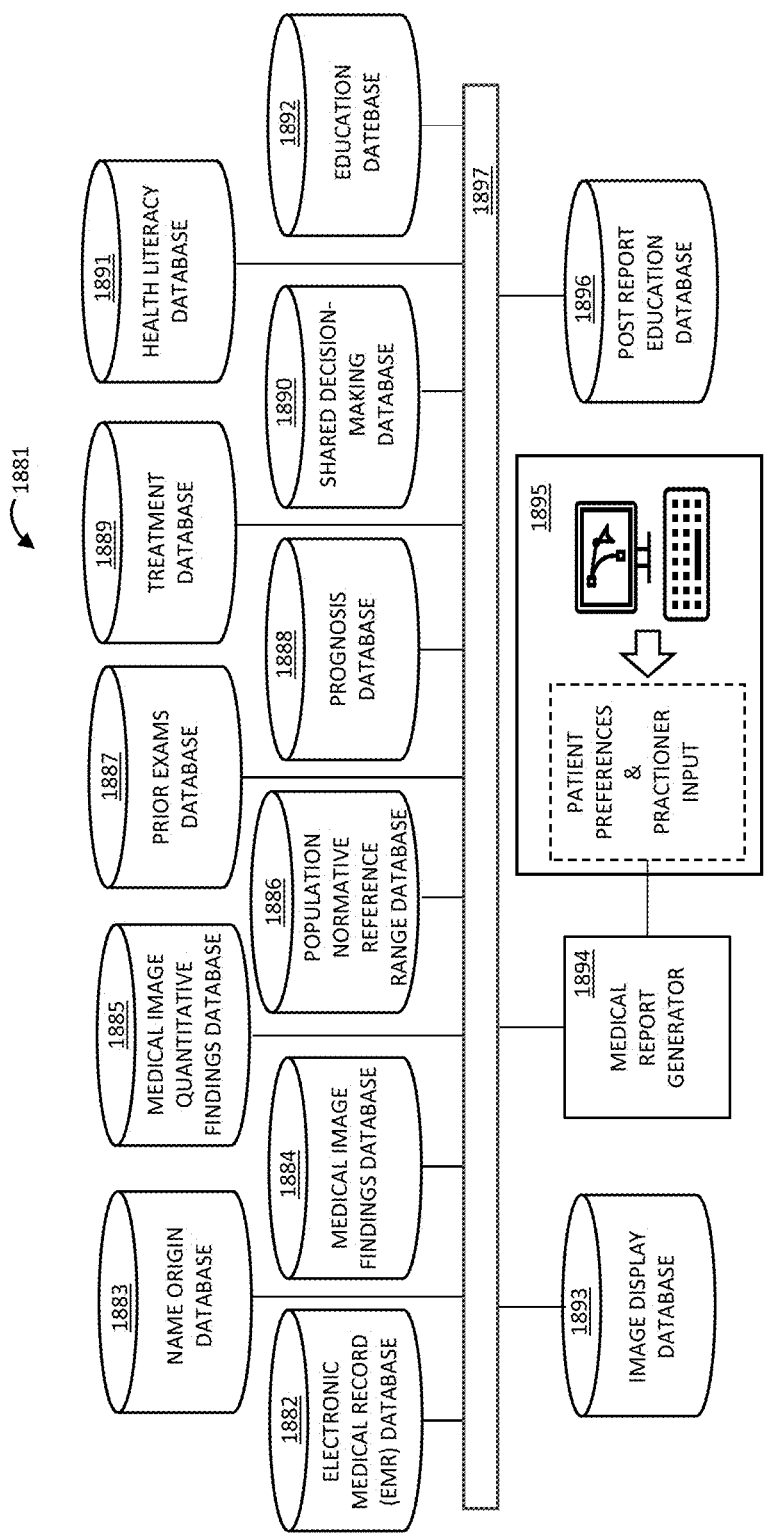
FIG. 18F is a diagram illustrating multiple structures for storing information that is used in a medical report, the information associated with a patient based on one or more characteristics of the patient, the patient's medical condition, and/or the input from the patient or a medical practitioner.

FIG. 18F is a diagram illustrating a representation of an example of a system 1881 having multiple structures for storing and accessing associated information that is used in a medical report, the information associated with a patient based on one or more of characteristics of the patient, the patient's medical condition, or an input from the patient and/or a medical practitioner. In some embodiments, the system 1881 is a representation of how the information used for generating a medical report is stored in systems of FIG. 16, 17, or 18E. In FIG. 18F, information is described as being stored in a plurality of databases. As used herein, a database refers to a way of storing information such that the information can be referenced by one or more values (e.g., other information) associated with stored information. In various embodiments, a "database" can be, for example, a database, a data storage structure, a linked list, a lookup table, etc.). In some embodiments, the database can be configured to store structured information (e.g., information of a predetermined size, for example, a name, age, gender, or other information with a predetermined maximum field size). In some embodiments, database can be configured to store structured or unstructured information (e.g., information that may or may not be predetermined, e.g., an image or a video). Stored information may be associated with any other information of the patient. For example, stored information can be associated with one or more of a characteristic of a patient (e.g., name, age, gender, ethnicity, geographic origin, education, weight, and/or height), one or more medical conditions of a patient, a prognosis for a patient's medical condition, medical treatments, etc. Although the example system 1881 in FIG. 18F illustrates having 13 different databases (e.g., for clarity of the description), in other embodiments such systems can have more or fewer databases, or certain information stored in illustrated databases can be combined with other information and stored together in the same database.

System 1881 includes a communication bus 1897, which allows the components to communicate with each other, as needed. One or more portions of the communication bus 1897 can be implemented as a wired communication bus, or implemented as a wireless communication bus. In various embodiments, the communication bus 1897 includes a plurality of communication networks, or one or more types (e.g., a larger are network (LAN), a wide area network (WAN), the Internet, or a local wireless network (e.g., Bluetooth). System 1881 also includes a medical report generator 1894, which is in communication with the communication bus 1897. The medical report generator 1894 is also in communication with one or more input components 1895, which can be used for a patient and/or a medical practitioner to interface with the medical report generator 1894 using a computer (e.g., a desktop computer, a laptop computer, a tablet computer, or a mobile device, e.g., a smart phone.

The medical report generator 1894 can communicate with any of the databases data structures using the communication bus 1897. In various embodiments, medical report generator 1894 can use information from one or more of the illustrated databases in a workflow, for generating a patient specific report, that includes patient identification, patient preferences, medical image findings, patient diagnosis, prognostication, clinical decision making, health literacy, patient education, image generation/display, and post-report education.

Patient identification is used by the medical report generator 1894 for generating an avatar that will be included in the medical report. For example, to be displayed during at least a portion of the medical report, or to be displayed and to "present" at least a portion of the medical report to the patient. Determining patient information can be based upon either active or passive methods.

Passive

In some embodiments, a medical report generator 1894 can be configured to automatically communicate with an electronic medical record (EMR) database 1893 to (for a certain patient) ascertain patient demographic characteristics to determine patient age, gender, ethnicity, and other potential relevant characteristics to understand patient biometrics (e.g., height, weight).

In some embodiments, the medical report generator 1894 can be configured to automatically query a proprietary or web-based name origin database 1883 containing names and ethnic origins of names to determine, wholly or in part, a patient's gender and ethnicity based on the patient's name and/or other patient information.

Active

In some embodiments, the medical report generator 1894 can receive input information from an interface system 1895, and the input information can be used to generate portions of the medical report. For example, a patient, family/friend member, or medical professional can enter patient age, gender and ethnicity, and other potential relevant characteristics. This can be done, for example, at the time of receiving report and in advance of playing the report; or at the time of registration of the patient into the system.

In some embodiments, the medical report generator 1894 can receive a picture of the patient through an interface system 1895, or via the communication bus 1897, and the picture can be used to generate portions of the medical report. For example, a picture of the patient can be input into the system or be taken (e.g., input as an electronic image, or input by scanning in a photograph), and the picture can be used by the medical report generator (or a system coupled to the medical report generator) to automatically morph the picture into a relevant avatar (e.g., relevant to the patient). The determination of characteristics of the avatar can done using linked image-based algorithms that determine or choose an avatar from a repository of avatars that exist within the data system, the avatar selected at least partially based on the picture of the patient.

In some embodiments, a QR code can be used for all products related to a company (e.g., Cleerly-related products) that can house information about the patient that can be used to generate the avatar.

Patient Preferences. In some embodiments, in this step the medical report generator 1902 can be configured to receive input from a patient, or a medical practitioner (e.g., via the interface system 1895) to identify the ideal or desired educational method to maximize patient understanding of the medical report. In some embodiments, the system generates graphical user interfaces (GUIs) that include options that can be selected by a patient. In some embodiments, GUIs can include one or more fields that a user (e.g., patient, medical practitioner, or another) can enter data related to a preference (e.g., the length of the report in minutes). Examples of inputs that can be received by a system are illustrated below:

Method of delivery—The patient may choose to view their medical report as a movie, in mixed reality (AR/VR), holography, podcast. In other embodiments, the method of delivery is determined at least in part by patient information.

Length of report. Some patients are more detailed than other, and would like more vs. less information.

Patients can select the length of their report (e.g., <5 minutes, 5-10 minutes, >10 minutes). In other embodiments, the length of the report is determined automatically at least in part using patient information.

Popularity of report. If patients do not know what type of report they want, the patients can select the "most popular" options. In other embodiments, the type of report is determined automatically at least in part using patient information.

Effectiveness of the report. If patients do not have a preference of what type of report they want, they can choose "most educational," which can be linked to report methods that have been demonstrated by patient voting or by scientific study to maximize healthy literacy. In other embodiments, the "effectiveness" of the report is determined automatically at least in part based on patient information.

Report delivery voice. Patients can select what type of voice they would like to hear for the report.

The medical report generator 1894 can also utilize a medical image findings database 1884 for the patient-specific medical report. There are a number of "medical image findings" that can be determined and stored in the medical image findings database 1884, and any one or more of them can be incorporated into the medical report. The following are some examples of the information that can be determined and stored in the medical image findings database 1884.

Image processing algorithms process the heart and heart arteries from a CT scan to segment:
  Coronary arteries—atherosclerosis, vascular morphology, ischemia
  Cardiovascular structures—left ventricular mass, left ventricular volume, atrial volumes, aortic dimensions, epicardial fat, fatty liver, valves Heart and heart artery findings are quantified by, for example, the following:
  Coronary artery plaque—e.g., plaque burden, volume; plaque type, percent atheroma volume, location, directionality, etc.
  Vascular morphology—e.g., lumen volume, vessel volume, arterial remodeling, anomaly, aneurysm, bridging, dissection, etc.
  Left ventricular mass—in grams or indexed to body surface area or body mass index
  Left ventricular volume—in ml or indexed to body surface area or body mass index
  Atrial volumes—in ml or indexed to body surface area or body mass index
  Aortic dimensions—in ml or indexed to body surface area or body mass index
  Epicardial fat—in ml or indexed to body surface area or body mass index
  Fatty liver—Hounsfield unit density alone or in relevance to spleen Quantified heart and heart artery findings are automatically sent to a medical image quantitative findings database 1885 that has well-defined areas for classification of each of these findings.

In some embodiments, the medical image quantitative findings database 1885 has an algorithm that links together relevant findings that comprise syndromes over single disease states.

In an example, the presence of left ventricular volume elevation, along with the presence of left atrial volume elevation, along with thickening of the mitral valve, along with a normal right atrial volume may suggest a patient with significant mitral regurgitation (or leaky mitral valve).

In another example, the presence of an increased aortic dimension and increased left ventricular mass may suggest a person has hypertension.

The medical image quantitative findings database 1885 can link to other electronic data source (e.g., company database, electronic health record, etc.) to identify potential associative relationships between study findings. For example, perhaps the electronic health record indicates the patient has hypertension, in which case, the report will automatically curate a health report card for patients specifically with hypertension, i.e., normality or left ventricular mass, atrial volume, ventricular volume, aortic dimensions.

The medical image quantitative findings database 1885 can link to the Internet to perform medical imaging finding-specific search (i.e., search is based upon the image data curation as described above). to retrieve information that may link relevant findings that comprise syndromes.

Diagnosis: morphologic classification of Heart and heart artery findings:
  Morphologic classification can be based upon:
  Comparison to a population-based normative reference range database 1886 which includes ranges that have the mean/95% confidence interval, median/interquartile interval; deciles for normality; quintiles of normality, etc. These data can also be reported in the medical report in "ages." For example, perhaps a patient's biological age is 50 years, while their heart age is 70 years based upon comparison to the age- and gender-based normative reference range database If the population-based normative reference range database 1886 does not exist in a system 1881, in some embodiments the system 1881 can search the Internet looking for these normative ranges, e.g., in PubMed search and by natural language processing and "reading" of the scientific papers.

Classification grades: can be done in many ways:
  presence/absent
  normal, mild, moderate, severe
  elevated or reduced
  percentile for age, gender and ethnicity
  Any of the above categorization systems, also accounting for other patient conditions (e.g., if a patient has hypertension, their expected plaque volume may be higher than for a patient without hypertension)

Temporal/Dynamic changes can be done and integrated into the medical report by automatic comparison of findings with a patient's prior study which exists in a specific prior exams database 1887, e.g., reporting the change that has occurred, and direct comparison to the population-based normative reference range database 1886 to determine whether this change in disease is expectedly normal, mild, moderate, severe, etc. (or other classification grading method).

Temporal/Dynamic changes may be done by comparison of >2 studies (e.g., 4 studies) in the database of patient's studies, in which changes can be reported by absolute, relative %, along a regression line, or by other mathematical transformation, with these findings compared to the population-based normative reference range database.

Prognostication

Automatic prognostication of patient outcomes can be done by integrating the medical imaging findings (±coupled to other patient data±coupled to normative reference range database) by direct interrogation of a prognosis database 1888 that exists with patient-level outcomes. The prognosis database 1888 may be a single database (e.g., of coronary plaque findings), or multiple databases (e.g., one database for coronary plaque, one database for ventricular findings, one database for non-coronary vascular findings, etc.).

In some embodiments, several and separate databases may exist for different types of prognosis, e.g., one database may exist for auto-calculation of risk of major adverse cardiovascular events (MACE), while another database may exist for auto-calculation of rapid disease progression. These databases may be interrogated sequentially, or they may be interactive with each other (e.g., a person who has a higher rate of rapid disease progression may also have a higher risk of MACE, but the presence of rapid disease progression may increase risk of MACE beyond that of someone who does not experience rapid disease progression).

Prognostic findings can be reported into the movie report by: elevated/reduced; % risk, hazards ratio, time-to-event Kaplan Meier curves, and others.

Clinical Decision Making

Automatic recommendation of treatments can be done by integrating the above findings with a treatment database 1889. The treatment database 1889 can house scientific and clinical evidence data to which a patient's medical image findings, diagnosis, syndromes and prognosis can be linked. Based upon these findings—as well as clinical trial inclusion/exclusion/eligibility criteria—a treatment recommendation can be given for a specific medication or procedure that may improve the patient's condition.

For example, perhaps a patient had a specific amount of plaque on the patient's $1^{st}$ study and that plaque progressed significantly on the patient's $2^{nd}$ study. The system will report the change as high, normal, or low based upon query of the normative reference range database and the prior studies database and, based upon this, render a prognosis. The system could then query the EMR database to see which medications the patient is currently taking, and the system finds out that the patient is taking a statin. The system could then examine the databases that would let the system know that adding a PCSK9 inhibitor medication on top of the statin medication would be associated with an XX % relative risk reduction. A similar example will be for a patient being considered for an invasive procedure.

In many cases, a treatment path is not 100% clear where there is benefit as well as risk for doing a specific kind of therapy. In this case, the system can query the shared decision database 1890, which lists the scientific evidence for treatment options, and lists all of the benefits as well as limitations of these approaches. The "pros" and "cons" of the different treatment approaches can be integrated into the patient medical report.

For example, based upon the medical image findings, normative reference comparison, prognosis evaluation and treatment query, perhaps an 81-year-old woman would highly benefit from a medication whose side effect is worsening of osteoporosis. In this case, the woman may have severe osteoporosis and for her, the benefits of the medication outweigh the risk as is illustrated and communicated through the shared decision making database. For these types of cases, an alternative may be provided.

For example, the shared decision making database may show comparative effectiveness of treatments, similar to the way Consumer Reports or amazon.com product options are listed so that the patient can understand the options, pros and cons.

The system 1881 can also include a health literacy database 1891. This portion of the workflow to produce a medical report can be an interactive "quiz" to ensure that the patient understood the study findings, the diagnosis, the prognosis, and the treatment decision making. If the patient fails the "quiz", then the system would automatically curate content into more and more simple terms so that the patient does understand their condition.

Thus, the health literacy database 1891 can be a tiered database of movies based upon simple to complex, and would be tailored to the patient's preferences as well as their score on the "quiz". This information can be kept for future movies for that patient.

The opposite can also occur. As an example, perhaps a patient passes the "quiz" and the system asks the patient whether they would like to know more about the condition. If the patient answers 'yes', then the system can extract more and more complex movies for display to the patient. In this way, the health literacy database 1891 is multilevel and interactive.

The system 1881 can also include an education database 1892, which has educational materials that are based upon science and medicine, and are redundant in content but different in delivery method.

As an example, if the system notes that the patient has a certain finding, the system can inquire with the patient whether they would like to learn more about a specific conditions. If the patient indicates 'yes,' then the system can inquire whether the patient would like to see a summary infographic page, a slide presentation, a movie, etc.

The system 1881 can also include an image display database 1893 that includes images that the medical report generator 1894 uses to morph medical images into cartoon formats, or simpler formats, that a patient can better understand.

The system can also include a post-report education database 1896 that continually uploads new information in real time related to specific medical conditions. The medical report generator 1894 can query this post-report education database 1896, and curate educational content (e.g., scientific articles, publications, presentations, etc.) that exist on the internet, and then modify them through the post-report education database 1896 to information that the patient would like to see, for example, as determined by the patient information or by a user input.

The medical report generator 1894 system can be interactive, not just passive. Different types of reports and information can be generated as a set of information for a medical report, and a user can interactively select what information to view using the interface system 1895 (e.g., a computer system of the user), and can select other information to be presented/displayed by providing input to the medical report generator 1894.

Systems and Methods for Imaging Methods of Non-Contiguous, or Different, Arterial Beds for Determining Atherosclerotic Cardiovascular Disease (ASCVD)

This portion of the disclosure relates to systems and methods for assessing atherosclerotic cardiovascular disease risk using sequential non-contiguous arterial bed imaging. Various embodiments described herein relate to quantification and characterization of sequential non-contiguous arterial bed images to generate a ASCVD assessment, or ASCVD risk score. Any risk score generated can be a suggested risk score, and a medical practitioner can use the suggested ASCVD risk score to provide a ASCVD risk score for a patient. In various embodiments, a suggested ASCVD risk score can be used to provide a ASCVD risk score to a patient based on the suggested ASCVD risk score, or with additional information.

In some embodiments, the ASCVD risk score is a calculation of your risk of having a cardiovascular problem over a duration of time, for example, 1 year, 3 years, 5 years, 10 years, or longer). In some embodiments, the cardiovascular problem can include one or more of a heart attack or stroke. However, other cardiovascular problems can also be included, that is, assessed as a risk. In some embodiments, this risk estimate considers age, sex, race, cholesterol levels, blood pressure, medication use, diabetic status, and/or smoking status. In some embodiments, the ASCVD risk score is given as a percentage. This is your chance of having heart disease or stroke in the next 10 years. There are different treatment recommendations depending on your risk score. As an example, an ASCVD risk score of 0.0 to 4.9 percent risk can be considered low. Eating a healthy diet and exercising will help keep your risk low. Medication is not recommended unless your LDL, or "bad" cholesterol, is greater than or equal to 190. An ASCVD risk score of 5.0 to 7.4 percent risk can be considered borderline. Use of a statin medication may be recommended if you have certain conditions, which may be referred to as "risk enhancers." These conditions may increase your risk of a heart disease or stroke. Talk with your primary care provider to see if you have any of the risk enhancers in the list below. An ASCVD risk score of 7.5 to 20 percent risk can be considered intermediate. Typically for a patient with a score in this range, it is recommended that a moderate-intensity statin therapy is started. An ASCVD risk score of greater than 20 percent risk can be considered high. When the ASCVD risk score indicates a high risk, it may be recommended that the patient start a high-intensity statin therapy.

Various embodiments described herein also relate to systems and methods for quantifying and characterizing ASCVD of different arterial beds, e.g., from a single imaging examination. In some embodiments, the systems and methods can quantify and characterize ASCVD of different arterial beds from two or more imaging examinations. Any of the imaging performed can be done in conjunction with a normalization device, described elsewhere herein. Various embodiments described herein also relate to systems and methods for determining an integrated metric to prognosticate ASCVD events by weighting findings from each arterial bed. Examples of systems and methods are described for quantifying and characterizing ASCVD burden, type and progression to logically guide clinical decision making through improved diagnosis, prognostication, and tracking of CAD after medical therapy or lifestyle changes. As such, some systems and methods can provide both holistic patient-level ASCVD risk assessment, as well as arterial bed-specific ASCVD burden, type and progression.

As an example relating to imaging of non-contiguous arterial beds that is done in conjunction with a normalization device, a normalization device is configured to normalize a medical image of a coronary region of a subject for an algorithm-based medical imaging analysis. In an example, a normalization device includes a substrate configured in size and shape to be placed in a medical imager along with a patient so that the normalization device and the patient can be imaged together such that at least a region of interest of the patient and the normalization device appear in a medical image taken by the medical imager, a plurality of compartments positioned on or within the substrate, wherein an arrangement of the plurality of compartments is fixed on or within the substrate, and a plurality of samples, each of the plurality of samples positioned within one of the plurality of compartments, and wherein a volume, an absolute density, and a relative density of each of the plurality of samples is known. The plurality of samples can include a set of contrast samples, each of the contrast samples comprising a different absolute density than absolute densities of the others of the contrast samples, a set of calcium samples, each of the calcium samples comprising a different absolute density than absolute densities of the others of the calcium samples, and a set of fat samples, each of the fat samples comprising a different absolute density than absolute densities of the others of the fat samples. The set contrast samples can be arranged within the plurality of compartments such that the set of calcium samples and the set of fat samples surround the set of contrast samples.

In an example, a computer implemented method for generating a risk assessment of atherosclerotic cardiovascular disease (ASCVD) uses a normalization device (as described herein) to improve accuracy of the algorithm-based imaging analysis. In some embodiments, the medical imaging method includes receiving a first set of images of a first arterial bed and a first set of images of a second arterial bed, the second arterial bed being noncontiguous with the first arterial bed, and wherein at least one of the first set of images of the first arterial bed and the first set of images of the second arterial bed are normalized using the normalization device, quantifying ASCVD in the first arterial bed using the first set of images of the first arterial bed, quantifying ASCVD in the second arterial bed using the first set of images of the second arterial bed, and determining a first ASCVD risk score based on the quantified ASCVD in the first arterial bed and the quantified ASCVD in the second arterial bed. In some embodiments, determining a first weighted assessment of the first arterial bed based on the quantified ASCVD of the first arterial bed and weighted adverse events for the first arterial bed, and determining a second weighted assessment of the second arterial bed based on the quantified ASCVD of the second arterial bed and weighted adverse events for the second arterial bed. Determining the first ASCVD risk score further comprises determining the ASCVD risk score based on the first weighted assessment and the second weighted assessment. In some embodiments, a method can further include receiving a second set of images of the first arterial bed and a second set of images of the second arterial bed, the second set of images of the first arterial bed generated subsequent to generating the first set of image of the first arterial bed, and the second set of images of the second arterial bed generated subsequent to generating the first set of image of the second arterial bed, quantifying ASCVD in the first arterial bed using the second set of images of the first arterial bed, quantifying ASCVD in the second arterial bed using the second set of images of the second arterial bed, and determining a second ASCVD risk score based on the quantified ASCVD in the first arterial bed using the second set of images, and the quantified ASCVD in the second arterial bed using the second set of images. Determining the second ASCVD risk score can be further based on the first ASCVD risk score. In some embodiments, the first arterial bed includes arteries of one of the aorta, carotid arteries, lower extremity arteries, renal arteries, or cerebral arteries. The second arterial bed includes arteries of one of the aorta, carotid arteries, lower extremity arteries, renal arteries, or cerebral arteries that are different than the arteries of the first arterial bed. Any of the methods described herein can be based on imaging using a normalization device to improve quality of the automatic image assessment of the generated images.

In an embodiment, an output of these methods can be a single patient-level risk score that can improve arterial bed-specific event-free survival in a personalized fashion. In some embodiments, any of the quantization of characterization techniques and processes described in U.S. patent application Ser. No. 17/142,120, filed Jan. 5, 2020, titled Systems, Methods, and Devices for Medical Image Analysis, Risk Stratification, Decision Making and/or Disease Tracking" (which is incorporated by reference herein), can be employed, in whole or in part, to generate a ASCVD risk assessment.

Traditional cardiovascular imaging using 3D imaging by computed tomography, magnetic resonance imaging, nuclear imaging or ultrasound have relied upon imaging single vascular beds (or territories) as regions of interest. Sometimes, multiple body parts may be imaged if they are contiguous, for example, chest-abdomen-pelvis CT, carotid and cerebral artery imaging, etc. Multi-body part imaging can be useful to identify disease processes that affect adjoining or geographically close anatomic regions. Multi-body part imaging can be used to enhance diagnosis, prognostication and guide clinical decision making of therapeutic interventions (e.g., medications, percutaneous interventions, surgery, etc.).

Additionally, methods that employ multi-body part imaging of non-contiguous arterial beds can be advantageous for enhancing diagnosis, prognostication and clinical decision making of atherosclerotic cardiovascular disease (ASCVD). ASCVD is a systemic disease that can affect all vessel beds, including coronary arteries, carotid arteries, aorta, renal arteries, lower extremity arteries, cerebral arteries and upper extremity arteries. While historically considered as a single diagnosis, the relative prevalence, extent, severity and type of ASCVD (and its consequent effects on vascular morphology) can exhibit very high variance between different arterial beds. As an example, patients with severe carotid artery atherosclerosis may have no coronary artery atherosclerosis. Alternatively, patients with severe coronary artery atherosclerosis may have milder forms of lower extremity atherosclerosis. As with the prevalence, extent and severity, so too can the types of atherosclerosis differ amongst vascular beds.

A significant body of research now clarifies the clinical significance of atherosclerotic cardiovascular disease (ASCVD) burden, type and progression, as quantified and characterized by advanced imaging. As an example, coronary computed tomographic angiography (CCTA) now allows for quantitative assessment of ASCVD and vascular morphology in all major vascular territories. Several research trials have demonstrated that not only the amount (or burden) of ASCVD, but also the type of plaque is important in risk stratification; in particular, low attenuation plaques (LAP) and non-calcified plaques which exhibit positive arterial remodeling are implicated in greater incidence of future major adverse cardiovascular events (MACE); calcified plaques and, in particular, calcified plaques of higher density appear to be more stable. Some studies that have evaluated this concept have been observational and within randomized controlled trials. Further, medication use has been associated with a reduction in LAP and an acceleration in calcified plaque formation in populations, with within-person estimates not yet reported. Medications such as statins, icosopent ethyl, and colchicine have been observed by coronary computed tomography angiography (CCTA) to be associated with modification of ASCVD in the coronary arteries. Similar findings relating the complexity or type of ASCVD in the carotid arteries has been espoused as an explanation for stroke, as well as for renal arteries and lower extremity arteries.

Accordingly, understanding the presence, extent, severity and type of ASCVD in each of the vascular arterial beds improves understanding of future risk of adverse cardiovascular events as well as the types of adverse cardiovascular events that will occur (e.g., heart attack versus stroke versus amputation, etc.), and can allow tracking of the effects of salutary medication and lifestyle modifications on the disease process in multiple arterial beds. Further, integrating the findings from non-contiguous arterial beds into a single prediction model can improve holistic assessment of an individual's risk and response to therapy over time in a personalized, precision-based fashion. In some examples, such assessments can include integrating an assessment of coronary arteries with an assessment of one or more other arterial beds, for example, one or more of the aorta, carotid arteries, lower extremity arteries, upper extremity arteries, renal arteries, and cerebral arteries. In some examples, such assessments can include integrating an assessment of any of the aorta, carotid arteries, lower extremity arteries, upper extremity arteries, renal arteries, or cerebral arteries with a different one of the aorta, carotid arteries, lower extremity arteries, upper extremity arteries, renal arteries, or cerebral arteries.

Various embodiments described herein relate to systems and methods for determining assessments that may be used for reducing cardiovascular risk and/or events. For example, such assessments can be used to, at least partly, determine or generate lifestyle, medication and/or interventional therapies based upon actual atherosclerotic cardiovascular disease (ASCVD) burden, ASCVD type, and/or and ASCVD progression. In some embodiments, the systems and methods described herein are configured to dynamically and/or automatically analyze medical image data, such as for example non-invasive CT, MRI, and/or other medical imaging data of the arterial beds of a patient, to generate one or more measurements indicative or associated with the actual ASCVD burden, ASCVD type, and/or ASCVD progression, for example using one or more artificial intelligence (AI) and/or machine learning (ML) algorithms. The arterial beds can include for example, coronary arteries, carotid arteries, and lower extremity arteries, renal arteries, and/or cerebral arteries. In some embodiments, the systems and methods described herein can further be configured to automatically and/or dynamically generate assessments that can be used in one or more patient-specific treatments and/or medications based on the actual ASCVD burden, ASCVD type, and/or ASCVD progression, for example using one or more artificial intelligence (AI) and/or machine learning (ML) algorithms.

In some embodiments, the systems and methods described herein are configured to utilize one or more CCTA algorithms and/or one or more medical treatment algorithms on two or more arterial bodies to quantify the presence, extent, severity and/or type of ASCVD, such as for example its localization and/or peri-lesion tissues. In some embodiments, the one or more medical treatment algorithms are configured to analyze any medical images obtained from any imaging modality, such as for example computed tomography (CT), magnetic resonance (MR), ultrasound, nuclear medicine, molecular imaging, and/or others. In some embodiments, the systems and methods described herein are configured to utilize one or more medical treatment algorithms that are personalized (rather than population-based), treat actual disease (rather than surrogate markers of disease, such as risk factors), and/or are guided by changes in CCTA-identified ASCVD over time (such as for example, progression, regression, transformation, and/or stabilization). In some embodiments, the one or more CCTA algorithms and/or the one or more medical treatment algorithms are computer-implemented algorithms and/or utilize one or more AI and/or ML algorithms.

In some embodiments, the systems and methods are configured to assess a baseline ASCVD in an individual using two or more arterial bodies. In some embodiments, the systems and methods are configured to evaluate ASCVD by utilizing coronary CT angiography (CCTA). In some embodiments, the systems and methods are configured to identify and/or analyze the presence, local, extent, severity, type of atherosclerosis, peri-lesion tissue characteristics, and/or the like. In some embodiments, the method of ASCVD evaluation can be dependent upon quantitative imaging algorithms that perform analysis of coronary, carotid, and/or other vascular beds (such as, for example, lower extremity, aorta, renal, and/or the like).

In some embodiments, the systems and methods are configured to categorize ASCVD into specific categories based upon risk. For example, some example of such categories can include: Stage 0, Stage I, Stage II, Stage III; or none, minimal, mild, moderate; or primarily calcified vs. primarily non-calcified; or X units of low density non-calcified plaque); or X % of NCP as a function of overall volume or burden. In some embodiments, the systems and methods can be configured to quantify ASCVD continuously. In some embodiments, the systems and methods can be configured to define categories by levels of future ASCVD risk of events, such as heart attack, stroke, amputation, dissection, and/or the like. In some embodiments, one or more other non-ASCVD measures may be included to enhance risk assessment, such as for example cardiovascular measurements (left ventricular hypertrophy for hypertension; atrial volumes for atrial fibrillation; fat; etc.) and/or non-cardiovascular measurements that may contribute to ASCVD (e.g., emphysema). In some embodiments, these measurements can be quantified using one or more CCTA algorithms.

In some embodiments, the systems and methods described herein can be configured to generate a personalized or patient-specific treatment based on an assessment of two or more arterial bodies. More specifically, in some embodiments, the systems and methods can be configured to generate therapeutic recommendations based upon ASCVD presence, extent, severity, and/or type. In some embodiments, rather than utilizing risk factors (such as, for example, cholesterol, diabetes), the treatment algorithm can comprise and/or utilize a tiered approach that intensifies medical therapy, lifestyle, and/or interventional therapies based upon ASCVD directly in a personalized fashion. In some embodiments, the treatment algorithm can be configured to generally ignore one or more conventional markers of success—such as lowering cholesterol, hemoglobin A1C, etc.—and instead leverage ASCVD presence, extent, severity, and/or type of disease to guide therapeutic decisions of medical therapy intensification. In some embodiments, the treatment algorithm can be configured to combine one or more conventional markers of success—such as lowering cholesterol, hemoglobin A1C, etc., with ASCVD presence, extent, severity, and/or type of disease to guide therapeutic decisions of medical therapy intensification. In some embodiments, the treatment algorithm can be configured to combine one or more novel markers of success—such as genetics, transcriptomics, or other 'omic measurements—with ASCVD presence, extent, severity, and/or type of disease to guide therapeutic decisions of medical therapy intensification. In some embodiments, the treatment algorithm can be configured to combine one or more other imaging markers of success—such as carotid ultrasound imaging, abdominal aortic ultrasound or computed tomography, lower extremity arterial evaluation, and others—with ASCVD presence, extent, severity, and/or type of disease to guide therapeutic decisions of medical therapy intensification.

In some embodiments, the systems and methods are configured to update personalized treatment based upon response assessment of two or more arterial bodies. In particular, in some embodiments, based upon the change in ASCVD between the baseline and follow-up CCTA, personalized treatment can be updated and intensified if worsening occurs or de-escalated/kept constant if improvement occurs. As a non-limiting example, if stabilization has occurred, this can be evidence of the success of the current medical regimen. Alternatively, as another non-limiting example, if stabilization has not occurred and ASCVD has progressed, this can be evidence of the failure of the current medical regimen, and an algorithmic approach can be taken to intensify medical therapy.

To facilitate an understanding of the systems and methods discussed herein, several terms are described below. These terms, as well as other terms used herein, should be construed to include the provided descriptions, the ordinary and customary meanings of the terms, and/or any other implied meaning for the respective terms, wherein such construction is consistent with context of the term. Thus, the descriptions below do not limit the meaning of these terms, but only provide example descriptions.

Presence of ASCVD: This can be the presence vs. absence of plaque; or the presence vs. absence of non-calcified plaque; or the presence vs. absence of low attenuation plaque Extent of ASCVD: This can include the following:
Total ASCVD Volume
Percent atheroma volume (atheroma volume/vessel volume×100)
Total atheroma volume normalized to vessel length (TAV-norm).
Diffuseness (% of vessel affected by ASCVD)
Severity of ASCVD: This can include the following:
ASCVD severity can be linked to population-based estimates normalized to age, gender, ethnicity, and/or CAD risk factors
Angiographic stenosis≥70% or ≥50% in none, 1-, 2-, or 3-VD
Type of ASCVD: This can include the following:
Proportion (ratio, %, etc.) of plaque that is non-calcified vs. calcified
Proportion of plaque that is low attenuation non-calcified vs. non-calcified vs. low density calcified vs. high-density calcified
Absolute amount of non-calcified plaque and calcified plaque
Absolute amount of plaque that is low attenuation non-calcified vs. non-calcified vs. low density calcified vs. high-density calcified
Continuous grey-scale measurement of plaques without ordinal classification
Vascular remodeling imposed by plaque as positive remodeling (≥1.10 or ≥1.05 ratio of vessel diameter/normal reference diameter; or vessel area/normal reference area; or vessel volume/normal reference volume) vs. negative remodeling (≤1.10 or ≤1.05)
Vascular remodeling imposed by plaque as a continuous ratio ASCVD Progression Progression can be defined as rapid vs. non-rapid, with thresholds to define rapid progression (e.g., >1.0% percent atheroma volume, >200 mm3 plaque, etc.)

Serial changes in ASCVD can include rapid progression; progression with primarily calcified plaque formation; progression with primarily non-calcified plaque formation; and regression.

Categories of Risk

Stages: 0, I, II, or III based upon plaque volumes associated with angiographic severity (none, non-obstructive, and obstructive 1VD, 2VD and 3VD)

Percentile for age and gender and ethnicity and presence of risk factor (e.g., diabetes, hypertension, etc.)

% calcified vs. % non-calcified as a function of overall plaque volume

X units of low density non-calcified plaque

Continuous 3D histogram analysis of grey scales of plaque by lesion, by vessel and by patient Risk can be defined in a number of ways, including risk of MACE, risk of angina, risk of ischemia, risk of rapid progression, risk of medication non-response, etc.

Certain features in embodiments of systems and methods relating to determining an assessment of non-contiguous arterial beds are described below.

Medical Imaging of Non-Contiguous Arterial Beds

Systems and methods described herein also relate to medical imaging of non-contiguous arterial beds. For example, imaging of non-contiguous arterial beds in a single imaging examination. In other embodiments, imaging of non-contiguous arterial beds in two or more imaging examinations, and the information from the generated images can be used to determine information relating to a patient's health. As an example, coronary artery and carotid arteries are imaged using the same contrast bolus. In this case, the coronary arteries can be imaged by CCTA. Immediately after CCTA image acquisition, the CT table moves and images the carotid artery using the same or supplemental contrast dose. The example here is given for CT imaging in a single examination, but can be also applied to combining information from multiple imaging examinations; or multi-modality imaging integration (e.g., ultrasound of the carotid; computed tomography of the coronary)

Automated Arterial Bed-Specific Risk Assessment

This is accomplished by an automated method for quantification and characterization of ASCVD in individual artery territories for improved diagnosis, prognostication, clinical decision making and tracking of disease changes over time. These findings may be arterial bed-specific. As an example, conversion of non-calcified plaque to calcified plaque may be a feature that is considered beneficial and a sign of effective medical therapy in the coronaries, but may be considered to be a pathologic process in the lower extremity arteries. Further, the prognostication enabled by the quantification and characterization of ASCVD in different artery territories may differ. As an example, untoward findings in the carotid arteries may prognosticate future stroke; while untoward findings in the coronary arteries may prognostic future myocardial infarction. Partial overlap of risk may occur, e.g., wherein adverse findings in the carotid arteries may be associated with an increase in coronary artery events.

Patient-Specific Risk Assessment

By combining the findings from each arterial bed, along with relative weighting of arterial bed findings, risk stratification, clinical decision making and disease tracking can be done with greater precision in a personalized fashion.

Thus, patient-level prediction models are based upon understanding the ASCVD findings of non-contiguous arterial beds but communicated as a single integrated metric (e.g., 1-100, mild/moderate/severe risk, etc.)

Longitudinal Updating of Arterial Bed- and Patient-Specific Risk

By longitudinal serial imaging after treatment changes (e.g., medication, lifestyle, and others), changes in ASCVD can be quantified and characterized and both arterial bed-specific as well as patient-level risk can be updated based upon the changes as well as the most contemporary ASCVD image findings.

Figure 19A:
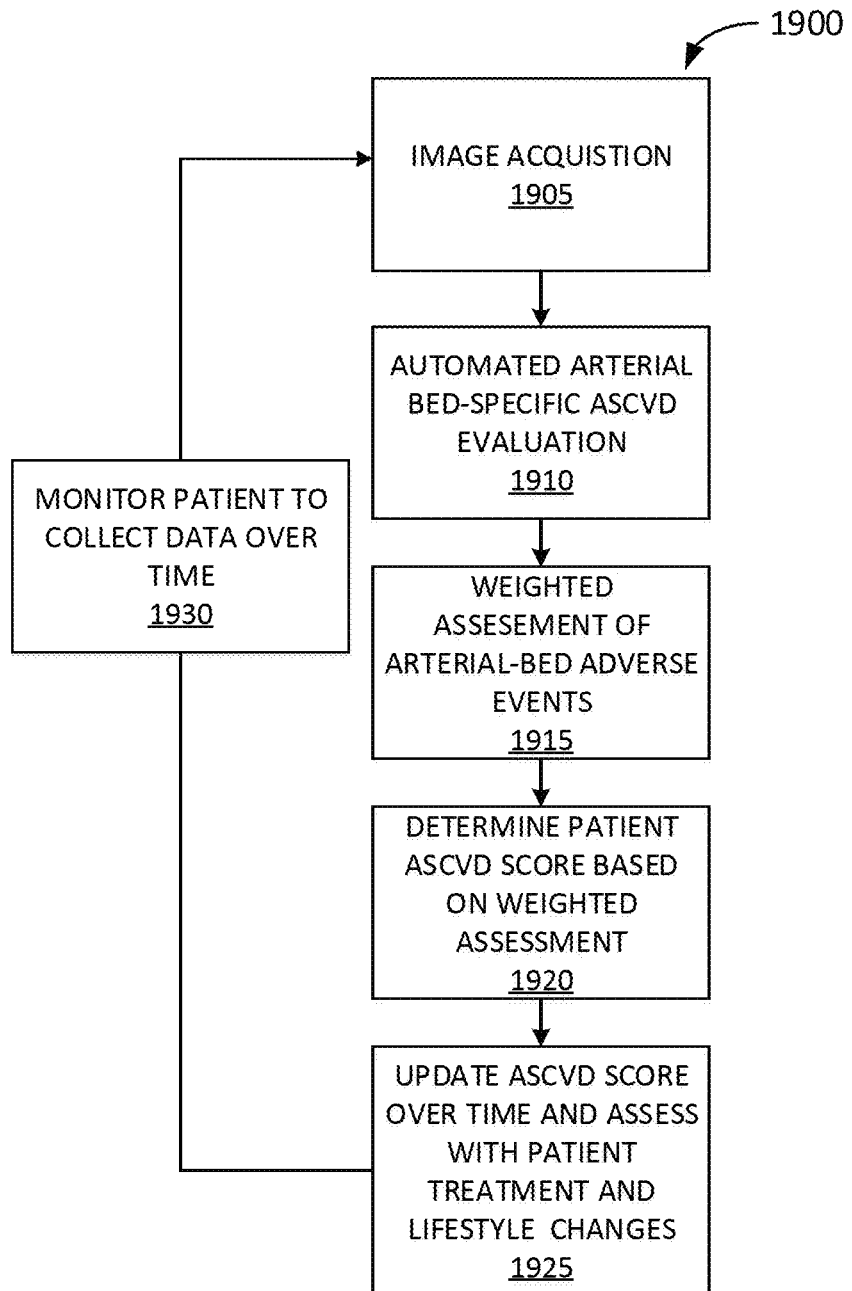
FIG. 19A illustrates an example of a process for determining a risk assessment using sequential imaging of non-contiguous arterial beds of a patient, according to some embodiments.

FIG. 19A illustrates an example of a process 1900 for determining a risk assessment using sequential imaging of noncontiguous arterial beds of patient, according to some embodiments. At block 1905, sequential imaging of non-contiguous arterial beds of a patient may be performed. An example, sequential imaging be noncontiguous first arterial bed second arterial bed performed. In some embodiments, the first arterial bed includes one of aorta, carotid arteries, lower extremity arteries, upper extremity arteries, renal arteries, or cerebral arteries, and the second arterial bed includes a different one of aorta, carotid arteries, lower extremity arteries, upper extremity arteries, renal arteries, or cerebral arteries. In some embodiments the third arterial bed may be imaged. In some embodiments a fourth arterial bed may be imaged. The third and fourth arterial beds may include one of aorta, carotid arteries, lower extremity arteries, upper extremity arteries, renal arteries, or cerebral arteries. The sequential imaging of the noncontiguous arterial beds may be done the same settings on the imaging machine, at different times, or with different imaging modalities, for example, CT and ultrasound).

At block 1910, the process 1900 automatically quantifies and characterizes ASCVD in the imaged arterial beds. In some embodiments, the ASCVD in the first arterial bed and the second arterial bed are quantified and characterized using any of the qualifications and characterization disclosed herein. For example, images of the first arterial bed are analyzed by a system configured with a machine learning program that has been trained on a plurality of arterial bed images and annotated features of arterial bed images. In other embodiments, the ASCVD and the first arterial bed and second arterial bed are quantified using other types of qualifications the characterizations.

At block 1915, the process 1900 generates a prognostic assessment of arterial bed specific adverse events. An example, for the coronary arteries the adverse event can be a heart attack. In another example, for the carotid arteries the adverse event is a stroke. In another example, for the lower extremity arteries the adverse event is amputation. The adverse events can be determined from patient information that is accessible to the system performing the assessment. For example, from archived patient medical information (e.g., patient medical information 1602 illustrated in FIG. 16) or any other stored information of a previous adverse event. Each event can be associated with a weight based on a predetermined scheme. The weights can be, for example, a value between 0.00 and 1.00. The weights associated with different adverse events can be stored in a non-transient storage medium, for example, a database. For a patient, a weighted assessment of each particular occurrence of an adverse event can be determined. In some embodiments, the weights are multiplied by the event. For example, for a $1^{st}$ occurrence of event 1 that has a weight of 0.05, one occurrence of that event results in a weighted assessment of 00.05. A second occurrence of event 1 may have the same weight, or a different weight. For example, an increased weight. In one example, a second occurrence of event 1 has a weight of 0.15, such that when two occurrences of the event occur the weighted assessment is the sum of the weights of the first and second occurrence (for example, 0.20). Other events can have difference weights, and the weighted assessment can include the sum of all of the weights for all of the events that occurred.

At block 1920, the process 1900 uses the arterial bed specific risk assessment to determine a patient level risk score, for example, an ASCVD risk score. In an example, the ASCVD risk score is based on a weighted assessment of an arterial bed. In an example, the ASCVD risk score is based on a weighted assessment of an arterial bed and other patient information.

At block 1925, the process 1900 tracks changes in ASCVD based upon treatment and lifestyle to determine beneficial or adverse changes in ASCVD. In some embodiments, as indicated in block 1930, the process 1900 uses additional sequential imaging, taken at a different time (e.g., days, weeks, months or years later) of one or more noncontiguous arterial beds and the process 1900 updates arterial bed and patient level risk assessments, and determines an updated ASCVD score based on the additional imaging. The baseline and updated assessment can also integrate non-imaging findings that are associated with arterial bed- and patient-specific risk. These may include laboratory tests (e.g., troponin, b-type natriuretic peptide, etc.); medication type, dose and duration (e.g., lovastatin 20 mg per day for 6 years); interactions between multiple medications (e.g., lovastatin alone versus lovastatin plus ezetimibe); biometric information (e.g., heart rate, heart rate variability, pulse oximetry, etc.) and patient history (e.g., symptoms, family history, etc.). By monitoring the ASCVD score and correlating changes in the ASCVD score with patient treatment(s) and patient lifestyle changes, better treatment protocols and lifestyle choices for that patient may be determined.

Figure 19B:
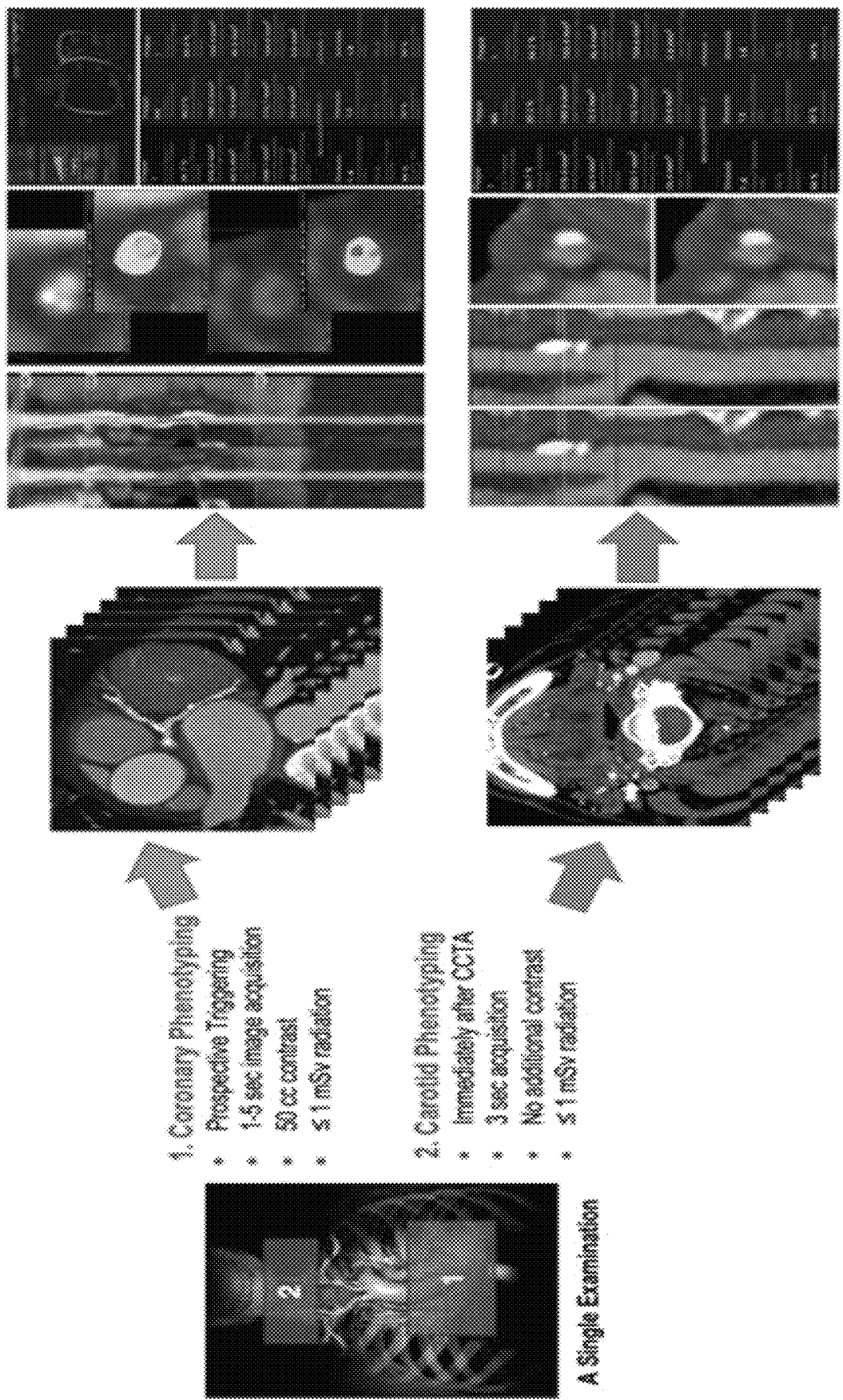
FIG. 19B illustrates an example where sequential non-contiguous arterial bed imaging is performed for the coronary arteries.

FIG. 19B illustrates an example where a sequential, non-contiguous arterial bed imaging is performed. In this example, a sequential, non-contiguous arterial bed imaging is performed for the (1) coronary arteries, and for the (2) carotid arteries. As can be seen in the quantification and characterization of the atherosclerosis in both the coronary and carotid arteries, the phenotypic makeup of the disease process is highly variable, with the coronary artery cross-sections showing both blue (calcified) and red (low-density non-calcified) plaque; and the carotid artery cross-sections only showing yellow (non-calcified) and red (low-density non-calcified plaque). Further, the amount of atherosclerosis is higher in the coronary arteries than the carotid arteries, indicating a differential risk of heart attack and stroke, respectively.

Figure 19C:
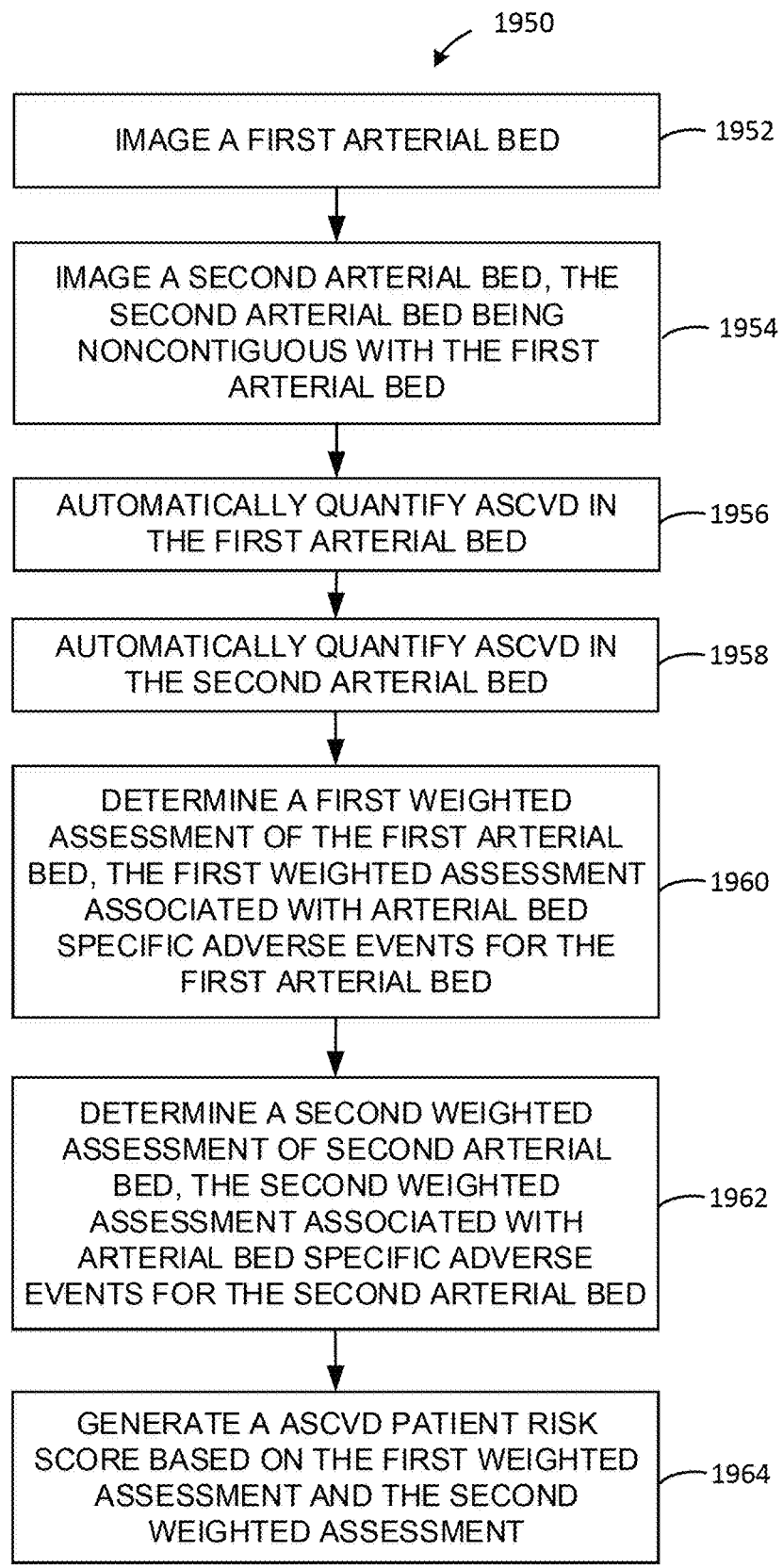
FIG. 19C is an example of a process for determining a risk assessment using sequential imaging of non-contiguous arterial beds, according to some embodiments.

FIG. 19C is an example of a process 1950 for determining a risk assessment of atherosclerotic cardiovascular disease (ASCVD) using sequential imaging of non-contiguous arterial beds, according to some embodiments. At block 1952 a first arterial bed of a patient is imaged. In some embodiments, the first arterial bed includes one of an aorta, carotid arteries, lower extremity arteries, upper extremity arteries, renal arteries, or cerebral arteries. In some embodiments, the imaging used can be digital subtraction angiography (DSA), duplex ultrasound (DUS), computed tomography (CT), magnetic resonance angiography (MRA), ultrasound, or magnetic resonance imaging (MRI), or another type of imaging that generates a representation of the arterial bed. At block 1954 the process 1950 images a second arterial bed. The imaging of the second arterial bed is noncontiguous with the first arterial bed. In some embodiments, the second arterial bed can be one of an aorta, carotid arteries, lower extremity arteries, upper extremity arteries, renal arteries, or cerebral arteries in his different than the first arterial bed. In some embodiments, imaging the second arterial bed can be performed by a DSA, DUS, CT, MRA, ultrasound, or MRI imaging process, or another imaging process. At block 1956 the process 1950 automatically quantifies ASCVD in the first arterial bed. At block 1958, the process 1950 automatically quantifies ASCVD in the second arterial bed. The quantification of ASCVD in the first arterial bed and the second arterial bed can be done using any of the quantification disclosed herein (e.g., using a neural network trained with annotated images) or other quantification.

At block 1960, the process 1950 determines a first weighted assessment of the first arterial bed, the first weighted assessment associated with arterial bed specific adverse events for the first arterial bed. At block 1962 the process 1950 determines a second weighted assessment of second arterial bed, the second weighted assessment associated with arterial bed specific adverse events for the second arterial bed. At block 1964 the process 1950 generates an ASCVD patient risk score based on the first weighted assessment and the second weighted assessment.

Figure 19D:
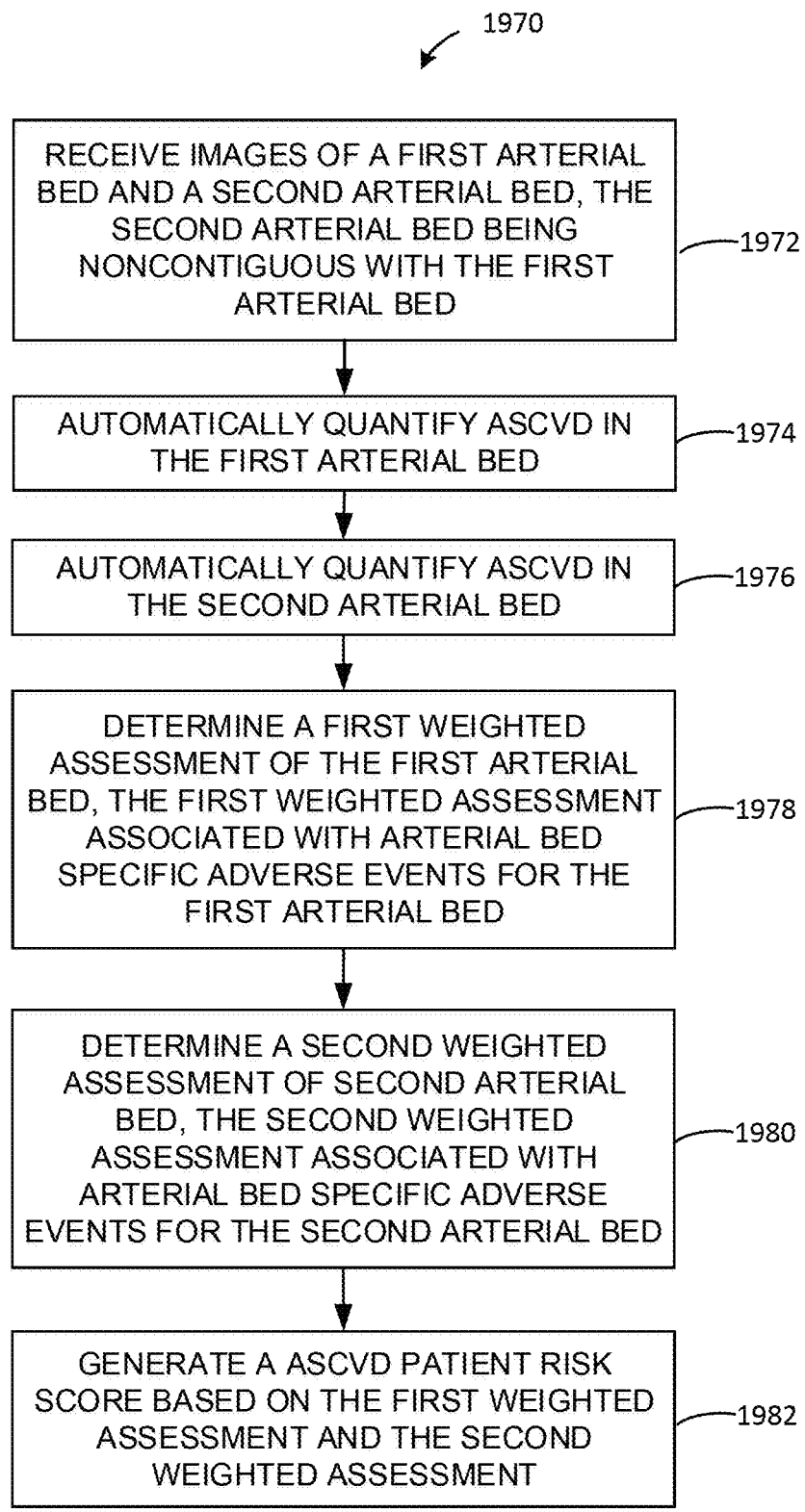
FIG. 19D is an example of a process for determining a risk assessment using sequential imaging of non-contiguous arterial beds, according to some embodiments.

FIG. 19D is an example of a process 1970 for determining a risk assessment using sequential imaging of non-contiguous arterial beds, according to some embodiments. At block 1972, the process 1970 receives images of the first arterial bed and a second arterial bed, the second arterial bed being noncontiguous with the first arterial bed and different than the first arterial bed. In some embodiments, the first arterial bed can be one of an aorta, carotid arteries, lower extremity arteries, upper extremity arteries, renal arteries, or cerebral arteries. The imaging of the second arterial bed is noncontiguous with the first arterial bed. In some embodiments, the images of the first arterial bed were generated by a DSA, DUS, CT, MRA, ultrasound, or MRI imaging process, or another imaging process. In some embodiments, the images of the second arterial bed were generated by a DSA, DUS, CT, MRA, ultrasound, or MM imaging process, or another imaging process. In some embodiments, the second arterial bed can be one of an aorta, carotid arteries, lower extremity arteries, upper extremity arteries, renal arteries, or cerebral arteries, and is different than the first arterial bed. In some embodiments, the images of the first arterial bed and the second arterial bed may be received from a computer storage medium that is configured to store patient images. In some embodiments, the images of the first arterial bed and the second arterial bed may be received directly from a facility which generates the images. In some embodiments, the images of the first arterial bed and second arterial bed may be received indirectly from a facility which generates the images. In some embodiments, images of first arterial bed may be received from a different source than images of second arterial bed.

At block 1974 the process 1970 automatically quantifies ASCVD in the first arterial bed. At block 1976, the process 1970 automatically quantifies ASCVD in the second arterial bed. The quantification of ASCVD in the first arterial bed and the second arterial bed can be done using any of the quantification disclosed herein, or other quantification.

At block 1978 the process 1970 determines a first weighted assessment of the first arterial bed, the first weighted assessment associated with arterial bed specific adverse events for the first arterial bed. At block 1980 the process 1970 determines a second weighted assessment of second arterial bed, the second weighted assessment associated with arterial bed specific adverse events for the second arterial bed. At block 1982 the process 1970 generates an ASCVD patient risk score based on the first weighted assessment and the second weighted assessment.

Figure 19E:
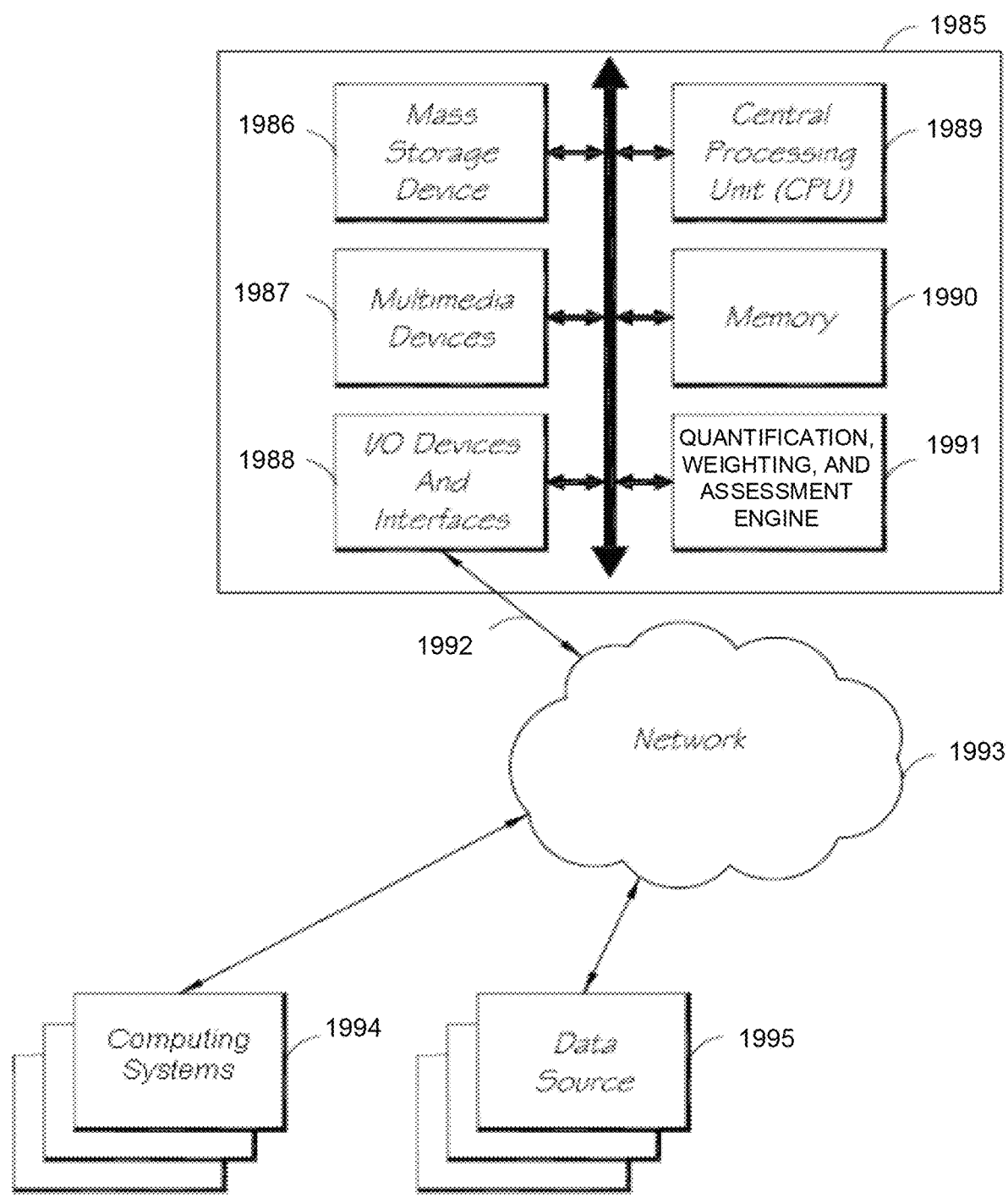
FIG. 19E is a block diagram depicting an embodiment of a computer hardware system configured to run software for implementing one or more embodiments of systems and methods for determining a risk assessment using sequential imaging of noncontiguous arterial beds of a patient.

FIG. 19E is a block diagram depicting an embodiment of a computer hardware system 1985 configured to run software for implementing one or more embodiments of systems and methods for determining a risk assessment using sequential imaging of noncontiguous arterial beds of a patient. In some embodiments, the systems, processes, and methods described herein are implemented using a computing system, such as the one illustrated in FIG. 19E. The example computer system 1985 is in communication with one or more computing systems 1994 and/or one or more data sources 1995 via one or more networks 1993. While FIG. 19E illustrates an embodiment of a computing system 1985, it is recognized that the functionality provided for in the components and modules of computer system 1985 can be combined into fewer components and modules, or further separated into additional components and modules.

The computer system 1985 can comprise a Quantification, Weighting, and Assessment Engine 1991 that carries out the functions, methods, acts, and/or processes described herein. For example, in some embodiments the functions of blocks 1956, 1958, 1960, 1962, and 1964 of FIG. 19C. In some embodiments, the functions of blocks 1972, 1974, 1976, 1978, 1980, and 1982 of FIG. 19D. The Quantification, Weighting, and Assessment Engine 1991 is executed on the computer system 1985 by a central processing unit 1989 discussed further below.

In general the word "engine," as used herein, refers to logic embodied in hardware or firmware or to a collection of software instructions, having entry and exit points. Such "engines" may also be referred to as a module, and are written in a program language, such as JAVA, C, or C++, or the like. Software modules can be compiled or linked into an executable program, installed in a dynamic link library, or can be written in an interpreted language such as BASIC, PERL, LAU, PHP or Python and any such languages. Software modules can be called from other modules or from themselves, and/or can be invoked in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems, and can be stored on or within any suitable computer readable medium, or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 1985 includes one or more processing units (CPU, GPU, TPU) 1989, which can comprise a microprocessor. The computer system 1985 further includes a physical memory 1990, such as random access memory (RAM) for temporary storage of information, a read only memory (ROM) for permanent storage of information, and a mass storage device 1986, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 1985 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1985 includes one or more input/output (I/O) devices and interfaces 1988, such as a keyboard, mouse, touch pad, and printer. The I/O devices and interfaces 1988 can include one or more display devices, such as a monitor, that allows the visual presentation of data to a user. More particularly, a display device provides for the presentation of GUIs as application software data, and multi-media presentations, for example. The I/O devices and interfaces 1988 can also provide a communications interface to various external devices. The computer system 1985 can comprise one or more multi-media devices 1985, such as speakers, video cards, graphics accelerators, and microphones, for example.

Computing System Device/Operating System

The computer system 1985 can run on a variety of computing devices, such as a server, a Windows server, a Structure Query Language server, a Unix Server, a personal computer, a laptop computer, and so forth. In other embodiments, the computer system 1985 can run on a cluster computer system, a mainframe computer system and/or other computing system suitable for controlling and/or communicating with large databases, performing high volume transaction processing, and generating reports from large databases. The computing system 1985 is generally controlled and coordinated by an operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 1985 illustrated in FIG. 19E is coupled to a network 1993, such as a LAN, WAN, or the Internet via a communication link 1992 (wired, wireless, or a combination thereof). Network 1993 communicates with various computing devices and/or other electronic devices. Network 1993 is communicating with one or more computing systems 1994 and one or more data sources 1995. For example, the computer system 1985 can receive image information (e.g., including images of arteries or an arterial bed, information associated to the images, etc.) from computing systems 1994 and/or data source 1995 via the network 1993 and store the received image information in the mass storage device 1986. The Quantification, Weighting, and Assessment Engine 1991 can then access the mass storage device 1986 as needed to. In some embodiments, the Quantification, Weighting, and Assessment Engine 1991 can access computing systems 1994 and/or data sources 1995, or be accessed by computing systems 1985 and/or data sources 1995, through a web-enabled user access point. Connections can be a direct physical connection, a virtual connection, and other connection type. The web-enabled user access point can comprise a browser module that uses text, graphics, audio, video, and other media to present data and to allow interaction with data via the network 1993.

The output module can be implemented as a combination of an all-points addressable display such as a cathode ray tube (CRT), a liquid crystal display (LCD), a plasma display, or other types and/or combinations of displays. The output module can be implemented to communicate with input devices 1988 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

Other Systems

The computing system 1985 can include one or more internal and/or external data sources (for example, data sources 1995). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1985 can also access one or more databases 1995. The data sources 1995 can be stored in a database or data repository. The computer system 1985 can access the one or more data sources 1995 through a network 1993 or can directly access the database or data repository through I/O devices and interfaces 1988. The data repository storing the one or more data sources 1995 can reside within the computer system 1985.

Additional Detail—General

In connection with any of the features and/or embodiments described herein, in some embodiments, the system can be configured to analyze, characterize, track, and/or utilize one or more plaque features derived from a medical image. For example, in some embodiments, the system can be configured to analyze, characterize, track, and/or utilize one or more dimensions of plaque and/or an area of plaque, in two dimensions, three dimensions, and/or four dimensions, for example over time or changes over time. In addition, in some embodiments, the system can be configured to rank one or more areas of plaque and/or utilize such ranking for analysis. In some embodiments, the ranking can be binary, ordinal, continuous, and/or mathematically transformed. In some embodiments, the system can be configured to analyze, characterize, track, and/or utilize the burden or one or more geometries of plaque and/or an area of plaque. For example, in some embodiments, the one or more geometries can comprise spatial mapping in two dimensions, three dimensions, and/or four dimensions over time. As another example, in some embodiments, the system can be configured to analyze transformation of one or more geometries. In some embodiments, the system can be configured to analyze, characterize, track, and/or utilize diffuseness of plaque regions, such as spotty v. continuous. For example, in some embodiments, pixels or voxels within a region of interest can be compared to pixels or voxels outside of the region of interest to gain more information. In particular, in some embodiments, the system can be configured to analyze a plaque pixel or voxel with another plaque pixel or voxel. In some embodiments, the system can be configured to compare a plaque pixel or voxel with a fat pixel or voxel. In some embodiments, the system can be configured to compare a plaque pixel or voxel with a lumen pixel or voxel. In some embodiments, the system can be configured to analyze, characterize, track, and/or utilize location of plaque or one or more areas of plaque. For example, in some embodiments, the location of plaque determined and/or analyzed by the system can include whether the plaque is within the left anterior descending (LAD), left circumflex artery (LCx), and/or the right coronary artery (RCA). In particular, in some embodiments, plaque in the proximal LAD can influence plaque in the mid-LAD, and plaque in the LCx can influence plaque in the LAD, such as via mixed effects modeling. As such, in some embodiments, the system can be configured to take into account neighboring structures. In some embodiments, the location can be based on whether it is in the proximal, mid, or distal portion of a vessel. In some embodiments, the location can be based on whether a plaque is in the main vessel or a branch vessel. In some embodiments, the location can be based on whether the plaque is myocardial facing or pericardial facing (for example as an absolute binary dichotomization or as a continuous characterization around 360 degrees of an artery), whether the plaque is juxtaposed to fat or epicardial fat or not juxtaposed to fat or epicardial fat, subtending a substantial amount of myocardium or subtending small amounts of myocardium, and/or the like. For example, arteries and/or plaques that subtend large amounts of subtended myocardium can behave differently than those that do not. As such, in some embodiments, the system can be configured to take into account the relation to the percentage of subtended myocardium.

In connection with any of the features and/or embodiments described herein, in some embodiments, the system can be configured to analyze, characterize, track, and/or utilize one or more peri-plaque features derived from a medical image. In particular, in some embodiments, the system can be configured to analyze lumen, for example in two dimensions in terms of area, three dimensions in terms of volume, and/or four dimensions across time. In some embodiments, the system can be configured to analyze the vessel wall, for example in two dimensions in terms of area, three dimensions in terms of volume, and/or four dimensions across time. In some embodiments, the system can be configured to analyze peri-coronary fat. In some embodiments, the system can be configured to analyze the relationship to myocardium, such as for example a percentage of subtended myocardial mass.

In connection with any of the features and/or embodiments described herein, in some embodiments, the system can be configured to analyze and/or use medical images obtained using different image acquisition protocols and/or variables. In some embodiments, the system can be configured to characterize, track, analyze, and/or otherwise use such image acquisition protocols and/or variables in analyzing images. For example, image acquisition parameters can include one or more of mA, kVp, spectral CT, photon counting detector CT, and/or the like. Also, in some embodiments, the system can be configured to take into account ECG gating parameters, such as retrospective v. prospective ECG helical. Another example can be prospective axial v. no gating. In addition, in some embodiments, the system can be configured to take into account whether medication was used to obtain the image, such as for example with or without a beta blocker, with or without contrast, with or without nitroglycerin, and/or the like. Moreover, in some embodiments, the system can be configured to take into account the presence or absence of a contrast agent used during the image acquisition process. For example, in some embodiments, the system can be configured to normalize an image based on a contrast type, contrast-to-noise ratio, and/or the like. Further, in some embodiments, the system can be configured to take into account patient biometrics when analyzing a medical image. For example, in some embodiments, the system can be configured to normalize an image to Body Mass Index (BMI) of a subject, normalize an image to signal-to-noise ratio, normalize an image to image noise, normalize an image to tissue within the field of view, and/or the like. In some embodiments, the system can be configured to take into account the image type, such as for example CT, non-contrast CT, MRI, x-ray, nuclear medicine, ultrasound, and/or any other imaging modality mentioned herein.

In connection with any of the features and/or embodiments described herein, in some embodiments, the system can be configured to normalize any analysis and/or results, whether or not based on image processing. For example, in some embodiments, the system can be configured to standardize any reading or analysis of a subject, such as those derived from a medical image of the subject, to a normative reference database. Similarly, in some embodiments, the system can be configured to standardize any reading or analysis of a subject, such as those derived from a medical image of the subject, to a diseased database, such as for example patients who experienced heart attack, patients who are ischemic, and/or the like. In some embodiments, the system can be configured to utilize a control database for comparison, standardization, and/or normalization purposes. For example, a control database can comprise data derived from a combination of subjects, such as 50% of subjects who experience heart attack and 50% who did not, and/or the like. In some embodiments, the system can be configured to normalize any analysis, result, or data by applying a mathematical transform, such as a linear, logarithmic, exponential, and/or quadratic transform. In some embodiments, the system can be configured to normalize any analysis, result, or data by applying a machine learning algorithm.

In connection with any of the features and/or embodiments described herein, in some embodiments, the term "density," can refer to radiodensity, such as in Hounsfield units. In connection with any of the features and/or embodiments described herein, in some embodiments, the term "density," can refer to absolute density, such as for example when analyzing images obtained from imaging modalities such as dual energy, spectral, photon counting CT, and/or the like. In some embodiments, one or more images analyzed and/or accessed by the system can be normalized to contrast-to-noise. In some embodiments, one or more images analyzed and/or accessed by the system can be normalized to signal-to-noise. In some embodiments, one or more images analyzed and/or accessed by the system can be normalized across the length of a vessel, such as for example along a transluminal attenuation gradient. In some embodiments, one or more images analyzed and/or accessed by the system can be mathematically transformed, for example by applying a logarithmic, exponential, and/or quadratic transformation. In some one or more images analyzed and/or accessed by the system can be transformed using machine learning.

In connection with any of the features and/or embodiments described herein, in some embodiments, the term "artery" can include any artery, such as for example, coronary, carotid, cerebral, aortic, renal, lower extremity, and/or upper extremity.

In connection with any of the features and/or embodiments described herein, in some embodiments, the system can utilize additional information obtained from various sources in analyzing and/or deriving data from a medical image. For example, in some embodiments, the system can be configured to obtain additional information from patient history and/or physical examination. In some embodiments, the system can be configured to obtain additional information from other biometric data, such as those which can be gleaned from wearable devices, which can include for example heart rate, heart rate variability, blood pressure, oxygen saturation, sleep quality, movement, physical activity, chest wall impedance, chest wall electrical activity, and/or the like. In some embodiments, the system can be configured to obtain additional information from clinical data, such as for example from Electronic Medical Records (EMR). In some embodiments, additional information used by the system can be linked to serum biomarkers, such as for example of cholesterol, renal function, inflammation, myocardial damage, and/or the like. In some embodiments, additional information used by the system can be linked to other omics markers, such as for example transcriptomics, proteomics, genomics, metabolomics, microbiomics, and/or the like.

In connection with any of the features and/or embodiments described herein, in some embodiments, the system can utilize medical image analysis to derive and/or generate assessment of a patient and/or provide assessment tools to guide patient assessment, thereby adding clinical importance and use. In some embodiments, the system can be configured to generate risk assessment at the plaque-level (for example, will this plaque cause heart attack and/or does this plaque cause ischemia), vessel-level (for example, will this vessel be the site of a future heart attack and/or does this vessel exhibit ischemia), and/or patient level (for example, will this patient experience heart attack and/or the like). In some embodiments, the summation or weighted summation of plaque features can contribute to segment-level features, which in turn can contribute to vessel-level features, which in turn can contribute to patient-level features.

In some embodiments, the system can be configured to generate a risk assessment of future major adverse cardiovascular events, such as for example heart attack, stroke, hospitalizations, unstable angina, stable angina, coronary revascularization, and/or the like. In some embodiments, the system can be configured to generate a risk assessment of rapid plaque progression, medication non-response (for example if plaque progresses significantly even when medications are given), benefit (or lack thereof) of coronary revascularization, new plaque formation in a site that does not currently have any plaque, development of symptoms (such as angina, shortness of breath) that is attributable to the plaque, ischemia and/or the like. In some embodiments, the system can be configured to generate an assessment of other artery consequences, such as for example carotid (stroke), lower extremity (claudication, critical limb ischemia, amputation), aorta (dissection, aneurysm), renal artery (hypertension), cerebral artery (aneurysm, rupture), and/or the like.

Additional Detail—Determination of Non-Calcified Plaque from a Medical Image(s)

As discussed herein, in some embodiments, the system can be configured to determine non-calcified plaque from a medical image, such as a non-contrast CT image and/or image obtained using any other image modality as those mentioned herein. Also, as discussed herein, in some embodiments, the system can be configured to utilize radiodensity as a parameter or measure to distinguish and/or determine non-calcified plaque from a medical image. In some embodiments, the system can utilize one or more other factors, which can be in addition to and/or used as an alternative to radiodensity, to determine non-calcified plaque from a medical image.

For example, in some embodiments, the system can be configured to utilize absolute material densities via dual energy CT, spectral CT or photon-counting detectors. In some embodiments, the system can be configured to analyze the geometry of the spatial maps that "look" like plaque, for example compared to a known database of plaques. In some embodiments, the system can be configured to utilize smoothing and/or transform functions to get rid of image noise and heterogeneity from a medical image to help determine non-calcified plaque. In some embodiments, the system can be configured to utilize auto-adjustable and/or manually adjustable thresholds of radiodensity values based upon image characteristics, such as for example signal-to-noise ratios, body morph (for example obesity can introduce more image noise), and/or the like. In some embodiments, the system can be configured to utilize different thresholds based upon different arteries. In some embodiments, the system can be configured to account for potential artifacts, such as beam hardening artifacts that may preferentially affect certain arteries (for example, the spine may affect right coronary artery in some instances). In some embodiments, the system can be configured to account for different image acquisition parameters, such as for example, prospective vs. retrospective ECG gating, how much mA and kvP, and/or the like. In some embodiments, the system can be configured to account for different scanner types, such as for example fast-pitch helical vs. traditional helical. In some embodiments, the system can be configured to account for patient-specific parameters, such as for example heart rate, scan volume in imaged field of view, and/or the like. In some embodiments, the system can be configured to account for prior knowledge. For example, in some embodiments, if a patient had a contrast-enhanced CT angiogram in the past, the system can be configured to leverage findings from the previous contrast-enhanced CT angiogram for a non-contrast CT image(s) of the patient moving forward. In some embodiments, in cases where epicardial fat is not present outside an artery, the system can be configured to leverage other Hounsfield unit threshold ranges to depict the outer artery wall. In some embodiments, the system can be configured to utilize a normalization device, such as those described herein, to account for differences in scan results (such as for example density values, etc.) between different scanners, scan parameters, and/or the like.

Additional Detail—Determination of Cause of Change in Calcium

As discussed herein, in some embodiments, the system can be configured to determine a cause of change in calcium level of a subject by analyzing one or more medical images. In some embodiments, the change in calcium level can be by some external force, such as for example, medication treatment, lifestyle change (such as improved diet, physical activity), stenting, surgical bypass, and/or the like. In some embodiments, the system is configured to include one or more assessments of treatment and/or recommendations of treatment based upon these findings.

In some embodiments, the system can be configured to determine a cause of change in calcium level of a subject and use the same for prognosis. In some embodiments, the system can be configured to enable improved diagnosis of atherosclerosis, stenosis, ischemia, inflammation in the pericoronary region, and/or the like. In some embodiments, the system can be configured to enable improved prognostication, such as for example forecasting of some clinical event, such as major adverse cardiovascular events, rapid progression, medication non-response, need for revascularization, and/or the like. In some embodiments, the system can be configured to enable improved prediction, such as for example enabling identification of who will benefit from what therapy and/or enabling monitoring of those changes over time. In some embodiments, the system can be configured to enable improved clinical decision making, such as for example which medications may be helpful, which lifestyle interventions might be helpful, which revascularization or surgical procedures may be helpful, and/or the like. In some embodiments, the system can be configured to enable comparison to one or more normative databases in order to standardize findings to a known ground truth database.

In some embodiments, a change in calcium level can be linear, non-linear, and/or transformed. In some embodiments, a change in calcium level can be on its own or in other words involve just calcium. In some embodiments, a change in calcium level can be in relation to one or more other constituents, such as for example, other non-calcified plaque, vessel volume/area, lumen volume/area, and/or the like. In some embodiments, a change in calcium level can be relative. For example, in some embodiments, the system can be configured to determine whether a change in calcium level is above or below an absolute threshold, whether a change in calcium level comprises a continuous change upwards or downwards, whether a change in calcium level comprises a mathematical transform upwards or downwards, and/or the like.

As discussed herein, in some embodiments, the system can be configured to analyze one or more variables or parameters, such as those relating to plaque, in determining the cause of a change in calcium level. For example, in some embodiments, the system can be configured to analyze one or more plaque parameters, such as a ratio or function of volume or surface area, heterogeneity index, geometry, location, directionality, and/or radiodensity of one or more regions of plaque within the coronary region of the subject at a given point in time.

As discussed herein, in some embodiments, the system can be configured to characterize a change in calcium level between two points in time. For example, in some embodiments, the system can be configured to characterize a change in calcium level as one of positive, neutral, or negative. In some embodiments, the system can be configured to characterize a change in calcium level as positive when the ratio of volume to surface area of a plaque region has decreased, as this can be indicative of how homogeneous and compact the structure is. In some embodiments, the system can be configured to characterize a change in calcium level as positive when the size of a plaque region has decreased. In some embodiments, the system can be configured to characterize a change in calcium level as positive when the density of a plaque region has increased or when an image of the region of plaque comprises more pixels with higher density values, as this can be indicative of stable plaque. In some embodiments, the system can be configured to characterize a change in calcium level as positive when there is a reduced diffuseness. For example, if three small regions of plaque converge into one contiguous plaque, that can be indicative of non-calcified plaque calcifying along the entire plaque length.

In some embodiments, the system can be configured to characterize a change in calcium level as negative when the system determines that a new region of plaque has formed. In some embodiments, the system can be configured to characterize a change in calcium level as negative when more vessels with calcified plaque appear. In some embodiments, the system can be configured to characterize a change in calcium level as negative when the ratio of volume to surface area has increased. In some embodiments, the system can be configured to characterize a change in calcium level as negative when there has been no increase in Hounsfield density per calcium pixel.

In some embodiments, the system can be configured to utilize a normalization device, such as those described herein, to account for differences in scan results (such as for example density values, etc.) between different scanners, scan parameters, and/or the like.

Additional Detail—Quantification of Plaque, Stenosis, and/or CAD-RADS Score

As discussed herein, in some embodiments, the system can be configured to generate quantifications of plaque, stenosis, and/or CAD-RADS scores from a medical image. In some embodiments, as part of such quantification analysis, the system can be configured to determine a percentage of higher or lower density plaque within a plaque region. For example, in some embodiments, the system can be configured to classify higher density plaque as pixels or voxels that comprise a Hounsfield density unit above 800 and/or 1000. In some embodiments, the system can be configured to classify lower density plaque as pixels or voxels that comprise a Hounsfield density unit below 800 and/or 1000. In some embodiments, the system can be configured to utilize other thresholds. In some embodiments, the system can be configured to report measures on a continuous scale, an ordinal scale, and/or a mathematically transformed scale.

In some embodiments, the system can be configured to utilize a normalization device, such as those described herein, to account for differences in scan results (such as for example density values, etc.) between different scanners, scan parameters, and/or the like.

Additional Detail—Disease Tracking

As discussed herein, in some embodiments, the system can be configured to track the progression and/or regression of an arterial and/or plaque-based disease, such as atherosclerosis, stenosis, ischemia, and/or the like. For example, in some embodiments, the system can be configured to track the progression and/or regression of a disease over time by analyzing one or more medical images obtained from two different points in time. As an example, in some embodiments, one or more normal regions from an earlier scan can turn into abnormal regions in the second scan and vice versa.

In some embodiments, the one or more medical images obtained from two different points in time can be obtained from the same modality and/or different modalities. For example, scans from both points in time can be CT, whereas in some cases the earlier scan can be CT while the later scan can be ultrasound.

Further, in some embodiments, the system can be configured to track the progression and/or regression of disease by identifying and/or tracking a change in density of one or more pixels and/or voxels, such as for example Hounsfield density and/or absolute density. In some embodiments, the system can be configured to track change in density of one or more pixels or voxels on a continuous basis and/or dichotomous basis. For example, in some embodiments, the system can be configured to classify an increase in density as stabilization of a plaque region and/or classify a decrease in density as destabilization of a plaque region. In some embodiments, the system can be configured to analyze surface area and/or volume of a region of plaque, ratio between the two, absolute values of surface area and/or volume, gradient(s) of surface area and/or volume, mathematical transformation of surface area and/or volume, directionality of a region of plaque, and/or the like.

In some embodiments, the system can be configured to track the progression and/or regression of disease by analyzing vascular morphology. For example, in some embodiments, the system can be configured to analyze and/or track the effects of the plaque on the outer vessel wall getting bigger or smaller, the effects of the plaque on the inner vessel lumen getting smaller or bigger, and/or the like.

In some embodiments, the system can be configured to utilize a normalization device, such as those described herein, to account for differences in scan results (such as for example density values, etc.) between different scanners, scan parameters, and/or the like.

Global Ischemia Index

Some embodiments of the systems, devices, and methods described herein are configured to determine a global ischemia index that is representative of risk of ischemia for a particular subject. For example, in some embodiments, the system is configured to generate a global ischemia index for a subject based at least in part on analysis of one or more medical images and/or contributors of ischemia as well as consequences and/or associated factors to ischemia along the temporal ischemic cascade. In some embodiments, the generated global ischemia index can be used by the systems, methods, and devices described herein for determining and/or predicting the outcome of one or more treatments and/or generating or guiding a recommended medical treatment, therapy, medication, and/or procedure for the subject.

In particular, in some embodiments, the systems, devices, and methods described herein can be configured to automatically and/or dynamically analyze one or more medical images and/or other data to identify one or more features, such as plaque, fat, and/or the like, for example using one or more machine learning, artificial intelligence (AI), and/or regression techniques. In some embodiments, one or more features identified from medical image data can be inputted into an algorithm, such as a second-tier algorithm which can be a regression algorithm or multivariable regression equation, for automatically and/or dynamically generating a global ischemia index. In some embodiments, the AI algorithm for determining a global ischemia index can be configured to utilize one or more variables as input, such as different temporal stages of the ischemia cascade as described herein, and compare the same to an output, such as myocardial blood flow, as a ground truth. In some embodiments, the output, such as myocardial blood flow, can be indicative of the presence or absence of ischemia as a binary measure and/or one or more moderations of ischemia, such as none, mild, moderate, severe, and/or the like.

In some embodiments, the system can be configured to utilize a normalization device, such as those described herein, to account for differences in scan results (such as for example density values, etc.) between different scanners, scan parameters, and/or the like.

In some embodiments, by utilizing one or more computer-implemented algorithms, such as for example one or more machine learning and/or regression techniques, the systems, devices, and methods described herein can be configured to analyze one or more medical images and/or other data to generate a global ischemia index and/or a recommended treatment or therapy within a clinical reasonable time, such as for example within about 1 minute, about 2 minutes, about 3 minutes, about 4 minutes, about 5 minutes, about 10 minutes, about 20 minutes, about 30 minutes, about 40 minutes, about 50 minutes, about 1 hour, about 2 hours, about 3 hours, and/or within a time period defined by two of the aforementioned values.

In generating the global ischemia index, in some embodiments, the systems, devices, and methods described herein are configured to: (a) temporally integrate one or more variables along the "ischemic" pathway and weight their input differently based upon their temporal sequence in the development and worsening of coronary ischemia; and/or (b) integrate the contributors, associated factors and consequences of ischemia to improve diagnosis of ischemia. Furthermore, in some embodiments, the systems, devices, and methods described herein transcend analysis beyond just the coronary arteries or just the left ventricular myocardium, and instead can include a combination one or more of: coronary arteries; coronary arteries after nitroglycerin or vasodilator administration; relating coronary arteries to the fractional myocardial mass; non-cardiac cardiac examination; relationship of the coronary-to-non-coronary cardiac; and/or non-cardiac examinations. In addition, in some embodiments, the systems, devices, and methods described herein can be configured to determine the fraction of myocardial mass or subtended myocardial mass to vessel or lumen volume, for example in combination with any of the other features described herein such as the global ischemia index, to further determine and/or guide a recommended medical treatment or procedure, such as revascularization, stenting, surgery, medication such as statins, and/or the like. As such, in some embodiments, the systems, devices, and methods described herein are configured to evaluate ischemia and/or provide recommended medical treatment for the same in a manner that does not currently exist today, accounting for the totality of information contributing to ischemia.

In some embodiments, the system can be configured to differentiate between micro and macro vascular ischemia, for example based on analysis of one or more of epicardial coronaries, measures of myocardium densities, myocardium mass, volume of epicardial coronaries, and/or the like. In some embodiments, by differentiating between micro and macro vascular ischemia, the system can be configured to generate different prognostic and/or therapeutic approaches based on such differentiation.

In some embodiments, when a medical image(s) of a patient is obtained, such as for example using CT, MM, and/or any other modality, not only information relating to coronary arteries but other information is also obtained, which can include information relating to the vascular system and/or the rest of the heart and/or chest area that is within the frame of reference. While certain technologies may simply focus on the information relating to coronary arteries from such medical scans, some embodiments described herein are configured to leverage more of the information that is inherently obtained from such images to obtain a more global indication of ischemia and/or use the same to generate and/or guide medical therapy.

In particular, in some embodiments, the systems, devices, and methods described herein are configured to examine both the contributors as well as consequences and associated factors to ischemia, rather than focusing only on either contributors or consequences. In addition, in some embodiments, the systems, devices, and methods described herein are configured to consider the entirety and/or a portion of temporal sequence of ischemia or the "ischemic pathway." Moreover, in some embodiments, the systems, devices, and methods described herein are configured to consider the non-coronary cardiac consequences as well as the non-cardiac associated factors that contribute to ischemia. Further, in some embodiments, the systems, devices, and methods described herein are configured to consider the comparison of pre- and post-coronary vasodilation. Furthermore, in some embodiments, the systems, devices, and methods described herein are configured to consider a specific list of variables, rather than a general theme, appropriately weighting their contribution to ischemia. Also, in some embodiments, the systems, devices, and methods described herein can be validated against multiple "measurements" of ischemia, including absolutely myocardial blood flow, myocardial perfusion, and/or flow ratios.

Generally speaking, ischemia diagnosis is currently evaluated by either stress tests (myocardial ischemia) or flow ratios in the coronary artery (coronary ischemia), the latter of which can include fractional flow reserve, instantaneous wave-free pressure ratio, hyperemic resistance, coronary flow, and/or the like. However, coronary ischemia can be thought of as only an indirect measure of what is going on in the myocardium, and myocardial ischemia can be thought of as only an indirect measure of what is going on in the coronary arteries.

Further certain tests measure only individual components of ischemia, such as contributors of ischemia (such as, stenosis) or sequelae of ischemia (such as, reduced myocardial perfusion or blood flow). However, there are numerous other contributors to ischemia beyond stenosis, numerous associated factors that increase likelihood of ischemia, and many other early and late consequences of ischemia.

One technical shortcoming of such existing techniques is that if you only look at factors that contribute or are associated with ischemia, then you are always too early—i.e., in the pre-ischemia stage. Conversely, if you only look at factors that are consequences/sequelae of ischemia, then you are always too late—i.e., in the post-ischemia stage.

And ultimately, if you do not look at everything (including associative factors, contributors, early and late consequences), you will not understand where an individual exists on the continuum of coronary ischemia. This may have very important implications in the type of therapy an individual should undergo—such as for example medical therapy, intensification of medical therapy, coronary revascularization by stenting, and/or coronary revascularization by coronary artery bypass surgery. As such, in some embodiments described herein, the systems, methods, and devices are configured to generate or determine a global ischemia index for a particular patient based at least in part on analysis of one or more medical images or data of the patient, wherein the generated global ischemia index is a measure of ischemia for the patient along the continuum of coronary ischemia or the ischemic cascade as described in further detail below. In other words, in some embodiments, unlike in existing technologies or techniques, the global ischemia index generated by the system can be indicative of a stage or risk or development of ischemia of a particular patient along the continuum of coronary ischemia or the ischemic cascade.

Further, there can be a relationship between the things that contribute/cause ischemia and the consequences/sequelae of ischemia that occur in a continuous and overlapping fashion. Thus, it can be much more accurate to identify ischemic individuals by combining various factors that contribute/cause ischemia with factors that are consequences/sequelae of ischemia.

As such, in some embodiments described herein, the systems, devices, and methods are configured to analyze one or more associative factors, contributors, as well as early and late consequences of ischemia in generating a global ischemia index, which can provide a more global indication of the risk of ischemia. Further, in some embodiments described herein, the systems, devices, and methods are configured to use such generated global ischemia index to determine and/or guide a type of therapy an individual should undergo, such as for example medical therapy, intensification of medical therapy, coronary revascularization by stenting, and/or coronary revascularization by coronary artery bypass surgery.

As discussed herein, in some embodiments, the systems, devices, and methods are configured to generate a global ischemia index indicative and/or representative of a risk of ischemia for a particular subject based on one or more medical images and/or other data. More specifically, in some embodiments, the system can be configured to generate a global ischemia index as a measurement of myocardial ischemia.

In some embodiments, the generated global ischemia index provides a much more accurate and/or direct measurement of myocardial ischemia compared to existing techniques. Ischemia, by its definition, is an inadequate blood supply to an organ or part of the body. By this definition, the diagnosis of ischemia can be best performed by examining the relationship of the coronary arteries (blood supply) to the heart (organ or part of the body). However, this is not the case as current generation tests measure either the coronary arteries (e.g., FFR, iFR) or the heart (e.g. stress testing by nuclear SPECT, PET, CMR or echo). Because current generation tests fail to examine the relationships of the coronary arteries, they do not account for the temporal sequence of events that occurs in the evolution of ischemia (from none-to-some, as well as from mild-to-moderate-to-severe) or the "ischemic pathway," as will be described in more detail herein. Quantifying the relationship of the coronary arteries to the heart and other non-coronary structures to the manifestation of ischemia, as well as the temporal findings associated with the stages of ischemia in the ischemic cascade, can improve our accuracy of diagnosis—as well as our understanding of ischemia severity—in a manner not possible with current generation tests.

As discussed above, no test currently exists for directly measuring ischemia; rather, existing tests only measure certain specific factors or surrogate markers associated with ischemia, such as for example hypoperfusion or fractional flow reserve (FFR) or wall motion abnormalities. In other words, the current approaches to ischemia evaluation are entirely too simplistic and do not consider all of the variables.

Ischemia has historically been "measured" by stress tests. The possible stress tests that exist include: (a) exercise treadmill ECG testing without imaging; (b) stress testing by single photon emission computed tomography (SPECT); (c) stress testing by positron emission tomography (PET); (d) stress testing by computed tomography perfusion (CTP); (e) stress testing by cardiac magnetic resonance (CMR) perfusion; and (f) stress testing by echocardiography. Also, SPECT, PET, CTP and CMR can measure relative myocardial perfusion, in that you compare the most normal appearing portion of the left ventricular myocardium to the abnormal-appearing areas. PET and CTP can have the added capability of measuring absolute myocardial blood flow and using these quantitative measures to assess the normality of blood supply to the left ventricle. In contrast, exercise treadmill ECG testing measures ST-segment depression as an indirect measure of subendocardial ischemia (reduced blood supply to the inner portion of the heart muscle), while stress echocardiography evaluates the heart for stress-induced regional wall motion abnormalities of the left ventricle. Abnormal relative perfusion, absolute myocardial blood flow, ST segment depression and regional wall motion abnormalities occur at different points in the "ischemic pathway."

Furthermore, in contrast to myocardial measures of the left ventricle, alternative methods to determine ischemia involve direct evaluation of the coronary arteries with pressure or flow wires. The most common 2 measurements are fractional flow reserve (FFR) or iFR. These techniques can compare the pressure distal to a given coronary stenosis to the pressure proximal to the stenosis. While easy to understand and potentially intuitive, these techniques do not account for important parameters that can contribute to ischemia, including diffuseness of "mild" stenoses, types of atherosclerosis causing stenosis; and these techniques take into account neither the left ventricle in whole nor the % left ventricle subtended by a given artery.

In some embodiments, the global ischemia index is a measure of myocardial ischemia, and leverages the quantitative information regarding the contributors, associated factors and consequences of ischemia. Further, in some embodiments, the system uses these factors to augment ischemia prediction by weighting their contribution accordingly. In some embodiments, the global ischemia index is aimed to serve as a direct measure of both myocardial perfusion and coronary pressure and to integrate these findings to improve ischemia diagnosis.

In some embodiments, unlike existing ischemia "measurement" techniques that focus only on a single factor or a single point in the ischemic pathway, the systems, devices, and methods described herein are configured to analyze and/or use as inputs one or more factors occurring at different points in the ischemic pathway in generating the global ischemia index. In other words, in some embodiments, the systems, devices, and methods described herein are configured to take into account the whole temporal ischemic cascade in generating a global ischemia index for assessing the risk of ischemia and/or generating a recommended treatment or therapy for a particular subject.

Figure 20A:
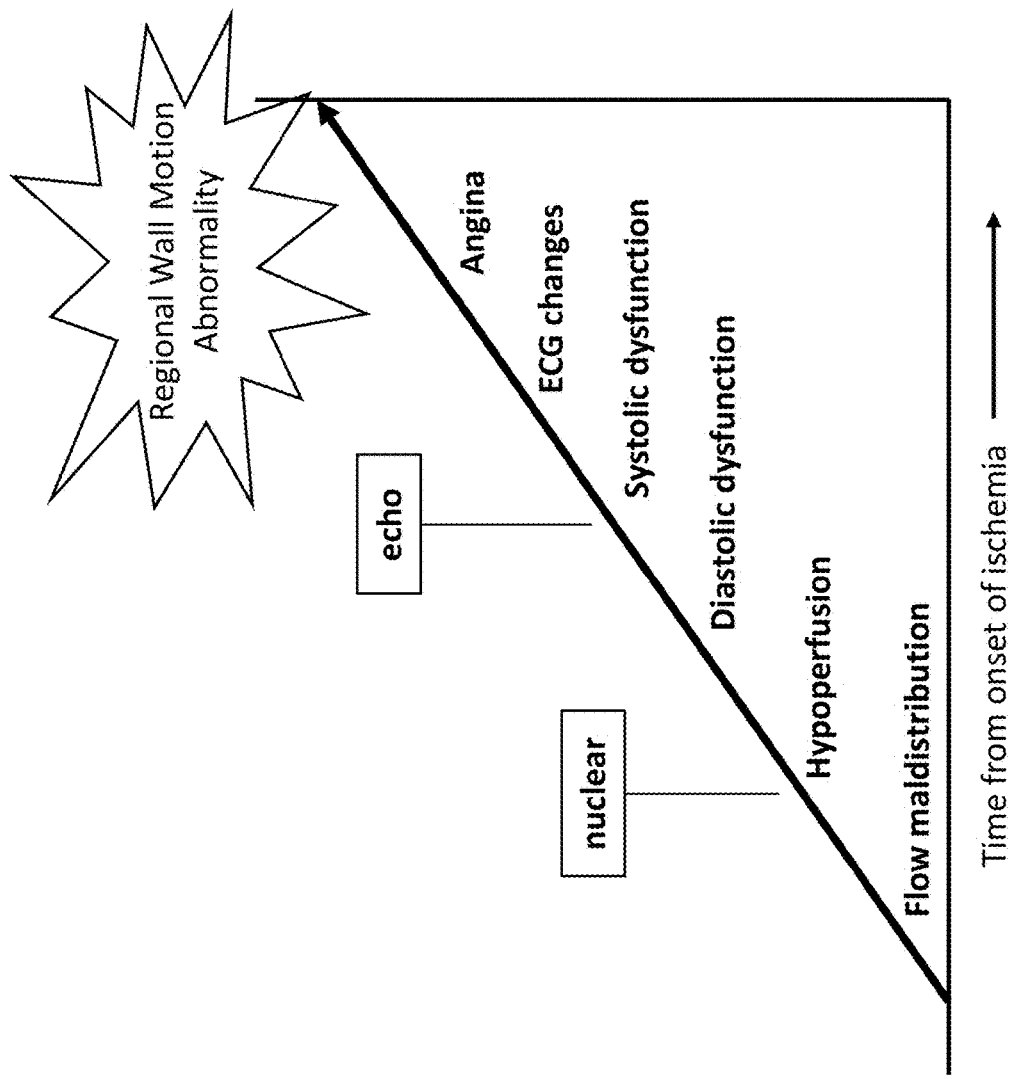
FIG. 20A illustrates one or more features of an example ischemic pathway.

FIG. 20A illustrates one or more features of an example ischemic pathway. While the ischemic pathway is not definitively proven, it is thought to be as shown in FIG. 20A. Having said this, this ischemic pathway may not actually occur in this exact sequence. The ischemic pathway may in fact occur in different order, or many of the events may occur simultaneously and overlap. Nonetheless, the different points along the ischemic pathway can occur at different points in time, thereby adding a temporal aspect in the development of ischemia that some embodiments described herein consider.

As illustrated in FIG. 20A, the ischemic pathway can illustrate different conditions that can occur when you have a blockage in a heart artery that reduces blood supply to the heart muscle. In other words, the ischemic pathway can illustrate a sequence of pathophysiologic events caused by coronary artery disease. As illustrated in FIG. 20A, ischemia can occur or gradually develop in a number of different steps rather than a binary concept. The ischemic pathway illustrates different conditions that may arise as a patient gets more and more ischemic.

Different existing tests can show ischemia at different stages along the ischemic pathway. For example, a nuclear stress test can show ischemia sooner rather than an echo test, because nuclear imaging probes hypoperfusion, which is an earlier event in the ischemic pathway, whereas a stress echocardiography probes a later event such as systolic dysfunction. Further, an exercise treadmill EKG testing can show ischemia sometime after an echo stress test, as if EKG testing becomes abnormal ECG changes will show. In addition, a PET scan can measure flow maldistribution, and as such can show signs of ischemia prior to before nuclear stress tests. As such, different tests exist for measuring different conditions and steps along the ischemic cascade. However, there does not exist a global technique that takes into account all of these different conditions that arise throughout the course of the ischemic pathway. As such, in some embodiments herein, the systems, devices and methods are configured to analyze multiple different measures along the temporal ischemic pathway and/or weight them differently in generating a global ischemia index, which can be used to diagnose ischemia and/or provide a recommended therapy and/or treatment. In some embodiments, such multiple measures along the temporal ischemic pathway can be weighted differently in generating the global ischemic index; for example, certain measures that come earlier can be weighted less than those measures that arise later in the ischemic cascade in some embodiments. More specifically, in some embodiments, one or more measures of ischemia can be weighted from less to more heavily in the following general order: flow maldistribution, hypoperfusion, diastolic dysfunction, systolic dysfunction, ECG changes, angina, and/or regional wall motion abnormality.

In some embodiments, the system can be configured to take the temporal sequence of the ischemic pathway and integrate and weight various conditions or events accordingly in generating the global ischemia index. Further, in some embodiments, the system can be configured to identify certain conditions or "associative factors" well before actual signs ischemia occur, such as for example fatty liver which is associated with diabetes which is associated with coronary disease. In other words, in some embodiments, the system can be configured to integrate one or more factors that are associated, causal, contributive, and/or consequential to ischemia, take into account the temporal sequence of the same and weight them accordingly to generate an index representative of and/or predicting risk of ischemia and/or generating a recommend treatment.

As discussed herein, the global ischemia index generated by some embodiments provide substantial technical advantages over existing techniques for assessing ischemia, which have a number of shortcomings. For example, coronary artery examination alone does not consider the wealth of potential contributors to ischemia, including for example: (1) 3D flow (lumen, stenosis, etc.); (2) endothelial function/vasodilation/vasoconstrictive ability of the coronary artery (e.g., plaque type, burden, etc.); (3) inflammation that may influence the vasodilation/vasoconstrictive ability of the coronary artery (e.g., epicardial adipose tissue surrounding the heart); and/or (4) location (plaques that face the myocardium are further away from the epicardial fat, and may be less influenced by the inflammatory contribution of the fat. Plaques that are at the bifurcation, trifurcation or proximal/ostial location may influence the likelihood of ischemia more than those that are not at the bifurcation, trifurcation or proximal/ostial location).

One important consideration is that current methods for determining ischemia by CT rely primarily on computational fluid dynamics which, by its definition, does not include fluid-structure interactions (FSI). However, the use of FSI requires the understanding of the material densities of coronary artery vessels and their plaque constituents, which is not known well.

Thus, in some embodiments described herein, one important component is that the lateral boundary conditions in the coronary arteries (lumen wall, vessel wall, plaque) can be known in a relative fashion by setting Hounsfield unit thresholds that represent different material densities or setting absolute material densities to pixels based upon comparison to a known material density (i.e., normalization device in our prior patent). By doing so, and coupling to a machine learning algorithm, some embodiments herein can improve upon the understanding of fluid-structure interactions without having to understand the exact material density, which may inform not only ischemia (blood flow within the vessel) but the ability of a plaque to "fatigue" over time.

In addition, in some embodiments, the system is configured to take into account non-coronary cardiac examination and data in addition to coronary cardiac data. The coronary arteries supply blood to not only the left ventricle but also the other chambers of the heart, including the left atrium, the right ventricle and the right atrium. While perfusion is not well measured in these chambers by current generation stress tests, in some embodiments, the end-organ effects of ischemia can be measured in these chambers by determining increases in blood volume or pressure (i.e., size or volumes). Further, if blood volume or pressure increases in these chambers, they can have effects of "backing up" blood flow due to volume overload into the adjacent chambers or vessels. So, as a chain reaction, increases in left ventricular volume may increase volumes in sequential order of: (1) left atrium; (2) pulmonary vein; (3) pulmonary arteries; (4) right ventricle; (5) right atrium; (6) superior vena cava or inferior vena cava. In some embodiments, by taking into account non-coronary cardiac examination, the system can be configured to differentiate the role of ischemia on the heart chambers based upon how "upstream" or "downstream" they are in the ischemic pathway.

Moreover, in some embodiments, the system can be configured to take into account the relationship of coronary arteries and non-coronary cardiac examination. Existing methods of ischemia determination limit their examination to either the coronary arteries (e.g., FFR, iFR) or the heart left ventricular myocardium. However, in some embodiments herein, the relationship of the coronary arteries with the heart chambers may act synergistically to improve our diagnosis of ischemia.

Further, in some embodiments, the system can be configured to take into account non-cardiac examination. At present, no method of coronary/myocardial ischemia determination accounts for the effects of clinical contributors (e.g., hypertension, diabetes) on the likelihood of ischemia. However, these clinical contributors can manifest several image-based end-organ effects which may increase the likelihood of an individual to manifest ischemia. These can include such image-based signs such as aortic dimension (aneurysms are a common end-organ effect of hypertension) and/or non-alcoholic steatohepatitis (fatty liver is a common end-organ effect of diabetes or pre-diabetes). As such, in some embodiments, the system can be configured to account for these features to augment the likelihood of ischemia diagnosis on a scan-specific, individualized manner.

Furthermore, at present, no method of myocardial ischemia determination incorporates other imaging findings that may not be ascertainable by a single method, but can be determined through examination by other methods. For example, the ischemia pathway is often thought to occur, in sequential order, from metabolic alterations (laboratory tests), perfusion abnormalities (stress perfusion), diastolic dysfunction (echocardiogram), systolic dysfunction (echocardiogram or stress test), ECG changes (ECG) and then angina (chest pain, human patient report). In some embodiments, the system can be configured to integrate these factors with the image-based findings of the CT scan and allow for improvements in ischemia determination by weighting these variables in accordance with their stage of the ischemic cascade.

As described herein, in some embodiments, the systems, methods, and devices are configured to generate a global ischemia index to diagnose ischemia. In some embodiments, the global ischemia index considers the totality of findings that contribute to ischemia, including, for example one or more of: coronary arteries+nitroglycerin/vasodilator administration+relating coronary arteries to the fractional myocardial mass+non-cardiac cardiac examination+relationship of the coronary-to-non-coronary cardiac+non-cardiac examinations, and/or a subset thereof. In some embodiments, the global ischemia index provides weighted increases of variables to contribution of ischemia based upon where the image-based finding is in the pathophysiology of ischemia. In some embodiments, in generating the global ischemia index, the system is configured to input into a regression model one or more factors that are associative, contributive, casual, and/or consequential to ischemia to optimally diagnose whether a subject ischemic or not.

Figure 20B:
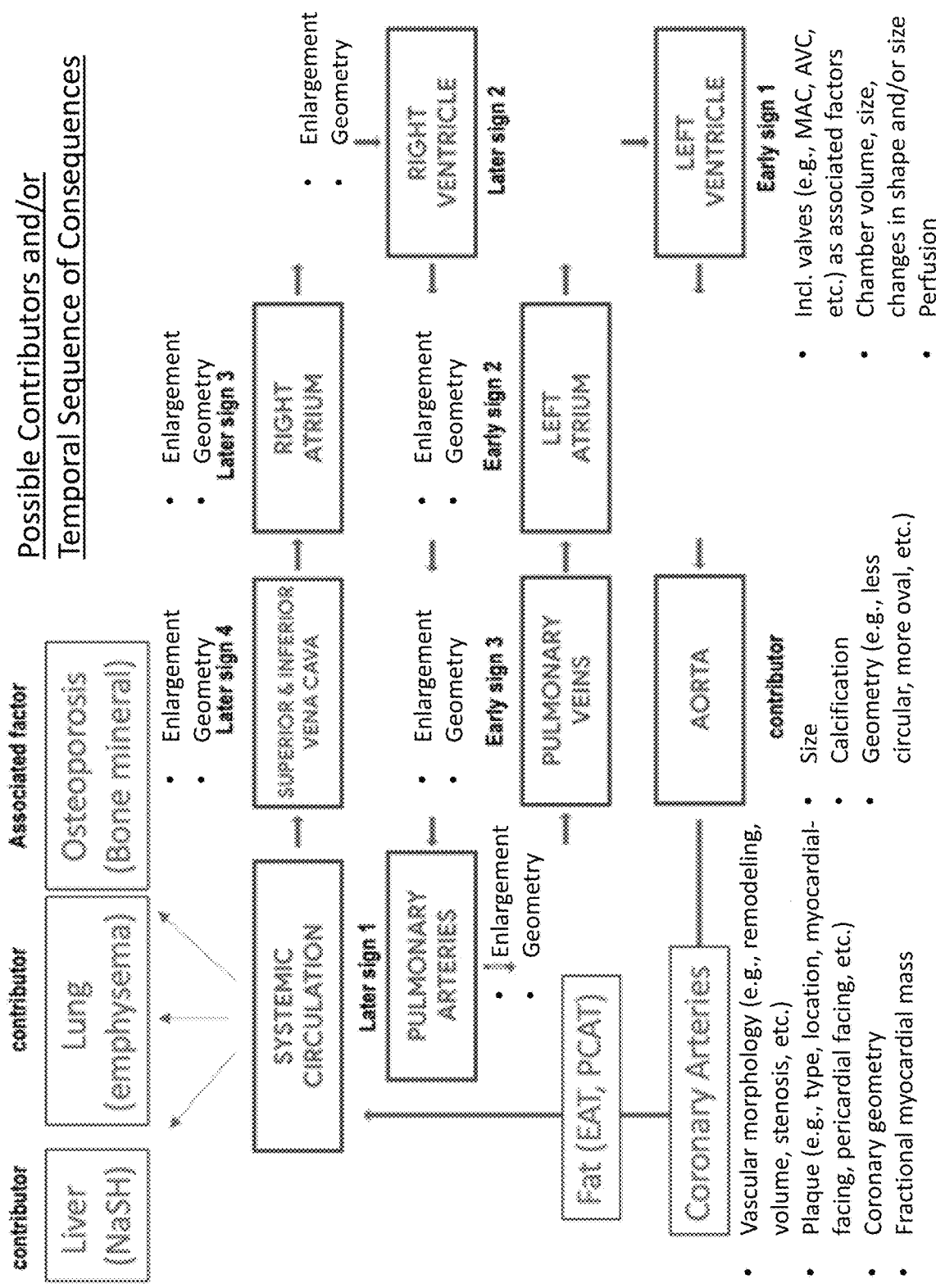
FIG. 20B is a block diagram depicting one or more contributors and one or more temporal sequences of consequences of ischemia utilized by an example embodiment(s) described herein.

FIG. 20B is a block diagram depicting one or more contributors and one or more temporal sequences of consequences of ischemia utilized by an example embodiment(s) described herein. As illustrated in FIG. 20B, in some embodiments, the system can be configured to analyze a number of factors, including contributors, associated factors, causal factors, and/or consequential factors of ischemia and/or use the same as input for generating the global ischemia index. Some of such factors can include those conditions shown in FIG. 20B. For example, signs of a fatty liver and/or emphysema in the lungs can be associated factors used by the system as inputs for generating the global ischemia index. Some examples of contributors used as an input(s) by the system can include the inability to vasodilate with nitric oxide and/or nitroglycerin, low density non-calcified plaque, small artery, and/or the like. Some examples of early consequences of ischemia used as an input(s) by the system can include reduced perfusion in the heart muscle, increase in size of the volume of the heart. An example of late consequences of ischemia used as an input(s) by the system can include blood starting to back up into other chambers of heart in addition to the left ventricle.

In some embodiments, the global ischemia index accounts for the direct contributors to ischemia, the early consequences of ischemia, the late consequences of ischemia, the associated factors with ischemia and other test findings in relation to ischemia. In some embodiments, one or more these factors can be identified and/or derived automatically, semi-automatically, and/or dynamically using one or more algorithms, such as a machine learning algorithm. Some example algorithms for identifying such features are described in more detail below. Without such trained algorithms, it can be difficult, if not impossible, to take into account all of these factors in generating the global ischemia index within a reasonable time.

In some embodiments, these factors, weighted differently and appropriately, can improve diagnosis of ischemia. FIG. 20C is a block diagram depicting one or more features of an example embodiment(s) for determining ischemia by weighting different factors differently. In some embodiments, in generating the global ischemia index, the system is configured to take into account the temporal aspect of the ischemic cascade and weight one or more factors according to the temporal aspect, for example where early signs of ischemia can be weighted less heavily compared to later signs of ischemia. In some embodiments, the system can automatically and/or dynamically determine the different weights for each factor, for example using a regression model. In some embodiments, the system can be configured to derive one or more appropriate weighting factors based on previous analysis of data to determine which factor should be more or less heavily weighted compared to others. In some embodiments, a user can guide and/or otherwise provide input for weighting different factors.

As described herein, in some embodiments, the global ischemia index can be generated by a machine learning algorithm and/or a regression algorithm that condenses this multidimensional information into an output of "ischemia" or "no ischemia" when compared to a "gold standard" of ischemia, as measured by myocardial blood flow, myocardial perfusion or flow ratios. In some embodiments, the system can be configured to output an indication of moderation of ischemia, such none, mild, moderate, severe, and/or the like. In some embodiments, the output indication of ischemia can be on a continuous scale.

Figure 20D:
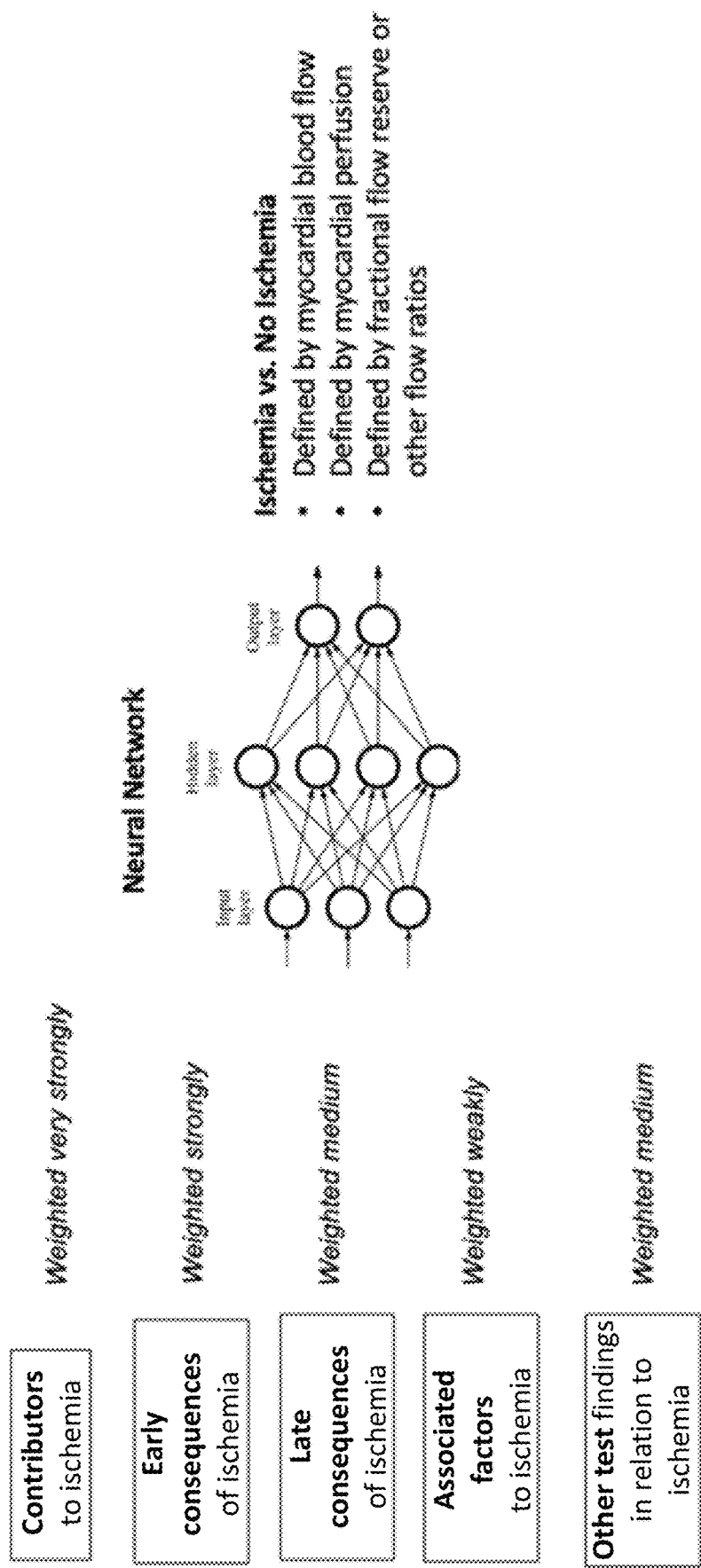
FIG. 20D is a block diagram depicting one or more features of an example embodiment(s) for calculating a global ischemia index.

FIG. 20D is a block diagram depicting one or more features of an example embodiment(s) for calculating a global ischemia index. As illustrated in FIG. 20D, in some embodiments, the system can be configured to validate the outputted global ischemia index against absolute myocardial blood flow, which can be measured for example by PET and/or CT scans to measure different regions of the heart to see if there are different flows of blood within different regions. As absolute myocardial blood flow can provide an absolute value of volume per time, in some embodiments, the system can be configured to compare the absolute myocardial blood flow of one region to another region, which would not be possible using relative measurements, such as for example using nuclear stress testing.

As discussed herein, in some embodiments, the systems, devices, and methods can be configured to utilize a machine learning algorithm and/or regression algorithm for analyzing and/or weighting different factors for generating the global ischemia index. By doing so, in some embodiments, the system can be configured to take into account one or more statistical and/or machine learning considerations. More specifically, in some embodiments, the system can be configured to deliberately duplicate the contribution of particular variables. For example, in some embodiments, non-calcified plaque (NCP), low density non-calcified plaque (LD-NCP), and/or high-risk plaque (HRP) may all contribute to ischemia. In traditional statistics, collinearity could be a reason to select only one out of these three variables, but by utilizing machine learning in some embodiments, the system may allow for data driven exploration of the contribution of multiple variables, even if they share a specific feature. In addition, in some embodiments, the system may take into account certain temporal considerations when training and/or applying an algorithm for generating the global ischemia index. For example, in some embodiments, the system can be configured to give greater weight to consequences/sequelae rather than causes/contributors, as the consequences/sequelae have already occurred.

In addition, in some situations, coronary vasodilation is induced before a coronary CT scan because it allows the coronary arteries to be maximum in their size/volume. Nitroglycerin is an endothelium-independent vasodilator as compared to, for example, nitric oxide, which is an endothelium-dependent vasodilator. As nitroglycerin-induced vasodilation occurs in the coronary arteries—and, because a "timing" iodine contrast bolus is often administered before the actual coronary CT angiogram, comparison of the volume of coronary arteries before and after a nitroglycerin administration may allow a direct evaluation of coronary vasodilatory capability, which may significantly augment accurate ischemia diagnosis. Alternatively, an endothelium-dependent vasodilator—like nitric oxide or carbon dioxide—may allow for augmentation of coronary artery size in a manner that can be either replaced or coupled to endothelium-independent vasodilation (by nitroglycerin) to maximize understanding of the ability of coronary arteries to vasodilate.

In some embodiments, the system can be configured to measure vasodilatory effects, for example by measuring the diameter of one or more arteries before and/or after administration of nitroglycerin and/or nitric oxide, and use such vasodilatory effects as a direct measurement or indication of ischemia. Alternatively and/or in addition to the foregoing, in some embodiments, the system can be configured to measure such vasodilatory effects and use the same as an input in determining or generating the global ischemia index and/or developing a recommended medical therapy or treatment for the subject.

Further, in some embodiments, the system can be configured to relate the coronary arteries to the heart muscle that it provides blood to. In other words, in some embodiments, the system can be configured to take into account fractional myocardial mass when generating a global ischemia index. For ischemia diagnosis, stress testing can be, at present, limited to the left ventricle. For example, in stress echocardiogram (ultrasound), the effects of stress-induced left ventricular regional wall motion abnormalities are examined, while in SPECT, PET and cardiac Mill, the effects of stress-induced left ventricular myocardial perfusion are examined. However, no currently existing technique relates the size (volume), geometry, path and relation to other vessels with the % fractional myocardial mass subtended by that artery. Further, one assumes that the coronary artery distribution is optimal but, in many people, it may not be. Therefore, understanding an optimization platform to compute optimal blood flow through the coronary arteries may be useful in guiding treatment decisions.

As such, in some embodiments, the system is configured to determine the fractional myocardial mass or the relationship of coronary arteries to the left ventricular myocardium that they subtend. In particular, in some embodiments, the system is configured to determine and/or tack into account the subtended mass of myocardium to the volume of arterial vessel. Historically, myocardial perfusion evaluation for myocardial ischemia has been performed using stress tests, such as nuclear SPECT, PET, cardiac Mill or cardiac CT perfusion. These methods have relied upon a 17-segment myocardial model, which classifies perfusion defects by location. There can be several limitations to this, including: (1) assuming that all 17 segments have the same size; (2) assuming that all 17 segments have the same prognostic importance; and (3) does not relate the myocardial segments to the coronary arteries that provide blood supply to them.

As such, to address such shortcomings, in some embodiments, the system can be configured to analyze fractional myocardial mass (FMM). Generally speaking, FMM aims to relate the coronary arteries to the amount of myocardium that they subtend. These can have important implications on prognostication and treatment. For example, a patient may have a 70% stenosis in an artery, which has been a historical cut point where coronary revascularization (stenting) is considered. However, there may be very important prognostic and therapeutic implications for patients who have a 70% stenosis in an artery that subtends 1% of the myocardium vs. a 70% stenosis in an artery that subtends 15% of the myocardium.

This FMM has been historically calculated using a "stem-and-crown" relationship between the myocardium on CT scans and the coronary arteries on CT scans and has been reported to have the following relationship: $M=kL3/4$, where M=mass, k=constant, and L=length.

However, this relationship, while written about quite frequently, has not been validated extensively. Nor have there been any cut points that can effectively guide therapy. The guidance of therapy can come in many regards, including: (1) decision to perform revascularization: high FMM, perform revascularization to improve event-free survival; low FMM, medical therapy alone without revascularization; (2) different medical therapy regimens: high FMM, give several medications to improve event-free survival; low FMM, give few medications; (3) prognostication: high FMM, poor prognosis; low FMM, good prognosis.

Further, in the era of 3D imaging, the $M=kL$ relationships should be expanded to the $M=kV$ relationship, where V=volume of the vessel or volume of the lumen. As such, in some embodiments, the system is configured to (1) describe the allometric scaling law in 3 dimensions, i.e., $M=kVn$; (2) use FMM as a cut point to guide coronary revascularization; and/or (3) use FMM cut points for clinical decision making, including (a) use of medications vs. not, (b) different types of medications (cholesterol lowering, vasodilators, heart rate slowing medications, etc.) based upon FMM cut points; (c) number of medications based upon FMM cut points; and/or (d) prognostication based upon FMM cut points. In some embodiments, the use of FMM cut points by 3D FMM calculations can improve decision making in a manner that improves event-free survival.

As described above, in some embodiments, the system can be configured to utilize one or more contributors or causes of ischemia as inputs for generating a global ischemia index. An example of a contributor or cause of ischemia that can be utilized as input and/or analyzed by the system can include vessel caliber. In particular, in some embodiments, the system can be configured to analyze and/or utilize as an input the percentage diameter of stenosis, wherein the greater the stenosis the more likely the ischemia. In addition, in some embodiments, the system can be configured to analyze and/or utilize as in input lumen volume, wherein the smaller the lumen volume, the more likely the ischemia. In some embodiments, the system can be configured to analyze and/or utilize as an input lumen volume indexed to % fractional myocardial mass, body surface area (BSA), body mass index (BMI), left ventricle (LV) mass, overall heart size, wherein the smaller the lumen volume, the more likely the ischemia. In some embodiments, the system can be configured to analyze and/or utilize as an input vessel volume, wherein the smaller the vessel volume, the more likely the ischemia. In some embodiments, the system can be configured to analyze and/or utilize as an input minimal luminal diameter (MLD), minimal luminal are (MLA), and/or a ratio between MLD and MLA, such as MLD/MLA.

Another example contributor or cause of ischemia that can be utilized as input and/or analyzed by the system can include plaque, which may have marked effects on the ability of an artery to vasodilate/vasoconstrict. In particular, in some embodiments, the system can be configured to analyze and/or utilize as an input non-calcified plaque (NCP), which may cause greater endothelial dysfunction and inability to vasodilate to hyperemia. In some embodiments, the system may utilize one or more arbitrary cutoffs for analyzing NCP, such as binary, trinary, and/or the like for necrotic core, fibrous, and/or fibrofatty. In some embodiments, the system may utilize continuous density measures for NCP. Further, in some embodiments, the system may analyze NCP for dual energy, monochromatic, and/or material basis decomposition. In some embodiments, the system can be configured to analyze and/or identify plaque geometry and/or plaque heterogeneity and/or other radiomics features. In some embodiments, the system can be configured to analyze and/or identify plaque facing the lumen and/or plaque facing epicardial fat. In some embodiments, the system can be configured to derive and/or identify imaging-based information, which can be provided directly to the algorithm for generating the global ischemia index.

In some embodiments, the system can be configured to analyze and/or utilize as an input low density NCP, which may cause greater endothelial dysfunction and inability to vasodilate to hyperemia, for example using one or more specific techniques described above in relation to NCP. In some embodiments, the system can be configured to analyze and/or utilize as an input calcified plaque (CP), which may cause more laminar flow, less endothelial dysfunction and less ischemia. In some embodiments, the system may utilize one or more arbitrary cutoffs, such as 1K plaque (plaques>1000 Hounsfield units), and/or continuous density measures for CP.

In some embodiments, the system can be configured to analyze and/or utilize as an input the location of plaque. In particular, the system may determine that myocardial facing plaque may be associated with reduced ischemia due to its proximity to myocardium (e.g., myocardial bridging rarely has atherosclerosis). In some embodiments, the system may determine that pericardial facing plaque may be associated with increased ischemia due to its proximity to peri-coronary adipose tissue. In some embodiments, the system may determine that bifurcation and/or trifurcation lesions may be associated with increased ischemia due to disruptions in laminar flow.

In some embodiments, visualization of three-dimensional plaques can be generated and/or provided by the system to a user to improve understanding to the human observer of where plaques are in relationship to each other and/or to the myocardium to the pericardium. For example, in a particular vein, the system may be configured to allow the visualization of all the plaques on a single 2D image. As such, in some embodiments, the system can allow for all of the plaques to be visualized in a single view, with color-coded and/or shadowed labels and/or other labels to plaques depending on whether they are in the 2D field of view, or whether they are further away from the 2D field of view. This can be analogous to the maximum intensity projection view, which highlights the lumen that is filled with contrast agent, but applies an intensity projection (maximum, minimum, average, ordinal) to the plaques of different distance from the field of view or of different densities.

In some embodiments, the system can be configured to visualize plaque using maximum intensity projection (MIP) techniques. In some embodiments, the system can be configured to visualize plaque in 2D, 3D, and/or 4D, for example using MIP techniques and/or other techniques, such as volume rendering techniques (VRT). More specifically, for 4D, in some embodiments, the system can be configured to visualize progression of plaque in terms of time. In some embodiments, the system can be configured to visualize on an image and/or on a video and/or other digital support the lumen and/or the addition of plaque in 2D, 3D, and/or 4D. In some embodiments, the system can be configured to show changes in time or 4D. In some embodiments, the system can be configured to take multiple scans taken from different points in time and/or integrate all or some of the information with therapeutics. In some embodiments, based on the same, the system can be configured to decide on changes in therapy and/or determine prognostic information, for example assessing for therapy success.

Another example contributor or cause of ischemia that can be utilized as input and/or analyzed by the system can include fat. In some embodiments, the system can be configured to analyze and/or utilize as an input peri-coronary adipose tissue, which may cause ischemia due to inflammatory properties that cause endothelial dysfunction. In some embodiments, the system can be configured to analyze and/or utilize as an input epicardial adipose tissue, which may be a cause of overall heart inflammation. In some embodiments, the system can be configured to analyze and/or utilize as input epicardial fat and/or radiomics or imaging-based information provided directly to the algorithm, such as for example heterogeneity, density, density change away from the vessel, volume, and/or the like.

As described above, in some embodiments, the system can be configured to utilize one or more consequences or sequelae of ischemia as inputs for generating a global ischemia index. An example consequence or sequelae of ischemia that can be utilized as input and/or analyzed by the system can be related to the left ventricle. For example, in some embodiments, the system can be configured to analyze the perfusion and/or Hounsfield unit density of the left ventricle, which can be global and/or related to the percentage of fractional myocardial mass. In some embodiments, the system can be configured to analyze the mass of the left ventricle, wherein the greater the mass, the greater the potential mismatch between lumen volume to LV mass, which can be global as well as related to the percentage of fractional myocardial mass. In some embodiments, the system can be the system can be configured to analyze the volume of the left ventricle, wherein an increase in the left ventricle volume can be a direct sign of ischemia. In some embodiments, the system can be configured to analyze and/or utilize as input density measurements of the myocardium, which can be absolute and/or relative, for example using a sticker or normalization device. In some embodiments, the system can be configured to analyze and/or use as input regional and/or global changes in densities. In some embodiments, the system can be configured to analyze and/or use as input endo, mid-wall, and/or epicardial changes in densities. In some embodiments, the system can be configured to analyze and/or use as input thickness, presence of fat and/or localization thereof, presence of calcium, heterogeneity, radiomic features, and/or the like.

Another example consequence or sequelae of ischemia that can be utilized as input and/or analyzed by the system can be related to the right ventricle. For example, in some embodiments, the system can be configured to analyze the perfusion and/or Hounsfield unit density of the right ventricle, which can be global and/or related to the percentage of fractional myocardial mass. In some embodiments, the system can be configured to analyze the mass of the right ventricle, wherein the greater the mass, the greater the potential mismatch between lumen volume to LV mass, which can be global as well as related to the percentage of fractional myocardial mass. In some embodiments, the system can be the system can be configured to analyze the volume of the right ventricle, wherein an increase in the right ventricle volume can be a direct sign of ischemia.

Another example consequence or sequelae of ischemia that can be utilized as input and/or analyzed by the system can be related to the left atrium. For example, in some embodiments, the system can be configured to analyze the volume of the left atrium, in which an increased left atrium volume can occur in patients who become ischemic and go into heart failure.

Another example consequence or sequelae of ischemia that can be utilized as input and/or analyzed by the system can be related to the right atrium. For example, in some embodiments, the system can be configured to analyze the volume of the right atrium, in which an increased right atrium volume can occur in patients who become ischemic and go into heart failure.

Another example consequence or sequelae of ischemia that can be utilized as input and/or analyzed by the system can be related to one or more aortic dimensions. For example, an increased aortic size as a long-standing contributor of hypertension may be associated with the end-organ effects of hypertension on the coronary arteries (resulting in more disease) and the LV mass (resulting in more LV mass-coronary lumen volume mismatch).

Another example consequence or sequelae of ischemia that can be utilized as input and/or analyzed by the system can be related to the pulmonary veins. For example, for patients with volume overload, engorgement of the pulmonary veins may be a significant sign of ischemia.

As described above, in some embodiments, the system can be configured to utilize one or more associated factors of ischemia as inputs for generating a global ischemia index. An example associated factor of ischemia that can be utilized as input and/or analyzed by the system can be related to the presence of fatty liver or non-alcoholic steatohepatitis, which is a condition that can be diagnosed by placing regions of interest (ROIs) in the liver to measure Hounsfield unit densities. Another example associated factor of ischemia that can be utilized as input and/or analyzed by the system can be related to emphysema, which is a condition that can be diagnosed by placing regions of interest in the lung to measure Hounsfield unit densities. Another example associated factor of ischemia that can be utilized as input and/or analyzed by the system can be related to osteoporosis, which is a condition that can be diagnosed by placing regions of interest in the spine. Another example associated factor of ischemia that can be utilized as input and/or analyzed by the system can be related to mitral annular calcification, which is a condition that can be diagnosed by identifying calcium (e.g., HU>350 etc.) in the mitral annulus. Another example associated factor of ischemia that can be utilized as input and/or analyzed by the system can be related to aortic valve calcification, which is a condition that can be diagnosed by identifying calcium in the aortic valve. Another example associated factor of ischemia that can be utilized as input and/or analyzed by the system can be related to aortic enlargement, often seen in hypertension, can reveal an enlargement in the proximal aorta due to long-standing hypertension. Another example associated factor of ischemia that can be utilized as input and/or analyzed by the system can be related to mitral valve calcification, which can be diagnosed by identifying calcium in the mitral valve.

As discussed herein, in some embodiments, the system can be configured to utilize one or more inputs or variables for generating a global ischemia index, for example by inputting the like into a regression model or other algorithm. In some embodiments, the system can be configured to use as input one or more radiomics features and/or imaging-based deep learning. In some embodiments, the system can be configured to utilize as input one or more of patient height, weight, sex, ethnicity, body surface, previous medication, genetics, and/or the like.

In some embodiments, the system can be configured to analyze and/or utilize as input calcium, separate calcium densities, localization calcium to lumen, volume of calcium, and/or the like. In some embodiments, the system can be configured to analyze and/or utilize as input contrast vessel attenuation. In particular, in some embodiments, the system can be configured to analyze and/or utilize as input average contrast in the lumen in the beginning of a segment and/or average contrast in the lumen at the end of that segment. In some embodiments, the system can be configured to analyze and/or utilize as input average contrast in the lumen in the beginning of the vessel to the beginning of the distal segment of that vessel, for example because the end can be too small in some instances.

In some embodiments, the system can be configured to analyze and/or utilize as input plaque heterogeneity. In particular, in some embodiments, the system can be configured to analyze and/or utilize as input calcified plaque volume versus and/or non-calcified plaque volume. In some embodiments, the system can be configured to analyze and/or utilize as input standard deviation of one or more of the 3 different components of plaque.

In some embodiments, the system can be configured to analyze and/or utilize as input one or more vasodilation metrics. In particular, in some embodiments, the system can be configured to analyze and/or utilize as input the highest remodeling index of a plaque. In some embodiments, the system can be configured to analyze and/or utilize as input the highest, average, and/or smallest thickness of plaque, and for example for its calcified and/or non-calcified components. In some embodiments, the system can be configured to analyze and/or utilize as input the highest remodeling index and/or lumen area. In some embodiments, the system can be configured to analyze and/or utilize as input the lesion length and/or segment length of plaque.

In some embodiments, the system can be configured to analyze and/or utilize as input bifurcation lesion, such as for example the presence of absence thereof. In some embodiments, the system can be configured to analyze and/or utilize as input coronary dominance, for example left dominance, right dominance, and/or codominance. In particular, in some embodiments, if left dominance, the system can be configured to disregard and/or weight less one or more right coronary metrics. Similarly, if right dominance, the system can be configured to disregard and/or weight less one or more left coronary metrics.

In some embodiments, the system can be configured to analyze and/or utilize as input one or more vascularization metrics. In particular, in some embodiments, the system can be configured to analyze and/or utilize as input the volume of the lumen of one or more, some, or all vessels. In some embodiments, the system can be configured to analyze and/or utilize as input the volume of the lumen of one or more secondary vessels, such as for example, non-right coronary artery (non-RCA), left anterior descending artery (LAD) vessel, circumflex (CX) vessel, and/or the like. In some embodiments, the system can be configured to analyze and/or utilize as input the volume of vessel and/or volume of plaque and/or a ratio thereof.

In some embodiments, the system can be configured to analyze and/or utilize as input one or more inflammation metrics. In particular, in some embodiments, the system can be configured to analyze and/or utilize as input the average density of one or more pixels outside a lesion, such as for example 5 pixels and/or 3 or 4 pixels of 5, disregarding the first 1 or 2 pixels. In some embodiments, the system can be configured to analyze and/or utilize as input the average density of one or more pixels outside a lesion Including the First ⅔ of Each Vessel that is not a Lesion or Plaque. In Some Embodiments, the system can be configured to analyze and/or utilize as input one or more pixels outside a lesion and/or the average of the same pixels on a 3 mm section above the proximal right coronary artery (R1) if there is no plaque in that place. In some embodiments, the system can be configured to analyze and/or utilize as input one or more ratios of any factors and/or variables described herein.

As described above, in some embodiments, the system can be configured to utilize one or more machine learning algorithms in identifying, deriving, and/or analyzing one or more inputs for generating the global ischemia index, including for example one or more direct contributors to ischemia, early consequences of ischemia, late consequences of ischemia, associated factors with ischemia, and other test findings in relation to ischemia. In some embodiments, one or more such machine learning algorithms can provide fully automated quantification and/or characterization of such factors.

As an example, in some embodiments, the system can be configured to utilize one or more machine learning algorithms to identify, derive, and/or analyze inferior vena cava from one or more medical images. Measures of inferior vena cava can be of high importance in patients with right-sided heart failure and tricuspid regurgitation.

In addition, in some embodiments, the system can be configured to utilize one or more machine learning algorithms to identify, derive, and/or analyze the interatrial septum from one or more medical images. Interatrial septum dimensions can be vital for patients undergoing left-sided transcatheter procedures.

In some embodiments, the system can be configured to utilize one or more machine learning algorithms to identify, derive, and/or analyze descending thoracic aorta from one or more medical images. Measures of descending thoracic aorta can be of critical importance in patients with aortic aneurysms, and for population-based screening in long-time smokers.

In some embodiments, the system can be configured to utilize one or more machine learning algorithms to identify, derive, and/or analyze the coronary sinus from one or more medical images. Coronary sinus dimensions can be vital for patients with heart failure who are undergoing biventricular pacing. In some embodiments, by analyzing the coronary sinus, the system can be configured to derive all or some myocardium blood flow, which can be related to coronary volume, myocardium mass. In addition, in some embodiments, the system can be configured to analyze, derive, and/or identify hypertrophic cardiomyopathy (HCM), other hypertrophies, ischemia, and/or the like to derive ischemia and/or microvascular ischemia.

In some embodiments, the system can be configured to utilize one or more machine learning algorithms to identify, derive, and/or analyze the anterior mitral leaflet from one or more medical images. For a patient being considered for surgical or transcatheter mitral valve repair or replacement, no current method currently exists to measure anterior mitral leaflet dimensions.

In some embodiments, the system can be configured to utilize one or more machine learning algorithms to identify, derive, and/or analyze the left atrial appendage from one or more medical images. Left atrial appendage morphologies are linked to stroke in patients with atrial fibrillation, but no automated characterization solution exists today.

In some embodiments, the system can be configured to utilize one or more machine learning algorithms to identify, derive, and/or analyze the left atrial free wall mass from one or more medical images. No current method exists to accurately measure left atrial free wall mass, which may be important in patients with atrial fibrillation.

In some embodiments, the system can be configured to utilize one or more machine learning algorithms to identify, derive, and/or analyze the left ventricular mass from one or more medical images. Certain methods of measuring left ventricular hypertrophy as an adverse consequence of hypertension rely upon echocardiography, which employs a 2D estimated formula that is highly imprecise. 3D imaging by magnetic resonance imaging (MRI) or computed tomography (CT) are much more accurate, but current software tools are time-intensive and imprecise.

In some embodiments, the system can be configured to utilize one or more machine learning algorithms to identify, derive, and/or analyze the left atrial volume from one or more medical images. Determination of left atrial volume can improve diagnosis and risk stratification in patients with and at risk of atrial fibrillation.

In some embodiments, the system can be configured to utilize one or more machine learning algorithms to identify, derive, and/or analyze the left ventricular volume from one or more medical images. Left ventricular volume measurements can enable determination of individuals with heart failure or at risk of heart failure.

In some embodiments, the system can be configured to utilize one or more machine learning algorithms to identify, derive, and/or analyze the left ventricular papillary muscle mass from one or more medical images. No current method currently exists to measure left ventricular papillary muscle mass.

In some embodiments, the system can be configured to utilize one or more machine learning algorithms to identify, derive, and/or analyze the posterior mitral leaflet from one or more medical images. For patients being considered for surgical or transcatheter mitral valve repair or replacement, no current method currently exists to measure posterior mitral leaflet dimensions.

In some embodiments, the system can be configured to utilize one or more machine learning algorithms to identify, derive, and/or analyze pulmonary veins from one or more medical images. Measures of pulmonary vein dimensions can be of critical importance in patients with atrial fibrillation, heart failure and mitral regurgitation.

In some embodiments, the system can be configured to utilize one or more machine learning algorithms to identify, derive, and/or analyze pulmonary arteries from one or more medical images. Measures of pulmonary artery dimensions can be of critical importance in patients with pulmonary hypertension, heart failure and pulmonary emboli.

In some embodiments, the system can be configured to utilize one or more machine learning algorithms to identify, derive, and/or analyze the right atrial free wall mass from one or more medical images. No current method exists to accurately measure right atrial free wall mass, which may be important in patients with atrial fibrillation.

In some embodiments, the system can be configured to utilize one or more machine learning algorithms to identify, derive, and/or analyze the right ventricular mass from one or more medical images. Methods of measuring right ventricular hypertrophy as an adverse consequence of pulmonary hypertension and/or heart failure do not currently exist.

In some embodiments, the system can be configured to utilize one or more machine learning algorithms to identify, derive, and/or analyze the proximal ascending aorta from one or more medical images. Aortic aneurysms can require highly precise measurements of the aorta, which are more accurate by 3D techniques such as CT and MIll. At present, current algorithms do not allow for highly accurate automated measurements.

In some embodiments, the system can be configured to utilize one or more machine learning algorithms to identify, derive, and/or analyze the right atrial volume from one or more medical images. Determination of right atrial volume can improve diagnosis and risk stratification in patients with and at risk of atrial fibrillation.

In some embodiments, the system can be configured to utilize one or more machine learning algorithms to identify, derive, and/or analyze the right ventricular papillary muscle mass from one or more medical images. No current method currently exists to measure right ventricular papillary muscle mass.

In some embodiments, the system can be configured to utilize one or more machine learning algorithms to identify, derive, and/or analyze the right ventricular volume from one or more medical images. Right ventricular volume measurements can enable determination of individuals with heart failure or at risk of heart failure.

In some embodiments, the system can be configured to utilize one or more machine learning algorithms to identify, derive, and/or analyze the superior vena cava from one or more medical images. No reliable method exists to date to measure superior vena cava dimensions, which may be important in patients with tricuspid valve insufficiency and heart failure.

In some embodiments, the system can be configured to utilize one or more machine learning algorithms to identify, derive, analyze, segment, and/or quantify one or more cardiac structures from one or more medical images, such as the left and right ventricular volume (LVV, RVV), left and right atrial volume (LAV, RAV), and/or left ventricular myocardial mass (LVM).

Further, in some embodiments, the system can be configured to utilize one or more machine learning algorithms to identify, derive, analyze, segment, and/or quantify one or more cardiac structures from one or more medical images, such as the proximal ascending and descending aorta (PAA, DA), superior and inferior vena cavae (SVC, IVC), pulmonary artery (PA), coronary sinus (CS), right ventricular wall (RVW), and left atrial wall (LAW).

In addition, in some embodiments, the system can be configured to utilize one or more machine learning algorithms to identify, derive, analyze, segment, and/or quantify one or more cardiac structures from one or more medical images, such as the left atrial appendage, left atrial wall, coronary sinus, descending aorta, superior vena cava, inferior vena cava, pulmonary artery, right ventricular wall, sinuses of Valsalva, left ventricular volume, left ventricular wall, right ventricular volume, left atrial volume, right atrial volume, and/or proximal ascending aorta.

Figure 20E:
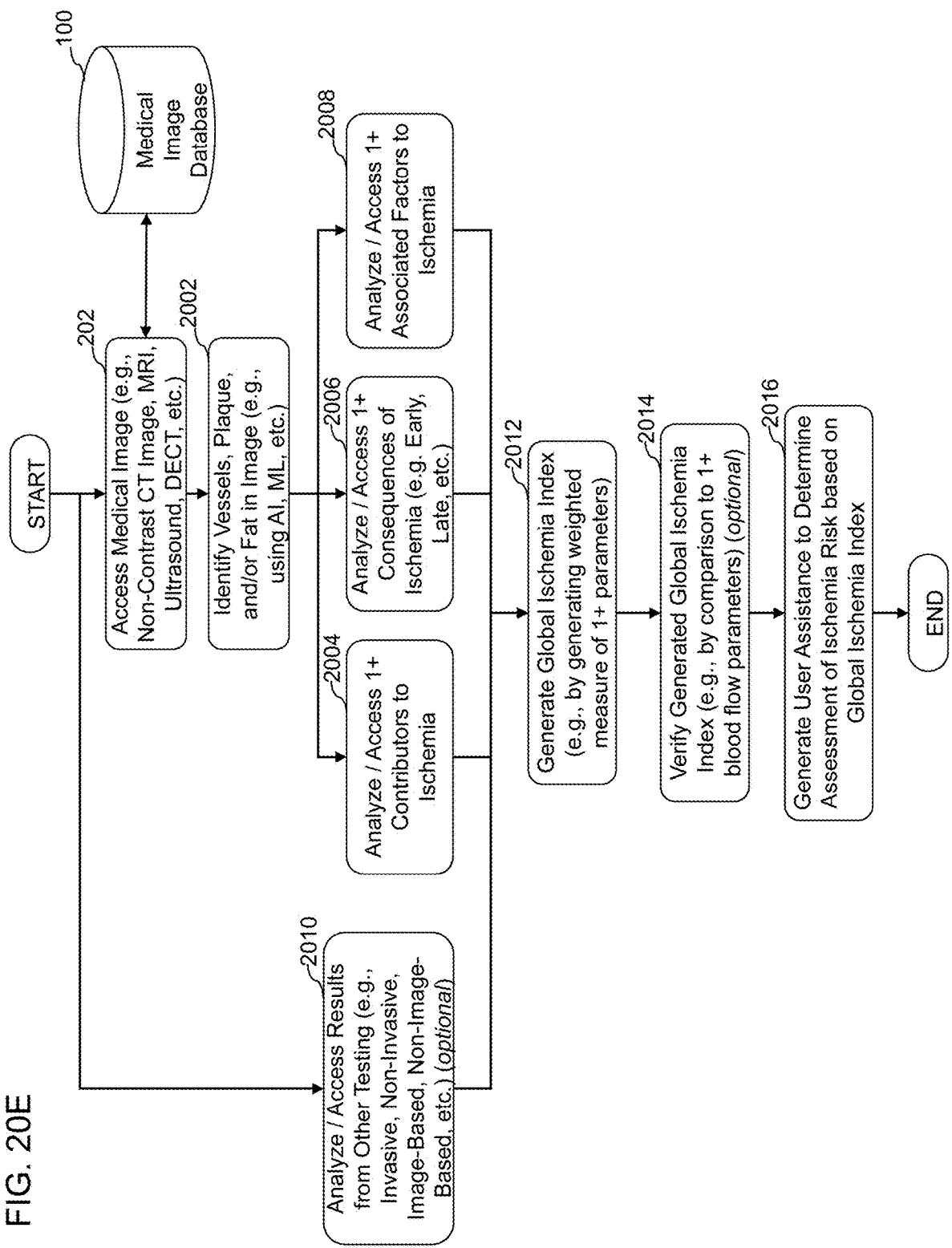
FIG. 20E is a flowchart illustrating an overview of an example embodiment(s) of a method for generating a global ischemia index for a subject and using the same to assist assessment of risk of ischemia for the subject.

FIG. 20E is a flowchart illustrating an overview of an example embodiment(s) of a method for generating a global ischemia index for a subject and using the same to assist assessment of risk of ischemia for the subject. As illustrated in FIG. 20E, in some embodiments, the system can be configured to access one or more medical images of a subject at block 202, in any manner and/or in connection with any feature described above in relation to block 202. In some embodiments, the system is configured to identify one or more vessels, plaque, and/or fat in the one or more medical images at block 2002. For example, in some embodiments, the system can be configured to use one or more AI and/or ML algorithms and/or other image processing techniques to identify one or more vessels, plaque, and/or fat.

In some embodiments, the system at block 2004 is configured to analyze and/or access one or more contributors to ischemia of the subject, including any contributors to ischemia described herein, for example based on the accessed one or more medical images and/or other medical data. In some embodiments, the system at block 2006 is configured to analyze and/or access one or more consequences of ischemia of the subject, including any consequences of ischemia described herein, including early and/or late consequences, for example based on the accessed one or more medical images and/or other medical data. In some embodiments, the system at block 2008 is configured to analyze and/or access one or more associated factors to ischemia of the subject, including any associated factors to ischemia described herein, for example based on the accessed one or more medical images and/or other medical data. In some embodiments, the system at block 2010 is configured to analyze and/or access one or more results from other testing, such as for example invasive testing, non-invasive testing, image-based testing, non-image based testing, and/or the like.

In some embodiments, the system at block 2012 can be configured to generate a global ischemia index based on one or more parameters, such as for example one or more contributors to ischemia, one or more consequences of ischemia, one or more associated factors to ischemia, one or more other testing results, and/or the like. In some embodiments, the system is configured to generate a global ischemia index for the subject by generating a weighted measure of one or more parameters. For example, in some embodiments, the system is configured to weight one or more parameters differently and/or equally. In some embodiments, the system can be configured weight one or more parameters logarithmically, algebraically, and/or utilizing another mathematical transform. In some embodiments, the system is configured to generate a weighted measure using only some or all of the parameters.

In some embodiments, at block 2014, the system is configured to verify the generated global ischemia index. For example, in some embodiments, the system is configured to verify the generated global ischemia index by comparison to one or more blood flow parameters such as those discussed herein. In some embodiments, at block 2016, the system is configured to generate user assistance to help a user determine an assessment of risk of ischemia for the subject based on the generated global ischemia index, for example graphically through a user interface and/or otherwise.

CAD Score(s)

Some embodiments of the systems, devices, and methods described herein are configured to generate one or more coronary artery disease (CAD) scores representative of a risk of CAD for a particular subject. In some embodiments, the risk score can be generated by analyzing and/or combining one or more aspects or characteristics relating to plaque and/or cardiovascular features, such as for example plaque volume, plaque composition, vascular remodeling, high-risk plaque, lumen volume, plaque location (proximal v. middle v. distal), plaque location (myocardial v. pericardial facing), plaque location (at bifurcation or trifurcation v. not at bifurcation or trifurcation), plaque location (in main vessel v. branch vessel), stenosis severity, percentage coronary blood volume, percentage fractional myocardial mass, percentile for age and/or gender, constant or other correction factor to allow for control of within-person, within-vessel, inter-plaque, plaque-myocardial relationships, and/or the like. In some embodiments, a CAD risk score(s) can be generated based on automatic and/or dynamic analysis of one or more medical images, such as for example a CT scan or an image obtained from any other modality mentioned herein. In some embodiments, data obtained from analyzing one or more medical images of a patient can be normalized in generating a CAD risk score(s) for that patient. In some embodiments, the systems, devices, and methods described herein can be configured to generate a CAD risk score(s) for different vessels, vascular territories, and/or patients. In some embodiments, the systems, devices, and methods described herein can be configured to generate a graphical visualization of risk of CAD of a patient based on a vessel basis, vascular territory basis, and/or patient basis. In some embodiments, based on the generated CAD risk score(s), the systems, methods, and devices described herein can be configured to generate one or more recommended treatments for a patient. In some embodiments, the system can be configured to utilize a normalization device, such as those described herein, to account for differences in scan results (such as for example density values, etc.) between different scanners, scan parameters, and/or the like.

In some embodiments, the systems, devices, and methods described herein can be configured to assess patients with suspected coronary artery disease (CAD) by use of one or more of a myriad of different diagnostic and prognostic tools. In particular, in some embodiments, the systems, devices, and methods described herein can be configured to use a risk score for cardiovascular care for patients without known CAD.

As a non-limiting example, in some embodiments, the system can be configured to generate an Atherosclerotic Cardiovascular Disease (ASCVD) risk score, which can be based upon a combination of age, gender, race, blood pressure, cholesterol (total, HDL and LDL), diabetes status, tobacco use, hypertension, and/or medical therapy (such as for example, statin and aspirin).

As another non-limiting example, in some embodiments, the system can be configured to generate a Coronary Artery Calcium Score (CACS), which can be based upon a non-contrast CT scan wherein coronary arteries are visualized for the presence of calcified plaque. In some embodiments, an Agatston (e.g., a measure of calcium in a coronary CT scan) score may be used to determine the CACS. In particular, in some embodiments, a CACS score can be calculated by: Agatston score=surface area×Hounsfield unit density (with brighter plaques with higher density receiving a higher score). However, in some embodiments, there may be certain limitations with a CACS score. For example, in some embodiments, because surface area to volume ratio decreases as a function of the overall volume, more spherical plaques can be incorrectly weighted as less contributory to the Agatston score. In addition, in some embodiments, because Hounsfield unit density is inversely proportional to risk of major adverse cardiac events (MACE), weighting the HU density higher can score a lower risk plaque as having a higher score. Moreover, in some embodiments, 2.5-3 mm thick CT "slices" can miss smaller calcified plaques, and/or no use of beta blocker results in significant motion artifact, which can increase the calcium score due to artifact.

In some embodiments, for symptomatic patients undergoing coronary CT angiography, the system can be configured to generate and/or utilize one or more additional risk scores, such as a Segment Stenosis Score, Segment Involvement Score, Segments-at-Risk Score, Duke Prognostic Index, CTA Score, and/or the like. More specifically, in some embodiments, a Segment Stenosis Score weights specific stenoses (0=0%, 1=1-24%, 2=25-49%, 3=50-69%, 4=>70%) across the entire 18 coronary segment, resulting in a total possible score of 72. In some embodiments, a Segment Involvement Score counts the number of plaques located in the 18 segments and has a total possible score of 18.

In some embodiments, a Segments-at-Risk Score reflects the potential susceptibility of all distal coronary segments subtended by severe proximal plaque. Thus, in some embodiments, all segments subtended by severe proximal plaque can be scored as severe as well, then summated over 18 segments to create a segment-at-risk score. For example, if the proximal portion of the LCx is considered severely obstructive, the segments-at-risk score for the LCx can be proximal circumflex (=3)+mid circumflex (=3)+distal circumflex (=3)+proximal obtuse marginal (=3)+mid obtuse marginal (=3)+distal obtuse marginal (=3), for a total circumflex segments-at-risk score of 18. In this individual, if the LAD exhibits mild plaque in the proximal portion (=1) and moderate plaque in the midportion (=2), the LAD segments-at-risk score can be 3. If the RCA exhibits moderate plaque in the proximal portion (=3), the RCA segments-at-risk score can be 2. Thus, for this individual, the total segments-at-risk score can be 23 out of a possible 48.

In some embodiments, a Duke Prognostic Index can be a reflection of the coronary artery plaque severity considering plaque location. In some embodiments, a modified Duke CAD index can consider overall plaque extent relating it to coexistent plaque in the left main or proximal LAD. In some embodiments, using this scoring system, individuals can be categorized into six distinct groups: no evident coronary artery plaque; ≥2 mild plaques with proximal plaque in any artery or 1 moderate plaque in any artery; 2 moderate plaques or 1 severe plaque in any artery; 3 moderate coronary artery plaques or 2 severe coronary artery plaques or isolated severe plaque in the proximal LAD; 3 severe coronary artery plaques or 2 severe coronary artery plaques with proximal LAD plaque; moderate or severe left main plaque.

In some embodiments, a CT angiography (CTA) Score can be calculated by determining CAD in each segment, such as for example proximal RCA, mid RCA, distal RCA, R-PDA, R-PLB, left main, proximal LAD, mid LAD, distal LAD, D1, D2, proximal LCX, distal LCX, IM/AL, OM, L-PL, L-PDA, and/or the like. In particular, for each segment, when plaque is absent, the system can be configured to assign a score of 0, and when plaque is present, the system can be configured to assign a score of 1.1, 1.2 or 1.3 according to plaque composition (such as calcified, non-calcified and mixed plaque, respectively). In some embodiments, these scores can be multiplied by a weight factor for the location of the segment in the coronary artery tree (for example, 0.5-6 according to vessel, proximal location and system dominance). In some embodiments, these scores can also be multiplied by a weight factor for stenosis severity (for example, 1.4 for >50% stenosis and 1.0 for stenosis<50%). In some embodiments, the final score can be calculated by addition of the individual segment scores.

In some embodiments, the systems, devices, and methods described herein can be configured to utilize and/or perform improved quantification and/or characterization of many parameters on CT angiography that were previously very difficult to measure. For example, in some embodiments, the system can be configured to determine stenosis severity leveraging a proximal/distal reference and report on a continuous scale, for example from 0-100%, by diameter, area, and/or volumetric stenosis. In some embodiments, the system can be configured to determine total atheroma burden, reported in volumes or as a percent of the overall vessel volume (PAV), including for example non-calcified plaque volume (for example, as a continuous variable, ordinal variable or single variable), calcified plaque volume (for example, as a continuous variable, ordinal variable or single variable), and/or mixed plaque volume (for example, as a continuous variable, ordinal variable or single variable).

In some embodiments, the system can be configured to determine low attenuation plaque, for example reported either as yes/no binary or continuous variable based upon HU density. In some embodiments, the system can be configured to determine vascular remodeling, for example reported as ordinal negative, intermediate or positive (for example, <0.90, 0.90-1.10, or >1.0) or continuous. In some embodiments, the system can be configured to determine and/or analyze various locations of plaque, such as for example proximal/mid/distal, myocardial facing vs. pericardial facing, at bifurcation v. not at bifurcation, in main vessel vs. branch vessel, and/or the like.

In some embodiments, the system can be configured to determine percentage coronary blood volume, which can report out the volume of the lumen (and downstream subtended vessels in some embodiments) as a function of the entire coronary vessel volume (for example, either measured or calculated as hypothetically normal). In some embodiments, the system can be configured to determine percentage fractional myocardial mass, which can relate the coronary lumen or vessel volume to the percentage downstream subtended myocardial mass.

In some embodiments, the system can be configured to determine the relationship of all or some of the above to each other, for example on a plaque-plaque basis to influence vessel behavior/risk or on a vessel-vessel basis to influence patient behavior/risk. In some embodiments, the system can be configured to utilize one or more comparisons of the same, for example to normal age- and/or gender-based reference values.

In some embodiments, one or more of the metrics described herein can be calculated on a per-segment basis. In some embodiments, one or more of the metrics calculated on a per-segment basis can then summed across a vessel, vascular territory, and/or patient level. In some embodiments, the system can be configured to visualize one or more of such metrics, whether on a per-segment basis and/or on a vessel, vascular territory, and/or patient basis, on a geographical scale. For example, in some embodiments, the system can be configured to visualize one or more such metrics on a graphical scale using 3D and/or 4D histograms.

Further, in some embodiments, cardiac CT angiography enables quantitative assessment of a myriad of cardiovascular structures beyond the coronary arteries, which may both contribute to coronary artery disease as well as other cardiovascular diseases. For example, these measurements can include those of one or more of: (1) left ventricle—e.g., left ventricular mass, left ventricular volume, left ventricle Hounsfield unit density as a surrogate marker of ventricular perfusion; (2) right ventricle—e.g., right ventricular mass, right ventricular volume; (3) left atrium—e.g., volume, size, geometry; (4) right atrium—e.g., volume, size, geometry; (5) left atrial appendage—e.g., morphology (e.g., chicken wing, windsock, etc.), volume, angle, etc.; (6) pulmonary vein—e.g., size, shape, angle of takeoff from the left atrium, etc.; (7) mitral valve—e.g., volume, thickness, shape, length, calcification, anatomic orifice area, etc.; (8) aortic valve—e.g., volume, thickness, shape, length, calcification, anatomic orifice area, etc.; (9) tricuspid valve—e.g., volume, thickness, shape, length, calcification, anatomic orifice area, etc.; (10) pulmonic valve—e.g., volume, thickness, shape, length, calcification, anatomic orifice area, etc.; (11) pericardial and pericoronary fat—e.g., volume, attenuation, etc.; (12) epicardial fat—e.g., volume, attenuation, etc.; (13) pericardium—e.g., thickness, mass, volume; and/or (14) aorta—e.g., dimensions, calcifications, atheroma.

Given the multitude of measurements that can help characterize cardiovascular risk, certain existing scores can be limited in their holistic assessment of the patient and may not account for many key parameters that may influence patient outcome. For example, certain existing scores may not take into account the entirety of data that is needed to effectively prognosticate risk. In addition, the data that will precisely predict risk can be multi-dimensional, and certain scores do not consider the relationship of plaques to one another, or vessel to one another, or plaques-vessels-myocardium relationships or all of those relationships to the patient-level risk. Also, in certain existing scores, the data may categorize plaques, vessels and patients, thus losing the granularity of pixel-wise data that are summarized in these scores. In addition, in certain existing scores, the data may not reflect the normal age- and gender-based reference values as a benchmark for determining risk. Moreover, certain scores may not consider a number of additional items that can be gleaned from quantitative assessment of coronary artery disease, vascular morphology and/or downstream ventricular mass. Further, within-person relationships of plaques, segments, vessels, vascular territories may not considered within certain risk scores. Furthermore, no risk score to date that utilizes imaging normalizes these risks to a standard that accounts for differences in scanner make/model, contrast type, contrast injection rate, heart rate/cardiac output, patient characteristics, contrast-to-noise ratio, signal-to-noise ratio, and/or image acquisition parameters (for example, single vs. dual vs. spectral energy imaging; retrospective helical vs. prospective axial vs. fast-pitch helical; whole-heart imaging versus non-whole-heart [i.e., non-volumetric] imaging; etc.). In some embodiments described herein, the systems, methods, and devices overcome such technical shortcomings.

In particular, in some embodiments, the systems, devices, and methods described herein can be configured to generate and/or a novel CAD risk score that addresses the aforementioned limitations by considering one or more of: (1) total atheroma burden, normalized for density, such as absolute density or Hounsfield unit (HU) density (e.g., can be categorized as total volume or relative volume, i.e., plaque volume/vessel volume×100%); (2) plaque composition by density or HU density (e.g., can be categorized continuously, ordinally or binarily); (3) low attenuation plaque (e.g., can be reported as yes/no binary or continuous variable based upon density or HU density); (4) vascular remodeling (e.g., can be reported as ordinal negative, intermediate or positive (<0.90, 0.90-1.10, or >1.0) or continuous); (5) plaque location—proximal v. mid v. distal; (6) plaque location—which vessel or vascular territory; (7) plaque location—myocardial facing v. pericardial facing; (8) plaque location—at bifurcation v. not at bifurcation; (9) plaque location—in main vessel v. branch vessel; (10) stenosis severity; (11) percentage coronary blood volume (e.g., this metric can report out the volume of the lumen (and downstream subtended vessels) as a function of the entire coronary vessel volume (e.g., either measured or calculated as hypothetically normal)); (12) percentage fractional myocardial mass (e.g., this metric can relate the coronary lumen or vessel volume to the percentage downstream subtended myocardial mass); (13) consideration of normal age- and/or gender-based reference values; and/or (14) statistical relationships of all or some of the above to each other (e.g., on a plaque-plaque basis to influence vessel behavior/risk or on a vessel-vessel basis to influence patient behavior/risk).

In some embodiments, the system can be configured to determine a baseline clinical assessment(s), including for such factors as one or more of: (1) age; (2) gender; (3) diabetes (e.g., presence, duration, insulin-dependence, history of diabetic ketoacidosis, end-organ complications, which medications, how many medications, and/or the like); (4) hypertension (e.g., presence, duration, severity, end-organ damage, left ventricular hypertrophy, number of medications, which medications, history of hypertensive urgency or emergency, and/or the like); (5) dyslipidemia (e.g., including low-density lipoprotein (LDL), triglycerides, total cholesterol, lipoprotein(a) Lp(a), apolipoprotein B (ApoB), and/or the like); (6) tobacco use (e.g., including what type, for what duration, how much use, and/or the like); (7) family history (e.g., including which relative, at what age, what type of event, and/or the like); (8) peripheral arterial disease (e.g., including what type, duration, severity, end-organ damage, and/or the like); (9) cerebrovascular disease (e.g., including what type, duration, severity, end-organ damage, and/or the like); (10) obesity (e.g., including how obese, how long, is it associated with other metabolic derangements, such as hypertriglyceridemia, centripetal obesity, diabetes, and/or the like); (11) physical activity (e.g., including what type, frequency, duration, exertional level, and/or the like); and/or (12) psychosocial state (e.g., including depression, anxiety, stress, sleep, and/or the like).

In some embodiments, a CAD risk score is calculated for each segment, such as for example for segment 1, segment 2, or for some or all segments. In some embodiments, the score is calculated by combining (e.g., by multiplying or applying any other mathematical transform or generating a weighted measure of) one or more of: (1) plaque volume (e.g., absolute volume such as in mm3 or PAV; may be weighted); (2) plaque composition (e.g., NCP/CP, Ordinal NCP/Ordinal CP; Continuous; may be weighted); (3) vascular remodeling (e.g., Positive/Intermediate/Negative; Continuous; may be weighted); (4) high-risk plaques (e.g., positive remodeling+low attenuation plaque; may be weighted); (5) lumen volume (e.g., may be absolute volume such as in mm3 or relative to vessel volume or relative to hypothetical vessel volume; may be weighted); (6) location—proximal/mid/distal (may be weighted); (7) location—myocardial vs. pericardial facing (may be weighted); (8) location—at bifurcation/trifurcation vs. not at bifurcation/trifurcation (may be weighted); (9) location—in main vessel vs. branch vessel (may be weighted); (10) stenosis severity (e.g., ><70%, < >50%, 1-24, 25-49, 50-69, >70%; 0, 1-49, 50-69, >70%; continuous; may use diameter, area or volume; may be weighted); (11) percentage Coronary Blood Volume (may be weighted); (12) percentage fractional myocardial mass (e.g., may include total vessel volume-to-LV mass ratio; lumen volume-to-LV mass ratio; may be weighted); (13) percentile for age- and gender; (14) constant/correction factor (e.g., to allow for control of within-person, within-vessel, inter-plaque, and/or plaque-myocardial relationships). As a non-limiting example, if Segment 1 has no plaque, then it can be weighted as 0 in some embodiments.

In some embodiments, to determine risk (which can be defined as risk of future myocardial infarction, major adverse cardiac events, ischemia, rapid progression, insufficient control on medical therapy, progression to angina, and/or progression to need of target vessel revascularization), all or some of the segments are added up on a per-vessel, per-vascular territory and per-patient basis. In some embodiments, by using plots, the system can be configured to visualize and/or quantify risk based on a vessel basis, vascular territory basis, and patient-basis.

In some embodiments, the score can be normalized in a patient- and scan-specific manner by considering items such as for example: (1) patient body mass index; (2) patient thorax density; (3) scanner make/model; (4) contrast density along the Z-axis and along vessels and/or cardiovascular structures; (5) contrast-to-noise ratio; (6) signal-to-noise ratio; (7) method of ECG gating (e.g., retrospective helical, prospective axial, fast-pitch helical); (8) energy acquisition (e.g., single, dual, spectral, photon counting); (9) heart rate; (10) use of pre-CT medications that may influence cardiovascular structures (e.g., nitrates, beta blockers, anxiolytics); (11) mA; and/or (12) kvp.

In some embodiments, without normalization, cardiovascular structures (coronary arteries and beyond) may have markedly different Hounsfield units for the same structure (e.g., if 100 vs. 120 kvp is used, a single coronary plaque may exhibit very different Hounsfield units). Thus, in some embodiments, this "normalization" step is needed, and can be performed based upon a database of previously acquired images and/or can be performed prospectively using an external normalization device, such as those described herein.

In some embodiments, the CAD risk score can be communicated in several ways by the system to a user. For example, in some embodiments, a generated CAD risk score can be normalized to a scale, such as a 100 point scale in which 90-100 can refer to excellent prognosis, 80-90 for good prognosis, 70-80 for satisfactory prognosis, 60-70 for below average prognosis, <60 for poor prognosis, and/or the like. In some embodiments, the system can be configured to generate and/or report to a user based on the CAD risk score(s) vascular age vs. biological age of the subject. In some embodiments, the system can be configured to characterize risk of CAD of a subject as one or more of normal, mild, moderate, and/or severe. In some embodiments, the system can be configured to generate one or more color heat maps based on a generated CAD risk score, such as red, yellow, green, for example in ordinal or continuous display. In some embodiments, the system can be configured to characterize risk of CAD for a subject as high risk vs. non-high-risk, and/or the like.

As a non-limiting example, in some embodiments, the generated CAD risk score for Lesion 1 can be calculated as Vol X Composition (HU)×RI×HRP×Lumen Volume×Location×Stenosis %×% CBV×% FMM×Age-/Gender Normal Value %×Correction Constant)×Correction factor for scan- and patient-specific parameters×Normalization factor to communicate severity of findings. Similarly, in some embodiments, the generated CAD risk score for Lesion 2 can be calculated as Vol×Composition (HU)×RI×HRP×Lumen Volume×Location x Stenosis %×% CBV×% FMM× Age-/Gender Normal Value %×Correction Constant)×Correction factor for scan- and patient-specific parameters× Normalization factor to communicate severity of findings. In some embodiments, the generated CAD risk score for Lesion 3 can be calculated as Vol×Composition (HU)×RI× HRP×Lumen Volume×Location x Stenosis %×% CBV×% FMM×Age-/Gender Normal Value %×Correction Constant)×Correction factor for scan- and patient-specific parameters×Normalization factor to communicate severity of findings. In some embodiments, the generated CAD risk score for Lesion 4 can be calculated as Vol×Composition (HU)×RI×HRP×Lumen Volume×Location×Stenosis %×% CBV×% FMM×Age-/Gender Normal Value %×Correction Constant)×Correction factor for scan- and patient-specific parameters×Normalization factor to communicate severity of findings. In some embodiments, a CAD risk score can similarly be generated for any other lesions.

In some embodiments, the CAD risk score can be adapted to other disease states within the cardiovascular system, including for example: (1) coronary artery disease and its downstream risk (e.g., myocardial infarction, acute coronary syndromes, ischemia, rapid progression, progression despite medical therapy, progression to angina, progression to need for target vessel revascularization, and/or the like); (2) heart failure; (3) atrial fibrillation; (4) left ventricular hypertrophy and hypertension; (5) aortic aneurysm and/or dissection; (6) valvular regurgitation or stenosis; (7) sudden coronary artery dissection, and/or the like.

Figure 21:
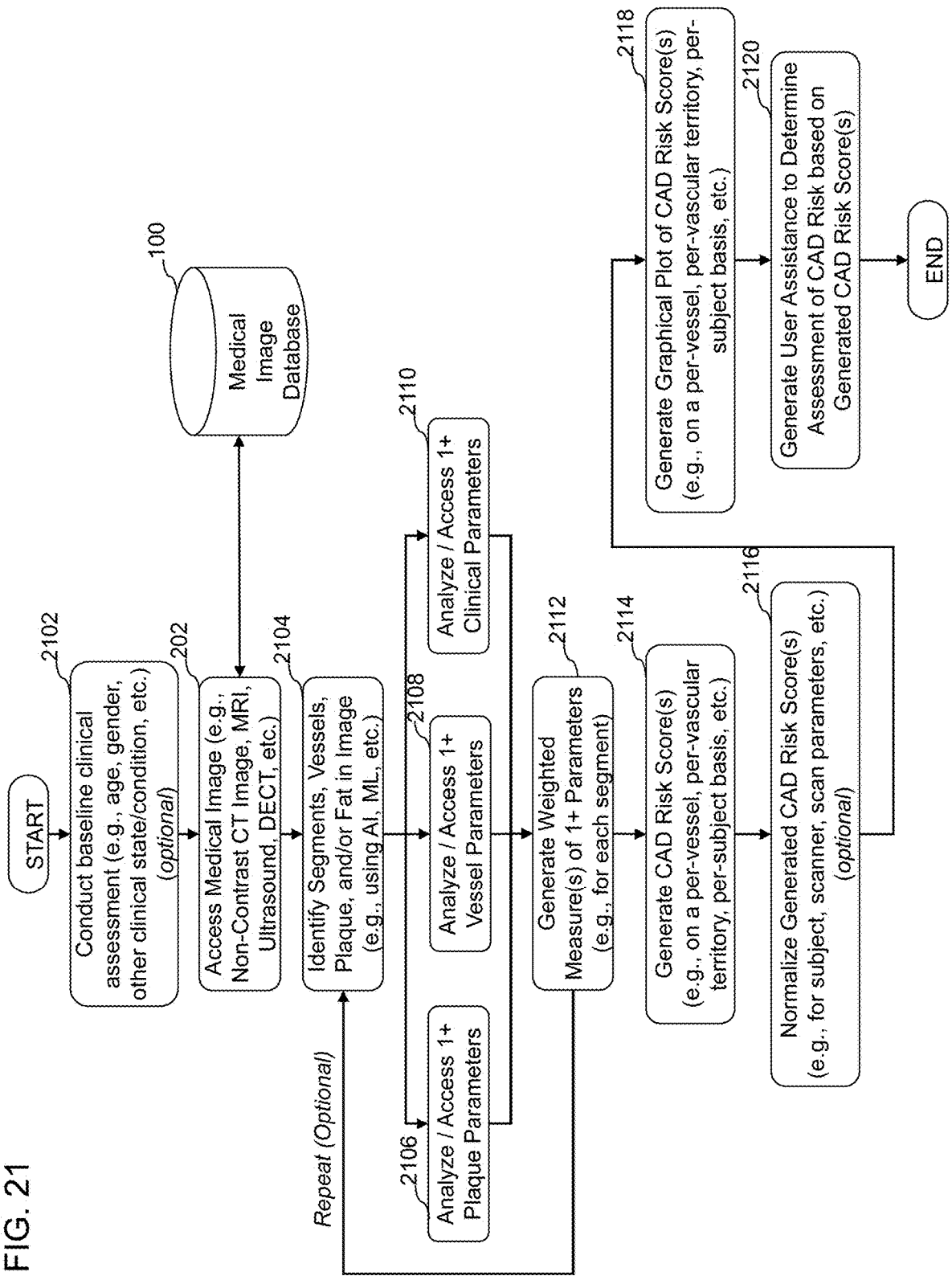
FIG. 21 is a flowchart illustrating an overview of an example embodiment(s) of a method for generating a coronary artery disease (CAD) Score(s) for a subject and using the same to assist assessment of risk of CAD for the subject.

FIG. 21 is a flowchart illustrating an overview of an example embodiment(s) of a method for generating a coronary artery disease (CAD) Score(s) for a subject and using the same to assist assessment of risk of CAD for the subject. As illustrated in FIG. 21, in some embodiments, the system is configured to conduct a baseline clinical assessment of a subject at block 2102. In particular, in some embodiments, the system can be configured to take into account one or more clinical assessment factors associated with the subject, such as for example age, gender, diabetes, hypertension, dyslipidemia, tobacco use, family history, peripheral arterial disease, cerebrovascular disease, obesity, physical activity, psychosocial state, and/or any details of the foregoing described herein. In some embodiments, one or more baseline clinical assessment factors can be accessed by the system from a database and/or derived from non-image-based and/or image-based data.

In some embodiments, at block 202, the system can be configured to access one or more medical images of the subject at block 202, in any manner and/or in connection with any feature described above in relation to block 202. In some embodiments, the system is configured to identify one or more segments, vessels, plaque, and/or fat in the one or more medical images at block 2104. For example, in some embodiments, the system can be configured to use one or more AI and/or ML algorithms and/or other image processing techniques to identify one or more segments, vessels, plaque, and/or fat.

In some embodiments, the system at block 2106 is configured to analyze and/or access one or more plaque parameters. For example, in some embodiments, one or more plaque parameters can include plaque volume, plaque composition, plaque attenuation, plaque location, and/or the like. In particular, in some embodiments, plaque volume can be based on absolute volume and/or PAV. In some embodiments, plaque composition can be determined by the system based on density of one or more regions of plaque in a medical image, such as absolute density and/or Hounsfield unit density. In some embodiments, the system can be configured to categorize plaque composition binarily, for example as calcified or non-calcified plaque, and/or continuously based on calcification levels of plaque. In some embodiments, plaque attenuation can similarly be categorized binarily by the system, for example as high attenuation or low attenuation based on density, or continuously based on attenuation levels of plaque. In some embodiments, plaque location can be categorized by the system as one or more of proximal, mid, or distal along a coronary artery vessel. In some embodiments, the system can analyze plaque location based on the vessel in which the plaque is located. In some embodiments, the system can be configured to categorize plaque location based on whether it is myocardial facing, pericardial facing, located at a bifurcation, located at a trifurcation, not located at a bifurcation, and/or not located at a trifurcation. In some embodiments, the system can be configured to analyze plaque location based on whether it is in a main vessel or in a branch vessel.

In some embodiments, the system at block 2108 is configured to analyze and/or access one or more vessel parameters, such as for example stenosis severity, lumen volume, percentage of coronary blood volume, percentage of fractional myocardial mass, and/or the like. In some embodiments, the system is configured to categorize or determine stenosis severity based on one or more predetermined ranges of percentage stenosis, for example based on diameter, area, and/or volume. In some embodiments, the system is configured to determine lumen volume based on absolute volume, volume relative to a vessel volume, volume relative to a hypothetical volume, and/or the like. In some embodiments, the system is configured to determine percentage of coronary blood volume based on determining a volume of lumen as a function of an entire coronary vessel volume. In some embodiments, the system is configured to determine percentage of fractional myocardial mass as a ratio of total vessel volume to left ventricular mass, a ratio of lumen volume to left ventricular mass, and/or the like.

In some embodiments, the system at block 2110 is configured to analyze and/or access one or more clinical parameters, such as for example percentile condition for age, percentile condition for gender of the subject, and/or any other clinical parameter described herein.

In some embodiments, the system at block 2112 is configured to generate a weighted measure of one or more parameters, such as for example one or more plaque parameters, one or more vessel parameters, and/or one or more clinical parameters. In some embodiments, the system is configured to generate a weighted measure of one or more parameters for each segment. In some embodiments, the system can be configured to generate the weighted measure logarithmically, algebraically, and/or utilizing another mathematical transform. In some embodiments, the system can be configured to generate the weighted measure by applying a correction factor or constant, for example to allow for control of within-person, within-vessel, inter-plaque, and/or plaque-myocardial relationships.

In some embodiments, the system at block 2114 is configured to generate one or more CAD risk scores for the subject. For example, in some embodiments, the system can be configured to generate a CAD risk score on a per-vessel, per-vascular territory, and/or per-subject basis. In some embodiments, the system is configured to generate one or more CAD risk scores of the subject by combining the generated weighted measure of one or more parameters.

In some embodiments, the system at block 2116 can be configured to normalize the generated one or more CAD scores. For example, in some embodiments, the system can be configured to normalize the generated one or more CAD scores to account for differences due to the subject, scanner, and/or scan parameters, including those described herein.

In some embodiments, the system at block 2118 can be configured to generate a graphical plot of the generated one or more per-vessel, per-vascular territory, or per-subject CAD risk scores for visualizing and quantifying risk of CAD for the subject. For example, in some embodiments, the system can be configured to generate a graphical plot of one or more CAD risk scores on a per-vessel, per-vascular, and/or per-subject basis. In some embodiments, the graphical plot can include a 2D, 3D, or 4D representation, such as for example a histogram.

In some embodiments, the system at block 2120 can be configured to assist a user to generate an assessment of risk of CAD for the subject based the analysis. For example, in some embodiments, the system can be configured to generate a scaled CAD risk score for the subject. In some embodiments, the system can be configured to determine a vascular age for the subject. In some embodiments, the system can be configured to categorize risk of CAD for the subject, for example as normal, mild, moderate, or severe. In some embodiments, the system can be configured to generate one or more colored heart maps. In some embodiments, the system can be configured to categorize risk of CAD for the subject as high risk or low risk.

Treat to the Image

Some embodiments of the systems, devices, and methods described herein are configured to track progression of a disease, such as a coronary artery disease (CAD), based on image analysis and use the results of such tracking to determine treatment for a patient. In other words, in some embodiments, the systems, methods, and devices described herein are configured to treat a patient or subject to the image. In particular, in some embodiments, the system can be configured to track progression of a disease in response to a medical treatment by analyzing one or more medical images over time and use the same to determine whether the medical treatment is effective or not. For example, in some embodiments, if the prior medical treatment is determined to be effectiveness based on tracking of disease progression based on image analysis, the system can be configured to propose continued use of the same treatment. On the other hand, in some embodiments, if the prior medical treatment is determined to be neutral or non-effective based on tracking of disease progression based on image analysis, the system can be configured to propose a modification of the prior treatment and/or a new treatment for the subject. In some embodiments, the treatment can include medication, lifestyle changes or actions, and/or revascularization procedures.

In particular, some embodiments of the systems, devices, and methods described herein are configured to determine one or more of the progression, regression or stabilization, and/or destabilization of coronary artery disease or other vascular disease over time in a manner that will reduce adverse coronary events. For example, in some embodiments, the systems, devices, and methods described herein are configured to provide medical analysis and/or treatment based on plaque attenuation tracking. In some embodiments, the systems, devices, and methods described herein can be configured to utilize a computer system and/or an artificial intelligence platform to track the attenuation of plaque, wherein an automatically detected transformation from low attenuation plaque to high attenuation plaque on a medical image, rather than regression of plaque, can be used as the main basis for generating a plaque attenuation score or status, which can be representative of the rate of progression and/or rate of increased/decreased risk of coronary disease. As such, in some embodiments, the systems, devices, and methods described herein can be configured to provide response assessment of medical therapy, lifestyle interventions, and/or coronary revascularization along the life course of an individual.

In some embodiments, the system can be configured to utilize computed tomography angiography (CCTA). Generally speaking, computed tomography angiography (CCTA) can enable evaluation of presence, extent, severity, location and/or type of atherosclerosis in the coronary and other arteries. These factors can change with medical therapy and lifestyle modifications and coronary interventions. As a non-limiting example, in some cases, Omega-3 fatty acids, after 38.6 months can lower high-risk plaque prevalence, number of high-risk plaques, and/or napkin-ring sign. Also, the CT density of plaque can be higher in omega-3 fatty acids group. As another non-limiting example, in some cases, icosapent ethyl can result in reduced low attenuation plaque (LAP) volume by 17% and overall plaque volume by 9% compared to baseline and placebo. In addition, as another non-limiting example, in some cases of HIV positive patients, higher non-calcified and high-risk plaque burden on anti-retroviral therapy can be higher and can involve higher cardiovascular risk. Further, as another non-limiting example, in some cases of patients taking statins, there can be slower rate of percent atheroma progression with more rapid progression of calcified percent atheroma volume. Other changes in plaque can also occur due to some other exposure. Importantly, in some instances, patients may often be taking combinations of these medications and/or living healthy or unhealthy lifestyles that may contribute multifactorially to the changes in plaque over time in a manner that is not predictable, but can be measurable, for example utilizing one or more embodiments described herein.

In some embodiments, the systems, methods, and devices described herein can be configured to analyze dichotomous and/or categorical changes in plaque (e.g., from non-calcified to calcified, high-risk to non-high-risk, and/or the like) and burden of plaque (e.g., volume, percent atheroma volume, and/or the like), as well as analyze serial continuous changes over time. In addition, in some embodiments, the systems, methods, and devices described herein can be configured to leverage the continuous change of a plaque's features as a longitudinal method for guiding need for intensification of medical therapy, change in lifestyle, and/or coronary revascularization. Further, in some embodiments, the systems, methods, and devices described herein can be configured to leverage the difference in these changes over time as a method to guide therapy in a manner that improves patient-specific event-free survival.

As such, in some embodiments, the systems, methods, and devices described herein can be configured to determine the progression, regression or stabilization, and/or destabilization of coronary artery disease and/or other vascular disease over time, for example in response to a medical treatment, in a manner that will reduce adverse coronary events. In particular, in some embodiments, the systems, methods, and devices described herein can be configured to analyze the density/signal intensity, vascular remodeling, location of plaques, plaque volume/disease burden, and/or the like. In some embodiments, the system can be configured to utilize a normalization device, such as those described herein, to account for differences in scan results (such as for example density values, etc.) between different scanners, scan parameters, and/or the like.

In some embodiments, the system can be configured to track imaging density (CT) and/or signal intensity (MM) of coronary atherosclerotic lesions over time by serial imaging.

In some embodiments, the system can be configured to leverage directionality changes in coronary lesions over time (e.g. lower-to-higher CT density, higher-to-even higher CT density, etc.) as measurements of stabilization of plaque. In some embodiments, the system can be configured to leverage directionality changes to link to risk of disease events (e.g., high CT density is associated with lower risk of heart attack). In some embodiments, the system can be configured to guide decision making as to whether to add another medication/intensity medical therapy. For example, if there is no change in density/signal intensity for a patient after 1 year, the system can be configured to propose addition of another medication. In some embodiments, the system can be configured to guide decision making in the above manner in order to reduce adverse coronary events (e.g., acute coronary syndrome, rapid progression, ischemia, and/or the like).

FIG. 22A illustrates an example(s) of tracking the attenuation of plaque for analysis and/or treatment of coronary artery and/or other vascular disease. As a non-limiting example, FIG. 22A illustrates example cross sections of arteries from a CT image. In the illustrated example embodiment, the yellow circles are the lumen, the orange circles are the outer vessel wall and everything in between is plaque tissue or similar. In the illustrated example embodiment, the "high-risk plaques" by CT are indicated to the left, where they are classified as such by having low attenuation plaque (e.g., <30 Hounsfield units) and positive (>1) vascular remodeling (e.g., cross-sectional area or diameter at the site of maximum plaque compared to cross-sectional area at the most proximal normal appearing cross-section). In some embodiments, positive arterial remodeling can be defined as >1.05 or >1.10.

As illustrated in the example embodiment of FIG. 22A, in some embodiments, plaques can be of continuously different density. In the left most cross-section of the illustrated example embodiment, the plaque is black, and turns progressively gray and then lighter and then brighter until it becomes very bright white, with a Hounsfield unit density of >1000 in the right most cross-section of the illustrated example embodiment. In some embodiments, this density can be reported out continuously as Hounsfield unit densities or other depending on the acquisition mode of the CT image, which can include single-energy, dual energy, spectral, and/or photon counting imaging.

In some embodiments, using imaging methods (e.g., by CT), darker plaques (e.g., with lower Hounsfield unit densities) can represent higher risk (e.g., of myocardial infarction, of causing ischemia, of progressing rapidly, and/or the like), while brighter plaques (e.g., with higher Hounsfield unit density) can represent lower risk.

In some embodiments, the system is configured to leverage the continuous scale of the plaque composition density as a marker for increased stabilization of plaque after treatment, and to leverage this information to continually update prognostic risk stratification for future coronary events (e.g., acute coronary syndromes, ischemia, etc.). Thus, in some embodiments, an individual's risk of a heart attack can be dependent on the density of the plaque, and changes in the density after treatment can attenuate that risk, increase that risk, and/or have no effect on risk.

In some embodiments, the system can be configured to generate and/or suggest treatment in a number of different forms, which may include: medications (e.g., statins, human immunodeficiency virus (HIV) medications, icosapent ethyl, bempedoic acid, rivaroxaban, aspirin, proprotein convertase subtilisin/kexin type 9 (PCSK-9) inhibitors, inclisaran, sodium-glucose cotransporter-2 (SGLT-2) inhibitors, glucagon-like peptide-1 (GLP-1) receptor agonists, low-density lipoprotein (LDL) apheresis, etc.); lifestyle (increased exercise, aerobic exercise, anaerobic exercise, cessation of smoking, changes in diet, etc.); and/or revascularization (after bypass grafting, stenting, bioabsorbable scaffolds, etc.).

In some embodiments, the system can be configured to generate and/or provide a "treat to the image" continuous approach that offers clinicians and patients a method for following plaque changes over time to ensure that the plaque is stabilizing and the prognosis is improving. For example, in some embodiments, a patient may be started on a statin medication after their CT scan. Over time (e.g., months), a plaque may change in Hounsfield unit density from 30 to 45 HUs. In some embodiments, this may represent a beneficial outcome of plaque stabilization and connote the efficacy of the statin medications on the plaque. Alternatively, over time, a plaque may not change in Hounsfield unit density, staying at 30 HU over time. In this case, in some embodiments, this may represent an adverse outcome wherein the statin medication is ineffective in stabilizing the plaque. In some embodiments, should a plaque not stabilize to medical therapy (e.g., HU density remains low, or is very slow to rise), then another medication (e.g., PCSK-9 inhibitor) may be added as the constancy in the HU ca be a titratable biomarker that is used to guide medical therapy intensification and, ultimately, improve patient outcomes (e.g., by reducing myocardial infarction, rapid progression, ischemia, and/or other adverse event).

In some embodiments, densities of plaques may be influenced by a number of factors that can include one or more of: scanner type, image acquisition parameters (e.g., mA, kVp, etc.), energy (e.g., single-, dual-, spectral, photon counting, etc.), gating (e.g., axial vs. retrospective helical, etc.), contrast, age, patient body habitus, surrounding cardiac structures, plaque type (e.g., calcium may cause partial volume artifact, etc.), and/or others. As such, in some embodiments, the system can be configured to normalize one or more of these factors to further standardize comparisons in plaque types over time.

In some embodiments, the system can be configured to track vascular remodeling of coronary atherosclerotic lesions over time using image analysis techniques. In some embodiments, the system can be configured to leverage directionality changes in remodeling (e.g., outward, intermediate, inward, and/or the like). In some embodiments, the system can be configured to evaluate directionality on a patient, vessel, segment, lesion and/or cross section basis. In some embodiments, the system can be configured to leverage directionality changes to link to risk of disease events. For example, in some embodiments, more outward remodeling can be indicative of a higher risk of heart attack, and/or the like. In some embodiments, the system can be configured to guide decision making as to whether to add another medication/intensify medical therapy and/or perform coronary revascularization based upon worsening or new positive remodeling. In some embodiments, the system can be configured to guide decision making in the above manner in order to reduce adverse coronary events (e.g., acute coronary syndrome, rapid progression, ischemia, and/or the like).

In some embodiments, a similar analogy for plaque composition can be applied to measures of vascular remodeling in a specific coronary lesion and/or across all coronary lesions within the coronary vascular tree. In particular, in some embodiments, the remodeling index can be a continuous measure and can be reported by one or more of diameter, area, and/or volume. As positive remodeling can be associated with lesions at the time of acute coronary syndrome and negative remodeling may not, in some embodiments, serial imaging (e.g., CT scans, etc.) can be followed across time to determine whether the plaque is causing more or less positive remodeling. In some embodiments, cessation and/or slowing of positive remodeling can be favorable sign that can be used to prognostically update an individual or a lesion's risk of myocardial infarction or other adverse coronary event (e.g., ischemia, etc.).

In some embodiments, the system can be configured to provide a "treat to the image" continuous approach that offers clinicians and patients a method for following plaque changes over time to ensure that the plaque is stabilizing and the prognosis is improving. For example, in some embodiments, a patient may be started on a statin medication after their CT scan. Over time (e.g., months, etc.), a plaque may change in remodeling index from 1.10 to 1.08. In some embodiments, this may represent a beneficial outcome of plaque stabilization and connote the efficacy of the statin medications on the plaque. Alternatively, over time, a plaque may not change in remodeling index over time, staying at 1.10. In this case, in some embodiments, this may represent an adverse outcome wherein the statin medication is ineffective in stabilizing the plaque. In some embodiments, should a plaque not stabilize to medical therapy (for example if the remodeling index remains high or is very slow to decrease), then another medication (e.g., PCSK-9 inhibitor, etc.) may be added, as the constancy in the remodeling can be a titratable biomarker that is used to guide medical therapy intensification and, ultimately, improve patient outcomes (e.g., by reducing myocardial infarction, rapid progression, ischemia, and/or other adverse event).

In some embodiments, remodeling indices of plaques may be influenced by a number of factors that can include one or more of: scanner type, image acquisition parameters (e.g., mA, kVp, etc.), energy (e.g., single-, dual-, spectral, photon counting, etc.), gating (e.g., axial vs. retrospective helical, etc.), contrast, age, patient body habitus, surrounding cardiac structures, plaque type (e.g., calcium may cause partial volume artifact, etc.), and/or the like. In some embodiments, the system can be configured to normalize to one or more of these factors to further standardize comparisons in plaque types over time.

In some embodiments, the system can be configured to track location of one or more regions of plaque over time. For example, in some embodiments, the system can be configured to track the location of one or more regions of plaque based on one or more of: myocardial facing vs. pericardial facing; at a bifurcation or trifurcation; proximal vs. mid vs. distal; main vessel vs. branch vessel; and/or the like. In some embodiments, the system can be configured to evaluate directionality on a patient, vessel, segment, lesion and/or cross section basis. In some embodiments, the system can be configured to leverage directionality changes to link to risk of disease events (e.g. more outward remodeling, higher risk of heart attack, and/or the like). In some embodiments, the system can be configured to guide decision making as to whether to add another medication/intensify medical therapy or perform coronary revascularization, and/or the like. In some embodiments, the system can be configured to guide decision making in the above manner in order to reduce adverse coronary events (e.g., acute coronary syndrome, rapid progression, ischemia, and/or the like).

In some embodiments, the system can be configured to identify and/or correlate certain coronary events as being associated with increased risk over time. For example, in some embodiments, pericardial facing plaque may have a higher rate of being a culprit lesion at the time of myocardial infarction than myocardial facing plaques. In some embodiments, bifurcation lesions can appear to have a higher rate of being a culprit lesion at the time of myocardial infarction than non-bifurcation/trifurcation lesions. In some embodiments, proximal lesions can tend to be more common than distal lesions and can also be most frequently the site of myocardial infarction or other adverse coronary event.

In some embodiments, the system can be configured to track each or some one of these individual locations of plaque and, based upon their presence, extent and severity, assign a baseline risk. In some embodiments, after treatment with medication, lifestyle or intervention, serial imaging (e.g., by CT, etc.) can be performed to determine changes in these features, which can be used to update risk assessment.

In some embodiments, the system can be configured to provide a "treat to the image" continuous approach that offers clinicians and patients a method for following plaque changes in location over time to ensure that the plaque is stabilizing and the prognosis is improving. For example, in some embodiments, a patient may be started on a statin medication after their CT scan. Over time (e.g., months, etc.), a plaque may regress in the pericardial-facing region but remain in the myocardial facing region. In some embodiments, this may represent a beneficial outcome of plaque stabilization and connote the efficacy of the statin medications on the plaque. Alternatively, over time, a plaque may not change in location over time and remain pericardial-facing. In this case, in some embodiments, this may represent an adverse outcome wherein the statin medication is ineffective in stabilizing the plaque. In some embodiments, should a plaque not stabilize to medical therapy (for example if the location of plaque remains pericardial-facing or is very slow to change), then another medication (e.g., PCSK-9 inhibitor or other) may be added, as the constancy in the location of plaque can be a titratable biomarker that is used to guide medical therapy intensification and, ultimately, improve patient outcomes (e.g., by reducing myocardial infarction, rapid progression, ischemia, or other adverse event).

In some embodiments, the CT appearance of plaque location may be influenced by a number of factors that may include one or more of: scanner type, image acquisition parameters (e.g., mA, kVp, etc.), energy (e.g., single-, dual-, spectral, photon counting, etc.), gating (e.g., axial vs. retrospective helical, etc.), contrast, age, patient body habitus, surrounding cardiac structures, plaque type (e.g., calcium may cause partial volume artifact, etc.), and/or others. In some embodiments, the system can be configured to normalize to one or more of these factors to further standardize comparisons in plaque types over time.

In some embodiments, the system can be configured to track plaque volume and/or plaque volume as a function of vessel volume (e.g., percent atheroma volume or PAV, etc.). In some embodiments, plaque volume and/or PAV can be tracked on a per-patient, per-vessel, per-segment or per-lesion basis. In some embodiments, the system can be configured to evaluate directionality of plaque volume or PAV (e.g., increasing, decreasing or staying the same). In some embodiments, the system can be configured to leverage directionality changes to link to risk of disease events. For example, in some embodiments, an increase in plaque volume or PAV can be indicative of higher risk. Similarly, in some embodiments, slowing of plaque progression can be indicative of lower risk and/or the like. In some embodiments, the system can be configured to guide decision making as to whether to add another medication/intensify medical therapy or perform coronary revascularization. For example, in some embodiments, in response to increasing plaque volume or PAV, the system can be configured to propose increased/intensified medical therapy, other treatment, increased medication dosage, and/or the like. In some embodiments, the system can be configured to guide decision making in order to reduce adverse coronary events (e.g., acute coronary syndrome, rapid progression, ischemia, and/or the like).

In some embodiments, the system can be configured to identify and/or correlate certain adverse coronary events as being associated with increased risk over time. For example, in some embodiments, higher plaque volume and/or higher PAV can result in high risk of CAD events.

In some embodiments, the system can be configured to track plaque volume and/or PAV and assign a baseline risk based at least in part on its presence, extent, and/or severity. In some embodiments, after treatment with medication, lifestyle or intervention, serial imaging (e.g., by CT) can be performed to determine changes in these features, which can be used to update risk assessment.

In some embodiments, the system can be configured to provide a "treat to the image" continuous approach that offers clinicians and patients a method for following plaque changes in location over time to ensure that the plaque is stabilizing and the prognosis is improving. For example, in some embodiments, in a patient may be started on a statin medication after their CT scan. Over time (e.g., months, etc.), a plaque may increase in volume or PAV. In some embodiments, this may represent an adverse outcome and connote the inefficacy of statin medications. Alternatively, over time, the volume of plaque may not change. In this case, in some embodiments, this may represent a beneficial outcome wherein the statin medication is effective in stabilizing the plaque. In some embodiments, should a plaque not stabilize to medical therapy (e.g., if plaque volume or PAV increases), then another medication (e.g., PCSK-9 inhibitor and/or other) may be added, as the constancy in the plaque volume or PAV can be a titratable biomarker that is used to guide medical therapy intensification and, ultimately, improve patient outcomes (e.g., by reducing myocardial infarction, rapid progression, ischemia, and/or other adverse event).

In some embodiments, the CT appearance of plaque location may be influenced by a number of factors that may include one or more of: scanner type, image acquisition parameters (e.g., mA, kVp, etc.), energy (e.g., single-, dual-, spectral, photon counting, etc.), gating (e.g., axial vs. retrospective helical, etc.), contrast, age, patient body habitus, surrounding cardiac structures, plaque type (e.g., calcium may cause partial volume artifact, etc.), and/or others. In some embodiments, the system can be configured to normalize to one or more of these factors to further standardize comparisons in plaque types over time.

In some embodiments, the system can be configured to analyze and/or report one or more of the overall changes described above related to plaque composition, vascular remodeling, and/or other features on a per-patient, per-vessel, per-segment, and/or per-lesion basis, for example to provide prognostic risk stratification either in isolation (e.g., just composition, etc.) and/or in combination (e.g., composition+remodeling+location, etc.).

In some embodiments, the system can be configured to update risk assessment and/or guide medical therapy, lifestyle changes, and/or interventional therapy based on image analysis and/or disease tracking. In particular, in some embodiments, the system can be configured to report in a number of ways changes to arteries/plaques that occur on a continuous basis as a method for tracking disease stabilization or worsening. In some embodiments, as a method of tracking disease, the system can be configured to report the risk of adverse coronary events. For example, in some embodiments, based upon imaging-based changes, a quantitative risk score can be updated from baseline at follow-up. In some embodiments, the system can be configured to utilize a 4-category method that analyzes: (1) progression—entails worsening (e.g., lower attenuation, greater positive remodeling, etc.); (2) regression—entails diminution (e.g., higher attenuation, lower positive remodeling, etc.); (3) mixed response—progression, but of more prognostically beneficial findings (e.g., higher volume of plaque over time, but with calcified 1K plaque dominant) (mixed response can also include plaque remodeling and location); and/or (4) mixed response—progression, but of more prognostically adverse findings (higher volume of plaque over time, but with more non-calcified low attenuation plaques) (mixed response can also include plaque remodeling and location). In some embodiments, for tracking disease as a method to guide therapy, intensification of medical therapy and/or institution of lifestyle changes or coronary revascularization may occur and be prompted by increased risk of adverse coronary events or being in the "progression" or "mixed response—progression of calcified plaque" categories for example. Further, in some embodiments, serial tracking of disease and appropriate intensification of medical therapy, lifestyle changes or coronary revascularization based upon composition, remodeling and/or location changes, can be provided as a guide to reduce adverse coronary events.

Figure 22B:
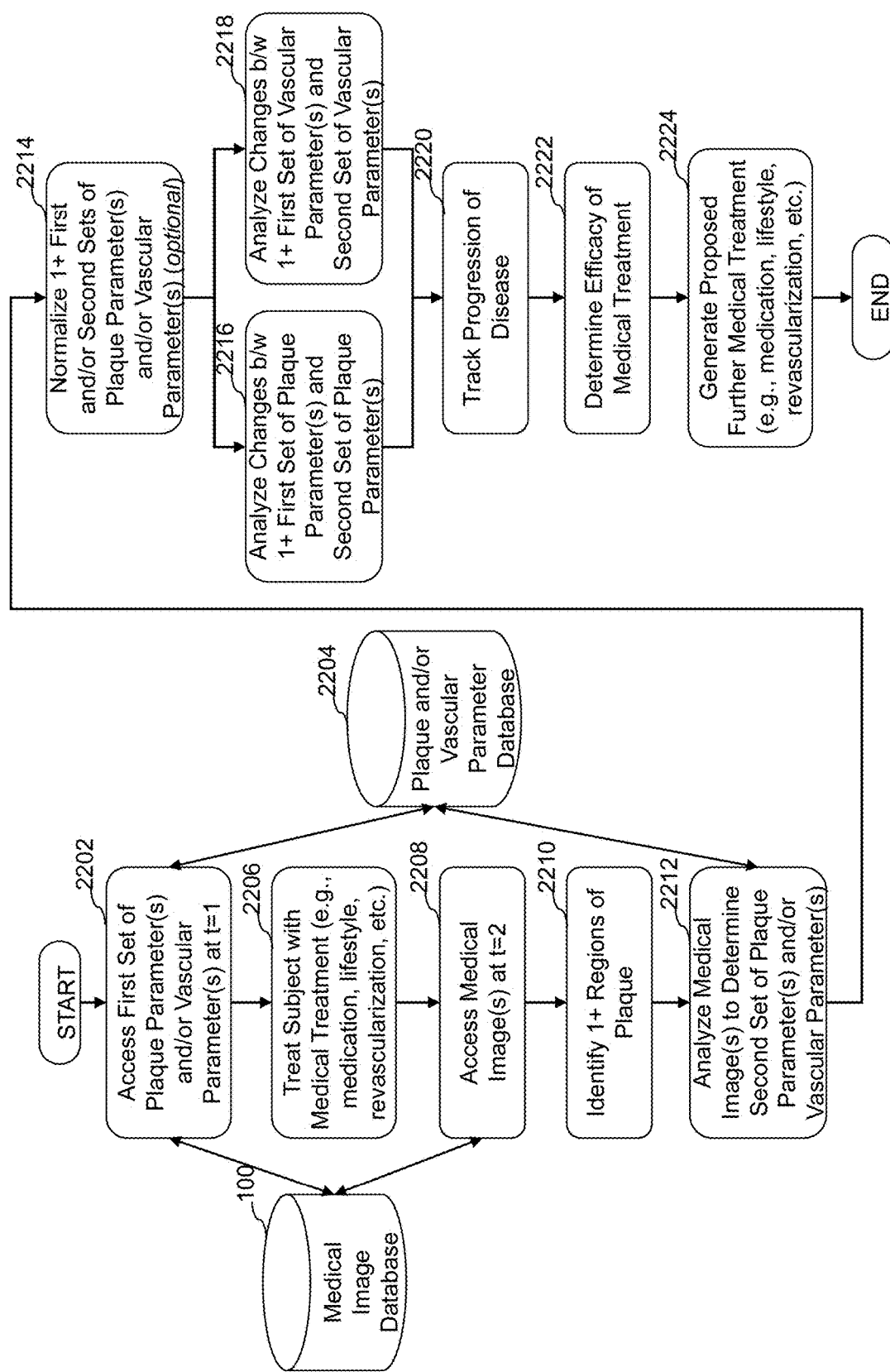
FIG. 22B is a flowchart illustrating an overview of an example embodiment(s) of a method for treating to the image.

FIG. 22B is a flowchart illustrating an overview of an example embodiment(s) of a method for treating to the image. As illustrated in FIG. 22B, in some embodiments, the system is configured to access a first set of plaque and/or vascular parameters of a subject, such as for example relating to the coronaries, at block 2202. In some embodiments, one or more plaque and/or vascular parameters can be accessed from a plaque and/or vascular parameter database 2204. In some embodiments, one or more plaque and/or vascular parameters can be derived and/or analyzed from one or more medical images being stored in a medical image database 100.

The one or more plaque parameters and/or vascular parameters can include any such parameters described herein. As a non-limiting example, the one or more plaque parameters can include one or more of density, location, or volume of one or more regions of plaque. The density can be absolute density, Hounsfield unit density, and/or the like. The location of one or more regions of plaque can be determined as one or more of myocardial facing, pericardial facing, at a bifurcation, at a trifurcation, proximal, mid, or distal along a vessel, or in a main vessel or branch vessel, and/or the like. The volume can be absolute volume, PAV, and/or the like. Further, the one or more vascular parameters can include vascular remodeling or any other vascular parameter described herein. For example, vascular remodeling can include directionality changes in remodeling, such as outward, intermediate, or inward. In some embodiments, vascular remodeling can include vascular remodeling of one or more coronary atherosclerotic lesions.

In some embodiments, at block 2206, the subject can be treated with some medical treatment to address a disease, such as CAD. In some embodiments, the treatment can include one or more medications, lifestyle changes or conditions, revascularization procedures, and/or the like. For example, in some embodiments, medication can include statins, human immunodeficiency virus (HIV) medications, icosapent ethyl, bempedoic acid, rivaroxaban, aspirin, proprotein convertase subtilisin/kexin type 9 (PCSK-9) inhibitors, inclisiran, sodium-glucose cotransporter-2 (SGLT-2) inhibitors, glucagon-like peptide-1 (GLP-1) receptor agonists, low-density lipoprotein (LDL) apheresis, and/or the like. In some embodiments, lifestyle changes or condition can include increased exercise, aerobic exercise, anaerobic exercise, cessation of smoking, change in diet, and/or the like. In some embodiments, revascularization can include bypass grafting, stenting, use of a bioabsorbable scaffold, and/or the like.

In some embodiments, at block 2208, the system can be configured to access one or more medical images of the subject taken after the subject is treated with the medical treatment for some time. The medical image can include any type of image described herein, such as for example, CT, MM, and/or the like. In some embodiments, at block 2210, the system can be configured to identify one or more regions of plaque on the one or more medical images, for example using one or more image analysis techniques described herein. In some embodiments, at block 2212, the system can be configured to analyze the one or more medical images to determine a second set of plaque and/or vascular parameters. The second set of plaque and/or vascular parameters can be stored and/or accessed from the plaque and/or vascular parameter database 2204 in some embodiments. The second set of plaque and/or vascular parameters can include any parameters described herein, including for example those of the first set of plaque and/or vascular parameters.

In some embodiments, the system at block 2214 can be configured to normalize one or more of the first set of plaque parameters, first set of vascular parameters, second set of plaque parameters, and/or second set of vascular parameters. As discussed herein, one or more such parameters or quantification thereof can depend on the scanner type or scan parameter used to obtain a medical image from which such parameters were derived from. As such, in some embodiments, it can be advantageous to normalize for such differences. To do so, in some embodiments, the system can be configured to utilize readings obtained from a normalization device as described herein.

In some embodiments, the system at block 2216 can be configured to analyze one or more changes between the first set of plaque parameters and the second set of plaque parameters. For example, in some embodiments, the system can be configured to analyze changes between a specific type of plaque parameter. In some embodiments, the system can be configured to generate a first weighted measure of one or more of the first set of plaque parameters and a second weighted measure of one or more of the second set of plaque parameters and analyze changes between the first weighted measure and the second weighted measure. The weighted measure can be generated in some embodiments by applying a mathematical transform or any other technique described herein.

In some embodiments, the system at block 2218 can be configured to analyze one or more changes between the first set of vascular parameters and the second set of vascular parameters. For example, in some embodiments, the system can be configured to analyze changes between a specific type of vascular parameter. In some embodiments, the system can be configured to generate a first weighted measure of one or more of the first set of vascular parameters and a second weighted measure of one or more of the second set of vascular parameters and analyze changes between the first weighted measure and the second weighted measure. The weighted measure can be generated in some embodiments by applying a mathematical transform or any other technique described herein.

In some embodiments, at block 2220, the system can be configured to track the progression of a disease, such as CAD, based on the analyzed changes between one or more plaque parameters and/or vascular parameters. In some embodiments, the system can be configured to determine progression of a disease based on analyzing changes between a weighted measure of one or more plaque parameters and/or vascular parameters as described herein. In some embodiments, the system can be configured to determine progression of a disease based on analyzing changes between one or more specific plaque parameters and/or vascular parameters. In particular, in some embodiments, an increase in density of the one or more regions of plaque can be indicative of disease stabilization. In some embodiments, a change in location of a region of plaque from pericardial facing to myocardial facing is indicative of disease stabilization. In some embodiments, an increase in volume of the one or more regions of plaque between the first point in time and the second point in time is indicative of disease stabilization. In some embodiments, more outward remodeling between the first point in time and the second point in time is indicative of disease stabilization. In some embodiments, disease progression is tracked on one or more of a per-subject, per-vessel, per-segment, or per-lesion basis. In some embodiments, disease progression can be determined by the system as one or more of progression, regression, mixed response—progression of calcified plaque, mixed response—progression of non-calcified plaque.

In some embodiments, at block 2222, the system can be configured to determine the efficacy of the medical treatment, for example based on the tracked disease progression. As such, in some embodiments, changes in one or more plaque and/or vascular parameters as derived from one or more medical images using image analysis techniques can be used as a biomarker for assessing treatment. In some embodiments, the system can be configured to determine efficacy of a treatment based on analyzing changes between a weighted measure of one or more plaque parameters and/or vascular parameters as described herein. In some embodiments, the system can be configured to determine efficacy of a treatment based on analyzing changes between one or more specific plaque parameters and/or vascular parameters. In particular, in some embodiments, an increase in density of the one or more regions of plaque can be indicative of a positive efficacy of the medical treatment. In some embodiments, a change in location of a region of plaque from pericardial facing to myocardial facing is indicative of a positive efficacy of the medical treatment. In some embodiments, an increase in volume of the one or more regions of plaque between the first point in time and the second point in time is indicative of a negative efficacy of the medical treatment. In some embodiments, more outward remodeling between the first point in time and the second point in time is indicative of a negative efficacy of the medical treatment.

In some embodiments, at block 2224, the system is configured to generate a proposed medical treatment for the subject based on the determined efficacy of the prior treatment. For example, if the prior treatment is determined to be positive or stabilizing the disease, the system can be configured to propose the same treatment. In some embodiments, if the prior treatment is determined to be negative or not stabilizing the disease, the system can be configured to propose a different treatment. The newly proposed treatment can include any of the types of treatment discussed herein, for example including those discussed in connection with the prior treatment at block 2206.

Determining Treatment(s) for Reducing Cardiovascular Risk and/or Events

Some embodiments of the systems, devices, and methods described herein are configured to determine a treatment(s) for reducing cardiovascular risk and/or events. In particular, some embodiments of the systems and methods described herein are configured to automatically and/or dynamically determine or generate lifestyle, medication and/or interventional therapies based upon actual atherosclerotic cardiovascular disease (ASCVD) burden, ASCVD type, and/or and ASCVD progression. As such, some systems and methods described herein can provide personalized medical therapy is based upon CCTA-characterized ASCVD. In some embodiments, the systems and methods described herein are configured to dynamically and/or automatically analyze medical image data, such as for example non-invasive CT, MRI, and/or other medical imaging data of the coronary region of a patient, to generate one or more measurements indicative or associated with the actual ASCVD burden, ASCVD type, and/or ASCVD progression, for example using one or more artificial intelligence (AI) and/or machine learning (ML) algorithms. In some embodiments, the systems and methods described herein can further be configured to automatically and/or dynamically generate one or more patient-specific treatments and/or medications based on the actual ASCVD burden, ASCVD type, and/or ASCVD progression, for example using one or more artificial intelligence (AI) and/or machine learning (ML) algorithms. In some embodiments, the system can be configured to utilize a normalization device, such as those described herein, to account for differences in scan results (such as for example density values, etc.) between different scanners, scan parameters, and/or the like.

In some embodiments of cardiovascular risk assessment of asymptomatic individuals, the system can be configured to use one or more risk factors to guide risk stratification and treatment. For example, some cardiovascular risk factors can include measurements of surrogate measures of coronary artery disease (CAD) of clinical states that contribute to CAD, including dyslipidemia, hypertension, diabetes, and/or the like. In some embodiments, such factors can form the basis of treatment recommendations in professional societal guidelines, which can have defined goals for medical treatment and lifestyle based upon these surrogate markers of CAD, such as total and LDL cholesterol (blood biomarkers), blood pressure (biometric) and hemoglobin A1C (blood biomarker). In some embodiments, this approach can improve population-based survival and reduces the incidence of heart attacks and strokes. However, in some embodiments, these methods also suffer a lack of specificity, wherein treatment can be more effective in populations but may not pinpoint individual persons who harbor residual risk. As an example, LDL has been found in population-based studies to explain only 29% of future heart attacks and, even in the pivotal statin treatment trials, those individuals treated effectively with statins still retain 70-75% residual risk of heart attacks.

As such, some embodiments described herein address such technical shortcomings by leveraging lifestyle, medication and/or interventional therapies based upon actual atherosclerotic cardiovascular disease (ASCVD) burden, ASCVD type, and/or and ASCVD progression. Given the multitude of medications available to target the ASCVD process through atherosclerosis, thrombosis and inflammatory pathways, in some embodiments, such direct precision-medicine ASCVD diagnosis and treatment approach can be more effective than treating surrogate markers of ASCVD at the individual level.

In some embodiments, the systems and methods described herein are configured to automatically and/or dynamically determine or generate lifestyle, medication and/or interventional therapies based upon actual atherosclerotic cardiovascular disease (ASCVD) burden, ASCVD type, and/or and ASCVD progression. In particular, in some embodiments, the systems and methods are configured to use coronary computed tomographic angiography (CCTA) for quantitative assessment of ASCVD in one or more or all vascular territories, including for example coronary, carotid, aortic, lower extremity, cerebral, renal arteries, and/or the like. In some embodiments, the systems and methods are configured to analyze and/or utilize not only the amount (or burden) of ASCVD, but also the type of plaque in risk stratification. For example, in some embodiments, the systems and methods are configured to associate low attenuation plaques (LAP) and/or non-calcified plaques (NCP) of certain densities with future major adverse cardiovascular events (MACE), whilst associating calcified plaques and, in particular, calcified plaques of higher density as being more stable. Further, in some embodiments, the systems and methods are configured to generate a patient-specific treatment plan that can include use of medication that has been associated with a reduction in LAP or NCP of certain densities and/or an acceleration in calcified plaque formation in populations, i.e., a transformation of plaque by compositional burden. In some embodiments, the systems and methods are configured to generate a patient-specific treatment plan that can include use of medications which can be observed by CCTA to be associated with modification of ASCVD in the coronary arteries, carotid arteries, and/or other arteries, such as for example statins, PCSK9 inhibitors, GLP receptor agonists, icosapent ethyl, and/or colchicine, amongst others.

As described herein, in some embodiments, the systems and methods are configured to leverage ASCVD burden, type, and/or progression to logically guide clinical decision making. In particular, in some embodiments, the systems and methods described herein are configured to leverage, analyze, and/or utilize ASCVD burden, type, and/or progression to guide medical therapy to reduce adverse ASCVD events and/or improve patient-specific event-free survival in a personalized fashion. For example, in some embodiments, the system can be configured to analyze and/or utilize ASCVD type, such as peri-lesion tissue atmosphere, localization, and/or the like.

More specifically, in some embodiments, the systems and methods described herein are configured to utilize one or more CCTA algorithms and/or one or more medical treatment algorithms that quantify the presence, extent, severity and/or type of ASCVD, such as for example its localization and/or peri-lesion tissues. In some embodiments, the one or more medical treatment algorithms are configured to analyze any medical images obtained from any imaging modality, such as for example computed tomography (CT), magnetic resonance (MR), ultrasound, nuclear medicine, molecular imaging, and/or others. In some embodiments, the systems and methods described herein are configured to utilize one or more medical treatment algorithms that are personalized (rather than population-based), treat actual disease (rather than surrogate markers of disease, such as risk factors), and/or are guided by changes in CCTA-identified ASCVD over time (such as for example, progression, regression, transformation, and/or stabilization). In some embodiments, the one or more CCTA algorithms and/or the one or more medical treatment algorithms are computer-implemented algorithms and/or utilize one or more AI and/or ML algorithms.

In some embodiments, the systems and methods are configured to assess a baseline ASCVD in an individual. In some embodiments, the systems and methods are configured to evaluate ASCVD by utilizing coronary CT angiography (CCTA). In some embodiments, the systems and methods are configured to identify and/or analyze the presence, local, extent, severity, type of atherosclerosis, peri-lesion tissue characteristics, and/or the like. In some embodiments, the method of ASCVD evaluation can be dependent upon quantitative imaging algorithms that perform analysis of coronary, carotid, and/or other vascular beds (such as, for example, lower extremity, aorta, renal, and/or the like).

In some embodiments, the systems and methods are configured to categorize ASCVD into specific categories based upon risk. For example, some example of such categories can include: Stage 0, Stage I, Stage II, Stage III; or none, minimal, mild, moderate/severe; or primarily calcified vs. primarily non-calcified; or X units of low density non-calcified plaque); or X % of NCP as a function of overall volume or burden. In some embodiments, the systems and methods can be configured to quantify ASCVD continuously. In some embodiments, the systems and methods can be configured to define categories by levels of future ASCVD risk of events, such as heart attack, stroke, amputation, dissection, and/or the like. In some embodiments, one or more other non-ASCVD measures may be included to enhance risk assessment, such as for example cardiovascular measurements (e.g., left ventricular hypertrophy for hypertension; atrial volumes for atrial fibrillation; fat; etc.) and/or non-cardiovascular measurements that may contribute to ASCVD (e.g., emphysema, etc.). In some embodiments, these measurements can be quantified using one or more CCTA algorithms.

In some embodiments, the systems and methods described herein can be configured to generate a personalized or patient-specific treatment. More specifically, in some embodiments, the systems and methods can be configured to generate therapeutic recommendations based upon ASCVD presence, extent, severity, and/or type. In some embodiments, rather than utilizing risk factors (such as, for example, cholesterol, diabetes), the treatment algorithm can comprise and/or utilize a tiered approach that intensifies medical therapy, lifestyle, and/or interventional therapies based upon ASCVD directly in a personalized fashion. In some embodiments, the treatment algorithm can be configured to generally ignore one or more conventional markers of success (e.g., lowering cholesterol, hemoglobin A1C, etc.) and instead leverage ASCVD presence, extent, severity, and/or type of disease to guide therapeutic decisions of medical therapy intensification. In some embodiments, the treatment algorithm can be configured to combine one or more conventional markers of success (e.g., lowering cholesterol, hemoglobin A1C, etc.) with ASCVD presence, extent, severity, and/or type of disease to guide therapeutic decisions of medical therapy intensification. In some embodiments, the treatment algorithm can be configured to combine one or more novel markers of success (e.g., such as genetics, transcriptomics, or other 'omics measurements, etc.) with ASCVD presence, extent, severity, and/or type of disease to guide therapeutic decisions of medical therapy intensification. In some embodiments, the treatment algorithm can be configured to combine one or more other imaging markers of success (e.g., such as carotid ultrasound imaging, abdominal aortic ultrasound or computed tomography, lower extremity arterial evaluation, and/or others) with ASCVD presence, extent, severity, and/or type of disease to guide therapeutic decisions of medical therapy intensification.

In some embodiments, the systems and methods are configured to perform a response assessment. In particular, in some embodiments, the systems and methods are configured to perform repeat and/or serial CCTA in order to determine the efficacy of therapy on a personalized basis, and to determine progression, stabilization, transformation, and/or regression of ASCVD. In some embodiments, progression can be defined as rapid or non-rapid. In some embodiments, stabilization can be defined as transformation of ASCVD from non-calcified to calcified, or reduction of low attenuation plaque, or reduction of positive arterial remodeling. In some embodiments, regression of ASCVD can be defined as a decrease in ASCVD volume or burden or a decrease in specific plaque types, such as non-calcified or low attenuation plaque.

In some embodiments, the systems and methods are configured to update personalized treatment based upon response assessment. In particular, in some embodiments, based upon the change in ASCVD between the baseline and follow-up CCTA, personalized treatment can be updated and intensified if worsening occurs or de-escalated/kept constant if improvement occurs. As a non-limiting example, if stabilization has occurred, this can be evidence of the success of the current medical regimen. Alternatively, as another non-limiting example, if stabilization has not occurred and ASCVD has progressed, this can be evidence of the failure of the current medical regimen, and an algorithmic approach can be taken to intensify medical therapy.

In some embodiments, the intensification regimen employs lipid lowering agents in a tiered fashion, and considers ASCVD presence, extent, severity, type, and/or progression. In some embodiments, the intensification regimen considers local and/or peri-lesion tissue. In some embodiments, the intensification regimen and use of the medications therein can be guided also by LDL cholesterol and triglyceride (TG) and Lp(a) and Apo(B) levels; or cholesterol particle density and size. For example, FIGS. 23F-G illustrate an example embodiment(s) of a treatment(s) employing lipid lowering medication(s) and/or treatment(s) generated by an example embodiment(s) of systems and methods for determining treatments for reducing cardiovascular risk and/or events.

In some embodiments, given the multidimensional nature of MACE contributors that include ASCVD, inflammation and thrombosis, the intensification regimen can incorporate anti-inflammatory medications (e.g., colchicine) and/or anti-thrombotic medications (e.g., rivaroxaban and aspirin) in order to control the ASCVD progress. In some embodiments, new diabetic medications that have salient effects on reducing MACE events—including SGLT2 inhibitors and GLP1R agonists—can also be incorporated. For example, FIGS. 23H-I illustrate an example embodiment(s) of a treatment(s) employing diabetic medication(s) and/or treatment(s) generated by an example embodiment(s) of systems and methods for determining treatments for reducing cardiovascular risk and/or events.

Figure 23A:
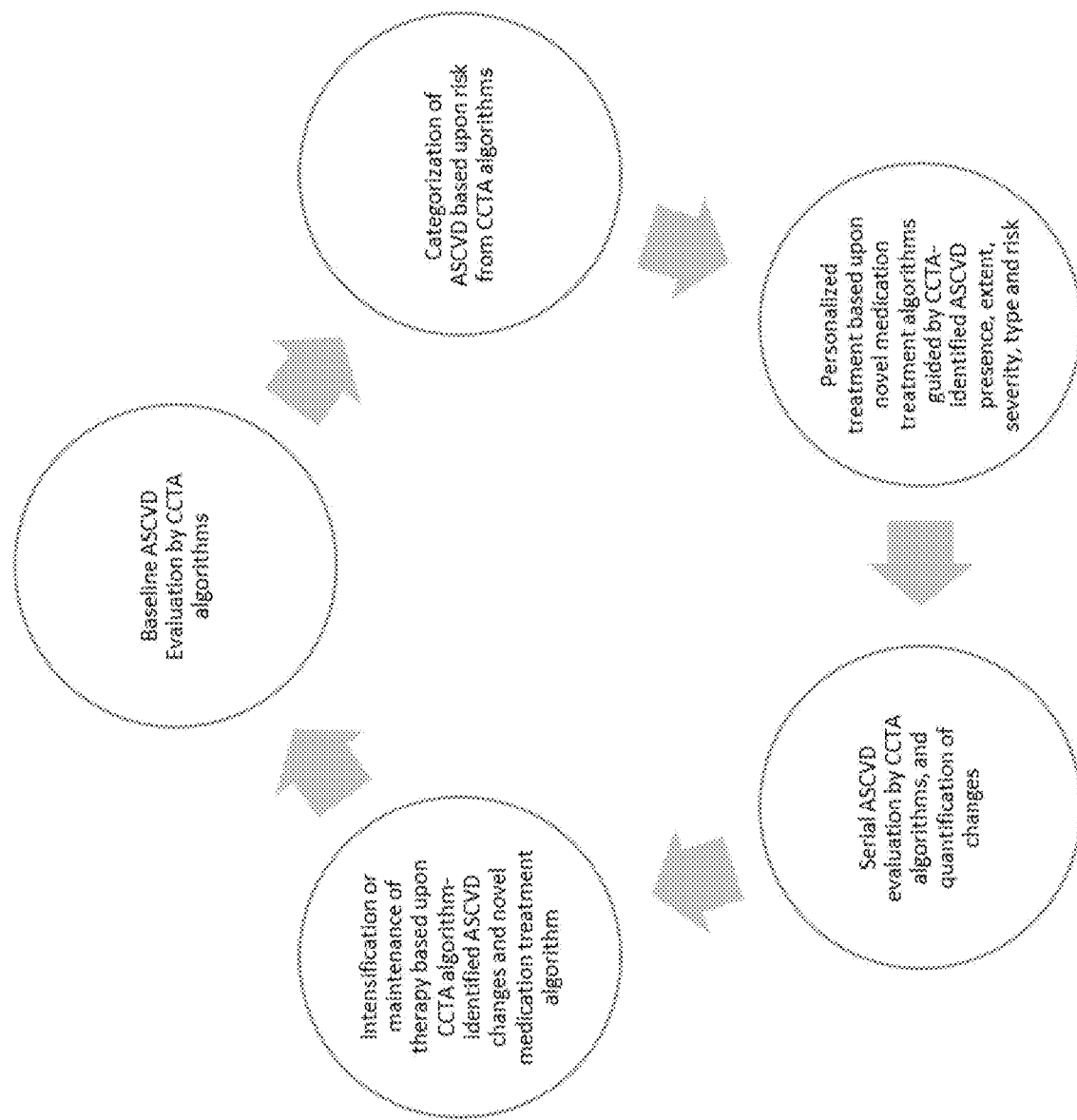
FIG. 23A illustrates an example embodiment(s) of systems and methods for determining treatments for reducing cardiovascular risk and/or events.
Figure 23G:
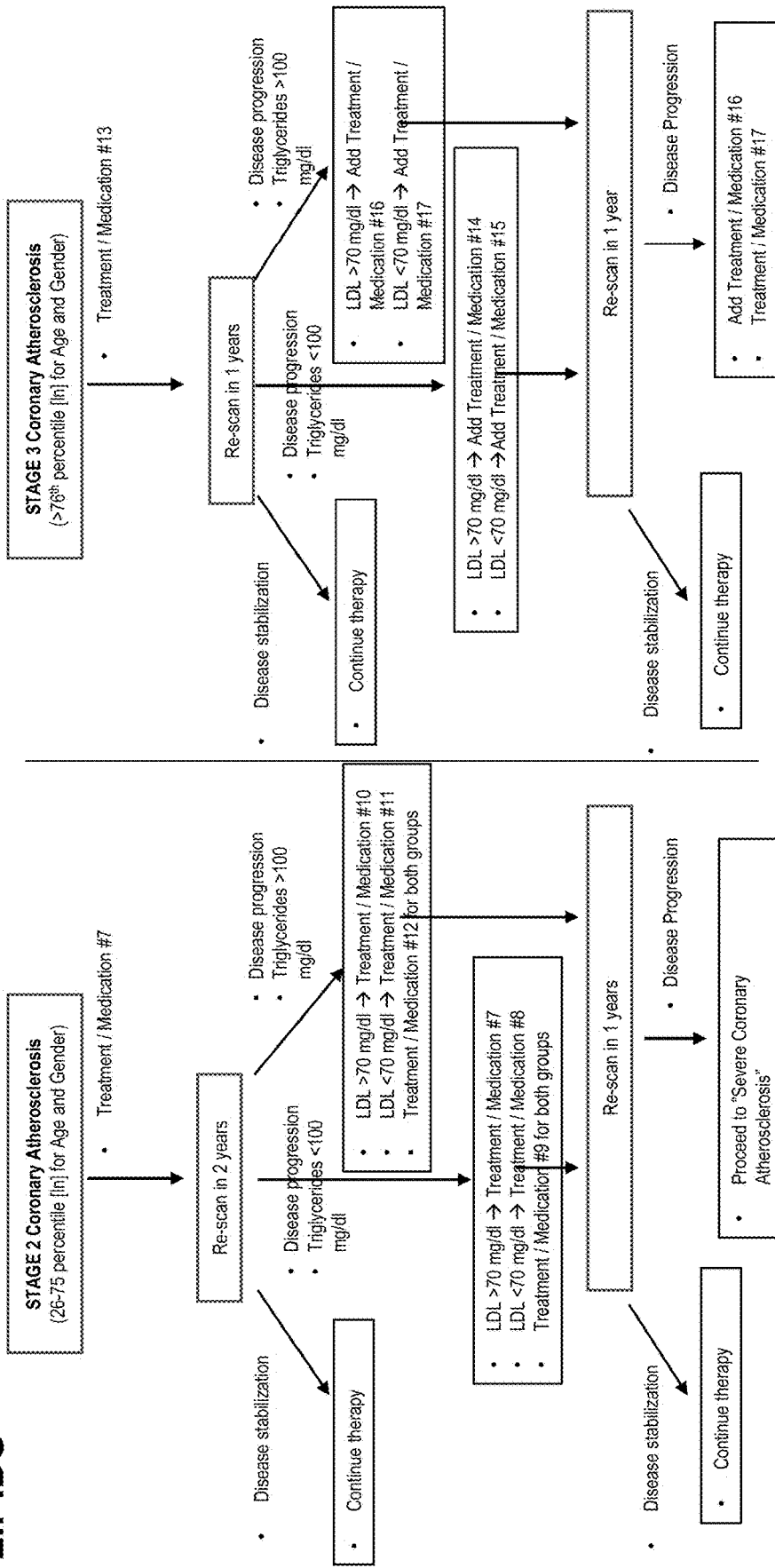
FIGS. 23F-G illustrate an example embodiment(s) of a treatment(s) employing lipid lowering medication(s) and/or treatment(s) generated by an example embodiment(s) of systems and methods for determining treatments for reducing cardiovascular risk and/or events.

FIG. 23A illustrates an example embodiment(s) of systems and methods for determining treatments for reducing cardiovascular risk and/or events. In some embodiments, the systems and methods described herein are configured to analyze coronaries. In some embodiments, the systems and methods can also be applied to other arterial bed as well, such as the aorta, carotid, lower extremity, renal artery, cerebral artery, and/or the like.

In some embodiments, the system can be configured to determine and/or utilize in its analysis the presence of ASCVD, which can be the presence vs. absence of plaque, the presence vs. absence of non-calcified plaque, the presence vs. absence of low attenuation plaque, and/or the like.

In some embodiments, the system can be configured to determine and/or utilize in its analysis the extent of ASCVD, which can include the total ASCVD volume, percent atheroma volume (atheroma volume/vessel volume×100), total atheroma volume normalized to vessel length (TAV-norm), diffuseness (% of vessel affected by ASCVD), and/or the like.

In some embodiments, the system can be configured to determine and/or utilize in its analysis severity of ASCVD. In some embodiments, ASCVD severity can be linked to population-based estimates normalized to age-, gender-, ethnicity-, CAD risk factors, and/or the like. In some embodiments, ASCVD severity can include angiographic stenosis>70% or >50% in none, 1-, 2-, and/or 3-VD.

In some embodiments, the system can be configured to determine and/or utilize in its analysis the type of ASCVD, which can include for example the proportion (ratio, %, etc.) of plaque that is non-calcified vs. calcified, proportion of plaque that is low attenuation non-calcified vs. non-calcified vs. low density calcified vs. high-density calcified, absolute amount of non-calcified plaque and calcified plaque, absolute amount of plaque that is low attenuation non-calcified vs. non-calcified vs. low density calcified vs. high-density calcified, continuous grey-scale measurement of plaques without ordinal classification, radiomic features of plaque, including heterogeneity and others, vascular remodeling imposed by plaque as positive remodeling (>1.10 or >1.05 ratio of vessel diameter/normal reference diameter; or vessel area/normal reference area; or vessel volume/normal reference volume) vs. negative remodeling (<1.10 or <1.05), vascular remodeling imposed by plaque as a continuous ratio, and/or the like.

In some embodiments, the system can be configured to determine and/or utilize in its analysis the locality of plaque, such as for example in the arterial bed, regarding vessel, segment, bifurcation, and/or the like.

In some embodiments, the system can be configured to determine and/or utilize in its analysis the peri-lesion tissue environment, such as for example density of the peri-plaque tissues such as fat, amount of fat in the peri-vascular space, radiomic features of peri-lesion tissue, including heterogeneity and others, and/or the like.

In some embodiments, the system can be configured to determine and/or utilize in its analysis ASCVD progression. In some embodiments, progression can be defined as rapid vs. non-rapid, with thresholds to define rapid progression (e.g., >1.0% percent atheroma volume, >200 mm3 plaque, etc.). In some embodiments, serial changes in ASCVD can include rapid progression, progression with primarily calcified plaque formation, progression with primarily non-calcified plaque formation, and regression.

In some embodiments, the system can be configured to determine and/or utilize in its analysis one or more categories of risk. In some embodiments, the system can be configured to utilize one or more stages, such as 0, I, II, or III based upon plaque volumes associated with angiographic severity (such as, for example, none, non-obstructive, and obstructive 1VD, 2VD and 3VD). In some embodiments, the system can be configured to utilize one or more percentiles, for example taking into account age, gender, ethnicity, and/or presence of one or more risk factors (such as, diabetes, hypertension, etc.). In some embodiments, the system can be configured to determine a percentage of calcified plaque vs. percentage of non-calcified plaque as a function of overall plaque volume. In some embodiments, the system can be configured to determine the number of units of low density non-calcified plaque. In some embodiments, the system can be configured to generate a continuous 3D histogram and/or geospatial map (for plaque geometry) analysis of grey scales of plaque by lesion, by vessel, and/or by patient. In some embodiments, risk can be defined in a number of ways, including for example risk of MACE, risk of angina, risk of ischemia, risk of rapid progression, risk of medication non-response, and/or the like.

In some embodiments, treatment recommendations can be based upon ASCVD presence, extent, severity type of disease, ASCVD progression, and/or the like. For example, FIGS. 23F-G illustrate an example embodiment(s) of a treatment(s) employing lipid lowering medication(s) and/or treatment(s) and FIGS. 23H-I illustrate an example embodiment(s) of a treatment(s) employing diabetic medication(s) and/or treatment(s) generated by an example embodiment(s) of systems and methods for determining treatments for reducing cardiovascular risk and/or events.

In some embodiments, the generated treatment protocols are aimed (e.g., based upon CCTA-based ASCVD characterization) to properly treat at the right point in time with medications aimed at ASCVD stabilization, inflammation reduction, and/or reduction of thrombosis potential. In some embodiments, the rationale behind this is that ASCVD events can be an inflammatory atherothrombotic phenomenon, but serum biomarkers, biometrics and conventional measures of angiographic stenosis severity can be inadequate to optimally define risk and guidance to clinical decision making. As such, some systems and methods described herein can provide personalized medical therapy is based upon CCTA-characterized ASCVD.

In some embodiments, the system can be configured to generate a risk score that combines one or more traditional risk factors, such as the ones described herein, together with one or more quantified ASCVD measures. In some embodiments, the system can be configured to generate a risk score that combines one or more genetics analysis with one or more quantified ASCVD measures, as some medications may work better on some people and/or people with particular genes. In addition, in some embodiments, the system can be configured to exclude or deduct certain plaque from the rest of disease. For example, in some embodiments, the system can be configured to ignore or exclude high density calcium that is so stable that the risk of having it can be better than having a disease without it, such that the existence of such plaque may impact risk negatively.

FIGS. 23B-C illustrate an example embodiment(s) of definitions or categories of atherosclerosis severity used by an example embodiment(s) of systems and methods for determining treatments for reducing cardiovascular risk and/or events.

FIG. 23D illustrates an example embodiment(s) of definitions or categories of disease progression, stabilization, and/or regression used by an example embodiment(s) of systems and methods for determining treatments for reducing cardiovascular risk and/or events.

FIG. 23E illustrates an example embodiment(s) of a time-to-treatment goal(s) for an example embodiment(s) of systems and methods for determining treatments for reducing cardiovascular risk and/or events.

Figure 23J:
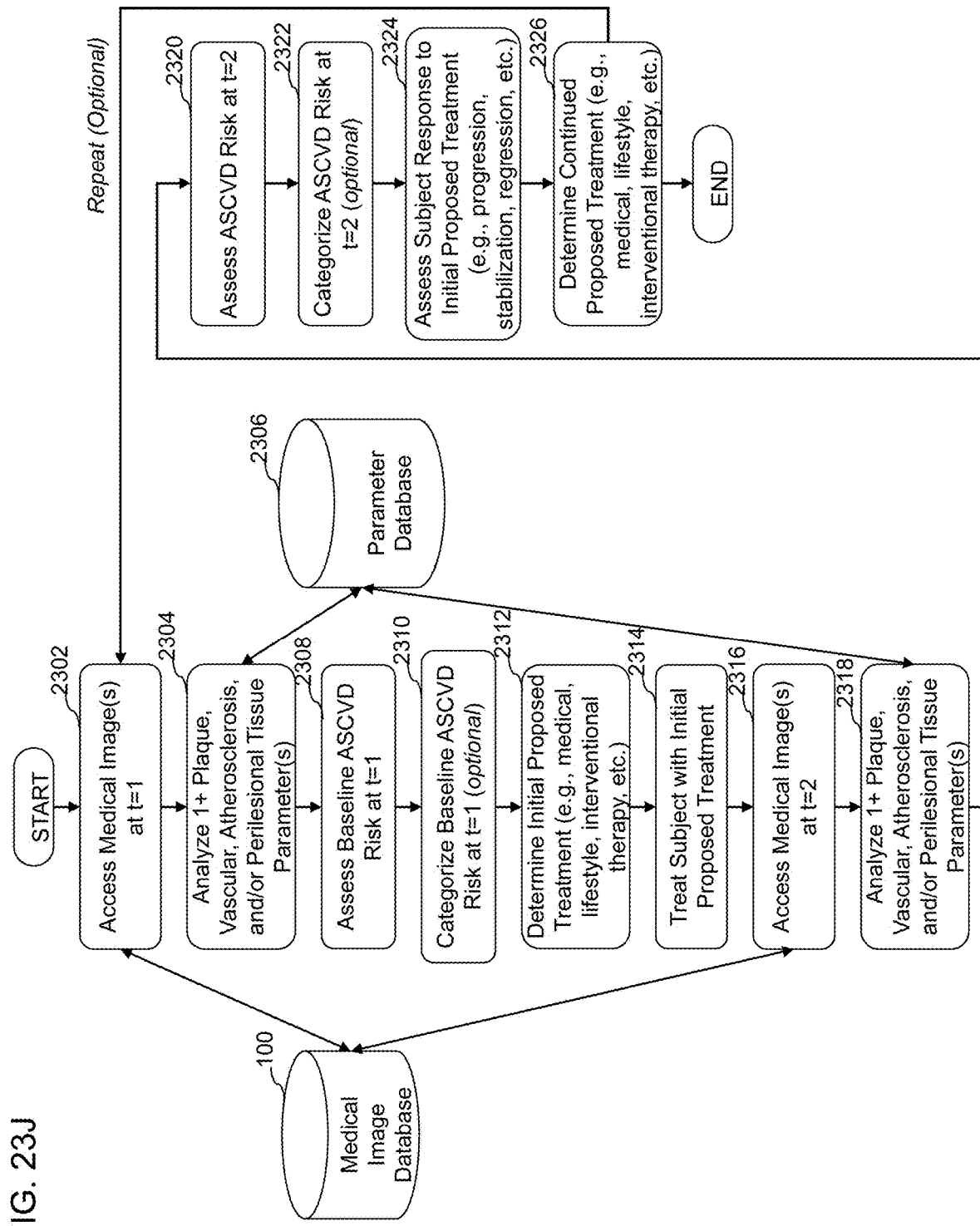
FIGS. 23B-C illustrate an example embodiment(s) of definitions or categories of atherosclerosis severity used by an example embodiment(s) of systems and methods for determining treatments for reducing cardiovascular risk and/or events.
FIG. 23D illustrates an example embodiment(s) of definitions or categories of disease progression, stabilization, and/or regression used by an example embodiment(s) of systems and methods for determining treatments for reducing cardiovascular risk and/or events.
FIG. 23E illustrates an example embodiment(s) of a time-to-treatment goal(s) for an example embodiment(s) of systems and methods for determining treatments for reducing cardiovascular risk and/or events.
FIGS. 23H-I illustrate an example embodiment(s) of a treatment(s) employing diabetic medication(s) and/or treatment(s) generated by an example embodiment(s) of systems and methods for determining treatments for reducing cardiovascular risk and/or events.

FIG. 23J is a flowchart illustrating an overview of an example embodiment(s) of a method for determining treatments for reducing cardiovascular risk and/or events. As illustrated in FIG. 23J, in some embodiments, the system is configured to determine a proposed personalized treatment for a subject to lower ASCVD risk based on CCTA analysis using one or more quantitative image analysis techniques and/or algorithms.

In particular, in some embodiments, the system can be configured to access one or more medical images taken from a first point in time at block 2302, for example from a medical image database 100. The one or more medical images can include images obtained using any imaging modality described herein. In some embodiments, the one or more medical images can include one or more arteries, such as for example coronary, carotid, lower extremity, upper extremity, aorta, renal, and/or the like.

In some embodiments, the system at block 2304 can be configured to analyze the one or more medical images. More specifically, in some embodiments, the system can be configured to utilize CCTA analysis and/or quantitative imaging algorithms to identify and/or derive one or more parameters from the medical image. In some embodiments, the system can be configured to store one or more identified and/or derived parameters in a parameter database 2306. In some embodiments, the system can be configured to access one or more such parameters from a parameter database 2306. In some embodiments, the system can be configured to analyze one or more plaque parameters, vascular parameters, atherosclerosis parameters, and/or perilesional tissue parameters. The plaque parameters and/or vascular parameters can include any one or more such parameters discussed herein.

In some embodiments, at block 2308, the system can be configured to assess a baseline ASCVD risk of the subject based on one or more such parameters. In some embodiments, at block 2310, the system can be configured to categorize the baseline ASCVD risk of the subject. In some embodiments, the system can be configured to categorize the baseline ASCVD risk into one or more predetermined categories. For example, in some embodiments, the system can be configured to categorize the baseline ASCVD risk as one of Stage 0, I, II, or III. In some embodiments, the system can be configured to categorize the baseline ASCVD risk as one of none, minimal, mild, or moderate. In some embodiments, the system can be configured to categorize the baseline ASCVD risk as one of primarily calcified or primarily non-calcified plaque. In some embodiments, the system can be configured to categorize the baseline ASCVD risk based on units of low density non-calcified plaque identified from the image. In some embodiments, the system is configured to categorize the baseline ASCVD risk on a continuous scale. In some embodiments, the system is configured to categorize the baseline ASCVD risk based on risk of future ASCVD events, such as heart attack, stroke, amputation, dissection, and/or the like. In some embodiments, the system is configured to categorize the baseline ASCVD risk based on one or more non-ASCVD measures, which can be quantified using one or more CCTA algorithms. For example, non-ASCVD measures can include one or more cardiovascular measurements (e.g., left ventricular hypertrophy for hypertension or atrial volumes for atrial fibrillation, and/or the like) or non-cardiovascular measurements that may contribute to ASCVD (e.g., emphysema, etc.).

In some embodiments, the system at block 2312 can be configured to determine an initial proposed treatment for the subject. In some embodiments, the system can be configured to determine an initial proposed treatment with or without analysis of cholesterol or hemoglobin A1C. In some embodiments, the system can be configured to determine an initial proposed treatment with or without analysis of low-density lipoprotein (LDL) cholesterol or triglyceride (TG) levels of the subject.

In some embodiments, the initial proposed treatment can include medical therapy, lifestyle therapy, and/or interventional therapy. For example, medical therapy can include one or more medications, such as lipid-lowering medications, anti-inflammatory medications (e.g., colchicine, etc.), anti-thrombotic medications (e.g., rivaroxaban, aspirin, etc.), diabetic medications (e.g., sodium-glucose cotransporter-2 (SGLT2) inhibitors, glucagon-like peptide-1 receptor (GLP1R) agonists, etc.), and/or the like. Lifestyle therapy and/or interventional therapy can include any one or more such therapies discussed herein. In some embodiments, at block 2314, the subject can be treated with one or more such medical treatments.

In some embodiments, the system at block 2316 can be configured to access one or more medical images taken from a second point in time after the subject is treated with the initial treatment, for example from a medical image database 100. The one or more medical images can include images obtained using any imaging modality described herein. In some embodiments, the one or more medical images can include one or more arteries, such as for example coronary, carotid, lower extremity, upper extremity, aorta, renal, and/or the like.

In some embodiments, the system at block 2318 can be configured to analyze the one or more medical images taken at the second point in time. More specifically, in some embodiments, the system can be configured to utilize CCTA analysis and/or quantitative imaging algorithms to identify and/or derive one or more parameters from the medical image. In some embodiments, the system can be configured to store one or more identified and/or derived parameters in a parameter database 2306. In some embodiments, the system can be configured to access one or more such parameters from a parameter database 2306. In some embodiments, the system can be configured to analyze one or more plaque parameters, vascular parameters, atherosclerosis parameters, and/or perilesional tissue parameters. The plaque parameters and/or vascular parameters can include any one or more such parameters discussed herein.

In some embodiments, at block 2320, the system can be configured to assess an updated ASCVD risk of the subject based on one or more such parameters. In some embodiments, at block 2322, the system can be configured to categorize the updated ASCVD risk of the subject. In some embodiments, the system can be configured to categorize the updated ASCVD risk into one or more predetermined categories. For example, in some embodiments, the system can be configured to categorize the updated ASCVD risk as one of Stage 0, I, II, or III. In some embodiments, the system can be configured to categorize the updated ASCVD risk as one of none, minimal, mild, or moderate. In some embodiments, the system can be configured to categorize the updated ASCVD risk as one of primarily calcified or primarily non-calcified plaque. In some embodiments, the system can be configured to categorize the updated ASCVD risk based on units of low density non-calcified plaque identified from the image. In some embodiments, the system is configured to categorize the updated ASCVD risk on a continuous scale. In some embodiments, the system is configured to categorize the updated ASCVD risk based on risk of future ASCVD events, such as heart attack, stroke, amputation, dissection, and/or the like. In some embodiments, the system is configured to categorize the updated ASCVD risk based on one or more non-ASCVD measures, which can be quantified using one or more CCTA algorithms. For example, non-ASCVD measures can include one or more cardiovascular measurements (e.g., left ventricular hypertrophy for hypertension or atrial volumes for atrial fibrillation, and/or the like) or non-cardiovascular measurements that may contribute to ASCVD (e.g., emphysema, etc.).

In some embodiments, the system at block 2324 can be configured to assess the subject's response to the initial proposed treatment. For example, in some embodiments, the system can be configured to compare differences or changes in ASCVD risk and/or categorized ASCVD risk between the first point in time and the second point in time. In some embodiments, the subject response is assessed based on one or more of progression, stabilization, or regression of ASCVD. In some embodiments, progression can include rapid and/or non-rapid progression. In some embodiments, stabilization can include transformation of ASCVD from non-calcified to calcified, reduction of low attenuation plaque, and/or reduction of positive arterial remodeling. In some embodiments, regression can include decrease in ASCVD volume or burden, decrease in non-calcified plaque, and/or decrease in low attenuation plaque.

In some embodiments, the system at block 2326 can be configured to determine a continued proposed treatment for the subject, for example based on the subject response to the initial treatment. In particular, in some embodiments, if the system determines that there was progression in ASCVD risk in response to the initial treatment, the system can be configured to propose a higher tiered treatment compared to the initial treatment. In some embodiments, if the system determines that there was stabilization or regression in ASCVD risk in response to the initial treatment, the system can be configured to propose the same initial treatment or a same or similar tiered alternative treatment or a lower tiered treatment compared to the initial treatment. In some embodiments, the system can be configured to determine a continued proposed treatment with or without analysis of cholesterol or hemoglobin A1C. In some embodiments, the system can be configured to determine a continued proposed treatment with or without analysis of low-density lipoprotein (LDL) cholesterol or triglyceride (TG) levels of the subject.

In some embodiments, the continued proposed treatment can include medical therapy, lifestyle therapy, and/or interventional therapy. For example, medical therapy can include one or more medications, such as lipid-lowering medications, anti-inflammatory medications (e.g., colchicine, etc.), anti-thrombotic medications (e.g., rivaroxaban, aspirin, etc.), diabetic medications (e.g., sodium-glucose cotransporter-2 (SGLT2) inhibitors, glucagon-like peptide-1 receptor (GLP1R) agonists, etc.), and/or the like. Lifestyle therapy and/or interventional therapy can include any one or more such therapies discussed herein.

In some embodiments, the system can be configured to repeat one or more processes described in connection with FIG. 23J at different points in time. In other words, in some embodiments, the system can be configured to apply serial analysis and/or tracking of treatments to continue to monitor ASCVD of a subject and the subject's response to treatment for continued treatment of the subject.

Determining Treatment(s) for Reducing Cardiovascular Risk and/or Events

Some embodiments of the systems, devices, and methods described herein are configured to determine stenosis severity and/or vascular remodeling in the presence of atherosclerosis. In particular, some embodiments of the systems, devices, and methods described herein are configured to determine stenosis severity and vascular remodeling, for example whilst accounting for presence of plaque, natural artery tapering, and/or 3D volumes. In some embodiments, the systems, devices, and methods described herein are configured to determine % fractional blood volume, for example for determining of contribution of specific arteries and/or branches to important pathophysiologic processes (such as, risk of size of myocardial infarction; ischemia, and/or the like), whilst accounting for the presence of plaque in non-normal arteries. In some embodiments, the systems, methods, and devices described herein are configured to determine ischemia, for example by applying the continuity equation, whilst accounting for blood flow across a range of physiologically realistic ranges (e.g., ranges for rest, mild/moderate/extreme exercise, and/or the like).

Generally speaking, coronary artery imaging can be a key component for diagnosis, prognostication and/or clinical decision making of patients with suspected or known coronary artery disease (CAD). More specifically, in some embodiments, an array of coronary artery imaging parameters can be useful for guiding and informing these clinical tasks and can include such measures of arterial narrowing (stenosis) and vascular remodeling.

In some embodiments, the system can be configured to define relative arterial narrowing (stenosis) due to coronary artery atherosclerotic lesions. In some embodiments, these measures can largely rely upon (1) comparisons to diseased regions to normal regions of coronary vessels, and/or (2) 2D measures of diameter or area reduction due to coronary artery lesions. However, limitations can exist in such embodiments.

For example, in some of such embodiments, relative narrowing can be difficult to determine in diseased vessels. Specifically, in some embodiments, coronary stenosis can be reported as a relative narrowing, i.e., Diameter disease/Diameter normal reference×100% or Area disease/Area normal reference×100%. However, in some instances, coronary vessels are diffusely diseased, which can render comparison of diseased, stenotic regions to "normal" regions of the vessel problematic and difficult when there is no normal region of the vessel without disease to compare to.

In addition, in some of such embodiments, stenosis measurements can be reported in 2D, not 3D. Specifically, some embodiments rely upon imaging methods which are two-dimensional in nature and thus, report out stenoses as relative % area narrowing (2D) or relative % diameter narrowing (2D). Some of such embodiments do not account for the marked irregularity in coronary artery lesions that are often present and do not provide information about the coronary artery lesion across the length of a vessel. In particular, if the x-axis is considered the axial distance along a coronary vessel, the y-axis the width of an artery wall, and the z-axis the irregular topology of plaque along the length of a vessel, then it can become evident that that a single % area narrowing or a single % diameter narrowing is inadequate to communicate the complexity of the coronary lesion.

In some of such embodiments, because % area and % diameter stenosis are based upon 2D measurements, certain methods that define stenosis severity can rely upon maximum % stenosis rather than the stenosis conferred by three-dimensional coronary lesions that demonstrate heterogeneity in length and degree of narrowing across their length (i.e., volume). As such, in some of such embodiments, tracking over time can be difficult (e.g., monitoring the effects of therapy) where changes in 2D would be much less accurate. A similar analogy can be when evaluating changes in a pulmonary nodule while the patient is in follow up, which can be much more accurate in 3D than 2D.

Furthermore, in some of such embodiments, the natural tapering of arteries may not be accounted for any and/or all forms of imaging. As illustrated in FIG. 24A, the coronary arteries can naturally get smaller along their length. This can be problematic for % area and % diameter measurements, as these approaches may not take into account that a normal coronary artery tapers gradually along its length. Hence, in some of such embodiments, the comparison to a normal reference diameter or normal reference area has been to use the most normal appearing vessel segment/cross-section proximal to a lesion. In this case, because the proximal cross-section is naturally larger (due to the tapering), the actual % narrowing (by area or diameter) can be lower than it actually is.

As such, in some of such embodiments, there are certain limitations to grading of coronary artery stenosis. Thus, it can be advantageous to account for the diffuseness of disease in a volumetric fashion, whilst accounting for natural vessel tapering, as in certain other embodiments described below. Instead, in some of such embodiments described above, certain formulas can be used to evaluate these phenomena in 2 dimensions rather than 3 dimensions, in which the relative degree of narrowing, also called stenosis or maximum diameter reduction, is determined by measuring the narrowest lumen diameter in the diseased segment and comparing it to the lumen diameter in the closest adjacent proximal disease-free section. In some of such embodiments, this is because with plaque present it can be no longer possible to measure directly what the lumen diameter at that point was originally.

Similarly, in some of such embodiments, the remodeling index can be problematic. In particular, in some of such embodiments, the remodeling index is determined by measuring the outer diameter of the vessel and this is compared to the diameter in the closest adjacent proximal disease-free section. In some of such embodiments, on CT imaging, the normal coronary artery wall is not resolved as it's thickness of ~0.3 mm is beyond the ability of being depicted on CT due to resolution limitations.

Some examples of these problems in some of such embodiments are illustrated in FIGS. 24B-G and accompanying text. For example, FIG. 24B illustrates such an embodiment(s) of determining % stenosis and remodeling index. In the illustrated embodiment(s), it is assumed that the diameter of the closest adjacent proximal disease-free section (R) accurately reflects what the diameter at the point of stenosis or outward remodeling would be. However, this simple formula may significantly overestimate the actual stenosis and underestimate the remodeling index. In particular, these simple formulas may not take into account that a normal coronary artery tapers gradually along its length as depicted in FIG. 24C. As illustrated in FIG. 24C, the coronary diameter may not be constant, but rather the vessel can taper gradually along its course. For example, the distal artery diameter (D2) may be less than 50% or more of the proximal diameter (D1).

Further, when there is a long atherosclerotic plaque present, the reference diameter R0 measured in a "normal" proximal part of the vessel may have a significantly larger diameter than the diameter that was initially present, especially when the measured stenosis or remodeling index is positioned far from the beginning of the plaque. This can introduce error into the Stenosis % equation, resulting in a percent diameter stenosis larger and remodeling index significantly lower than it should be. As illustrated in FIG. 24D, when there is a long plaque positioned proximal to the point of maximal stenosis (Lx) or positive remodeling (Wx), in some of such embodiments, the reference diameter R0 can be currently measured in the closest normal part of the vessel; however at this point the vessel can be significantly larger than it would have initially been at position x, introducing error.

Generally speaking, clinical decision making in cardiology is often guideline driven and decisions often take the quantitative percent stenosis or remodeling index into account. For example, in the case of percent stenosis, a threshold of 50 or 70% can be used to determine if additional diagnostic testing or intervention is required. As a non-limiting example, FIG. 24E depicts how an inaccurately estimated R0 could significantly affect the resulting percent stenosis and remodeling index. As illustrated in FIG. 24E, if the estimated R0 is larger than the true lumen at the site of stenosis or positive remodeling, significant error can be introduced.

In some embodiments, with current technology by imaging (including but not limited to CT, MM and others), the internal lumen (L) and outer (W) is continuously measurable along the entire length of a coronary artery. In some embodiments, when the lumen diameter is equal to the wall diameter, there is no atherosclerotic plaque present, the vessel is "normal." Conversely, in some embodiments, when the wall diameter is greater than the lumen diameter, plaque is present. This is illustrated in FIG. 24F. As illustrated in FIG. 24F, in some embodiments, both the lumen diameter and outer wall diameter are continuously measured using current imaging techniques, such as CT. In some embodiments, when L=W there is no plaque present.

In some embodiments, an estimated reference diameter can be calculated continuously at every point in the vessel where plaque is present. For example, by using the R0 just before plaque, and a Rn just after the end of the plaque, the degree of tapering along the length of the plaque can be calculated. In some embodiments, this degree of tapering is, in most cases, linear; but may also taper in other mathematically-predictable fashions (log, quadratic, etc.) and hence, the measurements may be transformed by certain mathematical equations, as illustrated in FIG. 24G. In some embodiments, using the formula in FIG. 24G, an Rx can then be determined at any position along the plaques length. In some embodiments, this assumes that the "normal" vessel would have tapered in a linear (or other mathematically predictable fashions) manner across its length. As illustrated in FIG. 24G, in some embodiments, the reference diameter can be better estimated continuously along the length of the diseased portion of the vessel as long as the diameter just before the plaque R0 and just after the plaque Rn is known.

In some embodiments, once the continuous Rx reference diameter is determined, a continuous percent stenosis and/or remodeling index across the plaque and be easily calculated, for example using the following.

$$\% \text{ Stenosis}_x = \frac{R_x - L_x}{R_x} \times 100$$

$$\text{Remodeling Index } RI_x = \frac{W_x}{R_x}$$

More specifically, in some embodiments, since the continuous lumen diameter Lx and wall diameter Wx are already known, continuous values for percent stenosis and remodeling index and be easily calculated once the Rx values have been generated.

As described above, in some embodiments, there are certain limitations to calculating stenosis severity and remodeling index in two dimensions. Further, even as improved upon with the accounting of the vessel taper and presence of plaque in some embodiments, these approaches may still be limited in that they are reliant upon 2D (areas, diameters) rather than 3D measurements (e.g., volume). Thus, as described in some embodiments herein, an improvement to this approach may be to calculate volumetric stenosis, volumetric remodeling, and/or comparisons of compartments of the coronary artery to each other in a volumetric fashion.

As such, in some embodiments, the systems, devices, and methods described herein are configured to calculate volumetric stenosis, volumetric remodeling, and/or comparisons of compartments of the coronary artery to each other in a volumetric fashion, for example by utilizing one or more image analysis techniques to one or more medical images obtained from a subject using one or more medical imaging scanning modalities. In some embodiments, the system can be configured to utilize a normalization device, such as those described herein, to account for differences in scan results (such as for example density values, etc.) between different scanners, scan parameters, and/or the like.

In particular, in some embodiments, volumetric stenosis is calculated as illustrated in FIGS. 24H and 24I. As illustrated in FIGS. 24H and 24I, in some embodiments, the system can be configured to analyze a medical image of a subject to identify one or more boundaries along a vessel. For example, in some embodiments, the system can be configured to identify the theoretically or hypothetically normal boundaries of the artery wall in the case a plaque was not present. In some embodiments, the system can be configured to identify the lumen wall and, in the absence of plaque, the vessel wall. In some embodiments, the system can be configured to identify an area of interrogation (e.g., site of maximum obstruction). In some embodiments, the system can be configured to determine a segment with the plaque.

Thus, in some embodiments as illustrated in FIG. 24I, % volumetric stenosis can be calculated by the following equation, which accounts for the 3D irregularity of contribution of the plaque to narrowing the lumen volume, whilst considering the normal vessel taper and hypothetically normal vessel wall boundary: Lumen volume accounting for plaque (which can be measured)/Volume of hypothetically normal vessel (which can be calculated)×100%=Volumetric % stenosis.

In some embodiments, an alternative method for % volume stenosis can be to include the entire vessel volume (i.e., that which is measured rather than that which is hypothetical). This can be governed by the following equation: Lumen volume accounting for plaque (which can be measured)/Volume of vessel (which can be measured)×100%=Volumetric % stenosis.

In some embodiments, another alternative method for determining % volumetric stenosis is to include the entire artery (i.e., that which is before, at the site of, and after a narrowing), as illustrated in FIG. 24I.

In some embodiments, the systems, devices, and methods described herein are configured to calculate volumetric remodeling. In particular, in some embodiments, volumetric remodeling can account for the natural tapering of a vessel, the 3D nature of the lesion, and/or the comparison to a proper reference standard. FIG. 24J is a schematic illustration of an embodiment(s) of determining volumetric remodeling. In the example of FIG. 24J, the remodeling index of Lesion #1, that is 5.2 mm in length, is illustrated.

As illustrated in FIG. 24J, in some embodiments, the system can be configured to identify from a medical image a length of Lesion #1 in which a region of plaque is present (note the natural 8% taper by area, diameter or volume). In some embodiments, the system can be configured to identify a lesion length immediately before Lesion #1 in a normal part of the vessel (note the natural 12% taper by area, diameter or volume). In some embodiments, the system can be configured to identify a lesion length immediately after Lesion #1 in a normal part of the vessel (note the natural 6% taper by area, diameter or volume). In some embodiments, the system can be configured to identify one or more regions of plaque. In some embodiments, the system can be configured to identify or determine a 3D volume of the vessel across the lesion length of 5.2 mm immediately before and/or after Lesion #1 and/or in Lesion #1.

In some embodiments, the system can be configured to calculate a Volumetric Remodeling Index by the following: (Volume within Lesion #1 had plaque not been present+ Volume of plaque in Lesion #1 exterior to the vessel wall)/Volume within Lesion #1 had plaque not been present. By utilizing this formula, in some embodiments, the resulting volumetric remodeling index can take into account tapering, as the volume within lesion #1 had plaque not been present takes into account any effect of tapering.

In some embodiments, the Volumetric Remodeling Index can be calculated using other methods, such as: Volume within Lesion #1 had plaque not been present/Proximal normal volume immediately proximal to Lesion #1×100%, mathematically adjusted for the natural vessel tapering. This volumetric remodeling index uses the proximal normal volume as the reference standard.

Alternatively, in some embodiments, a method of determining volumetric remodeling index that does not directly account for natural vessel tapering can be calculated by Volume within Lesion #1 had plaque not been present/ ((Proximal normal volume immediately proximal to Lesion #1+Distal normal volume immediately distal to Lesion #1))/2 in order to account for the natural tapering.

Further, in some embodiments, with the ability to evaluate coronary vessels in 3D, along with the ability to determine the hypothetically-normal boundaries of the vessel wall even in the presence of plaque, the systems, methods, and devices described herein can be configured to either measure (in the absence of plaque) or calculate the normal coronary vessel blood volume.

For example, in some embodiments, this coronary vessel blood volume can be assessed by one or more of the following: (1) Total coronary volume (which represents the total volume in all coronary arteries and branches); (2) Territory- or Artery-specific volume, or % fractional blood volume (which represents the volume in a specific artery or branch); (3) Segment-specific volume (which represents the volume in a specific coronary segment, of which there are generally considered 18 segments); and/or within-artery % fractional blood volume (which represents the volume in a portion of a vessel or branch, i.e., in the region of the artery before a lesion, in the region of the artery at the site of a lesion, in the region of the artery after a lesion, etc.).

FIG. 24K illustrates an embodiment(s) of coronary vessel blood volume assessment based on total coronary volume. FIG. 24L illustrates an embodiment(s) of coronary vessel blood volume assessment based on territory or artery-specific volume. For example, in the illustrated embodiment, the right the right coronary artery territory volume would be the volume within #1, #2, #3, #4, and #5, while the right coronary artery volume would be the volume within #1, #2, and #3. As an example of segment-specific volume-based assessment of coronary vessel blood volume, a segment-specific volume (e.g., mid-right coronary artery) can be the volume in #2. FIG. 24M illustrates an embodiment(s) of coronary vessel blood volume assessment based on within-artery % fractional blood volume, where the proximal and distal regions comprise portions of the artery fractional blood volume.

Numerous advantages exist for assessing fractional blood volume. In some embodiments, because this method allows for determination of coronary volume hypothetically-normal boundaries of the vessel wall even in the presence of plaque, these approaches allow for calculation of the % blood volume conferring potential risk to myocardium—comes the ability to either measure (in the absence of plaque) or calculate the normal coronary vessel blood volume. FIG. 24N illustrates an embodiment(s) of assessment of coronary vessel blood volume.

In some embodiments, based on one or more metrics described above, as well as the ability to determine the hypothetically normal boundaries of the vessel, the systems, devices, and methods described herein can be configured to determine the ischemia-causing nature of a vessel by a number of different methods.

In particular, in some embodiments, the system can be configured to determine % vessel volume stenosis, for example by: Measured lumen volume/Hypothetically normal vessel volume×100%. This is depicted in FIG. 24O.

In some embodiments, the system can be configured to determine pressure difference across a lesion using hypothetically normal artery, continuity equation and naturally occurring coronary flow rate ranges and/or other physiologic parameters. This is illustrated in FIG. 24P. In the embodiment illustrated in FIG. 24P, there is a plaque that extends into the lumen and narrows the lumen (at the maximum narrowing, it is R0). In some embodiments, the system can compare R0 to R-1, R-2, R-3 or any cross-section before the lesion.

In some embodiments, using this comparison, the system can apply the continuity equation either using actual measurements (e.g., at lines in FIG. 24P) or the hypothetically normal diameter of the vessel. The continuity equation applied to the coronary arteries is illustrated in FIG. 24Q.

As illustrated in FIG. 24Q, in some embodiments, the system, by using imaging (CT, MRI, etc.), can be configured to determine the cross-sectional area of artery at a defined point before the site of maximum narrowing (A1) and the cross-sectional area of artery at the site of maximum narrowing (A2) with high accuracy. However, in some embodiments, velocity and velocity time integral are unknown. Thus, in some embodiments, the velocity time integral (VTI) at a defined point before the site of maximum narrowing (V1) and the VTI at a defined point after the site of maximum narrowing (V2) are provided, for example in categorical outputs based upon what has been empirically measured for people at rest and during exertion (mild, moderate and extreme).

As a non-limiting example, at rest, the total coronary blood flow can be about ~250 ml/min (~0.8 ml/min*g of heart muscle), which represents ~5% of cardiac output. At increasing levels of exertion, the coronary blood flow can increase up to 5 times its amount (~1250 ml/min). Thus, in some embodiments, the system can categorize the flow into about 250 ml/min, about 250-500 ml/min, about 500-750 ml/min, about 750-1000 ml/min, and/or about 1250 ml/min. Other categorizations can exist, and these numbers can be reported in continuous, categorical, and/or binary expressions. Further, based upon the observations of blood flow, these relationships may not necessarily be linear, and can be transformed by mathematical operations (such as log transform, quadratic transform, etc.).

Further, in some embodiments, other factors can be calculated based upon ranges, binary expressions, and/or continuous values, such as for example heart rate, aortic blood pressure and downstream myocardial resistance, arterial wall/plaque resistance, blood viscosity, and/or the like. Empirical measurements of fluid behavior in these differing conditions can allow for putting together a titratable input for the continuity equation.

Further, in some embodiments, because imaging allows for evaluation of the artery across the entire cardiac cycle, measured (or assumed) coronary vasodilation can allow for time-averaged A1 and A2 measurements.

As such, in some embodiments, the system can be configured to utilize one or more of the following equations: (1) Q=area×velocity @ site of maximum obstruction (across a range of flows observed in empirical measurements); and (2) Q=area×velocity @ site proximal to maximum obstruction (across a range of flows observed in empirical measurements).

From the assumed flows and measured areas, in some embodiments, the system can then back-calculate the velocity. Then, the system can apply the simplified or full Bernoulli's equations to equal: Pressure change=$4(V2-V1)^2$. From this, in some embodiments, the system can calculate the pressure drop across a lesion and, of equal import, can assess this pressure change across physiologically-realistic parameters that a patient will face in real life (e.g., rest, mild/moderate/extreme exertion).

Further, in some embodiments, the system can apply a volumetric continuity equation to account for a volume of blood before and after a lesion narrowing, such as for example: (1) Q=volume×velocity @ site of maximum obstruction (across a range of flows observed in empirical measurements); and (2) Q=volume×velocity @ site proximal to maximum obstruction (across a range of flows observed in empirical measurements). From the assumed flows and measured volumes, in some embodiments, the system can then back-calculate the velocity and, if assuming or measuring heart rate, the system can then back-calculate the velocity time integral.

FIG. 24R is a flowchart illustrating an overview of an example embodiment(s) of a method for determining volumetric stenosis and/or volumetric vascular remodeling. As illustrated in FIG. 24R, in some embodiments, at block 2402 the system is configured to access one or more medical images, for example from a medical image database 100. The one or more medical images can be obtained using any one or more of the imaging modalities discussed herein. In some embodiments, at block 2404, the system can be configured to identify one or more segments of arteries and/or regions of plaque by analyzing the medical image.

In some embodiments, the system at block 2406 can be configured to determine a lumen wall boundary in the one or more segments where plaque is present. In some embodiments, the system at block 2406 can be configured to determine a hypothetical normal artery boundary if plaque were not present. In some embodiments, the system at block 2408 can be configured to quantify the lumen volume with plaque and/or a hypothetical normal vessel volume had plaque not been present. In some embodiments, using the foregoing, the system at block 2410 can be configured to determine volumetric stenosis of the one or more segments, taking into account tapering and true assessment of the vessel morphology based on image analysis.

In some embodiments, the system at block 2412 can be configured to quantify the volume of one or mor eregions of plaque. For example, in some embodiments, the system can be configured to quantify for a segment or lesion the total volume of plaque, volume of plaque inside the hypothetical normal artery boundary, volume of plaque outside the hypothetical normal artery boundary, and/or the like. In some embodiments, the system at block 2414 can be configured to utilize the foregoing to determine a volumetric remodeling index. For example, in some embodiments, the system can be configured to determine a volumetric remodeling index by dividing the sum of the hypothetical normal vessel volume and the plaque volume outside the hypothetical normal artery boundary by the hypothetical normal vessel volume.

In some embodiments, the system at block 2416 can be configured to determine a risk of CAD for the subject, for example based on one or more of the determined volumetric stenosis and/or volumetric vascular remodeling index.

FIG. 24S is a flowchart illustrating an overview of an example embodiment(s) of a method for determining ischemia. As illustrated in FIG. 24S, in some embodiments, the system can access a medical image at block 2402, identify one or more segments of arteries and/or region of plaque at block 2404, and/or determine the lumen wall boundary while taking into account the present plaque and/or a hypothetical normal artery boundary if plaque were not present at block 2406. In some embodiments, at block 2418, the system can be configured to quantify a proximal and/or distal cross-sectional area and/or volume along an artery. For example, in some embodiments, the system can be configured to quantify a proximal cross-sectional area and/or volume at a lesion that is proximal to a lesion of interest. In some embodiments, the lesion of interest can include plaque and/or a maximum narrowing of a vessel. In some embodiments, the system can be configured to quantify a distal cross-sectional area and/or volume of the lesion of interest.

In some embodiments, the system can be configured to apply an assumed velocity of blood flow at the proximal section at block 2420. In some embodiments, the assumed velocity of blood flow can be prestored or predetermined, for example based on different states, such as at rest, during mild exertion, during moderate exertion, during extreme exertion, and/or the like.

In some embodiments, at block 2422, the system can be configured to quantify the velocity of blood flow at the distal section, for example at the lesion that includes plaque and/or maximum narrowing of the vessel. In some embodiments, the system is configured to quantify the velocity of blood flow at the distal section by utilizing the continuity equation. In some embodiments, the system is configured to quantify the velocity of blood flow at the distal section by utilizing one or more of the quantified proximal cross-sectional area or volume, quantified distal cross-sectional area or volume, and/or assumed velocity of blood flow at the proximal section.

In some embodiments, the system at block 2424 is configured to determine a change in pressure between the proximal and distal sections, for example based on the assumed velocity of blood flow at the proximal section, the quantified velocity of blood flow at the distal section, the cross-sectional area at the proximal section, and/or the cross-sectional area at the distal section. In some embodiments, at block 2426, the system is configured to determine a velocity time integral (VTI) at the distal section, for example based on the quantified velocity of blood flow at the distal section. In some embodiments, the system at block 2428 is configured to determine ischemia for the subject, for example based on one or more of the determined change in pressure between the proximal and distal sections and/or VTI at the distal section.

Additional Example Embodiments

The following are non-limiting examples of certain embodiments of systems and methods of characterizing coronary plaque and/or other related features. Other embodiments may include one or more other features, or different features, that are discussed herein.

Certain Embodiments Relating to Normalization Devices

The following are non-limiting examples of certain embodiments of normalization devices and/or other related features. Other embodiments may include one or more other features, or different features, that are discussed herein.

Embodiment 1: A normalization device configured to normalize a medical image of a patient for an algorithm-based medical imaging analysis, the normalization comprising: a substrate configured in size and shape to be placed in a medical imager along with a patient so that the normalization device and the patient can be imaged together such that at least a region of interest of the patient and the normalization device appear in a medical image taken by the medical imager; a plurality of compartments positioned on or within the substrate, wherein an arrangement of the plurality of compartments is fixed on or within the substrate; and a plurality of samples, each of the plurality of samples positioned within one of the plurality of compartments, and wherein a volume, an absolute density, and a relative density of each of the plurality of samples is known.

Embodiment 2: The normalization device of embodiment 1, further comprising an attachment mechanism disposed on the substrate, the attachment mechanism configured to attach the normalization device to the patient so that the normalization device and the patient can be imaged together such that the region of interest of the patient and the normalization device appear in the medical image taken by the medical imager.

Embodiment 3: The normalization device of embodiments 1 or 2, wherein for at least some of the plurality of samples, the volume, the absolute density, and the relative density are selected based on a medical condition to be analyzed within the medical image.

Embodiment 4: The normalization device of embodiment 3, wherein for at least some of the plurality of samples, the volume, the absolute density, and the relative density are selected based on a type of the medical imager.

Embodiment 5: The normalization device of embodiment 4, wherein at least some of the plurality of samples comprise materials representative of materials to be analyzed with the algorithm-based medical imaging analysis.

Embodiment 6: The normalization device of any of embodiments 1-5, wherein the plurality of samples comprises a set of calcium samples, each calcium sample of the set of calcium samples comprising a different absolute densities than absolute densities of the others of the set of calcium samples.

Embodiment 7: The normalization device of embodiment 6, wherein the set of calcium samples are arranged within the plurality of compartments such that each calcium sample is positioned adjacent to at least another of the calcium samples.

Embodiment 8: The normalization device of embodiment 6, wherein a range of radio densities of the set of calcium samples is between about 130 Hounsfield Units and about 1000 Hounsfield units.

Embodiment 9: The normalization device of embodiment 6, wherein the plurality of samples comprises a set of contrast samples, each of the set of contrast samples comprising an absolute density different than absolute densities of the others of the contrast samples.

Embodiment 10: The normalization device of embodiment 9, wherein the set of contrast samples are arranged within the plurality of compartments such that each contrast sample is positioned adjacent to at least another of the contrast samples.

Embodiment 11: The normalization device of embodiment 10, wherein the set of contrast samples are arranged within the plurality of compartments such that each contrast sample is positioned adjacent to at least one of the calcium samples.

Embodiment 12: The normalization device of embodiment p, wherein the plurality of samples comprises a set of fat samples, each of the set of fat samples comprising an absolute density different than absolute densities of the others of the fat samples.

Embodiment 13: The normalization device of embodiment 13, wherein the set of fat samples are arranged within the plurality of compartments such that each fat sample is positioned adjacent to another of the fat samples.

Embodiment 14: The normalization device of embodiment 13, wherein the set of fat samples are arranged within the plurality of compartments such that each fat sample is positioned adjacent to one of the set of calcium samples.

Embodiment 15: The normalization device of embodiment 12, wherein the set of contrast samples is positioned arranged within the plurality of compartments such that the set of contrast samples is surrounded by the set of calcium samples and the set of fat samples.

Embodiment 16: The normalization device of embodiment 12, wherein the plurality of samples comprises at least one air sample.

Embodiment 17: The normalization device of embodiment 12, wherein the plurality of samples comprises at least one water sample.

Embodiment 18: A normalization device configured to normalize a medical image of a coronary region of a subject for an algorithm-based medical imaging analysis, the normalization device comprising: a substrate configured in size and shape to be placed in a medical imager along with a patient so that the normalization device and the patient can be imaged together such that at least a region of interest of the patient and the normalization device appear in a medical image taken by the medical imager; a plurality of compartments positioned on or within the substrate, wherein an arrangement of the plurality of compartments is fixed on or within the substrate; a plurality of samples, each of the plurality of samples positioned within one of the plurality of compartments, and wherein a volume, an absolute density, and a relative density of each of the plurality of samples is known, the plurality of samples comprising: a set of contrast samples, each of the contrast samples comprising a different absolute density than absolute densities of the others of the contrast samples; a set of calcium samples, each of the calcium samples comprising a different absolute density than absolute densities of the others of the calcium samples; and a set of fat samples, each of the fat samples comprising a different absolute density than absolute densities of the others of the fat samples; and wherein the set contrast samples are arranged within the plurality of compartments such that the set of calcium samples and the set of fat samples surround the set of contrast samples.

Embodiment 19: The normalization device of embodiment 18, further comprising an attachment mechanism disposed on the substrate, the attachment mechanism configured to attach the normalization device to the patient so that the normalization device and the patient can be imaged together such that the region of interest of the patient and the normalization device appear in the medical image taken by the medical imager.

Embodiment 20: The normalization device of embodiment 18, wherein: the set of contrast samples comprise four contrast samples; the set of calcium samples comprise four calcium samples; and the set of fat samples comprise four fat samples.

Embodiment 21: The normalization device of embodiment 20, wherein the plurality of samples further comprises at least one of an air sample and a water sample.

Embodiment 22: The normalization device of embodiment 18, wherein: the volume of a first contrast sample is different than a volume of a second contrast sample; the volume of a first calcium sample is different than a volume of a second calcium sample; and the volume of a first fat sample is different than a volume of a second fat sample.

Embodiment 23: The normalization device of embodiment 18, wherein a first contrast sample is arranged within the plurality of compartments so as to be adjacent to a second contrast sample, a first calcium sample, and a first fat sample.

Embodiment 24: The normalization device of embodiment 18, wherein a first calcium sample is arranged within the plurality of compartments so as to be adjacent to a second calcium sample, a first contrast sample, and a first fat sample.

Embodiment 25: The normalization device of embodiment 18, wherein a first fat sample is arranged within the plurality of compartments so as to be adjacent to a second fat sample, a first contrast sample, and a first calcium sample.

Embodiment 26: The normalization device of embodiment 18, wherein the set of contrast samples, the set of calcium samples, and the set of fat samples are arranged in a manner that mimics a blood vessel.

Certain Embodiments Relating to Generating a Medical Report

The following are non-limiting examples of certain embodiments of systems and methods of characterizing coronary plaque and/or other related features. Other embodiments may include one or more other features, or different features, that are discussed herein.

Embodiment 1: An apparatus for generating a multimedia medical report for a patient, the medical report associated with one or more tests of the patient, comprising: a non-transient memory configured to store computer-executable instructions; and one or more hardware processors in communication with the memory, wherein the computer-executable instructions, when executed by the one or more processors, configure the one or more processors to: receive an input of a request to generate the medical report for a patient, the request indicating a format for the medical report; receive patient information relating to the patient that is associated with the report generation request; determine one or more patient characteristics associated with the patient using the patient information; access associations between types of medical reports and patient medical information, wherein the patient medical information includes medical images relating to the patient and test results of one or more test performed on the patient; access report content associated with the patient's medical information and the medical report requested, wherein the report content comprises multimedia content that is not related to a specific patient, the multimedia content including a greeting segment in the language of the patient, an explanation segment explaining a type of test conducted, a results segment for conveying test results, and an explanation segment explaining results of the test, and a conclusion segment, wherein at least a portion of the multimedia content includes a test result and one or more medical images related to a test performed on the patient; and generate, based at least in part on the format of the medical report, the requested medical report using the patient information and report content.

Embodiment 2: The apparatus of embodiment 1, wherein the computer-executable instructions, when executed by the one or more processors, further configure the one or more processors to display the medical report.

Embodiment 3: The apparatus of embodiment 1, wherein the computer-executable instructions, when executed by the one or more processors, further configure the one or more processors to display the medical report on a user device of the patient.

Embodiment 4: The apparatus of embodiment 3, wherein user device is a smart phone, a laptop computer, a tablet computer, or a desktop computer.

Embodiment 5: The apparatus of embodiment 1, wherein the report content further comprises information for generating and displaying an avatar when the medical report is displayed.

Embodiment 6: The apparatus of embodiment 5, wherein the avatar based on the one or more patient characteristics.

Embodiment 7: The apparatus of embodiment 6, wherein the patient characteristics include one or more of age, race, or gender.

Embodiment 8: The apparatus of any one of embodiments 1-3 and 5-7, wherein the computer-executable instructions, when executed by the one or more processors, further configure the one or more processors to display the medical report on one or more displays of a computer system, receive user input while the medical report is displayed, and changing at least one portion of the medical report based on the received user input.

Embodiment 9: The apparatus of any one of embodiments 1-3 and 5-7, wherein the computer-executable instructions, when executed by the one or more processors, further configure the one or more processors to store the medical report.

Embodiment 10: The apparatus of any one of embodiments 1-3 and 5-7, wherein the computer-executable instructions, when executed by the one or more processors, further configure the one or more processors to access associations between types of medical reports and patient medical information comprises accessing one or more data structures storing associations between types of medical reports and patient medical information.

Embodiment 11: The apparatus of any one of embodiments 1-3 and 5-7, wherein the computer-executable instructions, when executed by the one or more processors, further configure the one or more processors to select multimedia content to include in the medical report based at least in part on a severity of the patient's medical condition.

Embodiment 12: The apparatus of any one of embodiments 1-3 and 5-7, wherein the computer-executable instructions, when executed by the one or more processors, further configure the one or more processors to select a greeting segment for the medical report based at least in part on one or more of the patient's race, age, gender, ethnicity, culture, language, education, geographic location, or severity of prognosis.

Embodiment 13: The apparatus of any one of embodiments 1-3 and 5-7, wherein the computer-executable instructions, when executed by the one or more processors, further configure the one or more processors to select an explanation segment based at least in part on one or more of the patient's race, age, gender, ethnicity, culture, language, education, geographic location, or severity of prognosis.

Embodiment 14: The apparatus of any one of embodiments 1-3, 5-7, and 13, wherein the computer-executable instructions, when executed by the one or more processors, further configure the one or more processors to select a results segment based at least in part on one or more of the patient's race, age, gender, ethnicity, culture, language, education, geographic location, and severity of prognosis.

Embodiment 15: The apparatus of any one of embodiments 1-3, 5-7, 13 and 14, wherein the computer-executable instructions, when executed by the one or more processors, further configure the one or more processors to select a conclusion segment based on one or more of the patient's race, age, gender, ethnicity, culture, language, education, geographic location, and severity of prognosis.

Embodiment 16: The apparatus of any one of embodiments 1-16, wherein the computer-executable instructions, when executed by the one or more processors, further configure the one or more processors to access one or more data structures configured to store associations related to normality, risk, treatment type, and treatment benefit of medical conditions, and wherein the computer-executable instructions, when executed by the one or more processors, further configure the one or more processors to automatically determine normality, risk, treatment type, and treatment benefit to include in the report based on the patients test results, and the stored associations related to normality, risk, treatment type, and treatment benefits.

Embodiment 17: The apparatus of any one of embodiments 1-17, wherein the computer-executable instructions, when executed by the one or more processors, further configure the one or more processors to generate an updated medical report based on a previously generated medical report, new patient medical information, and an input by a medical practitioner.

Embodiment 18: A non-transitory computer readable medium for generating a multi-media medical report for a patient, the medical report associated with one or more tests of the patient, the computer readable medium having program instructions for causing a hardware processor to perform a method of: receiving an input of a request to generate the medical report for a patient, the request indicating a format for the medical report; receiving patient information relating to the patient, the patient information associated with the report generation request; determining one or more patient characteristics associated with the patient using the patient information; accessing associations between types of medical reports and patient medical information, wherein the patient medical information includes medical images relating to the patient and test results of one or more test that were performed on the patient; accessing report content associated with the patient's medical information and the medical report requested, wherein the report content comprises multimedia content that is not related to a specific patient, the multimedia content including a greeting segment in the language of the patient, an explanation segment explaining a type of test conducted, a results segment for conveying test results, and an explanation segment explaining results of the test, and a conclusion segment, wherein at least a portion of the multimedia content includes a test result and one or more medical images that are related to a test performed on the patient; and in addition generating, based at least in part on the format of the medical report, the requested medical report using the patient information and report content.

Embodiment 19: The non-transitory computer readable medium of embodiment 18, wherein the computer-executable instructions, when executed by the one or more processors, further configure the one or more processors to display the medical report.

Embodiment 20: The non-transitory computer readable medium of embodiment 19, wherein the computer-executable instructions, when executed by the one or more processors, further configure the one or more processors to display the medical report on a user device of the patient.

Embodiment 21: The non-transitory computer readable medium of embodiment 19, wherein user device is a smart phone, a laptop computer, a tablet computer, or a desktop computer.

Embodiment 22: The non-transitory computer readable medium of embodiment 19, wherein the computer-executable instructions, when executed by the one or more processors, further configure the one or more processors to generate and display an avatar as part of the medical report.

Embodiment 23: The non-transitory computer readable medium of embodiment 22, wherein the avatar based on the one or more patient characteristics.

Embodiment 24: The non-transitory computer readable medium of embodiment 23, wherein the patient characteristics include one or more of age, race, or gender.

Embodiment 25: The non-transitory computer readable medium of any one of embodiments 19-21 and 23-25, wherein the computer-executable instructions, when executed by the one or more processors, further configure the one or more processors to display the medical report on one or more displays of a computer system, receive user input while the medical report is displayed, and change at least one portion of the medical report based on the received user input.

Embodiment 26: The non-transitory computer readable medium of any one of embodiments 19-21 and 23-25, wherein the computer-executable instructions, when executed by the one or more processors, further configure the one or more processors to store the medical report.

Embodiment 27: The non-transitory computer readable medium of any one of embodiments 19-21 and 23-25, wherein the computer-executable instructions, when executed by the one or more processors, further configure the one or more processors to access associations between types of medical reports and patient medical information comprises accessing one or more data structures storing associations between types of medical reports and patient medical information.

Embodiment 28: The non-transitory computer readable medium of any one of embodiments 19-21 and 23-25, wherein the computer-executable instructions, when executed by the one or more processors, further configure the one or more processors to select multimedia content to include in the medical report based at least in part on a severity of the patient's medical condition.

Embodiment 29: The non-transitory computer readable medium of any one of embodiments 19-21 and 23-25, wherein the computer-executable instructions, when executed by the one or more processors, further configure the one or more processors to select a greeting segment for the medical report based at least in part on one or more of the patient's race, age, gender, ethnicity, culture, language, education, geographic location, or severity of prognosis.

Embodiment 30: The non-transitory computer readable medium of any one of embodiments 19-21, 23-25, and 29, wherein the computer-executable instructions, when executed by the one or more processors, further configure the one or more processors to select an explanation segment based at least in part on one or more of the patient's race, age, gender, ethnicity, culture, language, education, geographic location, or severity of prognosis.

Embodiment 31: The non-transitory computer readable medium of any one of embodiments 19-21 23-25, 29 and 30, wherein the computer-executable instructions, when executed by the one or more processors, further configure the one or more processors to select a results segment based at least in part on one or more of the patient's race, age, gender, ethnicity, culture, language, education, geographic location, and severity of prognosis.

Embodiment 32: The non-transitory computer readable medium of any one of embodiments 19-21, 23-25, and 29-31, wherein the computer-executable instructions, when executed by the one or more processors, further configure the one or more processors to select a conclusion segment based on one or more of the patient's race, age, gender, ethnicity, culture, language, education, geographic location, and severity of prognosis.

Embodiment 33: The non-transitory computer readable medium of any one of embodiments 18-32, wherein the computer-executable instructions, when executed by the one or more processors, further configure the one or more processors to access one or more data structures configured to store associations related to normality, risk, treatment type, and treatment benefit of medical conditions, and wherein the computer-executable instructions, when executed by the one or more processors, further configure the one or more processors to automatically determine normality, risk, treatment type, and treatment benefit to include in the report based on the patients test results, and the stored associations related to normality, risk, treatment type, and treatment benefits.

Embodiment 34: The non-transitory computer readable medium of any one of embodiments 18-33, wherein the computer-executable instructions, when executed by the one or more processors, further configure the one or more processors to generate an updated medical report based on a previously generated medical report, new patient medical information, and a user input.

Embodiment 35: A method of generating a multi-media medical report for a patient, the medical report associated with one or more tests of the patient, the method comprising: receiving an input of a request to generate the medical report for a patient, the request indicating a format for the medical report; receiving patient information relating to the patient that is associated with the report generation request; determining one or more patient characteristics associated with the patient using the patient information; accessing associations between types of medical reports and patient medical information, wherein the patient medical information includes medical images relating to the patient and test results of one or more test performed on the patient; accessing report content associated with the patient's medical information and the medical report requested, wherein the report content comprises multimedia content that is not related to a specific patient, the multimedia content including a greeting segment in the language of the patient, an explanation segment explaining a type of test conducted, a results segment for conveying test results, and an explanation segment explaining results of the test, and a conclusion segment, wherein at least a portion of the multimedia content includes a test result and one or more medical images related to a test performed on the patient; and generating, based at least in part on the format of the medical report, the requested medical report using the patient information and report content, wherein the method is performed by one or more hardware processors executing program instruction on a non-transitory computer readable medium.

Embodiment 36: The method of embodiment 35, further comprising displaying the medical report.

Embodiment 37: The method of embodiment 35, further comprising displaying the medical report on a user device of the patient.

Embodiment 38: The non-transitory computer readable medium of embodiment 19, wherein user device is a smart phone, a laptop computer, a tablet computer, or a desktop computer.

Embodiment 39: The method of any one of embodiments 35-38, further comprising generating and displaying an avatar as part of the medical report.

Embodiment 40: The method of embodiment 39, wherein the avatar is based on the one or more patient characteristics.

Embodiment 41: The method of embodiment 40, wherein the patient characteristics include one or more of age, race, or gender.

Embodiment 42: The method of any one of embodiments 35-41, further comprising storing the medical report.

Embodiments of Systems and Methods of Sequential Non-Contiguous Arterial Bed Imaging and Atherosclerotic Cardiovascular Disease Evaluation Embodiment 1: An apparatus for generating a risk assessment of atherosclerotic cardiovascular disease (ASCVD), comprising: a non-transient memory configured to store computer-executable instructions; and one or more hardware processors in communication with the memory, wherein the computer-executable instructions, when executed by the one or more processors, configure the one or more processors to: receive images of a first arterial bed and a second arterial bed, the second arterial bed being noncontiguous with the first arterial bed; quantify ASCVD in the first arterial bed; quantify ASCVD in the second arterial bed; determine a first weighted assessment of the first arterial bed, the first weighted assessment generated using weighted adverse events for the first arterial bed; determine a second weighted assessment of the second arterial bed, the second weighted assessment generated using weighted adverse events for the first arterial bed; and determine an ASCVD patient risk score based on the first weighted assessment and the second weighted assessment.

Embodiment 2: The apparatus of embodiment 1, wherein the computer-executable instructions, when executed by the one or more processors, configure the one or more processors to generate a second ASCVD patient risk score of the patient based at least on another weighted assessment of the first arterial bed or another weighted assessment of the second arterial bed second weighted.

Embodiment 3: The apparatus of any one of embodiments 1 or 2, wherein the another weighted assessment is based on patient images taken after patient images used to determine the ACSVD patient risk score.

Embodiment 4: The apparatus of any one of embodiments 1-3, wherein the first arterial bed includes arteries of one of the aorta, carotid arteries, lower extremity arteries, renal arteries, and cerebral arteries.

Embodiment 5: The apparatus of any one of embodiments 1-4, wherein the second arterial bed includes arteries of one of the aorta, carotid arteries, lower extremity arteries, renal arteries, and cerebral arteries.

Embodiment 6: The apparatus of any one of embodiments 1-5, wherein the ASCVD patient risk score is based at least in part on the absence or presence of plaque.

Embodiment 7: The apparatus of any one of embodiments 1-6, wherein the ASCVD patient risk score is based at least in part on the absence or presence of non-calcified plaque.

Embodiment 8: The apparatus of any one of embodiments 1-7, wherein the ASCVD patient risk score is based at least in part on the absence or presence of low attenuation plaque.

Embodiment 9: The apparatus of any one of embodiments 1-8, wherein the ASCVD patient risk score is based at least in part on a measure of the extent of ASCVD in the first arterial bed and the second arterial bed.

Embodiment 10: The apparatus of any one of embodiments 1-9, wherein the ASCVD patient risk score is based at least in part on a measure of the total ASCVD volume in the first arterial bed and the second arterial bed.

Embodiment 11: The apparatus of any one of embodiments 1-10, wherein the ASCVD patient risk score is based at least in part on a measure of the percent atheroma volume in the first arterial bed and the second arterial bed.

Embodiment 12: The apparatus of embodiment 11, wherein the percent of atheroma volume is determined by the atheroma volume/vessel volume×100.

Embodiment 13: The apparatus of embodiment 1, wherein the ASCVD patient risk score is based at least in part on a total atheroma volume normalized to vessel length (TAVnorm) measure in the first arterial bed and the second arterial bed.

Embodiment 14: The apparatus of any one of embodiments 1-13, wherein the ASCVD patient risk score is based at least in part on a diffuseness measure in the first arterial bed and the second arterial bed.

Embodiment 15: The apparatus of embodiment 14, wherein the diffuseness measure is determined by percentage of vessel affected by ASCVD.

Embodiment 16: The apparatus of embodiment 14, wherein the diffuseness measure is determined by the severity of ASCVD.

Embodiment 17: The apparatus of any one of embodiments 1-16, wherein the computer-executable instructions, when executed by the one or more processors, configure the one or more processors to normalize the ASCVD patient risk score based on at least one of age, gender, ethnicity, and/or CAD risk factors.

Embodiment 18: The apparatus of any one of embodiments 1-17, wherein the ASCVD patient risk score is based on a angiographic stenosis determination in the first arterial bed and the second arterial bed.

Embodiment 19: The apparatus of any one of embodiments 1-18, wherein the ASCVD patient risk score is based on a proportion of plaque that is non-calcified vs. calcified.

Embodiment 20: The apparatus of any one of embodiments 1-19, wherein the ASCVD patient risk score is based on a proportion of plaque that is low attenuation non-calcified vs. non-calcified, vs. low density calcified vs. high-density calcified plaque.

Embodiment 21: The apparatus of any one of embodiments 1-20, wherein the ASCVD patient risk score is based on a proportion of the absolute amount of non-calcified plaque and calcified plaque.

Embodiment 22: The apparatus of any one of embodiments 1-21, wherein the ASCVD patient risk score is based on a proportion of plaque that is continuous grey-scale measurement of plaques without ordinal classification.

Embodiment 23: The apparatus of embodiment 1, wherein the ASCVD patient risk score is based on vascular remodeling imposed by plaque as positive remodeling, for example, ≥1.10 or ≥1.05 ratio of vessel diameter/normal reference diameter; vessel area/normal reference area; or [vessel volume/normal reference volume] vs. negative remodeling (≤1.10 or ≤1.05).

Embodiment 24: The apparatus of any one of embodiments 1-23, wherein the ASCVD patient risk score is based on vascular remodeling imposed by plaque as a continuous ratio.

Embodiment 25: The apparatus of any one of embodiments 1-24, wherein the ASCVD patient risk score is based on ASCVD progression.

Embodiment 26: The apparatus of any one of embodiments 1-25, wherein ASCVD progression is characterized as rapid or non-rapid.

Embodiment 27: The apparatus of any one of embodiments 1-26, wherein whether ASCVD progression is characterized as rapid or non-rapid is based on predetermined thresholds.

Embodiment 28: The apparatus of embodiment 27, wherein whether the predetermined thresholds relate to a percent atheroma volume.

Embodiment 29: The apparatus of embodiment 27, wherein whether the predetermined thresholds relate to a volume amount of plaque.

Embodiment 30: The apparatus of any one of embodiments 1-29, wherein whether the ASCVD progression is based on one or more or rapidness of progression, progression with primarily calcified plaque formation, progression with primarily non-calcified plaque formation, or regression.

Embodiment 31: The apparatus of any one of embodiments 1-30, wherein the ASCVD patient risk score is based on a categorization of the risk, including at least one of risk of MACE, risk of angina, risk of ischemia, risk of rapid progression, and risk of medication non-response.

Embodiment 32: A non-transitory computer readable medium for generating a risk assessment of atherosclerotic cardiovascular disease (ASCVD), the computer readable medium having program instructions for causing a hardware processor to perform a method of: receiving images of a first arterial bed and a second arterial bed, the second arterial bed being noncontiguous with the first arterial bed; quantifying ASCVD in the first arterial bed; quantifying ASCVD in the second arterial bed; determining a first weighted assessment of the first arterial bed, the first weighted assessment generated using weighted adverse events for the first arterial bed; determining a second weighted assessment of the second arterial bed, the second weighted assessment generated using weighted adverse events for the first arterial bed; and determining an ASCVD patient risk score based on the first weighted assessment and the second weighted assessment.

Embodiment 33: The non-transitory computer readable medium of embodiment 32, wherein the computer-executable instructions, when executed by the one or more processors, configure the one or more processors to generate a second ASCVD patient risk score of the patient based at least on another weighted assessment of the first arterial bed or another weighted assessment of the second arterial bed second weighted.

Embodiment 34: The non-transitory computer readable medium of embodiment 33, wherein the another weighted assessment is based on patient images taken after patient images used to determine the ACSVD patient risk score.

Embodiment 35: The non-transitory computer readable medium of embodiment 32, wherein the first arterial bed includes arteries of one of the aorta, carotid arteries, lower extremity arteries, renal arteries, and cerebral arteries.

Embodiment 36: The non-transitory computer readable medium of embodiment 32, wherein the second arterial bed includes arteries of one of the aorta, carotid arteries, lower extremity arteries, renal arteries, and cerebral arteries.

Embodiment 37: The non-transitory computer readable medium of embodiment 32, wherein the ASCVD patient risk score is based at least in part on the absence or presence of plaque.

Embodiment 38: The non-transitory computer readable medium of embodiment 32, wherein the ASCVD patient risk score is based at least in part on the absence or presence of non-calcified plaque.

Embodiment 39: The non-transitory computer readable medium of embodiment 32, wherein the ASCVD patient risk score is based at least in part on the absence or presence of low attenuation plaque.

Embodiment 40: The non-transitory computer readable medium of embodiment 32, wherein the ASCVD patient risk score is based at least in part on a measure of the extent of ASCVD in the first arterial bed and the second arterial bed.

Embodiment 41: The non-transitory computer readable medium of embodiment 32, wherein the ASCVD patient risk score is based at least in part on a measure of the total ASCVD volume in the first arterial bed and the second arterial bed.

Embodiment 42: The non-transitory computer readable medium of embodiment 32, wherein the ASCVD patient risk score is based at least in part on a measure of the percent atheroma volume in the first arterial bed and the second arterial bed.

Embodiment 43: The non-transitory computer readable medium of embodiment 32, wherein the ASCVD patient risk score is based at least in part on a diffuseness measure in the first arterial bed and the second arterial bed.

Embodiment 44: The non-transitory computer readable medium of embodiment 32, wherein the diffuseness measure is determined by percentage of vessel affected by ASCVD.

Embodiment 45: The non-transitory computer readable medium of embodiment 32, wherein the diffuseness measure is determined by the severity of ASCVD.

Embodiment 46: The non-transitory computer readable medium of embodiment 32, wherein the computer-executable instructions, when executed by the one or more processors, configure the one or more processors to normalize the ASCVD patient risk score based on at least one of age, gender, ethnicity, and/or CAD risk factors.

Embodiment 47: The non-transitory computer readable medium of embodiment 32, wherein the ASCVD patient risk score is based on a angiographic stenosis determination in the first arterial bed and the second arterial bed.

Embodiment 48: The non-transitory computer readable medium of embodiment 32, wherein the ASCVD patient risk score is based on a proportion of plaque that is non-calcified vs. calcified.

Embodiment 49: The non-transitory computer readable medium of embodiment 32, wherein the ASCVD patient risk score is based on a proportion of plaque that is low attenuation non-calcified vs. non-calcified, vs. low density calcified vs. high-density calcified plaque.

Embodiment 50: The non-transitory computer readable medium of embodiment 32, wherein the ASCVD patient risk score is based on a proportion of the absolute amount of non-calcified plaque and calcified plaque.

Embodiment 51: A computer implemented method for generating a risk assessment of atherosclerotic cardiovascular disease (ASCVD), the method comprising: receiving images of a first arterial bed and a second arterial bed, the second arterial bed being noncontiguous with the first arterial bed; quantifying ASCVD in the first arterial bed; quantifying ASCVD in the second arterial bed; determining a first weighted assessment of the first arterial bed, the first weighted assessment generated using weighted adverse events for the first arterial bed; determining a second weighted assessment of the second arterial bed, the second weighted assessment generated using weighted adverse events for the first arterial bed; and determining an ASCVD patient risk score based on the first weighted assessment and the second weighted assessment. The method may be performed by one or more hardware processors executing program instruction on a non-transitory computer readable medium. Embodiments of such methods can include functionality described herein relating to an apparatus for generating a risk assessment of atherosclerotic cardiovascular disease (ASCVD).

Embodiment 52: A computer implemented method for generating a risk assessment of atherosclerotic cardiovascular disease (ASCVD) using a normalization device for example as described herein, wherein normalization of the medical imaging improves accuracy of the algorithm-based imaging analysis. The method comprises receiving a first set of images of a first arterial bed and a first set of images of a second arterial bed, the second arterial bed being noncontiguous with the first arterial bed, and wherein at least one of the first set of images of the first arterial bed and the first set of images of the second arterial bed are normalized using the normalization device; quantifying ASCVD in the first arterial bed using the first set of images of the first arterial bed; quantifying ASCVD in the second arterial bed using the first set of images of the second arterial bed; and determining a first ASCVD risk score based on the quantified ASCVD in the first arterial bed and the quantified ASCVD in the second arterial bed. The method may be performed by one or more hardware processors executing program instruction on a non-transitory computer readable medium.

Embodiment 53: The method of embodiment 52, further comprising: determining a first weighted assessment of the first arterial bed based on the quantified ASCVD of the first arterial bed and weighted adverse events for the first arterial bed; and determining a second weighted assessment of the second arterial bed based on the quantified ASCVD of the second arterial bed and weighted adverse events for the second arterial bed, wherein determining the first ASCVD risk score further comprises determining the ASCVD risk score based on the first weighted assessment and the second weighted assessment.

Embodiment 54: The method of embodiment 53, the method further comprising: receiving a second set of images of the first arterial bed and a second set of images of the second arterial bed, the second set of images of the first arterial bed generated subsequent to generating the first set of image of the first arterial bed, and the second set of images of the second arterial bed generated subsequent to generating the first set of image of the second arterial bed; quantifying ASCVD in the first arterial bed using the second set of images of the first arterial bed; quantifying ASCVD in the second arterial bed using the second set of images of the second arterial bed; and determining a second ASCVD risk score based on the quantified ASCVD in the first arterial bed using the second set of images, and the quantified ASCVD in the second arterial bed using the second set of images.

Embodiment 55: The method of embodiment 54, wherein determining the second ASCVD risk score is further based on the first ASCVD risk score.

Embodiment 56: The method of embodiment 52, wherein the first arterial bed includes arteries of one of the aorta, carotid arteries, lower extremity arteries, renal arteries, or cerebral arteries.

Embodiment 57: The method of embodiment 56, wherein the second arterial bed includes arteries of one of the aorta, carotid arteries, lower extremity arteries, renal arteries, or cerebral arteries that are different than the arteries of the first arterial bed.

Certain Embodiments Relating to Generating a Global Ischemia Index

The following are non-limiting examples of certain embodiments of systems and methods of generating a global ischemia index and/or other related features. Other embodiments may include one or more other features, or different features, that are discussed herein.

Embodiment 1: A computer-implemented method of determining risk of ischemia for a subject by generating a global ischemia index based on multi-dimensional information derived from non-invasive medical image analysis, the method comprising: accessing, by a computer system, a medical image of a coronary region of a subject, wherein the medical image of the coronary region of the subject is obtained non-invasively; analyzing, by the computer system, the medical image of the coronary region of the subject to derive multidimensional information relating to ischemia, wherein the multidimensional information relating to ischemia comprises contributors to ischemia, consequences of ischemia, and associated factors of ischemia; generating, by the computer system using a machine learning algorithm, a global ischemia index for the subject by generating a weighted measure of the multidimensional information relating to ischemia, wherein the weighted measure of the multidimensional information relating to ischemia is generated by taking into account temporal considerations of one or more of contributors to ischemia, consequences of ischemia, or associated factors of ischemia; and assisting, by the computer system, an assessment of risk of ischemia of the subject based on the generated global ischemia index for the subject, wherein the computer system comprises a computer processor and an electronic storage medium.

Embodiment 2: The computer-implemented method of Embodiment 1, further comprising validating, by the computer system, the generated global ischemia index for the subject by comparison to an assessment of ischemia as measured by one or more of myocardial blood flow, myocardial perfusion, fractional flow reserve, or other blood flow ratio of the subject.

Embodiment 3: The computer-implemented method of Embodiments 1 or 2, wherein contributors to ischemia are weighted more heavily compared to consequences of ischemia or associated factors of ischemia when generating the weighted measure of the multidimensional information relating to ischemia.

Embodiment 4: The computer-implemented method of any one of Embodiments 1-3, wherein consequences of ischemia are weighted less heavily compared to contributors to ischemia, and wherein consequences of ischemia are weighted more heavily compared to associated factors of ischemia when generating the weighted measure of the multidimensional information relating to ischemia.

Embodiment 5: The computer-implemented method of any one of Embodiments 1-4, wherein consequences of ischemia comprise early consequences of ischemia and late consequences of ischemia, wherein early consequences of ischemia are weighted more heavily compared to late consequences of ischemia when generating the weighted measure of the multidimensional information relating to ischemia.

Embodiment 6: The computer-implemented method of any one of Embodiments 1-5, wherein associated factors of ischemia are weighted less heavily compared to contributors to ischemia and consequences of ischemia.

Embodiment 7: The computer-implemented method of any one of Embodiments 1-6, wherein contributors to ischemia comprise one or more vessel caliber parameters, plaque parameters, or fat parameters.

Embodiment 8: The computer-implemented method of Embodiment 7, wherein vessel caliber parameters comprise one or more of percentage diameter stenosis, absolute lumen volume, lumen volume indexed to percentage fractional myocardial mass, vessel volume, minimal luminal diameter (MLD), minimal luminal area (MLA), or ratio of MLD to MLA.

Embodiment 9: The computer-implemented method of Embodiment 7 or 8, wherein plaque parameters comprise one or more parameters related to one or more of non-calcified plaque, low density non-calcified plaque, calcified plaque, or location of plaque.

Embodiment 10: The computer-implemented method of Embodiment 9, wherein location of plaque comprises one or more of myocardial facing, pericardial facing, bifurcation lesions, or trifurcation lesions.

Embodiment 11: The computer-implemented method of any one of Embodiments 7-10, wherein fat parameters comprise one or more parameters related to peri-coronary adipose tissue or epicardial adipose tissue.

Embodiment 12: The computer-implemented method of any one of Embodiments 1-11, wherein consequences of ischemia comprise one or more left ventricular parameters, left atrial parameters, right ventricular parameters, right atrial parameters, aortic dimensions, or pulmonary vein parameters.

Embodiment 13: The computer-implemented method of Embodiment 12, wherein the left ventricular parameters and right ventricular parameters comprise one or more of perfusion or Hounsfield unit density, mass, or volume of the left ventricle or right ventricle.

Embodiment 14: The computer-implemented method of Embodiment 12 or 13, wherein the left atrial parameters and right atrial parameters comprise one or more of volume of the left atrium or right atrium.

Embodiment 15: The computer-implemented method of any one of Embodiments 1-14, wherein associated factors of ischemia comprise one or more of fatty liver or non-alcoholic steatohepatitis, emphysema, osteoporosis, mitral annular calcification, aortic valve calcification, aortic enlargement, or mitral valve calcification.

Embodiment 16: A system for determining risk of ischemia for a subject by generating a global ischemia index based on multi-dimensional information derived from non-invasive medical image analysis, the system comprising: one or more computer readable storage devices configured to store a plurality of computer executable instructions; and one or more hardware computer processors in communication with the one or more computer readable storage devices and configured to execute the plurality of computer executable instructions in order to cause the system to: access a medical image of a coronary region of a subject, wherein the medical image of the coronary region of the subject is obtained non-invasively; analyze the medical image of the coronary region of the subject to derive multidimensional information relating to ischemia, wherein the multidimensional information relating to ischemia comprises contributors to ischemia, consequences of ischemia, and associated factors of ischemia; generate using a machine learning algorithm a global ischemia index for the subject by generating a weighted measure of the multidimensional information relating to ischemia, wherein the weighted measure of the multidimensional information relating to ischemia is generated by taking into account temporal considerations of one or more of contributors to ischemia, consequences of ischemia, or associated factors of ischemia; and assisting, by the computer system, an assessment of risk of ischemia of the subject based on the generated global ischemia index for the subject.

Embodiment 17: The system of Embodiment 16, wherein the system is further caused to validate the generated global ischemia index for the subject by comparison to an assessment of ischemia as measured by one or more of myocardial blood flow, myocardial perfusion, fractional flow reserve, or other blood flow ratio of the subject.

Embodiment 18: The system of Embodiment 16 or 17, wherein contributors to ischemia are weighted more heavily compared to consequences of ischemia or associated factors of ischemia when generating the weighted measure of the multidimensional information relating to ischemia.

Embodiment 19: The system of any one of Embodiments 16-18, wherein consequences of ischemia are weighted less heavily compared to contributors to ischemia, and wherein consequences of ischemia are weighted more heavily compared to associated factors of ischemia when generating the weighted measure of the multidimensional information relating to ischemia.

Embodiment 20: The system of any one of Embodiments 16-19, wherein consequences of ischemia comprise early consequences of ischemia and late consequences of ischemia, wherein early consequences of ischemia are weighted more heavily compared to late consequences of ischemia when generating the weighted measure of the multidimensional information relating to ischemia.

Embodiment 21: The system of any one of Embodiments 16-20, wherein associated factors of ischemia are weighted less heavily compared to contributors to ischemia and consequences of ischemia.

Embodiment 22: The system of any one of Embodiments 16-21, wherein contributors to ischemia comprise one or more vessel caliber parameters, plaque parameters, or fat parameters.

Embodiment 23: The system of Embodiment 22, wherein vessel caliber parameters comprise one or more of percentage diameter stenosis, absolute lumen volume, lumen volume indexed to percentage fractional myocardial mass, vessel volume, minimal luminal diameter (MLD), minimal luminal area (MLA), or ratio of MLD to MLA.

Embodiment 24: The system of Embodiment 22 or 23, wherein plaque parameters comprise one or more parameters related to one or more of non-calcified plaque, low density non-calcified plaque, calcified plaque, or location of plaque.

Embodiment 25: The system of Embodiment 24, wherein location of plaque comprises one or more of myocardial facing, pericardial facing, bifurcation lesions, or trifurcation lesions.

Embodiment 26: The system of any one of Embodiments 22-25, wherein fat parameters comprise one or more parameters related to peri-coronary adipose tissue or epicardial adipose tissue.

Embodiment 27: The system of any one of Embodiments 16-26, wherein consequences of ischemia comprise one or more left ventricular parameters, left atrial parameters, right ventricular parameters, right atrial parameters, aortic dimensions, or pulmonary vein parameters.

Embodiment 28: The system of Embodiment 27, wherein the left ventricular parameters and right ventricular parameters comprise one or more of perfusion or Hounsfield unit density, mass, or volume of the left ventricle or right ventricle.

Embodiment 29: The system of Embodiment 27 or 28, wherein the left atrial parameters and right atrial parameters comprise one or more of volume of the left atrium or right atrium.

Embodiment 30: The system of any one of Embodiments 16-29, wherein associated factors of ischemia comprise one or more of fatty liver or non-alcoholic steatohepatitis, emphysema, osteoporosis, mitral annular calcification, aortic valve calcification, aortic enlargement, or mitral valve calcification.

Certain Embodiments Relating to Generating a Coronary Artery Disease (CAD) Risk Score The following are non-limiting examples of certain embodiments of systems and methods of generating a coronary artery disease (CAD) risk score and/or other related features. Other embodiments may include one or more other features, or different features, that are discussed herein.

Embodiment 1: A computer-implemented method of assessing a risk of coronary artery disease (CAD) for a subject by generating one or more CAD risk scores for the subject based on multi-dimensional information derived from non-invasive medical image analysis, the method comprising: accessing, by a computer system, a medical image of a coronary region of a subject, wherein the medical image of the coronary region of the subject is obtained non-invasively; identifying, by the computer system, one or more segments of coronary arteries within the medical image of the coronary region of the subject; determining, by the computer system, for each of the identified one or more segments of coronary arteries one or more plaque parameters, vessel parameters, and clinical parameters, wherein the one or more plaque parameters comprise one or more of plaque volume, plaque composition, plaque attenuation, or plaque location, wherein the one or more vessel parameters comprise one or more of stenosis severity, lumen volume, percentage of coronary blood volume, or percentage of fractional myocardial mass, and wherein the one or more clinical parameters comprise one or more of percentile health condition for age or percentile health condition for gender; generating, by the computer system, for each of the identified one or more segments of coronary arteries a weighted measure of the determined one or more plaque parameters, vessel parameters, and clinical parameters, wherein the weighted measure is generated by applying a correction factor; combining, by the computer system, the generated weighted measure of the determined one or more plaque parameters, vessel parameters, and clinical parameters for each of the identified one or more segments of coronary arteries to generate one or more per-vessel, per-vascular territory, or per-subject CAD risk scores; and generating, by the computer system, a graphical plot of the generated one or more per-vessel, per-vascular territory, or per-subject CAD risk scores for visualizing and quantifying risk of CAD for the subject on one or more of a per-vessel, per-vascular, or per-subject basis, wherein the computer system comprises a computer processor and an electronic storage medium.

Embodiment 2: The method of Embodiment 1, further comprising normalizing, by the computer system, the generated one or more per-vessel, per-vascular territory, or per-subject CAD risk scores to account for one or more of the subject, scanner, or scan parameters used to obtain the medical image.

Embodiment 3: The method of Embodiment 1 or 2, further comprising assisting, by the computer system, assessment of risk of CAD for the subject by generating a scaled CAD risk score for the subject based at least in part on the generated one or more per-vessel, per-vascular territory, or per-subject CAD risk scores.

Embodiment 4: The method of any one of Embodiments 1-3, further comprising assisting, by the computer system, assessment of risk of CAD for the subject by determining a vascular age for the subject based at least in part on the generated one or more per-vessel, per-vascular territory, or per-subject CAD risk scores.

Embodiment 5: The method of any one of Embodiments 1-4, further comprising assisting, by the computer system, assessment of risk of CAD for the subject by categorizing risk of CAD for the subject as one or more of normal, mild, moderate, or severe based at least in part on the generated one or more per-vessel, per-vascular territory, or per-subject CAD risk scores.

Embodiment 6: The method of any one of Embodiments 1-5, further comprising assisting, by the computer system, assessment of risk of CAD for the subject by generating one or more colored heat maps for the subject based at least in part on the generated one or more per-vessel, per-vascular territory, or per-subject CAD risk scores.

Embodiment 7: The method of any one of Embodiments 1-6, further comprising assisting, by the computer system, assessment of risk of CAD for the subject by categorizing risk of CAD for the subject as one or more of high risk or low risk based at least in part on the generated one or more per-vessel, per-vascular territory, or per-subject CAD risk scores.

Embodiment 8: The method of any one of Embodiments 1-7, wherein the plaque volume is determined as one or more of absolute plaque volume or percent atheroma volume (PAV).

Embodiment 9: The method of any one of Embodiments 1-8, wherein the plaque composition is determined based at least in part on density of one or more regions of plaque within the medical image.

Embodiment 10: The method of any one of Embodiments 1-9, wherein the density of the one or more regions of plaque comprises absolute density.

Embodiment 11: The method of any one of Embodiments 1-10, wherein the density of the one or more regions of plaque comprises Hounsfield unit density.

Embodiment 12: The method of any one of Embodiments 1-11, wherein the plaque composition is categorized binarily as one or more of non-calcified plaque or calcified plaque.

Embodiment 13: The method of any one of Embodiments 1-12, wherein the plaque composition is categorized ordinally based on calcification levels of plaque.

Embodiment 14: The method of any one of Embodiments 1-13, wherein the plaque composition is categorized continuously based on calcification levels of plaque.

Embodiment 15: The method of any one of Embodiments 1-14, wherein the plaque attenuation is categorized binarily as high attenuation or low attenuation plaque based on density.

Embodiment 16: The method of any one of Embodiments 1-15, wherein the plaque attenuation is categorized continuously based on attenuation levels of plaque.

Embodiment 17: The method of any one of Embodiments 1-16, wherein the plaque location is categorized as one or more of proximal, mid, or distal along a coronary artery vessel.

Embodiment 18: The method of any one of Embodiments 1-17, wherein the plaque location is categorized based on a coronary artery vessel in which a region of plaque is located.

Embodiment 19: The method of any one of Embodiments 1-18, wherein the plaque location is categorized as one or more of myocardial facing or pericardial facing.

Embodiment 20: The method of any one of Embodiments 1-19, wherein the plaque location is categorized as one or more of at bifurcation, at trifurcation, not at bifurcation, or not at trifurcation.

Embodiment 21: The method of any one of Embodiments 1-20, wherein the plaque location is categorized as one or more of in a main vessel or in a branch vessel.

Embodiment 22: The method of any one of Embodiments 1-21, wherein stenosis severity is categorized based on one or more predetermined ranges of percentage stenosis generated based on one or more of diameter, area, or volume.

Embodiment 23: The method of any one of Embodiments 1-22, wherein lumen volume comprises one or more of absolute volume, volume relative to a vessel volume, or volume relative to a hypothetical volume.

Embodiment 24: The method of any one of Embodiments 1-23, wherein percentage of coronary blood volume comprises a volume of lumen as a function of an entire coronary vessel volume.

Embodiment 25: The method of any one of Embodiments 1-24, wherein percentage of fractional myocardial mass comprises one or more of a ratio of total vessel volume to left ventricular mass or a ratio of lumen volume to left ventricular mass.

Embodiment 26: A system for assessing a risk of coronary artery disease (CAD) for a subject by generating one or more CAD risk scores for the subject based on multi-dimensional information derived from non-invasive medical image analysis, the system comprising: one or more computer readable storage devices configured to store a plurality of computer executable instructions; and one or more hardware computer processors in communication with the one or more computer readable storage devices and configured to execute the plurality of computer executable instructions in order to cause the system to: access a medical image of a coronary region of a subject, wherein the medical image of the coronary region of the subject is obtained non-invasively; identify one or more segments of coronary arteries within the medical image of the coronary region of the subject; determine for each of the identified one or more segments of coronary arteries one or more plaque parameters, vessel parameters, and clinical parameters, wherein the one or more plaque parameters comprise one or more of plaque volume, plaque composition, plaque attenuation, or plaque location, wherein the one or more vessel parameters comprise one or more of stenosis severity, lumen volume, percentage of coronary blood volume, or percentage of fractional myocardial mass, and wherein the one or more clinical parameters comprise one or more of age, gender, or other clinical assessment parameters; generate for each of the identified one or more segments of coronary arteries a weighted measure of the determined one or more plaque parameters, vessel parameters, and clinical parameters, wherein the weighted measure is generated by applying a correction factor; combine the generated weighted measure of the determined one or more plaque parameters, vessel parameters, and clinical parameters for each of the identified one or more segments of coronary arteries to generate one or more per-vessel, per-vascular territory, or per-subject CAD risk scores; and generate a graphical plot of the generated one or more per-vessel, per-vascular territory, or per-subject CAD risk scores for visualizing and quantifying risk of CAD for the subject on one or more of a per-vessel, per-vascular, or per-subject basis.

Embodiment 27: The system of Embodiment 26, wherein the system is further caused to normalize the generated one or more per-vessel, per-vascular territory, or per-subject CAD risk scores to account for one or more of the subject, scanner, or scan parameters used to obtain the medical image.

Embodiment 28: The system of Embodiment 26 or 27, wherein the system is further caused to assist assessment of risk of CAD for the subject by generating a scaled CAD risk score for the subject based at least in part on the generated one or more per-vessel, per-vascular territory, or per-subject CAD risk scores.

Embodiment 29: The system of any one of Embodiments 26-28, wherein the system is further caused to assist assessment of risk of CAD for the subject by determining a vascular age for the subject based at least in part on the generated one or more per-vessel, per-vascular territory, or per-subject CAD risk scores.

Embodiment 30: The system of any one of Embodiments 26-29, wherein the system is further caused to assist assessment of risk of CAD for the subject by categorizing risk of CAD for the subject as one or more of normal, mild, moderate, or severe based at least in part on the generated one or more per-vessel, per-vascular territory, or per-subject CAD risk scores.

Certain Embodiments Relating to Treating to an Image

The following are non-limiting examples of certain embodiments of systems and methods of treating to an image and/or other related features. Other embodiments may include one or more other features, or different features, that are discussed herein.

Embodiment 1: A computer-implemented method of tracking efficacy of a medical treatment for a plaque-based disease based on non-invasive medical image analysis, the method comprising: accessing, by a computer system, a first set of plaque parameters and a first set of vascular parameters associated with a subject, wherein the first set of plaque parameters and the first set of vascular parameters are derived from a first medical image of the subject comprising one or more regions of plaque, wherein the first medical image of the subject is obtained non-invasively at a first point in time, wherein the first set of plaque parameters comprises one or more of density, location, or volume of one or more regions of plaque from the medical image of the subject at the first point in time, and wherein the first set of vascular parameters comprises vascular remodeling of a vasculature at the first point in time; accessing, by the computer system, a second medical image of the subject, wherein the second medical image of the subject is obtained non-invasively at a second point in time after the subject is treated with a medical treatment, the second point in time being later than the first point in time, wherein the second medical image of the subject comprises the one or more regions of plaque; identifying, by the computer system, the one or more regions of plaque from the second medical image; determining, by the computer system, a second set of plaque parameters and a second of vascular parameters associated with the subject by analyzing the one or more regions of plaque from the second medical image, wherein the second set of plaque parameters comprises one or more of density, location, or volume of the one or more regions of plaque from the medical image of the subject at the second point in time, and wherein the second set of vascular parameters comprises vascular remodeling of the vasculature at the second point in time; analyzing, by the computer system, one or more changes between the first set of plaque parameters and the second set of plaque parameters; analyzing, by the computer system, one or more changes between the first set of vascular parameters and the second set of vascular parameters; tracking, by the computer system, progression of the plaque-based disease based on one or more of the analyzed one or more changes between the first set of plaque parameters and the second set of plaque parameters or the analyzed one or more changes between the first set of vascular parameters and the second set of vascular parameters; and determining, by the computer system, efficacy of the medical treatment based on the tracked progression of the plaque-based disease, wherein the computer system comprises a computer processor and an electronic storage medium.

Embodiment 2: The method of Embodiment 1, wherein progression of the plaque-based disease is tracked on one or more of a per-subject, per-vessel, per-segment, or per-lesion basis.

Embodiment 3: The method of Embodiment 1 or 2, wherein progression of the plaque-based disease is tracked as one or more of progression, regression, mixed response—progression of calcified plaque, mixed response—progression of non-calcified plaque.

Embodiment 4: The method of any one of Embodiments 1-3, further comprising generating, by the computer system, a further proposed medical treatment based at least in part on the efficacy of the medical treatment determined based on the tracked progression of the plaque-based disease.

Embodiment 5: The method of any one of Embodiments 1-4, wherein the further proposed medical treatment is different from the medical treatment when efficacy of the medical treatment determined based on tracked progression of the plaque-based disease is neutral or negative.

Embodiment 6: The method of any one of Embodiments 1-5, wherein the medical treatment comprises one or more of medication treatment, lifestyle treatment, or revascularization treatment.

Embodiment 7: The method of Embodiment 6, wherein medication treatment comprises one or more of statins, human immunodeficiency virus (HIV) medications, icosapent ethyl, bempedoic acid, rivaroxaban, aspirin, proprotein convertase subtilisin/kexin type 9 (PCSK-9) inhibitors, inclisiran, sodium-glucose cotransporter-2 (SGLT-2) inhibitors, glucagon-like peptide-1 (GLP-1) receptor agonists, or low-density lipoprotein (LDL) apheresis.

Embodiment 8: The method of Embodiment 6 or 7, wherein lifestyle treatment comprises one or more of increased exercise, aerobic exercise, anaerobic exercise, cessation of smoking, or change in diet.

Embodiment 9: The method of any one of Embodiments 6-8, wherein revascularization treatment comprises one or more of bypass grafting, stenting, or use of a bioabsorbable scaffold.

Embodiment 10: The method of any one of Embodiments 1-9, wherein one or more of the first set of plaque parameters, second set of plaque parameters, first set of vascular parameters, or second set of vascular parameters is normalized to account for one or more of scanner type, image acquisition parameters, energy, gating, contrast, age of subject, subject body habitus, surrounding cardiac structure, or plaque type.

Embodiment 11: The method of any one of Embodiments 1-10, wherein an increase in density of the one or more regions of plaque is indicative of a positive efficacy of the medical treatment.

Embodiment 12: The method of any one of Embodiments 1-11, wherein the density of the one or more regions of plaque comprises a Hounsfield unit density.

Embodiment 13: The method of any one of Embodiments 1-12, wherein the density of the one or more regions of plaque comprises absolute density.

Embodiment 14: The method of any one of Embodiments 1-13, wherein the location of the one or more regions of plaque comprises one or more of myocardial facing, pericardial facing, bifurcation, trifurcation, proximal, mid, distal, main vessel, or branch vessel.

Embodiment 15: The method of Embodiment 14, wherein a change in location of a region of plaque from pericardial facing to myocardial facing is indicative of a positive efficacy of the medical treatment.

Embodiment 16: The method of any one of Embodiments 1-15, wherein the volume of the one or more regions of plaque comprises one or more of absolute plaque volume or percent atheroma volume (PAV).

Embodiment 17: The method of any one of Embodiments 1-16, wherein an increase in volume of the one or more regions of plaque between the first point in time and the second point in time is indicative of a negative efficacy of the medical treatment.

Embodiment 18: The method of any one of Embodiments 1-17, wherein vascular remodeling of the vasculature comprises vascular remodeling of one or more coronary atherosclerotic lesions.

Embodiment 19: The method of any one of Embodiments 1-18, wherein vascular remodeling of the vasculature comprises one or more of directionality changes in remodeling, the directionality changes in remodeling comprising one or more of outward, intermediate, or inward.

Embodiment 20: The method of Embodiment 19, wherein more outward remodeling between the first point in time and the second point in time is indicative of a negative efficacy of the medical treatment.

Embodiment 21: A system for tracking efficacy of a medical treatment for a plaque-based disease based on non-invasive medical image analysis, the system comprising: one or more computer readable storage devices configured to store a plurality of computer executable instructions; and one or more hardware computer processors in communication with the one or more computer readable storage devices and configured to execute the plurality of computer executable instructions in order to cause the system to: access a first set of plaque parameters and a first set of vascular parameters associated with a subject, wherein the first set of plaque parameters and the first set of vascular parameters are derived from a first medical image of the subject comprising one or more regions of plaque, wherein the first medical image of the subject is obtained non-invasively at a first point in time, wherein the first set of plaque parameters comprises one or more of density, location, or volume of one or more regions of plaque from the medical image of the subject at the first point in time, and wherein the first set of vascular parameters comprises vascular remodeling of a vasculature at the first point in time; access a second medical image of the subject, wherein the second medical image of the subject is obtained non-invasively at a second point in time after the subject is treated with a medical treatment, the second point in time being later than the first point in time, wherein the second medical image of the subject comprises the one or more regions of plaque; identify the one or more regions of plaque from the second medical image; determine a second set of plaque parameters and a second of vascular parameters associated with the subject by analyzing the one or more regions of plaque from the second medical image, wherein the second set of plaque parameters comprises one or more of density, location, or volume of the one or more regions of plaque from the medical image of the subject at the second point in time, and wherein the second set of vascular parameters comprises vascular remodeling of the vasculature at the second point in time; analyze one or more changes between the first set of plaque parameters and the second set of plaque parameters; analyze one or more changes between the first set of vascular parameters and the second set of vascular parameters; track progression of the plaque-based disease based on one or more of the analyzed one or more changes between the first set of plaque parameters and the second set of plaque parameters or the analyzed one or more changes between the first set of vascular parameters and the second set of vascular parameters; and determine efficacy of the medical treatment based on the tracked progression of the plaque-based disease.

Embodiment 22: The system of Embodiment 21, wherein progression of the plaque-based disease is tracked on one or more of a per-subject, per-vessel, per-segment, or per-lesion basis.

Embodiment 23: The system of Embodiment 21 or 22, wherein the system is further caused to generate a further proposed medical treatment based at least in part on the efficacy of the medical treatment determined based on the tracked progression of the plaque-based disease.

Embodiment 24: The system of Embodiment 23, wherein the further generated medical treatment comprises one or more of medication treatment, lifestyle treatment, or revascularization treatment.

Embodiment 25: The system of Embodiment 24, wherein medication treatment comprises one or more of statins, human immunodeficiency virus (HIV) medications, icosapent ethyl, bempedoic acid, rivaroxaban, aspirin, proprotein convertase subtilisin/kexin type 9 (PCSK-9) inhibitors, inclisiran, sodium-glucose cotransporter-2 (SGLT-2) inhibitors, glucagon-like peptide-1 (GLP-1) receptor agonists, or low-density lipoprotein (LDL) apheresis, wherein lifestyle treatment comprises one or more of increased exercise, aerobic exercise, anaerobic exercise, cessation of smoking, or change in diet, and wherein revascularization treatment comprises one or more of bypass grafting, stenting, or use of a bioabsorbable scaffold.

Embodiment 26: The system of any one of Embodiments 21-25, wherein one or more of the first set of plaque parameters, second set of plaque parameters, first set of vascular parameters, or second set of vascular parameters is normalized to account for one or more of scanner type, image acquisition parameters, energy, gating, contrast, age of subject, subject body habitus, surrounding cardiac structure, or plaque type.

Embodiment 27: The system of any one of Embodiments 21-26, wherein an increase in density of the one or more regions of plaque is indicative of a positive efficacy of the medical treatment.

Embodiment 28: The system of any one of Embodiments 21-27, wherein the location of the one or more regions of plaque comprises one or more of myocardial facing, pericardial facing, bifurcation, trifurcation, proximal, mid, distal, main vessel, or branch vessel, and wherein a change in location of a region of plaque from pericardial facing to myocardial facing is indicative of a positive efficacy of the medical treatment.

Embodiment 29: The system of any one of Embodiments 21-28, wherein an increase in volume of the one or more regions of plaque between the first point in time and the second point in time is indicative of a negative efficacy of the medical treatment.

Embodiment 30: The system of any one of Embodiments 21-29, wherein vascular remodeling of the vasculature comprises one or more of directionality changes in remodeling, the directionality changes in remodeling comprising one or more of outward, intermediate, or inward, wherein more outward remodeling between the first point in time and the second point in time is indicative of a negative efficacy of the medical treatment.

Certain Embodiments Relating to Determining a Treatment for ASCVD

The following are non-limiting examples of certain embodiments of systems and methods of determining a treatment for ASCVD and/or other related features. Other embodiments may include one or more other features, or different features, that are discussed herein.

Embodiment 1: A computer-implemented method of determining continued personalized treatment for a subject with atherosclerotic cardiovascular disease (ASCVD) risk based on coronary CT angiography (CCTA) analysis using one or more quantitative imaging algorithms, the method comprising: assessing, by a computer system, a baseline ASCVD risk of the subject by analyzing baseline CCTA analysis results using one or more quantitative imaging algorithms, the baseline CCTA analysis results based at least in part on one or more atherosclerosis parameters or perilesional tissue parameters, the one or more atherosclerosis parameters comprising one or more of presence, locality, extent, severity, or type of atherosclerosis; categorizing, by the computer system, the baseline ASCVD risk of the subject into one or more predetermined categories of ASCVD risk; determining, by the computer system, an initial personalized proposed treatment for the subject based at least in part on the categorized baseline ASCVD risk of the subject, the initial personalized proposed treatment for the subject comprising one or more of medical therapy, lifestyle therapy, or interventional therapy; assessing, by the computer system, subject response to the determined initial personalized proposed treatment by subsequent CCTA analysis using one or more quantitative imaging algorithms and comparing the subsequent CCTA analysis results to the baseline CCTA analysis results, the subsequent CCTA analysis performed after applying the determined initial personalized proposed treatment to the subject, wherein the subject response is assessed based on one or more of progression, stabilization, or regression of ASCVD; and determining, by the computer system, a continued personalized proposed treatment for the subject based at least in part on the assessed subject response, the continued personalized proposed treatment comprising a higher tiered approach than the initial personalized proposed treatment when the assessed subject response comprises progression of ASCVD, the continued personalized proposed treatment comprising one or more of medical therapy, lifestyle therapy, or interventional therapy, wherein the computer system comprises a computer processor and an electronic storage medium.

Embodiment 2: The method of Embodiment 1, wherein the baseline CCTA analysis results are analyzed by applying the one or more quantitative imaging algorithms to one or more of coronary, carotid, lower extremity, upper extremity, aorta, or renal vascular beds.

Embodiment 3: The method of Embodiment 1 or 2, wherein the one or more atherosclerosis parameters comprises one or more plaque parameters or vascular parameters.

Embodiment 4: The method of any one of Embodiments 1-3, wherein the one or more predetermined categories of ASCVD risk comprises one or more of Stage 0, Stage I, Stage II, or Stage III.

Embodiment 5: The method of any one of Embodiments 1-4, wherein the one or more predetermined categories of ASCVD risk comprises one or more of none, minimal, mild, or moderate.

Embodiment 6: The method of any one of Embodiments 1-5, wherein the one or more predetermined categories of ASCVD risk comprises one or more of primarily calcified or primarily non-calcified plaque.

Embodiment 7: The method of any one of Embodiments 1-6, wherein the one or more predetermined categories of ASCVD risk is based at least in part on units of low density non-calcified plaque.

Embodiment 8: The method of any one of Embodiments 1-7, wherein the one or more predetermined categories of ASCVD risk is based at least in part on units of low density non-calcified plaque.

Embodiment 9: The method of any one of Embodiments 1-8, wherein the one or more predetermined categories of ASCVD risk is based at least in part on a continuous quantified scale.

Embodiment 10: The method of any one of Embodiments 1-9, wherein the one or more predetermined categories of ASCVD risk is based at least in part on levels of risk of future ASCVD events, the future ASCVD events comprising one or more of heart attack, stroke, amputation, or dissection.

Embodiment 11: The method of any one of Embodiments 1-10, wherein the ASCVD risk of the subject is categorized into one or more predetermined categories of ASCVD risk further based at least in part on one or more non-ASCVD measures, the one or more non-ASCVD measures quantified using one or more CCTA algorithms.

Embodiment 12: The method of Embodiment 11, wherein the one or more non-ASCVD measures comprise one or more cardiovascular measurements or non-cardiovascular measurements that may contribute to ASCVD, the one or more cardiovascular measurements comprising one or more of left ventricular hypertrophy for hypertension or atrial volumes for atrial fibrillation, and the one or more non-cardiovascular measurements comprising emphysema.

Embodiment 13: The method of any one of Embodiments 1-12, wherein the personalized proposed treatment for the subject is determined without analysis of cholesterol or hemoglobin A1C of the subject.

Embodiment 14: The method of any one of Embodiments 1-13, wherein progression of ASCVD comprises one or more of rapid or non-rapid progression.

Embodiment 15: The method of any one of Embodiments 1-14, wherein stabilization of ASCVD comprises one or more of transformation of ASCVD from non-calcified to calcified, reduction of low attenuation plaque, or reduction of positive arterial remodeling.

Embodiment 16: The method of any one of Embodiments 1-15, wherein regression of ASCVD comprises one or more of decrease in ASCVD volume or burden, decrease in non-calcified plaque, or decrease in low attenuation plaque.

Embodiment 17: The method of any one of Embodiments 1-16, wherein the continued personalized proposed treatment for the subject is further determined based at least in part on one or more of low-density lipoprotein (LDL) cholesterol or triglyceride (TG) levels of the subject.

Embodiment 18: The method of any one of Embodiments 1-17, wherein the one or more medical therapies comprise one or more anti-inflammatory medications, anti-thrombotic medications, or diabetic medications.

Embodiment 19: The method of Embodiment 18, wherein the one or more anti-inflammatory medications comprise colchicine, the one or more anti-thrombotic medications comprise one or more of rivaroxaban or aspirin, or the one or more diabetic medications comprise one or more of sodium-glucose cotransporter-2 (SGLT2) inhibitors or glucagon-like peptide-1 receptor (GLP1R) agonists.

Embodiment 20: The method of any one of Embodiments 1-19, wherein the continued personalized proposed treatment comprises a same or lower tiered approach than the initial personalized proposed treatment when the assessed subject response comprises stabilization or regression of ASCVD.

Embodiment 21: A system for determining continued personalized treatment for a subject with atherosclerotic cardiovascular disease (ASCVD) risk based on coronary CT angiography (CCTA) analysis using one or more quantitative imaging algorithms, the system comprising: one or more computer readable storage devices configured to store a plurality of computer executable instructions; and one or more hardware computer processors in communication with the one or more computer readable storage devices and configured to execute the plurality of computer executable instructions in order to cause the system to: assess a baseline ASCVD risk of the subject by analyzing baseline CCTA analysis results using one or more quantitative imaging algorithms, the baseline CCTA analysis results based at least in part on one or more atherosclerosis parameters or perilesional tissue parameters, the one or more atherosclerosis parameters comprising one or more of presence, locality, extent, severity, or type of atherosclerosis; categorize the baseline ASCVD risk of the subject into one or more predetermined categories of ASCVD risk; determine an initial personalized proposed treatment for the subject based at least in part on the categorized baseline ASCVD risk of the subject, the initial personalized proposed treatment for the subject comprising one or more of medical therapy, lifestyle therapy, or interventional therapy; assess subject response to the determined initial personalized proposed treatment by subsequent CCTA analysis using one or more quantitative imaging algorithms and comparing the subsequent CCTA analysis results to the baseline CCTA analysis results, the subsequent CCTA analysis performed after applying the determined initial personalized proposed treatment to the subject, wherein the subject response is assessed based on one or more of progression, stabilization, or regression of ASCVD; and determine a continued personalized proposed treatment for the subject based at least in part on the assessed subject response, the continued personalized proposed treatment comprising a higher tiered approach than the initial personalized proposed treatment when the assessed subject response comprises progression of ASCVD, the continued personalized proposed treatment comprising one or more of medical therapy, lifestyle therapy, or interventional therapy.

Embodiment 22: The system of Embodiment 21, wherein the continued personalized proposed treatment comprises a same or lower tiered approach than the initial personalized proposed treatment when the assessed subject response comprises stabilization or regression of ASCVD.

Embodiment 23: The system of Embodiment 21 or 22, wherein the results of the CCTA are analyzed by applying the one or more quantitative imaging algorithms to one or more of coronary, carotid, lower extremity, upper extremity, aorta, or renal vascular beds.

Embodiment 24: The system of any one of Embodiments 21-23, wherein the one or more atherosclerosis parameters comprises one or more plaque parameters or vascular parameters.

Embodiment 25: The system of any one of Embodiments 21-24, wherein the ASCVD risk of the subject is categorized into one or more predetermined categories of ASCVD risk further based at least in part on one or more non-ASCVD measures, the one or more non-ASCVD measures quantified using one or more CCTA algorithms.

Embodiment 26: The system of Embodiment 25, wherein the one or more non-ASCVD measures comprise one or more cardiovascular measurements or non-cardiovascular measurements that may contribute to ASCVD, the one or more cardiovascular measurements comprising one or more of left ventricular hypertrophy for hypertension or atrial volumes for atrial fibrillation, and the one or more non-cardiovascular measurements comprising emphysema.

Embodiment 27: The system of any one of Embodiments 21-26, wherein the personalized proposed treatment for the subject is determined without analysis of cholesterol or hemoglobin A1C of the subject.

Embodiment 28: The system of any one of Embodiments 21-27, wherein the continued personalized proposed treatment for the subject is further determined based at least in part on one or more of low-density lipoprotein (LDL) cholesterol or triglyceride (TG) levels of the subject.

Embodiment 29: The system of Embodiment 28, wherein the one or more anti-inflammatory medications comprise colchicine, the one or more anti-thrombotic medications comprise one or more of rivaroxaban or aspirin, or the one or more diabetic medications comprise one or more of sodium-glucose cotransporter-2 (SGLT2) inhibitors or glucagon-like peptide-1 receptor (GLP1R) agonists.

Embodiment 30: The system of any one of Embodiments 21-29, wherein the one or more predetermined categories of ASCVD risk is based at least in part on levels of risk of future ASCVD events, the future ASCVD events comprising one or more of heart attack, stroke, amputation, or dissection.

Certain Embodiments Relating to Determination of Stenosis Severity and/or Vascular Remodeling in the Presence of Atherosclerosis The following are non-limiting examples of certain embodiments of systems and methods of determining stenosis severity and/or vascular remodeling in the presence of atherosclerosis and/or other related features. Other embodiments may include one or more other features, or different features, that are discussed herein.

Embodiment 1: A computer-implemented method of determining volumetric stenosis severity and volumetric vascular remodeling in the presence of atherosclerosis based on non-invasive medical image analysis for risk assessment of coronary artery disease (CAD) for a subject, the method comprising: accessing, by a computer system, a medical image of a coronary region of a subject, wherein the medical image of the coronary region of the subject is obtained non-invasively; identifying, by the computer system, one or more segments of coronary arteries and one or more regions of plaque within the medical image of the coronary region of the subject; determining, by the computer system, for the identified one or more segments of coronary arteries a lumen wall boundary in the presence of the one or more regions of plaque and a hypothetical normal artery boundary in case the one or more regions of plaque were not present, wherein the determined lumen wall boundary and the hypothetical normal artery boundary comprise tapering of the one or more segments of coronary arteries, and wherein the determined lumen wall boundary further comprises a boundary of the one or more regions of plaque; quantifying, by the computer system, for the identified one or more segments of coronary arteries a lumen volume based on the determined lumen wall boundary, wherein the quantified lumen volume takes into account the tapering of the one or more segments of coronary arteries and the boundary of the one or more regions of plaque; quantifying, by the computer system, for the identified one or more segments of coronary arteries a hypothetical normal vessel volume based on the determined hypothetical normal artery boundary, wherein the quantified hypothetical normal vessel volume takes into account the tapering of the one or more segments of coronary arteries; determining, by the computer system, for the identified one or more segments of coronary arteries volumetric stenosis by determining a percentage or ratio of the quantified lumen volume compared to the hypothetical normal vessel volume; quantifying, by the computer system, a volume of the one or more regions of plaque outside of the determined hypothetical normal artery boundary; determining, by the computer system, for the identified one or more segments of coronary arteries a volumetric three-dimensional vascular remodeling index by dividing a sum of the quantified volume of the one or more regions of plaque outside of the determined hypothetical normal artery boundary and the quantified hypothetical normal vessel volume by the quantified hypothetical normal vessel volume; and determining, by the computer system, a risk of CAD for the subject based at least in part on the determined volumetric stenosis and the volumetric three-dimensional vascular remodeling index for the identified one or more segments of coronary arteries, wherein the computer system comprises a computer processor and an electronic storage medium.

Embodiment 2: The method of Embodiment 1, further comprising quantifying for the one or more segments of coronary arteries a hypothetical blood volume based at least in part on the hypothetical normal artery boundary and determining for the one or more segments a fractional blood volume by determining a percentage or ratio of actual blood volume to the quantified hypothetical blood volume.

Embodiment 3: The method of Embodiment 1 or 2, further comprising determining, by the computer system, ischemia based at least in part on the determined volumetric stenosis.

Embodiment 4: The method of any one of Embodiments 1-3, further comprising determining ischemia by: quantifying, by the computer system, a proximal cross-sectional area of a proximal section and a distal cross-sectional area of a distal section along the one or more segments of coronary arteries, wherein the proximal section does not comprise the one or more regions of plaque, and wherein the distal section comprises at least one of the one or more regions of plaque; accessing, by the computer system, an assumed velocity of blood flow at the proximal section; quantifying, by the computer system, a velocity of blood flow at the distal section based at least in part on the assumed velocity of blood flow at the proximal section, the quantified proximal cross-sectional area of the proximal section, and the distal cross-sectional area of the distal section along the one or more segments of coronary arteries; determining, by the computer system, a change in pressure between the proximal section and the distal section based at least in part on the assumed velocity of blood flow at the proximal section and the quantified velocity of blood flow at the distal section; and determining, by the computer system, ischemia along the one or more segments of coronary arteries based at least in part on the determined change in pressure between the proximal section and the distal section.

Embodiment 5: The method of Embodiment 4, wherein the assumed velocity of blood flow comprises one or more of an assumed velocity of blood flow at rest, an assumed velocity of blood flow during mild exertion, an assumed velocity of blood flow during moderate exertion, or an assumed velocity of blood flow during extreme exertion.

Embodiment 6: The method of Embodiment 5, wherein the assumed velocity of blood flow at rest comprises about 250 ml/min, the assumed velocity of blood flow during mild exertion comprises about 250-500 ml/min, the assumed velocity of blood flow during moderate exertion comprises about 500-750 ml/min, and the assumed velocity of blood flow during extreme exertion comprises about 1200 ml/min.

Embodiment 7: The method of any one of Embodiments 1-6, further comprising determining ischemia by: quantifying, by the computer system, a proximal volume of a proximal section and a distal volume of a distal section along the one or more segments of coronary arteries, wherein the proximal section does not comprise the one or more regions of plaque, and wherein the distal section comprises at least one of the one or more regions of plaque; accessing, by the computer system, an assumed velocity of blood flow at the proximal section; quantifying, by the computer system, a velocity of blood flow at the distal section based at least in part on the assumed velocity of blood flow at the proximal section, the quantified proximal volume of the proximal section, and the distal volume of the distal section along the one or more segments of coronary arteries; determining, by the computer system, a velocity time integral of blood flow at the distal section based at least in part on the quantified velocity of blood flow at the distal section; and determining, by the computer system, ischemia along the one or more segments of coronary arteries based at least in part on the determined velocity time integral of blood flow at the distal section.

Embodiment 8: The method of Embodiment 7, wherein the assumed velocity of blood flow comprises one or more of an assumed velocity of blood flow at rest, during mild exertion, during moderate exertion, or during extreme exertion.

Embodiment 9: The method of Embodiment 8, wherein the assumed velocity of blood flow at rest comprises about 250 ml/min, the assumed velocity of blood flow during mild exertion comprises about 250-500 ml/min, the assumed velocity of blood flow during moderate exertion comprises about 500-750 ml/min, and the assumed velocity of blood flow during extreme exertion comprises about 1200 ml/min.

Embodiment 10: A computer-implemented method of determining volumetric stenosis severity in the presence of atherosclerosis based on non-invasive medical image analysis for risk assessment of coronary artery disease (CAD) for a subject, the method comprising: accessing, by a computer system, a medical image of a coronary region of a subject, wherein the medical image of the coronary region of the subject is obtained non-invasively; identifying, by the computer system, one or more segments of coronary arteries and one or more regions of plaque within the medical image of the coronary region of the subject; determining, by the computer system, for the identified one or more segments of coronary arteries a lumen wall boundary in the presence of the one or more regions of plaque and a hypothetical normal artery boundary in case the one or more regions of plaque were not present, wherein the determined lumen wall boundary and the hypothetical normal artery boundary comprise tapering of the one or more segments of coronary arteries, and wherein the determined lumen wall boundary further comprises a boundary of the one or more regions of plaque; quantifying, by the computer system, for the identified one or more segments of coronary arteries a lumen volume based on the determined lumen wall boundary, wherein the quantified lumen volume takes into account the tapering of the one or more segments of coronary arteries and the boundary of the one or more regions of plaque; quantifying, by the computer system, for the identified one or more segments of coronary arteries a hypothetical normal vessel volume based on the determined hypothetical normal artery boundary, wherein the quantified hypothetical normal vessel volume takes into account the tapering of the one or more segments of coronary arteries; determining, by the computer system, for the identified one or more segments of coronary arteries volumetric stenosis by determining a percentage or ratio of the quantified lumen volume compared to the hypothetical normal vessel volume; and determining, by the computer system, a risk of CAD for the subject based at least in part on the determined volumetric stenosis for the identified one or more segments of coronary arteries, wherein the computer system comprises a computer processor and an electronic storage medium.

Embodiment 11: The method of Embodiment 10, further comprising determining, by the computer system, ischemia based at least in part on the determined volumetric stenosis.

Embodiment 12: A computer-implemented method of quantifying ischemia for a subject based on non-invasive medical image analysis, the method comprising: accessing, by a computer system, a medical image of a coronary region of a subject, wherein the medical image of the coronary region of the subject is obtained non-invasively; identifying, by the computer system, one or more segments of coronary arteries and one or more regions of plaque within the medical image of the coronary region of the subject; quantifying, by the computer system, a proximal cross-sectional area of a proximal section and a distal cross-sectional area of a distal section along the one or more segments of coronary arteries, wherein the proximal section does not comprise the one or more regions of plaque, and wherein the distal section comprises at least one of the one or more regions of plaque; accessing, by the computer system, an assumed velocity of blood flow at the proximal section; quantifying, by the computer system, a velocity of blood flow at the distal section based at least in part on the assumed velocity of blood flow at the proximal section, the quantified proximal cross-sectional area of the proximal section, and the distal cross-sectional area of the distal section along the one or more segments of coronary arteries; determining, by the computer system, a change in pressure between the proximal section and the distal section based at least in part on the assumed velocity of blood flow at the proximal section and the quantified velocity of blood flow at the distal section; and quantifying, by the computer system, ischemia along the one or more segments of coronary arteries based at least in part on the determined change in pressure between the proximal section and the distal section.

Embodiment 13: The method of Embodiment 12, wherein the assumed velocity of blood flow comprises one or more of an assumed velocity of blood flow at rest, during mild exertion, during moderate exertion, or during extreme exertion.

Embodiment 14: The method of Embodiment 13, wherein the assumed velocity of blood flow at rest comprises about 250 ml/min, the assumed velocity of blood flow during mild exertion comprises about 250-500 ml/min, the assumed velocity of blood flow during moderate exertion comprises about 500-750 ml/min, and the assumed velocity of blood flow during extreme exertion comprises about 1200 ml/min.

Embodiment 15: The method of any one of Embodiments 12-14, wherein the proximal cross-sectional area of the proximal section and the distal cross-sectional area of the distal section comprise time-averaged measurements.

Embodiment 16: A computer-implemented method of quantifying ischemia for a subject based on non-invasive medical image analysis, the method comprising: accessing, by a computer system, a medical image of a coronary region of a subject, wherein the medical image of the coronary region of the subject is obtained non-invasively; identifying, by the computer system, one or more segments of coronary arteries and one or more regions of plaque within the medical image of the coronary region of the subject; quantifying, by the computer system, a proximal volume of a proximal section and a distal volume of a distal section along the one or more segments of coronary arteries, wherein the proximal section does not comprise the one or more regions of plaque, and wherein the distal section comprises at least one of the one or more regions of plaque; accessing, by the computer system, an assumed velocity of blood flow at the proximal section; quantifying, by the computer system, a velocity of blood flow at the distal section based at least in part on the assumed velocity of blood flow at the proximal section, the quantified proximal volume of the proximal section, and the distal volume of the distal section along the one or more segments of coronary arteries; determining, by the computer system, a velocity time integral of blood flow at the distal section based at least in part on the quantified velocity of blood flow at the distal section; and quantifying, by the computer system, ischemia along the one or more segments of coronary arteries based at least in part on the determined velocity time integral of blood flow at the distal section.

Embodiment 17: The method of Embodiment 16, wherein the assumed velocity of blood flow comprises one or more of an assumed velocity of blood flow at rest, during mild exertion, during moderate exertion, or during extreme exertion.

Embodiment 18: The method of Embodiment 17, wherein the assumed velocity of blood flow at rest comprises about 250 ml/min, the assumed velocity of blood flow during mild exertion comprises about 250-500 ml/min, the assumed velocity of blood flow during moderate exertion comprises about 500-750 ml/min, and the assumed velocity of blood flow during extreme exertion comprises about 1200 ml/min.

Embodiment 19: The method of any one of Embodiments 16-18, wherein the proximal volume of the proximal section and the distal volume of the distal section comprise time-averaged measurements.

Embodiment 20: The method of any one of Embodiments 16-19, wherein the velocity time integral of blood flow at the distal section is further determined based at least in part on a measured heart rate of the subject.

Other Embodiment(s)

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or embodiments.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended embodiments. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. A computer-implemented method of tracking efficacy of a treatment for a plaque-based disease based on non-invasive medical image analysis, the method comprising:
    accessing, by a computer system, a first set of plaque parameters and a first set of vascular parameters associated with a subject, wherein the first set of plaque parameters and the first set of vascular parameters are derived from a first set of medical images of the subject comprising at least one axial image comprising one or more regions of plaque, wherein the first set of medical images of the subject is obtained non-invasively at a first point in time, wherein the first set of plaque parameters comprises density and volume of one or more regions of plaque derived from the first set of medical images of the subject obtained at the first point in time, and wherein the first set of vascular parameters comprises one or more of vascular volume, diameter, area, length, location, or remodeling derived from the first set of medical images of the subject obtained at the first point in time;
    generating, by the computer system, a first characterized region of plaque, wherein generating the first characterized region of plaque comprises characterizing the one or more regions of plaque derived from the first set of medical images of the subject obtained at the first point in time as calcified plaque, non-calcified plaque, or low density non-calcified plaque based on the first set of plaque parameters;
    accessing, by the computer system, a second set of medical images of the subject, wherein the second set of medical images of the subject is obtained non-invasively at a second point in time after the subject is treated with a treatment, the second point in time being later than the first point in time, wherein the second set of medical images of the subject comprises at least one axial image comprising the one or more regions of plaque;
    identifying, by the computer system, the one or more regions of plaque from the second set of medical images;
    determining, by the computer system, a second set of plaque parameters and a second set of vascular parameters associated with the subject by analyzing the one or more regions of plaque identified from the second set of medical images, the second set of plaque parameters determined based at least in part on graphical identification of vessel wall and lumen wall from the second set of medical images, wherein the second set of plaque parameters comprises density and volume of the one or more regions of plaque derived from the second set of medical images of the subject obtained at the second point in time, and wherein the second set of vascular parameters comprises one or more of vascular volume, diameter, area, length, location, or remodeling derived from the second set of medical images of the subject obtained at the second point in time;
    generating, by the computer system, a second characterized region of plaque, wherein generating the second characterized region of plaque comprises characterizing the one or more regions of plaque derived from the second set of medical images of the subject obtained at the second point in time as calcified plaque, non-calcified plaque, or low density non-calcified plaque based on the second set of plaque parameters;
    analyzing, by the computer system, one or more changes between the first characterized region of plaque and the second characterized region of plaque;
    analyzing, by the computer system, one or more changes between the first set of vascular parameters and the second set of vascular parameters; and
    generating, by the computer system, a graphical representation of tracking progression of the plaque-based disease based at least in part on the analyzed one or more changes between the first characterized region of plaque and the second characterized region of plaque and the analyzed one or more changes between the first set of vascular parameters and the second set of vascular parameters, wherein the generated graphical representation of tracking progression of the plaque-based disease is configured to be used to determine efficacy of the treatment, wherein the determined efficacy of the treatment is configured to be used to determine whether to change the treatment for the subject;
    wherein the computer system comprises a computer processor and an electronic storage medium.

2. The computer-implemented method of claim 1, wherein the graphical representation of tracking progression of the plaque-based disease is generated on one or more of a per-subject, per-vessel, per-segment, or per-lesion basis.

3. The computer-implemented method of claim 1, wherein the generated graphical representation of tracking progression of the plaque-based disease comprises a representation of one or more of progression, regression, mixed response—progression of calcified plaque, or mixed response—progression of non-calcified plaque.

4. The computer-implemented method of claim 1, further comprising determining the efficacy of the treatment based at least in part on the progression of the plaque-based disease.

5. The computer-implemented method of claim 4, further comprising generating a further proposed treatment based at least in part on the determined efficacy of the treatment determined based on the tracked progression of the plaque-based disease.

6. The computer-implemented method of claim 1, wherein the treatment comprises one or more of a medication treatment, lifestyle treatment, or revascularization treatment.

7. The computer-implemented method of claim 6, wherein the medication treatment comprises one or more of statins, icosapent ethyl, bempedoic acid, rivaroxaban, aspirin, proprotein convertase subtilisin/kexin type 9 (PCSK-9) inhibitors, inclisiran, sodium-glucose cotransporter-2 (SGLT-2) inhibitors, glucagon-like peptide-1 (GLP-1) receptor agonists, low-density lipoprotein (LDL) apheresis, or Lp(a) lowering medication.

8. The computer-implemented method of claim 6, wherein the lifestyle treatment comprises one or more of increased exercise, aerobic exercise, anaerobic exercise, cessation of smoking, or change in diet.

9. The computer-implemented method of claim 6, wherein the revascularization treatment comprises one or more of bypass grafting, stenting, or use of a bioabsorbable scaffold.

10. The computer-implemented method of claim 1, wherein one or more of the first set of plaque parameters, second set of plaque parameters, first set of vascular parameters, or second set of vascular parameters is normalized to account for one or more of scanner type, image acquisition parameters, energy, gating, contrast, age of subject, subject body habitus, surrounding cardiac structure, or plaque type.

11. The computer-implemented method of claim 1, wherein an increase in density of the one or more regions of plaque is indicative of a positive efficacy of the medical treatment.

12. The computer-implemented method of claim 11, wherein the density of the one or more regions of plaque comprises radiodensity.

13. The computer-implemented method of claim 11, wherein the density of the one or more regions of plaque comprises absolute density.

14. The computer-implemented method of claim 1, wherein the first set of plaque parameters and the second set of plaque parameters further comprise a location of the one or more regions of plaque, the location of the one or more regions of plaque comprising one or more of myocardial facing, pericardial facing, bifurcation, trifurcation, proximal, mid, distal, main vessel, or branch vessel.

15. The computer-implemented method of claim 14, wherein a change in location of a region of plaque from pericardial facing to myocardial facing is indicative of a positive efficacy of the medical treatment.

16. The computer-implemented method of claim 1, wherein the volume of the one or more regions of plaque comprises one or more of absolute plaque volume or percent atheroma volume (PAV).

17. The computer-implemented method of claim 1, wherein an increase in volume of the one or more regions of plaque between the first point in time and the second point in time is indicative of a negative efficacy of the medical treatment.

18. The computer-implemented method of claim 1, wherein vascular remodeling comprises vascular remodeling of one or more coronary atherosclerotic lesions.

19. The computer-implemented method of claim 1, wherein vascular remodeling comprises one or more directionality changes in remodeling, the one or more directionality changes in remodeling comprising one or more of outward, intermediate, or inward.

20. The computer-implemented method of claim 19, wherein more outward remodeling between the first point in time and the second point in time is indicative of a negative efficacy of the medical treatment.

21. A system for tracking efficacy of a treatment for a plaque-based disease based on non-invasive medical image analysis, the system comprising:
one or more computer readable storage devices configured to store a plurality of computer executable instructions; and
one or more hardware computer processors in communication with the one or more computer readable storage devices and configured to execute the plurality of computer executable instructions in order to cause the system to:
access a first set of plaque parameters and a first set of vascular parameters associated with a subject, wherein the first set of plaque parameters and the first set of vascular parameters are derived from a first set of medical images of the subject comprising at least one axial image comprising one or more regions of plaque, wherein the one or more plaque parameters are determined automatically based at least in part by applying a machine learning algorithm to the accessed first set of medical images, wherein the first set of medical images of the subject is obtained non-invasively at a first point in time, wherein the first set of plaque parameters comprises density and volume of one or more regions of plaque derived from the first medical image of the subject obtained at the first point in time, and wherein the first set of vascular parameters comprises one or more of volume, diameter, area, length, location, or remodeling derived from the first set of medical images of the subject obtained at the first point in time;
generate a first characterized region of plaque, wherein generating the first characterized region of plaque comprises characterizing the one or more regions of plaque in the first set of medical images of the subject obtained at the first point in time as calcified plaque, non-calcified plaque, or low density non-calcified plaque based on the first set of plaque parameters;
access a second set of medical images of the subject, wherein the second set of medical images of the subject is obtained non-invasively at a second point in time after the subject is treated with a treatment, the second point in time being later than the first point in time, wherein the second set of medical images of the subject comprises at least one axial image comprising the one or more regions of plaque;
identify the one or more regions of plaque from the second set of medical images;
determine a second set of plaque parameters and a second set of vascular parameters associated with the subject by analyzing the one or more regions of plaque identified from the second set of medical images, the second set of plaque parameters determined based at least in part on graphical identification of vessel wall and lumen wall from the second set of medical images, wherein the second set of plaque parameters comprises density and volume of the one or more regions of plaque derived from the second medical image of the subject obtained at the second point in time, and wherein the second set of vascular parameters comprises one or more of vascular volume, diameter, area, length, location, or remodeling derived from the second set of medical images of the subject obtained at the second point in time;

generate a second characterized region of plaque, wherein generating the first characterized region of plaque comprises characterizing the one or more regions of plaque in the second set of medical images of the subject obtained at the second point in time as calcified plaque, non-calcified plaque, or low density non-calcified plaque based on the first set of plaque parameters;

analyze one or more changes between the first characterized region of plaque and the second characterized region of plaque;

analyze one or more changes between the first set of vascular parameters and the second set of vascular parameters; and generate a graphical representation of tracking progression of the plaque-based disease based at least in part on the analyzed one or more changes between the first characterized region of plaque and the second characterized region of plaque and the analyzed one or more changes between the first set of vascular parameters and the second set of vascular parameters, wherein the generated graphical representation of tracking progression of the plaque-based disease is configured to be used to determine efficacy of the treatment, wherein the determined efficacy of the treatment is configured to be used to determine whether to change the treatment for the subject.

22. The system of claim 21, wherein the graphical representation of tracking progression of the plaque-based disease is generated on one or more of a per-subject, per-vessel, per-segment, or per-lesion basis.

23. The system of claim 21, wherein the system is further caused to determine the efficacy of the treatment based at least in part on the progression of the plaque-based disease.

24. The system of claim 23, wherein the system is further caused to generate a further proposed treatment based at least in part on the efficacy of the treatment determined based on the tracked progression of the plaque-based disease.

25. The system of claim 21, wherein the treatment comprises one or more of a medication treatment, lifestyle treatment, or revascularization treatment.

26. The system of claim 25, wherein the medication treatment comprises one or more of statins, icosapent ethyl, bempedoic acid, rivaroxaban, aspirin, proprotein convertase subtilisin/kexin type 9 (PCSK-9) inhibitors, inclisiran, sodium-glucose cotransporter-2 (SGLT-2) inhibitors, glucagon-like peptide-1 (GLP-1) receptor agonists, low-density lipoprotein (LDL) apheresis, or Lp(a) lowering medication, wherein the lifestyle treatment comprises one or more of increased exercise, aerobic exercise, anaerobic exercise, cessation of smoking, or change in diet, and wherein the revascularization treatment comprises one or more of bypass grafting, stenting, or use of a bioabsorbable scaffold.

27. The system of claim 21, wherein one or more of the first set of plaque parameters, second set of plaque parameters, first set of vascular parameters, or second set of vascular parameters is normalized to account for one or more of scanner type, image acquisition parameters, energy, gating, contrast, age of subject, subject body habitus, surrounding cardiac structure, or plaque type.

28. The system of claim 21, wherein the density of the one or more regions of plaque comprises radiodensity.

29. The system of claim 21, wherein the density of the one or more regions of plaque comprises absolute density.

30. The system of claim 21, wherein an increase in density of the one or more regions of plaque is indicative of a positive efficacy of the medical treatment.

* * * * *